US010874728B2

(12) United States Patent
Coukos et al.

(10) Patent No.: US 10,874,728 B2
(45) Date of Patent: Dec. 29, 2020

(54) TUMOR VASCULAR MARKER-TARGETED VACCINES

(71) Applicant: THE TRUSTEES OF THE UNIVERSITY OF PENNSYLVANIA, Philadelphia, PA (US)

(72) Inventors: George Coukos, Wynnewood, PA (US); Andrea Facciabene, Philadelphia, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

(21) Appl. No.: 15/075,451

(22) Filed: Mar. 21, 2016

(65) Prior Publication Data

US 2016/0331819 A1 Nov. 17, 2016

Related U.S. Application Data

(62) Division of application No. 13/121,638, filed on Aug. 25, 2011, now Pat. No. 9,290,556.

(60) Provisional application No. 61/101,083, filed on Sep. 29, 2008, provisional application No. 61/181,659, filed on May 27, 2009.

(51) Int. Cl.

| | |
|---|---|
| ***A61K 31/47*** | (2006.01) |
| ***G01N 33/574*** | (2006.01) |
| ***C12Q 1/68*** | (2018.01) |
| ***A61K 39/00*** | (2006.01) |
| ***C07H 21/04*** | (2006.01) |
| ***A61K 48/00*** | (2006.01) |
| ***A61K 51/10*** | (2006.01) |
| ***C07K 16/28*** | (2006.01) |
| ***C07K 14/47*** | (2006.01) |
| ***A61K 41/00*** | (2020.01) |

(52) U.S. Cl.

CPC ...... *A61K 39/0011* (2013.01); *A61K 41/0057* (2013.01); *A61K 48/00* (2013.01); *A61K 51/1045* (2013.01); *C07H 21/04* (2013.01); *C07K 14/4748* (2013.01); *C07K 16/2851* (2013.01); *A61K 2039/53* (2013.01); *A61K 2039/55516* (2013.01); *A61K 2039/58* (2013.01); *A61K 2039/62* (2013.01); *C07K 2317/24* (2013.01); *C07K 2319/55* (2013.01)

(58) Field of Classification Search

None

See application file for complete search history.

(56) References Cited

U.S. PATENT DOCUMENTS

| | | | | |
|---|---|---|---|---|
| 2004/0005563 | A1 | 1/2004 | Mack et al. | |
| 2004/0009154 | A1 | 1/2004 | Khan et al. | |
| 2005/0142138 | A1 | 6/2005 | St. Croix et al. | |
| 2006/0239911 | A1* | 10/2006 | Nicolaides | B82Y 5/00 424/1.49 |
| 2006/0286074 | A1 | 12/2006 | Tang et al. | |
| 2007/0154928 | A1 | 7/2007 | Mack et al. | |
| 2008/0181896 | A1 | 7/2008 | Khan et al. | |
| 2010/0183504 | A1* | 7/2010 | Chen | A61K 49/0002 424/1.29 |

FOREIGN PATENT DOCUMENTS

| | | |
|---|---|---|
| WO | WO 2002/086443 | 10/2002 |
| WO | WO 2003/042661 | 5/2003 |
| WO | WO 2005/077977 | 8/2005 |
| WO | WO 2007/042169 | 4/2007 |
| WO | WO 2008/105978 | 9/2008 |

OTHER PUBLICATIONS

Buckanovich et al., "Tumor Vascular Proteins As Biomarkers in Ovarian Cancer" J. of Clinical Oncology, vol. 25, No. 7, pp. 852-861.

Neri et al., "Tumour Vascular Targeting", Nature Reviews 5: 436-446, 2005.

* cited by examiner

*Primary Examiner* — Mark Halvorson

(74) *Attorney, Agent, or Firm* — Mark S. Cohen; Pearl Cohen Zedek Latzer Baratz LLP

(57) ABSTRACT

The present invention provides methods of immunizing a subject against a tumor, inhibiting tumor growth, inhibiting tumor recurrence, treating, suppressing the growth of, or decreasing the incidence of a tumor, overcoming tolerance to a tumor vasculature marker (TVM) in a subject comprising the step of administering a vaccine comprising a TVM or a nucleic acid encoding a TVM and related vaccines. The present invention also provides a method of targeting a tumor vasculature in a subject having a tumor comprising the step of contacting said subject with a labeled compound that binds a) a tumor vasculature marker (TVM) or b) a nucleic acid molecule encoding said TVM.

3 Claims, 18 Drawing Sheets

Specification includes a Sequence Listing.

| injection ID | 1 | 2 | 3 |
|---|---|---|---|
| Cell mixture | ID8 +MS1-fLuc | ID8 +MS1-TEM1/fLuc | ID8 |
| Each inj. (in 100uL) | 500K:5m | 500k:5m | 500k |

Left Right
3
1 2

Bioluminescence imaging,
1 wk after injection

Therapeutic administration of TEM-Dom DNA vaccine results in a significant Lewis Lung Carcinoma tumor growth impairment.

TUMOR VASCULAR MARKER-TARGETED VACCINES

CROSS-REFERENCE TO RELATED APPLICATIONS

This Application is a Divisional of U.S. patent application Ser. No. 13/121,638, filed Aug. 25, 2011 which is a National Phase Application of PCT International Application PCT/US09/58852, filed Sep. 29, 2009 that claims priority to U.S. provisional patent applications 61/101,083 and 61/181,659, filed Sep. 29, 2008 and May 27, 2009, respectively, all of which are incorporated herein by reference in their entirety.

GOVERNMENT INTEREST STATEMENT

This invention was made with government support under grant numbers CA098951, CA083638, TW000671, and HD043459 awarded by the National Institutes of Health. The government has certain rights in the invention.

FIELD OF THE INVENTION

The invention relates to compositions and methods for treating cancer. Specifically, the invention relates to a vaccine comprising a tumor vasculature marker (TVM) and methods of use thereof.

BACKGROUND OF THE INVENTION

A major hurdle to advances in treating cancer is the relative lack of agents that can selectively target the cancer, while sparing normal tissue. For example, radiation therapy and surgery, which generally are localized treatments, can cause substantial damage to normal tissue in the treatment field, resulting in scarring and, in severe cases, loss of function of the normal tissue. Chemotherapy, in comparison, which generally is administered systemically, can cause substantial damage to organs such as bone marrow, mucosae, skin and the small intestine, which undergo rapid cell turnover and continuous cell division. As a result, undesirable side effects such as nausea, loss of hair and drop in blood cell count occur as a result of systemically treating a cancer patient with chemotherapeutic agents. Such undesirable side effects often limit the amount of a treatment that can be administered. Thus, cancer remains a leading cause of patient morbidity and death.

Tumor malignancies accounts for 85% cancer mortality that was responsible for 23% of all deaths in US. Current approaches for the treatment of tumor malignancies with established agents and with the new targeted agents used alone and in combination are limited, in part, by inability to deliver cytotoxic agents selectively to the tumor tissue in sufficient concentrations critical for tumor cell kill that translate into meaningful and durable responses.

Cancers metastasize through tumor vasculature, which is diverse in both its cellular and molecular compositions, exhibiting variation in the type of cells that line the vessels and their complement of cell-surface receptors. Blood vessels are one type of tumor vasculature, and archetypal blood vessels are entirely lined with endothelial cells. Tumor blood vessels also can be mosaic or lined by both endothelial and tumor cells, while other vessels are formed entirely from tumor cells. Lymphatic vessels, which also occur within several tumor types, are a second type of tumor vasculature. The lymphatic vasculature is an important route for the spreading of cancer, and animal experiments have shown a positive correlation between metastasis and the number of lymphatic vessels in and around a tumor. The development of vascular-specific tools for cancer diagnosis and/or therapy has been hindered by the paucity of targets.

Accordingly, there exists a need for improved compositions and methods for treating cancer.

SUMMARY OF THE INVENTION

In one embodiment, the invention provides a vaccine comprising a polypeptide comprising a tumor vasculature marker (TVM) or immunogenic fragment thereof, wherein said vaccine is capable of abrogating the growth of a tumor whose vasculature expresses said TVM.

In another embodiment, the invention provides a vaccine comprising a nucleic acid construct comprising a nucleic acid sequence encoding a tumor vasculature marker (TVM) or immunogenic fragment thereof, wherein said vaccine is capable of abrogating the growth of a tumor whose vasculature expresses said TVM.

In another embodiment, the invention provides a method of immunizing a subject against a tumor, comprising administering to said subject a vaccine comprising a polypeptide comprising a tumor vasculature marker (TVM) or immunogenic fragment thereof, wherein said vaccine elicits an immune response to said TVM, thereby abrogating the growth of a tumor whose vasculature expresses said TVM.

In another embodiment, the invention provides a method of inhibiting the growth of a tumor in a subject, comprising administering to said subject a vaccine comprising a polypeptide comprising a tumor vasculature marker (TVM) or immunogenic fragment thereof, wherein said vaccine elicits an immune response to said TVM, thereby inhibiting the growth of a tumor whose vasculature expresses said TVM.

In another embodiment, the invention provides a method of inhibiting tumor recurrence in a subject, comprising administering to said subject a vaccine comprising a polypeptide comprising a tumor vasculature marker (TVM) or immunogenic fragment thereof, wherein said vaccine elicits an immune response to said TVM, thereby inhibiting the recurrence of a tumor whose vasculature expresses said TVM.

In another embodiment, the invention provides a method of treating, suppressing the growth of, or decreasing the incidence of a tumor in a subject, comprising administering to said subject a vaccine comprising a polypeptide comprising a tumor vasculature marker (TVM) or immunogenic fragment thereof, wherein said vaccine elicits an immune response to said TVM, thereby treating, suppressing the growth of, or decreasing the incidence of a tumor whose vasculature expresses said TVM.

In another embodiment, the invention provides a method of overcoming tolerance to a tumor vasculature marker (TVM) in a subject, comprising administering to said subject a vaccine comprising a polypeptide comprising a tumor vasculature marker (TVM) or immunogenic fragment thereof, wherein said vaccine elicits an immune response to said TVM, thereby overcoming tolerance to said TVM.

In another embodiment, the invention provides a nucleic acid encoding for TEM1-pDOM for the prevention and treatment of a tumor.

In another embodiment, the invention provides a method of inhibiting the growth of a tumor in a subject, wherein the vasculature supplying said tumor comprises a tumor vasculature marker (TVM), comprising the steps of: identifying expression of said TVM by said tumor by contacting said subject with a labeled compound that binds said TVM or a nucleic acid molecule encoding said TVM; detecting said label; contacting said subject with an antibody to said TVM, wherein said antibody is labeled with a radionuclide to deliver cytotoxic radiation to tumor vasculature expressing said TVM; and contacting said subject with said TVM or with a nucleic acid construct encoding said TVM to induce an immune response against said TVM.

In another embodiment, the invention provides a method of inhibiting tumor recurrence in a subject, wherein the vasculature supplying said tumor comprises a tumor vasculature marker (TVM), comprising the steps of: identifying expression of said TVM by said tumor by contacting said subject with a labeled compound that binds said TVM or a nucleic acid molecule encoding said TVM; detecting said label; contacting said subject with an antibody to said TVM, wherein said antibody is labeled with a radionuclide to deliver cytotoxic radiation to tumor vasculature expressing said TVM; and contacting said subject with said TVM or with a nucleic acid construct encoding said TVM to induce an immune response against said TVM.

In another embodiment, the invention provides a method of treating, inhibiting the growth of, suppressing the growth of, or decreasing the incidence of a tumor in a subject, wherein the vasculature supplying said tumor comprises a tumor vasculature marker (TVM), comprising the steps of: identifying expression of said TVM by said tumor by contacting said subject with a labeled compound that binds said TVM or a nucleic acid molecule encoding said TVM; detecting said label; contacting said subject with an antibody to said TVM, wherein said antibody is labeled with a radionuclide to deliver cytotoxic radiation to tumor vasculature expressing said TVM; and contacting said subject with said TVM or with a nucleic acid construct encoding said TVM to induce an immune response against said TVM.

In one embodiment, the nucleic acid sequence encoding said TVM is the sequences set forth in SEQ ID NO: 1-37. In one embodiment, the TVM is TEM-1. In one embodiment, the TVM is TEM-5, TEM-7, or TEM-8. In one embodiment, the detecting step is performed using positron emission tomography (PET) scanning. In one embodiment, the detecting step also utilizes computed tomography (CT) or magnetic resonance imaging (MRI) scanning. In one embodiment, the labeled compound is a labeled antibody.

In another embodiment, the invention provides a method of targeting a tumor vasculature in a subject having a tumor, the method comprising the step of contacting said subject with a labeled compound that binds a) a tumor vasculature marker (TVM) or b) a nucleic acid molecule encoding said TVM. In one embodiment, the method further comprises the step of detecting said labeled compound. In one embodiment, the labeled compound is an antibody.

In another embodiment, the invention provides a method of inhibiting the growth of a tumor in a subject, comprising administering to said subject a vaccine comprising one or more nucleic acid constructs comprising a nucleic acid sequence encoding a tumor vasculature marker (TVM) or immunogenic fragment thereof, wherein said vaccine elicits an immune response to said TVM, thereby inhibiting the growth of a tumor whose vasculature expresses said TVM In another embodiment, the invention provides a method of inhibiting tumor recurrence in a subject, comprising administering to said subject a vaccine comprising one or more nucleic acid constructs comprising a nucleic acid sequence encoding a tumor vasculature marker (TVM) or immunogenic fragment thereof, wherein said vaccine elicits an immune response to said TVM, thereby inhibiting the recurrence of a tumor whose vasculature expresses said TVM.

In another embodiment, the invention provides a method of treating, suppressing the growth of, or decreasing the incidence of a tumor in a subject, comprising administering to said subject a vaccine comprising one or more nucleic acid constructs comprising a nucleic acid sequence encoding a tumor vasculature marker (TVM) or immunogenic fragment thereof, wherein said vaccine elicits an immune response to said TVM, thereby treating, suppressing the growth of, or decreasing the incidence of a tumor whose vasculature expresses said TVM.

In another embodiment, the invention provides a method of overcoming tolerance to a tumor vasculature marker (TVM) in a subject, comprising administering to said subject a vaccine comprising one or more nucleic acid constructs comprising a nucleic acid sequence encoding a tumor vasculature marker (TVM) or immunogenic fragment thereof, wherein said vaccine elicits an immune response to said TVM, thereby overcoming tolerance to said TVM.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

FIG. 1.

FIG. 2. Establishment of human TEM1+ immortalized endothelial lines. MS1 and H5V murine endothelial lines were transfected with human TEM1.

FIG. 3.

FIG. 4.

DETAILED DESCRIPTION OF THE INVENTION

Figure 1A:
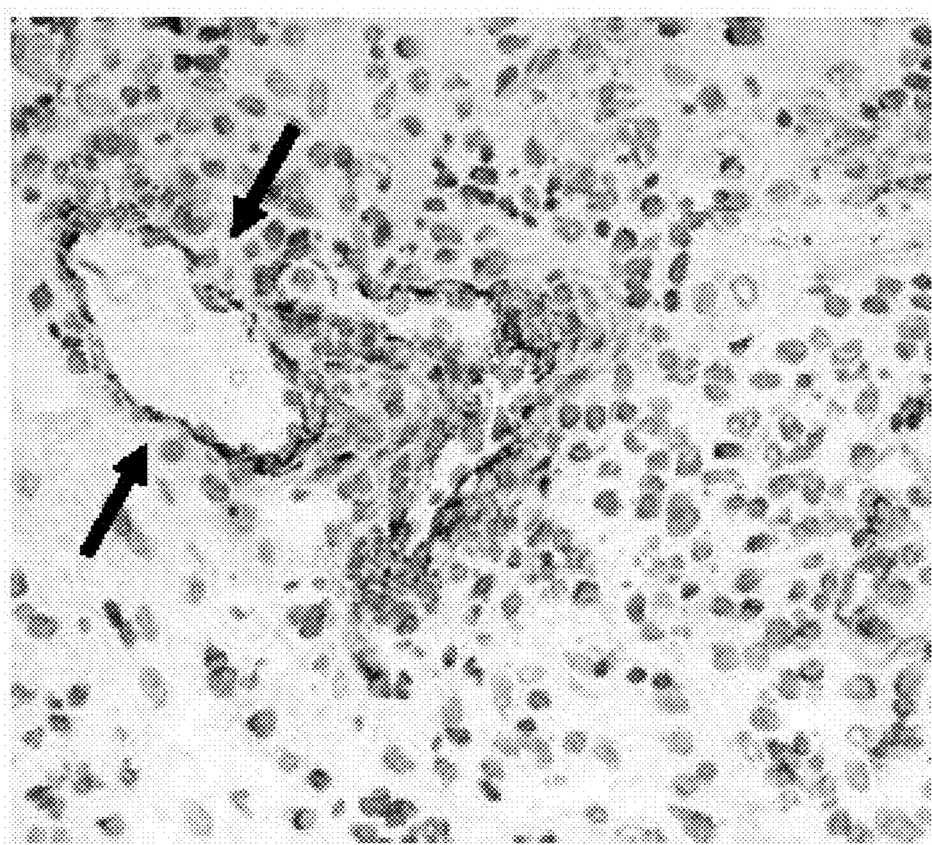
FIG. 1A, TEM1 expression in tumor vasculature in human ovarian cancer using MORAb-004.

The invention relates to compositions and methods for treating cancer. Specifically, the invention relates to a vaccine comprising a tumor vasculature marker (TVM) and methods of use thereof.

In one embodiment, provided herein is a vaccine comprising a polypeptide comprising a tumor vasculature marker (TVM) or immunogenic fragment thereof, wherein said vaccine can abrogate the growth of a tumor whose vasculature expresses said TVM.

In another embodiment, provided herein is a vaccine comprising a nucleic acid construct comprising a nucleic acid sequence encoding a tumor vasculature marker (TVM) or immunogenic fragment thereof, wherein said vaccine can abrogate growth of a tumor whose vasculature expresses said TVM.

In one embodiment, the TVM is encoded by a nucleic acid sequence as set forth in SEQ ID NO: 1-37. In another embodiment, the nucleic acid construct comprises a nucleic acid sequence as set forth in SEQ ID NO: 1-37. In one embodiment, the tumor is an ovarian tumor. In one embodiment, the TVM is encoded by a nucleic acid sequence as set forth in SEQ ID NO: 1-35. In another embodiment, the nucleic acid construct comprises a nucleic acid sequence as set forth in SEQ ID NO: 1-35. In one embodiment, the tumor is a renal tumor. In one embodiment, the TVM is encoded by a nucleic acid sequence as set forth in SEQ ID NO: 36. In another embodiment, the nucleic acid construct comprises a nucleic acid sequence as set forth in SEQ ID NO: 36. In one embodiment, the tumor is a breast tumor. In one embodiment, the TVM is encoded by a nucleic acid sequence as set forth in SEQ ID NO: 37. In another embodiment, the nucleic acid construct comprises a nucleic acid sequence as set forth in SEQ ID NO: 37. In an exemplary embodiment, the tumor is a solid tumor.

In one embodiment, the TVM of the present invention is ADAM12. In another embodiment, the TVM is Adlican. In another embodiment, the TVM is BLAME/SLAMF8. In another embodiment, the TVM is COL11A1. In another embodiment, the TVM is c14orf100. In another embodiment, the TVM is C14orf28. In another embodiment, the TVM is C2orf6. In another embodiment, the TVM is c6orf55. In another embodiment, the TVM is C6orf69. In another embodiment, the TVM is CDCP1-CUB. In another embodiment, the TVM is DKFZp762e1312. In another embodiment, the TVM is DR6. In another embodiment, the TVM is DSG2. In another embodiment, the TVM is EGFL6. In another embodiment, the TVM is EPSTI1. In another embodiment, the TVM is ESM1. In another embodiment, the TVM is FLJ46072. In another embodiment, the TVM is IVD10. In another embodiment, the TVM is GPR105. In another embodiment, the TVM is IVNS1ABP. In another embodiment, the TVM is KCNE3. In another embodiment, the TVM is KCNE4. In another embodiment, the TVM is KCNK5. In another embodiment, the TVM is KIAA1892. In another embodiment, the TVM is KIBRA. In another embodiment, the TVM is LOC51136. In another embodiment, the TVM is MS4A6A. In another embodiment, the TVM is OLFML2B. In another embodiment, the TVM is PCDHB2. In another embodiment, the TVM is SCGB2A1. In another embodiment, the TVM is SDC1. In another embodiment, the TVM is SEC23B. In another embodiment, the TVM is SLC11A1-NRAMP. In another embodiment, the TVM is SPP1. In another embodiment, the TVM is ST14. In another embodiment, the TVM is TNFAIP6. In another embodiment, the TVM is WFDC2.

In another embodiment, the TVM is tumor endothelial marker (TEM)-1, which in one embodiment, is endosialin. In one embodiment, the TVM is TEM-5, TEM-7, or TEM-8. In another embodiment, the TVM is TEM-9 or TEM-17.

As used herein, the term "tumor endothelial marker (TEM)" refers to a molecule preferentially expressed on tumor endothelial cells. TEM expression is absent or significantly lower on normal (non-tumor) vasculature.

In one embodiment, the target molecule is TEM 1. In one embodiment, TEM1, or endosialin, is a 165 kDa glycoprotein. In one embodiment, TEM 1 is a C-type lectin-like, type I membrane protein with a signal leader peptide, five globular extracellular domains, followed by a mucin-like region, a transmembrane segment and a short cytoplasmic tail. In one embodiment, the N-terminal shows homology to thrombomdulin, a receptor involved in regulating blood coagulation and to complement receptor ClqRp. In one embodiment, murine and human TEM 1 share 77.5% amino acid identity with 100% identity in the transmembrane region. In one embodiment, TEM 1 has a signal sequence at amino acids 1-17, its transmembrane domain is at amino acids 686-708, and its extracellular domain is at residues 1-685. In one embodiment, TEM 1 expression varies with cell density (or cell cycle). In one embodiment, TEM 1 is maximally expressed in confluent (Go) cells, the most relevant phase of the cell cycle in vivo. In one embodiment, the nucleic acid sequence of TEM 1 is tcgcgatgctgctgc-gcctgttgctggcctgggcggccgcagggcccacactgggccag-gacccctgggctgctgagccccgtgccgcc tgcggccccagcagctgc-tacgctctcttcccacggcgccgcaccttcctggaggcctggcggg-cctgccgcgagctgggggcgacct ggccactcctcggacccccgaggag-gcccagcgtgtggacagcctggtgggtgcgggcccagccagccggctgctgtg-gatcgggctg cagcggcaggcccggcaatgccagctgcagcgcc-cactgcgcggcttcacgtggaccacaggggaccaggacacggctttcaccaact gggcccagccagcctctggaggcccctgcccggcccagcgctgtgtggccctg-gaggcaagtggcgagcaccgctggctggagggct cgtgcacgctggct-gtcgacggctacctgtgccagtttggcttcgagggcgcctgcccggcgctgcaa-gatgaggcgggccaggccggc ccagccgtgtataccacgcccttc-cacctggtctccacagagtttgagtggctgcccttcggctctgtggccgctgtg-cagtgccaggctgg caggggagcctctctgctctgcgtgaagcagcctgagg-gaggtgtgggctggtcacgggctgggcccctgtgcctggggactggctgca gccctgacaacgggggctgcgaacacgaatgtgtggaggaggtggatggt-cacgtgtcctgccgctgcactgagggcttccggctggca gcagacgggcg-cagttgcgaggacccctgtgcccaggctccgtgcgagcagcagtgtgagccc-ggtgggccacaaggctacagctgcc actgtcgcctgggtttccggccagcg-gaggatgatccgcaccgctgtgtggacacagatgagtgccagattgccggtg-tgtgccagcagat gtgtgtcaactacgttggtggcttcgagtgttattgtagcg-agggacatgagctggaggctgatggcatcagctgcagccctgcaggggcc atgggtgcccaggcttcccaggacctcggagatgagttgctggatgacggggag-gatgaggaagatgaagacgaggcctggaaggcctt caacggtggctggacg-gagatgcctgggatcctgtggatggagcctacgcagccgcctgac-tttgccctggcctatagaccgagcttccca gaggacagagagccacagataccc-tacccggagcccacctggccacccccgctcagtgcccccagggtcccctac-cactcctcagtgctc tccgtcacccggcctgtggtggtctctgccacgcatcc-cacactgccttctgcccaccagcctcctgtgatccctgccacacacccagctttgt cccgtgaccaccagatccccgtgatcgcagccaactatccagatctgccttctgcc-taccaacccggtattctctctgtctctcattcagcaca gcctcctgcc-caccagccccctatgatctcaaccaaatatccggagctcttccctgcccaccag-tcccccatgtttccagacacccgggtcgc tggcacccagaccaccactcat-ttgcctggaatcccacctaaccatgcccctctggtcaccaccctcggtgcccagc-taccccctcaagccc cagatgcccttgtcctcagaacccaggccacccagcttcc-cattatcccaactgcccagccctctctgaccaccacctccaggtcccctgtgt ctcctgcccatcaaatctctgtgcctgctgccacccagcccgcagccctccc-cacctcctgccctctcagagccccactaaccagacctca cccatcagccctaca-catccccattccaaagcccccaaatcccaagggaagatggccccagtcc-caagttggccctgtggctgccctcac cagctcccacagcag-ccccaacagccctgggggaggctggtcttgccgagcacagccagagg-gatgaccggtggctgctggtggcact cctggtgccaacgtgtgtctttttggt-ggtcctgcttgcactgggcatcgtgtactgcacccgctgtggcccccatgcacc-caacaagcgcat cactgactgctatcgctgggtcatccatgctgg-gagcaagagcccaacagaacccatgcccccaggggcagcctcacag-gggtgcaga cctgcagaaccagcgtgtgatggggtgcagacccccctcatg-gagtatggggcgctggacacatggccggggctgcaccagggacccat gggggctgcccagctggacagatggcttcctgctccccaggcccagccagg-gtcctctctcaaccactagacttggctctcaggaactctg cttcctggccc-agcgctcgtgaccaaggatacaccaaagcccttaagacctcagggggcgg-gtgctggggtcttctccaataaatggggtg tcaaccttaaaaaaaaaaaaaa-aaaaaaaaaaaaa (SEQ ID NO: 38). In one embodiment, the amino acid sequence of TEM 1 is MLLRLLLA-WAAAGPTLGQDPWAAEPRAACGPSSCYALFPRRRT-FLEAWRACRELGGDL ATPRTPEEAQRVDSLVGAG-PASRLLWIGLQRQARQCQLQRPLRGFTWTTGDQD-TAFTN WAQPASGGPCPAQRCVALEASGEHRW-LEGSCTLAVDGYLCQFGFEGACPALQDEAGQ AGPAVYTTPFHLVSTEFEWLPFGSVAAVQCQAGR-GASLLCVKQPEGGVGWSRAGPLCL GTGCSPDN-GGCEHECVEEVDGHVSCRCTEGFRLAADGRSCEDP-CAQAPCEQQCEPGGP QGYSCHCRLGFRPAEDDPH-RCVDTDECQIAGVCQQMCVNYVGGFECYCSEGHE-LEAD GISCSPAGAMGAQASQDLGDELLDDGEDEED-EDEAWKAFNGGWTEMPGILWMEPTQP PDFALAY-RPSFPEDREPQIPYPEPTWPPPLSAPRVPYHSSVLSVT-RPVVVSATHPTLPSAH QPPVIPATHPALSRDHQIPVI-AANYPDLPSAYQPGILSVSHSAQPPAHQPPMIST-KYPELFP AHQSPMFPDTRVAGTQTTTHLPGIPPNHAP-LVTTLGAQLPPQAPDALVLRTQATQLPIIP TAQPSL-TTTSRSPVSPAHQISVPAATQPAALPTLLPSQSPTNQT-SPISPTHPHSKAPQIPRE DGPSPKLALWLPSPAPTAAP-TALGEAGLAEHSQRDDRWLLVALLVPTCVFLVVLLA-LGI VYCTRCGPHAPNKRITDCYRWVIHAGSKSPT-EPMPPRGSLTGVQTCRTSV (SEQ ID NO: 39).

Any biologically active fragment of a TVM, or in one embodiment, TEM, can be used in the present methods and compositions. As used herein, the term "biologically active fragment" refers to any portion of the TVM, or in one embodiment, TEM protein, and its corresponding encoding DNA sequence, that retains one or more of the biological activities of the full-length protein. Such fragments can include only a part of the full-length sequence and yet possess the same function, possibly to a greater or lesser extent. Such fragments can be evaluated for biological activities using the methods provided herein, in one embodiment, to assess immunogenicity.

Any analog or derivative of the TVM, or in one embodiment, TEM protein can be used in the methods herein. As used herein, the term "analog or derivative" refers to substituted proteins. Such mutations and substitutions can be designed and expressed by well-known laboratory methods and include conservative mutations and substitutions known to the skilled artisan. For example, deletion mutants of a TVM, or in one embodiment, TEM can be designed and expressed by well known laboratory methods. Such analogs and derivatives can be evaluated for maintaining their properties routinely using the assays provided herein as an indicator of biological activity.

The TVM, or in one embodiment, TEM protein or polypeptide can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography.

Typically, high performance liquid chromatography (HPLC) is employed for purification. Polypeptides useful in the methods provided herein include: products purified from natural sources, including bodily fluids, tissues and cells, whether directly isolated or cultured; products of chemical synthetic procedures; and products produced by recombinant techniques from a prokaryotic or eukaryotic host, including, but not limited to bacterial, yeast, higher plant, insect and mammalian cells. Depending upon the host employed in a recombinant production procedure, the polypeptides useful in the present methods may be glycosylated or may be non-glycosylated. In addition, TVM, or in one embodiment, TEM polypeptides may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins this prokaryotic removal process is inefficient, depending on the nature of the amino acid to which the N-terminal methionine is covalently linked.

It also will be recognized by one of ordinary skill in the art that some amino acid sequences of the TVM, or in one embodiment, TEM polypeptide can be varied without significant effect of the structure or function of the protein. Typically, conservative substitutions include the replacement of, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

To improve or alter the characteristics of TVM, or in one embodiment, TEM polypeptides, protein engineering may be employed. Recombinant DNA technology known to those skilled in the art can be used to create novel mutant proteins or muteins including single or multiple amino acid substitutions, deletions, additions or fusion proteins. Such modified polypeptides can show, e. g., enhanced activity or increased stability. In addition, they may be purified in higher yields and show better solubility than the corresponding natural polypeptide, at least under certain purification and storage conditions.

The DNA sequences useful in the present methods and compositions include any sequence that encodes a biologically active full length TVM, or in one embodiment, TEM, fragment, analog, or derivative thereof. The sequence may comprise a genomic sequence or a non-genomic sequence. Typically, the sequences will be a cDNA sequence. Exemplary sequences are found in U.S. Pat. No. 7,358,351 or U.S. Publication No. 20030017157, which are incorporated herein by reference.

Exogenous expression of the TVM, or in one embodiment, TEM protein can be transient, stable, or some combination thereof. Exogenous expression can be enhanced or maximized by co-expression with one or more additional proteins that increase its immunogenic activity.

In another embodiment, the TVM is FAD104; in another embodiment, the TVM is WARP; in another embodiment, the TVM is BCAP29; in another embodiment, the TVM is CDH1; in another embodiment, the TVM is FLJ10826; in another embodiment, the TVM is OPN3; in another embodiment, the TVM is HIATL2; in another embodiment, the TVM is IL28RA; in another embodiment, the TVM is TMEM19; in another embodiment, the TVM is C10orf69; in another embodiment, the TVM is FRAP1; in another embodiment, the TVM is CKLFSF6; in another embodiment, the TVM is MPHOSPH9; in another embodiment, the TVM is CLST11240; in another embodiment, the TVM is MS4A6A; in another embodiment, the TVM is SGPP2; in another embodiment, the TVM is SLC11A1; in another embodiment, the TVM is SLCO3A1; in another embodiment, the TVM is LOC51136; in another embodiment, the TVM is DKFZp564I1922; in another embodiment, the TVM is KCNE3; in another embodiment, the TVM is CALM3; in another embodiment, the TVM is KCNE4; in another embodiment, the TVM is MGC34647; in another embodiment, the TVM is MUC1; in another embodiment, the TVM is SDC1; in another embodiment, the TVM is SLC30A6; in another embodiment, the TVM is ST14; in another embodiment, the TVM is CDCP1; in another embodiment, the TVM is TLCD1; in another embodiment, the TVM is SPTB; in another embodiment, the TVM is FNDC3; in another embodiment, the TVM is SPRY1; in another embodiment, the TVM is MME; in another embodiment, the TVM is INSR; in another embodiment, the TVM is LPPR4; in another embodiment, the TVM is C14orf100; in another embodiment, the TVM is SLC9A5; in another embodiment, the TVM is SCGB2A1; in another embodiment, the TVM is FLT1; in another embodiment, the TVM is MOBK1B; in another embodiment, the TVM is TMEM2; in another embodiment, the TVM is TMEM8; in another embodiment, the TVM is SLC5A4; in another embodiment, the TVM is MEST; in another embodiment, the TVM is CHODL; in another embodiment, the TVM is TRIO; in another embodiment, the TVM is IL10RA; in another embodiment, the TVM is LGALS3BP; in another embodiment, the TVM is STK4; in another embodiment, the TVM is ERBB3; in another embodiment, the TVM is C14orf28; in another embodiment, the TVM is KIAA1024; in another embodiment, the TVM is KIAA1906; in another embodiment, the TVM is F3; in another embodiment, the TVM is PCDHB2; in another embodiment, the TVM is KIAA0703; in another embodiment, the TVM is C1orf10; in another embodiment, the TVM is POLYDOM; in another embodiment, the TVM is TUBAL3; in another embodiment, the TVM is GPR105; in another embodiment, the TVM is IL7R; in another embodiment, the TVM is ARHGAP18; in another embodiment, the TVM is GRM1; in another embodiment, the TVM is PREX1; in another embodiment, the TVM is MUC3A; in another embodiment, the TVM is EPSTI1; in another embodiment, the TVM is and UBE2J1.

In another embodiment, the TVM is DE1-B1; in another embodiment, the TVM is EPB41L3; in another embodiment, the TVM is F2RL1; in another embodiment, the TVM is GPM6B; in another embodiment, the TVM is SPON1; in another embodiment, the TVM is d STC2.

In another embodiment, the TVM is AML-1; in another embodiment, the TVM is LZTS1.

In one embodiment, the nucleic acid sequence encoding a TVM of the present invention is SEQ ID NO: 1. In another embodiment, the nucleic acid sequence encoding a TVM is SEQ ID NO: 2. In another embodiment, the nucleic acid sequence encoding a TVM is SEQ ID NO: 3 In another embodiment, the nucleic acid sequence encoding a TVM is SEQ ID NO: 4. In another embodiment, the nucleic acid sequence encoding a TVM is SEQ ID NO: 5. In another embodiment, the nucleic acid sequence encoding a TVM is SEQ ID NO: 6. In another embodiment, the nucleic acid sequence encoding a TVM is SEQ ID NO: 7. In another embodiment, the nucleic acid sequence encoding a TVM is SEQ ID NO: 8. In another embodiment, the nucleic acid sequence encoding a TVM is SEQ ID NO: 9. In another embodiment, the nucleic acid sequence encoding a TVM is SEQ ID NO: 10. In another embodiment, the nucleic acid sequence encoding a TVM is SEQ ID NO: 11. In another embodiment, the nucleic acid sequence encoding a TVM is SEQ ID NO: 12. In another embodiment, the nucleic acid sequence encoding a TVM is SEQ ID NO: 13. In another embodiment, the nucleic acid sequence encoding a TVM is SEQ ID NO: 14. In another embodiment, the nucleic acid sequence encoding a TVM is SEQ ID NO: 15. In another embodiment, the nucleic acid sequence encoding a TVM is SEQ ID NO: 16. In another embodiment, the nucleic acid sequence encoding a TVM is SEQ ID NO: 17. In another embodiment, the nucleic acid sequence encoding a TVM is SEQ ID NO: 18. In another embodiment, the nucleic acid sequence encoding a TVM is SEQ ID NO: 19. In another embodiment, the nucleic acid sequence encoding a TVM is SEQ ID NO: 20. In another embodiment, the nucleic acid sequence encoding a TVM is SEQ ID NO: 21. In another embodiment, the nucleic acid sequence encoding a TVM is SEQ ID NO: 22. In another embodiment, the nucleic acid sequence encoding a TVM is SEQ ID NO: 23. In another embodiment, the nucleic acid sequence encoding a TVM is SEQ ID NO: 24. In another embodiment, the nucleic acid sequence encoding a TVM is SEQ ID NO: 25. In another embodiment, the nucleic acid sequence encoding a TVM is SEQ ID NO: 26. In another embodiment, the nucleic acid sequence encoding a TVM is SEQ ID NO: 27. In another embodiment, the nucleic acid sequence encoding a TVM is SEQ ID NO: 28. In another embodiment, the nucleic acid sequence encoding a TVM is SEQ ID NO: 29. In another embodiment, the nucleic acid sequence encoding a TVM is SEQ ID NO: 30. In another embodiment, the nucleic acid sequence encoding a TVM is SEQ ID NO: 31. In another embodiment, the nucleic acid sequence encoding a TVM is SEQ ID NO: 32. In another embodiment, the nucleic acid sequence encoding a TVM is SEQ ID NO: 33. In another embodiment, the nucleic acid sequence encoding a TVM is SEQ ID NO: 34. In another embodiment, the nucleic acid sequence encoding a TVM is SEQ ID NO: 35. In another embodiment, the nucleic acid sequence encoding a TVM is SEQ ID NO: 36. In another embodiment, the nucleic acid sequence encoding a TVM is SEQ ID NO: 37.

In one embodiment, the nucleic acid sequence encoding a TVM is any sequence described in Table 1.

TABLE 1

| Embodiments of TVM sequences | |
|---|---|
| SEQ ID NO | Sequence |
| 1 | cactaacgctcttcctagtccccgggccaactcggacagtttgctcatttattgcaacggtcaaggctggcttgtgccagaacggcgcgcgcgcgacgcac<br>gcacacacacggggggaaactttttttaaaaatgaaaggctagaagagctcagcggcggcgcgggccgtgcgcgagggctccggagctgactcgccg<br>aggcaggaaatccctccggtcgcgacgcccggccccgctcggcgcccgcgtgggatggtgcagcgctcgccgccgggcccgagagctgctgcactg<br>aaggccggcgacgatggcagcgcgcccgctgcccgtgtcccccgcccgcgccctcctgctcgccctggccggtgctctgctcgcgccctgcgaggccc<br>gaggggtgagcttatggaaccaaggaagagctgatgaagttgtcagtgcctctgttcggagtggggacctctggatcccagtgaagagcttcgactccaa<br>gaatcatccagaagtgctgaatattcgactacaacgggaaagcaaagaactgatcataaatctggaaagaaatgaaggtctcattgccagcagtttcacg<br>gaaacccactatctgcaagacggtactgatgtctccctcgctcgaaattacacggtaattctgggtcactgttactaccatggacatgtacggggatattc<br>tgattcagcagtcagtctcagcacgtgttctggtctcaggggacttattgtgtttgaaaatgaaagctatgtcttagaaccaatgaaaagtgcaaccaaca<br>gatacaaactcttcccagcgaagaagctgaaaagcgtccggggatcatgtggatcacatcacaacacaccaaacctcgctgcaaagaatgtgtttccacca<br>ccctctcagacatgggcaagaaggcataaaagagagaccctcaaggcaactaagtatgtggagctggtgatcgtggcagacaaccgagagtttcagaggca<br>aggaaaagatctggaaaaagttaagcagcgattaatagagattgctaatcacgttgacaagttttacagaccactgaacattcggatcgtgttggtaggcgt<br>ggaagtgtggaatgacatggacaaatgctctgtaagtcaggacccattcaccagcctccatgaatttctggactggaggaagatgaagcttctacctcgca<br>aatcccatgacaatgcgcagcttgtcagtggggtttatttccaagggaccaccatcggcatggccccaatcatgagcatgtgcacggcagaccagtctgg<br>gggaattgtcatggaccattcagacaatccccttggtgcagccgtgaccctggcacatgagctgggccacaatttcgggatgaatcatgacacactggac<br>aggggctgtagctgtcaaatggcggttgagaaaggaggctgcatcatgaacgcttccaccgggtacccatttcccatggtgttcagcagttgcagcagga<br>aggacttggagaccagcctggagaaaggaatgggggtgtgcctgtttaacctgccggaagtcagggagtctttcgggggccagaagtgtgggaacag<br>atttgtggaagaaggagaggagtgtgactgtggggagccagaggaatgtatgaatcgctgctgcaatgccaccacctgtaccctgaagccggacgctgt<br>gtgcgcacatgggctgtgctgtgaagactgccagctgaagcctgcaggaacagcgtgcagggactccagcaactcctgtgacctcccagagttctgcac<br>aggggccagccctcactgcccagccaacgtgtacctgcacgatgggcactcatgtcaggatgtggacggctactgctacaatggcatctgccagactcac<br>gagcagcagtgtgtcacactctggggaccaggtgctaaacctgcccctgggatctgctttgagagagtcaattctgcaggtgatccttatggcaactgtgg<br>caaagtctcgaagagttcctttgccaaatgcgagatgagagatgctaaatgtggaaaaatccagtgtcaaggaggtgccagccggccagtcattggtacc<br>aatgccgtttccatagaaacaaacatccccctgcagcaaggaggccggattctgtgccgggggacccacgtgtacttgggcgatgacatgccggaccca<br>gggcttgtgcttgcaggcacaaagtgtgcagatggaaaaatctgcctgaatcgtcaatgtcaaaatattagtgtctttggggttcacgagtgtgcaatgcag<br>tgccacggcagaggggtgtgcaacaacaggaagaactgccactgcgaggcccactgggcacctcccttctgtgacaagtttggctttggaggaagcac<br>agacagcggccccatccggcaagcagataaccaaggtttaaccataggaattctggtgaccatcctgtgtcttcttgctgccggatttgtggtttatctca<br>aaaggaagaccttgatacgactgctgtttacaaataagaagaccaccattgaaaaactaaggtgtgtgcgcccttcccggccaccccgtggcttccaaccc<br>tgtcaggctcacctcggccaccttggaaaaggcctgatgaggaagccgccagattcctacccaccgaaggacaatcccaggagattgctgcagtgtcagaa<br>tgttgacatcagcagacccctcaacggcctgaatgtccctcagccccagtcaactcagcgagtgcttcctcccctccaccgggccccacgtgcacctagcg<br>tccctgccagacccctgccagccaagcctgcacttaggcaggcccaggggacctgtaagccaaacccccctcagaagcctctgcctgcagatcctctgg<br>ccagaacaactcggctcactcatgccttggccaggaccccaggacaatgggagactgggctccgcctggcacccctcagacctgctccacaatatccac<br>accaagtgcccagatccacccacaccgcctatattaagtgagaagccgacacctttttttcaacagtgaagacagaagtttgcactatctttcagctccagt<br>tggagtttttttgtaccaacttttaggatttttttttaatgtttaaaacatcattactataagaactttgagctactgccgtcagtgctgtgctgtgctatgg<br>tgctctgtctacttgcacaggtacttgtaaattattaatttatgcagaatgttgattacagtgcagtgcgctgtagtaggcatttttaccatcactgagtt<br>ttccatggcaggaaggcttgttgtgcttttagtattttagtgaacttgaaatatcctgcttgatgggattctggacaggatgtgtttgctttctgatcaag<br>gccttattggaaagcagtcccccaactacccccagctgtgcttatggtaccagatgcagctcaagagatcccaagtagaatctcagttgattttctggatt<br>ccccatctcaggccagagccaaggggcttcaggtccaggctgtgtttggctttcagggaggccctgtgccccttgacaactggcaggcaggctcccaggga<br>cacctgggagaaatctggcttctggccaggaagctttggtgagaacctgggttgcagacaggaatcttaaggtgtagccacaccaggatagagactggaac<br>actagacaagccagaacttgaccctgagctgaccagccgtgagcatgtttggaaggggtctgtagtgtcactcaaggcggtgcttgatagaaatgccaagc<br>acttctttttctcgctgtcctttctagagcactgccaccagtaggttatttagcttgggaaaggtggtgtttctgtaagaaacctactgcccaggcactgc<br>aaaccgccacctccctatactgcttggagctgagcaaatcaccacaaactgtaatacaatgatcctgtattcagacagatgaggactttccatgggaccac<br>aactattttcagatgtgaaccattaaccagatctagtcaatcaagtctgtttactgcaaggttcaacttattaacaattaggcagactctttatgcttgca<br>aaaactacaaccaatggaatgtgatgttcatgggtatagttcatgtctgctatcattattcgtagatattggacaaagaaccttctctatggggcatcctc<br>tttttccaacttggctgcaggaatctttaaaagatgcttttaacagagtctgaacctatttcttaaacacttgcaacctacctgttgagcatcacagaatg<br>tgataaggaaatcaacttgcttatcaacttcctaaatattatgagatgtggcttgggcagcatccccttgaactcttcactcttcaaatgcctgactaggg<br>agccatgtttcacaaggtctttaaagtgactaatggcatgagaaatacaaaaatactcagataaggtaaaatgccatgatgcctctgtcttctggactggt |

TABLE 1-continued

Embodiments of TVM sequences

| SEQ ID NO | Sequence |
|---|---|
| | tttcacattagaagacaattgacaacagttacataattcactctgagtgttttatgagaaagccttcttttggggtcaacagttttccatatgctttgaaa cagaaaaatatgtaccaagaatcttggtttgccttccagaaaacaaaactgcatttcactttcccggtgttccccactgtatctaggcaacatagtattca tgactatggataaactaaacacgtgacacaaacacacacaaaagggaacccagctctaatacattccaactcgtatagcatgcatctgtttattctatagt tattaagttctttaaaatgtaaagccatgctggaaaataatactgctgagatacatacagaattactgtaactgattacacttggtaattgtactaaagcc aaacatatatatactattaaaaaggtttacagaattttatggtgcattacgtgggcattgtctttttagatgcccaaatccttagatctggcatgttagcc cttcctccaattataagaggatatgaaccaaaaaaaaaaaaaaaaaa |
| 2 | atgcccaagcgcgcgcactggggggccctctccgtggtgctgatcctgctttggggccatccgcgagtggcgctggcctgcccgcatccttgtgcctgct acgtccccagcgaggtccactgcacgttccgatccctggcttccgtgcccgctggcattgctagacacgtggaaagaatcaatttggggtttaatagcatac aggccctgtcagaaacctcatttgcaggactgaccaagttggagctacttatgattcacggcaatgagatcccaagcatccccgatggagctttaagagac ctcagctctcttcaggttttcaagttcagctacaacaagctgagagtgatcacaggacagaccctccagggtctctctaacttaatgaggctgcacattga ccacaacaagatcgagtttatccaccctcaagctttcaacggcttaacgtctctgaggctactccatttggaaggaaatctcctccaccagctgcacccca gcaccttctccacgttcacattttggattatttcagactctccaccataaggcacctctacttagcagagaacatggttagaactcttcctgccagcatg cttcggaacatgccgcttctggagaatctttacttgcagggaaatccgtggacctgcgattgtgagatgagatggtttttggaatgggatgcaaaatccag aggaattctgaagtgtaaaaaggacaaagcttatgaaggcggtcagttgtgtgcaatgtgcttcagtccaaagaagttgtacaaacatgagatacacaagc tgaaggacatgacttgtctgaagccttcaatagagtcccctctgagacagaacaggagcaggagtattgaggaggagcaagaacaggaagaggatggtggc agccagctcatcctggagaaattccaactgccccagtggagcatctctttgaatatgaccgacgagcacgggaacatggtgaacttggtctgtgacatcaa gaaaccaatggatgtgtacaagattcacttgaaccaaacggatcctccagatattgacataaatgcaacagttgccttggactttgagtgtccaatgaccc gagaaaactatgaaaagctatggaaattgatagcatactacagtgaagttcccgtgaagctacacagagagctcatgctcagcaaagaccccagagtcagct accagtacaggcaggatgctgatgaggaagctctttactacacaggtgtgagagcccagattcttgcagaaccagaatgggtcatgcagccatccatagata tccagctgaaccgacgtcagagtacggccaagaaggtgctactttcctactacacccagtattctcaaacaatatccaccaaagatacaaggcaggctcggg gcagaagctgggtaatgattgagcctagtggagctgtgcaaagagatcagactgtcctggaaggggggtccatgccagttgagctgcaacgtgaaagctt ctgagagtccatctatcttctgggtgcttccagatggctccatcctgaaagcgcccatggatgacccagacagcaagttctccattctcagcagtggctggc tgaggatcaagtccatggagccatctgactcaggcttgtaccagtgcattgctcaagtgagggatgaaatggaccgcatggtatatagggtacttgtgcagt ctccctccactcagccagccgagaaagacacagtgacaattggcaagaacccaggggagtcggtgacattgccttgcaatgctttagcaatacccgaag cccaccttagctggattcttccaaacagaaggataattaatgatttggctaacacatcacatgtatacatgttgccaaatggaactctttccatcccaaggt ccaagtcagtgatagtggttactacagatgtgtggctgtcaaccagcaaggggcagaccattttacggtgggaatcacagtgaccaagaaagggtctggct tgccatccaaaagaggcagacgcccaggtgcaaaggctctttccagagtcagagaagacatcgtggaggatgaagggggctcgggcatgggagatga agagaacacttcaaggagacttctgcatccaaaggaccaagaggtgttcctcaaaacaaaggatgatgccatcaatggagacaagaaagccaagaaag ggagaagaaagctgaaactctggaagcattcggaaaaagaaccagagaccaatgttgcagaaggtcgcagagtgtttgaatctagacgaaggataaac atggcaaacaaacagattaatccggagcgctgggctgatattttagccaaagtccgtgggaaaaatctccctaagggcacagaagtaccccgttgatta aaaccacaagtcctccatccttgagcctagaagtcacaccaccttttcctgctgtttctccccctcagcatctcctgtgcagacagtaaccagtgctgaag aatcctcagcagatgtacctctacttggtgaagaagagcacgttttgggtaccatttcctcagccagcatggggctagaacacaaccacaatggagttattc ttgttgaacctgaagtaacaagcacacctctggaggaagttgttgatgacctttctgagaagactgaggagataacttccactgaaggagacctgaaggga cagcagcccctacacttatatctgagccttatgaaccatctcctactctgcacacattagacacagtctatgaaaagcccacccatgaagagacggcaaca gagggttggtctgcagcagatgttggatcgtcaccagagcccacatccagtgagtatgagcctccattggatgctgtctccttggctgagtctgagcccatg caatactttgacccagatttggagactaagtcacaaccagatgaggataagatgaaagaagacacctttgcacaccttactccaaccccccaccatctggg aatgactccagtacatcacagttatttgaggattctactatagggggaaccaggtgtcccaggccaatcacatctacaaggactgacagacaacatccacctt gtgaaaagtagtctaagcactcaagacaccttactgattaaaaagggtatgaaagagatgtctcagacactacagggaggaaatatgctagagggagac cccacacactccagaagttctgagagtgagggccaagagagcaaatccatcactttgcctgactccacactgggtataatgagcagtatgtctccagttaa gaagcctgcggaaaccacagttggtaccctcctagacaaagacaccacaacagtaacaacaacaccaaggcaaaaagttgctccgtcatccaccatgag cactcacccttctcgaaggagacccaacgggagaaggagattacgccccaacaaattccgccaccggcacaagcaaaccccacccacaacttttgcccc atcagagacttttctactcaaccaactcaagcacctgacattaagatttcaagtcaagtggagagttctctggttcctacagcttgggtggataacacagt taataccccaaacagttggaaatggagaagaatgcagaacccacatccaagggaacaccacggagaaaacacgggaagaggccaaacaaacatcgat ataccccttctacagtgagctcaagagcgtccggatccaagcccagcccttctccagaaaataaacatagaaacattgttactcccagttcagaaactatac ttttgcctagaactgtttctctgaaaactgagggcccttatgattccttagattacatgacaaccaccagaaaaatatattcatcttaccctaaagtccaag agacacttccagtcacatataaacccacatcagatggaaaagaaattaaggatgatgttgccacaaatgttgacaaacataaaagtgacattttagtcactg |

TABLE 1-continued

Embodiments of TVM sequences

| SEQ ID NO | Sequence |
|---|---|
| | gtgaatcaattactaatgccataccaacttctcgctccttggtctccactatgggagaatttaaggaagaatcctctcctgtaggctttccaggaactccaa<br>cctggaatccctcaaggacggcccagcctgggaggctacagacagacatacctgttaccacttctggggaaaatcttacagaccctccccttcttaaagagc<br>ttgaggatgtggatttcacttccgagtttttgtcctctttgacagtctccacaccatttcaccaggaagaagctggttcttccacaactctctcaagcataa<br>aagtggaggtggcttcaagtcaggcagaaaccaccacccttgatcaagatcatcttgaaaccactgtggctattctcctttctgaaactagaccacagaatc<br>acacccctactgctgcccggatgaaggagccagcatcctcgtccccatccacaattctcatgtctttgggacaaaccaccaccactaagccagcacttccca<br>gtccaagaatatctcaagcatctagagattccaaggaaaatgttttcttgaattatgtggggaatccagaaacagaagcaaccccagtcaacaatgaaggaa<br>cacagcatatgtcagggccaaatgaattatcaacaccctcttccgaccgggatgcatttaacttgtctacaaagctggaattggaaaagcaagtatttggta<br>gtaggagtctaccacgtggcccagatagccaacgccaggatggaagagttcatgcttctcatcaactaaccagagtccctgccaaacccatcctaccaacag<br>caacagtgaggctacctgaaatgtccacacaaagcgcttccagatactttgtaacttcccagtcacctcgtcactggaccaacaaaccggaaataactacat<br>atccttctggggctttgccagagaacaaacagtttacaactccaagattatcaagtacaacaattcctctcccattgcacatgtccaaacccagcattccta<br>gtaagtttactgaccgaagaactgaccaattcaatggttactccaaagtgtttggaaataacaacatccctgaggcaagaaacccagttggaaagcctccca<br>gtccaagaattcctcattattccaatggaagactccctttctctttaccaacaagactctttcttttccacagttgggagtcacccggagaccccagatacc<br>cacttctcctgccccagtaatgagagagagaaaagttattccaggttcctacaacaggatacattcccatagcaccttccatctggactttggccctccggc<br>acctccgttgttgcacactccgcagaccacgggatcaccctcaactaacttacagaatatccctatggtctcttccacccagagttctatctcctttataac<br>atcttctgtccagtcctcaggaagcttccaccagagcagctcaaagttctttgcaggaggacctcctgcatccaaattctggtctcttggggaaaagcccca<br>aatcctcaccaagtccccacagactgtgtccgtcaccgctgagacagacactgtgttcccctgtgaggcaacaggaaaaccaaagcctttcgttacttggac<br>aaaggtttccacaggagctcttatgactccgaataccaggatacaacggtttgaggttctcaagaacggtaccttagtgatacggaaggttcaagtacaaga<br>tcgaggccagtatatgtgcaccgccagcaacctgcacggcctggacaggatggtggtcttgctttcggtcaccgtgcagcaacctcaaatcctagcctccca<br>ctaccaggacgtcactgtctacctgggagacaccattgcaatggagtgtctggccaaagggaccccagcccccaaatttcctggatcttccctgacaggag<br>ggtgtggcaaactgtgtccccgtggagagccgcatcaccctgcacgaaaaccggaccctttccatcaaggaggcgtccttctcagacagaggcgtctataa<br>gtgcgtggccagcaatgcagccggggcggacagcctggccatccgcctgcacgtggcggcactgcccccgttatccaccaggagaagctggagaacatctc<br>gctgcccccggggctcagcattcacattcactgcactgccaaggctgcgcccctgcccagcgtgcgctgggtgctcggggacggtacccagatccgcccctc<br>gcagttcctccacgggaacttgttgttttccccaacgggacgctctacatccgcaacctcgcgcccaaggacagcgggcgctatgagtgcgtggccgccaac<br>ctggtaggctccgcgcgcaggacggtgcagctgaacgtgcagcgtgcagcagccaacgcgcgcatcacgggcacctccccgcggaggacggacgtc<br>aggtacggaggaaccctcaagctggactgcagcgcctcggggacccctggccgcgcatcctctggaggctgccgtccaagaggatgatcgacgcgc<br>tcttcagttttgatagcagaatcaaggtgtttgccaatgggaccctggtggtgaaatcagtgacggacaaagatgccggagattacctgtgcgtagctcga<br>aataaggttggtgatgactacgtggtgctcaaagtggatgtggtgatgaaaccggccaagattgaacacaaggaggagaacgaccacaaagtcttctac<br>gggggtgacctgaaagtggactgtgtggccaccgggcttcccaatcccgagatctcctggagcctcccagacgggagtctggtgaactccttcatgcagt<br>cggatgacagcggtggacgcaccaagcgctatgtcgtcttcaacaatgggacactctactttaacgaagtggggatgagggaggaaggagactacacct<br>gctttgctgaaaatcaggtcgggaaggacgagatgagagtcagagtcaaggtggtgacagcgcccgccacattccggaacaagacttacttggcggtt<br>caggtgccctatggagacgtggtcactgtagcctgtgaggccaaaggagaacccatgcccaaggtgacttggttgtccccaaccaacaaggtgatcccc<br>acctcctctgagaagtatcagatataccaagatggcactctccttattcagaaagcccagcgttctgacagcggcaactacacctgcctggtcaggaacag<br>cgcgggagaggataggaagacggtgtggattcacgtcaacgtccagccacccaagatcaacggtaaccccaaccccatcaccaccgtgcgggagata<br>gcagccgggggcagtcggaaactgattgactgcaaagctgaaggcatccccaccccgagggtgttatgggcttttcccgagggtgtggttctgccagctc<br>catactatggaaaccggatcactgtccatggcaacggttccctggacatcaggagtttgaggaagagcgactccgtccagctggtatgcatggcacgcaa<br>cgagggaggggaggcgaggttgatcgtgcagctcactgtcctggagcccatggagaaacccatcttccacgacccgatcagcgagaagatcacggcc<br>atggcgggccacaccatcagcctcaactgctctgccgcggggaccccgacacccagcctggtgtgggtccttcccaatggcaccgatctgcagagtgga<br>cagcagctgcagcgcttctaccacaaggctgacggcatgctacacattagcggtctctcctcggtggacgctggggcctaccgctgcgtggcccgcaatg<br>ccgctggccacacggagaggctggtctccctgaaggtgggactgaagccagaagcaaacaagcagtatcataacctggtcagcatcatcaatggtgag<br>accctgaagctcccctgcacccctcccggggctgggcagggacgtttctcctggacgctccccaatggcatgcatctggagggcccccaaaccctggga<br>cgcgtttctcttctggacaatggcaccctcacggttcgtgaggcctcggtgtttgacaggggtacctatgtatgcaggatggagacggagtacggcccttc<br>ggtcaccagcatccccgtgattgtgatcgcctatcctccccggatcaccagcgagcccaccccggtcatctacacccggcccgggaacaccgtgaaactg<br>aactgcatggctatggggattcccaaagctgacatcacgtgggagttaccggataagtcgcatctgaaggcaggggttcaggctcgtctgtatggaaaca<br>gatttcttcacccccagggatcactgaccatccagcatgccacacagagagatgccggcttctacaagtgcatggcaaaaaacattctcggcagtgactcc<br>aaaacaacttacatccacgtcttctgaaatgtggattccagaatgattgcttaggaactgacaacaaagcggggtttgtaagggaagccaggttggggaat<br>aggagctcttaaataatgtgtcacagtgcatggtggcctctggtgggtttcaagttgaggttgatcttgatctacaattgttgggaaaaggaagcaatgcag<br>acacgagaaggagggctcagccttgctgagacactttcttttgtgtttacatcatgccaggggcttcattcagggtgtctgtgctctgactgcaatttttct |

TABLE 1-continued

Embodiments of TVM sequences

| SEQ ID NO | Sequence |
|---|---|
| | tcttttgcaaatgccactcgactgccttcataagcgtccataggatatctgaggaacattcatcaaaaataagccatagacatgaacaacacctcactaccc |
| | cattgaagacgcatcacctagttaacctgctgcagtttttacatgatagactttgttccagattgacaagtcatctttcagttatttcctctgtcacttcaa |
| | aactccagcttgcccaataaggatttagaaccagagtgactgatatatatatatatattttaattcagagttacatacatacagctaccattttatatgaaa |
| | aaagaaaaacatttcttcctggaactcactttttatataatgtttttatatatatatttttttcctttcaaatcagacgatgagactagaaggagaaatacttt |
| | ctgtcttattaaaattaataaattattggtctttacaagacttggatacattacagcagacatggaaatataattttaaaaaatttctctccaacctccttc |
| | aaattcagtcaccactgttatattaccttctccaggaaccctccagtggggaaggctgcgatattagatttccttgtatgcaaagtttttgttgaaagctgt |
| | gctcagaggaggtgagaggagaggaaggagaaaactgcatcataactttacagaattgaatctagagtcttccccgaaaagcccagaaacttctctgcagta |
| | tctggcttgtccatctggtctaaggtggctgcttcttccccagccatgagtcagtttgtgcccatgaataatacacgacctgttatttccatgactgcttta |
| | ctgtatttttaaggtcaatatactgtacatttgataataaaataatattctcccaaaaaaaaaa |
| 3 | aggaagtggtgagttcggagtagagatggccgcgcttgcaccgctgcccccgctccccgcacagttcaagagcatacagcatcatctgaggacggctca |
| | ggagcatgacaagcgagaccctgtggtggcttattactgtcgtttatacgcaatgcagactggaatgaagatcgatagtaaaactcctgaatgtcgcaaatt |
| | tttatcaaagttaatggatcagttagaagctctaaagaagcagttgggtgataatgaagctattactcaagaaatagtgggctgtgcccatttggagaatta |
| | tgctttgaaaatgtttttgtatgcagacaatgaagatcgtgctggacgatttcacaaaaacatgatcaagtccttctatactgcaagtcttttgatagatgt |
| | cataacagtatttggagaactcactgatgaaaatgtgaaacacaggaagtatgccagatggaaggcaacatacatccataattgtttaaagaatggggagac |
| | tcctcaagcaggccctgttggaattgaagaagataatgatattgaagaaaatgaagatgctggagcagcctctctgcccactcagccaactcagccatcatc |
| | atcttcaacttatgacccaagcaacatgccatcaggcaactatactggaatacagattcctccgggtgcacacgctccagctaatacaccagcagaagtgcc |
| | tcacagcacaggtgtagcaagtaatactatccaacctactccacagactatacctgccattgatcccgcacttttcaatacaatttcccaggggggatgttcg |
| | tctaaccccagaagactttgctagagctcagaagtactgcaaatatgctggcagtgctttgcagtatgaagatgtaagcactgctgtccagaatctacaaaa |
| | ggctctcaagttactgacgacaggcagagaatgaagcctttgtatgacagacccatgtattttggcatgaggaactaacagtccattactctatcttcagc |
| | ctatcaggatcacagttttaaggaagacttggttttgttgaatatgacaatgaaatctgtgtgtatcagattttattgaagcattcatcagcagcctcaac |
| | cagttttcattgtccatttactagattcaatcgtctctgagtatatagggctgatgttagcaagaccctaaaaatgtccattgaaccctgcttcaaaaaatg |
| | aaaacacacctctataaaatgtgtactgggaataagctttgtatttacatacattaggggaatttttaaaatctgtaatgtttggacaaacagatgatatt |
| | actttgctataaaattataaatgtaacttttaataaagatagccagaatattctaaattagaaattacgtttttgtttccctcaagacataaaacaaatata |
| | aacattctaaactgctggatgaatctgaaaagacattaagttcaaattttaatttattctcatattaaatataactccattaaaagtttaaaatttcatggg |
| | agaaaatataataaggtaaagaggtagaatcactttcagacttaagaataatgttgatttcccaagtgctttaccttatctgttaaagcgtaagatgaattg |
| | gtatttgcttcataggcagtttgactgcatgtattagagaatgaaaagaagatatttgtagtaatgcctggaaacttggtgctttaaattaaggtactcctc |
| | tgctgctgtagaatggattccacacagtggatagctatgggtgattcagaatattatgtttagattcccatttgttaagtttataagttttgtggggaatta |
| | tgaacttactgtgtactacctgcatttgtgctgtgtgaaaaataaatacaaggattcgtttagctaattcaacttactacaaagacaaatgtctgtttttat |
| | ttgcctgctaggattgtctttttttaaaagtcatttttatttataggaatatgggtgtttctataggaagaaacaggtttttttgtttttttgtttttttaagata |
| | aatttgacaaagttaactgaaatttatctggtccattttattcatgctactaagatgggaatctttaaacacaagggtcagcaagctttggcccatggattg |
| | gccacctgttacgtaaataaagtttctttgaaacaagcctacactcattcatttatgttttgtctgtggttgctttccacaactgcagagttgtatggcttg |
| | caagtctaaaaacatttactatttggccctctaagaaaaagttaagacacctagtctaatggccttttgggaaaaaacaaatcactaactcataatcattta |
| | tatccattattttctgcataaatgtaatgctattgtacagggtttggtagaataaatattcagactgactaaactgttctaaatcctcacaaaaaagtcccc |
| | aaacaacatgcctcctaaaaaacattttcctatcttttacaagaggtatgaacatttgtagggttccacatttgcatctagaaatccaatgctctttagaat |
| | gttattacgaatagaaagatggccaggatgacctttagtgttacatgatgttcagcaaattttaattcaaaccttgatatgcctggacactgaaaagtaaac |
| | gcatcacctcctattttatacactaccttctggttcccaattgggagagcacatagagggaaggagacaatatagaaactacggagtccgctggtagtgggc |
| | tgcatggtgtgacagagcccttctctgtaaaatggaaatgacaccactagccatctcaatagttacaagaattaaaagagatacagtacctgaagtgcttag |
| | cgcatggtagcatttcataaatgtttagtgtcaatactaatgctctaataatgtaaattgttaataatttatttccctaatatcaggaaatcccagttgtct |
| | atgtggcccagtgcttaaaaacgccttcttgcatgaggggattgaactatacaatgtttgttaactttgtatttgtatttttttcctataaaatcttaaaata |
| | aaattaggagatgtgttccgaaaaaaaaaaaaaaaa |
| 4 | ccacgcgtccgaccaatgtcatccccaaaggaagggtgagctgaatggaaattaagcccagtcattttatttgatctattagctctgttatcagtgcatgat |
| | cacccagatcaccctcctcagcccacacagtgctgaaccatcttccctcctgttctccatggctattaatagtatagctaaatttagagtgcagagccagat |
| | ataagtattttggaattatctcccagtttgtggtagaagctgactggaatacaggttgagtatctcttatccaaaatgctagggaccagaaaggtttcagat |
| | tttttcagattttggaatacttaacagttgagcaccccaaatctgaaaggcttctgaacgtcatgtcagcactcaaaaaagtggattttggagcacttcaaa |
| | tttcggatttttggatttgggatgctcatcctgtgtaggagaggctactcgattccatttaatgactgtcctagtcataatcatccaaagataaaagccagg |

TABLE 1-continued

| Embodiments of TVM sequences | |
|---|---|
| SEQ ID NO | Sequence |
| | tagatgttgaaagctctttccagggctgaaaaagtgttcttacgttctctgcatgtgactagcatcactgtggaaattaatgctctgttcttcactagaatg<br>tagtaagtggttaaactgagctatcccccacctgatgactattggcatccatttgcaaggccaatggcctggattaagggttaggattatttgtagctagaa<br>ggtaattttatttctgtgaaactaattggctcatatttgaggttaggtgtggccttgaccttaccagtacatttatacccactaccagttgactagcccaga<br>taattgttaaatggtgcttcttttctgcttctcagtagacttccatgccattacaaaggaaatttgaattacctagtgtttgtatattccatgataactatg<br>tataacttctgttacacagcttatgtattgttaacatttaagtgtaaaccatgccacagctaacacttaaaaatgaaaactaattagttcttgcttagggaa<br>aatgccaggtatgaagtatggcatatacttgacactgtcctgtgtaaccctttactttgctcaggctttcaagattgagtctttttttcccccaaattaggtt<br>aacatgcatttgaccccaacctgtggggtttgagtaagctggaaatctgtgacggtaggctttctagtgtcacgaggtggtggtgactgaaggaaaagctgg<br>gatcacaggttccttctgatggagaggaaggtttatttctatgcccctcccaccaccctccacctagagctcacccaagcctgctccagtcccaggggcagg<br>ccattctgcaaaagcaggacctcacagaaacaagggctgggttgaggtcacccccttcagagttggttcctggccagatgggtaagaggcatttgtaatttt<br>aaaaatgtgaaacttgggtttggtgttttcttctaagtgcctaaataagcaagccaggctgttgatattttagccagagaaatcggcaagccaagattaacc<br>cgaatctgaagtttagaatcttgagtttgcatctgcatcatatcatgctgttttgatgaggaaacatttgccactgaggagttggagggagggcaagacgac<br>agtgttaagtcagatcatttaatggtttcccctaagccctggaaaaatatttgaaagaatggcagcaaaaaggttaagaaagcaagccagatttactgcaca<br>atatgcagtacccagtactactttaaatcccaagagaacagtgtgatgtctaatatatacaggtctatgaaaatactgtggaataagcccaggaaggttaga<br>tgtgtttgcaaataagttgcccaaagggtcccccctctaagtaaaacaaatattcagaccacaggctttaatgtaaactgtcaaaaagtgggatgtggaggat<br>ttttgttaagtgtcaatcgaagttaaaaagcaagggtttttggccaggcgtggtggctcacgcctgtaatcccagcactttgggaggccgaggccggcaaat<br>cacctaaggtcaggagttcgagaccagcctggccaacatggtgaaaccccgtctctactaaaaaaaaaaaaaaa |
| 5 | ggcgcggagcggtgcggcggcgggaggcggaggcgagggtgcgatggcgcggagcccgggacgcgcgtacgccctgctgcttctcctgatctgctt<br>taacgttggaagtggacttcacttacaggtcttaagcacaagaaatgaaaataagctgcttcctaaacatcctcatttagtgcggcaaaagcgcgcctggat<br>caccgcccccgtggctcttcgggagggagaggatctgtccaagaagaatccaattgccaagatacattctgatcttgcagaagaaagaggactcaaaatt<br>acttacaaatacactggaaaagggattacagagccaccttttggtatatttgtctttaacaaagatactggagaactgaatgttaccagcattcttgatcga<br>gaagaaacaccatttttctgctaacaggttacgctttggatgcaagaggaaacaatgtagagaaacccttagagctacgcattaaggttcttgatatcaat<br>gacaacgaaccagtgttcacacaggatgtctttgttgggtctgttgaagagttgagtgcagcacatactcttgtgatgaaaatcaatgcaacagatgcagat<br>gagcccaataccctgaattcgaaaatttcctatagaatcgtatctctggagcctgcttatcctccagtgttctacctaaataaagatacaggagagatttat<br>acaaccagtgttaccttggacagagaggaacacagcagctacactttgacagtagaagcaagagatggcaatggagaagttacagacaaacctgtaaaacaa<br>gctcaagttcagattcgtattttggatgtcaatgacaatatacctgtagtagaaaataaagtgcttgaagggatggttgaagaaaatcaagtcaacgtagaa<br>gttacgcgcataaaagtgttcgatgcagatgaaataggttctgataattggctggcaaattttacatttgcatcaggaaatgaaggaggttatttccacata<br>gaaacagatgctcaaactaacgaaggaattgtgacccttattaaggaagtagattatgaagaaatgaagaatcttgacttcagtgttattgtcgctaataaa<br>gcagcttttcacaagtcgattaggagtaaatacaagcctacacccattcccatcaaggtcaaagtgaaaaatgtgaaagaaggcattcattttaaaagcagc<br>gtcatctcaatttatgttagcgagagattggatagatcaagcaaaggccaaataattggaaattttcaagcttttgatgaggacactggactaccagcccat<br>gcaagatatgtaaaattagaagatagagataattggatctctgtggattctgtcacatctgaaattaaacttgcaaaacttcctgattttgaatctagatat<br>gttcaaaatggcacatacactgtaaagattgtggccatatcagaagattatcctagaaaaaccatcactggcacagtccttatcaatgttgaagacatcaac<br>gacaactgtcccaatctgatagagcctgtgcagacaatctgtcacgatgcagagtatgtgaatgttactgcagaggacctggatggacacccaaacagtggc<br>cctttcagtttctccgtcattgacaaaccacctggcatggcagaaaaatggaaaatagcacgccaagaaagtaccagtgtgctgctgcaacaaagtgagaaa<br>aagcttgggagaagtgaaattcagttcctgatttcagacaatcagggttttagttgtcctgaaaagcaggtccttacactcacagtttgtgagtgtctgcat<br>ggcagcggctgcagggaagcacagcatgactcctatgtgggcctgggacccgcagcaattgcgctcatgattttggcctttctgctcctgctattggtacca<br>cttttactgctgatgtgccattgcggaaagggcgccaaaggctttaccccatacctggcaccatagagatgctgcatccttggaataatgaaggagcacca<br>cctgaagacaaggtggtgccatcatttctgccagtggatcaagggggcagtctagtaggaagaaatggagtaggaggtatggccaaggaagccacgatgaaa<br>ggaagtagctctgcttccattgtcaaagggcaacatgagatgtccgagatggatggaaggtgggaagaacacagaagcctgctttctggtagagctacccag<br>tttaatggggccacaggcgctatcatgaccactgaaaccacgaagaccgcaagggccacaggggcttccagagacatggccggagctcaggcagctg<br>ctgttgcactgaacgaagaattcttaagaaattatttcactgataaagcggcctcttacactgaggaagatgaaaatcacacagccaaagattgccttctgg<br>tttattctcaggaagaaactgaatcgctgaatgcttctattggttgttgcagttttattgaaggagagctagatgaccgcttcttagatgatttggga<br>aagacactagctgaagtttgcctgggtcaaaaaatagatataaataaggaaattgagcagagacaaaaacctgccacagaaacaagtatgaacacagct<br>tcacattcactctgtgagcaaactatggttaattcagagaatacctactcctctggcagtagcttcccagttccaaaatctttgcaagaagccaatgcagag<br>aaagtaactcaggaaatagtcactgaaagatctgtgtcttctaggcaggcgcaaaaggtagctacacctcttcctgacccaatggcttctagaaatgtgata<br>gcaacagaaacttcctatgtcacagggtccactatgccaccaaccactgtgatcctgggtcctagccagccacagagccttattgtgacagagagggtgtat<br>gctccagcttctaccttggtagatcagccttatgctaatgaaggtacagttgtggtcactgaaagagtaatacagcctcatgggggtggatcgaatcctctg |

TABLE 1-continued

Embodiments of TVM sequences

| SEQ ID NO | Sequence |
|---|---|
| | gaaggcactcagcatcttcaagatgtaccttacgtcatggtgagggaaagagagagcttccttgcccccagctcaggtgtgcagcctactctggccatgcct<br>aatatagcagtaggacagaatgtgacagtgacagaaagagttctagcacctgcttccactctgcaatccagttaccagattcccactgaaaattctatgacg<br>gctaggaacaccacggtgtctggagctggagtccctggccctctgccagattttggtttagaggaatctggtcattctaattctaccataaccacatcttcc<br>accagagttaccaagcatagcactgtacagcattcttactcctaaacagcagtcagccacaaactgacccagagtttaattagcagtgactaatt |
| 6 | ccgcagaggagcctcggccaggctagccagggcgcccccagcccctccccaggccgcgagcgcccctgccgcggtgcctggcctcccctcccagact<br>gcagggacagcacccggtaactgcgagtggagcggaggacccgagcggctgaggagagaggaggcggcggcttagctgctacggggtccggccg<br>gcgccctcccgagggggctcaggaggaggaaggaggacccgtgcgagaatgcctctgccctggagccttgcgctcccgctgctgctctcctgggtgg<br>caggtggtttcgggaacgcggccagtgcaaggcatcacgggttgttagcatcggcacgtcagcctggggtctgtcactatggaactaaactggcctgctg<br>ctacggctggagaagaaacagcaagggagtctgtgaagctacatgcgaacctggatgtaagtttggtgagtgcgtgggaccaaacaaatgcagatgctt<br>tccaggatacaccgggaaaacctgcagtcaagatgtgaatgagtgtggaatgaaaccccggccatgccaacacagatgtgtgaatacacacggaagct<br>acaagtgcttttgcctcagtggccacatgctcatgccagatgctacgtgtgtgaactctaggacatgtgccatgataaactgtcagtacagctgtgaagaca<br>cagaagaagggccacagtgcctgtgtccatcctcaggactccgcctggccccaaatggaagagactgtctagatattgatgaatgtgcctctggtaaagtc<br>atctgtccctacaatcgaagatgtgtgaacacatttggaagctactactgcaaatgtcacattggtttcgaactgcaatatatcagtggacgatatgactgt<br>atagatataaatgaatgtactatggatagccatacgtgcagccaccatgccaattgcttcaatacccaagggtccttcaagtgtaaatgcaagcagggatat<br>aaaggcaatggacttcggtgttctgctatccctgaaaattctgtgaaggaagtcctcagagcacctggtaccatcaaagacagaatcaagaagttgcttgct<br>cacaaaaacagcatgaaaaagaaggcaaaaattaaaaatgttaccccagaacccaccaggactcctacccctaaggtgaacttgcagcccttcaactatgaa<br>gagatagtttccagaggcgggaactctcatggaggtaaaaaagggaatgaagagaaaatgaaagaggggcttgaggatgagaaaagagaagagaaa<br>gccctgaagaatgacatagaggagcgaagcctgcgaggagatgtgtttttccctaaggtgaatgaagcaggtgaattcggcctgattctggtccaaagga<br>aagcgctaacttccaaactggaacataaagatttaaatatctcggttgactgcagcttcaatcatgggatctgtgactggaaacaggatagagaagatgatt<br>ttgactggaatcctgctgatcgagataatgctattggcttctatatggcagttccggccttggcaggtcacaagaaagacattggccgattgaaacttctcc<br>tacctgacctgcaaccccaaagcaacttctgtttgctctttgattaccggctggccggagacaaagtcgggaaacttcgagtgtttgtgaaaaacagtaaca<br>atgccctggcatgggagaagaccacgagtgaggatgaaaagtggaagacagggaaaattcagttgtatcaaggaactgatgctaccaaaagcatcatttt<br>gaagcagaacgtggcaagggcaaaaccggcgaaatcgcagtggatggcgtcttgcttgtttcaggcttatgtccagatagccttttatctgtggatgactg<br>aatgttactatctttatatttgactttgtatgtcagttccctggtttttttgatattgcatcataggacctctggcattttagaattactagctgaaaaatt<br>gtaatgtaccaacagaaatattattgtaagatgcctttcttgtataagatatgccaatatttgctttaaatatcatatcactgtatcttctcagtcatttct<br>gaatctttccacattatattataaaatatggaaatgtcagtttatctcccctcctcagtatatctgatttgtataagtaagttgatgagcttctctctacaa<br>catttctagaaaatagaaaaaaaagcacagagaaatgtttaactgtttgactcttatgatacttcttggaaactatgacatcaaagatagacttttgcctaa<br>gtggcttagctgggtctttcataaaacttgtatatttaaattctttgtaataataatatccaaatcatcaaaaaaaaaaaaaaaa |
| 7 | accaggtgctccataatgagtcaaaagggagccccacctcggcttaccctgagcggaaggggagccccacgcctgggttttccactcgaagaggaagt<br>ccaactacaggatttatcgagcagaaggggagccccacctcagcctaccccgagcgcaggggtagtccggtgccccccgtgccggagcgcaggagca<br>gtccggtgccccccgtgccggagcgcaggggcagcctcacccttaccatctccggggagtccccgaaggccgggcccgcggaggaggggccgagc<br>ggccccatggaagtcttgcgcaaaggctccttgcgtcttaggcagctgctgagccccaagggcgagcggcgcatggaggatgagggtggcttcccagt<br>gccgcaggagaacggccaacccgagagcccgcggcgtctgtcactgggccagggtgacagcacggaggctgccacagaagagcggggtccgcgg<br>gcgcgcctgtcctcagccacggccaacgccttgtacagcagcaaccttcgggatgacacgaaggccattctggagcagatcagtgcccacggccagaa<br>gcaccgtgcggtccctgccccgagccccggcccgacccacaacagccccgagctaggccgtccaccggctgctggcgtcctggccccagatatgtccg<br>acaaggacaagtgttcagccatcttccgctcggacagcttggggacccagggccggctgagccgcacgctgccagccagcgcggaggagcgcgatcg<br>gctgctgcgccgcatggagagcatgcgcaaggagaagcgcgtgtacagccgcttcgaggtcttctgcaagaaagaggaggccagcagccctggggc<br>aggggaaggccccgcggaggagggcaccagggacagcaaggtgggcaagttcgtgcccaagatcctgggcacgttcaaaagcaagaagtgagtctt<br>ctggcctggcaacccaggccagggtgcccgcatcgctgccccggtcatccagaagccccgcggaacagagagccctgctcatgtgcttgagcagcgg<br>ctgtcaggccacggccgcttggggcttggctgagtgcgccagacctcggctccactggaggctcacctggcagctgccgtctctgccccctggcctcccc<br>aacgctggggctgcacccctcgccaccagtgcctttctcccctcagcaccttcatctctgcaccgtcagccttgcgtggcgcagcgtctggctccgccatct<br>ctttgtgcctcagtccccccgcccccttattttttgagatctagggctggagtgcagttgagcggtctgggctcactgcaacctctgcctcccgggttc<br>cagcgattctcctgcctcagcctcctgagtagctgggattacagatgtatgctaccacgcccaggtagtttttgtatttttagtagagacagggtttcacta<br>tgttggccaggctggtctccaactcctggcctcaaatgatcagcccgcttcagcctcccaaagtgggggattacaggcgtgagccttgcaccccgctaagt<br>cccctatcctcttgcaagggtctcacctctgtgcctcaattcctcattctctgggcccttctcctcctcagggcctcctgttctcagggcctccccctccc |

TABLE 1-continued

Embodiments of TVM sequences

| SEQ ID NO | Sequence |
| --- | --- |
| | cgctccctccctctctcaaggtctcctccttccctcccccccccccgtctccccctcccccgcctgggcttcacttcctttcctacttggattctcctgc<br>tcgctgcctcccagcatctttttggaggcccgtctcttgctgtggggaagactgggctggctgcgggcagtttgcaaggggtgggtggggcggggggggga<br>gctggaccagaagatgccccttggagtggcaaggaagctggacagggcaggcctctggggacgggacacagggaagcccgaaggggcgccttggccaggtct<br>gccatctcctccagcgaggctctggccagcactgggtgagagtggggagggggcactggcctttgcagcacagtaaaacatggtccagacaacctgtggc<br>cccggcctcatgagcacccccctgcacaggcccagcccaagccaggcgctagaagggctggttgtggagtgcttatccttgacaggtatggggccaggt<br>gagggcaggggacaaggtgcagctgaggccgagcccaactaggtcctgggcacccctgcaggtgggagtggtccttgtcctcctggtatccagcagac<br>acccccctctccccaccagccccattctcaggtcctttcctctttgtcaccaacaccaagaatctgtccagggttcttggcttatcttttatctcttttcac<br>tcctagagaggaattgcaattgactcagaatgacacattttggcaccacgtgtgtagaaagcccccactgttagatgatagcctcgtgaaattcatgtttct<br>gtattctcctatttcttttcaaaaactaattttttttttagtgtaataaatcctaagagggaactgatttaagaaacaaggccgccaaacaaaggcagcagt<br>tccgactccagcagctgggaaaggaaggaaagtgaccccactttcactcctgcacagcccactggttaccaaaaccaccgtgcaagtcgggatgacagcagg<br>gacttctggccaggtgggaaaggtgcctggaagcgggatgcgcctgtgcgtctcttggccatgatgttcttgtgggcatgttattcttggtgctgcctgggg<br>tgttgctgagcggacaggctctccagctggagtccatggagaggccagaggctggcggccctgcctgggccttcggagcctcctgcctgcaccctccacctc<br>ttctaaaccatgatgtggcacattttggtgttaataaaacacaacacacaaagtaaaaaaaaaaaaaaaaaa |
| 8 | acacgtccaacgccagcatgcagcgcccgggcccccgcctgtggctggtcctgcaggtgatgggctcgtgcgccgccatcagctccatggacatggag<br>cgcccgggcgacggcaaatgccagcccatcgagatcccgatgtgcaaggacatcggctacaacatgactcgtatgcccaacctgatgggccacgagaa<br>ccagcgcgaggcagccatccagttgcacgagttcgcgccgctggtggagtacggctgccacggccacctccgcttcttcctgtgctcgctgtacgcgccg<br>atgtgcaccgagcaggtctctaccccatccccgcctgccgggtcatgtgcgagcaggcccggctcaagtgctccccgattatggagcagttcaacttcaa<br>gtggcccgactccctggactgccggaaactccccaacaagaacgaccccaactacctgtgcatggaggcgcccaacaacggctcggacgagcccacc<br>cggggctcgggcctgttcccgccgctgttccggccgcagcggccccacagcgcgcaggagcacccgctgaaggacgggggcccgggcgcggcgg<br>ctgcgacaacccgggcaagttccaccacgtggagaagagcgcgtcgtgcgcgccgctctgcacgcccggcgtggacgtgtactggagccgcgagga<br>caagcgcttcgcagtggtctggctggccatctgggcggtgctgtgcttcttctccagcgccttcaccgtgctcaccttcctcatcgacccggcccgcttccg<br>ctaccccgagcgccccatcatcttcctctccatgtgctactgcgtctactccgtgggctacctcatccgcctcttcgccggcgccgagagcatcgcctgcga<br>ccgggacagcggccagctctatgtcatccaggagggactggagagcaccggctgcacgctggtcttcctggtcctctactacttcggcatggccagctcgct<br>gtggtgggtggtcctcacgctcacctggttcctggccgccggcaagaagtggggccacgaggccatcgaagccaacagcagctacttccacctggcag<br>cctgggccatcccggcggtgaagaccatcctgatcctggtcatgcgcagggtggcgggggacgagctcaccggggtctgctacgtgggcagcatgga<br>cgtcaacgcgctcaccggcttcgtgctcattcccctggcctgctacctggtcatcggcacgtccttcatcctctcgggcttcgtggccctgttccacatccg<br>gagggtgatgaagacgggcggcgagaacacggacaagctggagaagctcatggtgcgtatcgggctcttctctgtgctgtacaccgtgccggccacctgtg<br>tgatcgcctgctactttacgaacgcctcaacatggattactggaagatcctggcggcgcagcacaagtgcaaaatgaacaaccagactaaaacgctgga<br>ctgcctgatggccgcctccatccccgccgtggagatcttcatggtgaagatctttatgctgctggtggtggggatcaccagcgggatgtggatttggacctc<br>caagactctgcagtcctggcagcaggtgtgcagccgtaggttaaagaagaagagccggagaaaaccggccagcgtgatcaccagcggtgggatttac<br>aaaaaagcccagcatccccagaaaactcaccacgggaaatatgagatccctgcccagtcgcccacctgcgtgtgaacagggctggagggaagggcac<br>aggggcgcccggagctaagatgtggtgcttttcttggttgtgtttttctttcttcttcttcttttttttttttttataaaagcaaaagagaaatacataaaa<br>aagtgtttaccctgaaattcaggatgctgtgatacactgaaaggaaaaatgtacttaaagggttttgttttgttttggttttccagcgaagggaagctcctc<br>cagtgaagtagcctcttgtgtaactaatttgtggtaaagtagttgattcagccctcagaagaaaacttttgtttagagccctccgtaaatatacatctgtgt<br>atttgagttggctttgctacccatttacaaataagaggacagataactgctttgcaaattcaagagcctcccctgggttaacaaatgagccatccccagggc<br>ccacccccaggaaggccacagtgctgggcggcatccctgcagaggaaagacaggacccggggcccgcctcacaccccagtggatttggagttgcttaaaata<br>gactctggccttcaccaatagtctctctgcaagacagaaacctccatcaaacctcacatttgtgaactcaaacgatgtgcaatacatttttttctctttcct<br>tgaaaataaaaagagaaacaagtattttgctatatataaagacaacaaaagaaatctcctaacaaaagaactaagaggcccagccctcagaaacccttcagt<br>gctacattttgtggctttttaatggaaaccaagccaatgttatagacgtttggactgatttgtggaaaggagggggaagagggagaaggatcattcaaaag<br>ttacccaaagggcttattgactctttctattgttaaacaaatgatttccacaaacagatcaggaagcactaggttggcagagacactttgtctagtgtattc<br>tcttcacagtgccaggaaagagtggtttctgcgtgtgtatatttgtaatatatgatatttttcatgctccactattttattaaaaataaaatatgttcttta<br>aaaaaa |
| 9 | agtgttaccttggagcctacaatgagaggtatttcaaaatgagtgaagcatgactctcacagatgaaggcctagacgcaggatctttaatgaaaaaacactt<br>gggccacttcaagacgacaaacgctcactgggcaaaacaccttcactgaaaagagacctcatattatgcaaaaaaaatcttaaaaggcctctgccttcaga<br>agttacaagatgatcaattcaacctccacacagcctccagatgaatcctgctctcagaacctcctgatcactcagcagatcattcctgtgctgtactgtatg |

TABLE 1-continued

Embodiments of TVM sequences

| SEQ ID NO | Sequence |
|---|---|
| | gtcttcattgcaggaatcctactcaatggagtgtcaggatggatattcttttacgtgcccagctctgagagtttcatcatctatctcaagaacattgttatt<br>gctgactttgtgatgagcctgacttttcctttcaagatccttggtgactcaggccttggtccctggcagctgaacgtgtttgtgtgcagggtctctgccgtg<br>ctcttctacgtcaacatgtacgtcagcattgtgttctttgggctcatcagctttgacagatattataaaattgtaaagcctctttggacttctttcatccag<br>tcagtgagttacagcaaacttctgtcagtgatagtatggatgctcatgctcctccttgctgttccaaatattattctcaccaaccagagtgttagggaggtt<br>acacaaataaaatgtatagaactgaaaagtgaactgggacggaagtggcacaaagcatcaaactacatcttcgtggccatcttctggattgtgtttcttttg<br>ttaatcgttttctatactgctatcacaaagaaaatctttaagtcccaccttaagtcaagtcggaattccacttcggtcaaaaagaaatctagccgcaacata<br>ttcagcatcgtgtttgtgtttttttgtctgttttgtaccttaccatattgccagaatcccctacacaaagagtcagaccgaagctcattacagctgccagtca<br>aaagaaatcttgcggtatatgaaagaattcactctgctactatctgctgcaaatgtatgcttggaccctattatttatttctttctatgccagccgtttagg<br>gaaatcttatgtaagaaattgcacattccattaaaagctcagaatgacctagacatttccagaatcaaaagaggaaatacaacacttgaaagcacagatact<br>ttgtgagttcctaccctcttccaaagaaagaccacgtgtgcatgttgtcatcttcaattacataacagaaatcaataagatatgtgccctcatcataaatat<br>catctctagcactgccatccaatttagttcaataaaattcaaatataagtttccatgctttttttgtaacatcaaagaaaacatacccatcagtaatttctct<br>aatactgacctttctattctctattaataaaaaattaatacatacaattattcaattctattatattaaaataagttaaagtttataaccactagtctggtc<br>agttaatgtagaaatttaaatagtaaataaaacacaacataatcaaagacaactcactcaggcatcttctttctctaaataccagaatctagtatgtaattg<br>ttttcaacactgtccttaaagactaacttgaaagcaggcacagtttgatgaagggctagagagctgtttgcaataaaaagtcaggtttttttcctgatttga<br>agaagcaggaaaagctgacacccagacaatcacttaagaaacccccttattgatgtatttcatggcactgcaaaggaagaggaatattaattgtatacttagc<br>aagaaaatttttttttctgatagcactttgaggatattagatacatgctaaatatgttttctacaaagacttacgtcatttaatgagcctggggttctggt<br>gttagaatattttaagtaggctttactgagagaaactaaatattggcatacgttatcagcaacttcccctgttcaatagtatgggaaaaataagatgactg<br>ggaaaaagacacacccacaccgtagaacatatattaatctactggcgaatgggaaaggagaccatttcttagaaagcaaataaacttgatttttttaaatc<br>taaaatttacattaatgagtgcaaaataacacataaaatgaaaattcacacatcacatttttctggaaaacagacggattttacttctggagacatggcata<br>cggttactgacttatgagctaccaaaactaaattctttctctgctattaactggctagaagacattcatctatttttcaaatgttctttcaaaacattttta<br>taagtaatgtttgtatctatttcatgctttactgtctatatactaataaagaaatgttttaataccgaaaaaaaaaaaaaaaa |
| 10 | gaagcgggctgggaggcgtcggcggcggcagcgcacgtggtgacgtgcgagggggtgcggcgcgagcggtcggcggcggcggaggcagtgtctc<br>ccggtcgcgcgtggaggtcggtcgctcagagctgctgggcgcagtttctccgcctgctgcttcggcgcggctgtatcggcgagcgagcgagttcccgcg<br>agttctcggtggcgctccccccttcctttcagtctccacggactggcccctcgtccttctacttgaccgctcccgtcttccgccgccttctggcgctttccgt<br>tgggccgattcccgcccgcttcctcctgcttcccatcgaagctctagaaatgaatgtttccatctcttcagagatgaaccagattatgatgcatcattatca<br>cagaagaaattcgtgtctatagcttttaaggacttgattacatcattttcaagcctgatagttttggaatcaccattagagcttaagacacacctgccttca<br>tttcaaccacctgtcttcataccctgacgaagtgcaccttttaacactcctttgtccttggattacttaagagttcccagaaatacatttgccaccaacaga<br>gtagccaaatttataaggaaaaatgattcccaatggatatttgatgtttgaggatgaaaattttattgagtcttctgttgccaaattaaatgccctgaggaa<br>aagtggccagttctgtgatgttcgacttcaggtctgtggccatgaaatgttagcacacagagcagtgctagcttgctgcagtccctatttatttgaaatctt<br>taatagtgatagtgatcctcatggaatttctcacgttaaatttgatgatctcaatccagaagctgttgaagtcttgttgaattatgcctacactgctcagtt<br>gaaagcagataaggaattggtaaaagatgtttattctgcagcaaaaaagctgaagatggatcgagtaaagcaggtttgtggtgattatttactgtctagaat<br>ggatgttaccagctgcatctcttaccgaaattttgcaagttgtatgggagactcccgtttgttgaataaggttgatgcttatattcaggagcatttgttaca<br>aatttctgaagaggaggagtttcttaagcttccaaggctaaagttggaggtaatgcttgaagataatgtttgcttgcccagcaatggcaaattatatacaaa<br>ggtaatcaactgggtgcagcgtagcatctgggagaatggagacagtctggaagagctgatggaagaggttcaaaccttgtactactcagctgatcacaagct<br>gcttgatgggaacctactagatggacaggctgaggtgtttggcagtgatgatgaccacattcagtttgtgcagaaaaagccaccacgtgagaatggccataa<br>gcagataagtagcagttcaactggatgtctctcttctccaaatgctacagtacaaagccctaagcatgagtggaaaatcgttgcttcagaaaagacttcaaa<br>taacacttacttgtgcctggctgtgctggatggtatattctgtgtcatttttcttcatgggagaaacagcccacagagctcaccaacaagtactccaaaact<br>aagtaagagtttaagctttgagatgcaacaagatgagctaatcgaaaagcccatgtctcctatgcagtacgcacgatctggtctgggaacagcagagatgaa<br>tggcaaactcatagctgcaggtggctataacagagaggaatgtcttcgaacagtcgaatgctataatccacatacagatcactggtcctttcttgctcccat<br>gagaacaccaagagcccgatttcaaatggctgtactcatgggccagctctatgtggtaggtggatcaaatggccactcagatgacctgagttgtggagagat<br>gtatgattcaaacatagatgactggattcctgttccagaattgagaactaaccgttgtaatgcaggagtgtgtgctctgaatggaaagttatacatcgttgg<br>tggctctgatccatatggtcaaaaaggactgaaaaattgtgatgtatttgatcctgtaacaaagttgtggacaagctgtgcccctcttaacattcggagaca<br>ccagtctgcagtctgtgagcttggtggttatttgtacataatcggaggtgcagaatcttggaattgtctgaacacagtagaacgatacaatcctgaaaataa<br>tacctggactttaattgcacccatgaatgtggctaggcgaggagctggagtggctgttcttaatggaaaactgtttgtatgtggtggctttgatggttctca<br>tgccatcagttgtgtggaaatgtatgatccaactagaaatgaatggaagatgatgggaaatatgacttcaccaaggagcaatgctgggattgcaactgtagg<br>gaacaccatttatgcagtgggaggattcgatggcaatgaatttctgaatacggtggaagtctataaccttgagtcaaatgaatggagcccctatacaaagat |

TABLE 1-continued

Embodiments of TVM sequences

| SEQ ID NO | Sequence |
|---|---|
| | tttccagttttaacaaatttaagaccctctcaaactaacaggcttagtgatgtaattatggttagtagaggtacacttgtgaataaagagggtgggtgggta |
| | tagatgttgctaacagcaacacaaagcttttgcatattgcatactattaaacatgctgtacatactttttgggtttatttggaaaggaatgcaaagatgaag |
| | gtctgttttgtgtacttttaagactttggttattttacttttggaaaagaataaaccaagaattgattgggcacatcatttcaagaagtcccctctcctcc |
| | acatttgttttgccaatttgcacattaaatgactcttccctcaaatgtgtactatggggtaaaggggtagggtttaaagatgtagacagttgggtttttta |
| | agggccctttttcaataactggaacactctataacaaaggatacttatttaaatagatgacattgactatttttgtttttattaaaaggaagcttacatgcc |
| | taccaatatttaatcttttatgattgcctttttataactttttatattctcagcagagtgctttaccaattgaagtaaaatgtggcaggctggagttattga |
| | agcagagtggcagtcttcagtttgcagagtaggggtctgtcttttaaactctgagtgcaaacttcagagttcttgccttggctgcagtttttttccttcaag |
| | aatgcagtactaacatttatttgagtggagttactgaacagtaacatagctgtgattttggtatttgaaacactggttttaaatatttgacttgttgagg |
| | gtatgttttatatagcaagacattatatagcagtaaaaaatggtgttttatcttctatataattcctgtttttattattaacaaaacagtcctaaatagcag |
| | ccctcaattgtgaaaaaatttactttaaactacattaggttgtgaatgcaggttttatcagaactatgtttttgttcagtttatctgttcatatggataaat |
| | attggttgggatgacttggtgtctaatgtgtagtgctacacacctaacttatggggccaaaatagcatgtcctaatgcttgctgctgatttaaacacattaa |
| | aggtactttgcaggaaatccttgcaccatgggattaatatccaattgctgcttgtacactcattcattactaaaagttttgagaaattttttttccagtaa |
| | tgagcttaagaaatttgtggaaaataactcacctggcatcttacatctgaaataaggaatgatataaggttttttttctcacagaagatgaagcacacagg |
| | aacctaatgggccaactgggatgaggtgactattctgagatgactattcagtggctaacttgggttaggaagaaaataattaggtattttctccaaatg |
| | ttcactggtactctgccactttatttctctcatctgttacacaaagaaccaccaggaaagcaaatcagtttggttggtaactctgtaattcctaactatcac |
| | tggtttggttctggactaaaactacattgacagattgaatttgcctaatatgatgactgtttttaatatggatctgtatgtgttctattcagcacaaggaaa |
| | taaaattttagttgaggattcagcactaaaaaaaaaa |
| 11 | gcatactgctagtggcgcgcggaggagcgacgcgtggagaagcggcccacgtgtctgcccagagtcaagtcctgtgttcttcccgctccttacgcatccg |
| | cggtccagggcgccctttcagccccgctggtgttcgcccaccccgggccgcgtgagtggggccccacgcagctccccgcactccgtgggccaacttgg |
| | ccaagcaactctgtccggggagcggtgcttgcgggggggtgagtaccgggcactgcgcatgcggagctccaaattcaaacagctgttttcagaggctgga |
| | gggcgggcggactggtagcagctggggctaggagaggctttctctaggaggcggccgctcgggagccatggtggaccggggccctctgctcacctcg |
| | gccatcatcttctacctggccatcggggcggcgatcttcgaagtgctggaggagccacactggaaggaggccaagaaaaactactacacacagaagct |
| | gcatctgctcaaggagttcccgtgcctgggtcaggagggcctggacaagatcctagaggtggtatctgatgctgcaggacagggtgtggccatcacagg |
| | gaaccagaccttcaacaactggaactggcccaatgcaatgatttttgcagcgaccgtcattaccaccattggatatggcaatgtggctcccaagacccccg |
| | ccggtcgcctcttctgtgttttctatggtctcttcggggtgccgctctgcctgacgtggatcagtgccctgggcaagttcttcgggggacgtgccaagagac |
| | tagggcagttccttaccaagagaggtgtgagtctgcggaaggcgcagatcacgtgcacagtcatcttcatcgtgtggggcgtcctagtccacctggtgatc |
| | ccacccttcgtattcatggtgactgaggggtggaactacatcgagggcctctactactccttcatcaccatctccaccatcggcttcggtgactttgtggcc |
| | ggtgtgaaccccagcgccaactaccacgccctgtaccgctacttcgtggagctctggatctacttggggctggcctggctgtccctttttgtcaactggaag |
| | gtgagcatgtttgtggaagtccacaaagccattaagaagcggcggcggcgacggaaggagtcctttgagagctccccacactcccggaaggccctgcagg |
| | tgaaggggagcacagcctccaaggacgtcaacatcttcagctttctttccaagaaggaagagacctacaacgacctcatcaagcagatcgggaagaagg |
| | ccatgaagacaagcgggggtggggagacgggcccgggcccagggctggggcctcaaggcggcggtgggctcccagcactgccccccttccctggtgccc |
| | tggtagtctactccaagaaccgggtgcccaccttggaagaggtgtcacagacactgaggagcaaaggccacgtatcaaggtccccagatgaggaggct |
| | gtggcacgggcccctgaagacagctcccctgcccccgaggtgttcatgaaccagctggaccgcatcagcgaggaatgcgagccatgggacgcccagg |
| | actaccacccactcatcttccaggacgccagcatcaccttcgtgaacacggaggctggcctctcagacgaggagacctccaagtcctcgctagaggaca |
| | acttggcaggggaggagagccccccagcagggggctgaagccaaggcgcccctgaacatgggcgagttcccctcctcctccgagtccaccttcaccagc |
| | actgagtctgagctctctgtgccttacgaacagctgatgaatgagtacaacaaggctaacagccccaagggcacatgaggcagggccggctccccaccc |
| | cacctttgatggcctcttccccctcaccctagggtgtcccgagatgaccgggacgcctggcccctggtgggggggcagcctcggaactgggagtgggg |
| | ggccaggggccttcctaaccttccatcatcctcagctagatgtatgcccgggacagggcctctgttctccagctgaaccataccctggctgtgggggcatct |
| | gtcctgagcttggctggtgtatctcacaatgcaaagacatgctggctggcgggacaggtgggcaggactgaccctgaggaggccttgcctgcagggtctt |
| | tgtctcaccatttggtggagtatcacacggttctctgaggtctggggcctcagctgtttaagtttaccggtattactgagctcggcatttggagagggagct |
| | ctgaagtgtctggggaggtaccgctgtgcgtggggtcaggtgtttccgtaccacagcaggagcagggcccgcccgcatcccagctgtgggcctgccggtc |
| | aggtcgggcacctactacaaaccgtagtggggtggaggctgctggaggtgggagtgaggagatgagggcagggtctcaaacagtcctgactcacagg |
| | gcctggaaacaagtcctatgtgggcctggggcctggggtcctcatcctccttgttggtctactcaggcccagcccagagctgtgttccctgtctcaggtcaa |
| | gcagtggcagacgcaaggctttctgtgggcccccaagtggtaggagggagagtagcagagcatgggttactggaagccgggactgctagggctggtg |
| | gccagggagctgcaagagtgaggctcagctctggctggttctgcccttacccctcctgcccgcctgagaactgcacaccctgcccgctggccccaggac |
| | ctgcactcccaatcctgctgtcttctccttccctgtgccctgaacaaggacctcactgcccgccttcccctcccaccagccccccttgggccaggcagggtga |

TABLE 1-continued

Embodiments of TVM sequences

| SEQ ID NO | Sequence |
|---|---|
| | ggccaaattgctcttggcccacaaatgggtgatggtcagatatgtgaatcaagctcctttctctagctagtgtttgatgtgcacgtgtgtgtgcacagtgcg |
| | tgtgtgcacacgcacacctgtgcactcgtgtgtgtttaagaaaggaaaggatttgggctggggagcaaaagataatgtgaaactgttggtggactctctggt |
| | gaggggtgggcagaacttgctgctactagagttcttgggttctccatgatgttcaccctggggctggcccactgtgtcctgaatgttttgttatttttttgt |
| | tttattttttaaacaaactgctgtttttatatacctggaatctgttgttggcttcagagccagtggttaaagagcagggtcccaaggattgggagatctagt |
| | gtctgccctcctgccctgcaactcaattgggcctttttcggtgacctcatccaaggccatgatgtcaagggccatgtccccaagcagaggtggagaagggga |
| | cactgaggtgagcaaaagcaggaaggggcatccactgcgggtgactggaggccgggcaggaagcaagtcatcagagccgctcagctccgttcactctctgcc |
| | ttctgccccactactgtggggcagtggggccagagcccacctccccaacatgtgaagacagtgatgggcacgtgcccacacccccacttctctagccgtttg |
| | cagaggccgccacccagcaggggcctgaaaaggagctgcctcgtatttttctgtgaaatgttttaatgaaccatgttgttgctggttgtcctggcatcgcgc |
| | acactgtatgtacatactggcaacgatgtcaaatgtaatttattttaacatttttacaataaaacatgaggtggacaggcaaaaaaaaaaaaaaa |
| 12 | gcccgcgccgccaccgcctcttccctccccgtgtccggtccccgtgcgtcccgaggctccccgccgcccgtcccggcgcgcaccgcgggcgtctgtccg |
| | aacgccttccagccacctgagccctcctgcgggcgactcgctcagctagcccgtgcccgcctccaccttctccgtcatcccctcttccttgcgtccggctct |
| | ccactggggctgcacagtcgagggctgctcgcgtcgggaaggagatgcccagagtctctggggcgcaccctcccgtcccgctcagccgcacccagcttt |
| | agaaggtgctctcagcagccactttcgggctctagcgaggacaccctctcgcagaagtccttgccgagacccccgccccagccattctctgaaggggct |
| | gaggacactcttatcgcgcccctcatggccaagcctcggctgctagttctctacttcgctctgattgtggttccggcctgggtgtccagcattgtcctcaca |
| | gggacaagcgagcccccagatgcgcagacagtggcgcctgcggaggacgagactctgcaaaacgaggcggacaaccaggagaacgttttatctcagttg |
| | ctgggggactatgacaaggtcaaggctatgtctgagggctcggactgtcagtgcaagtgtgtggtgagacccctgggccgggatgcctgccagaggatc |
| | aatgcgggggcctccaggaaggaagacttctataccgtggaaaccatcacctcaggctcgtcgtgcaagtgtgcctgtgtagcacccccatcggccctca |
| | atccctgcgagggagacttcaggctccagaagctgcgggaggcagacagccaggacttgaagctctccacaatcatagacatgttggaaggagcgttct |
| | atggcctggatctcctgaagctacattcagtcaccaccaaactggtggggcgagtggataaactggaggaggaagtgtctaaaaacctcaccaaggaaa |
| | acgaacaaatcaaagaggacatggaagaaattcgaaccgagatgaataagcgaggcaaagaaaattgctctgaaaacatcctagatagcatgccagac |
| | atccgctcagccctgcagagggatgcagcagcagcctacgcccacccagagtatgaagagcggtttctgcaggaagaaaccgtgtcccagcagatcaa |
| | ctccatcgaacttctgcagacgcgacccctggctctgcctgaggtggtgaagtcacagcggcccctgcagaggcaggtccacctgagaggccggccgg |
| | cctcccagcccactgtcatccggggcatcacctactataaagccaaggtctctgaagaagagaatgacattgaagagcagcaagatgagtttttcagcggt |
| | gacaatggagtggatttgctgattgaagatcagctcctgagacacaacggcctgatgaccagtgtcacccggaggcctgcagccacccgtcagggacac |
| | agcactgctgtgacaagcgacctgaacgctcggaccgcaccctggtcctcagcactgccacagccctcgacctcagatcccagcatcgccaaccatgcct |
| | cagtgggaccaacactccaaacaacctcggtgtctccagatcccacaagggagtcagtcctgcagccttctcctcaggtaccagccaccactgtggccca |
| | cacagccacccagcaaccagcagccccagctcctccggcagtgtctcccagggaggcattgatggaagctatgcacacagtcccagtgcctcccaccac |
| | agtcagaacagactcgctggggaaagatgctcctgctgggtggggaacaacccctgccagccccacgctgagccccgaagaagaagatgacatccgg |
| | aatgtcataggaaggtgcaaggacactctctccacaatcacggggccgaccacccagaacacatatgggcggaatgaaggggcctggatgaaggacc |
| | ccctggccaaggatgagcggatttacgtaaccaactattactacggcaacaccctggtagagttccggaacctggagaacttcaaacaaggtcgctggag |
| | caattcctacaagctcccgtacagctggatcggcacaggccacgtggtatacaatggcgccttctactacaatcgcgccttcacccgcaacatcatcaagta |
| | cgacctgaagcagcgctacgtggctgcctgggccatgctgcatgacgtggcctacgaggaggccacccccctggcgatggcagggccactcagacgtg |
| | gactttgctgtggacgagaatggcctatggctcatctacccggccctggacgatgagggcttcagccaggaggtcattgtcctgagcaagctcaatgccg |
| | cggacctgagcacacagaaggagaccacatggcgcacggggctccggaggaatttctacggcaactgcttcgtcatctgtggggtgctgtatgccgtgg |
| | atagctacaaccagcggaatgccaacatctcctacgctttcgacacccacaccaacacacagatcgtccccaggctgctgttcgagaatgagtattcctata |
| | cgacccagatagactacaaccccaaggaccgcctgctctatgcctgggacaatggccaccaggtcacttaccatgtcatctttgcctactgacacccttgtc |
| | cccacaagcagaagcacagaggggtcactagcaccttgtgtgtatgtgtgtgcgcgcacgtgtgtgtaggtgggtatgtgttgtttaaaaatatatattatt |
| | ttgtataatattgcaaatgtaaaatgacaatttgggtctatttttttatatggattgtagatcaatccatacgtgtatgtgctggtctcatcctccccagtt |
| | tatattttgcaaatgaacttctccttttgaccagtaaccaccttccttcaagccttcagcccctccagctccaagtctcagatctcgaccattgaaaaggtt |
| | tcttcatctgggtcttgcaggaggcaggcaacaccaggagcagaaatgaaagaggcaagaaagaagtgctatgtggcgagaaaaaaagttttaatgtattgg |
| | agaagttttaaaaaacccagaaaaacgcttttttttttaataaagaagaaatttaaaatcaaaaaaaaaaaaaaaaaaaaaaaaaaaaaaaaaaaaaaaaa |
| | aaaaaaaaaaaaaaaaaaaaaaaaaaaaaaaaaaaaaaaa |
| 13 | acttttgggacatcctgttctgagtcaagattcctccttctgaacatgggactttccagaaggaccacagctcctcccgtgcatccactcggcctgggaggt |
| | tctggattttggctgtcgagggagtttgcctgcctctccagagaaagatggtcatgaggcccctgtggagtctgcttctctgggaagccctacttccca |
| | gttactggtgcccaagtgctgagcaaagtcgggggctcggtgctgctggtggcagcgcgtccccctggcttccaagtccgtgaggctatctggcgatctct |

TABLE 1-continued

Embodiments of TVM sequences

| SEQ ID NO | Sequence |
|---|---|
| | ctggccttcagaagagctcctggccacgtttttccgaggctccctagagactctgtaccattcccgcttcctgggccgagcccagctacaatgcaacctcag |
| | cctggagctcgggccgctggagtctggagacagcggcaacttctccgtgttgatggtggacacaaggggccagccctggacccagaccctccagctca |
| | aggtgtacgatgcagtgcccaggcccgtggtacaagtgttcattgctgtagaaagggatgctcagccctccaagacctgccaggttttcttgtcctgttggg |
| | cccccaacatcagcgaaataacctatagctggcgacgggagacaaccatggactttggtatggaaccacacagcctcttcacagacggacaggtgctga |
| | gcatttccctgggaccaggagacagagatgtggcctattcctgcattgtctccaaccctgtcagctgggacttggccacagtcacgccctgggatagctgtc |
| | atcatgaggcagcaccagggaaggcctcctacaaagatgtgctgctggtggtggtgcctgtctcgctgctcctgatgctggttactctcttctctgcctggc |
| | actggtgcccctgctcagggaaaaagaaaaaggatgtccatgctgacagagtgggtccagagacagagaaccccccttgtgcaggatctgccataaagga |
| | caatatgaactgatgcctggactatcagtaaccccactgcacaggcacacgatgctctgggacataactggtgcctggaaatcaccatggtcctcatatctc |
| | ccatgggaatcctgtcctgcctcgaaggagcagcctgggcagccatcacaccacgaggacaggaagcaccagcacgtttcacacctccccttccctctc |
| | ccatcttctcatatcctggctcttctctgggcaagatgagccaagcagaacattccatccaggacactggaagttctccaggatccagatccatggggacat |
| | taatagtccaaggcattccctcccccaccactattcataaagtattaaccaactggcaccaaggaattgcctccagcctgagtcctaggctctaaaagatat |
| | tacatatttgaactaatagaggaactctgagtcacccatgccagcatcagcttcagccccagaccctgcagtttgagatctgatgcttcctgagggccaagg |
| | cattgctgtaagaaaaggtctagaaataggtgaaagtgagaggtgggggacaggggtttctctttctggcctaaggactttcaggtaatcagagttcatggg |
| | ccctcaaaggtagattgcagttgtagacaccgaggatggttgacaacccatggttgagatgggcaccgttttgcaggaaacaccatattaatagacatcct |
| | caccatctccatccgctctcacgcctcctgcaggatctgggagtgagggtggagagtctttcctcacgctccagcacagtggccaggaaaagaaatactg |
| | aatttgccccagccaacaggacgttcttgcacaacttcaagaaaagcagctcagctcaggatgagtcttcctgcctgaaactgagagagtgaagaaccat |
| | aaaacgctatgcagaaggaacattatggagagaaagggtactgaggcactctagaatctgccacattcattttcaaatgcaaatgcagaagacttacctta |
| | gttcaaggggaggggacaaagaccccacagcccaacagcaggactgtagaggtcactctgactccatcaaactttttattgtggccatcttaggaaaatac |
| | attctgcccctgaatgattctgtctagaaaagctctggagtattgatcactactggaaaaacacttaaggagctaaacttaccttcggggattattagctga |
| | taaggttcacagtttctctcacccaggtgtaactggattttctggggcctcaatccagtcttgataacagcgaggaaagaggtattgaagaaacaggggtg |
| | ggtttgaagtactattttcccagggtggcttcaatctccccacctaggatgtcagccctgtccaaggaccttccctcttctccccagttcctgggcaatcac |
| | ttcaccttggacaaaggatcagcacagctggcctccagatccacatcaccactcttccactcgattgttcccagatcctccctgcctggcctgctcagaggt |
| | tccctgttggtaacctggctttatcaaattctcatccctttcccacacccacttctctcctatcaccttcccccaagattacctgaacagggtccatggcca |
| | ctcaacctgtcagcttgcaccatccccacctgccacctacagtcaggccacatgcctggtcactgaatcatgcaaaactggcctcagtccctaaaaatgatg |
| | tggaaaggaaagcccaggatctgacaatgagccctggtggatttgtggggaaaaaatacacagcactccccacctttctttcgttcatctccagggccccac |
| | ctcagatcaaagcagctctggatgagatgggacctgcagctctccctccacaaggtgactcttagcaacctcatttcgacagtggtttgtagcgtggtgcac |
| | cagggccttgttgaacagatccacactgctctaataaagttcccatccttaatgaag |
| 14 | cagtcacatttcagccactgctctgagaatttgtgagcagcccctaacaggctgttacttcactacaactgacgatatgatcatcttaatttacttatttct |
| | cttgctatgggaagacactcaaggatggggattcaaggatggaatttttcataactccatatggcttgaacgagcagccggtgtgtaccacagagaagcacg |
| | gtctggcaaatacaagctcacctacgcagaagctaaggcggtgtgtgaatttgaaggcggccatctcgcaacttacaagcagctagaggcagccagaaaaat |
| | tggatttcatgtctgtgctgctggatggatggctaagggcagagttggataccccattgtgaagccagggcccaactgtggatttggaaaaactggcattat |
| | tgattatggaatccgtctcaataggagtgaaagatgggatgcctattgctacaacccacacgcaaaggagtgtggtggcgtctttacagatccaaagcaaa |
| | tttttaaatctccaggcttcccaaatgagtacgaagataaccaaatctgctactggcacattagactcaagtatggtcagcgtattcacctgagtttttttag |
| | agaccttgaagatgacccaggttgcttggctgattatgttgaaatatatgacagttacgatgatgtccatggctttgtgggaagatactgtggagatgagct |
| | tccagatgacatcatcagtacaggaaatgtcatgaccttgaagtttctaagtgatgcttcagtgacagctggaggtttccaaatcaaatatgttgcaatgga |
| | tcctgtatccaaatccagtcaaggaaaaaatacaagtactacttctactggaaataaaaactttttagctggaagatttagccacttataaaaaaaaaaaaa |
| | aggatgatcaaaacacacagtgtttatgttggaatcttttggaactcctttgatctcactgttattattaacatttatttattatttttctaaatgtgaaag |
| | caatacataatttagggaaaattggaaaatataggaaactttaaacgagaaaatgaaacctctcataatcccactgcatagaaataacaagcgttaacattt |
| | tcatattttttctttcagtcatttttctatttgtggtatatgtatatatgtacctatatgtatttgcatttgaaattttggaatcctgctctatgtacagt |
| | tttgtattatactttttaaatcttgattataaacattttctgaaatcattgattattctacaaaaacatgattttaaacagctgtaaaatattctatgatat |
| | gaatgttttatgcattatttaagcctgtctctattgttggaatttcaggtcattttcataaatattgttgcaataaatatccttgaacacaaaaaaaaaaaa |
| | aaaaaa |
| 15 | gccaccttgtctgtgagctccctgtgccccccatacggtgtgtcctgtgggttggggtgtgcggaagaaagggacagagactgaggatgtgcggtgtaag |
| | cagtgtgctcggggtaccttctcagatgtgccttctagtgtgatgaaatgcaaagcatacacagactgtctgagtcagaacctggtggtgatcaagccggg |
| | gaccaaggagacagacaacgtctgtggcacactcccgtccttctccagctccacctcaccttcccctggcacagccatctttccacgccctgagcacatgg |

TABLE 1-continued

Embodiments of TVM sequences

| SEQ ID NO | Sequence |
|---|---|
| | aaacccatgaagtcccttcctccacttatgttcccaaaggcatgaactcaacagaatccaactcttctgcctctgttagaccaaaggtactgagtagcatcc aggaagggacagtccctgacaacacaagctcagcaaggggaaggaagacgtgaacaagaccctcccaaaccttcaggtagtcaaccaccagcaagg cccccaccacagacacatcctgaagctgctgccgtccatggaggccactgggggcgagaagtccagcacgcccatcaagggccccaagaggggacat cctagacagaacctacacaagcattttgacatcaatgagcatttgccctggatgattgtgcttttcctgctgctggtgcttgtggtgattgtggtgtgcagt atccggaaaagctcgaggactctgaaaaaggggccccggcaggatcccagtgccattgtggaaaaggcagggctgaagaaatccatgactccaacccaga accgggagaaatggatctactactgcaatggccatggtatcgatatcctgaagcttgtagcagcccaagtgggaagccagtggaaagatatctatcagttt ctttgcaatgccagtgagagggaggttgctgctttctccaatgggtacacagccgaccacgagcgggcctacgcagctctgcagcactggaccatccgg ggccccgaggccagcctcgcccagctaattagcgccctgcgccagcaccggagaaacgatgttgtggagaagattcgtgggctgatggaagacacca cccagctggaaactgacaaactagctctcccgatgagccccagcccgcttagcccgagccccatccccagccccaacgcgaaacttgagaattccgctct cctgacggtggagccttccccacaggacaagaacaagggcttcttcgtggatgagtcggagccccttctccgctgtgactctacatccagcggctcctccg cgctgagcaggaacggttcctttattaccaaagaaaagaaggacacagtgttgcggcaggtacgcctggacccctgtgacttgcagcctatctttgatgac atgctccactttctaaatcctgaggagctgcgggtgattgaagagattccccaggctgaggacaaactagaccggctattcgaaattattggagtcaagag ccaggaagccagccagaccctcctggactctgtttatagccatcttcctgacctgctgtagaacatagggatactgcattctggaaattactcaatttagtg gcagggtggtttttaattttcttctgtttctgattttgttgtttggggtgtgtgtgtgtgtttgtgtgtgtgtgtgtgtgtgtgtgtgtgtgtttaac aggccagtgcttgagttctttctccttctctctctctcttttttttttaaataactcttctgggaagttggtttataacctttgccaggtgtaactgttgtg aaatacccaccactaaagtttttaagttccatatttctccattttgccttcttatgtattttcaagattattctgtgcactttaaatttacttaacttac cataaatgcagtgtgacttttcccacacactggattgtgaggctcttaacttcttaaaagtataatggcatcttgtgaatcctataagcagtctttatgtct cttaacattcacacctactacaaatattattactatttttattattgtttgtcctttataaatttcttaaagattaagaaaatttaagaccccattgagtt actgtaatgcaattcaactttgagttatcttttaaatatgtcttgtatagttcatattcatggctgaaacttgaccacactattgctgattgtatggttttc acctggacaccgtgtagaatgcttgattacttgtactcttcttatgctaatatgctctgggctggagaaatgaaatcctcaagccatcaggatttgctattt aagtggcttgacaactgggccaccaaagaacttgaacttcaccttttaggatttgagctgttctggaacacattgctgcactttggaaagtcaaaatcaagt gccagtggcgccctttccatagagaatttgcccagctttgctttaaaagatgtcttgtttttatatacacataatcaataggtccaatctgctctcaaggc cttggtcctggtgggattccttcaccaattactttaattaaaaatggctgcaactgtaagaacccttgtctgatatatttgcaactatgctcccatttacaa atgtaccttctaatgctcagttgccaggttccaatgcaaaggactccctttgtgtgggtggggtttgtgggtagtggtgaaggaccgatatcagaaaaatgc cttcaagtgtactaatttattaataaacattaggtgtttgttaaaaaaaaaaaaaaa |
| 16 | gggaggtaagtagaaaccgttgatgggactgagaaaccagagttaaaacctctttggagcttctgagggctcagctggaaccaacgggcacagttggca acaccatcatgacatcacaacctgttcccaatgagaccatcatagtgctcccatcaaatgtcatcaacttctcccaagcagagaaacccgaacccaccaac caggggcaggatagcctgaagaaacatctacacgcagaaatcaaagttattgggactatccagatcttgtgtggcatgatggtattgagcttggggatcat tttggcatctgcttccttctctccaaatttacccaagtgacttctacactgttgaactctgcttacccattcataggacccttttttttttatcatctctgg ctctctatcaatcgccacagagaaaaggttgaccaagcttttggtgcatagcagcctggttggaagcattctgagtgctctgtctgccctggtgggtttcat tatcctgtctgtcaaacaggccaccttaaatcctgcctcactgcagtgtgagttggacaaaaataatataccaacaagaagttatgtttcttacttttatca tgattcactttataccacggactgctatacagccaaagccagtctggctggatccctctctctgatgctgatttgcactctgctggaattctgcctagctgt gctcactgctgtgctgcggtggaaacaggcttactctgacttccctgggagtgtacttttcctgcctcacagttacattggtaattctggcatgtcctcaaa aatgactcatgactgtggatatgaagaactattgacttcttaagaaaaaagggagaaatattaatcagaaagttgattcttatgataatatggaaaagttaa ccattatagaaaagcaaagcttgagtttcctaaatgtaagcttttaaagtaatgaacattaaaaaaaaccattatttcactgtcatttaagatatgtgttca ttggggatctcttgatttgcctgacattgacttcagcaaaagcacggggctgtaaattaccatttactagattagccaaatagtctgaatttccagaaaaca aggcagaatgatcattcccagaaacatttcccagaaaatgtttcccagaaaactagacagaatgatcattcaatggatcacagtgaagcaaaggacacaact ttttattgtaccccttaattgtcaacaggagttaactgatttgttgtggtgctcagactttttttatacaggtgctagtgttttatcctatgtattttaactc attagtgcataaaggcaagccccatataatgaagtctcagggtatatgaaagtagctggcttcaaaataaaatttttgagtgcaaaaaaaaaaaaaaaaaaaa aaaaaaaaaa |
| 17 | ggctgaggagctgcccagagcaccgctcacactcccagagtacctgaagtcggcatttcaatgacaggtgacaagggtccccaaaggctaagcgggtc cagctatggttccatctccagcccgaccagcccgaccagcccagggccacagcaagcacctcccagagagacctacctgagtgagaagatccccatcc cagacacaaaaccgggcaccttcagcctgcggaagctatgggccttcacggggcctggctttctcatgagcattgctttcctggacccaggaaacatcga gtcagatcttcaggctggcgccgtggcgggattcaaacttctctgggtgctgctctgggccaccgtgttgggcttgctctgccagcgactggctgcacgtct gggcgtggtgacaggcaaggacttgggcgaggtctgccatctctactaccctaagtcggagtctcgctccgtcgcccagtcaggagtgcaatggtgcgat |

TABLE 1-continued

Embodiments of TVM sequences

| SEQ ID NO | Sequence |
|---|---|
| | gtcagctcactgcaacctctacctcccaggtgccccgcaccgtcctctggctgaccatcgagctagccattgtgggctccgacatgcaggaagtcatcggc<br>acggccattgcattcaatctgctctcagctggacgaatcccactctggggtggcgtcctcatcaccatcgtggacaccttcttcttcctcttcctcgataac<br>tacgggctgcggaagctggaagctttttttggactccttataaccattatggccttgacctttggctatgagtatgtggtggcgcgtcctgagcagggagcg<br>cttcttcggggcctgttcctgccctcgtgcccgggctgcggccaccccgagctgctgcaggcggtgggcattgttggcgccatcatcatgccccacaacatc<br>tacctgcactcggccctggtcaagtctcgagagatagaccgggcccgccgagcggacatcagagaagccaacatgtacttcctgattgaggccaccatcgcc<br>ctgtccgtctcctttatcatcaacctctttgtcatggctgtctttgggcaggccttctaccagaaaaccaaccaggctgcgttcaacatctgtgccaacagc<br>agcctccacgactacgccaagatcttccccatgaacaacgccaccgtggccgtggacatttaccagggggcgtgatcctgggctgcctgttcggccccgcg<br>gccctctacatctgggccataggtctcctggcggctgggcagagctccaccatgacgggcacctacgcgggacagttcgtgatggagggcttcctgagg<br>ctgcggtggtcacgcttcgcccgtgtcctcctcacccgctcctgcgccatcctgcccaccgtgctcgtggctgtcttccgggacctgagggacttgtcgggc<br>ctcaatgatctgctcaacgtgctgcagagcctgctgctcccgttcgccgtgctgcccatcctcacgttcaccagcatgcccaccctcatgcaggagtttgcc<br>aatggcctgctgaacaaggtcgtcacctcttccatcatggtgctagtctgcgccatcaacctctacttcgtggtcagctatctgcccagcctgccccaccct<br>gcctacttcggccttgcagccttgctggccgcagcctacctgggcctcagcacctacctggtctggacctgttgccttgcccacggagccacctttctggcc<br>cacagctcccaccaccacttcctgtatgggctccttgaagaggaccagaaaggggagacctctggctaggcccacaccagggcctggctgggagtggcat<br>gtatgacgtgactggcctgctggatgtggaggggcgcgtgcaggcagcaggatggagtgggacagttcctgagaccagccaacctgggggctttag<br>ggacctgctgtttcctagcgcagccatgtgattaccctctgggtctcagtgtcctcatctgtaaaatggagacaccaccacccttgccatggaggttaagca<br>ctttaacacagtgtctggcacttgggacaaaaacaaacaaacaaacaaaaaacaaaaaaaaaaaaaaaaaaaaaaaaaaaaaaaaaaaaaaaaaaaaaa<br>aaaaaaaaaaaaaaaaaaaaaaaaaa |
| 18 | gagcgcgcgcgccgccgccgttgccgccgggctgagagaagagcttgcggggtttgcggttgatggccccgactgaagggctggaggcggtgtatgc<br>cgctgttcttgctgtcgctcccgacacctccgtccgcttctggtcatgagaggagacagaggcctgaagcaaagacatctgggtcagagaaaaagtattta<br>agggccatgcaagccaatcgtagccaactgcacagtcctccaggaactggaagcagtgaggatgcctcaacccctcagtgtgtccacacaagattgaca<br>ggagagggttcttgccctcattctggagatgttcatatccagataaactccatacctaaagaatgtgcagaaaatgcaagctccagaaatataaggtcaggt<br>gtccatagctgtgcccatggatgtgtacacagtcgcttacggggtcactcccacagtgaagcaaggctgactgatgatactgccgcagaatctggagatca<br>tggtagtagctccttctcagaattccgctatctcttcaagtggctgcaaaaaagtcttccatatattttgattctgagcgtcaaacttgttatgcagcatat<br>aacaggaatttctcttggaattgggctgctaacaacttttatgtatgcaaacaaaagcattgtaaatcaggtttttctaagagaaaggtcctcaaagattca<br>gtgtgcttggttactggtattcttagcaggatcttctgttcttttatattacacctttcattctcagtcactttattacagcttaatttttttaaatcctac<br>tttggaccatttgagcttctgggaagtattttggattgttggaattacagacttcattctgaaattctttttcatgggcttaaaatgccttattttattggt<br>gccttctttcatcatgccttttaaatctaagggttactggtatatgcttttagaagaattgtgtcaatactaccgaacttttgttcccataccagtttggtt<br>tcgctaccttataagctatggggagtttggtaacgtaactagatggagtcttgggatactgctggctttactctacctcatattaaaacttttggaattttt<br>tgggcatctgagaactttcagacaggttttacgaatatttttttacacaaccaagttatggagtggctgccagcaagagacagtgttcagatgtggatgatat<br>ttgttcaatatgtcaagctgaatttcagaagccaattcttctcatttgtcagcatatattttgtgaagagtgcatgaccttatggtttaacagagagaaaac<br>atgtccactctgcagaactgtgatttcagaccatataaacaaatggaaggatggagccacttcatcacaccttcaaatatattaagttgtataaactatcaa<br>ggccacaaaatactaatgtcatttggtcataatgactactgataaggcatcagaatggattttcagggctaccagaaaaatgtttccagatggttttagaat<br>gtaggacttatgatccaattcaccaaaagattaaatgaaaccaccctgtgttttaaaatatatataatgttcaacctaatgtatatgcaacatttattctat<br>tctaattatttgacaggtaactgcagtgttaaattgtaaatgtgttttctttatgttaccaaaacagcaatttgaaattagaactagtggttttagagaact<br>caggtattctttcctgacattgttttcagaataaagaatatttttcataatattttaagatacatactatctaaaagtagaattttgttcagcattgacttt<br>tataattcccatcctaaaaattcttaatattttcataaaatttgtatttttaaatgaaaattctaaatgttgtattttatcagtaacattttctaagtgaag<br>attaatttactgaggatgatacattatagtattgtattattctctgtagtaagattagtaataagtgaaaataaatgatttaaattcaaaaaaaaaaaaaa<br>a |
| 19 | gagcccagagccagagagcgcgctgggcggtgctgggcacccgcggagtggaacggggctggtggaatgcacagggtcgcagcgcttgggccacc<br>ctcggtcagagggcgccgtgtccagcgagcaaacgggcgccccggagccttgctgagaggcagctctgggctttcccagctccgaagtcaatactgag<br>atcccagatgtgtccagagacatcctgaagaggctcgggggtggaggagccttagtgtgtccacaaagggactcctgaaactgactgagagccagtgg<br>atttgccagcagtctgagcttctaccgagtcttcccccacctcaatccctgttgctatggagactaccaatggaacggagacctggtatgagagcctgcatg<br>ccgtgctgaaggctctaaatgccactcttcacagcaatttgctctgccggccagggccagggctggggccagacaaccagactgaagagaggcgggcc<br>agcctacctggccgtgatgacaactcctacatgtacattctctttgtcatgtttctatttgctgtaactgtgggcagcctcatcctgggatacacccgctcc<br>cgcaaagtggacaagcgtagtgacccctatcatgtgtatatcaagaaccgtgtgtctatgatctaacacgagagggctgggacggtggaagaccaagacacc |

TABLE 1-continued

Embodiments of TVM sequences

| SEQ ID NO | Sequence |
| --- | --- |
| | tggggattgcgtctggggcctccagaactctgctgtggactgcatcaggtctcagtgtccctatctgtaagatcaacaagaaacacggttaagggaggtcgt<br>cactggggtgggagaagaggggctggtagaccgaagccttgtgcataaggatttttcccaggaaaagatagactttataaacagtgggagcccatgaa<br>caaacatataaaagtagcaacagataatgaccaataactggttcagtggctggagtattaggggcctggggattggagaacggagaagaagttgtagca<br>gagggaaatgagacaggaagatgctctggggacacatttttatgtgttatcttcagccatgagaagcagtgatgactatcccatatcacagatatgattta<br>ccaccaccaccctgcccccgctcccgtgaagaaagcagggcaagtgctgtgctgcccatttgggcctgcatagtgccatgattggaacccaggaactctgg<br>tctccttgcctagtgcttttcaaaactctgtgctacacaggagtggatccaggcctgaaggtcatacaattctggggactctctttaagaaaaagaattcta<br>aaatatcttacttttgcaaacattatgaaaatatactgccacattaatatgttgctagggcccctgctaggaccttaagaaggagctcatgtgagtcaggac<br>cctgaatgttaggcctcgttagctctatggttcatatgcttcttgaaccaagtcacagggcacttcccagccacattgccaggcaacaggactaaactacct<br>ccaaagcaagcagtcttttcagttttgactgagtgatgtgagaaacttcttttcttttcttttcttttttttttttgagacagtctccctatgtcacccag<br>gctgtggtgcagcaacccaatcttggctcactgcaaccccacctcccgggttcaagcaattatcctgcctcagccacctgagtagctgggattacaggttc<br>ctgtcaccacacccagttaatttatatatatatatatatatatatttaagtagagacagggtttcacatgttgcccaggctggtctcgaactcctgtcct<br>caagttatctgcccattttggtctcccaaagtgctgggattacaagtgtaagccaccacgactatctgagagaagttttctgatgtcatgttgaatctgctt<br>ctaaaagactgatactgccaaggtgggcggatcacctgaggtcaggagttcgagaccagcctggccaacatggtgaaaccccatctactaaaaaaatacaaa<br>aattagccagacctggtggcgggtgcccgtattcccagctacttgggaggctgaggcaggagaattgtttgaacccgggaggtggaggttgcagtaagccaa<br>gatcacgccactgcactccagcctgggtgacagagcaaggctctgtctcaaaaaaaaacaaaaacaaaaacaaaaaagactgatatcgcacctaaattatta<br>ttatattaaaagaagcagagtatgagagacaggtacatggtccagtaggaagagaagcagccctgattctaccacttaaggtgatgtatgatcttaggctgg<br>acacttctctccctcatccgttttcctcttcaacataatgaaatagacttgaaagtctctaaggctctatcagttctgacattctaggcttcatatacatta<br>agttgagccatatgtaatcactgtgtttgtaggttagaaacagctgagtatcgtagtttcatatatggttccagctaatacatgcaatgtggctggtgaaca<br>cttctgaattcagaaactatcccagatctcagctagaaccatccactgttctgtttgtccagtttcaacttaagggatctccatgcggtccctggaagtacc<br>cattgaaacatgcgtatttgtgtatagcagaactctgaaataatattctgacagcagttatctctgaggaattgggttataggtgattttccctttccgcat<br>gataaatttatgtaatatttgactgacttgaccgtaagtatgttacttgtataataaaaggaaaaaaggtacttctattttgaaaaaataaaaataaaagcc<br>tttgggttcttgaatggaggatcatggaacacatttgctgccatatgcagttatgttgatgctctgcaaacctgtgctgagccctgttgctcaagcccttcc<br>tcatctcttcttgagggagaaggtggagacttccttaaggagatgtgacatatgggaagacaacagattcagaaatttacgtggataggactttagacacca<br>cccagcccaaacttccaaataaaatatggaacgcaa |
| 20 | agcagaagaaccctcttggactggacgatttgggaattcaaaacttgggacaaactgtcagccttgcccctgctgtggaggcagcctcaatgctgaaaatg<br>gagcctctgaacagcacgcaccccggcaccgccgcctccagcagcccctggagtcccgtgcggccggtggcggcagcggcaatggcaacgagtac<br>ttctacattctggttgtcatgtccttctacggcattttcttgatcggaatcatgctgggctacatgaaatccaagaggcgggagaagaagtccagcctcctg<br>ctgctgtacaaagacgaggagcggctctgggggaggccatgaagccgctgcccgtggtgtcgggcctgaggtcggtgcaggtgcccctgatgctgaac<br>atgctgcaggagagcgtggcgcccgcgctgtcctgcaccctctgttccatggaaggggacagcgtgagctccgagtcctcctccccggacgtgcacctc<br>accattcaggaggagggggcagacgaggagctggaggagacctcggagacgcccctcaacgagagcagcgaagggtcctcggagaacatccatca<br>gaattcctagcacccccgggacccctgcgggtggctccatcagccagcaaccttagagagaggaaagacagttttcaagtgtctggtttcactttcacagt<br>gcggctgccactttgaagagacccttggtaaacccctgattcggggtggggtgggggactaggctcagccggaaccagcacctccaaggagtccggga<br>ggtgcctgtggtttgcacccaccactgaaaaagccgcggagatgcgcagcgcgtacactgactttggggcctgggtgttggggttctgatcagaatttgg<br>cgggatgatatgcttgccattttctcactggatgccctgggtagctcctgcagggtctgcctgttcccagggctgccgaatgcttaggacacgctgagagac<br>tagttgtgatttgctatttgcctagagctttgtccttctagatctgattggctgtaagtatctctactgtgtacctgtggcattccttcacagtgggttac<br>aagcttcttttggattagaggggatttttgatgggagaaagctggagatctgaacccagcccatttgcacactaaaaaaaaaaaaaaaaaaaaaaaaaa<br>aaaaaaa |
| 21 | ttcagcccctctcccgggctgcgcctccgcactccgggcccgggcagaagggggtgcgcctcggccccaccacccagggagcagccgagctgaaag<br>gccgggaaccgcggcttgcggggaccacagctcccgaaagcgacgttcggccaccggaggagcgggagccaagcaggcggagctcggcgggaga<br>ggtgcgggccgaatccgagccgagcggagaggaatccggcagtagagacggactccagccggcggaccctgcagccctcgcctgggacagcggc<br>gcgctgggcaggcgcccaagagagcatcgagcagcggaacccgcgaagccggcccgcagccgcgacccgcgcagcctgccgctctcccgccgccg<br>gtccgggcagcatgaggcgcgcggcgctctggctctggctgtgcgcgctggcgctgagcctgcagccggccctgccgcaaattgtggctactaatttgc<br>cccctgaagatcaagatggctctggggatgactctgacaacttctccggctcaggtgcaggtgctttgcaagatatcaccttgtcacagcagacccccctcca<br>cttggaaggacacgcagctcctgacggctattcccacgtctccagaacccaccggcctggaggctacagctgcctccacctccaccctgccggctggag<br>aggggcccaaggagggagaggctgtagtcctgccagaagtggagcctggcctcaccgcccgggagcaggaggccaccccccgacccagggagac |

TABLE 1-continued

Embodiments of TVM sequences

| SEQ ID NO | Sequence |
|---|---|
| | cacacagctcccgaccactcatcaggcctcaacgaccacagccaccacggcccaggagcccgccacctcccacccccacagggacatgcagcctggc caccatgagacctcaacccctgcaggacccagccaagctgaccttcacactccccacacagaggatggaggtccttctgccaccgagagggctgctgag gatggagcctccagtcagctcccagcagcagagggctctggggagcaggacttcacctttgaaacctcgggggagaatacggctgtagtggccgtgga gcctgaccgccggaaccagtccccagtggatcaggggccacgggggcctcacagggcctcctggacaggaaagaggtgctgggaggggtcattgc cggaggcctcgtggggctcatctttgctgtgtgcctggtgggtttcatgctgtaccgcatgaagaagaaggacgaaggcagctactccttggaggagccg aaacaagccaacggcggggcctaccagaagcccaccaaacaggaggaattctatgcctgacgcgggagccatgcgcccctccgccctgccactcact aggcccccacttgcctcttccttgaagaactgcaggccctggcctcccctgccaccaggccacctccccagcattccagcccctctggtcgctcctgcccac ggagtcgtggggtgtgctgggagctccactctgcttctctgacttctgcctggagacttagggcaccaggggtttctcgcataggacctttccaccacagcc agcacctggcatcgcaccattctgactcggtttctccaaactgaagcagcctctccccaggtccagctctggaggggagggggatccgactgctttggacc taaatggcctcatgtggctggaagatcctgcgggtggggcttggggctcacacacctgtagcacttactggtaggaccaagcatcttgggggggtggcc gctgagtggcaggggacaggagtccactttgtttcgtggggaggtctaatctagatatcgacttgtttttgcacatgtttcctctagttctttgttcatagc ccagtagaccttgttacttctgaggtaagttaagtaagttgattcggtatcccccatcttgcttccctaatctatggtcgggagacagcatcagggttaag aagactttttttttttttttaaactaggagaaccaaatctggaagccaaaatgtaggcttagtttgtgtgttgtctcttgagtttgtcgctcatgtgtgc aacagggtatggactatctgtctggtggccccgtttctggtggtctgttggcaggctggccagtccaggctgccgtggggccgccgcctctttcaagcagtc gtgcctgtgtccatgcgctcagggccatgctgaggcctgggccgctgccacgttggagaagcccgtgtgagaagtgaatgctgggactcagccttcagacag agaggactgtgggtgtcttgggcagagctggctctgagcgcctccatccaaggccaggttctccgttagctcctgtggccccaccctgggccctgggctgga atcaggaatattttccaaagagtgatagtcttttgcttttggcaaaactctacttaatccaatgggtttttccctgtacagtagattttccaaatgtaataa actttaatataaagtcctgtgaatgccactgccttcgcttcttgcctctgtgctgtgtgtgacgtgaccggacttttctgcaaacaccaacatgttgggaaa cttggctcgaatctctgtgccttcgtctttcccatggggagggattctggttccagggtccctctgtgtatttgctttttttgttttggctgaaattctcctg gaggtcggtaggttcagccaaggttttataaggctgatgtcaatttctgtgttgccaagctccaagccccatcttctaaatggcaaaggaaggtggatggcc ccagcacagcttgacctgaggctgtggtcacagcggaggtgtggagccgaggcctaccccgcagacaccttggacatcctcctcccacccggctgcagaggc cagaggcccccagcccagggctcctgcacttacttgcttatttgacaacgtttcagcgactccgttggccactccgagaggtgggccagtctgtggatcaga gatgcaccaccaagccaagggaacctgtgtccggtattcgatactgcgactttctgcctggagtgtatgactgcacatgactcggggggtggggaaaggggtc ggctgaccatgctcatctgctggtccgtgggacggtgcccaagccagaggctgggttcatttgtgtaacgacaataaacggtacttgtcatttcggcaaaa aaaaaaaaaaaaaa |
| 22 | cgctgggcctgcccggaatcccgccgcctgcgccccgcgccccgcgccctgcgggccatgggagccggccgccggcagggacgacgcctgtgaga cccgcgagcggcctcggggaccatggggagcgatcgggcccgcaagggcggagggggcccgaaggacttcggcgcgggactcaagtacaactcc cggcacgagaaagtgaatggcttggaggaaggcgtggagttcctgccagtcaacaacgtcaagaaggtggaaaagcatggcccggggcgctgggtg gtgctggcagccgtgctgatcggcctcctcttggtcttgctggggatcggcttcctggtgtggcatttgcagtaccgggacgtgcgtgtccagaaggtc aatggctacatgaggatcacaaatgagaattttgtggatgcctacgagaactccaactccactgagtttgtaagcctggccagcaaggtgaaggacgcgc tgaagctgctgtacagcggagtcccattcctgggcccctaccacaaggagtcggctgtgacggccttcagcgagggcagcgtcatcgcctactactggtc tgagttcagcatcccgcagcacctggtggaggaggccgagcgcgtcatggccgaggagcgcgtagtcatgctgcccccgcgggcgcgctccctgaag tcctttgtggtcacctcagtggtggctttccccacggactccaaaacagtacagaggacccaggacaacagctgcagctttggcctgcacgcccgcggtgt ggagctgatgcgcttcaccacgcccggcttccctgacagcccctaccccgctcatgcccgctgccagtgggccctgcgggggacgccgactcagtgct gagcctcaccttccgcagctttgaccttgcgtcctgcgacgagcgcggcagcgacctggtgacggtgtacaacaccctgagccccatggagccccacgc cctggtgcagttgtgtggcacctaccctccctcctacaacctgaccttccactcctcccagaacgtcctgctcatcacactgataaccaacactgagcggcg gcatcccggctttgaggccaccttcttccagctgcctaggatgagcagctgtggaggccgcttacgtaaagcccaggggacattcaacagcccctactac ccaggccactacccacccaacattgactgcacatggaacattgaggtgcccaacaaccagcatgtgaaggtgcgcttcaaattcttctacctgctggagcc cggcgtgcctgcgggcacctgccccaaggactacgtggagatcaatggggagaaatactgcggagagaggtcccagttcgtcgtcaccagcaacagc aacaagatcacagttcgcttccactcagatcagtcctacaccgacaccggcttcttagctgaatacctctcctacgactccagtgacccatgcccggggcag ttcacgtgccgcacggggcggtgtatccggaaggagctgcgctgtgatggctgggccgactgcaccgaccacagcgatgagctcaactgcagttgcga cgccggccaccagttcacgtgcaagaacaagttctgcaagcccctcttctgggtctgcgacagtgtgaacgactgcggagacaacagcgacgagcagg ggtgcagttgtccggcccagaccttcaggtgttccaatgggaagtgcctctcgaaaagccagcagtgcaatgggaaggacgactgtggggacggctcc gacgaggcctcctgccccaaggtgaacgtcgtcacttgtaccaaacacacctaccgctgcctcaatgggctctgcttgagcaagggcaaccctgagtgtg acgggaaggaggactgtagcgacggctcagatgagaaggactgcgactgtgggctgcggtcattcacgagacaggctcgtgttgttgggggcacgga tgcggatgagggcgagtggccctggcaggtaagcctgcatgctctgggccagggccacatctgcggtgcttccctcatctctcccaactggctggtctctg |

TABLE 1-continued

Embodiments of TVM sequences

| SEQ ID NO | Sequence |
|---|---|
| | ccgcacactgctacatcgatgacagaggattcaggtactcagaccccacgcagtggacggccttcctgggcttgcacgaccagagccagcgcagcgcc<br>cctggggtgcaggagcgcaggctcaagcgcatcatctcccaccccttcttcaatgacttcaccttcgactatgacatcgcgctgctggagctggagaaacc<br>ggcagagtacagctccatggtgcggcccatctgcctgccggacgcctcccatgtcttccctgccggcaaggccatctgggtcacgggctggggacacac<br>ccagtatggaggcactggcgcgctgatcctgcaaaagggtgagatccgcgtcatcaaccagaccacctgcgagaacctcctgccgcagcagatcacgc<br>cgcgcatgatgtgcgtgggcttcctcagcggcggcgtggactcctgccagggtgattccggggggacccctgtccagcgtggaggcggatgggcggatc<br>ttccaggccggtgtggtgagctggggagacggctgcgctcagaggaacaagccaggcgtgtacacaaggctccctctgtttcgggactggatcaaaga<br>gaacactggggtataggggccggggccacccaaatgtgtacacctgcggggccacccatcgtccaccccagtgtgcacgcctgcaggctggagactg<br>gaccgctgactgcaccagcgcccccagaacatacactgtgaactcaatctccagggctccaaatctgcctagaaaacctctcgcttcctcagcctccaaag<br>tggagctgggaggtagaaggggaggacactggtggttctactgacccaactgggggcaaaggtttgaagacacagcctcccccgccagccccaagct<br>gggccgaggcgcgtttgtgcatatctgcctcccctgtctctaaggagcagcgggaacggagcttcggggcctcctcagtgaaggtggtggggctgccgg<br>atctgggctgtggggcccttgggccacgctcttgaggaagcccaggctcggaggaccctggaaaacagacgggtctgagactgaaattgttttaccagct<br>cccagggtggacttcagtgtgtgtatttgtgtaaatgagtaaaacattttatttctttttaaaaaaaaaaaaaaaaaaaaaaaaaaaaaaaaaaaaaaa<br>aaaaaaaa |
| 23 | gggcggggctcgggccggtccgcccgcgcgcaggtgagtgagccagggcggagcgcagctgcgccgggcttgggcgcctggggccgccgctccc<br>caccgtcgttttccccaccgaggccgaggcgtcccggagtcatggccggcctgaactgcggggtctctatcgcactgctaggggttctgctgctgggtgc<br>ggcgcgcctgccgcgcggggcagaagcttttgagattgctctgccacgagaaagcaacattacagttctcataaagctggggaccccgactctgctggc<br>aaaaccctgttacatcgtcatttctaaaagacatataaccatgttgtcaggcccatgtccttttggggaggttcagcttcagccctcgacatcgttgttgcc<br>taccctcaacaactttgtcatagagatccagaaaaatattgactgtatgtcaggcccatgtccttttggggaggttcagcttcagccctcgacatcgttgtt<br>gcctaccctcaacagaactttcatctgggatgtcaaagctcataagagcatcggtttagagctgcagttttccatccctcgcctgaggcagatcggtccggg<br>tgagagctgcccagacggagtcactcactccatcagcggccgaatcgatgccaccgtggtcaggatcggaaccttctgcagcaatggcactgtgtcccggat<br>caagatgcaagaaggagtgaaaatggccttacacctcccatggttccaccccagaaatgtctccggcttcagcattgcaaaccgctcatctataaaacgtct<br>gtgcatcatcgagtctgtgtttgagggtgaaggctcagcaaccctgatgtctgccaactacccagaaggcttccctgaggatgagctcatgacgtggcagtt<br>tgtcgttcctgcacacctgcgggccagcgtctccttcctcaacttcaacctctccaactgtgagaggaaggaggagcgggttgaatactacatcccgggctc<br>caccaccaaccccgaggtgttcaagctggaggacaagcagcctgggaacatggcggggaacttcaacctctctctgcaaggctgtgaccaagatgcccaaag<br>tccagggatcctccggctgcagttccaagttttggtccaacatccacaaaatgaaagcagtgagtgagccccactttcctttttcttcctcctccagcacct<br>tcgttgtttcctgggtagtctgcctgggtgaggctcccttcctgtttctcatctgtggcttctgaaacacttagactctggacccagcaagagtttcaggaa<br>gtgggttgctaggcagttagacaggcttgttggtgaacacccggtatgtagttccatttcagcacaataaaaagaaatcttgcattcaaaaaaaaaaaaaa<br>aaaa |
| 24 | caccatgcctgcttgtcgcctaggcccgctagccgccgccctcctcctcagcctgctgctgttcggcttcaccctagtctcaggcacaggagcagagaaga<br>ctggcgtgtgccccgagctccaggctgaccagaactgcacgcaagagtgcgtctcggacagcgaatgcgccgacaacctcaagtgctgcagcgcggg<br>ctgtgccaccttctgctctctgcccaatgataaggagggttcctgcccccaggtgaacattaactttccccagctcggcctctgtcgggaccagtgccaggt<br>ggacagccagtgtcctggccagatgaaatgctgccgcaatggctgtgggaaggtgtcctgtgtcactcccaatttctgagctccagccaccaccaggctg<br>agcagtgaggagagaaagtttctgcctggccctgcatctggttccagcccacctgccctccccttttttcgggactctgtattccctcttgggctgaccacag<br>cttctccctttcccaaccaataaagtaaccactttcagcaaaaaaaaaaaaaaaaaaaaaaaaa |
| 25 | agcagcaggaggaggcagagcacagcatcgtcgggaccagactcgtctcaggccagttgcagccttctcagccaaacgccgaccaaggaaaactcac<br>taccatgagaattgcagtgatttgcttttgcctcctaggcatcacctgtgccataccagttaaacaggctgattctggaagttctgaggaaaagcagcttta<br>caacaaatacccagatgctgtggccacatggctaaaccctgacccatctcagaagcagaatctcctagccccacagacccttccaagtaagtccaacgaaag<br>ccatgaccacatggatgatatggatgatgaagatgatgatgaccatgtggacagccaggactccattgactcgaacgactctgatgatgtagatgacactg<br>atgattctcaccagtctgatgagtctcaccattctgatgaatctgatgaactggtcactgattttcccacggacctgccagcaaccgaagttttcactccag<br>ttgtccccacagtagacacatatgatggccgaggtgatagtgtggtttatggactgaggtcaaaatctaagaagtttcgcagacctgacatccagtaccctg<br>atgctacagacgaggacatcacctcacacatggaaagcgaggagttgaatggtgcatacaaggccatccccgttgcccaggacctgaacgcgccttctgatt<br>gggacagccgtgggaaggacagttatgaaacgagtcagctggatgaccagagtgctgaaacccacagccacaagcagtccagattatataagcggaa<br>agccaatgatgagagcaatgagcattccgatgtgattgatagtcaggaactttccaaagtcagccgtgaattccacagccatgaatttcacagccatgaag<br>atatgctggttgtagaccccaaaagtaaggaagaagataaacacctgaaatttcgtatttctcatgaattagatagtgcatcttctgaggtcaattaaaagg |

TABLE 1-continued

Embodiments of TVM sequences

| SEQ ID NO | Sequence |
|---|---|
| | agaaaaaatacaatttctcactttgcatttagtcaaaagaaaaaatgctttatagcaaaatgaaagagaacatgaaatgcttctttctcagtttattggttg aatgtgtatctatttgagtctggaaataactaatgtgtttgataattagtttagtttgtggcttcatggaaactccctgtaaactaaaagcttcagggttat gtctatgttcattctatagaagaaatgcaaactatcactgtattttaatatttgttattctctcatgaatagaaatttatgtagaagcaaacaaaatacttt tacccacttaaaaagagaatataacattttatgtcactataatcttttgtttttaagttagtgtatattttgttgtgattatctttttgtggtgtgaataa atcttttatcttgaatgtaataagaaaaaaaaaaaaaaaataaaaaaaaaaaaaaaaaaaaaaaaaaaa |
| 26 | gtggcccggatgttcggtgcagctgccagatccgctgatctagtgcttctcgaaaaaaaccttcaggcggcccatggcatgccttggactttattgtgggaa gaccctattatttaaaaatggctcaactgaaatatatggagaatgtggggtatgcccaagaggacagagaacgaatgcacagaaatattgtcagccttgca cagaatctcctgaactttatgattggctctatcttggatttatggcaatgcttcctctggttttacattggttcttcattgaatggtactcggggaaaaaga gttccagcgcacttttccaacacatcactgcattatttgaatgcagcatggcagctattatcaccttacttgtgagtgatccagttggtgttctttatattc gttcatgtcgagtattgatgctttctgactggtacacgatgctttacaacccaagtccagattacgttaccacagtacactgtactcatgaagccgtctacc cactatataccattgtatttatctattacgcattctgcttggtattaatgatgctgctccgacctcttctggtgaagaagattgcatgtgggttagggaaat ctgatcgatttaaaagtatttatgctgcactttacttcttcccaattttaaccgtgcttcaggcagttggtggaggccttttatattacgccttcccataca ttatattagtgttatctttggttactctggctgtgtacatgtctgcttctgaaatagagaactgctatgatcttctggtcagaaagaaaagacttattgttc tcttcagccactggttacttcatgcctatggaataatctccatttccagagtggataaacttgagcaagatttgccccttttggctttggtacctacaccag cccttttttacttgttcactgcaaaatttaccgaaccttcaaggatactctcagaaggagccaatggacactgagtgtagacatgtgaaatgccaaaaacct gagaagtgctcctaataaaaaagtaaatcaatcttaacagtgtatgagaactattctatcatatatgggaacaagattgtcagtatatcttaatgtttgggt ttgtctttgttttgtttatggttagacttacagacttggaaaatgcaaaactctgtaatactctgttacacagggtaatattatctgctacactggaaggcc gctaggaagcccttgcttctctcaacagttcagctgttctttagggcaaaatcatgtttctgtgtacctagcaatgtgttcccattttattaagaaaagctt taacacgtgtaatctgcagtccttaacagtggcgtaattgtacgtacctgttgtgtttcagtttgtttttcacctataatgaattgtaaaaacaaacatact tgtggggtctgatagcaaacatagaaatgatgtatattgtttttttgttatctatttattttcatcaatacagtattttgatgtattgcaaaaatagataata atttatataacaggttttctgtttatagattggttcaagatttgtttggattattgttcctgtaaagaaaacaataataaaaagcttacctacaaaaaaaaa aaaaaaaaaaaaaaaaaaaa |
| 27 | ggggacagcaacttccttgatccctgccacgcacgactgaacacagacagcagccgcctcgccatgaagctgctgatggtcctcatgctggcggccctc ctcctgcactgctatgcagattctggctgcaaactcctggaggacatggttgaaaagaccatcaattccgacatatctatacctgaatacaaagagcttctt caagagttcatagacagtgatgccgctgcagaggctatggggaaattcaagcagtgtttcctcaaccagtcacatagaactctgaaaaactttggactgatg atgcatacagtgtacgacagcatttggtgtaatatgaagagtaattaactttacccaaggcgtttggctcagagggctacagactatggccagaactcatct gttgattgctagaaaccacttttctttcttgtgttgtctttttatgtggaaactgctagacaactgttgaaacctcaaattcatttccatttcaataaacta actgcaaatctaaaaaaaaaaaaaaaaaaaaaaaaaaa |
| 28 | gaggcgggcaaggcgggcgccgaggtttgcaaaggctcgcagcggccagaaacccggctccgagcggcggcggcccggcttccgctgcccgtgag ctaaggacggtccgctccctctagccagctccgaatcctgatccaggcgggggccaggggcccctcgcctcccctctgaggaccgaagatgagcttcct cttcagcagccgctcttctaaaacattcaaaccaaagaagaatatccctgaaggatctcatcagtatgaactcttaaaacatgcagaagcaactctaggaag tgggaatctgagacaagctgttatgttgcctgagggagaggatctcaatgaatggattgctgtgaacactgtggatttctttaaccagatcaacatgttata tggaactattacagaattctgcactgaagcaagctgtccagtcatgtctgcaggtccgagatatgaatatcactgggcagatggtactaatattaaaaagcc aatcaaatgttctgcaccaaaatacattgactatttgatgacttgggttcaagatcagcttgatgatgaaactctttttccttctaagattggtgtcccatt tcccaaaaactttatgtctgtggcaaagactattctaaagcgtctgttcagggtttatgcccatatttatcaccagcactttgattctgtgatgcagctgca agaggggggcccacctcaacacctcctttaagcactttattttctttgttcaggagtttaatctgattgataggcgtgagctggcacctcttcaagaattaat agagaaacttggatcaaaagacagataaatgtttcttctagaacacagttaccccttgcttcatctattgctagaactatctcattgctatctgttataga gctagtgatacaaactttaaaaaacaggataaaaagatacccattgcctgtgtctactgataaaattatcccaaaggtaggttggtgtgatagtttccgagt aagaccttaaggacacagccaaatcttaagtactgtgtgaccactcttgttgttatcacatagtcatacttggttgtaatatgtgatggttaacctgtagct tataaatttacttattattcttttactcatttactcagtcatttctttacaagaaaatgattgaatctgttttaggtgacagcacaatggacattaagaatt tccatcaataatttatgaataagtttccagaacaaatttcctaataacacaatcagattggttttattcttttattttacgaataaaaaatgtatttttcag tatccttgagatttagaacatctgtgtcacttcagataacattttagtttcaagtttgtatggtagtgtttttatagataagatacgtctatttttcaaaa ttcatgattgcagtttaaatcatcatatgacgtgtgggtgggagcaaccaaagttatttttacagggactttatttttgatctttatttgagattgttttc atatctatctaaattattaggagtgtgtgtatcagaagtaatttttaatgtcttctaaggatggtcttccaggcttttaaactgaaaagcttaattcagat |

TABLE 1-continued

Embodiments of TVM sequences

| SEQ ID NO | Sequence |
|---|---|
| | agtagcttttggctgagaaaaggaatccaaaatattaataaatttagatctcaaaaccactatttttattatttcattatttttcagaggccttaaaattct<br>ggataagagaatggaggaaaatactcagagtacttgattattttatttccttttattaaaaaattacttctatgtttttattgtctcttgagccttagttaa<br>gagtagtgtagaaatgcatgaacttcatcctaataaggataaaacttaaggaaaaccacaataaaccatgaaggtgtacacatcctataacacagataaagt<br>tttggtgtgctacctattcttgagagagtgagtgagtgtatgtgtttaaaggaaacaaaatgggagaaataagttttaaaaaaatcctcattttgttaatat<br>tcaaaagatggactgagcttccacttgggttttatcttgttttaattgtttttgtatcaaaacttgaaattcctctatttctattgggatataaaagccttc<br>cccttcagtgaagaaaacatttatttttatttgattcctaggatttagtaaactctagctgtctatttaaaatgtactgaggcacaacaagtattatactg<br>gaagacttgccaaactggcaaagctttaagttcatcagcattctatgtggttcagagctgtgattttttgcaaagtattttaccaacctcctcgatggctttg<br>ataaaggttagatttgatgtttttttttagatttatttttcttactccactaaactataaagaaaataattacttagaaactccattttaaataatcattt<br>cctagaaattcttaaatatatacagaattttaaagaaaacatttcatctgatttagttagcatccacatatcattgaggaattaaagtgtgggacagtcatt<br>att |
| 29 | aagaagcgacgtgtcccactgtcctggctccgtgggtccagtgagattgggcctgggcgctggagctgctgtggctcccgccgcggcggctgccatgga<br>ggccatgccagagcccagaactcacgccgggggaggccgagacagccggcggtactcatagatgaggcagcggcggcggcggcggcggca<br>gcccgggctctccatgagcaggcggcggcggcgacgggtgcggcggcaccggcagttttcggtccccagggaggatgaagacactgtttgaagagat<br>caaagcatcaattaaaaataactataaccaagatcgatcattttgtaggcctgttcttccttgggggggtgtttttactatcaaagctggccgcaaagcagt<br>atcctgtacaccactctatgttgaaataagactgaaaaatacctgcaccatagatggattcttgatgttattatatgtcattcttaatgaaaatgaaaactt<br>ccctagggaactctctcttcattttggtagagagtttgtagactgttttctttacttaatggacacctacagttttacaactgtgaagctactttggatttg<br>aggacaagatggaaaacagcaatacaaatctgaagtccataaagcttcattaataattgatttgtttgggaatgagcatgataattttacaaaaaatcttga<br>aaatctcatgtctaccattcaagagagttactgttccaactggcgatgcccaactcgagtgcaggaggatcagcagcgcacaattaatataaatcctcccca<br>agaaattccacatggaaacttgataagactggctgtgaatgagttattctgttccaagattgaactgtgtgaagagcatgggtgtggtggcttaagagaatt<br>ttcccaacgaattttctgccatggggcacccccttttgttgtcttaaatatgcaacattggaaatctgaagatctggcgtatgtaccctattacttggattt<br>tggaaggtgccacattatttaacaaagaggaacatcattattctgcagctttccagattggtggacattggatgcactatgatgggctcagaaatgtgaatt<br>gtctgatcacaagtatttgttaattttgttaaataaaccccccagagtttctcctcttgtcatcattggtttatattcgagcaacagagaaataaatatagat<br>tgatgctaaaagttgttttccctcctgcccatgctctcccagatgaagggctttttatttgtgtatacttggtatccaagaaaatagttcaactatactagt<br>ttcagaagtgtattttcagtgtttaaccccaggtaaatgttttatatagaggatctgtgcaaaaatgtttgtaattttttttatatttcctgagttattttta<br>tatgagcatattttatgttggaataaaatatatcttgtggcctttgtattttttatttatatgtacctcaaagatttttacaattctgtctttgaattcaag<br>aaatactttgtcatctgaattctaaatttttctttttggatattcgagtaaaacctaggtaaaagtattttaagtttatataatttaacagttcaaaatata<br>tctgactgtatttctttgccctacctcactataatccaaagtgcactatttgatctagtatggatttgaatgtacaatttatcgatggcttagtttattagt<br>tcgatttgcctagtatccctgcagcaatttttttaaaatgtctgagaaatttttcagagcttaaactatttctttataatggcaaattacttttaactacttc<br>ctaaagtattataaacctgccagtggatttaagtgatagctaagcttccaagcttaattcacgttattacaaataaattatataactatcttaaatgttta<br>tcttataattaaatgtaatttgaaatgctctaatgtattttgcagataaaacaactataaacaatattaggcaactggatgtttactagtgtcggactagca<br>atagaaatgcactttaaatatatatttaaggggaaatgcgtgcctggaaatacttcttttcctagtgaagttttatattgacacagagaaaagaatacttaa<br>aattttgagtgatgtctactggcttccttgtaagtagtgattgatagcatgcggctttgacttgcaatacaaatcattacgattttatagttatcagaacat<br>tacgtttctttataaagaccctaaggtcactcttctttttgcaacttaagggaaaaaatattctcaagggaaaatacttttttgaaatttatcacc<br>atttagtgtttacatttcaataaatagttcacttcaggtttgggattgagattagttgcaatatatttagaagctcctacatgacagcacagatcactgcc<br>atctgctgaactgctaaagtgcttggtgccatgttgagaaaacttacccaagaatggataaatatgggtgaaacattactgagaatgcctcacgttagcaaa<br>tactatgaaaattcttgtttatatatcaaactgatttattttacaaaaaaaaaaaaattcaccccaagatttatttagtttcccaagtgtatctgattaggat<br>ttaatttagagtaaacttttctggggacacctgattgcatgaactgaagtatacaataacacaaatattacagtaaacataaatggtgtcattaacaaaatt<br>attcctaatgcagatttattctttcaggaaatgcactttatttggaatactagtttatcatgaaacaatgacttacctacctcacagggttgttgtgaggat<br>taagatgtttgttaaaatcttgactaccttgaacatgctaataaaaaaacatttttctacctcttttatttgca |
| 30 | ggaagaggaggctttctaaggcggtcgctccgggaaatccgggccctaggattgtccactcatcccagtatcagcgagatacggggagatagagttagc<br>gacaacgtgagccagagctggagcacgtttggtgagagaccagaaagcaatggaggccggagaggggaaggagcgcgttccgaaacaaaggcaa<br>gtcctgatattctttgttttgctgggcatagctcaggctagttgccagcctaggcactattcagtggccgaggaaacggagagtggctcctttgtggccaat<br>ttgttaaaagacctggggctggagataggagaacttgctgtgagggggggccagggtcgtttccaaaggaaaaaaaatgcatttgcagttcgataggcagac<br>cggggatttgttgttaaatgagaaattggaccgggaggagctgtgcggccccacagagccctgtgtcctacctttccaggtgttactagaaaatcccttgca<br>gtttttttcaggcggagctacggattagggacgtaaatgatcattccccagttttcctagacaaagaaatacttttgaaaattccagaaagtatcactcctgg |

TABLE 1-continued

| SEQ ID NO | Embodiments of TVM sequences<br>Sequence |
|---|---|
| | aactactttcttaatagaacgtgcccaggacttggatgtaggaaccaacagtctccaaaattacacaatcagtcccaatttccactttcatcttaatttaca<br>agacagtctcgatggcataatattaccacagctggtgctgaacagagccctggatcgcgaggagcagcctgagatcaggttaaccctcacagcgctagatgg<br>cgggagtccacccaggtccggcacggccctggtacggattgaagttgtggacatcaatgacaacgtcccagagtttgcaaagctgctctatgaggtgcagat<br>cccggaggacagccccgttggatcccaggttgccatcgtctctgccagggatttagacattggaactaatggagaaatatcttatgcattttcccaagcatc<br>tgaagacattcgcaaaacgtttcgattaagtgcaaaatcgggagaactgcttttaagacagaaactggatttcgaatccatccagacatacacagtaaatat<br>tcccggaggacagccccgttggatcccaggttgccatcgtctctgccagggatttagacattggaactaatggagaaatatcttatgcattttcccaagcat<br>ctatcagatcccagaaaacttgcaggacaccctcattgctgtattcagcgtttcagatcctgactccggagacaacggaaggatggtgtgctccatccaaga<br>tgatcttcctttttttcttgaaaccttctgttgagaacttttacactctggtgataagcacggccctggaccgggagaccagatccgaatacaacatcaccat<br>caccgtcaccgacttcgggacacccaggctgaaaaccgagcacaacataaccgtgctggtctccgacgtcaatgacaacgcccccgccttcacccaaacctc<br>ctacaccctgttcgtccgcgagaacaacagccccgccctgcacatcggcagcgtcagcgccacagacagagactcgggcaccaacgcccaggtcacct<br>actcgctgctgccgccccaggacccgcacctgcccctcgcctccctggtctccatcaacgcggacaacggccacctgttcgctctccagtcgctggactac<br>gaggccctgcaggcgttcgagttccgcgtgggcgccgcagaccgcggctccccggcgttgagcagcgaggcgctggtgcgcgtgctggtgctggacg<br>ccaacgacaactcgcccttcgtgctgtacccgctgcagaacggctccgcgccctgcaccgagctggtgccccgggcggccgagccgggctacctggtg<br>accaaggtggtggcggtggacggcgactcgggccagaacgcctggctgtcgtaccagctgctcaaggccacggagcccgggctgttcggcgtgtggg<br>cgcacaatggcgaggtgcgcaccgccaggctgctgagggagcgcgacgctgccaagcagaggctggtggtgctggtcaaggacaatggcgagcctc<br>cgcgctcggccaccgccacgctgcacgtgctcctggtggacggcttctcccagccctacctgctgctcccggaggcggcaccggcccaggcccaggcc<br>gacttgctcaccgtctacctggtggtggcattggcctcggtgtcttcgctcttcctcttctcggtgctcctgttcgtggcggtgcggctgtgcaggaggagc<br>agggcggcctcggtgggtcgctgctcggtgcccgagggcccctttccagggcagatggtggacgtgagcggcaccgggaccctgtcccagagctacca<br>gtacgaggtgtgtctgactggagaatccgggacaaatgagttcaagttcctgaagccaattatccccaacttcgttgctcagggtgcagagagggttagcg<br>aggcaaatcccagtttcaggaagagctttgaattcacttaagtgttaataaggatctactgaggctagtctcgtttaatttgtggaaagtcctttttactg<br>ctttgcccattggaggtgtctccttttattagaaagtaaccatcttattccaattctatgcatgttactggtatttataaatgtatgagtttttttgcggta<br>taataaatgtaaattttctttgtattctaaaaaaaaaaaaaaaaaaaaaa |
| 31 | cgctaagcgtcccagccgcatccctcccgcagcgacggcggcccgggacccgcgggctgtgaaccatgaacacccgcaatagagtggtgaactccgg<br>gctcggcgcctcccctgcctcccgcccgacccgggatccccaggacccttctgggcggcaaggggagctgagccccgtggaagaccagagagaggg<br>tttggaggcagcccctaagggcccttcgcgggagagcgtcgtgcacgcgggccagaggcgcacaagtgcatacaccttgatagcaccaaatataaacc<br>ggagaaatgagatacaaagaattgcggagcaggagctggccaacctggagaagtggaaggagcagaacagagctaaaccggttcacctggtgccca<br>gacggctaggtggaagccagtcagaaactgaagtcagacagaaacaacaactccagctgatgcaatctaaatacaagcaaaagctaaaaagagaaga<br>atctgtaagaatcaagaaggaagctgaagaagctgaactccaaaaaatgaaggcaattcagagagagaagagcaataaactggaggagaaaaaaag<br>acttcaagaaaaccttagaagagaagcatttagagagcatcagcaatacaaaaccgctgagttcttgagcaaactgaacacagaatcgccagacagaag<br>tgcctgtcaaagtgctgtttgtggcccacaatcctcaacatggaaacttcctatcctgcctagggatcacagctgggccagaagctgggcttacagagattc<br>tctaaaggcagaagaaaacagaaaattgcaaaagatgaaggatgaacaacatcaaaagagtgaattactggaactgaaacggcagcagcaagagcaa<br>gaaagagccaaaatccaccagactgaacacaggagggtaaataatgcttttctggaccgactccaaggcaaaagtcaaccaggtggcctcgagcaatct<br>ggaggctgttggaatatgaatagcggtaacagctggggttctctattagtttttttcgaggcacctaagggtatatgagaaaatattgactcctatctggcct<br>tcatcaactgacctcgaaaagcctcatgagatgctttttcttaatgtgattttgttcagcctcactgtttttaccttaatttcaactgcccacacacttgac<br>cgtgcagtcaggagtgactggcttctccttgtcctcatttatgcatgtttggaggagctgattcctgaactcatatttaatctctactgccagggaaatgct<br>acattatttttctaattggaagtataattagagtgatgttggtagggtagaaaaagagggagtcacttgatgctttcaggttaatcagagctatgggtgcta<br>caggcttgtctttctaagtgacatattcttatctaattctcagatcaggttttgaaaagctttgggggtctttttagattttaatccctactttctttatgg<br>tacaaatatgtaataaagaaaaaggtcttatattcttttacacaaatttataaataaattttgaactccttctgtaaaaaaaaaaaaaaaaaaaaaa |
| 32 | ctggagccgctgagcccccgctgcggccgggagctgcatgggggagcgccggcagcgcttgggaagatgccccggccggagctgcccctgccgga<br>gggctgggaggaggcgcgcgacttcgacggcaaggtctactacatagaccacacgaaccgcaccaccagctggatcgacccgcgggacaggtacac<br>caaaccgctcacctttgctgactgcattagtgatgagttgccgctaggatgggaagaggcatatgacccacaggttggagattacttcatagaccacaaca<br>ccaaaaccactcagattgaggatcctcgagtacaatggcggcgggagcaggaacatatgctgaaggattacctggtggtggcccaggaggctctgagt<br>gcacaaaaggagatctaccaggtgaagcagcagcgcctggagcttgcacagcaggagtaccagcaactgcatgccgtctgggagcataagctgggct<br>cccaggtcagcttggtctctggttcatcatccagctccaagtatgaccctgagatcctgaaagctgaaattgccactgcaaaatcccgggtcaacaagctga<br>agagagagatggttcacctccagcacgagctgcagttcaaagagcgtggctttcagaccctgaagaaaatcgataagaaaatgtctgatgctcagggca |

TABLE 1-continued

| Embodiments of TVM sequences | |
|---|---|
| SEQ ID NO | Sequence |
| | gctacaaactggatgaagctcaggctgtcttgagagaaacaaaagccatcaaaaaggctattacctgtggggaaaaggaaaagcaagatctcattaaga |
| | gccttgccatgttgaaggacggcttccgcactgacagggggtctcactcagacctgtggtccagcagcagctctctggagagttcgagtttcccgctaccg |
| | aaacagtacctggatgtgagctcccagacagacatctcgggaagcttcggcatcaacagcaacaatcagttggcagagaaggtcagattgcgccttcgat |
| | atgaagaggctaagagaaggatcgccaacctgaagatccagctggccaagcttgacagtgaggcctggcctggggtgctggactcagagagggaccg |
| | gctgatccttatcaacgagaaggaggagctgctgaaggagatgcgcttcatcagcccccgcaagtggacccagggggaggtggagcagctggagatg |
| | gcccggaagcggctggaaaaggacctgcaggcagcccgggacacccagagcaaggcgctgacggagaggttaaagttaaacagtaagaggaacca |
| | gcttgtgagagaactggaggaagccacccggcaggtggcaactctgcactcccagctgaaaagtctctcaagcagcatgcagtccctgtcctcaggcag |
| | cagccccggatccctcacgtccagccggggctccctggttgcatccagcctggactcctccacttcagccagcttcactgacctctactatgacccctttga |
| | gcagctggactcagagctgcagagcaaggtggagttcctgctcctggagggggccaccggcttccggccctcaggctgcatcaccaccatccacgagga |
| | tgaggtggccaagacccagaaggcagagggaggtggccgcctgcaggctctgcgttccctgtctggcaccccaaagtccatgacctccctatccccacg |
| | ttcctctctctcctccccctccccaccctgttcccctctcatggctgacccccctcctggctggtgatgccttcctcaactccttggagtttgaagacccgga |
| | gctgagtgccactctttgtgaactgagccttggtaacagcgcccaggaaagataccggctggaggaaccaggaacggagggcaagcagctgggccaagct |
| | gtgaatacggcccaggggtgtggcctgaaagtggcctgtgtctcagccgccgtatcggacgagtcagtggctggagacagtggtgtgtacgaggcttcc |
| | gtgcagagactgggtgcttcagaagctgctgcatttgacagtgacgaatcggaagcagtgggtgcgacccgaattcagattgccctgaagtatgatgaga |
| | agaataagcaatttgcaatattaatcatccagctgagtaacctttctgctctgttgcagcaacaagaccagaaagtgaatatccgcgtggctgtccttcctt |
| | gctctgaaagcacaacctgcctgttccggacccggcctctggacgcctcagacactctagtgttcaatgaggtgttctgggtatccatgtcctatccagccc |
| | ttcaccagaagaccttaagagtcgatgtctgtaccaccgacaggagccatctggaagagtgcctgggaggcgcccagatcagcctggcggaggtctgccg |
| | gtctggggagaggtcgactcgctggtacaaccttctcagctacaaatacttgaagaagcagagcagggagctcaagccagtgggagttatggcccctgc |
| | ctcagggcctgccagcacggacgctgtgtctgctctgttggaacagacagcagtggagctggagaagaggcaggagggcaggagcagcacacagac |
| | actggaagacagctggaggtatgaggagaccagtgagaatgaggcagtagccgaggaagaggaggaggaggtggaggaggaggagggagaaga |
| | ggatgttttcaccgagaaagcctcacctgatatggatgggtacccagcattaaaggtggacaaagagaccaacacggagaccccggccccatcccccac |
| | agtggtgcgacctaaggaccggagagtgggcaccccgtcccaggggccatttcttcgagggagcaccatcatccgctctaagaccttctccccaggacc |
| | ccagagccagtacgtgtgccggctgaatcggagtgatagtgacagctccactctgtccaaaaagccaccttttgttcgaaactccctggagcgacgcagc |
| | gtccggatgaagcggccttcctcggtcaagtcgctgcgctccgagcgtctgatccgtacctcgctggacctggagttagacctgcaggcgacaagaacct |
| | ggcacagccaactgacccaggagatctcggtgctgaaggagctcaaggagcagctggaacaagccaagagccacggggagaaggagctgccacag |
| | tggttgcgtgaggacgagcgtttccgcctgctgctgaggatgctggagaagcggcagatggaccgagcggagcacaagggtgagcttcagacagaca |
| | agatgatgagggcagctgccaaggatgtgcacaggctccgaggccagagctgtaaggaaccccccagaagttcagtctttcagggagaagatggcatttt |
| | tcacccggcctcggatgaatatcccagctctctctgcagatgacgtctaatcgccagaaaagtatttcctttgttccactgaccaggctgtgaacattgact |
| | gtggctaaagttatttatgtggtgttatatgaaggtactgagtcacaagtcctctagtgctcttgttggtttgaagatgaaccgacttttttagtttggg |
| | gttattaaaaacagaacaaaaacaaaacacacacacacacaaaaacagaaacaaaaaaaaccagcattaaaataataagattgtatagtttgtatatttag |
| | gagtgtatttttgggaaagaaaatttaaatgaactaaagcagtattgagttgctgctcttcttaaaatcgtttagattttttttggtttgtacagctccacc |
| | ttttagaggtcttactgcaataagaagtaatgcctgggggacggtaatcctaataggacgtcccgcacttgtcacagtacagctaatttttcctagttaaca |
| | tattttgtacaatattaaaaaaatgcacagaaaccattgggggggattcagaggtgcatccacggatcttcttgagctgtgacgtgtttttatgtggctgcc |
| | caacgtggagcgggcagtgtgataggctgggtgggctaagcagcctagtctatgtgggtgacaggccacgctggtctcagatgcccagtgaagccactaaca |
| | gtgagtgagggagggctgtggggaactccattcagttttatctccatcaataaagtggcctttcaaaaagaaaaaaaaaaaaaaaaaaaaaaa |
| 33 | aatcggttgagagctgagctggacttggcggtgggagccggagcctgcttgttgcagctgtgggtgaggacggctctagctagttccctttttagactatgg |
| | cgacatacctggagttcatccagcagaatgaagaacgggatggtgtgcgttttagttggaacgtgtggccttccagccggctggaggctacaagaatggt |
| | tgtacccctggcttgtctccttactcctttgaaagaacgtccagacctacctcctgtacaatatgaacctgtgctttgcagcaggccaacttgtaaagctgt |
| | tctcaacccactttgtcaggttgattatcgagcaaaactttgggcctgtaatttctgttttcaaagaaatcagtttcctccagcttatggaggcatatctga |
| | ggtgaatcaacctgccgaattgatgccccagttttctacaattgagtacgtgatacagcgaggtgctcagtcccctctgatctttctctatgtggttgacac |
| | atgcctggaggaagatgaccttcaagcactcaaagagtccctgcagatgtccctgagtcttcttcctccagatgctctggtgggtctgatcacatttggaag |
| | gatggtgcaggttcatgagctaagctgtgaaggaatctccaaaagttatgtcttccgagggaccaaggatttaactgcaaagcaaatacaggatatgttggg |
| | cctgaccaagccagccatgcccatgcagcaagcacgacctgcacaaccacaggagcacccttttgcttcaagcagatttctgcagcctgttcacaagattga |
| | tatgaacctcactgatcttcttggggagctacagagggacccatggccagtaactcaggggaagagacctttgcgatccactggtgtggctttgtccattgc |
| | tgttggcttgctggagggcacttttccaaacacaggagccaggatcatgctgtttactggaggtcccccctacccaagggcctggcatggtggttggagatga |
| | attaaagattcctattcgttcttggcatgatattgagaaagataatgcacgattcatgaaaaaggcaaccaagcactatgagatgcttgctaatcgaacagc |

TABLE 1-continued

Embodiments of TVM sequences

| SEQ ID NO | Sequence |
| --- | --- |
| | tgcaaatggtcactgcattgatatttatgcttgtgcccttgatcaaactggacttttggagatgaagtgttgtgcaaatcttactggaggctacatggtaat gggagattctttcaacacttctctcttcaagcagacattccaaagaatctttactaaagattttaatggagatttccgaatggcatttggtgctactttgga cgtaaagacctctcgggaactgaagattgcaggagccattggtccatgcgtatctctgaatgtgaaaggactgtgtgtgtcagaaaatgagcttggtgttgg tggcacgagtcagtggaaaatctgtggcctagatcctacatctacacttggcatctattttgaagttgtcaatcagcacaacaccccgatcccccaaggagg cagaggagccatccagtttgtcacgcattatcagcactccagcacccagagacgcatccgcgtgaccaccatcgcccgaaattgggcagatgtacagagtca gctcaggcacatagaagcagcatttgaccaggaggctgcggcagtgttgatggcacggcttggggtgttccgagcggagtcagaggagggcccgatgtgct ccggtggctggaccgacaactcatccgactgtgtcaaaagtttggacagtataacaaagaagaccccacttcttttaggttatcagattccttttctctata tcctcagtttatgttccatctgagaagatctccatttcttcaagtgtttaacaacagtcctgatgagtcgtcatattacagacatcattttgcccggcagga cctgacccagtccctcatcatgatccagcccattctctactcttactcctttcatgggccaccagagccagtactcttggatagcagcagcattctagctga cagaattttgctgatggatactttctttcaaattgtcatttatcttggtgagaccatagcccagtggcgtaaagctggctaccaggacatgcccgagtatga aaacttcaagcaccttctgcaggcaccactggatgatgctcaagaaattctgcaagcacgcttcccgatgccacgttacatcaacacggagcatggaggcag tcaggctcgattccttttgtccaaagtgaacccatctcagacacacaataacctgtatgcttggggacaggaaactggagcacccatcctaactgatgatgt tagcctgcaggtgttcatggaccatttgaagaagctggctgtctccagtgcctgttaagctgaggatacaaccaggaaatgcaacggtgtcagattgtgttc aaaatgtctagaaaggcttgataacattcctgttacttttctagcagattttaacaaataatcaaggacattttatatgtaactctttagattataatttat ttgtattcctgtctttgtccttttttcttgcactataaaattataaggtcataaatgttttggtacttgtagatgtttatgtgcttttttgtatcctaactttt agaatctaaataaaatcagaggtaatgtattttggcagcttgtttaggtgagaatcttaatgatcataaaaggaaataaatctagatgcagaaagtactggc taaaatattgctaatacaaatgtgatttcctgaggtctctgtgtgagtgtgtatgtgttttaagtgacttccttaagaggtgtttcctgaacctaattctca taattaaagtaatgtatatgcaggatcaaaatgaaacaaatataccttatcctaaagagctcataacaaataagttacctccactctataaactcagaccta ctttttgaagataactgcttttaacctctccttacaagatgatgtatttaattttagcccatgtctcaattctcattttcaaagaatcaatatattaatata caaaaaaaaaaaaaaaa |
| 34 | atgctgggtacgctgcgcgccatggagggcgaggacgtggaagacgaccagctgctgcagaagctcagggccagtcgccgccgcttccagaggcgc atgcagcggctgatagagaagtacaaccagcccttcgaggacaccccggtggtgcaaatggccacgctgacctacgagacgccacagggattgagaat ttggggtggaagactaataaaggaaagaaacaaaggagagatccaggactcctccatgaagcccgcggacaggacagatggctccgtgcaagctgca gcctggggtcctgagcttccctcgcaccgcacagtcctgggagccgattcaaaaagcggtgaggtcgatgccacgtcagaccaggaagagtcagttgct tgggccttagcacctgcagtgcctcaaagccctttgaaaaatgaattaagaaggaaatacttgacccaagtggatatactgctacaaggtgatgagtatttt gagtgtgcaggtaacagagctggaagggatgtacgtgtgactccgctgccttcactggcctcacctgccgtgcctgcccccggatactgcagtcgtatctc cggaaagagtcctggtgacccagcgaaaccagcttcatctcccagagaatgggatcctttgcatccttcctccacagacatggccttagtacctagaaatg acagcctctccctacaagagaccagtagcagcagcttcttaagcagccagccctttgaagatgatgacatttgcaatgtgaccatcagtgacctgtacgca gggatgctgcactccatgagccggctgttgagcacaaagccatcaagcatcatctccaccaaaacgttcatcatgcaaaactggaactgcaggaggagg cacagatataagagcaggatgaacaaaacatattgcaaaggagccagacgttctcagaggagctccaaggagaacttcataccctgctctgagcctgtg aaagggacaggggcattaagagattgcaagaacgtattagatgtttcttgccgtaagacaggtttaaaattggaaaaagcttttcttgaagtcaacagaccc caaatccataagttagatccaagttggaaggagcgcaaagtgacaccctcgaagtattcttccttgatttacttcgactccagtgcaacatataatcttgat gaggaaaatagatttaggacattaaaatggttaatttctcctgtaaaaatagtttccagaccaacaatacgacagggccatggagagaaccgtcagagggag attgaaatccgatttgatcagcttcatcgggaatattgcctgagtcccaggaaccagcctcgccggatgtgcctcccggactcctgggccatgaacatgtac agagggggtcctgcgagtcctggtggccttcagggcttagaaacccgcaggctgagtttaccttccagcaaagcaaaagcaaaaagtttaagtgaggctt ttgaaaacctaggcaaaagatctctggaagcaggtaggtgcctgcccaagagcgattcatcttcatcacttccaaagaccaaccccacacacagcgcaac tcgcccgcagcagacatctgaccttcacgttcagggaaatagttctggaatatttagaaagtcagtgtcacccagcaaaactctttcagtcccagataaaga agtgccaggccacggaaggaatcgttacgatgaaattaaagaagaatttgacaagcttcatcaaaagtattgcctcaaatctcctgggcagatgacagtgc ctttatgtattggagtgtctacagataaagcaagtatggaagttcgatatcaaacagaaggcttcttaggaaaattaaatccagaccctcacttccagggtt tccagaagttgccatcatcacccctggggtgcagaaaaagtctactgggctcaactgcaattgaggctccttcatctacatgtgttgctcgtgccatcacga gggatggcacgagggaccatcagttccctgcaaaaagacccaggctatcagaaccccagggctccggacgccagggcaattccctgggtgcctcagatgg ggtggacaacaccgtcagaccgggagaccagggcagctcttcacagcccaactcagaagagagaggagagaacacgtcttacaggatggaagagaa aagtgatttcatgctagaaaaattggaaactaaaagtgtgtagctaggttatttcggagtgttatttatcttcccacttgctctctgtttgtatttttgttt tgtttttgattcttgagactgtgaggacttggttgacttctctgcccttaaagtaaatattagtgaaattggttccatcagagataacctcgagttcttggt gtagagaataaagttgctcaattagaaaaaaaaaaaaaaaaaaaaa |

TABLE 1-continued

Embodiments of TVM sequences

| SEQ ID NO | Sequence |
| --- | --- |
| 35 | ccgctcgccgtccttgcaggctctgccgtcggaaagccgctcattctcgcttccccttccctttcccggctcaagtccttcctctctctttcctttctttcc<br>gcctatctttttctgctgccgctccgggtccgggccattttccgggccgggcgcactaaggtgcgcggccccggggcccagtatatgacccgccgtcctgc<br>tatccttcgcttcccccgccccatgtggctgcggggccgcggcggcgctgcccactatggcccggaaagtagttagcaggaagcggaaagcgcccgcctcgc<br>cgggagctgggagcgacgctcagggcccgcagtttggctgggatcactcgcttcacaaaaggaaaagacttcctcctgtgaagagatccttagtatactac<br>ttgaagaaccgggaagtcaggctacagaatgaaaccagctactctcgagtgttgcatggttatgcagcacagcaacttcccagtctcctgaaggagagag<br>agtttcaccttgggacccttaataaagtgtttgcatctcagtggttgaatcataggcaagtggtgtgtggcacaaaatgcaacacgctatttgtcgtagatg<br>tccagacaagccagatcaccaagatccccattctgaaagaccaggagcctggaggtgtgacccagcagggctgtggtatccatgccatcgagctgaatcct<br>tctagaacactgctagccactggaggagacaaccccaacagtcttgccatctatcgactacctacgctggatcctgtgtgtgtaggagatgatggacacaa<br>ggactggatcttttccatcgcatggatcagcgacactatggcagtgtctggctcacgtgatggttctatgggactctgggaggtgacagatgatgttttgac<br>caaaagtgatgcgagacacaatgtgtcacgggtccctgtgtatgcacacatcactcacaaggccttaaaggacatccccaaagaagacacaaaccctgac<br>aactgcaaggttcgggctctggccttcaacaacaagaacaaggaactgggagcagtgtctctggatggctactttcatctctggaaggctgaaaatacact<br>atctaagctcctctccaccaaactgccatattgccgtgagaatgtgtgtctggcttatggtagtgaatggtcagtttatgcagtgggctcccaagctcatgt<br>ctccttcttggatccacggcagccatcatacaacgtcaagtctgtctgttccagggagcgaggcagtggaatccggtcagtgagtttctacgagcacatcat<br>cactgtgggaacagggcagggctccctgctgttctatgacatccgagctcagagatttctggaagagaggctctcagcttgttatgggtccaagcccagact<br>agcaggggagaatctgaaactaaccactggcaaaggctggctgaatcatgatgaaacctggaggaattacttttcagacattgacttcttccccaatgctgt<br>ttacacccactgctacgactcgtctggaacgaaactctttgtggcaggaggtcccctcccttcagggctccatggaaactatgctgggctctggagttaatg<br>acaactccccaaatgcagagatttacactaacttccattctcagtttccttgtttcttttgatttttttttcctaattgtgtgaggctcttgtgttttagt<br>gggaacaccaaagtttgcctatagtttaggcacttaataggaagaagctctgtacagaaatctgaaagttgttttgctttttgttttcccctttggtaatca<br>aaattttactatctttttctggcttttcaaccaaacattgttgctaatccctatttttctttaagtgacacacattctcctgtctctggcttcttcaggctg<br>aaatgacatagtctttctcacccttacttcactcttgagaggtagggctcctttataattacatggttgctctcagactttctgtgaaagtttgggagctgt<br>gtgtgtctgtgtgtgtgtgagagagagatcttgtctgcgtgtgtgtgtgtgatcttgtgtgcctgtaggtactgtgtgtcactgaaattacctggagtgagg<br>attacttgtaattaaaatatttataaaagaaacaactttattcacagagtccagctttgggactagtctgtatcttgtttttttaagtctaacaacactgata<br>ataggaagtaaaaacagaaaggaaaagaaattaccactgggaaaatctttttagttagattgtaggcttcctggggcctcccatgccaggactgcaaagtga<br>tccagccctacctgtcttcccacctgtgtgtcccccgtgtgggaagttggtgtcacttccccttcccaccctcacatctgcttagccagtagccacacccct<br>aaaacatcagactcaccatccaggtgcagctccagaggctacaaaaggcttcatgggacttgaatccccatcctagcttctctctccttcccctcaagacct<br>gatctggttttaaggggcctggagctgggagtctcaagtctgctaagattcacatccatagcccccatggctttgaggagaatcctctctgccattcttcca<br>atctccccagtgggttttgctattattttctaaattgggttaagtctaagaaggtgggggtgagcagggggtttatctgtgtgtagtgagtgcttcatgtgt<br>ggaatattcattttcttactgcagtgggacttggggttgaagccacccctcctactctgttggcttagccctgagatggtgacaggctggcctgcagtcagc<br>atcattgtgcatgtgacagcatcaatgtgattagtaatttgtctgttcctcccttgaactgtctgtttagtctgaggtttttaaacttgcaggcagctgact<br>gtgatgtccacttgttccctgatttttacacatcatgtcaaagataacagctgttcccacccaccagttcctctaagcacatactctgcttttctgtcaaca<br>tcccattttggggaaaggaaaagtcatatttattcctgcaccccagtttttttaacttgttctcccagttgtcccccctcttctctgggtgtaagaagggaaat<br>tggaaaaaaaattatatatatattctccttttaatggtgggggggctactggagaggagagacagcaagtccaccctaacttgttacacagcacataccacag<br>gttctggaattctcatcttcgaacctagagaaataggtgctataaacagggaattaagcaaaatgctggatgctatagatcttttaattgtcttaattttttt<br>ttctattattaaactacaggctgtagatttcttagttctcacagaacttctatcattttaaactgacttgtatatttaaaaaaaaaatcttcagtaggatgt<br>tttgtactattgctagaccctcttctgtaatgggtaatgcgtttgattgtttgagattttctgtttttaaaaatgtagcacttgactttttgccaaggaaaa<br>aaataaaaattattccagtgcaaaaaaaaaaaaaaaaaaaaaaaaaaaaaaaaaaaa |
| 36 | gctgcttcccaccagcaaagaccacgactggagagccgagccggaggcagctgggaaacatgaagagcgtcttgctgctgaccacgctcctcgtgcct<br>gcacacctggtggccgcctggagcaataattatgcggtggactgccctcaacactgtgacagcagtgagtgcaaaagcagcccgcgctgcgagaggac<br>agtgctcgacgactgtggctgctgccgagtgtgcgctgcagggcggggagaaacttgctaccgcacagtctcaggcatggatggcatgaagtgtggcc<br>cggggctgaggtgtcagccttctaatggggaggatccttttggtgaagagtttggtatctgcaaagactgtccctacggcaccttcgggatggattgcaga<br>gagacctgcaactgccagtcaggcatctgtgacagggggacgggaayatgcctgaaattccccttcttccaatattcagtaaccaagtcttccaacagattt<br>gtttctctcacggagcatgacatggcatctggagatggcaatattgtgagagaagaagttgtgaaagagaatgctgccgggtctcccgtaatgaggaaat<br>ggttaaatccacgctgatcccggctgtgatttctgagagaaggctctattttcgtgattgttcaacacacagccaacattttaggaactttctagattatag<br>cataaggacatgtaattttttgaagaccaaatgtgatgcatggtggatccagaaaacaaaaagtaggatacttacaatccataacatccatatgactgaacac<br>ttgtatgtgtttgttaaatattcgaatgcatgtagatttgttaaatgtgtgtgtatagtaacactgaagaactaaaaatgcaatttaggtaatcttacatgg<br>agacaggtcaaccaaagagggagctaggcaaagctgaagaccgcagtgagtcaaattagttctttgactttgatgtacattaatgttgggatatggaatgaa |

TABLE 1-continued

| SEQ ID NO | Sequence |
|---|---|
| | gacttaagagcaggagaagatggggagggggtgggagtgggaaataaaatatttagcccttccttggtaggtagcttctctagaatttaattgtgcttttttttttggctttgggaaaagtcaaaataaaacaaccagaaaacccctgaaggaagtaagatgtttgaagcttatggaaatttgagtaacaaacagctttgaactgagagcaatttcaaaaggctgctgatgtagttcccgggttacctgtatctgaaggacggttctggggcataggaaacacatacacttccataaatagctttaacgtatgccacctcagagataaatctaagaagtattttacccctggtggtttgtgtgtgtatgaaggtaaatatttatatatatttttataaataaatgtgttagtgcaagtcatcttccctacccatatttatcatcctcttgaggaaagaaatctagtattatttgttgaaaatggttagaataaaactatgactctataaggttttcaaacatctgaggcatgataaatttattatccataattatagtaataataaccttaataagcataagaaaaacagagtcactctggatttcaaaaatgtcaaaaaaaaaaaaaaa |
| 37 | acacagtactctcagcttgttggtggaagcccctcatctgccttcattctgaaggcagggcccggcagaggaaggatcagagggtcgcggccggagggtcccggccggtggggccaactcagagggagaggaaagggctagagacacgaagaacgcaaaccatcaaatttagaagaaaaagccctttgactttttccccctctccctccccaatggctgtgtagcaaacatccctggcgataccttggaaaggacgaagttggtctgcagtcgcaatttcgtgggttgagttcacagttgtgagtgcggggctcggagatggagccgtggtcctctaggtggaaaacgaaacggtggctctgggatttcaccgtaacaaccctcgcattgaccttcctcttccaagctagagaggtcagaggagctgctccagttgatgtactaaaagcactagattttcacaattctccagagggaatatcaaaaacaacggattttgcacaaacagaaagaattctaaaggctcagatactgcttacagagtttcaaagcaagcacaactcagtgccccaacaaaacagttatttccaggtggaactttcccagaagacttttcaatactatttacagtaaaaccaaaaaaaggaattcagtctttccttttatctatatataatgagcatggtattcagcaaattggtgttgaggttgggagatcacctgtttttctgtttgaagaccacactggaaaacctgccccagaagactatcccctcttcagaactgttaacatcgctgacgggaagtggcatcgggtagcaatcagcgtggagaagaaaactgtgacaatgattgttgattgtaagaagaaaaccacgaaaccacttgatagaagtgagagagcaattgttgataccaatggaatcacggtttttggaacaaggattttggatgaagaagtttttgagggggacattcagcagtttttgatcacaggtgatcccaaggcagcatatgactactgtgagcattatagtccagactgtgactcttcagcacccaaggctgctcaagctcaggaacctcagatagatgagtatgcaccagaggatataatcgaatatgactatgagtatggggaagcagagtataaagaggctgaaagtgtaacagagggacccactgtaactgaggagacaatagcacagacggaggcaaacatcgttgatgattttcaagaatacaactatggaacaatggaaagttaccagacagaagctcctaggcatgtttctgggacaaatgagccaaatccagttgaagaaatatttactgaagaatatctaacgggagaggattatgattcccagaggaaaaattctgaggatacactatatgaaaacaaagaaatagacggcagggattctgatcttctggtagatggagatttaggcgaatatgatttttatgaatataaagaatatgaagataaaccaacaagcccccctaatgaagaatttggtccaggtgtaccagcagaaactgatattacagaaacaagcataaatggccatggtgcatatggagagaaaggacagaaaggagaaccagcagtggttgagcctggtatgcttgtcgaaggaccaccaggaccagcaggacctgcaggtattatgggtcctccaggtctacaaggccccactggacccctggtgaccctggcgataggggcccccaggacgtcctggcttaccaggggctgatggtctacctggtcctcctggtactatgttgatgttaccgttccgttatggtggtgatggttccaaaggaccaaccatctctgctcaggaagctcaggctcaagctattcttcagcaggctcggattgctctgagaggcccacctggcccaatgggtctaactggaagaccaggtcctgtgggggggcctggttcatctggggccaaaggtgagagtggtgatccaggtcctcagggccctcgaggcgtccagggtcccccctggtccaacgggaaaacctggaaaaaggggtcgtccaggtgcagatggaggaagaggaatgccaggagaacctggggcaaagggagatcgagggtttgatggacttccgggtctgccaggtgacaaaggtcacaggggtgaacgaggtcctcaaggtcctccaggtcctcctggtgatgatggaatgaggggagaagatggagaaattggaccaagaggtcttccaggtgaagctggcccacgaggtttgctgggtccaaggggaactccaggagctccagggcagcctggtatggcaggtgtagatggcccccaggaccaaaagggaacatgggtccccaaggggagcctgggcctccaggtcaacaagggaatccaggacctcagggtcttcctggtccacaaggtccaattggtcctcctggtgaaaaaggaccacaaggaaaaccaggacttgctggacttcctggtgctgatgggcctcctggtcatcctgggaaagaaggccagtctggagaaaaggggggctctgggtcccccctggtccacaaggtcctattggatacccgggcccccggggagtaaagggagcagatggtgtcagaggtctcaagggatctaaaggtgaaaagggtgaagatggttttccaggattcaaaggtgacatgggtctaaaaggtgacagaggagaagttggtcaaattggcccaagaggggaagatggccctgaaggacccaaaggtcgagcaggcccaactggagacccaggtccttcaggtcaagcaggagaaaagggaaaacttggagttccaggattaccaggatatccaggaagacaaggtccaaagggttccactggattccctgggtttccaggtgccaatggagagaaaggtgcacggggagtagctggcaaaccaggccctcggggtcagcgtggtccaacgggtcctcgaggttcaagaggtgcaagaggtcccactgggaaacctgggccaaagggcacttcaggtggcgatggccctcctggccctccaggtgaaagaggtcctcaaggacctcagggtccagttggattccctggaccaaaaggccctcctggaccacctgggaaggatgggctgccaggacaccctgggcaacgtggggagactggatttcaaggcaagaccggccctcctgggccagggggagtggttggaccacagggaccaaccggtgagactggtccaataggggaacgtgggcatcctggccctcctggccctcctggtgagcaaggtcttcctggtgctgcaggaaaagaaggtgcaaagggtgatccaggtcctcaaggtatctcagggaaagatggaccagcaggattacgtggtttcccaggggaaagaggtcttcctggagctcagggtgcacctggactgaaaggaggggaaggtccccagggcccaccaggtccagttggctcaccaggagaacgtgggtcagcaggtacagctggcccaattggtttaccagggcgcccgggacctcagggtcctcctggtccagctggagagaaaggtgctcctggagaaaaaggtccccaagggcctgcagggagagatggagttcaaggtcctgttggtctcccagggccagctggtcctgccggctcccctggggaagacggagacaagggtgaaattggtgagccgggacaaaaaggcagcaagggtgacaagggagaaaatggccctcccggtcccccaggtcttcaaggaccagttggtgcccctggaattgctggaggtgatggtgaaccaggtcctagaggacagcaggggatgtttggcaaaaaggtgatga |

TABLE 1-continued

| SEQ ID NO | Embodiments of TVM sequences<br>Sequence |
|---|---|
| | gggtgccagaggcttccctggacctcctggtccaataggtcttcagggtctgccaggcccacctggtgaaaaaggtgaaaatggggatgttggtcccatg<br>gggccacctggtcctccaggcccaagaggccctcaaggtcccaatggagctgatggaccacaaggacccccagggtctgttggttcagttggtggtgtt<br>ggagaaaagggtgaacctggagaagcagggaacccagggcctcctggggaagcaggtgtaggcggtcccaaaggagaaagaggagagaaaggg<br>gaagctggtccacctggagctgctggacctccaggtgccaaggggccaccaggtgatgatggccctaagggtaacccgggtcctgttggttttcctgga<br>gatcctggtcctcctggggaacctggccctgcaggtcaagatggtgttggtggtgacaagggtgaagatggagatcctggtcaaccgggtcctcctggcc<br>catctggtgaggctggcccaccaggtcctcctggaaaacgaggtcctcctggagctgcaggtgcagagggaagacaaggtgaaaaaggtgctaaggg<br>ggaagcaggtgcagaaggtcctcctggaaaaaccggcccagtcggtcctcagggacctgcaggaaagcctggtccagaaggtcttcggggcatccctg<br>gtcctgtgggagaacaaggtctccctggagctgcaggccaagatggaccacctggtcctatgggacctcctggcttacctggtctcaaaggtgaccctgg<br>ctccaagggtgaaaagggacatcctggtttaattggcctgattggtcctccaggagaacaaggggaaaaaggtgaccgagggctccctggaactcaag<br>gatctccaggagcaaaggggatgggggaattcctggtcctgctggtcccttaggtccacctggtcctccaggtttaccaggtcctcaaggcccaaaggg<br>taacaaaggctctactggacccgctggccagaaaggtgacagtggtcttccagggcctcctgggtctccaggtccacctggtgaagtcattcagcctttac<br>caatcttgtcctccaaaaaaacgagaagacatactgaaggcatgcaagcagatgcagatgataatattcttgattactcggatggaatggaagaaatatttg<br>gttccctcaattccctgaaacaagacattgagcatatgaaatttccaatgggtactcagaccaatccagcccgaacttgtaaagacctgcaactcagccatc<br>ctgacttcccagatggtgaatattggattgatcctaaccaaggttgctcaggagattccttcaaagtttactgtaatttcacatctggtggtgagacttgca<br>tttatccagacaaaaaatctgagggagtaagaatttcatcatggccaaaggagaaaccaggaagttggtttagtgaatttaagaggggaaaactgctttcat<br>acttagatgttgaaggaaattccatcaatatggtgcaaatgacattcctgaaacttctgactgcctctgctcggcaaaatttcacctaccactgtcatcagt<br>cagcagcctggtatgatgtgtcatcaggaagttatgacaaagcacttcgcttcctgggatcaaatgatgaggagatgtcctatgacaataatccttttatca<br>aaacactgtatgatggttgtgcgtccagaaaaggctatgaaaagactgtcattgaaatcaatacaccaaaaattgatcaagtacctattgttgatgtcatga<br>tcaatgactttggtgatcagaatcagaagttcggatttgaagttggtcctgtttgttttcttggctaagattaagacaaagaacatatcaaatcaacagaaa<br>atataccttggtgccaccaacccattttgtgccacatgcaagttttgaataaggatggtatagaaaacaacgctgcatatacaggtaccatttaggaaatac<br>cgatgcctttgtgggggcagaatcacatggcaaaagctttgaaaatcataaagatataagttggtgtggctaagatggaaacagggctgattcttgattccc<br>aattctcaactctccttttcctatttgaatttctttggtgctgtagaaaacaaaaaaagaaaaatatatattcataaaaaatatggtgctcattctcatcca<br>tccaggatgtactaaaacagtgtgtttaataaattgtaattatttgtgtacagttctatactgttatctgtgtccatttccaaaacttgcacgtgtccctg<br>aattccatctgactctaattttatgagaattgcagaactctgatggcaataaatatatgtattatgaaaaaataaagttgtaatttctgatgactctaagtc<br>cctttctttggttaataataaaatgcctttgtatatattgatgttgaagagttcaattatttgatgtcgccaacaaaattctcagagggcaaaaatctggaa<br>gacttttggaagcacactctgatcaactcttctctgccgacagtcattttgctgaatttcagccaaaaatattatgcattttgatgctttattcaaggctat<br>acctcaaactttttcttctcagaatccaggatttcacaggatacttgtatatatggaaaacaagcaagtttatatttttggacagggaaatgtgtgtaagaa<br>agtatattaacaaatcaatgcctccgtcaagcaaacaatcatatgtatactttttttctacgttatctcatctccttgttttcagtgtgcttcaataatgca<br>ggttaatattaaagatggaaattaagcaattatttatgaatttgtgcaatgttagattttcttatcaatcaagttcttgaatttgattctaagttgcatatt<br>ataacagtctcgaaaattattttacttgcccaacaaatattactttttttcctttcaagataattttataaatcatttgacctacctaattgctaaatgaata<br>acatatggtggactgttattaagagtatttgttttaagtcattcaggaaaatctaaacttttttttccactaaggtatttactttaaggtagcttgaaatag<br>caatacaatttaaaaattaaaaactgaattttgtatctattttaagtaatatatgtaagacttgaaaataaatgttttatttcttatataaagtgttaaatt<br>aattgataccagatttcactggaacagtttcaactgataatttatgacaaaagaacatacctgtaatattgaaattaaaaagtgaaatttgtcataaagaat<br>ttcttttatttttgaaatcgagtttgtaaatgtccttttaagaagggagatatgaatccaataaataaactcagga |
| 52 | ctccaaaggagccagcgtctccccagttcctgaaatcctgggtgttgcctgccagtcgccatgagaacttcctaccttctgctgtttactctctgcttactt<br>ttgtctgagatggcctcaggtggtaactttctcacaggccttggccacagatctgatcattacaattgcgtcagcagtggagggcaatgtctctattctgcc<br>tgcccgatctttaccaaaattcaaggcacctgttacagagggaaggccaagtgctgcaagtgagctgggagtgaccagaagaaatgacgcagaagtgaaatg<br>aactttttataagcattcttttaataaaggaaaattgcttttgaagtataaaaaaaaaaaaaaaaaaaaaaaaaaaaaaaa |
| 53 | atttacaataaatgaagattaccctcaaatgctagaagctgtctaggtccgtccggtgtgtcagattttcctcagattagatgtgccaataaccaagtttat<br>tcagtaaacaacttgtacttgtttcatctggttttattactctcacccataaacaggyatgactctttgaccctctggaaatatgtaatgcttccaatcttg<br>ctttgtgtatctcatttaatttgttataaggtagtactgattttagcatattaatgcgatttcttccttgttgtttgctttggtctgtgttcaatccagaga<br>gcttaaattgtcattattttgggaagaaaacctgtatttttgttagtttacaatattatgaaatttcacttcaggagaaactgctgggcttcctgtggcttt<br>gttttcttagttacttttccgtgccgtgtatttttaattgatttttcttcttttacttgaaaagaaagtgttttattttcaaatctggtccatatttaca<br>ttctagttcagagccaagccttaaactgtacagaatttccactgtaattaaaactatttagtgttagttataaatagccttcaaaaagagagattctccatt<br>cacgatcacctgcatcacagcccatggtgaatgtatgtttctgcatagcgaaataaaaatggcaaatgcaaaaaaaaaaaaaaaaaaaaaaaaaaa |

TABLE 1-continued

Embodiments of TVM sequences

| SEQ ID NO | Sequence |
|---|---|
| 54 | ctgactttctctcggtgcgtccagtggagctctgagtttcgaatcggtggcggcggattccccgcgcgcccggcgtcggggcttccaggaggatgcggag<br>ccccagcgcggcgtggctgctggggggccgccatcctgctagcagcctctctctcctgcagtggcaccatccaaggaaccaatagatcctctaaaggaag<br>aagccttattggtaaggttgatggcacatcccacgtcactggaaaaggagttacagttgaaacagtcttttctgtggatgagttttctgcatctgtcctcac<br>tggaaaactgaccactgtcttccttccaattgtctacacaattgtgtttgtggtgggtttgccaagtaacggcatggccctgtgggtctttcttttccgaac<br>taagaagaagcaccctgctgtgatttacatggccaatctggccttggctgacctcctctctgtcatctggttccccttgaagattgcctatcacatacatgg<br>caacaactggatttatggggaagctctttgtaatgtgcttattggctttttctatggcaacatgtactgttccattctcttcatgacctgcctcagtgtgca<br>gaggtattgggtcatcgtgaaccccatggggcactccaggaagaaggcaaacattgccattggcatctccctggcaatatggctgctgattctgctggtcac<br>catccctttgtatgtcgtgaagcagaccatcttcattcctgccctgaacatcacgacctgtcatgatgttttgcctgagcagctcttggtgggagacatgtt<br>caattacttcctctctctggccattggggtctttctgttcccagccttcctcacagcctctgcctatgtgctgatgatcagaatgctgcgatcttctgccat<br>ggatgaaaactcagagaagaaaaggaagagggccatcaaactcattgtcactgtcctggccatgtacctgatctgcttcactcctagtaaccttctgcttgt<br>ggtgatttattttctgattaagagccagggccagagccatgtctatgccctgtacattgtagccctctgcctctctacccttaacagctgcatcgacccctt<br>tgtctattactttgtttcacatgatggatcatgcaaagaacgctctcctttgccgaagtgtccgcactgtaaagcagatgcaagtatccctcacctcaaaga<br>aacactccaggaaatccagctcttactcttcaagttcaaccactgttaagacctcctattgagttttccaggtcctcagatgggaattgcacagtaggatgt<br>ggaacctgtttaatgttatgaggacgtgtctgttatttcctaatcaaaaaggtctcaccacataccatgtggatgcagcacctctcaggattgctaggagct<br>cccctgtttgcatgagaaaagtagtcccccaaattaacatcagtgtctgtttcagaatctctctactcagatgaccccagaaactgaaccaacagaagcaga<br>cttttcagaagatggtgaagacagaaacccagtaacttgcaaaaagtagacttggtgtgaagactcacttctcagctgaaattatatatatacacatatata<br>tatatattttacatctgggatcatgatagacttgttagggcttcaaggccctcagagatgatcagtccaactgaacgaccttacaaatgaggaaaccaagat<br>aaatgagctgccagaatcaggtttccaatcaacagcagtgagatgggattggacagtagaatttcaatgtccagtgagtgaggttcttgtaccacttcatca<br>aaatcatggatcttggctgggtgcggtgcctcatgcctgtaatcctagcactttgggaggctgaggcaggcaatcacttgaggtcaggagttcgagaccagc<br>ctggccatcatggcgaaacctcatctctactaaaaatacaaaagttaaccaggtgtgtggtgcacgtttgtaatcccagttactcaggaggctgaggcacaa<br>gaattgagtatcactttaactcaggaggcagaggttgcagtgagccgagattgcaccactgcactccagcttgggtgataaaataaaataaaatagtcgtga<br>atcttgttcaaaatgcagattcctcagattcaataatgagagctcagactgggaacagggcccaggaatctgtgtggtacaaacctgcatggtgtttatgca<br>cacagagatttgagaaccattgttctgaatgctgcttccatttgacaaagtgccgtgataattttgaaaagagaagcaaacaatggtgtctcttttatgtt<br>cagcttataatgaaatctgtttgttgacttattagactttgaattatttctttattaaccctctgagtttttgtatgtattattattaaagaaaaatgcaat<br>caggattttaaacatgtaaatacaaattttgtataacttttgatgacttcagtgaaattttcaggtagtctgagtaatagattgttttgccacttagaatat<br>tttaaaaaataattgttggagtatttattgtcagttttgttcacttgttatctaatacaaaattataaagccttcagagggtttggaccacatctctttgga<br>aaatagtttgcaacatatttaagagatacttgatgccaaaatgactttatacaacgattgtatttgtgacttttaaaaataattattttattgtgtaattga<br>tttataaataacaaaatttttttacaacttaaaaaaaaaa |
| 55 | ggagtccaaaagaaaaggaagaggaggaaaaacaagtgtgtgttgggggggaacagggggaaaagcatttttggtggatggtatgaagccagccatg<br>gaaactgcagccgaggaaaatactgaacaaagccaagagagaaaaggctgctttgaatgctgcatcaagtgtctgggaggagtcccctacgcctccctg<br>gtggccaccatcctctgcttctccggggtggccttattctgcggctgtgggcatgtggctctcgcaggcaccgtggcgattcttgagcaacacttctccacc<br>aacgccagtgaccatgccttgctgagcgaggtgatacaactgatgcagtatgtcatctatggaattgcgtcctttttcttcttgtatgggatcattctgttg<br>gcagaaggcttttacaccacaagtgcagtgaaagaactgcacggtgagtttaaaacaaccgcttgtggccgatgcatcagtggaatgttcgttttcctcacc<br>tatgtgcttggagtggcctggctgggtgtgtttggtttctcagcggtgcccgtgtttatgttctacaacatatggtcaacttgtgaagtcatcaagtcaccg<br>cagaccaacgggaccacgggtgtggagcagatctgtgtggatatccgacaatacggtatcattccttggaatgctttccccggaaaaatatgtggctctgcc<br>ctggagaacatctgcaacacaaacgagttctacatgtcctatcacctgttcattgtggcctgtgcaggagctggtgccaccgtcattgccctgctgatctac<br>atgatggctactacatataactatgcggttttgaagtttaagagtcgggaagattgctgcactaaattctaaattgcataaggagttttagagagctatgct<br>ctgtagcatgaaatatcactgacactccagactaaagcagagtctaggtttctgcaattttgttacagtaatttgtaaatagctttagtaaactcaccttgc<br>atggtagattaataagatgacttactgtacatgaattacacaataatgagatctggtggctatttccacattttgaaaaggattcagttatttactgacagt<br>ggtgagcatcctttttaaaataatgttctcatacttaaacattagagagcagtatctttaaatgaattattaacactttggaatacttacattttctgttat<br>ttttgattgcctgataaccagtttcaatgatgaaaatgaaaacaagtgctgaagatgaaatggaagagaaccgttttaatctggattttgttttgtcacacc<br>tggaaaatactttgcaaatatgttctaaattgaaaacaatttttttatgatcacatggttcactaccaaatgaccctcaaataagccagatgaaaatttga<br>agaaaaaggtcacccagttctctggaaaaaaaaaaaaaaaaaaaaaaaaaaaa |

TABLE 1-continued

Embodiments of TVM sequences

| SEQ ID NO | Sequence |
|---|---|
| 56 | ccgccaagcatattgctaggcacagagcaggtgtgcaacaaaagttatttctcaggctttccctcctctgagcgccgtcctccagagggtccggagtgtag ctggggggttggagcagcagcctcctaggcgatgggacagagcccacagggtccggtatgccacggtttcttcgtcagaccctgggaatccaacgtcgca aaataaacacggccgcgccgctaatcgccagttcggaggaaacaaaacagcgctgcgctgggggatctgggcaaaatcagccctccctcctcccgctc cttcgccgcggccctcccctcctcgcgctgctctcgttcgcttggctcagctcagctcagctcagcgcagctccgcggccgccaagccgaggcgggcacg gtctccgagtcgcggacgccagctccgagctccctctctccgccgcgcctccgccaggtcgcgccttcgtcgggaccacttcgggcaggagtcgcgtgg cgaaggcctgcggccgcggcacaaagttgggggccgcgaagatgaggctgtccccggcgcccctgaagctgagccggactccggcactgctggccc tggcgctgcccctggccgcggcgctggccttctccgacgagaccctggacaaagtgcccaagtcagagggctactgcagccgtatcctgcgcgcccag ggcacgcggcgcgagggctacaccgagttcagcctccgcgtggagggcgaccccgacttctacaagccgggaaccagctaccgcgtaacactttcag ctgctcctccctcctacttcagaggattcacattaattgccctcagagagaacagagagggtgataaggaagaagaccatgctgggaccttccagatcata gacgaagaagaaactcagtttatgagcaattgccctgttgcagtcactgaaagcactccacggaggaggacccggatccaggtgttttggatagcaccac cagcgggaacaggctgcgtgattctgaaggccagcatcgtacaaaaacgcattatttattttcaagatgagggctctctgaccaagaaactttgtgaacaa gattccacatttgatggggtgactgacaaacccatcttagactgctgtgcctgcggaactgccaagtacagactcacattttatgggaattggtccgagaag acacacccaaaggattaccctcgtcgggccaaccactggtctgcgatcatcggaggatcccactccaagaattatgtactgtgggaatatggaggatatgc cagcgaaggcgtcaaacaagttgcagaattgggctcacccgtgaaaatggaggaagaaattcgacaacagagtgatgaggtcctcaccgtcatcaaag ccaaagcccaatggccagcctggcagcctctcaacgtgagagcagcaccttcagctgaattttccgtggacagaacgcgccatttaatgtccttcctgacc atgatgggccctagtcccgactggaacgtaggcttatctgcagaagatctgtgcaccaaggaatgtggctgggtccagaaggtggtgcaagacctgattc cctgggacgctggcaccgacagcggggtgacctatgagtcacccaacaaacccaccattccccaggagaaaatccggcccctgaccagcctggaccat cctcagagtcctttctatgacccagagggtgggtccatcactcaagtagccagagttgtcatcgagagaatcgcacggaagggtgaacaatgcaatattgt acctgacaatgtcgatgatattgtagctgacctggctccagaagagaaagatgaagatgacacccctgaaacctgcatctactccaactggtccccatggt ccgcctgcagctcctccacctgtgacaaaggcaagaggatgcgacagcgcatgctgaaagcacagctggacctcagcgtcccctgccctgacacccag gacttccagccctgcatgggccctggctgcagtgacgaagacggctccacctgcaccatgtccgagtggatcacctggtcgccctgcagcatctcctgcg gcatgggcatgaggtcccgggagaggtatgtgaagcagttcccggaggacggctccgtgtgcacgctgcccactgaggaaacggagaagtgcacggt caacgaggagtgctctcccagcagctgcctgatgaccgagtggggcgagtgggacgagtgcagcgccacctgcggcatgggcatgaagaagcggca ccgcatgatcaagatgaaccccgcagatggctccatgtgcaaagccgagacatcacaggcagagaagtgcatgatgccagagtgccacaccatcccat gcttgctgtccccatggtccgagtggagtgactgcagcgtgacctgcgggaagggcatgcgaacccgacagcggatgctcaagtctctggcagaacttg gagactgcaatgaggatctggagcaggtggagaagtgcatgctccctgaatgccccattgactgtgagctcaccgagtggtcccagtggtcggaatgta acaagtcatgtgggaaaggccacgtgattcgaacccggatgatccaaatggagcctcagtttggaggtgcaccctgcccagagactgtgcagcgaaaa aagtgccgcatccgaaaatgccttcgaaatccatccatccaaaagctacgctggagggaggcccgagagagccggcggagtgagcagctgaaggaa gagtctgaaggggagcagttcccaggttgtaggatgcgcccatggacggcctggtcagaatgcaccaaactgtgcggaggtggaattcaggaacgtta catgactgtaaagaagagattcaaaagctcccagtttaccagctgcaaagacaagaaggagatcagagcatgcaatgttcatccttgttagcaagggtac gagttccccagggctgcactctagattccagagtcaccaatggctggattatttgcttgtttaagacaatttaaattgtgtacgctagttttcatttttgca gtgtggttcgcccagtagtcttgtggatgccagagacatcctttctgaatacttcttgatgggtacaggctgagtggggcgccctcacctccagccagcctc ttcctgcagaggagtagtgtcagccaccttgtactaagctgaaacatgtccctctggagcttccacctggccagggaggacggagactttgacctactccac atggagaggcaaccatgtctggaagtgactatgcctgagtcccagggtgcggcaggtaggaaacattcacagatgaagacagcagattccccacattctcat ctttggcctgttcaatgaaaccattgtttgcccatctcttcttagtggaactttaggtctcttttcaagtctcctcagtcatcaatagttcctggggaaaaa cagagctggtagacttgaagaggagcattgatgttgggtggcttttgttctttcactgagaaattcggaatacatttgtctcacccctgatattggttcctg atgcccccccaacaaaaataaataaataaattatggctgctttatttaaatataaggtagctagtttttacacctgagataaataataagcttagagtgtat ttttcccttgcttttggggggttcagaggagtatgtacaattcttctgggaagccagccttctgaactttttggtactaaatccttattggaaccaagacaaa ggaagcaaaattggtctctttagagaccaatttgcctaaattttaaaatcttcctacacacatctagacgttcaagtttgcaaatcagtttttagcaagaaa acatttttgctatacaaacatttttgctaagtctgcccaaagccccccaatgcattccttcaacaaaatacaatctctgtactttaaagttattttagtcat gaaattttatatgcagagagaaaaagttaccgagacagaaaacaaatctaagggaaaggaatattatgggattaagctgagcaagcaattctggtggaaagt caaacctgtcagtgctccacaccagggctgtggtcctcccagacatgcataggaatggccacaggtttacactgccttcccagcaattataagcacaccaga ttcagggagactgaccaccaagggatagtgtaaaaggacattttctcagttgggtccatcagcagtttttcttcctgcatttattgttgaaaactattgttt catttcttcttttataggccttattactgcttaatccaaatgtgtaccattggtgagacacatacaatgctctgaatacactacgaatttgtattaaacaca tcagaatatttccaaatacaacatagtatagtcctgaatatgtacttttaacacaagagagactattcaataaaaactcactgggtctttcatgtctttaag ctaagtaagtgttcagaaggttctttttttatattgtcctccacctccatcattttcaataaaagatagggcttttgctcccttgttcttggagggaccatta |

TABLE 1-continued

Embodiments of TVM sequences

| SEQ ID NO | Sequence |
|---|---|
| | ttacatctctgaactacctttgtatcctttgtatccaacatgttttaaatccttaaatgaattgctttctcccaaaaaaagcacaatataaagaaacacaag<br>atttaattatttttctacttgggggaaaaaagtcctcatgtagaagcacccacttttgcaatgttgttctaagctatctatctaactctcagcccatgata<br>aagttccttaagctggtgattcctaatcaaggacaagccaccctagtgtctcatgtttgtatttggtcccagttgggtacattttaaaatcctgattttgga<br>gacttaaaaccaggttaatggctaagaatgggtaacatgactcttgttggattgttatttttgtttgcaatggggaatttataagaagcatcaagtctctt<br>tcttaccaaagtcttgttaggtggtttatagttcttttggctaacaaatcattttggaaataaagatttttactacaaaaatgaaatttgtttggacttcc<br>acttgagacagtaaagagagtattagacacccagtaaaaactgccatataaagaagttgtaattgtttgttgtgtatgtatttttttcaatgccaaaccagc<br>tgtgatccaatttacatccacattttaggtccaacagcaagaagttcagagagagatttcccaaccagacattgggtcactcactggtcaccttgccagtgc<br>attttattagaagggaatctgttgtagcaaatgggaataaacctgggtttctatagacccagaactgaaaaaataaaaaaaaaaaaaaaaa |
| 57 | catccctgccattgccgggcactcgcggcgctgctaacggcctggtcacatgctctccggagagctacgggagggcgctgggtaacctctatccgagcc<br>gcggccgcgaggaggagggaaaaggcgagcaaaaaggaagagtgggaggaggaggggaagcggcgaaggaggaagaggaggaggaggaag<br>aggggagcacaaaggatccaggtctcccgacgggaggttaataccaagaaccatgtgtgccgagcggctgggccagttcatgaccctggctttggtgtt<br>ggccacctttgacccggcgcgggggaccgacgccaccaacccacccgagggtccccaagacaggagctcccagcagaaaggccgcctgtccctgca<br>gaatacagcggagatccagcactgtttggtcaacgctggcgatgtggggtgtggcgtgtttgaatgtttcgagaacaactcttgtgagattcggggcttaca<br>tgggatttgcatgacttttctgcacaacgctggaaaatttgatgcccagggcaagtcattcatcaaagacgccttgaaatgtaaggcccacgctctgcggca<br>caggttcggctgcataagccggaagtgcccggccatcagggaaatggtgtcccagttgcagcgggaatgctacctcaagcacgacctgtgcgcggctg<br>cccaggagaacacccgggtgatagtggagatgatccatttcaaggacttgctgctgcacgaaccctacgtggacctcgtgaacttgctgctgacctgtgg<br>ggaggaggtgaaggaggccatcacccacagcgtgcaggttcagtgtgagcagaactggggaagcctgtgctccatcttgagcttctgcacctcggccat<br>ccagaagcctcccacggcgcccccgagcgccagccccaggtggacagaaccaagctctccagggcccaccacggggaagcaggacatcacctccc<br>agagcccagcagtagggagactggccgaggtgccaagggtgagcgaggtagcaagagccacccaaacgcccatgcccgaggcagagtcgggggc<br>cttggggctcagggaccttccggaagcagcgagtgggaagacgaacagtctgagtattctgatatccggaggtgaaatgaaaggcctggccacgaaat<br>ctttcctccacgccgtccattttcttatctatggacattccaaaacatttaccattagagagggggggatgtcacacgcaggattctgtggggactgtggact<br>tcatcgaggtgtgtgttcgcggaacggacaggtgagatggagacccctggggccgtggggtctcaggggtgcctggtgaattctgcacttacacgtactca<br>agggagcgcgcccgcgttatcctcgtacctttgtcttctttccatctgtggagtcagtgggtgtcggccgctctgttgtgggggaggtgaaccaggga<br>gcagggcaaggcagggcccccagagctgggccacacagtgggtgctgggcctcgccccgaagcttctggtgcagcagcctctggtgctgtctccgcg<br>gaagtcagggcggctggattccaggacaggagtgaatgtaaaaataaatatcgcttagaatgcaggagaagggtggagaggaggcaggggccgagg<br>gggtgcttggtgccaaactgaaattcagtttcttgtgtggggccttgcggttcagagctcttggcgagggtggagggaggagtgtcatttctatgtgtaatt<br>tctgagccattgtactgtctgggctgggggggacactgtccaagggagtggcccctatgagtttatattttaaccactgcttcaaatctcgatttcactttt<br>tttatttatccagttatatctacatatctgtcatctaaataaatggctttcaaacaaaaaaaaaaaaaaaaaa |

In one embodiment, the TVM is an ovarian TVM, and in one embodiment, the TVM is ADAM12, Adlican, BLAME/SLAMF8, c14orf100, C14orf28, C2orf6, c6orf55, C6orf69, CDCP1-CUB, DKFZp762e1312, DR6, DSG2, EGFL6, EPSTI1, FLJ46072, FZD10, GPR105, IVNS1ABP, KCNE3, KCNE4, KCNK5, KIAA1892, KIBRA, LOC51136, MS4A6A, OLFML2B, PCDHB2, SCGB2A1, SDC1, SEC23B, SLC11A1-NRAMP, SPP1, ST14, TNFAIP6, WFDC2, and in one embodiment, the nucleic acid sequence is SEQ ID NO: 1-35. In another embodiment, the TVM is a renal TVM, and in one embodiment, the TVM is ESM1, and in one embodiment, the nucleic acid sequence is SEQ ID NO: 36. In another embodiment, the TVM is a breast TVM, and in one embodiment, the TVM is COL11A1, and in one embodiment, the nucleic acid sequence is SEQ ID NO: 37.

In one embodiment, the tumor is an ovarian tumor, and in one embodiment, the TVM is ADAM12, Adlican, BLAME/SLAMF8, c14orf100, C14orf28, C2orf6, c6orf55, C6orf69, CDCP1-CUB, DKFZp762e1312, DR6, DSG2, EGFL6, EPSTI1, FLJ46072, FZD10, GPR105, IVNS1ABP, KCNE3, KCNE4, KCNK5, KIAA1892, KIBRA, LOC51136, MS4A6A, OLFML2B, PCDHB2, SCGB2A1, SDC1, SEC23B, SLC11A1-NRAMP, SPP1, ST14, TNFAIP6, or WFDC2, and in one embodiment, the nucleic acid sequence is SEQ ID NO: 1-35. In another embodiment, the tumor is a renal tumor, and in one embodiment, the TVM is ESM1, and in one embodiment, the nucleic acid sequence is SEQ ID NO: 36. In another embodiment, the tumor is a breast tumor, and in one embodiment, the TVM is COL11A1, and in one embodiment, the nucleic acid sequence is SEQ ID NO: 37.

The nucleic acid molecule for the compositions and methods of the present invention, has, in another embodiment, a sequence selected from the sequences set forth in SEQ ID No: 2, 13-15, 37, 41, and 52-57. In another embodiment, the nucleic acid molecule has a sequence selected from the sequences set forth in SEQ ID No: 2, 6, 8, 55, and 56. In another embodiment, the nucleic acid molecule has the sequence set forth in SEQ ID No: 13. Each possibility represents a separate embodiment of the present invention.

In another embodiment, the TVM is encoded by a sequence set forth in Table 6 of WO 2007/089513 of WO 2007/089513, which is incorporated by reference herein in its entirety. In another embodiment, the TVM is encoded by a sequence comprising a sequence set forth in Table 6 of WO 2007/089513. In another embodiment, the TVM is encoded by a sequence comprising a partial gene sequence set forth in Table 6 of WO 2007/089513. In another embodiment, the TVM is encoded by a sequence comprising a partial transcript sequence set forth in Table 6 of WO 2007/089513. In another embodiment, the TVM is encoded by a sequence set forth in a GenBank entry whose Accession Number appears in Table 6 of WO 2007/089513. In another embodiment, the TVM is encoded by a sequence comprising a sequence set forth a GenBank entry whose Accession Number appears in Table 6 of WO 2007/089513. In another embodiment, the TVM is encoded by a sequence comprising a partial gene sequence set forth in a GenBank entry whose Accession Number appears in Table 6 of WO 2007/089513. In another embodiment, the TVM is encoded by a sequence comprising a partial transcript sequence set forth in a GenBank entry whose Accession Number appears in Table 6 of WO 2007/089513.

In another embodiment, the TVM is encoded by a sequence set forth in Table 7 of WO 2007/089513. In another embodiment, the TVM is encoded by a sequence comprising a sequence set forth in Table 7 of WO 2007/089513. In another embodiment, the TVM is encoded by a sequence comprising a partial gene sequence set forth in Table 7 of WO 2007/089513. In another embodiment, the TVM is encoded by a sequence comprising a partial transcript sequence set forth in Table 7 of WO 2007/089513. In another embodiment, the TVM is encoded by a sequence set forth in a GenBank entry whose Accession Number appears in Table 7 of WO 2007/089513. In another embodiment, the TVM is encoded by a sequence comprising a sequence set forth a GenBank entry whose Accession Number appears in Table 7 of WO 2007/089513. In another embodiment, the TVM is encoded by a sequence comprising a partial gene sequence set forth in a GenBank entry whose Accession Number appears in Table 7 of WO 2007/089513. In another embodiment, the TVM is encoded by a sequence comprising a partial transcript sequence set forth in a GenBank entry whose Accession Number appears in Table 7 of WO 2007/089513.

In another embodiment, a nucleic acid molecule of the present invention encodes a TVM. In another embodiment, the nucleic acid molecule is a TVM. Each possibility represents a separate embodiment of the present invention.

The protein for the compositions and methods of the present invention, is, in another embodiment, encoded by a nucleic acid molecule having a sequence selected from the sequences set forth in SEQ ID No: 2, 13-15, 37, 40, 44, and 52-57. In another embodiment, the protein is encoded by a nucleic acid molecule having a sequence selected from the sequences set forth in SEQ ID No: 2, 6, 8, 55, and 56. In another embodiment, the protein is encoded by a nucleic acid molecule having the sequence set forth in SEQ ID No: 13. In another embodiment, the protein is a tumor vasculature marker. In another embodiment, the protein has one of the sequences set forth below. Each possibility represents a separate embodiment of the present invention.

In another embodiment, the tumor vasculature marker (TVM) is an Adlican protein. In another embodiment, the marker is a nucleic acid molecule encoding an Adlican protein. In another embodiment, the Adlican protein is encoded by a nucleic acid molecule having the sequence set forth in SEQ ID No: 2. In another embodiment, the Adlican protein is encoded by a nucleic acid molecule having a sequence set forth in GenBank Accession No. AF245505. In another embodiment, the Adlican protein has an amino acid (AA) sequence set forth in GenBank Accession No. AF245505. In another embodiment, the Adlican protein is an MXRA5 protein. In another embodiment, the Adlican protein is encoded by any other Adlican gene sequence known in the art. In another embodiment, the Adlican protein is any other Adlican protein known in the art. In another embodiment, the TVM is an isoform of an Adlican protein. In another embodiment, the TVM is a homologue of an Adlican protein. In another embodiment, the TVM is a variant of an Adlican protein. In another embodiment, the TVM is a fragment of an Adlican protein. In another embodiment, the TVM is a fragment of an isoform, homologue, or variant of an Adlican protein. Each possibility represents a separate embodiment of the present invention.

In another embodiment, the TVM is an AML1 protein. In another embodiment, the marker is a nucleic acid molecule encoding an AML1 protein. In another embodiment, the AML1 protein is encoded by a nucleic acid molecule having the sequence set forth in SEQ ID No: 40. In another embodiment, the AML1 protein is encoded by a nucleic acid molecule having a sequence set forth in GenBank Accession No. NM_001001890. In another embodiment, the AML1 protein is encoded by a nucleic acid molecule having a sequence selected from those set forth in GenBank Accession No. NM_001754 and NM_001987. In another embodiment, the AML1 protein has an AA sequence set forth in one of the above GenBank entries. In another embodiment, the AML1 protein is encoded by a nucleic acid molecule comprising a sequence set forth in DQ224380, DQ224379, DQ224378, DQ207762, DQ207763, DQ207764, DQ207765, DQ207766, DQ207767, DQ207768, DQ207769, DQ207770, DQ100455, DQ100456, DQ100457, AJ888032, AJ888033, AJ888034, AJ888035, AJ888036, AJ888037, AJ888038, AJ888039, AJ888040, or AJ888041. In another embodiment, the AML1 protein has an AA sequence comprising an AA sequence set forth in one of the above GenBank entries. In another embodiment, the AML1 protein is encoded by any other AML1 gene sequence known in the art. In another embodiment, the AML1 protein is any other AML1 protein known in the art. In another embodiment, the TVM is an isoform of an AML1 protein. In another embodiment, the TVM is a homologue of an AML1 protein. In another embodiment, the TVM is a variant of an AML1 protein. In another embodiment, a TEL/AML1 protein is utilized in methods and compositions of the present invention. In another embodiment, the TEL/AML1 protein is encoded by any TEL/AML1 gene sequence known in the art. In another embodiment, the TEL/AML1 protein is any TEL/AML1 protein known in the art. In another embodiment, the TVM is an isoform of a TEL/AML1 protein. In another embodiment, the TVM is a homologue of a TEL/AML1 protein. In another embodiment, an ETV6/RUNX1 protein is utilized in methods and compositions of the present invention. In another embodiment, the ETV6/RUNX1 protein is encoded by any ETV6/RUNX1 gene sequence known in the art. In another embodiment, the ETV6/RUNX1 protein is any ETV6/RUNX1 protein known in the art. In another embodiment, the TVM is an isoform of an ETV6/RUNX1 protein. In another embodiment, the TVM is a homologue of an ETV6/RUNX1 protein. In another embodiment, the TVM is a fragment of an AML1, TEL/AML1, or ETV6/RUNX1 protein. In another embodiment, the TVM is a fragment of an isoform, homologue, or variant of an AML1, TEL/AML1, or ETV6/RUNX1 protein. Each possibility represents another embodiment of the present invention.

In another embodiment, the TVM is a COL11A1 protein. In another embodiment, the marker is a nucleic acid molecule encoding a COL11A1 protein. In another embodiment, the COL11A1 protein is encoded by a nucleic acid molecule having the sequence set forth in SEQ ID NO: 41. In another embodiment, the COL11A1 protein is encoded by a nucleic acid molecule with the following sequence:

(SEQ ID NO: 41)

```
acacagtactctcagcttgaggtggaagcccctcatctgccacattctga
aggcagggcccggcagaggaaggatcagagggtcgcggccggagggtccc
ggccggtggggccaactcagagggagaggaaagggctagagacacgaaga
acgcaaaccatcaaatttagaagaaaaagcccatgactattccccctctc
cctccccaatggctgtgtagcaaacatccctggcgataccaggaaaggac
gaagaggtctgcagtcgcaatttcgtgggttgagttcacagagtgagtgc
ggggctcggagatggagccgtggtcctctaggtggaaaacgaaacggtgg
ctctgggatttcaccgtaacaaccctcgcattgaccacctcaccaagcta
```

-continued

```
gagaggtcagaggagctgctccagttgatgtactaaaagcactagatttt
cacaattctccagagggaatatcaaaaacaacgggattagcacaaacaga
aagaattctaaaggctcagatactgcttacagagatcaaagcaagcacaa
ctcagtgccccaacaaaacagttataccaggtggaactacccagaagact
atcaatactatttacagtaaaaccaaaaaaaggaattcagtctaccatta
tctatatataatgagcatggtattcagcaaattggtgagaggagggagat
cacctgatactgatgaagaccacactggaaaacctgccccagaagactat
cccctcacagaactgttaacatcgctgacgggaagtggcatcgggtagca
atcagcgtggagaagaaaactgtgacaatgattgagattgtaagaagaaa
accacgaaaccacttgatagaagtgagagagcaattgagataccaatgga
atcacggataggaacaaggattaggatgaagaagtattgaggggacatt
cagcagtattgatcacaggtgatcccaaggcagcatatgactactgtgag
cattatagtccagactgtgactcacagcacccaaggctgctcaagctcag
gaacctcagatagatgagtatgcaccagaggatataatcgaatatgacta
tgagtatggggaagcagagtataaagaggctgaaagtgtaacagagggac
ccactgtaactgaggagacaatagcacagacggaggcaaacatcgttgat
gattttcaagaatacaactatggaacaatggaaagttaccagacagaagc
tcctaggcatgtttctgggacaaatgagccaaatccagttgaagaaatat
ttactgaagaatatctaacgggagaggattatgattcccagaggaaaaat
tctgaggatacactatatgaaaacaaagaaatagacggcagggattctga
tcttctggtagatggagatttaggcgaatatgatttttatgaatataaag
aatatgaagataaaccaacaagccccccctaatgaagaatttggtccaggt
gtaccagcagaaactgatattacagaaacaagcataaatggccatggtgc
atatggagagaaaggacagaaaggagaaccagcagtggttgagcctggta
tgcttgtcgaaggaccaccaggaccagcaggacctgcaggtattatgggt
cctccaggtctacaaggccccactggacccccctggtgaccctggcgatag
gggcccccccaggacgtcctggcttaccaggggctgatggtctacctggtc
tcctggtactatgttgatgttaccgttccgttatggtggtgatggttcca
aaggaccaaccatctctgctcaggaagctcaggctcaagctattcttcag
caggctcggattgctctgagaggcccacctggcccaatgggtctaactgg
aagaccaggtcctgtgggggggcctggttcatctggggccaaaggtgaga
gtggtgatccaggtcctcagggccctcgaggcgtccagggtccccctggt
ccaacgggaaaacctggaaaaaggggtcgtccaggtgcagatggaggaag
aggaatgccaggagaacctggggcaaagggagatcgagggtttgatggac
ttccgggtctgccaggtgacaaaggtcacaggggtgaacgaggtcctcaa
ggtcctccaggtcctcctggtgatgatggaatgaggggagaagatggaga
aattggaccaagaggtcttccaggtgaagctggcccacgaggtttgctgg
gtccaaggggaactccaggagctccagggcagcctggtatggcaggtgta
gatggcccccccaggaccaaaagggaacatgggtccccaaggggagcctgg
gcctccaggtcaacaagggaatccaggacctcagggtcttcctggtccac
aaggtccaattggtcctcctggtgaaaaaggaccacaaggaaaaccagga
```

-continued cttgctggacttcctggtgctgatgggcctcctggtcatcctgggaaaga aggccagtctggagaaaaggggggctctgggtccccctggtccacaaggtc ctattggatacccgggcccccggggagtaaagggagcagatggtgtcaga ggtctcaagggatctaaaggtgaaaagggtgaagatggttttccaggatt caaaggtgacatgggtctaaaaggtgacagaggagaagttggtcaaattg gcccaagaggggaagatggccctgaaggacccaaaggtcgagcaggccca actggagacccaggtccttcaggtcaagcaggagaaaagggaaaacttgg agttccaggattaccaggatatccaggaagacaaggtccaaagggttcca ctggattccctgggtttccaggtgccaatggagagaaaggtgcacgggga gtagctggcaaaccaggccctcggggtcagcgtggtccaacgggtcctcg aggttcaagaggtgcaagaggtcccactgggaaacctgggccaaagggca cttcaggtggcgatggccctcctggccctccaggtgaaagaggtcctcaa ggacctcagggtccagttggattccctggaccaaaaggccctcctggacc acctgggaaggatgggctgccaggacaccctgggcaacgtggggagactg gatttcaaggcaagaccggccctcctgggccagggggagtggttggacca cagggaccaaccggtgagactggtccaataggggaacgtgggcatcctgg ccctcctggccctcctggtgagcaaggtcttcctggtgctgcaggaaaag aaggtgcaaagggtgatccaggtcctcaaggtatctcagggaaagatgga ccagcaggattacgtggtttcccaggggaaagaggtcttcctggagctca gggtgcacctggactgaaaggaggggaaggtccccagggcccaccaggtc cagttggctcaccaggagaacgtgggtcagcaggtacagctggcccaatt ggtttaccagggcgcccgggacctcagggtcctcctggtccagctggaga gaaaggtgctcctggagaaaaaggtccccaagggcctgcagggagagatg gagttcaaggtcctgttggtctcccagggccagctggtcctgccggctcc cctggggaagacggagacaagggtgaaattggtgagccgggacaaaaagg cagcaagggtgacaagggagaaaatggccctcccggtcccccaggtcttc aaggaccagttggtgcccctggaattgctggaggtgatggtgaaccaggt cctagaggacagcaggggatgtttgggcaaaaaggtgatgagggtgccag aggcttccctggacctcctggtccaataggtcttcagggtctgccaggcc cacctggtgaaaaaggtgaaaatggggatgttggtcccatggggccacct ggtcctccaggcccaagaggccctcaaggtcccaatggagctgatggacc acaaggacccccagggtctgttggttcagttggtggtgttggagaaaagg gtgaacctggagaagcagggaacccagggcctcctggggaagcaggtgta ggcggtcccaaaggagaaagaggagagaaaggggaagctggtccacctgg agctgctggacctccaggtgccaaggggccaccaggtgatgatggcccta agggtaacccgggtcctgaggattcctggagatcctggtcctcctgggga acctggccctgcaggtcaagatggtgaggtggtgacaagggtgaagatgg agatcctggtcaaccgggtcctcctggcccatctggtgaggctggcccac caggtcctcctggaaaacgaggtcctcctggagctgcaggtgcagaggga agacaaggtgaaaaaggtgctaaggggaagcaggtgcagaaggtcctcc -continued tggaaaaaccggcccagtcggtcctcagggacctgcaggaaagcctggtc cagaaggtcacggggcatccctggtcctgtgggagaacaaggtctccctg gagctgcaggccaagatggaccacctggtcctatgggacctcctggctta cctggtctcaaaggtgaccctggctccaagggtgaaaagggacatcctgg ataattggcctgattggtcctccaggagaacaaggggaaaaaggtgaccg agggctccctggaactcaaggatctccaggagcaaaaggggatgggggaa ttcctggtcctgctggtcccttaggtccacctggtcctccaggataccag gtcctcaaggcccaaagggtaacaaaggctctactggacccgctggccag aaaggtgacagtggtcaccagggcctcctgggtctccaggtccacctggt gaagtcattcagccataccaatcagtcctccaaaaaaacgagaagacata ctgaaggcatgcaagcagatgcagatgataatattcttgattactcggat ggaatggaagaaatataggaccctcaattccctgaaacaagacattgagc atatgaaataccaatgggtactcagaccaatccagcccgaacttgtaaag acctgcaactcagccatcctgacttcccagatggtgaatattggattgat cctaaccaaggagctcaggagattccacaaagatactgtaatttcacatc tggtggtgagacttgcatttatccagacaaaaaatctgagggagtaagaa tttcatcatggccaaaggagaaaccaggaagaggatagtgaatttaagag gggaaaactgcatcatacttagatgagaaggaaattccatcaatatggtg caaatgacattcctgaaacactgactgcctctgctcggcaaaatttcacc taccactgtcatcagtcagcagcctggtatgatgtgtcatcaggaagtta tgacaaagcacttcgcacctgggatcaaatgatgaggagatgtcctatga caataatccattatcaaaacactgtatgatggagtgcgtccagaaaaggc tatgaaaagactgtcattgaaatcaatacaccaaaaattgatcaagtacc tattgagatgtcatgatcaatgactaggtgatcagaatcagaagttcgga tttgaagaggtcctgatgattcaggctaagattaagacaaagaacatatc aaatcaacagaaaatataccaggtgccaccaacccattagtgccacatgc aagattgaataaggatggtatagaaaacaacgctgcatatacaggtacca tttaggaaataccgatgcctagtgggggcagaatcacatggcaaaagcat gaaaatcataaagatataagaggtgtggctaagatggaaacagggctgat tcttgattcccaattctcaactctccattcctatttgaatactaggtgct gtagaaaacaaaaaaagaaaaatatatattcataaaaaatatggtgctca ttctcatccatccaggatgtactaaaacagtgtgataataaattgtaatt attagtgtacagactatactgttatctgtgtccataccaaaacttgcacg tgtccctgaattccatctgactctaatatatgagaattgcagaactctga tggcaataaatatatgtattatgaaaaaataaagagtaatactgatgact ctaagtccctactaggttaataataaaatgcctagtatatattgatgaga agagttcaattatttgatgtcgccaacaaaattctcagagggcaaaaatc tggaagacttaggaagcacactctgatcaactcactctgccgacagtcaa ttgctgaatttcagccaaaaatattatgcattagatgcatattcaaggct atacctcaaactattcactcagaatccaggatttcacaggatacagtata tatggaaaacaagcaagatatatattggacagggaaatgtgtgtaagaaa -continued

```
gtatattaacaaatcaatgcctccgtcaagcaaacaatcatatgtatact
attactacgttatctcatctccttgattcagtgtgcttcaataatgcagg
ttaatattaaagatggaaattaagcaattatttatgaatagtgcaatgtt
agattacttatcaatcaagacttgaatttgattctaagagcatattataa
cagtctcgaaaattatatacttgcccaacaaatattactataccatcaag
ataatatataaatcatttgacctacctaattgctaaatgaataacatatg
gtggactgttattaagagtatttgattaagtcattcaggaaaatctaaac
ttattaccactaaggtatttactttaaggtagcttgaaatagcaatacaa
tttaaaaattaaaaactgaattagtatctatataagtaatatatgtaaga
cttgaaaataaatgattatacttatataaagtgttaaattaattgatacc
agatttcactggaacagatcaactgataatttatgacaaaagaacatacc
tgtaatattgaaattaaaaagtgaaatagtcataaagaatactatatatt
gaaatcgagtagtaaatgtccttttaagaagggagatatgaatccaataa
ataaactcaagtcttggctacctgga.
```

In another embodiment, the COL11A1 protein is encoded by a nucleic acid molecule having a sequence set forth in GenBank Accession No. NM_001854. In another embodiment, the COL11A1 protein is encoded by a nucleic acid molecule having a sequence selected from those set forth in GenBank Accession No. NM_080629, NM_080630, J04177, AB208844, and AB208844. In another embodiment, the COL11A1 protein has an AA sequence set forth in one of the above GenBank entries. In another embodiment, the COL11A1 protein has an AA sequence set forth in GenBank Accession No. NP_542196, NP_542197, AAA51891, or BAD92081. In another embodiment, the COL11A1 protein is encoded by a COL11A transcript variant A. In another embodiment, the COL11A1 protein is encoded by a COL11A transcript variant B. In another embodiment, the COL11A1 protein is encoded by a COL11A transcript variant C. In another embodiment, the COL11A1 protein is a COL11A isoform A. In another embodiment, the COL11A1 protein is a COL11A isoform B. In another embodiment, the COL11A1 protein is a COL11A isoform C. In another embodiment, the COL11A1 protein is encoded by any other COL11A1 gene sequence known in the art. In another embodiment, the COL11A1 protein is any other COL11A1 protein known in the art. In another embodiment, the TVM is an isoform of a COL11A1 protein. In another embodiment, the TVM is a homologue of a COL11A1 protein. In another embodiment, the TVM is a variant of a COL11A1 protein. In another embodiment, the TVM is a fragment of a COL11A1 protein. In another embodiment, the TVM is a fragment of an isoform, homologue, or variant of a COL11A1 protein. Each possibility represents another embodiment of the present invention.

In another embodiment, the TVM is a DEEB1 protein. In another embodiment, the marker is a nucleic acid molecule encoding a DE1-B1 protein. In another embodiment, the DE1-B1 protein is encoded by a nucleic acid molecule having a sequence set forth in GenBank Accession No. BC033298. In another embodiment, the DEFB1 protein is encoded by a nucleic acid molecule having a sequence selected from those set forth in GenBank Accession No. BC047677, NM_005218, U73945, Z50788, and X92744. In another embodiment, the DE1-B1 protein has an AA sequence set forth in one of the above GenBank entries. In another embodiment, the DE1-131 protein has an AA sequence selected from the sequences set forth in GenBank Accession No. NP_005209, AAH33298, AAH47677, CAA63405, and CAA90650. In another embodiment, the DEEB1 protein is encoded by any other DEEB1 gene sequence known in the art. In another embodiment, the DEFB1 protein is any other DEFB1 protein known in the art. In another embodiment, the TVM is an isoform of a DE1-B1 protein. In another embodiment, the TVM is a homologue of a DEFB1 protein. In another embodiment, the TVM is a variant of a DEEB1 protein. In another embodiment, the TVM is a fragment of a DEFB1 protein. In another embodiment, the TVM is a fragment of an isoform, homologue, or variant of a DE1-B1 protein. Each possibility represents another embodiment of the present invention.

In another embodiment, the TVM is an EPB41L3 protein. In another embodiment, the marker is a nucleic acid molecule encoding an EPB41L3 protein. In another embodiment, the TVM is a homologue of an EPB41L3 precursor protein. In another embodiment, the TVM is a variant of an EPB41L3 precursor protein. In another embodiment, the TVM is an isoform of an EPB41L3 precursor protein. In another embodiment, the TVM is a fragment of an EPB41L3 protein. In another embodiment, the TVM is a fragment of an isoform, homologue, or variant of an EPB41L3 protein. Each possibility represents another embodiment of the present invention.

In another embodiment, the TVM is an F2RL1 protein. In another embodiment, the marker is a nucleic acid molecule encoding an F2RL1 protein. In another embodiment, the F2RL1 protein is encoded by a nucleic acid molecule having a sequence set forth in GenBank Accession No. BC012453. In another embodiment, the F2RL1 protein is encoded by a nucleic acid molecule having a sequence selected from those set forth in GenBank Accession No. BC018130, U34038, BC012453, BC018130, BT009856, AY336105, and NM_005242. In another embodiment, the F2RL1 protein has an AA sequence set forth in one of the above GenBank entries. In another embodiment, the F2RL1 protein has an AA sequence selected from the sequences set forth in GenBank Accession No. NP_005233, AAB47871, AAH12453, AAH18130, AAP88858, and AAP97012. In another embodiment, the F2RL1 protein is encoded by any other F2RL1 gene sequence known in the art. In another embodiment, the F2RL1 protein is any other F2RL1 protein known in the art. In another embodiment, the TVM is an isoform of an F2RL1 protein. In another embodiment, the TVM is a homologue of an F2RL1 protein. In another embodiment, the TVM is a variant of an F2RL1 protein. In another embodiment, a coagulation factor II (thrombin) receptor-like 1 (F2RL1) precursor protein is utilized in methods and compositions of the present invention. In another embodiment, the F2RL1 precursor protein is encoded by a gene having a sequence set forth in GenBank Accession No. NP_005233. In another embodiment, the F2RL1 precursor protein is encoded by any F2RL1 precursor gene sequence known in the art. In another embodiment, the F2RL1 precursor protein is any F2RL1 precursor protein known in the art. In another embodiment, the TVM is an isoform of a F2RL1 precursor protein. In another embodiment, the TVM is a fragment of an F2RL1 protein or precursor thereof. In another embodiment, the TVM is a fragment of an isoform, homologue, or variant of an F2RL1 protein or precursor thereof. Each possibility represents another embodiment of the present invention.

In another embodiment, the TVM is a GPM6B protein. In another embodiment, the marker is a nucleic acid molecule encoding a GPM6B protein. In another embodiment, the GPM6B protein is encoded by a nucleic acid molecule having a sequence set forth in GenBank Accession No. BC008151. In another embodiment, the GPM6B protein is encoded by a nucleic acid molecule having a sequence selected from those set forth in GenBank Accession No. BC047295, NM_005278, NM_001001994, NM_001001995, NM_001001996, AK095657, AB209525, and U45955. In another embodiment, the GPM6B protein has an AA sequence set forth in one of the above GenBank entries. In another embodiment, the GPM6B protein has an AA sequence selected from the sequences set forth in GenBank Accession No. NP_005269, AAH08151, BAC04600, BAD92762, and AAB16888. In another embodiment, the GPM6B protein is encoded by a transcript variant 1 of a GPM6B-encoding RNA. In another embodiment, the GPM6B protein is encoded by a transcript variant 2 of a GPM6B-encoding RNA. In another embodiment, the GPM6B protein is encoded by a transcript variant 3 of a GPM6B-encoding RNA. In another embodiment, the GPM6B protein is encoded by a transcript variant 4 of a GPM6B-encoding RNA. In another embodiment, the GPM6B protein is encoded by any other GPM6B gene sequence known in the art. In another embodiment, the GPM6B protein is a GPM6B isoform 1. In another embodiment, the GPM6B protein is a GPM6B isoform 2. In another embodiment, the GPM6B protein is an M6b-2. In another embodiment, the GPM6B protein is a GPM6B isoform 3. In another embodiment, the TVM is another isoform of a GPM6B protein. In another embodiment, the GPM6B protein is any other GPM6B protein known in the art. In another embodiment, the TVM is a homologue of a GPM6B protein. In another embodiment, the TVM is a variant of a GPM6B protein. In another embodiment, the TVM is a fragment of a GPM6B protein. In another embodiment, the TVM is a fragment of an isoform, homologue, or variant of a GPM6B protein. Each possibility represents another embodiment of the present invention.

In another embodiment, the TVM is an LZTS1 protein. In another embodiment, the marker is a nucleic acid molecule encoding a LZTS1 protein. In another embodiment, the LZTS1 protein is encoded by a nucleic acid molecule having a sequence set forth in GenBank Accession No. NM_021020. In another embodiment, the LZTS1 protein is encoded by a nucleic acid molecule having a sequence selected from those set forth in GenBank Accession No. AF123659, BC075006, AF123654, AF123655, AF123656, AF123657, AF123658, BC075006, BC075007, and BC075007. In another embodiment, the LZTS1 protein has an AA sequence set forth in one of the above GenBank entries. In another embodiment, the LZTS1 protein has an AA sequence selected from the sequences set forth in NP_066300, AAD23833, AAD23835, AAD23836, AAD23837, AAD23838, AAD23839, AAD23840, AAH75006 and AAH75007. In another embodiment, the LZTS1 protein is encoded by any other LZTS1 gene sequence known in the art. In another embodiment, the LZTS1 protein is any other LZTS1 protein known in the art. In another embodiment, the TVM is an isoform of a LZTS1 protein. In another embodiment, the TVM is a homologue of a LZTS1 protein. In another embodiment, the TVM is a variant of a LZTS1 protein. In another embodiment, an E16T8 FEZ1 or a fasciculation and elongation protein zeta 1 (FEZ1) protein is utilized in methods and compositions of the present invention. In another embodiment, the FEZ1 protein is encoded by any FEZ1 gene sequence known in the art. In another embodiment, the FEZ1 protein is any FEZ1 protein known in the art. In another embodiment, the TVM is an isoform of a FEZ1 protein. In another embodiment, the TVM is a homologue of a FEZ1 protein. In another embodiment, a zygin I protein is utilized in methods and compositions of the present invention. In another embodiment, the zygin I protein is encoded by any zygin I gene sequence known in the art. In another embodiment, the zygin I protein is any zygin I protein known in the art. In another embodiment, the TVM is an isoform of a zygin I protein. In another embodiment, the TVM is a homologue of a zygin I protein. In another embodiment, a LAPSER1 protein is utilized in methods and compositions of the present invention. In another embodiment, the LAPSER1 protein is encoded by any LAPSER1 gene sequence known in the art. In another embodiment, the LAPSER1 protein is any LAPSER1 protein known in the art. In another embodiment, the TVM is an isoform of a LAPSER1 protein. In another embodiment, the TVM is a homologue of a LAPSER1 protein. In another embodiment, the TVM is a fragment of a LZTS1, FEZ1, zygin I, or LAPSER1 protein. In another embodiment, the TVM is a fragment of an isoform, homologue, or variant of a LZTS1, FEZ1, zygin I, or LAPSER1 protein. Each possibility represents another embodiment of the present invention.

In another embodiment, the TVM is a BLAME protein. In another embodiment, the marker is a nucleic acid molecule encoding a BLAME protein. In another embodiment, the BLAME protein is encoded by a nucleic acid molecule having a sequence set forth in GenBank Accession No. AK074669. In another embodiment, the BLAME protein is encoded by a nucleic acid molecule having a sequence selected from those set forth in GenBank Accession No. BC109194, NM_020125, AF144235, or AF146761. In another embodiment, the BLAME protein is encoded by a FLJ90188 cDNA. In another embodiment, the BLAME protein has an AA sequence set forth in one of the above GenBank entries. In another embodiment, the BLAME protein has an AA sequence selected from the sequences set forth in GenBank Accession No. NP_064510, AAD33923, AAF67470, AAI09195, and BAC11123. In another embodiment, the BLAME protein is referred to as "SLAMF8." In another embodiment, the BLAME protein is encoded by any other BLAME gene sequence known in the art. In another embodiment, the BLAME protein is any other BLAME protein known in the art. In another embodiment, the TVM is an isoform of a BLAME protein. In another embodiment, the TVM is a homologue of a BLAME protein. In another embodiment, the TVM is a variant of a BLAME protein. In another embodiment, a BCM-like membrane protein precursor or IgSF protein is utilized in methods and compositions of the present invention. In another embodiment, the protein is encoded by any BCM-like membrane protein precursor or IgSF protein gene sequence known in the art. In another embodiment, the protein is any BCM-like membrane protein precursor or IgSF protein known in the art. In another embodiment, the TVM is an isoform of a BCM-like membrane protein precursor or IgSF protein. In another embodiment, the TVM is a homologue of a BCM-like membrane protein precursor or IgSF protein. In another embodiment, an FLJ20442 protein is utilized in methods and compositions of the present invention. In another embodiment, the FLJ20442 protein is encoded by any FLJ20442 gene sequence known in the art. In another embodiment, the FLJ20442 protein is any FLJ20442 protein known in the art. In another embodiment, the TVM is an isoform of an FLJ20442 protein. In another embodiment, the TVM is a homologue of an FLJ20442 protein. In another embodiment, the TVM is a fragment of a BLAME, IgSF, or FLJ20442 protein. In another embodiment, the TVM is a fragment of an isoform, homologue, or variant of a BLAME, IgSF, or FLJ20442 protein. Each possibility represents another embodiment of the present invention.

In another embodiment, the TVM is a SPON1 protein. In another embodiment, the marker is a nucleic acid molecule encoding a SPON1 protein. In another embodiment, the SPON1 protein is encoded by a nucleic acid molecule having a sequence set forth in GenBank Accession No. NM_006108. In another embodiment, the SPON1 protein is encoded by a nucleic acid molecule having a sequence selected from those set forth in GenBank Accession No. NM_006108, AB051390, AK074803, AK074803, NP_006099, and BC041974. In another embodiment, the SPON1 protein is encoded by a FLJ90322 cDNA. In another embodiment, the SPON1 protein has an AA sequence set forth in one of the above GenBank entries. In another embodiment, the SPON1 protein has an AA sequence selected from the sequences set forth in GenBank Accession No. BAA34482, BAB18461, BAC11217, AAH19825, and AAH41974. In another embodiment, the SPON1 protein is encoded by a nucleic acid molecule comprising a sequence set forth in BC019825, BC041974, and AB018305. In another embodiment, the SPON1 protein has an AA sequence comprising an AA sequence set forth in one of the above GenBank entries. In another embodiment, the SPON1 protein is encoded by any other SPON1 gene sequence known in the art. In another embodiment, the SPON1 protein is any other SPON1 protein known in the art. In another embodiment, the TVM is an isoform of a SPON1 protein. In another embodiment, the TVM is a homologue of a SPON1 protein. In another embodiment, the TVM is a variant of a SPON1 protein. In another embodiment, a VSGP/F-spondin protein is utilized in methods and compositions of the present invention. In another embodiment, the protein is encoded by any VSGP/F-spondin gene sequence known in the art. In another embodiment, the protein is any VSGP/F-spondin protein known in the art. In another embodiment, the TVM is an isoform of a VSGP/F-spondin protein. In another embodiment, the TVM is a homologue of a VSGP/F-spondin protein. In another embodiment, a KIAA0762 protein is utilized in methods and compositions of the present invention. In another embodiment, the protein is encoded by any KIAA0762 gene sequence known in the art. In another embodiment, the protein is any KIAA0762 protein known in the art. In another embodiment, the TVM is an isoform of a KIAA0762 protein. In another embodiment, the TVM is a homologue of a KIAA0762 protein. In another embodiment, the TVM is a fragment of a SPON1, VSGP/F-spondin, or KIAA0762 protein. In another embodiment, the TVM is a fragment of an isoform, homologue, or variant of a SPON1, VSGP/F-spondin, or KIAA0762 protein. Each possibility represents another embodiment of the present invention.

In another embodiment, the TVM is an STC2 protein. In another embodiment, the marker is a nucleic acid molecule encoding an STC2 protein. In another embodiment, the STC2 protein is encoded by a nucleic acid molecule having a sequence set forth in GenBank Accession No. BC000658. In another embodiment, the STC2 protein is encoded by a nucleic acid molecule having a sequence selected from those set forth in GenBank Accession No. BC006352, BC013958, AF055460, AB012664, AK027390, AK075406, AF098462, AF031036, BT019591, CR541825, NP_003705, and AK095891. In another embodiment, the STC2 protein is encoded by a cDNA selected from FLJ14484 fis, PSEC0097 fis, and FLJ38572 fis. In another embodiment, the STC2 protein has an AA sequence set forth in one of the above GenBank entries. In another embodiment, the STC2 protein has an AA sequence set forth in GenBank Accession No. AAC27036, AAC97948, AAD01922, AAH00658, AAH06352, AAH13958, AAV38398, BAA33489, and CAG46624. In another embodiment, the STC2 protein is encoded by any other STC2 gene sequence known in the art. In another embodiment, the STC2 protein is any other STC2 protein known in the art. In another embodiment, the TVM is an isoform of an STC2 protein. In another embodiment, the TVM is a homologue of an STC2 protein. In another embodiment, a STC2 precursor protein is utilized in methods and compositions of the present invention. In another embodiment, the protein is encoded by any STC2 precursor gene sequence known in the art. In another embodiment, the protein is any STC2 precursor protein known in the art. In another embodiment, the TVM is an isoform of an STC2 precursor protein. In another embodiment, the TVM is a homologue of an STC2 precursor protein. In another embodiment, the TVM is a variant of an STC2 protein. In another embodiment, the TVM is a fragment of a STC2 protein or precursor thereof. In another embodiment, the TVM is a fragment of an isoform, homologue, or variant of a STC2 protein or precursor thereof. Each possibility represents another embodiment of the present invention.

In another embodiment, the TVM is a TNFAIP6 protein. In another embodiment, the marker is a nucleic acid molecule encoding a TNFAIP6 protein. In another embodiment, the TNFAIP6 protein is encoded by a nucleic acid molecule having a sequence set forth in GenBank Accession No. BC030205. In another embodiment, the TNFAIP6 protein is encoded by a nucleic acid molecule having a sequence selected from those set forth in GenBank Accession No. NM_007115, M31165, AJ421518, and AJ419936. In another embodiment, the TNFAIP6 protein has an AA sequence set forth in one of the above GenBank entries. In another embodiment, the TNFAIP6 protein has an AA sequence selected from the sequences set forth in GenBank entries NP_009046, AAB00792, AAH30205, CAD12353, and CAD13434. In another embodiment, the TNFAIP6 protein is encoded by a nucleic acid molecule comprising a sequence set forth in GenBank entry BC039384. In another embodiment, the TNFAIP6 protein has an AA sequence comprising an AA sequence set forth in GenBank entry BC039384. In another embodiment, the TNFAIP6 protein is encoded by any other TNFAIP6 gene sequence known in the art. In another embodiment, the TNFAIP6 protein is any other TNFAIP6 protein known in the art. In another embodiment, the TVM is an isoform of a TNFAIP6 protein. In another embodiment, the TVM is a homologue of a TNFAIP6 protein. In another embodiment, the TVM is a variant of a TNFAIP6 protein. In another embodiment, a TNFAIP6 precursor protein is utilized in methods and compositions of the present invention. In another embodiment, the protein is encoded by any TNFAIP6 precursor gene sequence known in the art. In another embodiment, the protein is any TNFAIP6 precursor protein known in the art. In another embodiment, the TVM is an isoform of a TNFAIP6 precursor protein. In another embodiment, the TVM is a homologue of a TNFAIP6 precursor protein. In another embodiment, a tumor necrosis factor-stimulated gene 6 (TSG-6) protein is utilized in methods and compositions of the present invention. In another embodiment, the protein is encoded by any TSG-6 gene sequence known in the art. In another embodiment, the protein is any TSG-6 protein known in the art. In another embodiment, the TVM is an isoform of a TSG-6 protein. In another embodiment, the TVM is a homologue of a TSG-6 protein. In another embodiment, the TVM is a fragment of a TNFAIP6 or TSG-6 protein. In another embodiment, the TVM is a fragment of an isoform, homologue, or variant of a TNFAIP6 or TSG-6 protein. Each possibility represents another embodiment of the present invention.

In another embodiment, the TVM is a TNFRSF21 protein. In another embodiment, the marker is a nucleic acid molecule encoding a TNFRSF21 protein. In another embodiment, the TNFRSF21 protein is encoded by a nucleic acid molecule having a sequence set forth in GenBank Accession No. BC010241. In another embodiment, the TNFRSF21 protein is encoded by a nucleic acid molecule having a sequence selected from those set forth in GenBank Accession No. BC017730, NM_014452, AY358304, BC005192, BC015466, AB209394, AJ420531, AF068868, AF208860, BC010241, BT007420, NP_055267, or CR457190. In another embodiment, the TNFRSF21 protein has an AA sequence set forth in one of the above GenBank entries. In another embodiment, the TNFRSF21 protein is encoded by any other TNFRSF21 gene sequence known in the art. In another embodiment, the TNFRSF21 protein is any other TNFRSF21 protein known in the art. In another embodiment, the TVM is an isoform of a TNFRSF21 protein. In another embodiment, the TVM is a homologue of a TNFRSF21 protein. In another embodiment, the TVM is a variant of a TNFRSF21 protein. In another embodiment, a TNFR-related death receptor-6 (DR6) protein is utilized in methods and compositions of the present invention. In another embodiment, the protein is encoded by any DR6 gene sequence known in the art. In another embodiment, the protein is any DR6 protein known in the art. In another embodiment, the TVM is an isoform of a DR6 protein. In another embodiment, the TVM is a homologue of a DR6 protein. In another embodiment, a TNFRSF21 precursor protein is utilized in methods and compositions of the present invention. In another embodiment, the protein is encoded by any TNFRSF21 precursor gene sequence known in the art. In another embodiment, the protein is any TNFRSF21 precursor protein known in the art. In another embodiment, the TVM is an isoform of a TNFRSF21 precursor protein. In another embodiment, the TVM is a homologue of a TNFRSF21 precursor protein. In another embodiment, the TVM is a fragment of a TNFRSF21 protein, DR6 protein, or precursor thereof. In another embodiment, the TVM is a fragment of an isoform, homologue, or variant of a TNFRSF21 protein, DR6 protein, or precursor thereof. Each possibility represents another embodiment of the present invention.

In another embodiment, the TVM is an FZD10 protein. In another embodiment, the marker is a nucleic acid molecule encoding an FZD10 protein. In another embodiment, the FZD10 protein is encoded by a nucleic acid molecule having a sequence set forth in GenBank Accession No. AB027464. In another embodiment, the FZD10 protein is encoded by a nucleic acid molecule having a sequence selected from those set forth in GenBank Accession No. BC070037, BC074997, BC074998, NP_009128, and NM_007197. In another embodiment, the FZD10 protein has an AA sequence set forth in one of the above GenBank entries. In another embodiment, the FZD10 protein is encoded by any other FZD10 gene sequence known in the art. In another embodiment, the FZD10 protein is any other FZD10 protein known in the art. In another embodiment, the TVM is an isoform of an FZD10 protein. In another embodiment, the TVM is a homologue of an FZD10 protein. In another embodiment, the TVM is a variant of an FZD10 protein. In another embodiment, the TVM is a fragment of an FZD10 protein. In another embodiment, the TVM is a fragment of an isoform, homologue, or variant of an FZD10 protein. Each possibility represents another embodiment of the present invention.

In another embodiment, the TVM is an HOXA9 protein. In another embodiment, the marker is a nucleic acid molecule encoding an HOXA9 protein. In another embodiment, the HOXA9 protein is encoded by a nucleic acid molecule having the sequence: agtttcataatttccgtgggtcgggccgggcgggccaggcgctgggcacggtgatggccaccactggggccctgggcaactactacgtg gactcgttcctgctgggcgccgacgccgcggatgagctgagcgttggccgctatgcgccggggaccctgggccagcctccccggcagg cggcgacgctggccgagcaccccgacttcagcccgtgcagcttccagtccaaggcgacggtgtttggcgcctcgtggaacccagtgcac gcggcgggcgccaacgctgtacccgctgcggtgtaccaccaccatcaccaccacccctacgtgcacccccaggcgcccgtggcggcgg cggcgccggacggcaggtacatgcgctcctggctggagcccacgcccggtgcgctctccttcgcgggcttgccctccagccggccttatg gcattaaacctgaaccgctgtcggccagaaggggtgactgtcccacgcttgacactcacactttgtccctgactgactatgcttgtggttctcc tccagttgatagagaaaaacaacccagcgaaggcgccttctctgaaaacaatgctgagaatgagagcggcggagacaagcccccccatcga tcccaataacccagcagccaactggcttcatgcgcgctccactcggaaaaagcggtgcccctatacaaaacaccagaccctggaactgga gaaagagtttctgttcaacatgtacctcaccagggaccgcaggtacgaggtggctcgactgctcaacctcaccgagaggcaggtcaagatc tggttccagaaccgcaggatgaaaatgaagaaaatcaacaaagaccgagcaaaagacgagtgatgccatttgggcttatttagaaaaaagg gtaagctagagagaaaaagaaagaactgtccgtccccccttccgccttctcccttttctcacccccaccctagcctccaccatccccgcacaaa gcggctctaaacctcaggccacatcttttccaaggcaaaccctgttcaggctggctcgtaggcctgccgctttgatggaggaggtattgtaag ctttccattttctataagaaaaaggaaaagttgagggggggcattagtgctgatagctgtgtgtgttagcttgtatatatatttttaaaaatctacctgttcctgacttaaaacaaaaggaaagaaactaccttttataatgcacaactgttgatggtaggctgtatagtttttagtctgtgtagttaattta atttgcagtttgtgcggcagattgctctgccaagatacttgaacactgtgttttattgtggtaattatgttttgtgattcaaacttctgtgtactgggt gatgcacccattgtgattgtggaagatagaattcaatttgaactcaggttgtttatgaggggaaaaaaacagttgcatagagtatagctctgtag tggaatatgtcttctgtataactaggctgttaacctatgattgtaaagtagctgtaagaatttcccagtgaaataaaaaaaaattttaagtgttctcg gggatgcatagattcatcattttctccaccttaaaaatgcgggcatttaagtctgtccattatctatatagtcctgtcttgtctattgtatatataatct atatgattaaagaaaatatgcataatcagacaagcttgaatattgtttttgcaccagacgaacagtgaggaaattcggagctatacatatgtgca gaaggttactacctagggtttatgcttaattttaatcggaggaaatgaatgctgattgtaacggagttaattttattgataataaattatacactatg aaaccgccattgggctactgtagatttgtatccttgatgaatctggggtttccatcagactgaacttacactgtatattttgcaatagttacctcaa ggcctactgaccaaattgttgtgttgagatgatatttaactttttgccaaataaaatatattgattcttttctaaaaaaaaaaaaaaaaaaa (SEQ ID No: 42). In another embodiment, the HOXA9 protein is encoded by a nucleic acid molecule having a sequence set forth in GenBank Accession No. BC006537. In another embodiment, the HOXA9 protein is encoded by a nucleic acid molecule having a sequence selected from those set forth in GenBank Accession No. BC010023, NM_152739, U41813, NM_002142, U82759, and BT006990. In another embodiment, the HOXA9 protein has an AA sequence set forth in one of the above GenBank entries. In another embodiment, the HOXA9 protein is encoded by any other HOXA9 gene sequence known in the art. In another embodiment, the HOXA9 protein is any other HOXA9 protein known in the art. In another embodiment, the TVM is an isoform of an HOXA9 protein. In another embodiment, the TVM is a homologue of an HOXA9 protein. In another embodiment, the TVM is a variant of an HOXA9 protein. In another embodiment, the TVM is a fragment of an HOXA9 protein. In another embodiment, the TVM is a fragment of an isoform, homologue, or variant of an HOXA9 protein. Each possibility represents another embodiment of the present invention.

In another embodiment, the TVM is an SLPI protein. In another embodiment, the marker is a nucleic acid molecule encoding an SLPI protein. In another embodiment, the SLPI protein is encoded by a nucleic acid molecule having the sequence: agagtcactcctgccttcaccatgaagtccagcggcc- tcttccccttcctggtgctgcttgccctgggaactctggcaccttgggctgtggaa ggctctggaaagtccttcaaagctggagtctgtcctcctaagaaatctgcccagtg- ccttagatacaagaaacctgagtgccagagtgactg gcagtgtccagg- gaagaagagatgttgtcctgacacttgtggcatcaaatgcctggatcctgttg- acaccccaaacccaacaaggaggaag cctgggaagtgcccagtgacttatggc- caatgtttgatgcttaaccccccaatttctgtgagatggatggccagt- gcaagcgtgacttgaag tgttgcatgggcatgtgtgggaaatcctgcgtttcc- cctgtgaaagcttgattcctgccatatggaggaggctctggagtcctgctctgtgtgg tccaggtcctttccaccctgagacttggctccaccactgatatcctcctttggg- gaaaggcttggcacacagcaggctttcaagaagtgccag ttgatcaat- gaataaataaacgagcctatttctctttgcaaaaaaaaaaaaaaaaaaaa- aaaaaaaa (SEQ ID No: 43). In another embodiment, the SLPI protein is encoded by a nucleic acid molecule having a sequence set forth in GenBank Accession No. BC020708. In another embodiment, the SLPI protein is encoded by a nucleic acid molecule having a sequence selected from those set forth in GenBank Accession No. NM_003064, X04470, X04503, and AF114471. In another embodiment, the SLPI protein has an AA sequence set forth in one of the above GenBank entries. In another embodiment, the SLPI protein is encoded by any other SLPI gene sequence known in the art. In another embodiment, the SLPI protein is any other SLPI protein known in the art. In another embodiment, the TVM is an isoform of an SLPI protein. In another embodiment, the TVM is a homologue of an SLPI protein. In another embodiment, the TVM is a variant of an SLPI protein. In another embodiment, the TVM is a fragment of an SLPI protein. In another embodiment, the TVM is a fragment of an isoform, homologue, or variant of an SLPI protein. Each possibility represents another embodiment of the present invention.

In another embodiment, the TVM is a KIBRA protein. In another embodiment, the marker is a nucleic acid molecule encoding a KIBRA protein. In another embodiment, the KIBRA protein is encoded by a nucleic acid molecule having the sequence: caaccttctcagctacaaatactt- gaagaaacagagcagggagctcaagccagtgggagtcatggcccct- gcctcagggcctgccagcac ggacgctgtgtctgctctgttggaaca- gacagcagtggagctggagaagaggcaggagggcaggagcagcacaca- gacactggaagac agctggaggtatgaggagaccagtgagaat- gaggcagtagccgaggaagaggaggaggaggtggaggaggaggagggag- aagagg atgttttcaccgagaaagcctcacctgatatggatgggtacccagcat- taaaggtggacaaagagaccaacacggagaccccggccccatc ccc- cacagtggtgcgacctaaggaccggagagtgggcaccccgtcccaggggccat- ttcttcgagggagcaccatcatccgctctaagac cttctccccaggac- cccagagccagtacgtgtgccggctgaatcggagtgatagtgacagctc- cactctgtccaaaaagccaccttttgttcg aaactccctggagcgacgc- agcgtccggatgaagcggccttcctcggtcaagtcgctgcgctccgagcgtct- gatccgtacctcgctggac ctggagttagacctgcaggcgacaagaacct- ggcacagccaattgacccaggagatctcggtgctgaaggagctcaaggagc- agctgga acaagccaagagccacggggagaaggagctgccacagtggtt- gcgtgaggacgagcgtttccgcctgctgctgaggatgctggagaag cggca- gatggaccgagcggagcacaagggtgagcttcagacagacaagatgat- gagggcagctgccaaggatgtgcacaggctccga ggccagagctgtaa- ggaacccccagaagttcagtctttcagggagaagatggcatttttcacccgg- cctcggatgaatatcccagctctctct gcagatgacgtctaatcgccagaaaagt- atttcctttgttccactgaccaggctgtgaacattgactgtggctaaagttatt- tatgtggtgttatat gaaggtactgagtcacaagtcctctagtgctcttgttggttt- gaagatgaaccgactttttagtttgggtcctactgttgttattaaaaaaaaaaaa aaaacaaaaaaaaaaaaaaaaaaaaaaaaaa (SEQ ID No: 44). In another embodiment, the KIBRA protein is encoded by a nucleic acid molecule having a sequence set forth in GenBank Accession No. BC004394. In another embodiment, the KIBRA protein is encoded by a nucleic acid molecule having a sequence selected from those set forth in GenBank Accession No. AK001727, NM_015238, BC017746, AF506799, AY189820, AF530058, AB020676, and BX640827. In another embodiment, the KIBRA protein has an AA sequence set forth in one of the above GenBank entries. In another embodiment, the KIBRA protein is encoded by any other KIBRA gene sequence known in the art. In another embodiment, the KIBRA protein is any other KIBRA protein known in the art. In another embodiment, the TVM is an isoform of a KIBRA protein. In another embodiment, the TVM is a homologue of a KIBRA protein. In another embodiment, the TVM is a variant of a KIBRA protein. In another embodiment, the TVM is a fragment of a KIBRA protein. In another embodiment, the TVM is a fragment of an isoform, homologue, or variant of a KIBRA protein. Each possibility represents another embodiment of the present invention.

In another embodiment, the TVM is an IL10RA protein. In another embodiment, the marker is a nucleic acid molecule encoding an IL10RA protein. In another embodiment, the IL10RA protein is encoded by a nucleic acid molecule having the sequence: tggaggcgcgcaggccggctccgctccg- gccccggacgatgcggcgcgcccaggatgctgccgtgcctcgtagtgctg- ctggcggcgc tcctcagcctccgtcttggctcagacgctcatgggacag- agctgcccagccctccgtctgtgtggtttgaagcagaatttttccaccacatcct ccactggacacccatcccaaatcagtctgaaagtacctgctatgaagtggca- ctcctgaggtatggaatagagtcctggaactccatctccaa ctgtagccagaccct- gtcctatgaccttaccgcagtgaccttggacctgtaccacagcaatggctaccgg- gccagagtgcgggctgtggac ggcagccggcactccaactggaccgtcac- caacacccgcttctctgtggatgaagtgactctgacagttggcagtgtgaacc- tagagatcc acaatggcttcatcctcgggaagattcagctacccaggcccaa- gatggcccccgcaaatgacacatatgaaagcatcttcagtcacttccga gagtat- gagattgccattcgcaaggtgccgggaaacttcacgttcacacacaaga- aagtaaaacatgaaaacttcagcctcctaacctctgg agaagtgggagagt- tctgtgtccaggtgaaaccatctgtcgcttcccgaagtaacaaggggatgtggtc- taaagaggagtgcatctccctca ccaggcagtatttcaccgtgaccaacgtcat- catcttctttgcctttgtcctgctgctctccggagccctcgcctactgcctggccc- tccagctg tatgtgcggcgccgaaagaagctacccagtgtcctgctctt- caagaagcccagccccttcatcttcatcagccagcgtccctccccagagac ccaagacaccatccacccgcttgatgaggaggcctttttgaaggtgtccccag- agctgaagaacttggacctgcacggcagcacagacagt ggctttggcagcac- caagccatccctgcagactgaagagccccagttcctcctccctgaccct- cacccccaggctgacagaacgctggga aacggggagcccctgtgctg- gggacagctgcagtagtggcagcagcaatagcacagacagcgggatctg- cctgcaggagcccagcc tgagccccagcacagggcccacctgg- gagcaacaggtggggagcaacagcaggggccaggatgacagtggcattgact- tagttcaaaa ctctgagggccgggctggggacacacagggtggctcggccttg- ggccaccacagtcccccggagcctgaggtgcctggggaagaaga cccag- ctgctgtggcattccagggttacctgaggcagaccagatgtgct- gaagagaaggcaaccaagacaggctgcctggaggaagaat cgccccttgaca- gatggccttggccccaaattcgggagatgcctggttgatgaggcaggcttgcatc- caccagccctggccaagggctattt gaaacaggatcctctagaaatg- actctggcttcctcaggggccccaacgggacagtggaaccagcccactgag- gaatggtcactcctggc cttgagcagctgcagtgacctgggaatatctgactg- gagtttgcccatgaccttgcccctctaggctgtgtggcagccccaggtggtctcct gggcagctttaactcagacctggtcaccctgcccctcatctctagcctgcagt- caagtgagtgactcgggctgagaggctgcttttgattttag ccatgcctgc- tcctctgcctggaccaggaggagggcccctggggcagaagttaggcacg- aggcagtctgggcacttttctgcaagtccact ggggctggccccagccagg- ccctgcagggctggtcagggtgtctggggcaggaggaggccaactcactgaactagtgcagggtatgtg ggtggcactgacctgttctgttgactggggc-
cctgcagactctggcagagctgagaagggcagggaccttctccctcctag-
gaactctttcc tgtatcataaaggattatttgctcaggggaaccatggggctttctg-
gagttgtggtgaggccaccaggctgaagtcagctcagacccagacc tccctgct-
taggccactcgagcatcagagcttccagcaggaggaagggctgtaggaatgga-
agcttcagggccttgctgctggggtcatttt taggggaaaaggaggatat-
gatggtcacatggggaacctcccctcatcgggcctctggggcaggaagcttgt-
cactggaagatcttaag gtatatattttctggacactcaaacacatcataatggatt-
cactgaggggagacaaagggagccgagaccctggatggggcttccagctcag
aacccatccctctggtgggtacctctggcacccatctgcaaatatctccctctctc-
caacaaatggagtagcatccccctggggcacttgctga ggccaagccactca-
catcctcactttgctgccccaccatcttgctgacaacttccagagaagccatggtt-
ttttgtattggtcataactcagccct ttgggcggcctctgggcttgggcaccagct-
catgccagccccagagggtcagggttggaggcctgtgcttgtgttt-
gctgctaatgtccagc tacagacccagaggataagccactgggcactg-
ggctggggtccctgccttgttggtgttcagctgtgtgattttggactagc-
cacttgtcaga gggcctcaatctcccatctgtgaaataaggactccacctt-
taggggaccctccatgtttgctgggtattagccaagctggtcctgggagaatg
cagatactgtccgtggactaccaagctggcttgtttcttatgccagaggctaaca-
gatccaatgggagtccatggtgtcatgccaagacagta tcagacacag-
ccccagaagggggcattatgggccctgcctccccataggccatttggactct-
gccttcaaacaaaggcagttcagtccaca ggcatggaagctgtgaggg-
gacaggcctgtgcgtgccatccagagtcatctcagccctgcctttctctggagcat-
tctgaaaacagatattct ggcccagggaatccagccatgacccccacccctctgc-
caaagtactcttaggtgccagtctggtaactgaactccctctggaggcaggcttg
agggaggattcctcagggttcccttgaaagctttatttatttattttgttcatttattt-
attggagaggcagcattgcacagtgaaagaattctggat atctcag-
gagccccgaaattctagctctgactttgctgtttccagtggtatgaccttggagaagt-
cacttatcctcttggagcctcagtttcctcat ctgcagaataatgac-
tgacttgtctaattcgtagggatgtgaggttctgctgaggaaatgggtat-
gaatgtgccttgaacacaaagctctgtca ataagtgatacatgtttttattc-
caataaattgtcaagaccacaaaaaaaaaaaaaaaaaaaaaaa-
aaaaaaaaaaaaaaaaaaaaaaaaa aaaaaaaaaaaaaa (SEQ ID No: 45). In another embodiment, the IL10RA protein is encoded by a nucleic acid molecule having a sequence set forth in GenBank Accession No. BC028082. In another embodiment, the IL10RA protein is encoded by a nucleic acid molecule having a sequence selected from those set forth in GenBank Accession No. NM_001558, AB209626, U00672, and BC028082. In another embodiment, the IL10RA protein has an AA sequence set forth in one of the above GenBank entries. In another embodiment, the IL10RA protein is encoded by any other IL10RA gene sequence known in the art. In another embodiment, the IL10RA protein is any other IL10RA protein known in the art. In another embodiment, the TVM is an isoform of an IL10RA protein. In another embodiment, the TVM is a homologue of an IL10RA protein. In another embodiment, the TVM is a variant of an IL10RA protein. In another embodiment, the TVM is a fragment of an IL10RA protein. In another embodiment, the TVM is a fragment of an isoform, homologue, or variant of an IL10RA protein. Each possibility represents another embodiment of the present invention.

In another embodiment, the TVM is an ADAM12 protein. In another embodiment, the marker is a nucleic acid molecule encoding an ADAM12 protein. In another embodiment, the ADAM12 nucleotide is a long isoform of ADAM12. In another embodiment, the ADAM12 nucleotide is a short isoform of ADAM12. In another embodiment, the ADAM12 protein is encoded by a nucleic acid molecule having the sequence: cactaacgctcttcctagtccccgggc-
caactcggacagtttgctcatttattgcaacggtcaaggctggcttgtgc-
cagaacggcgcgcgc gcgacgcacgcacacacacgggggggaaactttttt-
taaaaatgaaaggctagaagagctcagcggcggcgcgggccgt-
gcgcgagggct ccggagctgactcgccgaggcaggaaatccctccgg-
tcgcgacgcccggccccgctcggcgcccgcgtgggatggtgcagcgctcgcc
gccgggcccgagagctgctgcactgaaggccggcgacgatggcagcgcg-
cccgctgcccgtgtcccccgcccgcgccctcctgctcgc cctggccgg-
tgctctgctcgcgccctgcgaggcccgaggggtgagcttatggaaccaagg-
aagagctgatgaagttgtcagtgcctctgtt cggagtggggacctctg-
gatcccagtgaagagcttcgactccaagaatcatccagaagtgctgaatattcgac-
tacaacgggaaagcaaag aactgatcataaatctggaaagaaatgaaggtctcat-
tgccagcagtttcacggaaacccactatctgcaagacggtactgatgtctccctcg
ctcgaaattacacggtaattctgggtcactgttactaccatggacatgtacggggat-
attctgattcagcagtcagtctcagcacgtgttctggt ctcaggggacttattgtgttt-
gaaaatgaaagctatgtcttagaaccaatgaaaagtgcaaccaacagata-
caaactcttcccagcgaagaag ctgaaaagcgtccggggatcatgt-
ggatcacatcacaacacaccaaacctcgctgcaaagaatgtgtttccac-
caccctctcagacatgggc aagaaggcataaaagagagaccct-
caaggcaactaagtatgtggagctggtgatcgtggcagacaaccgaga-
gtttcagaggcaaggaa aagatctggaaaaagttaagcagcgattaatagagat-
tgctaatcacgttgacaagttttacagaccactgaacattcggatcgtgttggtagg
cgtggaagtgtggaatgacatggacaaatgctctgtaagtcaggacccatt-
caccagcctccatgaatttctggactggaggaagatgaagc ttc-
tacctcgcaaatcccatgacaatgcgcagcttgtcagtggggtttatttccaaggg-
accaccatcggcatggccccaatcatgagcatgt gcacggcagaccagt-
ctgggggaattgtcatggaccattcagacaatccccttggtgcagccg-
tgaccctggcacatgagctgggccaca atttcgggatgaatcatgacaca-
ctggacaggggctgtagctgtcaaatggcggttgagaaaggaggctgcatcat-
gaacgcttccaccgg gtacccatttcccatggtgttcagcagttgcagcag-
gaaggacttggagaccagcctggagaaaggaatgggggtgtgcctgtt-
taacctgc cggaagtcagggagtctttcgggggccagaagtgtggga-
acagatttgtggaagaaggagaggagtgtgactgtggggagccagagga
atgtatgaatcgctgctgcaatgccaccacctgtaccctgaagccggac-
gctgtgtgcgcacatgggctgtgctgtgaagactgccagctga agcctgcag-
gaacagcgtgcagggactccagcaactcctgtgacctcccagagactgc-
acaggggccagccctcactgcccagccaac gtgtacctgcacgatgggcact-
catgtcaggatgtggacggctactgctacaatggcatctgccagact-
cacgagcagcagtgtgtcacact ctggggaccaggtgctaaacctgcccctgg-
gatctgctttgagagagtcaattctgcaggtgatccttatggcaactgtggcaaag-
tctcgaa gagaccatgccaaatgcgagatgagagatgctaaatgtg-
gaaaaatccagtgtcaaggaggtgccagccggccagtcattggtaccaatg
ccgtaccatagaaacaaacatcccccctgcagcaaggaggccggat-
tctgtgccgggggacccacgtgtacttgggcgatgacatgccgg
acccagggcagtgcttgcaggcacaaagtgtgcagatggaaaaatctgcct-
gaatcgtcaatgtcaaaatattagtgtctaggggttcacga gtgtgcaat-
gcagtgccacggcagaggggtgtgcaacaacaggaagaactgccactgcga-
ggcccactgggcacctcccactgtgaca agtaggctaggaggaagcaca-
gacagcggccccatccggcaagcagataaccaaggataaccataggaat-
tctggtgaccatcctgtgt cacttgctgccggatagtggatatctcaaaaggaa-
gaccttgatacgactgctgatacaaataagaagaccaccattgaaaaactaaggtg
tgtgcgcccacccggccaccccgtggcaccaaccctgtcaggctcacctcggc-
caccaggaaaaggcctgatgaggaagccgccagat tcctacc-
caccgaaggacaatcccaggagattgctgcagtgtcagaatgagacatcagca-
gacccctcaacggcctgaatgtccctcagcc ccagtcaactcagcg-
agtgcacctcccctccaccgggccccacgtgcacctagcgtccctgcca-
gacccctgccagccaagcctgcactt aggcaggcccaggggacctgtaagc-
caaaccccccctcagaagcctctgcctgcagatcctctggccagaacaactcggct-
cactcatgcc aggccaggaccccaggacaatgggagactgggctccgc-
ctggcacccctcagacctgctccacaatatccacaccaagtgcccagatcc acc-
cacaccgcctatattaagtgagaagccgacaccattacaacagtgaa-
gacagaagtagcactatcatcagctccagaggagattag taccaactataggat-
tatataatgataaaacatcattactataagaactagagctactgccgtcagtgctgt-
gctgtgctatggtgctctgtcta cagcacaggtacttgtaaattattaatt-
tatgcagaatgagattacagtgcagtgcgctgtagtaggcattataccatcact-
gagattccatgg caggaaggcttgagtgcattagtatatagtgaactt-
gaaatatcctgcttgatgggattctggacaggatgtgatgctactgatcaaggcctt
attggaaagcagtcccccaactacccccagctgtgcttatggtaccagatgcagct-
caagagatcccaagtagaatctcagttgattactgga accc-
catctcaggccagagccaaggggcttcaggtccaggctgtgtaggcatcagg-
gaggccctgtgccccttgacaactggcaggca ggctcccagggaca-
cctgggagaaatctggcactggccaggaagctaggtgagaacctgggagca-
gacaggaatcttaaggtgtagcc acaccaggatagagactggaacacta-
gacaagccagaacttgaccctgagctgaccagccgtgagcatgtaggaaggggtctgtagtgtc actcaaggcggtgcttgatagaaatgccaagc- acactattctcgctgtccatctagagcactgccaccagtaggttatttagcagg- gaaag gtggtgatctgtaagaaacctactgcccaggcactgcaaaccgc- cacctccctatactgcaggagctgagcaaatcaccacaaactgtaat acaat- gatcctgtattcagacagatgaggactaccatgggaccacaactattacagatgtg- aaccattaaccagatctagtcaatcaagtctg atactgcaaggacaacttat- taacaatt- aggcagactcatatgcttgcaaaaactacaaccaatggaatgt- gatgacatgggtatagttcatg tctgctatcattattcgtagatattggacaaagaac- cactctatggggcatcctcataccaacttggctgcaggaatcataaaagatgcatta acagagtctgaacctatacttaaacacttgcaacctacctgagagcat- cacagaatgtgataaggaaatcaacttgcttatcaacttcctaaat attat- gagatgtggcagggcagcatccccttgaactcacactcacaaatgcctgactagg- gagccatgatcacaaggtcataaagtgact aatggcatgagaaa- tacaaaaatactcagataaggtaaaatgccatgatgcctctgtcactggactggatt- cacattagaagacaattgacaa cagttacataattcactctgagtgattat- gagaaagccacttaggggtcaacagattcctatgcatgaaacagaaaa- atatgtaccaagaat cttggtttgccttccagaaaacaaaactgcattt- cactttcccggtgttccccactgtatctaggcaacatagtattcatgactatgga- taaactaa acacgtgacacaaacacacacaaaagggaacccagctctaatacat- tccaactcgtatagcatgcatctgtttattctatagttattaagttcttt aaaatgtaaagccatgctggaaaataatactgctgagatacatacagaat- tactgtaactgattacacttggtaattgtactaaagccaaacata tatatactat- taaaaaggtttacagaattttatggtgcattacgtgggcattgtctttttagatgcc- caaatccttagatctggcatgttagcccttcc tccaattataagaggat- atgaaccaaaaaaaaaaaaaaaaaa (SEQ ID No: 1). In another embodiment, the ADAM12 protein is a long isoform of ADAM12. In another embodiment, the ADAM12 protein is a short isoform of ADAM12. In another embodiment, the ADAM12 protein is encoded by a nucleic acid molecule having a sequence set forth in GenBank Accession No. AF023476. In another embodiment, the ADAM12 protein is encoded by a nucleic acid molecule having a sequence set forth in GenBank Accession No. AF023477. In another embodiment, the ADAM12 protein is encoded by a nucleic acid molecule having a sequence set forth in GenBank Accession No. NM_003474. In another embodiment, the ADAM12 protein has an AA sequence set forth in 1 of the above GenBank entries. In another embodiment, the ADAM12 protein is encoded by any other ADAM12 gene sequence known in the art. In another embodiment, the ADAM12 protein is any other ADAM12 protein known in the art. In another embodiment, the TVM is an isoform of an ADAM12 protein. In another embodiment, the TVM is a homologue of an ADAM12 protein. In another embodiment, the TVM is a variant of an ADAM12 protein. In another embodiment, the TVM is a fragment of an ADAM12 protein. In another embodiment, the TVM is a fragment of an isoform, homologue, or variant of an ADAM12 protein. Each possibility represents another embodiment of the present invention.

In another embodiment, the TVM is a PCDH17 protein. In another embodiment, the marker is a nucleic acid molecule encoding a PCDH17 protein. In another embodiment, the PCDH17 protein is encoded by a nucleic acid molecule having a sequence set forth in GenBank Accession No. AL137505. In another embodiment, the PCDH17 protein has an AA sequence set forth in GenBank Accession No. AL137505. In another embodiment, the PCDH17 protein is encoded by any other PCDH17 gene sequence known in the art. In another embodiment, the PCDH17 protein is any other PCDH17 protein known in the art. In another embodiment, the TVM is an isoform of a PCDH17 protein. In another embodiment, the TVM is a homologue of a PCDH17 protein. In another embodiment, the TVM is a variant of a PCDH17 protein. In another embodiment, the TVM is a fragment of a PCDH17 protein. In another embodiment, the TVM is a fragment of an isoform, homologue, or variant of a PCDH17 protein. Each possibility represents another embodiment of the present invention.

In another embodiment, the TVM is an AML-1 protein. In another embodiment, the marker is a nucleic acid molecule encoding an AML-1 protein. In another embodiment, the AML-1 protein is encoded by a nucleic acid molecule having the sequence: catagagccagcgggcgcgggcggg- acgggcgccccgcggccggacccagccagggcaccacgctgcccggcc- ctgcgccgccag gcacttctttccggggctcctagggacgccagaaggaagt- caacctctgctgcttctccttggcctgcgttggaccttcctttttttgttgtttttt ttgtttttcccctttcttccttttgaattaactggcttcttggctggatgtttt- caacttctttcctggctgcgaacttttccccaattgttttccttttaca acagggg- gagaaagtgctctgtggtccgaggcgagccgtgaagttgcgtgtg- cgtggcagtgtgcgtggcaggatgtgcgtgcgtgtgta acccgagccgccc- gatctgtttcgatctgcgccgcggagccctccctcaaggcccgctc- cacctgctgcggttacgcggcgctcgtgggt gttcgtgcctcg- gagcagctaaccggcgggtgctgggcgacggtggaggagtatcgtctcgctg- ctgcccgagtcagggctgagtcacc cagctgatgtagacagtggctg- ccttccgaagagtgcgtgtttgcatgtgtgtgactctgcggctgctcaactcc- caacaaaccagaggacc agccacaaacttaaccaacatccccaaacccgagtt- cacagatgtgggagagctgtagaaccctgagtgtcatcgactgggccttcttatgat tgttgttttaagattagctgaagatctctgaaacgctgaattttctgcact- gagcgttttgacagaattcattgagagaacagagaacatgacaa gtacttctagctcagcactgctccaactactgaagctgattttcaaggctact- taaaaaaatctgcagcgtacattaatggatttctgttgtgttta aattctccacagat- tgtattgtaaatattttatgaagtagagcatatgtatatatttatatatacgtgcacata- cattagtagcactacctttggaagt ctcagctcttgcttttcgggactgaag- ccagttttgcatgataaaagtggccttgttacgggagataattgtgttctgttg- ggactttagacaaaa ctcacctgcaaaaaactgacaggcattaactactg- gaacttccaaataatgtgtttgctgatcgttttactcttcgcataaatattttaggaagtgt atgagaattttgccttcaggaacttttctaacagccaaagacagaacttaacctct- gcaagcaagattcgtggaagatagtctccactttttaatg cactaagcaat- cggttgctaggagcccatcctgggtcagaggccgatccgcagaaccaga- acgttttcccctcctggactgttagtaacttag tctccctcctcccctaac- cacccccgcccccccccacccccccgcagtaataaaggcccctgaacgtgta- tgttggtctcccgggagctgctt gctgaagatccgcgcccctgtcgccgt- ctggtaggagctgtttgcagggtcctaactcaatcggcttgttgt- gatgcgtatccccgtagatgc cagcacgagccgccgcttcacgccgccttc- caccgcgctgagcccaggcaagatgagcgaggcgttgccgc- tgggcgccccggacgcc ggcgctgccctggccggcaagctgag- gagcggcgaccgcagcatggtggaggtgctggccgac- cacccgggcgagctggtgcgcacc gacagccccaacttcctctgct- ccgtgctgcctacgcactggcgctgcaacaagaccctgcccatcgcttt- caaggtggtggccctagggg atgttccagatggcactctggtcactgt- gatggctggcaatgatgaaaactactcggctgagctgagaaatgctaccgcagc- catgaagaac caggttgcaagatttaatgacctcaggtttgtcggtcga- agtggaagagggaaaagcttcactctgaccatcactgtcttcacaaacccaccg caagtcgccacctaccacagagccatcaaaatcacagtggatgggccccg- agaacctcgaagacatcggcagaaactagatgatcagacc aagcccgg- gagcttgtccttttccgagcggctcagtgaactggagcagctgcggcgcacagc- catgagggtcagcccacaccacccagc ccccacgcccaaccctcgtgc- ctccctgaaccactccactgcctttaaccctcagcctcagagtcagatgcaggata- caaggcagatccaac catccccaccgtggtcctacgatcagtcctac- caatacctgggatccattgcctctccttctgtgcacccagcaacgcccattt- cacctggacg tgccagcggcatgacaaccctctctgcagaactttc- cagtcgactctcaacggcacccgacctgacagcgttcagcgacccgcgccagttc cccgcgctgccctccatctccgacccccgcatgcactatccaggcgccttcacc- tactccccgacgccggtcacctcgggcatcggcatcg gcatgtcggc- catgggctcggccacgcgctaccacacctacctgccgccgccc- taccccggctcgtcgcaagcgcagggaggcccgttc caagccagctcg- ccctcctaccacctgtactacggcgcctcggccggctcctaccagactc- catggtgggcggcgagcgctcgccgccg cgcatcctgccgccctgcac- caacgcctccaccggctccgcgctgctcaaccccagcctcccg- aaccagagcgacgtggtggaggccga gggcagccacagcaactcccccac- caacatggcgccctccgcgcgcctggaggaggccgtgtggaggccctact- gaggcgccaggcct ggcccggctgggccccgcgggccgccgccacgcctccgggcgcgcgggcctcctgacgcgacaagcccgccgg-
gatcccgggccc tgggcccggccaccgtcctggggccgagggcgcc-
cgacggccaggatctcgctgtaggtcaggcccgcgcagcctcctgcgcccagaa
gcccacgccgccgccgtctgctggcgccccggccctcgcggaggtgtc-
cgaggcgacgcacctcgagggtgtccgccggccccagca cccaggggac-
gcgctggaaagcaaacaggaagattcccggagggaaactgtgaatgcactgatt-
tagcaatgctgtgaataaaagaaa gatatatacccttgacttaactattaac-
caagttgatattccaaagagtgtggaattaggaggggtgggggagaggagg-
gatgcaactc gccctgtttggcatctaattcttatttttaatttttccgc-
accttatcaattgcaaaatgcgtatttgcatttgggtggtttttatttttatatacgtttatat
aaatatatataaattgagcttgcttctttcttgctttgaccatggaaagaaatatgat-
tcccttttctttaagttttatttaacttttcttttggacttttgg gtagttgttttttttt-
gttttgttttgtttttttgagaaacagctacagctttgggtcatttttaactactgtat-
tcccacaaggaatccccagatatttat gtatcttgatgttcagacatttatgtgttga-
taattttttaattatttaaatgtacttatattaagaaaaatatcaagtactacat-
tttcttttgttcttgata gtagccaaagttaaatgtatcacattgaagaaggcta-
gaaaaaaagaatgagtaatgtgatcgcaggttatccagaagtattgatacattaaa
ctcccatcatgttaatcaaacaagtgagtagctcacgcagcaacgtattaataggat-
tatagacactgagggtcactccaaggatcagaagt atggaattactgccaggct-
caacaagggtctcatatctaacttcctccttaaaacagagaaggtcaatcta-
gaccagagggagaggcaggt gccaataattacatctaggagaggatttga-
tactgcccagggatttgctcaccccaaggtcatctgataatttcaca-
gatgctgtgtaacagaa cacagccaaagtaaactgtgtaggggagccacattta-
cataggaaccaaatcaatgaatttaggggttacgattatagcaatttaagggccac
cagaagcaggcctcgaggagtcaatttgcctctgtgtgcctcagtgga-
gacaagtgggaaaacatggtcccacctgtgcgagacccccctgt cctgtgctgct-
cactcaacaacatctagtgagcatcaccaggctgagaccctaccc-
tatggggtatatgggcattacctgtgcaccagtgtg acaggaaagattc-
atgtcactactgtccgtggctacaattcaaaggtatccaatgtcgctgta-
aatatatggcactattatattggaggatttgg tcagaatgcagttgagtacaactcat-
aaatactaactgctgattagacacatgtgtgctccaaatgatctggtggttatt-
taacgtacctcttaaa attcgttgaaacgatttcaggtcaactctgaagagtattt-
gaaagcaggacttcagaacagtgatgattatatatataaatttaagcattcaaatt
aggcaaatctaggctgcaggcagcaaaaacagctggacttatttaaaacaactt-
gatttgagattcttatatatatattgattatttgattacaca catgcagtag-
cactaggtaagagttaaagagtaaagcagcttatgagtcaggtcgact-
tatctagagaagagctatagcagatctcggaca aactcagaatatattcactacat-
attgacaggattccctccacaactcagatcatatattattccgtattacatat-
tgcagctaaattaccataaa atgtcagcaaatgtaaaaatttaatactga-
aaagcaccattagcccatacccccaaattaaacgtaaatgattattcagcacatgt-
taccatgt ctgacctgcaaaaatgctggagaaaaatgaaggaaaaaattatgat-
ttcagataattctgttaactgaagatattccaactcaaaaccagcctc atgctct-
gattagataatcattacattgaaccatactctcaaagccatgtgtggagggggca-
gtcactattgtaggctcactggattggtcattt agagatcacagactcttaccag-
catatatagtatttaattgatcaaaaaaaatcaaactgtagttgattggcgataggtct-
cacgcaacacattt agtatgtgtgtgtgtgtgcgtgtgtgtgtgtgtgtgaaaaat-
tgcattcattgacttcaggtagattaaggtatctattattcattgccctcagg
aaagttaaggtatcaatgagacccttaagccaatcatgtaataactgcatgtgt-
ctggtccaggagaagtattgaataagccatactactgctt actcatgtccctatttat-
gatttcaacatggatacatatttcagttctttctttttctcactatctgaaaatacat-
ttccctccctctcttccccccaatat ctccctttttttctctcttcctctatcttc-
caaaccccactttctccctcctccttttcctgtgttctcttaagcagatagcacataccccc-
cacccagta ccaaatttcagaacacaagaaggtccagttcttccccccttc-
acataaaggaacatggtttgtcagcctttctcctgtttatgggtttcttccagca
gaacagagacattgccaaccatattggatctgcttgctgtccaaaccagcaa-
actttcctgggcaaatcacaatcagtgagtaaatagacagc ctttctgctgcctt-
gggtttctgtgcagataaacagaaatgctctgattagaaaggaaatgaatggttc-
cactcaaatgtcctgcaatttaggatt gcagatttctgccttgaaatacctgtttct-
ttgggacattccgtcctgatgatttttatttttgttggtttttatttttggggggaatga-
catgtttgggt cttttatacatgaaaatttgtttgacaataatctcacaaaacatattta-
catctgaacaaaatgcctttttgtttaccgtagcgtatacatttgttttgg gat-
tttgtgtgtttgttgggaattttgtttttagccaggtcagtattgatgaggctgatcattt-
ggctcttttttttccttccagaagagttgcatcaac aaagttaattgtatt-
tatgtatgtaaatagattttaagcttcattataaaatattgttaatgcctataactttttttt-
caatttttttgtgtgtgtttctaagga ctttttcttaggtttgctaaatactgtagg-
gaaaaaaatgcttctttctactttgtttattttagactttaaaatgagctacttcttatt-
cacttttgtaaac agctaatagcatggttccaatutttttaagtt-
cactttttttgttctaggggaaatgaatgtgcaaaaaaagaaaaagaactgttggttat-
ttgtgtt attctggatgtataaaaatcaatggaaaaaaataaacttt-
caaattgaaatgacggtataacacatctactgaaaaagcaacgggaaatgtggt
cctatttaagccagcccccacctagggtctatttgtgtggcagttattgggtttggt-
cacaaaacatcctgaaaattcgtgcgtgggcttctttct ccctggtacaaacgtatg-
gaatgcttcttaaaggggaactgtcaagctggtgtcttcagccagatgacat-
gagagaatatcccagaaccctct ctccaaggtgtttctagatagcacagg-
agagcaggcactgcactgtccacagtccacggtacacagtcgggtgggc-
cgcctcccctctcct gggagcattcgtcgtgcccagcctgagcagggcag-
ctggactgctgctgttcaggagccaccagagccttcctctctttgtaccacagtttct
tctgtaaatccagtgttacaatcagtgtgaatggcaaataaacagtttgacaagta-
catacaccataaaaaaaaaaaaaaaaa (SEQ ID No: 40). In another embodiment, the AML-1 protein is encoded by a nucleic acid molecule having a sequence set forth in GenBank Accession No. NM_001001890. In another embodiment, the AML-1 protein is encoded by a nucleic acid molecule having a sequence set forth in GenBank Accession No. NM_001754. In another embodiment, the AML-1 protein has an AA sequence set forth in 1 of the above GenBank entries. In another embodiment, the AML-1 protein is encoded by any other AML-1 gene sequence known in the art. In another embodiment, the AML-1 protein is any other AML-1 protein known in the art. In another embodiment, the TVM is an isoform of an AML-1 protein. In another embodiment, the TVM is a homologue of an AML-1 protein. In another embodiment, the TVM is a variant of an AML-1 protein. In another embodiment, the TVM is a fragment of an AML-1 protein. In another embodiment, the TVM is a fragment of an isoform, homologue, or variant of an AML-1 protein. Each possibility represents another embodiment of the present invention.

In another embodiment, the TVM is a SLIT2 protein. In another embodiment, the marker is a nucleic acid molecule encoding a SLIT2 protein. In another embodiment, the SLIT2 protein is encoded by a nucleic acid molecule having the sequence: cagagcagggtggagagggcggtgggaggcgtgtgcct-
gagtgggctctactgccttgaccatattattagtgcacattaccctggcact ctgg-
gagctagccccgccgggcactgggcctcagacactgcgcggaccctcg-
gagcagcaagctaaagaaagcccccagtgccggcg aggaaggagg-
cggcggggaaagatgcgcggcgaggctggcagatgctgtccctgt-
cgctggggttagtgctggcgatcctgaacaagg tggcaccgcaggcg-
tgcccggcgcagtgctcttgctcgggcagcacagtggactgtcacgggctg-
gcgctgcgcagcgtgcccaggaat atcccccgcaacaccgagagactggatt-
taaatggaaataacatcacaagaattacgaagacagattagctggtcttaga-
catctaagagttc ttcagcttatggagaataagattagcaccattgaaagaggag-
cattccaggatcttaaagaactagagagactgcgataaacagaaatcacc
ttcagctgatcctgagagctgatcagggactgcgaagctatacaggcttgatctc-
agtgaaaaccaaattcaggcaatcccaaggaaagct accgtggggcagttga-
cataaaaaatttgcaactggattacaaccagatcagctgtattgaagatggggcat-
tcagggctctccgggacctg gaagtgctcactctcaacaataacaacattacta-
gactactgtggcaagatcaaccatatgcctaaacttaggactatcgactgcattca-
aac aacctgtattgtgactgccacctggcctggctctccgactggcttcgc-
caaaggcctcgggaggtctgtacactcagtgtatgggcccctcc cacct-
gagaggccataatgtagccgaggacaaaaacgagaatagtctgcagtggt-
caccagtcatttatggctccacttgtagtgattgca ctgccctgccgcc-
tgtacctgtagcaacaatatcgtagactgtcgtgggaaaggtctcactgagatccc-
cacaaatcaccagagaccatcac agaaatacgtaggaacagaacacaat-
caaagtcatccctcctggagctactcaccatataaaaagcttagacgaattgacct-
gagcaataat cagatctctgaacttgcaccagatgctaccaaggacta-
cgctctctgaattcacttgtcctctatggaaataaaatcacagaactccccaaaag
atatttgaaggactgattccttacagctcctattattgaatgccaacaaga-
taaactgccacgggtagatgcattcaggatctccacaacttga accactctccc-
tatatgacaacaagcttcagaccatcgccaaggggaccattcacctcacgggc-
cattcaaactatgcataggcccagaac cccatatagtgactgccatctc-
aagtggctagcggattatctccataccaacccgattgagaccagtggtgcccgag-
caccagcccccgcc gcctggcaaacaaaagaattggacagat-
caaaagcaagaaattccgttgacagctaaagaacagtatttcattccaggtacagaagattatc gatcaaaattaagtggagactgctagcggatctggcttgccct-
gaaaagtgtcgctgtgaaggaaccacagtagattgctctaatcaaaagc
tcaacaaaatcccggagcacattccccagtacactgcagagagcgtct-
caataataatgaatttaccgtgaggaagccacaggaatcataa gaaacttcct-
caattacgtaaaataaactttagcaacaataagatcacagatattgaggagggag-
catttgaaggagcatctggtgtaaatgaa atacacttacgagtaatcgtagga-
aaatgtgcagcataagatgacaagggattggaaagcctcaaaactagat-
gagagaagcaatcgaat aacctgtgtggggaatgacagatcataggactca-
gactgtgcgtagctactagtatgataatcaaattactacagagcaccaggggcattt
gatactctccattcatatctactctaaacctcaggccaatccattaactgtaactgc-
tacctggcaggagggagagtggctgagaaagaag agaattgtcacgg-
gaaatcctagatgtcaaaaaccatacttcctgaaagaaatacccatccag-
gatgtggccattcaggacttcacttgtgatg acggaaatgatgacaata-
gagctccccactactcgctgtcctactgaatgtacttgcaggatacagtcgtcc-
gatgtagcaacaagggatg aaggtcagccgaaaggtattccaagagatgt-
cacagagagtatctggatggaaaccaatttacactggacccaaggaactctc-
caactaca aacatttaacacttatagacttaagtaacaacagaat-
aagcacgctactaatcagagcttcagcaacatgacccagctcctcaccttaattctta
gttacaaccgtctgagatgtattcctcctcgcaccatgatggattaaagtctcacgat-
tactactctacatggaaatgacatactgagtgcctg aaggtgcatcaatgatc-
tactgcattatcacatctagcaattggagccaaccctcatactgtgattgtaa-
catgcagtggttatccgactgggt gaagtcggaatataaggagc-
ctggaattgctcgagtgctggtcctggagaaatggcagataaactatact-
cacaactccctccaaaaaattt acctgtcaaggtcctgtggatgtcaatat-
tctagctaagtgtaaccccctgcctatcaaatccgtgtaaaaatgatggca-
catgtaatagtgatcc agttgactataccgatgcacctgtccatatggatc-
aaggggcaggactgtgatgtcccaattcatgcctgcatcagtaacccatgtaaa-
catg gaggaacttgccacttaaaggaaggagaagaagatggat-
tctggtgtatagtgctgatggatttgaaggagaaaattgtgaagtcaacgag
atgattgtgaagataatgactgtgaaaataattctacatgtgtcgatggcat-
taataactacacatgccatgcccacctgagtatacaggtgagt tgtgtgag-
gagaagctggacactgtgcccaggacctgaacccctgccagcacgatt-
caaagtgcatcctaactccaaagggattcaaatgt gactgcacaccagggta-
cgtaggtgaacactgcgacatcgattagacgactgccaagacaacaagtgt-
aaaaacggagcccactgcaca gatgcagtgaacggctatacgtg-
catatgccccgaaggttacagtggcttgactgtgagattctccacc-
catggtcctccctcgtaccagcc cctgtgataattttgattgtcagaatg-
gagctcagtgtatcgtcagaataaatgagccaatatgtcagtgtttgcctggctatc-
agggagaaaag tgtgaaaaattggttagtgtgaatatataaacaaagagt- cttat-
cacagattcatcagccaaggacggcctcagacgaacataacacttcag attgc-
cacagatgaagacagcggaatcctcctgtataagggtgacaaagac-
catatcgcggtagaactctatcgggggcgtgacgtgcca gctatgacaccg-
gctctcatccagcactgccatttacagtgtggagacaatcaatgatggaaacttcca-
cattgtggaactacttgccaggat cagagtctctctagtccgtggatggtgg-
gaaccccaaaatcatcactaacttgtcaaagcagtccactctgaattagactctc-
cactctatgta ggaggcatgccagggaagagtaacgtggcatctctgc-
gccaggcccctgggcagaacggaaccagatccacggctgcatccggaacct
ttacatcaacagtgagctgcaggacttccagaaggtgccgatgcaaacaggcatt-
agcctggctgtgagccatgccacaagaaggtgtgtg cccatggca-
catgccagcccagcagccaggcaggcttcacctgcgagtgccaggaaggatg-
gatggggcccctctgtgaccaacggac caatgaccdtgcca-
ggaaataaatgcgtacatggcacctgcttgcccatcaatgcgactccta-
cagctgtaagtgatggagggccatgga ggtgtcctctgtgatgaagaggag-
gatctgataacccatgccaggcgatcaagtgcaagcacgggaagtgcagg-
catcaggtctggggc agccctactgtgaatgcagcagtggatac-
acgggggacagctgtgatcgagaaatctcagtcgaggggaaaggataagagatt-
attacca aaagcagcagggctatgctgcttgccaaacaaccaagaaggtgtccc-
gattagagtgcagaggtgggtgtgcaggagggcagtgctgtg gaccgctgag-
gagcaagcggcggaaatactattcgaatgcactgacggctcctcctagtggacg-
aggagagaaagtggtgaagtgcgg
ctgtacgaggtgtgtgtcctaaacacactccc- ggcagctctgtctag-
gaaaaggagtatacacttgaccatgtgggactaatgaatgcttcat agtggaaat-
atttgaaatatattgtaaaatacagaacagacttattatattatgagaataaagactat-
tactgcatttg (SEQ ID No: 46). In another embodiment, the SLIT2 protein is encoded by a nucleic acid molecule having a sequence set forth in GenBank Accession No. NM_004787. In another embodiment, the SLIT2 protein is encoded by a nucleic acid molecule having a sequence selected from those set forth in GenBank Accession No. AB017168 and AK027326. In another embodiment, the SLIT2 protein has an AA sequence set forth in 1 of the above GenBank entries. In another embodiment, the SLIT2 protein is encoded by any other SLIT2 gene sequence known in the art. In another embodiment, the SLIT2 protein is any other SLIT2 protein known in the art. In another embodiment, the TVM is an isoform of a SLIT2 protein. In another embodiment, the TVM is a homologue of a SLIT2 protein. In another embodiment, the TVM is a variant of a SLIT2 protein. In another embodiment, the TVM is a fragment of a SLIT2 protein. In another embodiment, the TVM is a fragment of an isoform, homologue, or variant of a SLIT2 protein. Each possibility represents another embodiment of the present invention.

In another embodiment, the TVM is SLC11A1 (Solute carrier family 11; proton-coupled divalent metal ion transporters, member 1; NRAMP). In another embodiment, the TVM is a nucleotide molecule encoding SLCA1. In another embodiment, the TVM is an isoform of a SLC11A1 protein. In another embodiment, the TVM is a homologue of a SLC11A1 protein. In another embodiment, the TVM is a variant of a SLC11A1 protein. In another embodiment, the TVM is a fragment of a SLC11A1 protein. In another embodiment, the TVM is a fragment of an isoform, homologue, or variant of a SLC11A1 protein. Each possibility represents another embodiment of the present invention.

In another embodiment, the TVM is SEC23B. In another embodiment, the TVM is a nucleotide molecule encoding SEC23B. In another embodiment, the TVM is an isoform of a SEC23B protein. In another embodiment, the TVM is a homologue of a SEC23B protein. In another embodiment, the TVM is a variant of a SEC23B protein. In another embodiment, the TVM is a fragment of a SEC23B protein. In another embodiment, the TVM is a fragment of an isoform, homologue, or variant of a SEC23B protein. Each possibility represents another embodiment of the present invention.

In another embodiment, the TVM is DKFZp762E1312. In another embodiment, the TVM is a nucleotide molecule encoding DKFZp762E1312. In another embodiment, the TVM is an isoform of a DKFZp762E1312 protein. In another embodiment, the TVM is a homologue of a DKFZp762E1312 protein. In another embodiment, the TVM is a variant of a DKFZp762E1312 protein. In another embodiment, the TVM is a fragment of a DKFZp762E1312 protein. In another embodiment, the TVM is a fragment of an isoform, homologue, or variant of a DKFZp762E1312 protein. Each possibility represents another embodiment of the present invention.

In another embodiment, the TVM is KIAA1892. In another embodiment, the TVM is a nucleotide molecule encoding KIAA1892. In another embodiment, the TVM is a protein encoded by KIAA1892. In another embodiment, the TVM is an isoform of a KIAA1892 protein. In another embodiment, the TVM is a homologue of a KIAA1892 protein. In another embodiment, the TVM is a variant of a KIAA1892 protein. In another embodiment, the TVM is a fragment of a KIAA1892 protein. In another embodiment, the TVM is a fragment of an isoform, homologue, or variant of a KIAA1892 protein. Each possibility represents another embodiment of the present invention.

In another embodiment, the TVM is MS4A6A (Membrane-spanning 4-domains, subfamily A, member 6A). In another embodiment, the TVM is a nucleotide molecule encoding MS4A6A. In another embodiment, the TVM is an isoform of a MS4A6A protein. In another embodiment, the TVM is a homologue of a MS4A6A protein. In another embodiment, the TVM is a variant of a MS4A6A protein. In another embodiment, the TVM is a fragment of a MS4A6A protein. In another embodiment, the TVM is a fragment of an isoform, homologue, or variant of a MS4A6A protein. Each possibility represents another embodiment of the present invention.

In another embodiment, the TVM is KCNE3 (Potassium voltage-gated channel, Isk-related family, member 3). In another embodiment, the TVM is a nucleotide molecule encoding KCNE3. In another embodiment, the TVM is an isoform of a KCNE3 protein. In another embodiment, the TVM is a homologue of a KCNE3 protein. In another embodiment, the TVM is a variant of a KCNE3 protein. In another embodiment, the TVM is a fragment of a KCNE3 protein. In another embodiment, the TVM is a fragment of an isoform, homologue, or variant of a KCNE3 protein. Each possibility represents another embodiment of the present invention.

In another embodiment, the TVM is KCNE4 (Potassium voltage-gated channel, Isk-related family, member 4). In another embodiment, the TVM is a nucleotide molecule encoding KCNE4. In another embodiment, the TVM is an isoform of a KCNE4 protein. In another embodiment, the TVM is a homologue of a KCNE4 protein. In another embodiment, the TVM is a variant of a KCNE4 protein. In another embodiment, the TVM is a fragment of a KCNE4 protein. In another embodiment, the TVM is a fragment of an isoform, homologue, or variant of a KCNE4 protein. Each possibility represents another embodiment of the present invention.

In another embodiment, the TVM is SDC1 (Syndecan 1). In another embodiment, the TVM is a nucleotide molecule encoding SDC1. In another embodiment, the TVM is an isoform of a SDC1 protein. In another embodiment, the TVM is a homologue of a SDC1 protein. In another embodiment, the TVM is a variant of a SDC1 protein. In another embodiment, the TVM is a fragment of a SDC1 protein. In another embodiment, the TVM is a fragment of an isoform, homologue, or variant of a SDC1 protein. Each possibility represents another embodiment of the present invention.

In another embodiment, the TVM is ST14 (Suppression of tumorigenicity 14 (colon carcinoma)). In another embodiment, the TVM is a nucleotide molecule encoding ST14. In another embodiment, the TVM is an isoform of a ST14 protein. In another embodiment, the TVM is a homologue of a ST14 protein. In another embodiment, the TVM is a variant of a ST14 protein. In another embodiment, the TVM is a fragment of a ST14 protein. In another embodiment, the TVM is a fragment of an isoform, homologue, or variant of a ST14 protein. Each possibility represents another embodiment of the present invention.

In another embodiment, the TVM is CDCP1 (CUB domain containing protein 1). In another embodiment, the TVM is a nucleotide molecule encoding CDCP1. In another embodiment, the CDCP1 nucleotide is a short isoform of CDCP1. In another embodiment, the CDCP1 nucleotide is a long isoform of CDCP1. In another embodiment, the CDCP1 protein is encoded by a nucleic acid molecule having the sequence: gggcggggctcgggccggtccgcccgcgc-gcaggtgagtgagccagggcggagcgcagctgcgccgggcttgggcgc-ctggggcc gccgctccccaccgtcgttttccccaccgaggccgaggcgtcccg-gagtcatggccggcctgaactgcggggtctctatcgcactgctag gggttctgctgctgggtgcggcgcgcctgccgcgcggggcagaagctttt-gagattgctctgccacgagaaagcaacattacagttctcata aagctggggaccccgactctgctggcaaaaccctgttacatcgtcatttctaaaa-gacatataaccatgttgtccatcaagtctggagaaaga atagtctttacctt-tagctgccagagtcctgagaatcactttgtcatagagatccagaaaatat-tgactgtatgtcaggcccatgtccttttggg gaggttcagcttcag-ccctcgacatcgttgttgcctaccctcaacagaactttcatctgggatgtcaaagct-cataagagcatcggtttagagc tgcagttttccatccctcgcctgaggca-gatcggtccgggtgagagctgcccagacggagtcactcactccatcagc-ggccgaatcgatgc caccgtggtcaggatcggaaccttctgcagcaatgg-cactgtgtcccggatcaagatgcaagaaggagtgaaaatggccttacacctccca tggttccaccccagaaatgtctccggcttcagcattgcaaaccgctcatc-tataaaacgtctgtgcatcatcgagtctgtgtttgagggtgaag gctcagcaa-ccctgatgtctgccaactacccagaaggcttccctgaggatgagct-catgacgtggcagtttgtcgttcctgcacacctgcgg gccagcgtctccttcct-caacttcaacctctccaactgtgagaggaaggaggagcgggttgaatacta-catcccgggctccaccaccaaccc cgaggtgttcaagctggaggacaagcag-cctgggaacatggcggggaacttcaacctctctctgcaaggctgtgaccaa-gatgcccaaag tccagggatcctccggctgcagttccaagttttggtccaacatc-cacaaaatgaaagcagtgagtgagccccactttccttttcttcctcctcc agcaccttcgttgtttcctgggtagtctgcctgggtgaggctcccttcctgtttct-catctgtggcttctgaaacacttagactctggacccagca agagtttcag-gaagtgggttgctaggcagttagacaggcttgttggt-gaacacccggtatgtagttccatttcagcacaataaaaagaaatctt gcattcaaaaaaaaaaaaaaaaaa (SEQ ID No: 47). In another embodiment, the CDCP1 protein is a short isoform of CDCP1. In another embodiment, the CDCP1 protein is a long isoform of CDCP1. In another embodiment, the CDCP1 protein is encoded by a nucleic acid molecule having a sequence set forth in GenBank Accession No. AK026329. In another embodiment, the sequence of the CDCP1-encoding nucleotide is set forth in GenBank Accession No. NM_178181. In another embodiment, the sequence of the CDCP1-encoding nucleotide is set forth in GenBank Accession No. BC021099. In another embodiment, the sequence of the CDCP1-encoding nucleotide is set forth in GenBank Accession No. BC069254. In another embodiment, the sequence of the CDCP1-encoding nucleotide is set forth in GenBank Accession No. AY026461. In another embodiment, the sequence of the CDCP1-encoding nucleotide is set forth in GenBank Accession No. AF468010. In another embodiment, the sequence of the CDCP1-encoding nucleotide is set forth in GenBank Accession No. AY167484. In another embodiment, the CDCP1 protein has an AA sequence set forth in 1 of the above GenBank entries. In another embodiment, the CDCP1 protein is encoded by any other CDCP1 gene sequence known in the art. In another embodiment, the CDCP1 protein is any other CDCP1 protein known in the art. In another embodiment, the TVM is an isoform of a CDCP1 protein. In another embodiment, the TVM is a homologue of a CDCP1 protein. In another embodiment, the TVM is a variant of a CDCP1 protein. In another embodiment, the TVM is a fragment of a CDCP1 protein. In another embodiment, the TVM is a fragment of an isoform, homologue, or variant of a CDCP1 protein. Each possibility represents another embodiment of the present invention.

In another embodiment, the TVM is a homologue of a CDCP1 protein. In another embodiment, the TVM is a variant of a CDCP1 protein. In another embodiment, the TVM is a fragment of a CDCP1 protein. In another embodiment, the TVM is a fragment of an isoform, homologue, or variant of a CDCP1 protein. Each possibility represents another embodiment of the present invention.

In another embodiment, the TVM is MOBK1B (C2orf6; MOB1, Mps One Binder kinase activator-like 1B). In another embodiment, the TVM is an isoform of a MOBK1B protein. In another embodiment, the TVM is a homologue of a MOBK1B protein. In another embodiment, the TVM is a variant of a MOBK1B protein. In another embodiment, the TVM is a fragment of a MOBK1B protein. In another embodiment, the TVM is a fragment of an isoform, homologue, or variant of a MOBK1B protein. Each possibility represents another embodiment of the present invention.

In another embodiment, the TVM is a protein encoded by C14orf28. In another embodiment, the TVM is C14orf28. In another embodiment, the TVM is a nucleotide molecule encoding a protein encoded by C14orf28. In another embodiment, the TVM is an isoform of a C14orf28 protein. In another embodiment, the TVM is a homologue of a C14orf28 protein. In another embodiment, the TVM is a variant of a C14orf28 protein. In another embodiment, the TVM is a fragment of a C14orf28 protein. In another embodiment, the TVM is a fragment of an isoform, homologue, or variant of a C14orf28 protein. Each possibility represents another embodiment of the present invention.

In another embodiment, the TVM is PCDHB2 (Protocadherin beta 2). In another embodiment, the TVM is a nucleotide molecule encoding PCDHB2. In another embodiment, the TVM is an isoform of a PCDHB2 protein. In another embodiment, the TVM is a homologue of a PCDHB2 protein. In another embodiment, the TVM is a variant of a PCDHB2 protein. In another embodiment, the TVM is a fragment of a PCDHB2 protein. In another embodiment, the TVM is a fragment of an isoform, homologue, or variant of a PCDHB2 protein. Each possibility represents another embodiment of the present invention.

In another embodiment, the TVM is GPR105 (Purinergic receptor P2Y, G-protein coupled, 14). In another embodiment, the TVM is a nucleotide molecule encoding GPR105. In another embodiment, the TVM is an isoform of a GPR105 protein. In another embodiment, the TVM is a homologue of a GPR105 protein. In another embodiment, the TVM is a variant of a GPR105 protein. In another embodiment, the TVM is a fragment of a GPR105 protein. In another embodiment, the TVM is a fragment of an isoform, homologue, or variant of a GPR105 protein. Each possibility represents another embodiment of the present invention.

In another embodiment, the TVM is CSPG2 (chondroitin sulfate proteoglycan 2). In another embodiment, the TVM is a nucleotide molecule encoding CSPG2. In another embodiment, the TVM is an isoform of a CSPG2 protein. In another embodiment, the TVM is a homologue of a CSPG2 protein. In another embodiment, the TVM is a variant of a CSPG2 protein. In another embodiment, the TVM is a fragment of a CSPG2 protein. In another embodiment, the TVM is a fragment of an isoform, homologue, or variant of a CSPG2 protein. Each possibility represents another embodiment of the present invention.

In another embodiment, the TVM is ESM1 (Endothelial cell-specific molecule 1). In another embodiment, the TVM is a nucleotide molecule encoding ESM1. In another embodiment, the TVM is an isoform of a ESM1 protein. In another embodiment, the TVM is a homologue of a ESM1 protein. In another embodiment, the TVM is a variant of a ESM1 protein. In another embodiment, the TVM is a fragment of a ESM1 protein. In another embodiment, the TVM is a fragment of an isoform, homologue, or variant of a ESM1 protein. Each possibility represents another embodiment of the present invention.

In another embodiment, the TVM is WFDC2 (WAP four-disulfide core domain 2). In another embodiment, the TVM is a nucleotide molecule encoding WFDC2. In another embodiment, the TVM is an isoform of a WFDC2 protein. In another embodiment, the TVM is a homologue of a WFDC2 protein. In another embodiment, the TVM is a variant of a WFDC2 protein. In another embodiment, the TVM is a fragment of a WFDC2 protein. In another embodiment, the TVM is a fragment of an isoform, homologue, or variant of a WFDC2 protein. Each possibility represents another embodiment of the present invention.

In another embodiment, the TVM is SPP1 (Secreted phosphoprotein 1 (osteopontin, bone sialoprotein I, early T-lymphocyte activation 1)). In another embodiment, the TVM is a nucleotide molecule encoding SPP1. In another embodiment, the TVM is an isoform of a SPP1 protein. In another embodiment, the TVM is a homologue of a SPP1 protein. In another embodiment, the TVM is a variant of a SPP1 protein. In another embodiment, the TVM is a fragment of a SPP1 protein. In another embodiment, the TVM is a fragment of an isoform, homologue, or variant of a SPP1 protein. Each possibility represents another embodiment of the present invention.

Figure 11:
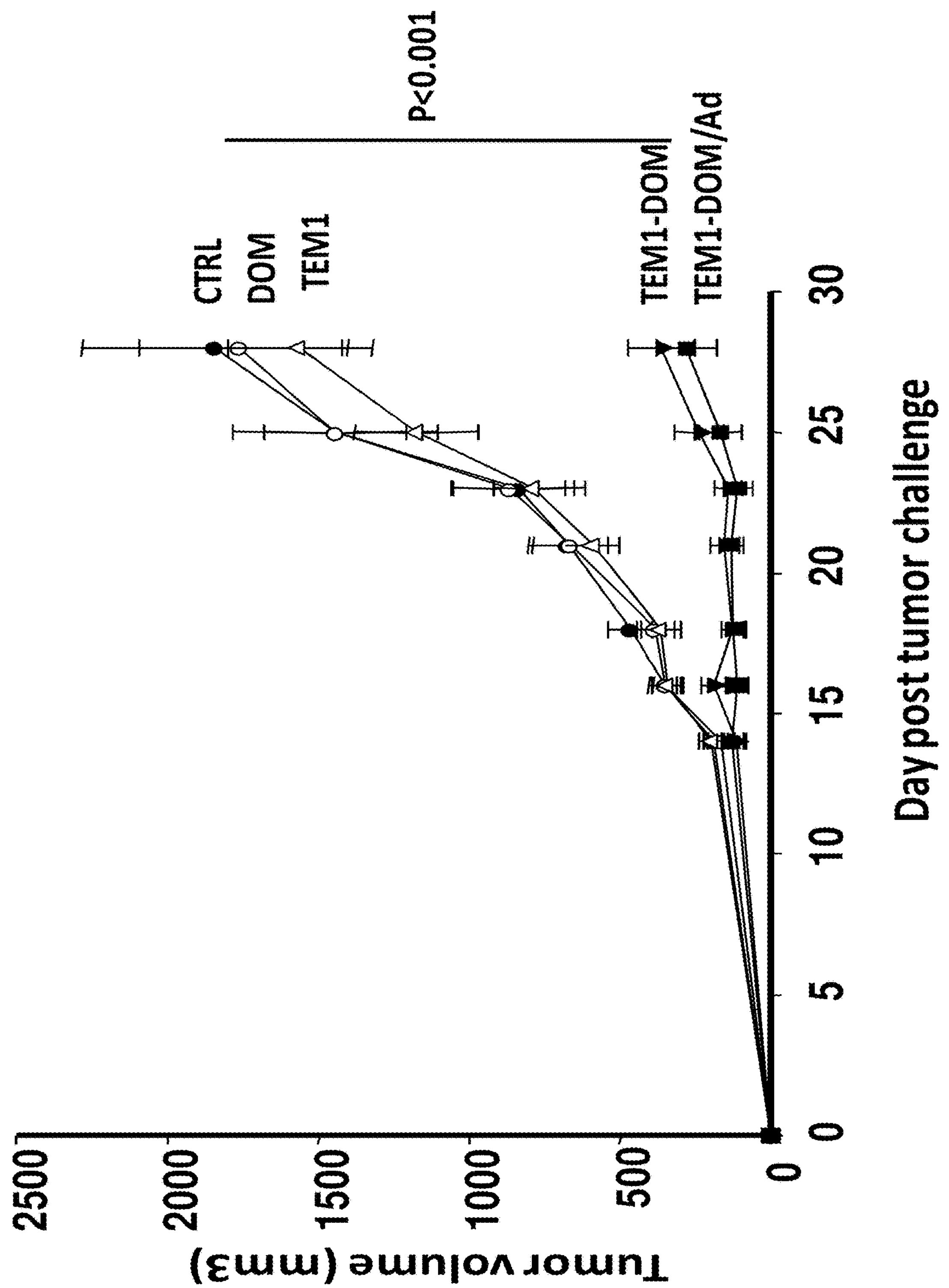
FIG. 11. Therapeutic vaccination with a TEM1-pDOM DNA vaccine results in 50% tumor rejection and tumor delay.

In another embodiment, the TVM is a TM protein listed in FIG. 11. In another embodiment, the TVM is MGAT4A. In another embodiment, the TVM is a nucleotide molecule encoding MGAT4A. In another embodiment, the TVM is AFAP. In another embodiment, the TVM is a nucleotide molecule encoding AFAP. In another embodiment, the TVM is CXCR4. In another embodiment, the TVM is a nucleotide molecule encoding CXCR4. In another embodiment, the TVM is UCP2. In another embodiment, the TVM is a nucleotide molecule encoding UCP2. In another embodiment, the TVM is TWIST. In another embodiment, the TVM is a nucleotide molecule encoding TWIST. In another embodiment, the TVM is SLC2A3. In another embodiment, the TVM is a nucleotide molecule encoding SLC2A3. In another embodiment, the TVM is MYO1B. In another embodiment, the TVM is a nucleotide molecule encoding MYO1B. In another embodiment, the TVM is COL4A2. In another embodiment, the TVM is a nucleotide molecule encoding COL4A2. In another embodiment, the TVM is MGC4677. In another embodiment, the TVM is a nucleotide molecule encoding MGC4677. In another embodiment, the TVM is G1P2. In another embodiment, the TVM is a nucleotide molecule encoding G1P2. In another embodiment, the TVM is BHLHB3. In another embodiment, the TVM is a nucleotide molecule encoding BHLHB3. In another embodiment, the TVM is NEDL2. In another embodiment, the TVM is a nucleotide molecule encoding NEDL2. In another embodiment, the TVM is ITGA1. In another embodiment, the TVM is a nucleotide molecule encoding ITGA1. Each possibility represents a separate embodiment of the present invention.

Figure 12:
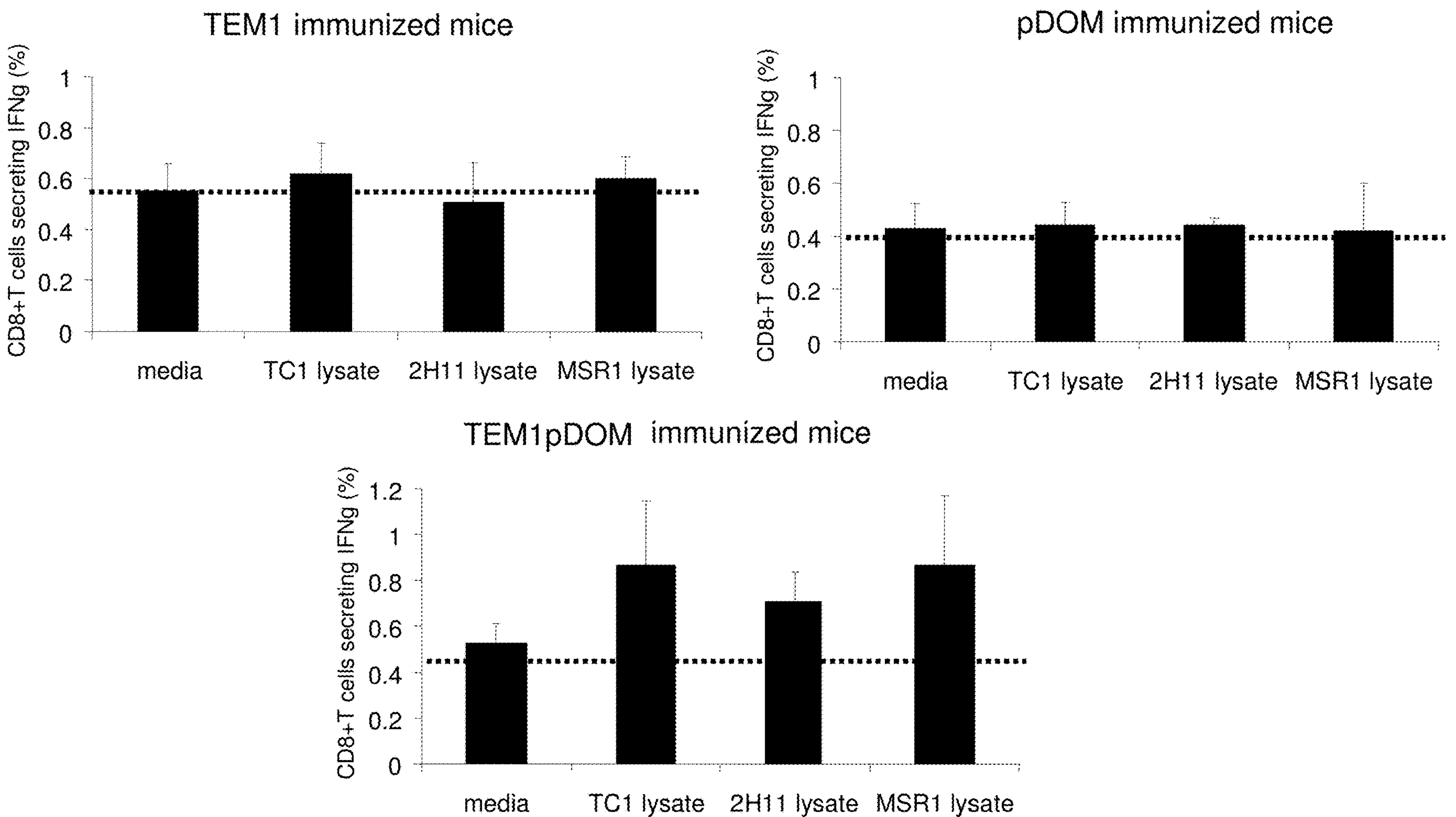
FIG. 12. TEM1-pDOM immunization results in a higher number of CD8 T cells secreting IFN-gamma.

In another embodiment, the TVM is a TM protein listed in FIG. 12. In another embodiment, the TVM is MUC16. In another embodiment, the TVM is a nucleotide molecule encoding MUC16. In another embodiment, the TVM is FLJ20171. In another embodiment, the TVM is a nucleotide molecule encoding FU20171. In another embodiment, the TVM is TAP1. In another embodiment, the TVM is a nucleotide molecule encoding TAP1. In another embodiment, the TVM is C11orf5. In another embodiment, the TVM is a nucleotide molecule encoding C11orf5. In another embodiment, the TVM is SLC30A5. In another embodiment, the TVM is a nucleotide molecule encoding SLC30A5. In another embodiment, the TVM is CST5. In another embodiment, the TVM is a nucleotide molecule encoding CST5. In another embodiment, the TVM is TNFAIP1. In another embodiment, the TVM is a nucleotide molecule encoding TNFAIP1. In another embodiment, the TVM is AKAP8. In another embodiment, the TVM is a nucleotide molecule encoding AKAP8. In another embodiment, the TVM is PSAT1. In another embodiment, the TVM is a nucleotide molecule encoding PSAT1. In another embodiment, the TVM is FLJ20171. In another embodiment, the TVM is a nucleotide molecule encoding FU20171. In another embodiment, the TVM is RP2. In another embodiment, the TVM is a nucleotide molecule encoding RP2. In another embodiment, the TVM is LOC132671. In another embodiment, the TVM is a nucleotide molecule encoding LOC132671. In another embodiment, the TVM is HES2. In another embodiment, the TVM is a nucleotide molecule encoding HES2. In another embodiment, the TVM is APCDD1. In another embodiment, the TVM is a nucleotide molecule encoding APCDD1. In another embodiment, the TVM is LOC286334. In another embodiment, the TVM is a nucleotide molecule encoding LOC286334. In another embodiment, the TVM is FLJ11526. In another embodiment, the TVM is a nucleotide molecule encoding FU11526. In another embodiment, the TVM is KIAA2022. In another embodiment, the TVM is a nucleotide molecule encoding KIAA2022. In another embodiment, the TVM is MGC3032. In another embodiment, the TVM is a nucleotide molecule encoding MGC3032. In another embodiment, the TVM is FLJ22795. In another embodiment, the TVM is a nucleotide molecule encoding FLJ22795. In another embodiment, the TVM is KIAA1909. In another embodiment, the TVM is a nucleotide molecule encoding KIAA1909. In another embodiment, the TVM is FLJ30277. In another embodiment, the TVM is a nucleotide molecule encoding FLJ30277. In another embodiment, the TVM is LOC284801. In another embodiment, the TVM is a nucleotide molecule encoding LOC284801. In another embodiment, the TVM is LOC158135. In another embodiment, the TVM is a nucleotide molecule encoding LOC158135. In another embodiment, the TVM is LOC254531. In another embodiment, the TVM is a nucleotide molecule encoding LOC254531. In another embodiment, the TVM is OR7E47P. In another embodiment, the TVM is a nucleotide molecule encoding OR7E47P. In another embodiment, the TVM is UBPH. In another embodiment, the TVM is a nucleotide molecule encoding UBPH. In another embodiment, the TVM is FU35801. In another embodiment, the TVM is a nucleotide molecule encoding FLJ35801. In another embodiment, the TVM is LOC150271. In another embodiment, the TVM is a nucleotide molecule encoding LOC150271. In another embodiment, the TVM is SIPA1L3. In another embodiment, the TVM is a nucleotide molecule encoding SIPA1L3. In another embodiment, the TVM is LOC158563. In another embodiment, the TVM is a nucleotide molecule encoding LOC158563. In another embodiment, the TVM is NAV1. In another embodiment, the TVM is a nucleotide molecule encoding NAV1. In another embodiment, the TVM is LOC401022. In another embodiment, the TVM is a nucleotide molecule encoding LOC401022. In another embodiment, the TVM is C9orf113. In another embodiment, the TVM is a nucleotide molecule encoding C9orf113. In another embodiment, the TVM is GPT2. In another embodiment, the TVM is a nucleotide molecule encoding GPT2. In another embodiment, the TVM is PHLDB1. In another embodiment, the TVM is a nucleotide molecule encoding PHLDB1. In another embodiment, the TVM is FU12748. In another embodiment, the TVM is a nucleotide molecule encoding FLJ12748. In another embodiment, the TVM is LOC130355. In another embodiment, the TVM is a nucleotide molecule encoding LOC130355. In another embodiment, the TVM is BECN1. In another embodiment, the TVM is a nucleotide molecule encoding BECN1. In another embodiment, the TVM is LOC283713. In another embodiment, the TVM is a nucleotide molecule encoding LOC283713. Each possibility represents a separate embodiment of the present invention.

In another embodiment, the TVM is a TM protein listed in Table 6 of WO 2007/089513. In another embodiment, the TVM is a TM protein listed in Table 7 of WO 2007/089513. In another embodiment, the TVM is a plasma-membrane-associated (PM) protein listed in Table 6 of WO 2007/089513. In another embodiment, the TVM is a PM protein listed in Table 7 of WO 2007/089513. In another embodiment, a PM protein of the present invention is a TM protein. In another embodiment, the PM protein is associated with the intracellular face of the PM. In another embodiment, the PM protein is associated with the extracellular face of the PM. Each possibility represents a separate embodiment of the present invention.

In another embodiment, the TVM is FAD104 (FNDC3B; Fibronectin type III domain containing 3B). In another embodiment, the TVM is a nucleotide molecule encoding FAD104. In another embodiment, the TVM is WARP (Von Willebrand factor A domain containing 1). In another embodiment, the TVM is a nucleotide molecule encoding WARP. In another embodiment, the TVM is B-cell receptor-associated protein 29 (BCAP29). In another embodiment, the TVM is a nucleotide molecule encoding BCAP29. In another embodiment, the TVM is CDH1 (Cadherin 1, type 1, E-cadherin (epithelial). In another embodiment, the TVM is a nucleotide molecule encoding CDH1. In another embodiment, the TVM is FLJ10826 (OGFOD1; 2-oxoglutarate and iron-dependent oxygenase domain containing 1). In another embodiment, the TVM is a nucleotide molecule encoding FLJ10826. In another embodiment, the TVM is OPN3 (Opsin 3; encephalopsin, panopsin). In another embodiment, the TVM is a nucleotide molecule encoding OPN3. In another embodiment, the TVM is HIATL2 (Hippocampus abundant gene transcript-like 2). In another embodiment, the TVM is a nucleotide molecule encoding HIATL2. In another embodiment, the TVM is IL28RA (Interleukin 28 receptor, alpha; interferon, lambda receptor). In another embodiment, the TVM is a nucleotide molecule encoding IL28RA. In another embodiment, the TVM is TMEM19 (Transmembrane protein 19). In another embodiment, the TVM is a nucleotide molecule encoding TMEM19. In another embodiment, the TVM is C10orf69 (SPFH domain family, member 1). In another embodiment, the TVM is a nucleotide molecule encoding C10orf69. In another embodiment, the TVM is FRAP1 (FK506 binding protein 12-rapamycin associated protein 1). In another embodiment, the TVM is a nucleotide molecule encoding FRAP1. In another embodiment, the TVM is CKLFSF6 (CKLF-like MARVEL transmembrane domain containing 6). In another embodiment, the TVM is a nucleotide molecule encoding CKLFSF6. In another embodiment, the TVM is MPHOSPH9 (M-phase phosphoprotein 9). In another embodiment, the TVM is a nucleotide molecule encoding MPOHSPH9. In another embodiment, the TVM is CLST11240 (HIGD1B; HIG1 domain family, member 1B). In another embodiment, the TVM is a nucleotide molecule encoding CLST11240. In another embodiment, the TVM is SGPP2 (Sphingosine-1-phosphate phosphotase 2). In another embodiment, the TVM is a nucleotide molecule encoding SGPP2. In another embodiment, the TVM is SLCO3A1 (Solute carrier organic anion transporter family, member 3A1). In another embodiment, the TVM is a nucleotide molecule encoding SLCO3A1. In another embodiment, the TVM is LOC51136 (PTD016 protein). In another embodiment, the TVM is a nucleotide molecule encoding LOC51136. In another embodiment, the TVM is DKFZp564I1922 (MXRA5 (Matrix-remodelling associated 5). In another embodiment, the TVM is a nucleotide molecule encoding DKFZp564I1922. In another embodiment, the TVM is CALM3 (Calmodulin 3; phosphorylase kinase, delta). In another embodiment, the TVM is a nucleotide molecule encoding CALM3. In another embodiment, the TVM is MGC34647. In another embodiment, the TVM is a nucleotide molecule encoding MGC34647. In another embodiment, the TVM is MUC1 (Mucin 1, transmembrane). In another embodiment, the TVM is a nucleotide molecule encoding MUC1. In another embodiment, the TVM is SLC30A6 (Solute carrier family 30 (zinc transporter), member 6). In another embodiment, the TVM is a nucleotide molecule encoding SLC30A6. In another embodiment, the TVM is TLCD1 (LOC116238). In another embodiment, the TVM is a nucleotide molecule encoding TLCD1. In another embodiment, the TVM is SPTB (Spectrin, beta, erythrocytic (includes spherocytosis, clinical type I)). In another embodiment, the TVM is a nucleotide molecule encoding SPTB. In another embodiment, the TVM is FNDC3 (Fibronectin type III domain containing 3A). In another embodiment, the TVM is a nucleotide molecule encoding FNDC3. In another embodiment, the TVM is SPRY1 (Sprouty homolog 1, antagonist of FGF signaling (*Drosophila*). In another embodiment, the TVM is a nucleotide molecule encoding SPRY1. In another embodiment, the TVM is MME (Membrane metallo-endopeptidase; neutral endopeptidase, enkephalinase, CALLA, CD10). In another embodiment, the TVM is a nucleotide molecule encoding MME. In another embodiment, the TVM is INSR (Insulin receptor). In another embodiment, the TVM is a nucleotide molecule encoding INSR. In another embodiment, the TVM is LPPR4 (Plasticity related gene 1). In another embodiment, the TVM is a nucleotide molecule encoding LPPR1. In another embodiment, the TVM is a C14orf100-encoded protein. In another embodiment, the TVM is a nucleotide molecule encoding a C14orf100-encoded protein. In another embodiment, the TVM is a C14orf100 nucleotide molecule. In another embodiment, the TVM is SLC9A5 (Solute carrier family 9 (sodium/hydrogen exchanger), member 5). In another embodiment, the TVM is a nucleotide molecule encoding SLC9A5. In another embodiment, the TVM is SCGB2A1 (Secretoglobin, family 2A, member 1). In another embodiment, the TVM is a nucleotide molecule encoding SCGB2A1. In another embodiment, the TVM is FLT1 (Fms-related tyrosine kinase 1 (vascular endothelial growth factor/vascular permeability factor receptor). In another embodiment, the TVM is a nucleotide molecule encoding FLT1. In another embodiment, the TVM is a nucleotide molecule encoding MOBK1B. In another embodiment, the TVM is TMEM2 (Transmembrane protein 2). In another embodiment, the TVM is a nucleotide molecule encoding TMEM2. In another embodiment, the TVM is TMEM8 (Transmembrane protein 8; five membrane-spanning domains) In another embodiment, the TVM is a nucleotide molecule encoding TMEM8. In another embodiment, the TVM is SLC5A4 (Solute carrier family 5 (low affinity glucose cotransporter), member 4). In another embodiment, the TVM is a nucleotide molecule encoding SLC5A4. In another embodiment, the TVM is MEST (Mesoderm specific transcript homolog (mouse). In another embodiment, the TVM is a nucleotide molecule encoding MEST. In another embodiment, the TVM is CHODL (Chondrolectin). In another embodiment, the TVM is a nucleotide molecule encoding CHODL. In another embodiment, the TVM is TRIO (Triple functional domain (PTPRF interacting)). In another embodiment, the TVM is a nucleotide molecule encoding TRIO. In another embodiment, the TVM is IL10RA (Interleukin 10 receptor, alpha). In another embodiment, the TVM is a nucleotide molecule encoding IL10RA. In another embodiment, the TVM is LGALS3BP (Lectin, galactoside-binding, soluble, 3 binding protein). In another embodiment, the TVM is a nucleotide molecule encoding LGALS3BP. In another embodiment, the TVM is STK4 (Serine/threonine kinase 4). In another embodiment, the TVM is a nucleotide molecule encoding STK4. In another embodiment, the TVM is ERBB3 (V-erb-b2 erythroblastic leukemia viral oncogene homolog 3 (avian). In another embodiment, the TVM is a nucleotide molecule encoding ERBB3. In another embodiment, the TVM is KIAA1024. In another embodiment, the TVM is a nucleotide molecule encoding KIAA1024. In another embodiment, the TVM is KIAA1906. In another embodiment, the TVM is a nucleotide molecule encoding KIAA1906. In another embodiment, the TVM is F3 (Coagulation factor III (thromboplastin, tissue factor)). In another embodiment, the TVM is a nucleotide molecule encoding F3. In another embodiment, the TVM is KIAA0703. In another embodiment, the TVM is a nucleotide molecule encoding KIAA0703. In another embodiment, the TVM is C1orf10 (CRNN; Cornulin). In another embodiment, the TVM is a nucleotide molecule encoding C1orf10. In another embodiment, the TVM is POLYDOM (SVEP1 (Sushi, von Willebrand factor type A, EGF and pentraxin domain containing 1). In another embodiment, the TVM is a nucleotide molecule encoding POLYDOM. In another embodiment, the TVM is TUBAL3 (Tubulin, alpha-like 3). In another embodiment, the TVM is a nucleotide molecule encoding TUBAL3. In another embodiment, the TVM is IL7R (Interleukin 7 receptor). In another embodiment, the TVM is a nucleotide molecule encoding IL7R. In another embodiment, the TVM is ARHGAP18 (Rho GTPase activating protein 18). In another embodiment, the TVM is a nucleotide molecule encoding ARHGAP18. In another embodiment, the TVM is GRM1 (Glutamate receptor, metabotropic 1). In another embodiment, the TVM is a nucleotide molecule encoding GRM1. In another embodiment, the TVM is PREX1 (Phosphatidylinositol 3,4,5-trisphosphate-dependent RAC exchanger 1). In another embodiment, the TVM is a nucleotide molecule encoding PREX1. In another embodiment, the TVM is MUC3A (Mucin 3A, intestinal). In another embodiment, the TVM is a nucleotide molecule encoding MUC3A. In another embodiment, the TVM is EPSTI1 (Epithelial stromal interaction 1 (breast)). In another embodiment, the TVM is a nucleotide molecule encoding EPSTI1. In another embodiment, the TVM is UBE2J1 (Ubiquitin-conjugating enzyme E2, J1 (UBC6 homolog, yeast). In another embodiment, the TVM is a nucleotide molecule encoding UBE2J1. Each possibility represents a separate embodiment of the present invention.

As provided herein, the long isoform of ADAM12 was particularly efficacious, under the conditions utilized, in distinguishing between tumor vasculature and healthy tissue (Example 20). In another embodiment, the ADAM12 nucleotide of methods and compositions of the present invention is a long isoform thereof. In another embodiment, the ADAM12 nucleotide is a short isoform. In another embodiment, the ADAM12 nucleotide is any other ADAM12 nucleotide known in the art. Each possibility represents a separate embodiment of the present invention.

An ADAM12 protein of methods and compositions of the present invention is, in another embodiment, a long isoform thereof. In another embodiment, the ADAM12 protein is a short isoform. In another embodiment, the ADAM12 protein is any other ADAM12 protein known in the art. Each possibility represents a separate embodiment of the present invention.

As provided herein, the short isoform of CDCP1-CUB was particularly efficacious, under the conditions utilized, in distinguishing between tumor vasculature and healthy tissue (Example 20). In another embodiment, the CDCP1-CUB nucleotide of methods and compositions of the present invention is a short isoform thereof. In another embodiment, the CDCP1-CUB nucleotide is a long isoform. In another embodiment, the CDCP1-CUB nucleotide is any other CDCP1-CUB nucleotide known in the art. Each possibility represents a separate embodiment of the present invention.

A CDCP1-CUB protein of methods and compositions of the present invention is, in another embodiment, a short isoform thereof. In another embodiment, the CDCP1-CUB protein is a long isoform. In another embodiment, the CDCP1-CUB protein is any other CDCP1-CUB protein known in the art. Each possibility represents a separate embodiment of the present invention.

In another embodiment, a TVM for the compositions and methods of the present invention is encoded by a sequence selected from the sequences set forth in SEQ ID No: 1-16, 18-23, 25-26, 28-32, 34-46, 48-58, 60-66, 68-70, and 85-211 of WO 2007/089513. In another embodiment, the TVM has an AA sequence encoded by a nucleotide sequence set forth in Table 6 of WO 2007/089513, or in a GenBank entry which Accession Number appears therein. In another embodiment, the TVM has an AA sequence comprising an AA sequence encoded by a nucleotide sequence set forth in Table 6 of WO 2007/089513, or in a GenBank entry which Accession Number appears therein. Each possibility represents a separate embodiment of the present invention.

In another embodiment of compositions and methods of the present invention, the TVM is expressed at detectable levels only in the tumor vasculature cells (TVC), but not in the surrounding tissue. In another embodiment, the TVC is expressed at significantly higher levels in the TVC, relative to the surrounding tissue. In another embodiment, the TVM is expressed at detectable levels only in the TVC, but not in other body tissues. In another embodiment, the TVC is expressed at significantly higher levels in the TVC, relative to other body tissues. Each possibility represents a separate embodiment of the present invention.

In one embodiment, a transmembrane (TM) protein of the present invention is accessible to antibodies and/or non-cell membrane-permeable agents and ligands and thus is useful for the vaccines and methods of the present invention. In another embodiment, a plasma membrane-associated protein of the present invention is accessible to antibodies and/or non-cell membrane-permeable agents and ligands. In another embodiment, a plasma membrane-associated protein of the present invention is a TM protein. In another embodiment, the plasma membrane-associated protein is an extracellular peripheral membrane protein. In another embodiment, the plasma membrane-associated protein is an intracellular peripheral membrane protein. Each possibility represents a separate embodiment of the present invention.

In another embodiment, a TVM of the present invention is specific for vasculogenesis. In another embodiment, a TVM is associated with vasculogenesis. "Vasculogenesis" refers, in another embodiment, to recruitment of endothelial progenitors of hematopoietic origin. In another embodiment, the term refers to de novo formation of tumor vasculature. In another embodiment, a method of present invention is capable to detecting or localizing vasculogenesis. In another embodiment, a method of present invention is capable to inhibiting vasculogenesis. Each possibility represents a separate embodiment of the present invention.

In another embodiment, the TVM is a secreted protein. In another embodiment, the TVM is an extracellular matrix (ECM) protein. In another embodiment, the TVM is a protein associated with the plasma membrane of the TVC, on the extracellular side. In another embodiment, the TVM is capable of shedding from the shed into a bodily fluid. In another embodiment, the TVM can be detected in a bodily fluid. In another embodiment, the bodily fluid is blood. In another embodiment, the bodily fluid is lymph. In another embodiment, the bodily fluid is saliva. In another embodiment, the bodily fluid is sperm. In another embodiment, the bodily fluid is cerebro-spinal fluid. In another embodiment, the bodily fluid is cervico-vaginal fluid. In another embodiment, the bodily fluid is any other bodily fluid known in the art. Each possibility represents a separate embodiment of the present invention.

In another embodiment, the TVM is IBSP (Integrin-binding sialoprotein). In another embodiment, the TVM is a nucleotide molecule encoding IBSP. In another embodiment, the TVM is CKLFSF6 (CKLF-like MARVEL transmembrane domain containing 6). In another embodiment, the TVM is a nucleotide molecule encoding CKLFSF6. In another embodiment, the TVM is HAPLN1 (Hyaluronan and proteoglycan link protein 1). In another embodiment, the TVM is a nucleotide molecule encoding HAPLN1. In another embodiment, the TVM is FLT1 (Fms-related tyrosine kinase 1 (vascular endothelial growth factor/vascular permeability factor receptor). In another embodiment, the TVM is a nucleotide molecule encoding FLT1. In another embodiment, the TVM is LGALS3BP (Lectin, galactoside-binding, soluble, 3 binding protein). In another embodiment, the TVM is a nucleotide molecule encoding LGALS3BP. In another embodiment, the TVM is CCL15 (chemokine (C—C motif) ligand 15). In another embodiment, the TVM is a nucleotide molecule encoding CCL15. In another embodiment, the TVM is PLA2G2D (Phospholipase A2, group IID). In another embodiment, the TVM is a nucleotide molecule encoding PLA2G2D. In another embodiment, the TVM is MUC3A (Mucin 3A, intestinal). In another embodiment, the TVM is a nucleotide molecule encoding MUC3A. In another embodiment, the TVM is LTBP2 (Latent transforming growth factor beta binding protein 2). In another embodiment, the TVM is a nucleotide molecule encoding LTBP2. In another embodiment, the TVM is CELSR2 (Cadherin, EGF LAG seven-pass G-type receptor 2). In another embodiment, the TVM is a nucleotide molecule encoding CELSR2. Each possibility represents a separate embodiment of the present invention.

Figure 8:
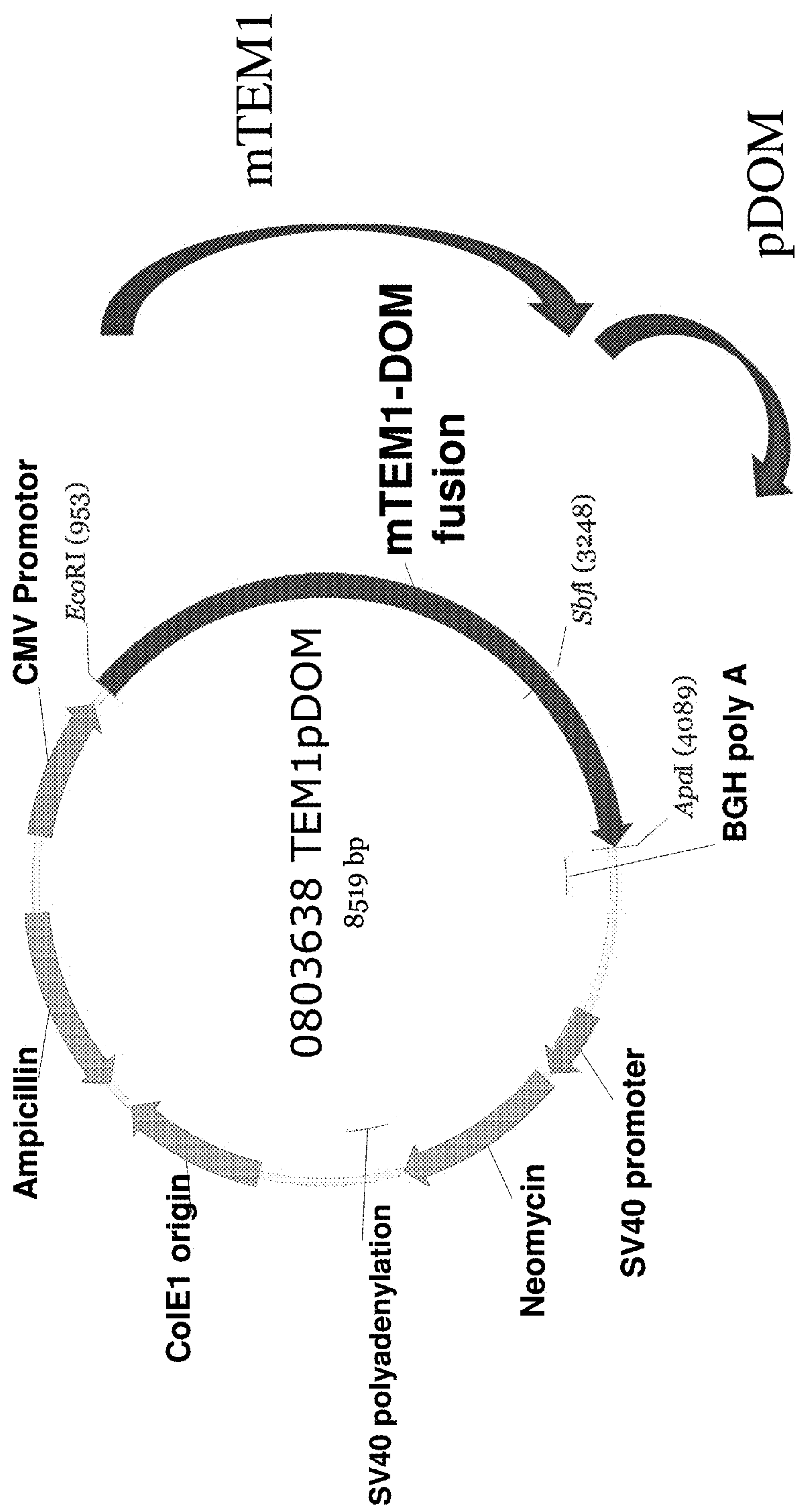
FIG. 8. TEM1-pDOM codon optimized DNA plasmid map.

In another embodiment, the TVM is another nucleotide molecule listed in FIG. 8. In another embodiment, the TVM is a protein encoded by a nucleotide molecule listed in FIG. 8. Each possibility represents a separate embodiment of the present invention.

In another embodiment, the TVM is a solute carrier (SLC) family protein. As provided herein, several SLC proteins (SLC9A5, SLC30A6, SLC11A1) were identified as TVM, showing that proteins belonging to this family are efficacious TVM.

In another embodiment, the TVM is a TMEM protein. In another embodiment, the TVM is a protein containing a TMEM region of homology. In another embodiment, the TVM is a protein containing a TMEM domain. As provided herein, several TMEM proteins (TMEM8, TMEM2, TMEM19) were identified as TVM.

In another embodiment, the TVM is a KCN family protein. As provided herein, several KCN proteins (KCNE3, KCNE4) were identified as TVM, indicating that proteins belonging to this family are TVM.

In another embodiment, the TVM is a CD74 protein. As provided herein, CD74 is a marker of tumor vasculature.

In another embodiment, the TVM is an SYCP1 (Synaptonemal complex protein 1).

In another embodiment, the TVM is a CTD (carboxy-terminal domain, RNA polymerase II, polypeptide A) small phosphatase 1.

Each of TVM disclosed herein, refers, in one embodiment, to a human TVM. In another embodiment, TVMs of the present invention are homologues of proteins known by a different name in another species, as indicated herein.

Each TVM, nucleic acid molecule, and protein represents a separate embodiment of the present invention.

The cancer treated by a method of present invention is, in another embodiment, a cervical cancer tumor. In another embodiment, the cancer is a head and neck cancer tumor. In another embodiment, the cancer is a breast cancer tumor. In another embodiment, the cancer is an ano-genital cancer tumor. In another embodiment, the cancer is a melanoma. In another embodiment, the cancer is a sarcoma. In another embodiment, the cancer is a carcinoma. In another embodiment, the cancer is a lymphoma. In another embodiment, the cancer is a leukemia. In another embodiment, the cancer is mesothelioma. In another embodiment, the cancer is a glioma. In another embodiment, the cancer is a germ cell tumor. In another embodiment, the cancer is a choriocarcinoma. In another embodiment, the cancer is pancreatic cancer. In another embodiment, the cancer is ovarian cancer. In another embodiment, the cancer is gastric cancer. In another embodiment, the cancer is a carcinomatous lesion of the pancreas. In another embodiment, the cancer is pulmonary adenocarcinoma. In another embodiment, the cancer is colorectal adenocarcinoma. In another embodiment, the cancer is pulmonary squamous adenocarcinoma. In another embodiment, the cancer is gastric adenocarcinoma. In another embodiment, the cancer is an ovarian surface epithelial neoplasm (e.g. a benign, proliferative or malignant variety thereof). In another embodiment, the cancer is an oral squamous cell carcinoma. In another embodiment, the cancer is non small-cell lung carcinoma. In another embodiment, the cancer is an endometrial carcinoma. In another embodiment, the cancer is a bladder cancer. In another embodiment, the cancer is a head and neck cancer. In another embodiment, the cancer is a prostate carcinoma. In another embodiment, the cancer is an acute myelogenous leukemia (AML). In another embodiment, the cancer is a myelodysplastic syndrome (MDS). In another embodiment, the cancer is a non-small cell lung cancer (NSCLC). In another embodiment, the cancer is a Wilms' tumor. In another embodiment, the cancer is a leukemia. In another embodiment, the cancer is a lymphoma. In another embodiment, the cancer is a desmoplastic small round cell tumor. In another embodiment, the cancer is a mesothelioma (e.g. malignant mesothelioma). In another embodiment, the cancer is a gastric cancer. In another embodiment, the cancer is a colon cancer. In another embodiment, the cancer is a lung cancer. In another embodiment, the cancer is a breast cancer. In another embodiment, the cancer is a germ cell tumor. In another embodiment, the cancer is an ovarian cancer. In another embodiment, the cancer is a uterine cancer. In another embodiment, the cancer is a thyroid cancer. In another embodiment, the cancer is a hepatocellular carcinoma. In another embodiment, the cancer is a thyroid cancer. In another embodiment, the cancer is a liver cancer. In another embodiment, the cancer is a renal cancer. In another embodiment, the cancer is a kaposis sarcoma. In another embodiment, the cancer is a sarcoma. In another embodiment, the cancer is another carcinoma or sarcoma. Each possibility represents a separate embodiment of the present invention.

In another embodiment, the cancer is an ovarian cancer. In one embodiment, symptoms of ovarian cancer alleviated by the compositions and methods of the present invention include: abdominal pressure, fullness, swelling or bloating; urinary urgency; pelvic discomfort or pain; persistent indigestion, gas or nausea; unexplained changes in bowel habits, including diarrhea or constipation; changes in bladder habits, including a frequent need to urinate; loss of appetite; unexplained weight loss or gain; increased abdominal girth or clothes fitting tighter around your waist; pain during intercourse (dyspareunia); a persistent lack of energy; low back pain.

In another embodiment, the cancer is a renal cancer. In one embodiment, symptoms of renal cancer alleviated by the compositions and methods of the present invention include: blood in the urine; rapid, unexplained weight loss; low back pain (not caused by an injury); loss of appetite; swelling of ankles and legs; mass or lump in the belly; fatigue; recurrent fever (not caused by a cold or the flu); high blood pressure (less frequently); anemia (less frequently); unrelieved pain in the side.

In another embodiment, the cancer is a breast cancer. In one embodiment, symptoms of breast cancer alleviated by the compositions and methods of the present invention include: lumps in breast; nipple changes; cysts in breast; breast pain.

In another embodiment, a TVM of the present invention is particularly efficacious for treating, localizing, or diagnosing a particular tumor type. In another embodiment, a TVM of the present invention is efficacious for treating, localizing, or diagnosing multiple tumor types. In another embodiment, collagen 11α1 is particularly useful for breast tumors. In another embodiment, collagen 11α1 is particularly useful for lung tumors. In another embodiment, LZTS1 is particularly useful for melanoma. In another embodiment, LZTS1 is particularly useful for ovarian cancer. In another embodiment, FZD10 is particularly useful for ovarian tumors. In another embodiment, EMBPL1 is particularly useful for ovarian tumors. In another embodiment, BLAME is particularly useful for a tumor selected from ovarian, adrenal, and testis tumors. In another embodiment, ESM1 is particularly useful for a tumor selected from ovarian, adrenal, and renal tumors. In another embodiment, DSG2 is particularly useful for a tumor selected from colon and recto-sigmoid. In another embodiment, EPSTI1 is particularly useful for a tumor selected from adrenal and testes. In another embodiment, MS4A6A is particularly useful for a tumor selected from adrenal and testes. In another embodiment, LOC51136 is particularly useful for a tumor selected from adrenal, breast, and liver. In another embodiment, EGFL6 is particularly useful for a tumor selected from uterine corpus, lung and omentum. In another embodiment, KCNE3 is particularly useful for a tumor selected from recto-sigmoid, stomach, kidney, and adrenal. In another embodiment, KCNE4 is particularly useful for a tumor selected from breast, pancreas, and adrenal. In another embodiment, c14orf100 is particularly useful for adrenal tumors. In another embodiment, BLAME is particularly useful for a tumor selected from recto-sigmoid and adrenal. In another embodiment, FZD10 is particularly useful for a corpus uteri malignancy. In another embodiment, ST14 is particularly useful for a tumor selected from colon, liver, recto-sigmoid, and adrenal. In another embodiment, PCDHB2 is particularly useful for a tumor selected from adrenal, brain, renal, lung, pancreas, and stomach. In another embodiment, OLFML2B is particularly useful for a tumor selected from adrenal and corpus uteri. In another embodiment, GPR105 is particularly useful for a tumor selected from stomach and testes. In another embodiment, IVNS1ABP is particularly useful for a tumor selected from adrenal, kidney, and testes. In another embodiment, SPP1 is particularly useful for a tumor selected from adrenal, kidney, and liver. In another embodiment, KIAA1892 is particularly useful for a testicular tumor. In another embodiment, C6orf69 is particularly useful for an adrenal malignancy. In another embodiment, KIBRA is particularly useful for a tumor selected from kidney and prostate. Each possibility represents a separate embodiment of the present invention.

In another embodiment, a nucleic acid molecule or peptide of the present invention is homologous to a nucleic acid molecule or peptide disclosed herein. The terms "homology," "homologous," etc, when in reference to any protein or peptide, refer, in one embodiment, to a percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Methods and computer programs for the alignment are well known in the art.

Homology is, in another embodiment, determined by computer algorithm for sequence alignment, by methods well described in the art. For example, computer algorithm analysis of nucleic acid sequence homology may include the utilization of any number of software packages available, such as, for example, the BLAST, DOMAIN, BEAUTY (BLAST Enhanced Alignment Utility), GENPEPT and TREMBL packages.

In another embodiment, "homology" refers to identity to a sequence of greater than 70%. In another embodiment, "homology" refers to identity to a sequence of greater than 72%. In another embodiment, "homology" refers to identity to a sequence of greater than 75%. In another embodiment, "homology" refers to identity to a sequence of greater than 78%. In another embodiment, "homology" refers to identity to a sequence of greater than 80%. In another embodiment, "homology" refers to identity to a sequence of greater than 82%. In another embodiment, "homology" refers to identity to a sequence of greater than 83%. In another embodiment, "homology" refers to identity to a sequence of greater than 85%. In another embodiment, "homology" refers to identity to a sequence of greater than 87%. In another embodiment, "homology" refers to identity to a sequence of greater than 88%. In another embodiment, "homology" refers to identity to a sequence of greater than 90%. In another embodiment, "homology" refers to identity to a sequence of greater than 92%. In another embodiment, "homology" refers to identity to a sequence of greater than 93%. In another embodiment, "homology" refers to identity to a sequence of greater than 95%. In another embodiment, "homology" refers to identity to a sequence of greater than 96%. In another embodiment, "homology" refers to identity to a sequence of greater than 97%. In another embodiment, "homology" refers to identity to a sequence of greater than 98%. In another embodiment, "homology" refers to identity to a sequence of greater than 99%. In another embodiment, "homology" refers to identity to a sequence of 100%. Each possibility represents a separate embodiment of the present invention.

In another embodiment, homology is determined via determination of candidate sequence hybridization, methods of which are well described in the art (See, for example, "Nucleic Acid Hybridization" Hames, B. D., and Higgins S. J., Eds. (1985); Sambrook et al., 2001, Molecular Cloning, A Laboratory Manual, Cold Spring Harbor Press, N.Y.; and Ausubel et al., 1989, Current Protocols in Molecular Biology, Green Publishing Associates and Wiley Interscience, N.Y). For example methods of hybridization may be carried out under moderate to stringent conditions, to the complement of a DNA encoding a native caspase peptide. Hybridization conditions being, for example, overnight incubation at 42° C. in a solution comprising: 10-20% formamide, 5×SSC (150 mM NaCl, 15 mM trisodium citrate), 50 mM sodium phosphate (pH 7.6), 5×Denhardt's solution, 10% dextran sulfate, and 20 μg/ml denatured, sheared salmon sperm DNA.

As used herein, the terms "complementary" or "complementarity" are used in reference to "polynucleotides" and "oligonucleotides" (which are interchangeable terms that refer to a sequence of nucleotides) related by the base-pairing rules. For example, for the sequence 5'-AGT-3' is complementary to the sequence 5'-ACT-3'. Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands.

Protein and/or peptide homology for any amino acid sequence listed herein is determined, in another embodiment, by methods well described in the art, including immunoblot analysis, or via computer algorithm analysis of amino acid sequences, utilizing any of a number of software packages available, via established methods. Some of these packages may include the FASTA, BLAST, MPsrch or Scanps packages, and may employ the use of the Smith and Waterman algorithms, and/or global/local or BLOCKS alignments for analysis, for example. Each method of determining homology represents a separate embodiment of the present invention.

In one embodiment, "variant" refers to an amino acid or nucleic acid sequence (or in other embodiments, an organism or tissue) that is different from the majority of the population but is still sufficiently similar to the common mode to be considered to be one of them, for example splice variants. In one embodiment, the variant may a sequence conservative variant, while in another embodiment, the variant may be a functional conservative variant. In one embodiment, a variant may comprise an addition, deletion or substitution of 1 amino acid. In one embodiment, a variant may comprise an addition, deletion, substitution, or combination thereof of 2 amino acids. In one embodiment, a variant may comprise an addition, deletion or substitution, or combination thereof of 3 amino acids. In one embodiment, a variant may comprise an addition, deletion or substitution, or combination thereof of 4 amino acids. In one embodiment, a variant may comprise an addition, deletion or substitution, or combination thereof of 5 amino acids. In one embodiment, a variant may comprise an addition, deletion or substitution, or combination thereof of 7 amino acids. In one embodiment, a variant may comprise an addition, deletion or substitution, or combination thereof of 10 amino acids. In one embodiment, a variant may comprise an addition, deletion or substitution, or combination thereof of 2-15 amino acids. In one embodiment, a variant may comprise an addition, deletion or substitution, or combination thereof of 3-20 amino acids. In one embodiment, a variant may comprise an addition, deletion or substitution, or combination thereof of 4-25 amino acids.

In one embodiment, the term "fragment" is used herein to refer to a protein or polypeptide that is shorter or comprises fewer amino acids than the full length protein or polypeptide. In another embodiment, fragment refers to a nucleic acid that is shorter or comprises fewer nucleotides than the full length nucleic acid. In another embodiment, the fragment is an N-terminal fragment. In another embodiment, the fragment is a C-terminal fragment. In one embodiment, the fragment is an intrasequential section of the protein, peptide, or nucleic acid. In another embodiment, the fragment is an immunogenic intrasequential section of the protein, peptide or nucleic acid. In another embodiment, the fragment is a functional intrasequential section within the protein, peptide or nucleic acid. In another embodiment, the fragment is an N-terminal immunogenic fragment. In one embodiment, the fragment is a C-terminal immunogenic fragment. In another embodiment, the fragment is an N-terminal functional fragment. In another embodiment, the fragment is a C-terminal functional fragment.

Thus, in one embodiment, an "immunogenic fragment" of a protein as described in the present invention refers to a portion of the protein that is immunogenic, in one embodiment and in another embodiment, elicits a protective immune response when administered to a subject.

In one embodiment, "isoform" refers to a version of a molecule, for example, a protein, with only slight differences to another isoform of the same protein. In one embodiment, isoforms may be produced from different but related genes, or in another embodiment, may arise from the same gene by alternative splicing. In another embodiment, isoforms are caused by single nucleotide polymorphisms.

In one embodiment, the present invention provides vaccines for inducing an immune response against a tumor vasculature, while in another embodiment, the present invention provides compositions for inducing an immune response against a tumor vasculature.

In one embodiment, the term "vaccine" refers to an immunological composition given to a subject to elicit an immune response against a specific antigen, which in one embodiment, is a tumor vaculature marker.

In one embodiment, the vaccine is a DNA vaccine. In another embodiment, the vaccine is a plasmid vector. In another embodiment, the vaccine is a mini-circle DNA vaccine. In one embodiment, the vaccine is a recombinant viral vaccine. In one embodiment, the recombinant viral vaccine is a recombinant adenoviral vaccine. In another embodiment, the vaccine is a live whole virus vaccine. In another embodiment, the vaccine is killed whole virus vaccine. In another embodiment, the vaccine is a subunit vaccine, which in one embodiment is a peptide vaccine in which the peptide encodes an antigen, which in one embodiment, is purified or recombinant. In another embodiment, the vaccine is an anti-idiotype antibody.

In one embodiment, the recombinant viral vaccine is an adenovirus, alphavirus or simian virus, or vaccinia virus-based vaccine. In another embodiment, viruses contemplated as useful vectors in the present methods and compositions include, but are not limited to lentiviruses, retroviruses, coxsackie viruses, herpes viruses (see, e. g., Geller, A. I. et al., ProcNatl. Acad. Sci.: U.S.A 90: 7603 (1993); Geller, A. I., et al., ProcNat. Acad. Sci USA 87: 1149 (1990), adenoviruses (see, e. g., LaSalle et al., Science, 259: 988 (1993); Davidson, et al., Nat. Genet 3: 219 (1993); Yang, et al., J. Virol. 69: 2004 (1995), adeno-associated viruses (see, e. g., Kaplitt, M. G., et al., Nat. Genet. 8: 148 (1994)) and the like, all of which are hereby incorporated by reference.

In accordance with this invention, the TVM fusion expression cassette is inserted into a vector. The vector is preferably an adenoviral or plasmid vector, although linear DNA linked to a promoter, or other vectors, such as adeno-associated virus or a modified vaccinia virus, retroviral or lentiviral vector may also be used. In one embodiment, the adenovirus vector is a first-generation adenoviral vector, which in one embodiment, is characterized by having a non functional E1 gene region, and preferably a deleted adenoviral E1 gene region. In some embodiments, the expression cassette is inserted in the position where the adenoviral E1 gene is normally located. In addition, in one embodiment, these vectors optionally have a non-functional or deleted E3 region.

In one embodiment, the vector is a replication-defective adenovirus. Techniques for preparing replication defective adenoviruses are well known in the art, as exemplified by Quantin, et al., Proc. Natl. Acad. Sci. USA, 89: 2581-2584 (1992); Stratford-Perricadet, et al., J. Clin. Invest., 90: 626-630 (1992); and Rosenfeld, et al., Cell, 68: 143-155 (1992). In such an adenovirus, a viral gene essential for replication and/or packaging is deleted from the adenoviral vector construct, allowing the TVM, or in one embodiment, TEM expression region to be introduced in its place. Any gene, whether essential (e. g., E1A, E1B, E2 and E4) or non-essential (e. g., E3) for replication, may be deleted and replaced with the TVM, or in one embodiment, TEM DNA sequence.

In one embodiment, vectors and virions in which the E1A and E1B regions of the adenovirus vector have been deleted and the TVM, or in one embodiment, TEM DNA sequence introduced in their place.

It is also well known that various cell lines may be used to propagate recombinant adenoviruses, so long as they complement any replication defect that may be present. One exemplary cell line is the human 293 cell line, but any other cell line that is permissive for replication, e. g., in the preferred case, which expresses E1A and E1B may be employed. Further, the cells can be propagated either on plastic dishes or in suspension culture, in order to obtain virus stocks thereof. In one embodiment of the invention, a replication-defective, helper-independent adenovirus is created that expresses the TVM, or in one embodiment, TEM protein under the control of the human cytomegalovirus promoter.

The adenoviruses can be multiplied in known cell lines which express the viral E1 gene, such as 293 cells, or PERC.6 cells, or in cell lines derived from 293 or PE1IC.6 cell. For example, when using constructs that have a controlled gene expression, such as a tetracycline regulatable promoter system, the cell line may express components involved in the regulatory system. One example of such a cell line is TRex-293, others are known in the art.

For convenience in manipulating the adenoviral vector, the adenovirus may be in a shuttle plasmid form. This invention is also directed to a shuttle plasmid vector which comprises a plasmid portion and an adenovirus portion, the adenovirus portion comprising an adenoviral genome which has a deleted E1 and optional E3 deletion, and has an inserted expression cassette comprising a TVM fusion protein encoding nucleotide sequence. In preferred embodiments, there is a restriction site flanking the adenoviral portion of the plasmid so that the adenoviral vector can easily be removed. The shuffle plasmid may be replicated in prokaryotic cells or eukaryotic cells.

In another embodiment, the adenovirus used in the methods and compositions of the present invention is a helper-dependent Ad (hdAd), or in another embodiment, a gutless adenovirus, which is well-known in the art.

Standard techniques of molecular biology for preparing and purifying DNA constructs enable the preparation of the adenoviruses, shuttle plasmids, and DNA immunogens of this invention.

In one of the invention, the adenovirus vector is an Ad 5 vector. In another embodiment of the invention, the adenovirus vector is an Ad 6 vector. In yet another preferred embodiment, the adenovirus vector is an Ad 24 vector. In another embodiment, the adenovirus is derived from Ad5, Ad11, Ad26, Ad34, Ad35, Ad48, Ad49 or Ad50 serotype. In another embodiment, the adenovirus may be of any of the 42 different known serotypes or subgroups A-F.

Also contemplated for use in the present invention is an adenovirus vaccine vector comprising an adenovirus genome that naturally infects a species other than human, including, but not limited to, chimpanzee adenoviral vectors. In one embodiment, the adenovirus vector is a chimp Ad 3 vaccine vector.

"Nucleic acid molecule" and "nucleotide" refer, in another embodiment, to an RNA molecule. In another embodiment, the terms refer to a DNA molecule. In another embodiment, the terms refer to any other type of nucleic acid molecule enumerated herein. In another embodiment, the terms refer to any other type of nucleic acid molecule known in the art. Each possibility represents a separate embodiment of the present invention.

The terms "amino acid sequence" and "polypeptide sequence" are used interchangeably herein to refer to a sequence of amino acids.

An oligonucleotide, as used herein, is a nucleic acid molecule of less than about 100 nucleotides, and a polynucleotide is a nucleic acid molecule of more than about 100 nucleotides. Also included herein are nucleic acids which incorporate unusual nucleotides, as well as nucleic acid analogs, such as peptide nucleic acids (PNAs), locked nucleic acids, and synthetic nucleic acid binding molecules, such as N-methylimidazole and N-methylpyrrole amino acid sequences that bind in the minor groove of DNA. These analogs are well known in the art. See, e.g., Larsen et al. (1999) Biochem. Biophys. Acta 1489, 159; Wengel et al. (1999) Nucleosides Nucleotides 18, 1365; Braasch et al. (2000) Chem. Biol. 55, 1; Trauger, J. W. et al. (1996) Nature, 382, 559; Nielsen et al. (1991) Science 254, 1497; Wittung et al. (1997) Nucleosid. Nucleotid. 16, 559; U.S. Pat. Nos. 6,201,103; 6,204,326. Also included are molecules comprising a nucleotide moiety along with other components, such as saccharides, dyes, haptens, etc.

A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169-176). Several nucleic acid analogs are described in Rawls, C & E News Jun. 2, 1997 page 35. Nucleic acid analogs also include "locked nucleic acids". All of these references are hereby expressly incorporated by reference. These modifications of the ribose-phosphate backbone may be done to facilitate the addition of electron transfer moieties, or to increase the stability and half-life of such molecules in physiological environments As used herein in the specification and in the examples section which follows the term "peptide" includes native peptides (either degradation products, synthetically synthesized peptides or recombinant peptides) and peptidomimetics (typically, synthetically synthesized peptides), such as peptoids and semipeptoids which are peptide analogs, which may have, for example, modifications rendering the peptides more stable while in a body or more capable of penetrating into bacterial cells. Such modifications include, but are not limited to N terminus modification, C terminus modification, peptide bond modification, including, but not limited to, CH2-NH, CH2-S, CH2-S═O, O═C—NH, CH2-O, CH2-CH2, S═C—NH, CH═CH or CF═CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH═CH—), retro amide bonds (—NH—CO—), peptide derivatives (—N(R)—CH2-

CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted for synthetic non-natural acid such as TIC, naphthylelanine (Nol), ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 2 and 3 below list naturally occurring amino acids (Table 2) and non-conventional or modified amino acids (Table 3) which can be used with the present invention.

TABLE 2

| Amino Acid | Three-Letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| Glycine | Gly | G |
| Histidine | His | H |
| Isoleucine | Iie | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid as above | Xaa | X |

TABLE 3

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-Carboxylate | Cpro | L-N-methylasparagine | Nmasn |
| | | L-N-methylaspartic acid | Nmasp |
| aminoisobutyric acid | Aib | L-N-methylcysteine | Nmcys |
| aminonorbornyl-Carboxylate | Norb | L-N-methylglutamine | Nmgin |
| | | L-N-methylglutamic acid | Nmglu |
| Cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |

TABLE 3-continued

| Non-conventional amino acid | Code | Non-conventional amino acid | Code |
|---|---|---|---|
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl) glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α ethylvaline | Mtrp | L-α-methyltyrosine | Mtyr |
| L-α-methylleucine | Mval | L-N-methylhomophenylalanine | Nmhphe |
| | Nnbhm | | |
| N-(N-(2,2-diphenylethyl) carbamylmethyl-glycine | Nnbhm | N-(N-(3,3-diphenylpropyl) carbamylmethyl(1)glycine | Nnbhe |
| 1-carboxy-1-(2,2-diphenyl ethylamino)cyclopropane | Nmbc | | |

In one embodiment, the nucleic acid sequence of TVM is wild-type, while in another embodiment, the nucleic acid sequence of TVM comprises a modification. The term "wild-type" when made in reference to a nucleic acid sequence refers to a nucleic acid sequence which has the characteristics of that nucleic acid sequence when isolated from a naturally occurring source. A wild-type nucleic acid sequence is that which is most frequently observed in a population and is thus arbitrarily designed the "normal" or "wild-type" form of the nucleic acid sequence. In contrast, the term "modified nucleic acid sequence" or "mutant nucleic acid sequence" refers to a nucleic acid sequence which displays modifications in sequence and/or functional properties (i.e., altered characteristics) when compared to the wild-type nucleic acid sequence. For example, a mutant nucleic acid sequence refers to a nucleic acid sequence which contains a mutation. It is noted that naturally-occurring mutants can be isolated; these are identified by the fact that they have altered characteristics when compared to the wild-type nucleic acid sequence.

A "modification" as used herein in reference to a nucleic acid sequence refers to any change in the structure of the nucleic acid sequence. Changes in the structure of a nucleic acid sequence include changes in the covalent and non-covalent bonds in the nucleic acid sequence. Illustrative of these changes are point mutations, mismatches, strand breaks, as well as covalent and non-covalent interactions between a nucleic acid sequence, which contains unmodified and/or modified nucleic acids, and other molecules. Illustrative of a covalent interaction between a nucleic acid sequence and another molecule are changes to a nucleotide base (e.g., formation of thumine glycol) and covalent cross-links between double-stranded DNA sequences which are introduced by ultraviolet radiation or by cis-platinum. Yet another example of a covalent interaction between a nucleic acid sequence and another molecule includes covalent binding of two nucleic acid sequences to psoralen following ultraviolet irradiation. Non-covalent interactions between a nucleic acid sequence and another molecule include non-covalent interactions of a nucleic acid sequence with a molecule other than a nucleic acid sequence and other than a polypeptide sequence. Non-covalent interactions between a nucleic acid sequence with a molecule other than a nucleic acid sequence and other than a polypeptide sequence are illustrated by non-covalent intercalation of ethidium bromide or of psoralen between the two strands of a double-stranded deoxyribnucleic acid sequence.

As used herein, the term "mutation" refers to a deletion, insertion, or substitution. A "deletion" is defined as a change in a nucleic acid sequence in which one or more nucleotides is absent. An "insertion" or "addition" is that change in a nucleic acid sequence which has resulted in the addition of one or more nucleotides. A "substitution" results from the replacement of one or more nucleotides by a molecule which is different molecule from the replaced one or more nucleotides. For example, a nucleic acid may be replaced by a different nucleic acid as exemplified by replacement of a thymine by a cytosine, adenine, guanine, or uridine. Alternatively, a nucleic acid may be replaced by a modified nucleic acid as exemplified by replacement of a thymine by thymine glycol.

In one embodiment, the vaccine further comprises an adjuvant. In another embodiment, the nucleic acid construct further comprises a nucleic acid sequence encoding an adjuvant. In one embodiment, the adjuvant is DOM, pDOM FcIgG, CT, LTA, or LTB or an immunogenic fragment thereof. In one embodiment, the adjuvant is the N-terminal domain of fragment C of tetanus toxoid (DOM). In one embodiment, the adjuvant is fused to said polypeptide. In another embodiment, the adjuvant is fused to said nucleic acid sequence. In one embodiment, the polypeptide comprises a tumor endothelial marker (TEM)-1 protein or variant thereof fused to the N-terminal domain of fragment C of tetanus toxoid (DOM). In another embodiment, the nucleic acid construct comprises a nucleic acid sequence encoding a tumor endothelial marker (TEM)-1 protein or variant thereof fused in frame to a nucleic acid sequence encoding the N-terminal domain of fragment C of tetanus toxoid (DOM). In another embodiment, provided herein is a nucleic acid encoding a TEM1-pDOM fusion (FIG. 8), wherein in other embodiments, the TEM1-pDOM is murine TEM1-pDOM. In another embodiment, provided herein is a nucleic acid encoding a TEM-7R-DOM fusion.

In one embodiment, the vaccines of the present invention comprise an adjuvant, while in another embodiment, the vaccines do not comprise an adjuvant. "Adjuvant" refers, in another embodiment, to compounds that, when administered to an individual or tested in vitro, increase the immune response to an antigen in the individual or test system to which the antigen is administered. In another embodiment, an immune adjuvant enhances an immune response to an antigen that is weakly immunogenic when administered alone, i.e., inducing no or weak antibody titers or cell-mediated immune response. In another embodiment, the adjuvant increases antibody titers to the antigen. In another embodiment, the adjuvant lowers the dose of the antigen effective to achieve an immune response in the individual.

In one embodiment, the adjuvant utilized in the methods and compositions of the present inventions is DOM, pDOM, FcIgG, CT, LTA, or LTB or an immunogenic fragment thereof. In one embodiment, the abbreviation "DOM" refers generally to the N-terminal domain of fragment C of tetanus toxoid.

In one embodiment, the abbreviation "LT" refers generally to the heat labile enterotoxin of *E. coli*. "LT" may refer to the complete enterotoxin, comprising subunits A and B or a substantial portion of subunit A, or a substantial portion of subunit B. The abbreviation "LTA" refers to the A subunit of the heat labile enterotoxin of *E. coli*, or substantial portion thereof, including subunits which are truncated on the C-terminal or N-terminal end but maintain biological activity, as well as subunits that contain internal amino acid insertions, deletions, or substitutions but maintain biological activity. The abbreviation "LTB" refers to the B subunit of the heat labile enterotoxin of *E. coli*, or substantial portion thereof, including subunits which are truncated on the C-terminal or N-terminal end but maintain biological activity, as well as subunits that contain internal amino acid insertions, deletions, or substitutions but maintain biological activity.

In one embodiment, an adjuvant of the present invention is heat shock protein (HSP) 70, lysosome-associated membrane protein (LAMP), fragment C of tetanus toxoid (FrC), the N-terminal domain of FrC (DOM), the heavy fragment of constant chain of immune globulin G1 (FcIgG), the vesicular stomatitis virus glycoprotein (VSV-G), cholera toxin (CT) from *Vibrio cholerae*, or heat labile enterotoxin of *E. coli* (LT).

The adjuvant utilized in methods and compositions of the present invention is, in another embodiment, a CpG-containing nucleotide sequence. In another embodiment, the adjuvant is a CpG-containing oligonucleotide. In another embodiment, the adjuvant is a CpG-containing oligodeoxynucleotide (CpG ODN). In another embodiment, the adjuvant is ODN 1826, which in one embodiment, is acquired from Coley Pharmaceutical Group.

"CpG-containing nucleotide," "CpG-containing oligonucleotide," "CpG oligonucleotide," and similar terms refer, in another embodiment, to a nucleotide molecule of 8-50 nucleotides in length that contains an unmethylated CpG moiety. In another embodiment, any other art-accepted definition of the terms is intended.

In other embodiments, the adjuvant of the methods and compositions of the present invention is Montanide ISA 51. Montanide ISA 51 contains a natural metabolizable oil and a refined emulsifier. In another embodiment, the adjuvant is GM-CSF. In another embodiment, the adjuvant is KLH. Recombinant GM-CSF is a human protein grown, in another embodiment, in a yeast (*S. cerevisiae*) vector. GM-CSF promotes clonal expansion and differentiation of hematopoietic progenitor cells, APC, and dendritic cells and T cells.

In another embodiment, the adjuvant is a cytokine. In another embodiment, the adjuvant is a growth factor. In another embodiment, the adjuvant is a cell population. In another embodiment, the adjuvant is QS21. In another embodiment, the adjuvant is Freund's incomplete adjuvant. In another embodiment, the adjuvant is aluminum phosphate. In another embodiment, the adjuvant is aluminum hydroxide. In another embodiment, the adjuvant is BCG. In another embodiment, the adjuvant is alum, which in another embodiment, is potassium aluminum sulfate. In another embodiment, the adjuvant is an interleukin. In another embodiment, the adjuvant is an unmethylated CpG oligonucleotide. In another embodiment, the adjuvant is quill glycosides. In another embodiment, the adjuvant is monophosphoryl lipid A. In another embodiment, the adjuvant is liposomes. In another embodiment, the adjuvant is a bacterial mitogen. In another embodiment, the adjuvant is a bacterial toxin. In another embodiment, the adjuvant is a chemokine. In another embodiment, the adjuvant is any other type of adjuvant known in the art. In another embodiment, the vaccine of methods and compositions of the present invention comprises two of the above adjuvants. In another embodiment, the vaccine comprises more than two of the above adjuvants. Each possibility represents a separate embodiment of the present invention.

In one embodiment, the vaccine additionally comprises one or more tumor associated antigens. In one embodiment, the tumor associated antigen is a Her/2-neu antigen, High Molecular Weight Melanoma Associated Antigen (HMW-MAA), carcinoembryonic antigen (CEA), Melanoma-associated antigen (MAGE-A), Carcinoma-associated mucin (MUC-1), Renal tumor antigen 1 (RAGE), Breakpoint cluster region protein (BCR), kidney-associated antigen 1; or Carbonate dehydratase IX (CALX).

In one embodiment, said vaccine additionally comprises one or more tumor associated antigens. In one embodiment, said tumor associated antigen is a Her/2-neu antigen, a Prostate Specific Antigen (PSA), Prostate Stem Cell Antigen (PSCA), a Stratum Corneum Chymotryptic Enzyme (SCCE) antigen, Wilms tumor antigen 1 (WT-1), human telomerase reverse transcriptase (hTERT), Proteinase 3, Tyrosinase Related Protein 2 (TRP2), High Molecular Weight Melanoma Associated Antigen (HMW-MAA), synovial sarcoma, X (SSX)-2, carcinoembryonic antigen (CEA), MAGE-A, interleukin-13 Receptor alpha (IL13-R alpha), Carbonic anhydrase IX (CALX), survivin, GP100, or Testisin. In another embodiment, said tumor associated antigen is Human Papilloma Virus E6 or E7.

In another embodiment, said tumor associated antigen is Baculoviral IAP repeat-containing protein 7; Baculoviral IAP repeat-containing protein 5 (BIRCS); Kidney-associated antigen 1; Carbonate dehydratase IX; Renal tumor antigen 1 (RAGE); Scm-like with four MBT domains protein 1 (SFMBT1); Breakpoint cluster region protein (BCR); Met proto-oncogene (hepatocyte growth factor receptor) (MET); RING finger protein 43 precursor (RNF43). In another embodiment, said tumor associated antigen is kinase anchor protein 13 (AKAP13); Ankyrin repeat domain-containing protein 30A (ANKRD30A); Adenomatosis polyposis coli (APC); Baculoviral IAP repeat-containing protein 5 (BIRCS); CAN protein; Calcium activated chloride channel family member 2 (CLCA2); Fibronectin 1 (FN1); Glycoprotein NMB (GPNMB); Melanoma-associated antigen 1 (MAGEA1); Melanoma-associated antigen 4 (MAGEA4); Milk fat globule-EGF factor 8 (MFGE8); Carcinoma-associated mucin (MUC1); Oculocutaneous albinism II (pink-eye dilution (murine) homolog) (OCA2); Peroxiredoxin-5 (PRDXS); Parathyroid hormone-like hormone (PTHLH); TGF-beta receptor type II (TG1-BR2); Tropomyosin 4 (TPM4); Zinc finger, UBR1 type 1-fragment (ZUBR1).

In another embodiment, the tumor associated antigen is ERBB2 (CD340 antigen; MLN 19; NEU proto-oncogene; Tyrosine kinase-type cell surface receptor HER2; c-erb B2; c-erbB2/neu protein; neuroblastoma/glioblastoma derived oncogene homolog; tyrosine kinase-type cell surface receptor; v-erb-b2 avian erythroblastic leukemia viral oncogene homolog; neuro/glioblastoma derived oncogene homolog; v-erb-b2 erythroblastic leukemia viral oncogene homolog; neuo/glioblastoma derived oncogene homolog (avain); c-erbB-2; EC 2.7.10.1; HER-2; HER-2/neu; HER2; NEU; NGL; TKR1; erb-2; herstatin; p185erbB2); BIRCS (Survivin; Apoptosis inhibitor 4; Apoptosis inhibitor survivin; apoptosis inhibitor 4 (survivin); baculoviral IAP repeat-containing 5; API4; EPR-1; IAP4; SVV5); CEACAM5 (CEA; 5CD66e antigen; Carcinoembryonic antigen; Carcinoembryonic antigen-related cell adhesion molecule 5 precursor; Meconium antigen 100; CD66e; CEA; DKFZp781M239); WDR46 (WD repeat protein BING4; WDR46; BING4; C6Orf1; FP221); BAGE (antigen MZ2-BA; B melanoma antigen 1 precursor; BAGE1; BAGE); CSAG2 (CSAG family, member 2; Taxol-resistant-associated protein 3; taxol resistance associated gene 3; CSAG2; MGC149851; MGC149852; TRAG-3; TRAG3); DCT (dopachrome delta-isomerase; tyrosinase-related protein 2; L-dopachrome Delta-isomerase; L-dopachrome tautomerase precursor; Tyrosinase-related protein 2; dopachrome tautomerase; dopachrome delta-isomerase; tyrosine related proteins; DCT; EC5.3.3.12; TRP-2; TYRP2); GAGE1 (MZ2-F antigen; GAGE-1; MGC33825); GAGE2 (GAGE-2; MGC120097; MGC96883; MGC96930; MGC96942); GAGE3 (GAGE-3); GAGE4 (GAGE-4); GAGE5 (GAGE-5); GAGE6 (GAGE-6); GAGE7 (G antigen 7B; AL4; GAGE-7; GAGE-7B; GAGE-8; GAGE7; GAGE7B); GAGE8 (GAGE-8; CTD-2248C21.2); IL13RA2 (CD213a2 antigen; IL-13 receptor; Interleukin-13-binding protein; interleukin 13 binding protein; interleukin 13 receptor alpha 2 chain; interleukin 13 receptor; alpha 2; CD213A2; CD213a2; IL-13R; IL-13BP; IL13R; IL13RA2); MAGEA1 (Antigen MZ2-E; MAGE-1 antigen; melanoma antigen MAGE-1; melanoma antigen family A,1; melanoma antigen famiily A; 1 (direct expression of antigen MZ2-E; melanoma, antigen family A; 1 (direct expression of antigen MZ2-E; melanoma-associated antigen MZ2-E; MAGE1; MAGE1A; MGC9326; MAGEA1; MAGE-A1); MAGEA2 (MAGE-2 antigen; melanoma antigen 2; melanoma antigen-family A, 2; melanoma antigen; family A, 2; MAGE2; MAGEA2A; MAGEA2B; MGC131923; MAGEA2; MAGE-A2); MAGEA3 (Antigen MZ2-D; MAGE-3 antigen; melanoma antigen family A, 3; Melanoma antigen, family A, 3; HIPS; HYPD; MAGE3; MGC14613; MAGEA3; MAGE-A3); MAGEA4 (MAGE-4 antigen; melanoma antigen family A,4; melanoma antigen family A,4; MAGE-41; MAGE-X2; MAGE4; MAGE4A; MAGE4B; MGC21336; MAGEA4; MAGE-A4); MAGEA6 (MAGE-6 antigen; melanoma antigen family A, 6; MAGE-3B; MAGE3B; MAGE6; MGC52297; MAGEA6; MAGE-A6); MAGEA9 (MAGE-9 antigen; melanoma associated family A, 9; melanoma antigen, family A, 9; MAGE9; MGC8421; MAGEA9; MAGE-A9); MAGEA10 (MAGE-10 antigen; melanoma associated family A, 10; melanoma antigen, family A, 10; MAGE10; MGC10599; MAGEA10; MAGE-A10); MAGEA12 (MAGE-12 antigen; melanoma associated family A, 12; melanoma antigen, family A, 12; MAGE12; MAGE12F; MAGEA12; MAGE-A12); MAGEB1 (DSS-AHC critical interval MAGE superfamily 10; DSS/AHC critical interval MAGE superfamily 10; MAGE-B1 antigen; MAGE-XP; MAGE-like gene on Xp; melanoma antigen family B, 1; melanoma antigen, family B, 1; DAM10; MAGE-Xp; MAGEL1; MAGEXP; MG9322); MAGEB2 (DSS-AHC critical interval MAGE superfamily 6; DSS/AHC critical interval MAGE superfamily 6; MAGE-B2 antigen; MAGE-XP2; MAGE-like gene on Xp; melanoma antigen family B, 2; melanoma antigen, family B, 2; DAM6; MAGE-XP-2; MGC26438); MAGEC2 (Cancer-testis antigen 10; Hepatocellular carcinoma-associated antigen 587; MAGE-C2 antigen; MAGE-E1 antigen; cancer-testis antigen CT10; hepatocellular cancer antigen 587; melanoma antigen family C, 2; melanoma antigen, family E, 1 protein; melanoma antigen, family E, 1, cancer/testis specific; melanoma-associated antigen E1); TP53 (Antigen NY—CO-13; Cellular tumor antigen p53; Phosphoprotein p53; p53 tumor suppressor; tumor protein p53; tumor protein p53 (Li-Fraumeni syndrome); LFS1; P53; TRP53; P53); TYR (Monophenol monooxygenase; Tumor rejection antigen AB; Tyrosinase precursor; tyrosinase (oculocutaneous albinism IA); TYR; EC 1.14.18.1; LB24-AB; OCA1A; OCAIA; SK29-AB); TYRP1 (5,6-Dihydroxyindole-2-carboxylic acid oxidase precirsor; Catalase B; DHICA oxidase; Glycoprotein 75; associated with iris pigmentation; CAS2; CATB; EC1.14.18.-; GP75; TRP; TRP-1; TRP1; TYRP; TYRRP; b-PROTEIN); SAGE1 (Cancer/testis antigen 14; CT14; SAGE); SYCP1 (HOM-TES-14; MGC104417; SCP-1; SCP1; SYCP1); SSX2 (Protein SSX2; synovial sarcoma, X breakpoint 2; synovial sarcoma, X brakpoint 2 isoform b; synovial sarcoma, X breakpoint 2B; HD21; HOM-MEL-40; MGC119055; MGC15364; MGC3884; SSX2); SSX4 (Protein SSX4; MGC119056; MGC12411); KRAS (K-Ras 2; K-ras p21 protein; Kirsten rat sarcoma-2 viral (v-Ki-ras2) oncogene homolog; PR310 c-K-ras oncogene; c-K-ras2 protein; c-Kirsten-ras protein; cellular c-Ki-ras2 proto-oncogene; oncogene KRAS; tansforming protein p21; v-Ki-ras2 Kirsten rat sarcoma 2 viral oncogene homolog; v-Ki-ras2 Kirsten rat sarcoma viral oncogene homolog KRAS; C—K-RAS, K-RAS2A; K-RAS2B; K-RAS4A; K-RAS4B; KI-RAS; KRAS1; KRAS2; Ki-Ras; NS3; RASK2; c-K-RAS; C-Ki-RAS); PRAME (Melanoma antigen preferentially expressed in tumors; OPA-interacting protein 4; Opa-interacting protein OIP4; Preferentially expressed antigen of melanoma; preferentially expressed antigen in melanoma; PRMAE; MAPE; OIP4); NRAS (N-ras protein part 4; Transforming protein N-Ras; neuroblastoma RAS viral (v-ras) oncogene homolog; v-ras neuroblastoma RAS viral oncogene homolog; N-ras); ACTN4 (F-actin cross-linking protein; actinin, alpha4; ACTN4; DKFZp686k23158; FSGS; FSGS1); CTNNB1 (catenin; caherin-associated protein beta 1(88 kD); Beta-catenin; CTNNB; CTNNB1; FLJ25606); CASP8 (Apototic cysteine protease; Apoptotic protease Mch-5; FADD-homologous ICE/CED-3-like protease; FADD-like YCE; *H. sapeins* mRNA for MACH-alpha-2 protein; ICE-like apoptotic protease 5; MACH-alpha1/2/3 protein; MACH-beta-1/2/3/4 protein MORT1-associated CED-3 homolog; Mch5 isoform alpha; caspase 8; apoptosis-related cysteine peptidase; apoptotic-related cysteine protease; CAP4; CASP8; CASP-8; EC 3.4.22.-; FLICE; MACH; MCHS; MGC78473; procaspase-8); CDC27 (Cell division cycle protein 27 homolog; anaphase-promoting complex; protein 3; cell division 27 homolog (*S. cerevisiae*); cell division cycle protein 27; nuc2 homolog; APC3; CDC27; CDC27Hs; DOS1430E; D17S978E; H-NUC; HNUC); CDK4 (cell division kinase 4; cyclin-dependent kinase 4; malnoma cutaneous malignant 3; CMM3; CDK4; EC2.7.11.22; MGC14458; PSK-J3); EEF2 (eukaryotic translation elongation factor 2; polypeptidyl-tRNA translocase; EEF-2; EEF2; EF2; EF2); FN1 (Cold-insoluble globulin; Fibronectin precuror; migration stimulating factor; migration-stimulating factor; CIG; DKFZp686F10164; DKFZp686H0342; DKFZp686I1370; DKFZp686O13149; FINC; FN; LETS; MSF); HSPA1B (Heat shock 70 kDa protein 1; heat shock 70 kD protein 1; heat shock 70 kDa protein 1B; HSP70-1/HSP70-2; HSP70-2; HSP70.1; HSPA1; HSPA1A); LPGAT1 (family with sequence similarity 34, member A; lysophosphatidylglyceraol, acyl transferase 1; EC 2.3.1.-; FAM34A; FAM34A1; KIAA0205; LPGAT1); ME1 (MALATE OXIDOREDUCTASE; Malic enzyme; cytoplasmic, NADP-dependent malic enzyme; malate dehydrogenase; malic enzyme 1; NADP(+)dependent, cytosolic, malic enzyme 1; soluble, pyruvic-malic carboxylase; M1; EC 1.1.1.40; HUMNDME; MES; NADP-ME); HHAT (Melanoma antigen recognized by T cells 2; Protein-cysteine N-palmitoyltransferase HHAT; Skinny hedehog protein 1; melanoma antigen recognized by T cells; skinny hedhehog *Drosophila*, homolog of; EC 2.3.1.-, FLJ10724; FLJ34867; GUP2; MART-2; MART2; SKR; HHAT; Skn; rasp; sit; ski); TRAPPC1 (BETS homolog; Multiple myeloma protein 2; Trafficking proteinparticle complex subunit1; BETS; MUM-2; MUM2); MUM3 (ASC-1 complex subunit p200; Helicase, ATP binding 1; TRIP4 complex subunit p200; activating signal cointegrator 1 complex subunit 3; ASC1p200; B630009I04Rik; DJ467N11.1; EC 3.6.1.-; HELIC1; MGC26074; RNAH; dJ121G13.4; ASCC3); MYO1B (myosin IB; mysosin-I alpha; MMI-alpha, MMIa; MYH-1 c; Myosin-Ib; myr1); PAPOLG (Apolymerase gamma; neopoly; PAP gamma; Polunycleotide adenyltransferase gamma; SRP RNA 3'adenylating enzyme; SRP RNA 3' adenylating enzyme/pap2; nuclear poly (A) polymerase gamma; EC 2.7.7.19; FU11805; FLJ13482; FLJ14187; MGC133307; MGC133308; Neo-PAP; PAP2; PAPG; Poly; PAPOLG); OS9 (Amplified in osteosarcoma 9; amplified in osteosarcoma); PTPRK (*H. sapiens* mRNA for phosphotyrosine phosphatase kappa; Protein-tyrosine phosphatase kappa; Receptor-type tyrosine phosphase kappa precursor; dJ480J14.2.1 (protein tyrosine phosphatase kappa; protein tyrosine phosphatase kappa; protein tyrosine phosphatase; receptor type, K; protein-tyrosine phosphatase; receptor type, kappa; DKFZp686C2268; DKFZp779N1045; EC 3.1.3.48; OTTHUMP00000040306; PTPK; R_PTP-kappa; PTPRK); TPI1 (Triosephosphate isomerase; triosphosphaye isomerase1; EC 5.3.1.1; MGC88108; TIM; TPI1); ADFP (Adipophilin; AGC10598; adipophilin; ADFP; ADRP); AFP (Alpha-fetoprotein precursor; herdity persistence of alpha-fetoprotein AFP, Alpha-fetoglobulin; FETA; HPAFP; alpha-1-fetoprotein; alpha-fetoglobulin; alpha-fetoprotein); AIM2 (Interferon-inducible protein AIM2; Weakly similar to interferon gamma-inducible protein IFI16 [*H. sapeins*]; AIM2-PEN; PHIN4; AIM2); ANXA2 (Annexin II; Calpactin heavy chain; Lipocirtin II; Placental anticoagulant protein IV; Protein I; annexin II (lipocortin II); sulfatase B; calpactin I heavy polypeptide; calpactin I heavy polypeptide (p36); chromobindin 8 ANXA2; ANX2; ANX2L4; CAL1H; Chromobidin-8; LIP2; LPC2; LPC2D; P36; PAP-IV; p36); ART4 (NIN1/RPN12 binding protein 1 homolog (*S. cerevisiae*); PSMD8 binding protein 1; Phosphorylation regulatory protein HP-10; Protein ART-4; RNA-binding protein NOB1; nin one binding protein); CLCA2 (calcium actived chloride channel 2; chloride channel, calcium channel; calcium activated, 2, chloride channel; calcium activared family member 2; CaCC); CPSF1 (CPSF 160 kDa subunit; Cleavage and polyadenylation specificity factor 160 kDa subunit; Highly similar to cleavage and polyadenylation specificity facotr; 160 KD SUBUNIT [*H. sapiens*]; cleavage and polyadenylation specific factor 1; 160 kD subunit, cleavage and polyadenylation specific factor 1, 160 kDa; cleavage and polyadenylation specificity factor; polyadenylation specificity factor; CPSF160; HSU37012; P/c1.18); PPIB (Cyclophilin B; Peptidyl-prolyl cis-trans isomerase B precursor; cyclophilin-like protein; peptidylprolyl isomerase B; peptidylprolyl isomerase B (cyclophilin B) CYP-S1; CYPB; EC 5.2.1.8; MGC14109; MGC2224; PPIase; Rotamase; S-cyclophilin; SCYLP; rotamase); EPHA2 (EPH receptor A2; Epithelial cell kinase; Tyrosine-protein kinase receptor ECK; ephrin receptor EPHA2; epithelial cell receptor protein tyosine kinase; protein tyrosine kinase; protein tyrosine kinase; receptor protein tyrosine kinase regulated by p53 and E2F-1; EC2.7.10.1; ECK); EPHA3 (EPH receptor A3; TYRO4 protein tyrosine kinase; Tyrosine-protein kinase receptor ETK1; eph-like tyrosine kinase 1; eph-like tyrosine kinase (human embryo kinase 1); ephrin receptor EphA3 and human embryo kinase 1; EC 2.7.10.1; ETK; ETK1; EphA3; HEK; HEK4; TYRO4); FGFS (fibroblast frowth factor 5; heparin-binding growth factor 5; FGFS; HBGF-5; Smag-82); CA9 (Carbonic anhydrase 9 precursor; *H. sapiens* MaTu MN mRNA for p54/58N protein; Membrane antigen MN; renal cell carcinoma-associated antigen G250; renal cell carcinoma-associated protein G250; Renal cell carcinoma-associated antigen G250; carbonic anhydrase IX; cabonic dehydratase; CA9; CA-IX; CALX; EC 4.2.1.1; G250; MN; P54/58N; pMW1); TERT (Telomerase catalytic subunit; Telomerase-associated protein 2; EC 2.7.7.49; EST2; HEST2; TCS1; TP2; TRT; TERT; hEST2; hTERT); MGAT5 (Alpha-mannoside beta-1,6-N-acetylgluco saminyltransferase; Alpha-1,6-mannosylglycoprotein 6-beta-N-acetylglucosaminyltransferase V; GlcNAc-T V; N-acetylglucosaminytransferase V; alpha-1,3(6)-mannosylglycoprotein; beta-mannoside beta-1,6-N-acetylglucosaminyltransferase; mannosyl (alpha-1,6)-glycoprotein; beta-1,6-N-acetyl-glucosaminyltransferase; mannosyl (alpha-1,6-)-glycoprotein; beta-1,6-N-acetylglucosaminyltransferase; EC 2.4.1.155; GGNT5; GNT-V); CEL (caboxylesterase 2; carboxylesterase 2(intestinal, liver); intestinal carboxylesterase; liver carboxylesterase CEL; CE-2; CES2A1; EC 3.1.1.1; ICE; PCE-2; hCE-2; iCE); F4.2 ( ); CAN (214 kDa nucleoporin; CAN protein; putative oncogene; Nuclear pore complex protein Nup214; Nucleoporin Nup214; nucleoporin Nup214; nucleoporin 214 kD; nucleoporin 214 kD(CAIN); nucleoporin 214 kDa; CAIN; CAN; DS46E; KIAA0023; MGC104525; N214; OTTHUMP00000064563; P250); ETV6 (ETS-related protein Tell; TEL1 oncogene; Transcription factor ETV6; ets variant gene 6; ets variant gene 6 (TEL oncogene); ETV6; TEL; TEL/ABL; TEL1; Tel); BIRC7 (Kidney inhibitor of apoptosis protein; Kidney inhibitor of apoptosis protein; Melanoma inhibitor of apoptosis protein; RING finger protein 50; baculovial IAP repeat-containing 7 (livin); Livin inhibitor of apoptosis; livin inhibitor-of-apoptosis BIRC7; KIAP; LIVIN; Livin; ML-IAP; MLIAP; RNF50; mliap); CSF1 (M-CSF; colony stimulating factor 1; colony stimulating factor 1 (macrophage); macrophage colony stimulating factor; CSF-1; Lanimostim; M-CSF; MCSF; MGC31930); OGT (O-GlcNAc transferase p110 subunit; O-linked N-acetylglucosamine (GlcNAc) transferase; UDP-N-acetylglucosamine; polypeptide-N-acetylglucosaminyl transferase; UDP-N-acetylglucosamine-peptide N-acetylglucosaminyltransferase 110 kDa subunit; uridinediphospho-N-acetylglucosamine; polypeptide beta-N-acetylglucosaminyl transferase; OGT; EC 2.4.1.-; FLJ23071; HRTNT1; MG22921; O-GLCNAC); MUC1 (Breast carcinoma-associated antigen DF3; CD227 antien; DF3 antigen; H23 antigen CD227; EMA; Epsialin; H23AG; MAM6; MUC-1; MUC1; MUC-1/SEC; MUC-1/X; MUC-1/Y; MUC-1/Z; MUC-1/ZD; PEM; PEMT; PUM; episialin); MUC2 (Mucin-2 precursor; mucin 2; mucin; intestinal/tracheal mucin 2; oligomeric mucus/gel-forming; mucin-like protein; MLP; SMUC); MUM1 (CDNA FLJ14868 fis; clone PLACE1002395; weakly similar to *Mus musculus*; UBE-1c1; UBE-1c2; UBE1c3; CDNA); CTAG1A (Autoimmunogenic cancer/testis antigen NY-ESO-1; L antigen family member 2; LAGE-2 protein; LAGE-2 protein; New York esophagous squamous cell carcinoma 1; cancer antigen 3; cancer/testis antigen 1B; CTAG; CTAG1; ESO1; LAGE-2; LAGE2; LAGE2A; LAGE2B; NY-ESO-1; CTAG1A); CTAG2 (ESO-2 protein; Human autoimmunogenic cancer/testis antigen NY-ESO-1 mRNA, complete cds; L antigen family member 1; LAGE-1 protein; LAGE-1a protein transcript variant 1; LAGE-1a protein transcript variant 2; cancer/testis antigen 2; CAMEL; ESO2; LAGE-1; LAGE-2b; LAGE1; MGC138724; MGC3803; CTAG2); CTAG (ESO-2 protein; Human autoimmunogenic cancer/testis antigen NY-ESO-1 mRNA, complete cds; L antigen family member 1; LAGE-1 protein; LAGE-1a protein transcript variant 1; LAGE-1a protein transcript variant 2; cancer/testis antigen 2; CAMEL; ESO2; LAGE-1; LAGE-2b; LAGE1; MGC138724; MGC3803; CTAG2); MRPL28 (39S ribosomal protein L28; mitochondrial precursor; Melanoma antigen p15; Melanoma-associated antigen recognized by T lymphocytes, melanoma-associated antigen recognised by cytotoxic T lymphocytes; L28mt; MAAT1; MGC8499; MRP-L28; MRPL28; p15); FOLH1 (Folylpoly-gamma-glutamate carboxypeptidase, Glutamate carboxypeptidase 2; Glutamate carboxypeptidase II; Membrane glutamate carboxypeptidase; N-acetylated-alpha-linked acidic dipeptidase I; N-acetylated alpha-linked acidic dipeptidase 1; NAALADase I; Prostate-specific membrane antigen; Pteroylpoly-gamma-glutamate carboxypeptidase; folate hydrolase (prostate-specific membrane antigen) 1; folate hydrolase 1 (prostate-specific membrane antigen); folylpoly-gamma-glutamate carboxypeptidase; glutamate carboxylase II; prostate-specific membrane antigen; EC 3.4.17.21; FGCP; FOLH1; GCP2; GCPII; NAALAD1, NAALAdase, PSM, PSMA, mGCP); RAGE (Human renal cell carcinoma antigen RAGE-2 mRNA; complete putative cds; LE-9211-A antigen; MAPK/MAK/MRK overlapping kinase; MOK protein kinase; antigen recognized by autologous cytolytic T lymphocytes; renal cell carcinoma antigen (MOK protein kinase); renal tumor antigen; EC 2.7.11.22; MOK; RAGE-1; RAGE); SFMBT1 (Renal ubiquitous protein 1; Scm-like with four mbt domains 1; Scm-related gene containing four mbt domains 2; Scm-related gene product containing four mbt domains; DKFZp434L243; RU1); KAAG1 (RU2 antisense gene protein; kidney asociated antigen 1; KAAG1; MGC78738; RU2; RU2AS); SART1 (IgE autoantigen; SART1(259) protein; SART1(800) protein; U4/U6.U5 tri-snRNP-associated 110 kDa protein; U4/U6.U5 tri-snRNP-associated protein 1; squamous cell carcinoma antigen recognised by T cells; squamous cell carcinoma antigen recognized by T cells; ARA1; Ara1; HOMS1; MGC2038; SART-1; SART1259; Snu66; hSART-1; hSnu66); TSPYL1 (DS epimerase; Dermatan-sulfate epimerase precursor; Squamous cell carcinoma antigen recognized by T-cells 2; dermatan sulfate epimerase; squamous cell carcinoma antigen recognized by T cells 2; DSEPI, EC 5.1.3.19; OTTHUMP00000040406; SART-2; SART2); SART3 (Similar to *X. laevis* NUCLEOLIN; Tat-interacting protein of 110 kDa; squamous cell carcinoma antigen recognised by T cells 3; KIAA0156; MGC138188; RP11-13G14; SART-3; TIP110; Tip110; hSART-3; p110(nrb)); SOX10 (SRY-related HMG-box gene 10; Transcription factor SOX-10; dominant megacolon, mouse, human homolog of; DOM; MGC15649; OTTHUMP00000028515; WS4; SOX10); TRG ( ); WT1 (Wilms' tumor protein; GUD; WAGR; WIT-2; WT33; WT1); TACSTD1 (Adenocarcinoma-associated antigen; CD326 antigen; Cell surface glycoprotein Trop-1; Epithelial cell surface antigen; Epithelial glycoprotein; KS 1/4 antigen; MAJOR GASTROINTESTINAL TUMOR-ASSOCIATED PROTEIN GA733-2 PRECURSOR; MK-1 antigen; Major gastrointestinal tumor-associated protein GA733-2; precursor, antigen identified by monoclonal antibody AUA1; human epithelial glycoprotein-2; membrane component, chromosome 4, surface marker (35 kD glycoprotein); CD326; CO17-1A; EGP; EGP40; Ep-CAM; GA733-2; KSA; Ly74; M1S2; M4S1; MIC18; MK-1; TROP1; hEGP-2); SILV (95 kDa melanocyte-specific secreted glycoprotein; ME20-M/ME20-S; Melanocyte lineage-specific antigen GP100; Melanocyte protein Pmel 17 precursor; Melanocyte protein mel 17; Melanoma-associated ME20 antigen; PMEL 17 PROTEIN PRECURSOR 5 Pmel 17; Silver, mouse, homolog of, melanosomal matrix proteinl7; silver (mouse homolog)-like; silver homolog (mouse); D12S53E; ME20; ME20M/ME20S; PMEL17; Pme117; SI; SIL; gp100); SCGB2A2 (Mammaglobin-A precursor; mammaglobin 1; mammaglobin A; secretoglobin, family 2A, member 2; MGB1; Mammaglobin-1; UGB2); MC1R (Melanocyte-stimulating hormone receptor; Melanotropin receptor; melanocortin 1 receptor; melanocortin 1 receptor (alpha melanocyte stimulating hormone receptor); melanocyte stimulating hormone receptor; MC1-R; MGC14337; MSH-R; MSHR); MLANA (Antigen LB39-AA; Antigen SK29-AA; Melanoma antigen recognized by T-cells 1; MART-1; MART1; melan-A; MLANA); GPR143 (G-protein coupled receptor 143; Ocular albinism type 1 protein; ocular albinism 1 (Nettleship-Falls); ocular albinism-1; Nettleship-Falls type; OA1; GPR143); OCA2 (Melanocyte-specific transporter protein; P protein; Pink-eyed dilution protein homolog; oculocutaneous albinism II (pink-eye dilution homolog, mouse); BOCA, D15S12, EYCL3, P, PED, OCA2); KLK3 (P-30 antigen; Prostate-specific antigen precursor; antigen, prostate specific, kallikrein 3, (prostate specific antigen); kallikrein-related peptidase; prostate specific antigen; KLK3; APS; EC 3.4.21.77; Gamma-seminoprotein; KLK2A1; PSA; Semenogelase; Seminin; gamma-seminoprotein; hK3; semenogelase; seminin); SUPT7L (Adenocarcinoma antigen ART1; SPTF-associated factor 65 gamma; STAGA complex 65 gamma subunit; STAGA complex 65 subunit gamma; suppressor of Ty 7 (*S. cerevisiae*)-like; SUPTL; ART1; KIAA0764; MGC90306; SPT7L; STAF65; STAF65(gamma); STAF65gamma); BRAF (94 kDa B-raf protein; B-raf, Murine sarcoma viral (v-raf) oncogene homolog B1; v-raf murine sarcoma viral oncogene homolog B1; BRAF; B-Raf; B-raf-1; BRAF1; EC 2.7.11.1; MGC126806; MGC138284; RAFB1; p94); CASP5 (Caspase-5 precursor; *H. sapiens* mRNA for TY protease; ICH-3 protease; TY protease; caspase 5, apoptosis-related cysteine peptidase; CASP-5; EC 3.4.22.-; ICE; ICE (rel)III; ICEREL-III; ICErel-III; ICH-3 2; ICH3; MGC141966; relIII); CDKN2A (CDK4 inhibitor p16-INK4; isoform 4, Cyclin-dependent kinase 4 inhibitor A; Cyclin-dependent kinase inhibitor 2A, isoforms 1/2/3; Multiple tumor suppressor 1; cell cycle negative regulator beta; cyclin-dependent kinase inhibitor 2A; cyclin-dependent kinase inhibitor 2A (melanoma, p16, inhibits CDK4); cyclin-dependent kinase inhibitor p16; ARF; CDK4I; CDKN2; CDKN2A; CMM2; INK4; INK4a; MLM; MTS1; P16; TP16; p14; p14ARF; p16; p16-INK4; p16-INK4a; p16INK4; p16INK4A; p16INK4a; p19; p19ARF); UBXD5 (Hypothetical protein DKFZp686F04228; UBXD5 protein; colorectal tumor-associated antigen-1; COA-1; DKFZp686F04228; PP2243; SOC; socius); EFTUD2 (116 kDa U5 small nuclear ribonucleoprotein component; U5 snRNP specific protein; 116 kD; U5 snRNP-specific protein, 116 kDa; U5-116 kDa; elongation factor Tu GTP binding domain containing; DKFZp686E24196; FLJ44695; KIAA0031; SNRP116; Snrp116; Snu114; U5-116 KD; hSNU114); GPNMB (Transmembrane glycoprotein HGFIN; Transmembrane glycoprotein NMB precursor; glycoprotein (transmembrane) nmb; glycoprotein nmb-like protein; transmembrane glycoprotein; HGFIN, GPNMB, NMB); NFYC (CAAT-box DNA-binding protein subunit C; CCAAT binding factor subunit C; CCAAT transcription binding factor subunit gamma; CCAAT-binding factor, C subunit; Nuclear transcription factor Y subunit gamma; Transactivator HSM-1/2; histone H1 transcription factor large subunit 2A; homologous to rat CCAAT binding factor subunit C (rCBF-C); nuclear transcription factor Y; gamma, transactivator HSM-1; transcription factor NF-Y; C subunit CBF-C; CBFC; DKFZp667G242; FLJ45775; H1TF2A; HAPS; HSM; NF-Y; hCBF-C; NFYC); PRDXS (Mu co-repressor; Mu corepressor; Antioxidant enzyme B166; Liver tissue 2D-page spot 71B; mitochondrial precursor; Peroxisomal antioxidant enzyme; TPx type VI; Thioredoxin peroxidase PMP20; Thioredoxin reductase; peroxiredoxin 5; ACR1; AOEB166; B166; EC 1.11.1.15; MGC117264; MGC142283; MGC142285; PLP; PMP20; PRDX6; PRXV; Prx-V; SBBI10; PRDXS); ZUBR1 (CDNA FLJ12260 fis; clone MAMMA1001551; ZUBR1 protein; ZUBR1 protein—Fragment; retinoblastoma-associated factor 600; retinoblastoma-associated factor 600-like protein; zinc finger, UBR1 type; FLJ41863; KIAA0462; KIAA1307; RBAF600; RP5-1126H10.1; p600; ZUBR1); SIRT2 (NAD-dependent deacetylase sirtuin-2; SIR2 (silent mating type information regulation 2, *S. cerevisiae*, homolog)-like; SIR2 (silent mating type information regulation 2, *S. cerevisiae*, homolog)-like SIR2-like protein 2; silencing information regulator 2-like 2; sir2-related protein type 2; sirtuin 2; sirtuin silent mating type information regulation 2 homolog 2 (*S. cerevisiae*); sirtuin type 2; EC 3.5.1.-; SIR2-like; SIR2L; SIR2L2); SNRPD1 (Sm-D autoantigen; Small nuclear ribonucleoprotein Sm D1; small nuclear ribonucleoprotein D1 polypeptide (16 kD); snRNP core protein D1; HsT2456; SMD1; SNRPD; Sm-D1; SNRPD1); HERV-K-MEL ( ); CXorf61 (Kita-kyushu lung cancer antigen 1; KK-LC-1; LOC203413; RP3-452H17.2); CCDC110 (Cancer/testis antigen KM-HN-1; KM-HN-1 protein; KM-HN-1; KMHN1; MGC33607; CCDC110); VENTXP1 (Cancer/testis antigen 18; CT18; NA88; VENTX2P1); SPA17 (Sperm surface protein Sp17; sperm autoantigenic protein 17; SP17; SP17-1; Sp17-1; SPA17); KLK4 (Enamel matrix serine proteinase 1; Kallikrein-like protein 1; Serine protease 17; androgen-regulated message 1; enamel matrix serine protease 1; kallikrein 4 (prostase, enamel matrix, prostate); kallikrein-related peptidase 4; protease, serine, 17 ARM1, EC 3.4.21.-, EMSP, EMSP1, KLK-L1, MGC116827, MGC116828, PRSS17, PSTS, Prostase 3, KLK4); ANKRD30A (Serologically defined breast cancer antigen NY-BR-1; ankyrin repeat domain 30A; breast cancer antigen NY-BR-1; NY-BR-1, RP11-20F24.1; ANKRD30A); RAB38 (Antigen NY-MEL-1; member RAS oncogene family; Ras-related protein Rab-38; NY-MEL-1; rrGTPbp; RAB38);

CCND1 (B-cell CLL/lymphoma; BCL-1 oncogene; G1/S-specific cyclin D1; G1/S-specific cyclin-D1; PRAD1 oncogene; cyclin D1 (PRAD1-parathyroid adenomatosis 1); parathyroid adenomatosis; BCL1; D11S287E; PRAD1; U21B31); CYP1B1 (GLC3A (Primary Congenital Glaucoma or Buphthalmos); aryl hydrocarbon hydroxylase; cytochrome P450, family 1, subfamily B, polypeptide 1; cytochrome P450, subfamily I (dioxin-inducible), polypeptide 1; (glaucoma 3, primary infantile); flavoprotein-linked monooxygenase; microsomal monooxygenase; xenobiotic monooxygenase; CP1B; EC 1.14.14.1; GLC3A); MDM2 (Double minute 2 protein, Mdm2, transformed 3T3 cell double minute 2, p53 binding protein (mouse), Oncoprotein Mdm2, Ubiquitin-protein ligase E3 Mdm2, mouse double minute 2 homolog, human homolog of; p53-binding protein; p53-binding protein Mdm2; EC 6.3.2.-; HDM2; HDMX; Hdm2; MGC71221; MDM2); MMP2 (72 kDa gelatinase; 72 kDa type IV collagenase precursor; 72 kD type IV collagenase; Gelatinase A; Matrix metalloproteinase-2; TBE-1; collagenase type IV-A; matrix metallopeptidase 2 (gelatinase A, 72 kDa gelatinase, 72 kDa type IV collagenase); matrix metalloproteinase 2 (gelatinase A, 72 kDa gelatinase, 72 kDa type IV collagenase); matrix metalloproteinase-II; neutrophil gelatinase; CLG4; CLG4A; EC 3.4.24.24; MMP-2; MMP2; MMP-II; MONA; TBE-1); ZNF395 (HD gene regulatory region-binding protein 2; HD-regulating factor 2; Huntington disease gene regulatory region-binding protein 2; Huntington's disease gene regulatory region-binding protein 2; Papillomavirus regulatory factor 1; Papillomavirus-binding factor; papillomavirus regulatory factor PRF-1; DKFZp434K1210; HDBP-2; HDBP2; HDRF-2; PBF; PRF-1; PRF1; Si-1-8-14; ZNF395); RNF43 (ring finger protein 43; DKFZp781H02126; DKFZp781H0392; FLJ20315; MGC125630; RNF124; Urenal cell carcinoma;); SCRN1 (KIAA0193; SES1; Secernin-1); STEAP1 (Metalloreductase STEAP1; six transmembrane epithelial antigen of the prostate; EC 1.16.1.-; MGC19484; PRSS24); 707-AP ( ); TGFBR2 (TGF-beta receptor type IIB; TGF-beta receptor type-2 precursor; TGF-beta type II receptor; Transforming growth factor-beta receptor type II; transforming growth factor beta receptor type IIC; transforming growth factor, beta receptor II; transforming growth factor, beta receptor II (70-80 kD); transforming growth factor, beta receptor II (70/80 kDa); AAT3; EC 2.7.11.30; FAA3; HNPCC6; MFS2; RIIC 2; TAAD2; TGFR-2; TGFBR2; TGFbeta-RII; TbetaR-II); PXDNL (PXDN protein—Fragment; p53-responsive gene; peroxidasin homolog; peroxidasin homolog (*Drosophila*); D2S448; D2S448E; KIAA0230; MG50; PRG2; PXN); AKAP13 (Lymphoid blast crisis oncogene A kinase (PRKA) anchor protein 13; A-kinase anchor protein 13; A-kinase anchoring protein, AKAP 13; Breast cancer nuclear receptor-binding auxiliary protein; Guanine nucleotide exchange factor Lbc; Human thyroid-anchoring protein 31; LBC oncogene; Lymphoid blast crisis oncogene; Non-oncogenic Rho GTPase-specific GTP exchange factor; PROTO-LB LBC; Protein kinase A-anchoring protein 13; AKAP-Lbc; BRX; FLJ11952; FLJ43341; HA-3; HT31; Ht31; LBC; P47; PROTO-LB; PROTO-LBC; c-lbc; AKAP13); PRTN3 (C-ANCA antigen; Myeloblastin precursor; Neutrophil proteinase 4; Wegener autoantigen; proteinase 3 (serine proteinase, neutrophil, Wegener granulomatosis autoantigen); ACPA; AG7; C-ANCA; EC 3.4.21.76; MBN; MBT; NP-4; P29; PR-3; PR3; PRTN3; myeloblastin); PSCA (prostate stem cell antigen; PRO232); RHAMM (CD168 antigen; Hyaluronan mediated motility receptor; Intracellular hyaluronic acid-binding protein; hyaluronan-mediated motility receptor; hyaluronan-mediated motility receptor (RHAMM); intracellular hyaluronic acid binding protein; CD168; IHABP; MGC119494; MGC119495; RHAMM); ACPP (acid phosphatase; prostate, prostatic acid phosphatase; prostatic acid phosphotase; ACP-3; ACP3; EC 3.1.3.2; PAP; ACPP); ACRBP (Cancer testis antigen OY-TES-1; Proacrosin-binding protein sp32; Weakly similar to proacrosin-binding protein [*M. musculus*]; acrosin binding protein; proacrosin binding protein sp32 2; proacrosin binding protein sp32 precursor; HLA-B associated transcript 3; OY-TES-1; SP32); LCK (Proto-oncogene tyrosine-protein kinase LCK; T cell-specific protein-tyrosine kinase; T-lymphocyte specific protein tyrosine kinase p56lck; lymphocyte-specific protein tyrosine kinase; p56(LSTRA) protein-tyrosine kinase; EC 2.7.10.2; LSK; YT16; p56-LCK; p56lck; pp58lck; LCK); RCVRN (Cancer-associated retinopathy protein; Protein CAR; cancer associated retinopathy antigen; RCV1; RCVRN); RPS2 (40S ribosomal protein S2; LLRep3 protein; LLREP3; MGC102851; MGC117344; MGC117345; OK/KNS-c1.6; RPS4; RPS2; S4); RPL10A (60S ribosomal protein L10a; Neural precursor cell expressed developmentally down-regulated protein 6; Protein NEDD6; neural precursor cell expressed, developmentally down-regulated 6; CSA-19; Csa-19; NEDD-6; NEDD6); SLC45A3 (Prostate cancer-associated protein 6; prostate cancer associated protein 6; prostate cancer-associated gene 6; solute carrier family 45, member; IPCA-6; IPCA6; PCANAP6; PRST; Prostein; prostein; SLC45A3); BCL2L1 (Apoptosis regulator Bcl-X; Bcl-2-like 1 protein; BCL-XUS; BCL2L; BCLX; Bcl-X; DKFZp781P2092; bcl-xL; bcl-xS); DKK1 (dickkopf (*Xenopus laevis*) homolog 1; dickkopf homolog 1; dickkopf homolog 1 (*Xenopus laevis*); dickkopf related protein-1; dickkopf-1 like; DKK-1; Dickkopf-1; Dkk-1; SK 1; dickkopf-1; hDkk-1); ENAH (enabled homolog; enabled homolog (*Drosophila*); FLJ10773; MENA; NDPP1); CSPG4 (Chondroitin sulfate proteoglycan NG2; Melanoma chondroitin sulfate proteoglycan; Melanoma-associated chondroitin sulfate proteoglycan; chondroitin sulfate proteoglycan 4; chondroitin sulfate proteoglycan 4 (melanoma-associated); HMW-MAA; MCSP; MCSPG; MEL-CSPG; MSK16; NG2); RGSS (Highly similar to REGULATOR OF G-PROTEIN SIGNALLING 2 [*Homo sapiens*]; Regulator of G-protein signaling 5; regulator of G-protein signalling 5; MST092; MST106; MST129; MSTP032; MSTP092; MSTP106; MSTP129); BCR (Renal carcinoma antigen NY-REN-26; breakpoint cluster region; ALL; BCR1; CML; D22S11; D22S662; EC 2.7.11.1; FLJ16453; PHL); BCR-ABL ( ); DEK (DEK gene; DEK oncogene (DNA binding); Protein DEK; D6s231E; OTTHUMP00000039357); DEK-CAN ( ); ETV6-AML1 ( ); LDLR-FUT ( ); NPM1-ALK1 ( ); PML-RARA ( ); SYT-SSX1 ( ); SYT-SSX2 ( ); FLT3 (CD135 antigen; FL cytokine receptor; FL cytokine receptor precursor; Stem cell tyrosine kinase 1; fetal liver kinase 2; fms-related tyrosine kinase 3; growth factor receptor tyrosine kinase type III; CD135; EC 2.7.10.1; FLK2; OTTHUMP00000042340; STK-1; STK1); ABL1 (Abelson murine leukemia viral oncogene homolog 1; Proto-oncogene tyrosine-protein kinase ABL1; bcr/c-abl oncogene protein; c-ABL; v-abl Abelson murine leukemia viral oncogene homolog 1; ABL; ABL1; EC 2.7.10.2; JTK7; c-ABL; p150; v-abl); AML1 (Acute myeloid leukemia 1 protein; CBF-alpha 2; Core-binding factor; alpha 2 subunit; Oncogene AML-1; PEA2-alphaB; PEBP2-alpha B; Polyomavirus enhancer-binding protein 2 alpha B subunit; Runt-related transcription factor 1; SL3-3 enhancer factor 1 alpha B subunit; SL3-3 enhancer factor 1 alpha B subunit; SL3/AKV core-binding factor alpha B subunit; acute myeloid leukemia 1 gene; acute myeloid leukemia 1 protein (oncogene AML-1), core-binding factor, alpha subunit; aml1 oncogene; core-binding factor, runt domain, alpha subunit 2; core-binding factor, runt domain, alpha subunit 2 (acute myeloid leukemia 1; aml1 oncogene); runt-related transcription factor 1 (acute myeloid leukemia 1; aml1 oncogene); RUNX1; AML1-EVI-1; AMLCR1; CBFA2; EVI-1; PEBP2A2; PEBP2aB); LDLR (LDL receptor; LDLR precursor; Low-density lipoprotein receptor precursor; low density lipoprotein receptor (family hypercholesterolemia); FH; FHC; LDLR); FUT1 (Blood group H alpha 2-fucosyltransferase; GDP-L-fucose); NPM1 (Nucleolar phosphoprotein B23; Nucleolar protein NO38; nucleophosmin (nucleolar phosphoprotein B23, numatin); nucleophosmin/nucleoplasmin family, member 1; B23; MGC104254; NPM; Nucleophosmin; Numatrin; numatin); ALK (ALK tyrosine kinase receptor precursor; CD246 antigen; TRK-fused gene-anplastic lymphoma kinase fusion protein; anaplastic lymphoma kinase (Ki-1); anaplastic lymphoma kinase Ki-1; CD246; EC 2.7.10.1; TFG/ALK); PML1 (Probable transcription factor PML; RING finger protein 71; Tripartite motif-containing protein 19; promyelocytic leukemia; promyelocytic leukemia, inducer of; tripartite motif protein TRIM19; MYL; PP8675; RNF71; TRIM19); RARA (NuMA-RARA fusion; Retinoic acid receptor alpha; alpha polypeptide; nuclear mitotic apparatus protein-retinoic acid receptor alpha fusion protein; nucleophosmin-retinoic acid receptor alpha fusion protein NPM-RAR; nucleophosmin-retinoic acid receptor alpha fusion protein NPM-RAR long form; retinoic acid receptor, alpha; NR1B1; RAR; RAR-alpha); SYT (SSXT protein; SSXT/SSX4v fusion; SYT/SSX4v fusion; SYT/SSX4v fusion protein; Synovial sarcoma, translocated to X chromosome; fusion protein SYT-SSX1; fusion protein SYT-SSX2; synovial sarcoma translocation, chromosome 18; MGC116875; SSXT; SYT; SYT-SSX1; SYT-SSX2); SSX1 (Protein SSX1; synovial sarcoma, X breakpoint 1; MGC150425; MGC5162; SSRC); MSLN (CAKantigen; Megakaryocyte potentiating factor; Pre-pro-megakaryocyte-potentiaitng factor; CAK1; MPF; SMR; mesothelin); UBE2V1 (DNA-binding protein; Human putative DNA-binding protein mRNA, partial cds; TRAF6-regulated IKK activator 1 beta Uev1A; Ubiquitin-conjugating enzyme variant Kua; Ubiquitin-conjugating enzyme E2 variant; CIRQ; CROC-1; CROC1; UBE2V; UEV-1; UEV1; UEV1A); HNRPL (hnRNP L; FLJ35509; P/OKcI.14; hnRNP-L); WHSC2 (Negative factor elongation factor A; Wolf-Herschhorn syndrome candidate 2 protein; FLJ10442; FU25112; NELF-A; NELFA; P/Okc1.15); EIF4EBP1 (Phosphorylated heat-and-stable protein regulated by insulin 1; eIF4E-binding protein 1; eukaryotic translation initiation factor 4E binding protein 1; 4E-BP1; 4EBP1; BP-1; MGC4316; PHAS-I); WNK2 (Protein kinase lysine deficient 2; serine/threonine-protein kinase WNK2 WNK lysine deficient protein kinase 2; mitogen-activated peotein kinase kinase kinase; protein kinase lysine deficient 2; serologically defined colon cancer antigen 43; EC 2.7.11.1; KIAA1760; NY-CO-43; P/Okc1.13; PRKWNK2; SDCCAG43); OAS3 (2'-5'-oligoadenylate synthetase 3 (100 kD); 2'-5'-oligoadenylate synthetase 3, 100 kDa; 2'-5'oligoadenylate synthetase 3, 2'-5'oligoadenylate synthetase p100; 2-5A synthetase 3; Asynthetase 3; p100 OAS 2-5'ligo; EC 2.7.7.-; MGC133260 2; p100 2; P100oas); BCL-2 (B-cell CLL/lymphoma 2; B-cell lymphoma protein 2); MCL1 (Bcl-2-related protein EAT/mcl1; INDUCED MYELOID LEUKEMIA CELL DIFFERENTIATION PROTEIN MCL1; Induced myeloid leukemia cell differentiation protein Mcl-1; myeloid cell leukemia sequence; myeloid cell leukemia sequence 1 (BCL2-related); EAT; MCL1L; MCL1S; MGC104264; MGC1839; TM; mcl1/EAT); CTSH (N-benzoylarginine-beta-naphthylamide hydrolase; cathepsin B3; cathepsin BA; cathepsin H ACC-4; ACC-5; CPSB; DKFZp686B24257; EC 3.4.22.16; MGC1519; aleurain; minichain); ABCC3 (ATP-binding cassette sub-family C member 3; ATP-binding cassette, sub-family C (CFTR/MRP), member 3; ATP-binding cassette, sub-family C, member 3; Canalicular multispecific organic anion transporter 2; Highly similar to MULTIDRUG RESISTANCE-ASSOCIATED PROTEIN 1 [*Homo sapiens*]; Multi-specific organic anion transporter-D; Multidrug resistance-associated protein 3; canicular multispecific organic anion transporter; multidrug resistance associated protein; ABC31; CMOAT2; EST90757; MLP2; MOAT-D; MRP3; cMOAT2); BST2 (cd317; HM1.24); MFGE8 (Breast epithelial antigen BA46; Human breast epithelial antigen BA46 mRNA, complete cds; Lactadherin precursor; O-acetyl disialoganglioside synthase; milk fat globule-EGF factor 8 protein; BA46; EDIL1; HMFG; HsT19888; MFG-E8; MFGM; OAcGD3S; lactadherin; medin; MFGE8); TPBG (5T4 oncofetal antigen; 5T4 oncofetal trophoblast glycoprotein; 5T4 oncotrophoblast glycoprotein; *H. sapiens* 5T4 gene for 5T4 oncofetal antigen; trophoblast glycoprotein; 5T4; 5T4-AG; 5T4 antigen; M6P1); FMOD (Collagen-binding 59 kDa protein; KSPG fibromodulin; Keratan sulfate proteoglycan fibromodulin; fibromodulin proteoglycan; FM 3; SLRR2E; fibromodulin); XAGE1 (G antigen family D member 2; G antigen, family D, 2; Protein XAGE-1; xage-1 p16; GAGED2; XAGE-1); RPSA (34/67 kDa laminin receptor; 40S ribosomal protein SA; 67 kD, Colon carcinoma laminin-binding protein; Multidrug resistance-associated protein MGr1-Ag; laminin receptor 1; laminin receptor 1 (67 kD, ribosomal protein SA); ribosomal protein SA 1; OFA-iLR; 37LRP; 67LR; LAMBR; LAMR1; LRP; NEM/1CHD4; p40); COTL1 (coactosin-like 1; coactosin-like 1 (Dictyostelium); CLP; FLJ43657; MGC19733; KM-PA-4); CALR3 (CRT2; Calreticulin-2; FLJ25355; MGC26577; Calreticulin-3 precursor; calreticulin 2; calreticulin 3); PA2G4 (EBP1; HG4-1; hG4-1; p38-2G4; Cell cycle protein p38-2G4 homolog; ErbB-3 binding protein 1; ErbB3-binding protein 1; ErbB3-binding protein Ebp1; Proliferation-associated protein 2G4; proliferation-associated 2G4, 38 kD; proliferation-associated 2G4, 38 kDa); EZH2 (ENX-1; EZH1; MGC9169; Enhancer of zeste homolog 2; enhancer of zeste (*Drosophila*) homolog 2; enhancer of zeste 2; enhancer of zeste homolog 2 (*Drosophila*)); FMNL1 (C17orf1; C17orf1B; FHOD4; FMNL; KW-13; MGC133052; MGC1894; MGC21878; formin-like; CLL-associated antigen KW-13; CLL-associated antigen KW-13; Formin-like protein 1; Leukocyte formin; formin-like 1); HPSE (EC 3.2.-.-; HEP; HPA; HPA1; HPR1; HPSE1; HSE1; Heparanase-1; Hpa1; heparanase; heparanase-1; Endo-glucoronidase; Heparanase precursor); APC (DP2; DP2.5; DP3; FAP; FPC; GS; Adenomatous polyposis coli protein; Protein APC; adenomatosis polyposis coli; adenomatosis polyposis coli tumor suppressor); UBE2A (EC 6.3.2.19; HHR6A; HR6A; RAD6A; UBC2; hHR6A; Ubiquitin carrier protein A; Ubiquitin-conjugating enzyme E2 A; Ubiquitin-protein ligase A; ubiquitin-conjugating enzyme E2A; ubiquitin-conjugating enzyme E2A (RAD6 homolog)); BCAP31 (6C6-AG; 6C6-Ag; BAP31; CDM; DXS1357E; 6C6-AG tumor-associated antigen; B-cell receptor-associated protein 31; BCR-associated protein Bap31; Protein CDM; accessory protein BAP31; p28 Bap31); TOP2A (EC 5.99.1.3; TOP2; TP2A; DNA topoisomerase 2-alpha; DNA topoisomerase II, 170 kD; DNA topoisomerase II, alpha isozyme; topoisomerase (DNA) II alpha (170 kD); topoisomerase (DNA) II alpha 170 kDa; topoisomerase II alpha 170 kDa); TOP2B (EC 5.99.1.3; TOPIIB; top2beta; DNA topoisomerase 2-beta; DNA topoisomerase II beta; DNA topoisomerase II, 180 kD; DNA topoisomerase II, beta isozyme; U937 associated antigen; antigen MLAA-44; topo II beta; topoisomerase (DNA) II beta (180 kD); topoisomerase (DNA) II beta 180 kDa; topoisomerase II beta; topoisomerase II beta 180 kDa; topoisomerase IIb); ITGB8 (Integrin beta-8 precursor; integrin, beta 8); RPA1 (HSSB; REPA1; RF-A; RP-A; RPA70; p70; Replication factor-A protein 1; Replication protein A 70 kDa DNA-binding subunit; Single-stranded DNA-binding protein; replication protein A1 (70 kD); replication protein A1, 70 kDa); ABI2 (ABI-2; ABI2B; AIP-1; ARGBPIA; Abi-2; AblBP3; ArgBP1; SSH3BP2; argBPIA; argBPIB; Abelson interactor 2; Abl-binding protein 3; Arg-binding protein 1; abl binding protein 3; abl interactor 2; abl-interacting protein 1 (SH3-containing protein); abl-interactor 2; abl-interactor protein 2b; arg protein tyrosine kinase-binding protein); CCNI (CYC1; CYI; Cyclin-I; Highly similar to CALNEXIN PRECURSOR [*Homo sapiens*]; cyclin I; cyclin ITI); CDC2 (CDC28A; CDK1; DKFZp686L20222; EC 2.7.11.22; EC 2.7.11.23; MGC111195; Cell division control protein 2 homolog; Cyclin-dependent kinase 1; cell cycle controller CDC2; cell division cycle 2 protein; cell division cycle 2; G1 to S and G2 to M; p34 protein kinase); SEPT2 (DIFF6; KIAA0158; NEDDS; Pnut13; Septin-2; hNedd5; Protein NEDDS; neural precursor cell expressed; developmentally down-regulated 5; septin 2); STAT1 (DKFZp686B04100; ISGF-3; STAT91; Signal transducer and activator of transcription 1-alpha/beta; Transcription factor ISGF-3 components p91/p84; signal transducer and activator of transcription 1; signal transducer and activator of transcription 1, 91 kD; signal transducer and activator of transcription 1, 91 kDa; signal transducer and activator of transcription-1; transcription factor ISGF-3); LRP1 (A2MR; APOER; APR; CD91; FLJ16451; LRP; MGC88725; TG1-BR5; Alpha-2-macroglobulin receptor; Apolipoprotein E receptor; CD91 antigen; Low-density lipoprotein receptor-related protein 1 precursor; low density lipoprotein-related protein 1; low density lipoprotein-related protein 1 (alpha-2-macroglobulin receptor); type V tgf-beta receptor); ADAM17 (CD156B; CD156b; CSVP; EC 3.4.24.86; MGC71942; TACE; cSVP; A disintegrin and metalloproteinase domain 17; ADAM 17 precursor; ADAM metallopeptidase domain 17; ADAM metallopeptidase domain 17 (tumor necrosis factor, alpha, converting enzyme); CD156b antigen; Snake venom-like protease; TNF-alpha convertase; TNF-alpha converting enzyme; TNF-alpha-converting enzyme; a disintegrin and metalloproteinase domain 17 (tumor necrosis factor, alpha, converting enzyme); tumor necrosis factor, alpha, converting enzyme); JUP (CTNNG; DP3; DPIII; Desmoplakin-3; PDGB; PKGB; gamma-catenin; Catenin gamma; Desmoplakin III; catenin (cadherin-associated protein), gamma (80 kD); catenin (cadherin-associated protein), gamma 80 kDa; junction plakoglobin); DDR1 (CAK; CD167; DDR; EC 2.7.10.1; EDDR1; HGK2; MCK10; NEP; NTRK4; PTK3; PTK3A; RTK6; TRKE; trkE; CD167a antigen; Cell adhesion kinase; Discoidin receptor tyrosine kinase; Epithelial discoidin domain receptor 1; Epithelial discoidin domain-containing receptor 1 precursor; PTK3A protein tyrosine kinase 3A; Protein-tyrosine kinase RTK 6; TRK E; Tyrosine kinase DDR; Tyrosine-protein kinase CAK; discoidin domain receptor DDR1d; discoidin domain receptor family; member 1; mammarian carcinoma kinase 10; neuroepithelial tyrosine kinase; neurotrophic tyrosine kinase, receptor, type 4); ITPR2 (IP3R2; InsP3R2; IP3 receptor isoform 2; Inositol 1,4,5-trisphosphate receptor type 2; Type 2 InsP3 receptor; Type 2 inositol 1,4,5-trisphosphate receptor; inositol 1,4,5-triphosphate receptor, type 2); HMOX1 (EC 1.14.99.3; HO; HO-1; HO1; OTTHUMP00000028925; bK286B10; Heme oxygenase 1; heme oxygenase (decycling) 1; heme oxygenase (decyclizing) 1); TPM4 (TM30p1; Tropomyosin-4; Tropomyosin alpha-4 chain; tropomyosin 4); BAAT (BACAT; BAT; EC 2.3.1.65; EC 3.1.2.2; FLJ20300; MGC104432; Bile acid CoA); DNAJC8 (HSPC331; SPF31; DnaJ (Hsp40) homolog, subfamily C, member 8; DnaJ homolog subfamily C member 8; Splicing protein spf31); TAPBP (NGS-17; NGS17; TAPA; TAPA-SIN; TPN; TPSN; tapasin; TAP binding protein (tapasin); TAP-associated protein; TAP-binding protein; Tapasin precursor); LGALS3BP (90K; M2BP; MAC-2-BP; MAC2BP; Galectin-3-binding protein precursor; L3 antigen; Lectin galactoside-binding soluble 3-binding protein; Mac-2 BP; Mac-2-binding protein; Tumor-associated antigen 90K; galectin 3 binding protein; lectin, galactoside-binding, soluble, 3 binding protein; lectin, galactoside-binding, soluble, 3 binding protein (galectin 6 binding protein); serum protein 90K); PAGE4 (FLJ35184; GAGE-9; GAGEC1; JM27; PAGE-1; PAGE-4; G antigen family C member 1; G antigen, family C, 1; P antigen family, member 4 (prostate associated); Prostate-associated gene 4 protein; prostate-associated gene protein 4); PAK2 (EC 2.7.11.1; Gamma-PAK; PAK-2; PAK65; PAKgamma; hPAK65; 56/H4 kinase; Serine/threonine-protein kinase PAK 2; p21 (CDKN1A)-activated kinase 2; p21-activated kinase 2); CDKN1A (CAP20; CDKN1; CIP1; MDA-6; MDA6; P21; PIC1; SDH; WAF1; p21; p21CIP1; CDK-interacting protein 1; CDK-interaction protein 1; Cyclin-dependent kinase inhibitor 1; DNA synthesis inhibitor; Melanoma differentiation-associated protein 6; cyclin-dependent kinase inhibitor 1A; cyclin-dependent kinase inhibitor 1A (p21, Cip1); melanoma differentiation associated protein 6; wild-type p53-activated fragment 1); PTHLH (107-139); HHM; MGC14611; PLP; PTH-rP; PTHR; PTHRP; PTHrP; osteostatin; 1-36 PTHrP; 38-94 Osteostatin; PTH-related protein; Parathyroid hormone-related protein precursor; humoral hypercalcemia of malignancy; parathyroid hormone-like hormone; parathyroid hormone-like protein; parathyroid hormone-like related protein; parathyroid hormone-related protein; parathyroid-like protein); SOX2 (ANOP3; MCOPS3; MGC2413; SRY (sex determining region Y)-box 2; SRY-related HMG-box gene 2; Transcription factor SOX-2; sex-determining region Y-box 2; transcription factor SOX2); SOX11 (SRY (sex determining region Y)-box 11; SRY (sex-determining region Y)-box 11; SRY-box 11; SRY-related HMG-box gene 11; Transcription factor SOX-11); TRPM8 (CMR1; LTRPC6; LTrpC6; MGC2849; TRPP8; Trp-p8; trp-p8; Long transient receptor potential channel 6; Transient receptor potential cation channel subfamily M member 8; Transient receptor potential-p8; cold-menthol receptor type 1; short form of the TRPM8 cationic channel; transient receptor potential cation channel, subfamily M, member 8; transient receptor potential subfamily M member 8); TYMS (EC 2.1.1.45; HsT422; MGC88736; TMS; TS; TSase; Tsase; Thymidylate synthase; thymidylate synthetase); ATIC (AICAR; AICARFT; AICARFT/IMPCHASE; IMPCHASE; PURH; 5-aminoimidazole-4-carboxamide ribonucleotide formyltransferase/IMP cyclohydrolase; Bifunctional purine biosynthesis protein PURH); PGK1 (EC 2.7.2.3; MGC117307; MGC142128; MGC8947; MIG10; OK/SW-c1.110; PGKA; Cell migration-inducing gene 10 protein; PRP 2; Primer recognition protein 2; migration-inducing gene 10 protein; phosphoglycerate kinase 1); SOX4 (EVI16; OTTHUMP00000039358; SRY (sex determining region Y)-box 4; SRY-related HMG-box gene 4; Transcription factor SOX-4; ecotropic viral integration site 16); TOR3A (ADIR; ADIR2; FLJ22345; MGC111104; TORP2; ATP-dependant interferon response protein 1; ATP-dependant interferon responsive; ATP-dependent interferon-responsive protein; Torsin family 3 member A; Torsin-3A precursor; torsin family 3, member A); TRGC2 (TCRGC2; TRGC2(2×); TRGC2(3×); T cell receptor gamma constant 2; T-cell receptor gamma chain C region PT-gamma-1/2; T-cell receptor; gamma; constant region C2); BTBD2 (BTB (POZ) domain containing 2; BTB domain containing 2; BTB/POZ domain-containing protein 2; Weakly similar to F38H4.7 [*C. elegans*]); SLBP (HBP; HBP-PEN; Histone RNA hairpin-binding protein; Histone stem-loop-binding protein; hairpin binding protein; histone; heparing binding protein (HBp17); histone stem-loop binding protein; stem-loop (histone) binding protein); EGFR (EC 2.7.10.1; ERBB; ERBB1; mENA; Epidermal growth factor receptor precursor; Receptor tyrosine-protein kinase ErbB-1; avian erythroblastic leukemia viral (v-erb-b) oncogene homolog; cell growth inhibiting protein 40; epidermal growth factor receptor; epidermal growth factor receptor (avian erythroblastic leukemia viral (v-erb-b) oncogene homolog); epidermal growth factor receptor (erythroblastic leukemia viral (v-erb-b) oncogene homolog, avian)); IER3 (DIF-2; DIF2; GLY96; IEX-1; IEX-1L; IEX1; PRG1; Differentiation-dependent gene 2 protein; Immediate early protein GLY96; Immediate early response 3 protein; PACAP-responsive gene 1; PACAP-responsive gene 1 protein; Protein DIF-2; Protein PRG1; Radiation-inducible immediate-early gene IEX-1; anti-death protein; differentiation-dependent gene 2; expressed in pancreatic carcinoma; gly96, mouse, homolog of; immediate early response 3; immediately early gene X-1); TTK (EC 2.7.12.1; ESK; FLJ38280; MPS1L1; PYT; Dual specificity protein kinase TTK; Phosphotyrosine picked threonine-protein kinase; TTK protein kinase; phosphotyrosine picked threonine kinase (PYT)); LY6K (CO16; FLJ35226; HSJ001348; LY6K protein—Fragment; Lymphocyte antigen 6 complex locus protein K-Fragment; lymphocyte antigen 6 complex, locus K); IGF2BP3 (DKFZp686F1078; IMP-3; IMPS; KOC1; VICKZ3; hKOC; IGF II mRNA binding protein 3; IGF-II mRNA-binding protein 3; IGF2 mRNA-binding protein 3; Insulin-like growth factor 2 mRNA-binding protein 3; KH domain containing protein overexpressed in cancer; KH domain-containing protein overexpressed in cancer; VICKZ family member 3; insulin-like growth factor 2 mRNA binding protein 3); GPC3 (DGSX; GTR2-2; MXR7; OCI-5; OCI5; OTTHUMP00000062492; SDYS; SGB; SGBS; SGBS1; glypican-3; Glypican-3 precursor; Intestinal protein OCI-5; glypican 3; glypican proteoglycan 3); SLC35A4 (DKFZp586D071; MGC2541; solute carrier family 35 (UDP-galactose transporter), member A4; solute carrier family 35, member A4; tumor rejection antigen); SERPINB8 (Histocompatibility (minor) serpin domain containing; Uncharacterized protein ENSP00000383162 (Serpin peptidase inhibitor, clade B (Ovalbumin), member 8, isoform CRA_b)); H3F3A (H3.3A; H3.3B; H3F3; H3F3B; MGC87782; MGC87783; Histone H3.3); ALDH1A1 (ALDC; ALDH-E1; ALDH1; ALDH11; ALHDII; EC 1.2.1.36; MGC2318; PUMB1; RALDH1; Ra1DH1; ALDH class 1; ALDH1A1 aldehyde dehydrogenase 1 family, member A1; Aldehyde dehydrogenase family 1 member A1; Aldehyde dehydrogenase; cytosolic; RALDH 1; Retinal dehydrogenase 1; acetaldehyde dehydrogenase 1; aldehyde dehydrogenase 1 family, member A1; aldehyde dehydrogenase 1, soluble; aldehyde dehydrogenase 1A1; aldehyde dehydrogenase, liver cytosolic); MFI2 (CD228; FLJ38863; MAP97; MGC4856; MTF1; Antigen p97 (melanoma associated) identified by monoclonal antibodies 133.2 and 96.5; CD228 antigen; Melanoma-associated antigen p97; Melanotransferrin precursor; antigen p97 (melanoma associated) identified by monoclonal antibodies 133.2 and 96.5; melanoma-associated antigen p97, isoform 2); MMP14 (EC 3.4.24.80; MMP-14; MMP-X1; MT1-MMP; MT1MMP; MTMMP1; MMP-X1; MT-MMP 1; Matrix metalloproteinase-14 precursor; Membrane-type matrix metalloproteinase 1; Membrane-type-1 matrix metalloproteinase; matrix metallopeptidase 14 (membrane-inserted); matrix metalloproteinase 14; matrix metalloproteinase 14 (membrane-inserted); membrane type 1 metalloprotease); SDCBP (MDA-9; MDA9; ST1; SYCL; Syntenin-1; TACIP18; syntenin; Human scaffold protein Pbpl mRNA; complete cds; Melanoma differentiation-associated protein 9; Pro-TGF-alpha cytoplasmic domain-interacting protein 18; Scaffold protein Pbpl; Syndecan-binding protein 1; melanoma differentiation associated protein-9; syndecan binding protein (syntenin)); MAGED4 (KIAA1859; MAGE-E1; MAGE1; MAGED4B; MAGEE1; MGC3210; MGC88639; MAGE-D4 antigen; MAGE-E1 antigen; Melanoma-associated antigen D4; melanoma antigen family D, 4; melanoma antigen family D, 4B); PARP12 (EC 2.4.2.30; FLJ22693; MST109; MSTP109; PARP-12; Poly; ZC3H1; ZC3HDC1; ADP-ribosepolymerase 12; Zinc finger CCCH domain-containing protein 1; poly (ADP-ribose) polymerase family; member 12; zinc finger CCCH type domain containing 1; zinc finger CCCH-type domain containing 1); MET (AUTS9; EC 2.7.10.1; HG1-R; RCCP2; c-Met; HGF receptor; HGF/SF receptor; Hepatocyte growth factor receptor precursor; Met proto-oncogene tyrosine kinase; Oncogene MET; SF receptor; Scatter factor receptor; met proto-oncogene; met proto-oncogene (hepatocyte growth factor receptor)); CCNB1 (CCNB; G2/MITOTIC-SPECIFIC CYCLIN B1; G2/mitotic-specific cyclin-B1; cyclin B1); PAX3-FKHR ( ); PAX3 (PAX3/FKHR fusion; paired box gene 3; paired box gene 3 (Waardenburg syndrome 1); paired box homeotic gene 3; paired box homeotic gene 3 (Waardenburg syndrome 1); paired domain gene 3; paired domain gene HuP2; CDHS; HUP2; MGC120381; MGC120382; MGC120383; MGC120384; MGC134778; WS1); FOXO1 (Forkhead in rhabdomyosarcoma; forkhead box O1; forkhead box O1A (rhabdomyosarcoma); forkhead homolog in rhabdomyosarcoma; forkhead, *Drosophila*, homolog of, in rhabdomyosarcoma; FKH1; FKHR; FOXO1A); or combination thereof. In another embodiment, an immunogenic portion of the tumor associated antigen is used in the vaccines and methods of the present invention, as is known in the art.

In one embodiment, the present invention provides an isolated or recombinant polynucleotide encoding a codon-optimized tumor endothelial marker (TEM)-1.

In one embodiment, the present invention provides a vector comprising the polynucleotide, which in one embodiment, is an adenovirus vector or a plasmid vector, which in one embodiment, is an Ad 5 vector. In one embodiment, the present invention provides a cell comprising the vector, which in one embodiment, is *E. coli.*

In one embodiment, the DOM portion of the TVM-DOM fusion protein is codon-optimized for high-level expression in human cells. In other preferred embodiments, the TVM portion of the TVM fusion is codon-optimized for high-level expression in human cells. In still further preferred embodiments, both the TVM and the DOM portions are codon-optimized for high-level expression in human cells.

Following expression of a TVM fusion in a host cell, TVM fusion protein may be recovered to provide TVM fusion protein in active form. Several protein purification procedures are available and suitable for use. Recombinant protein may be purified from cell lysates and extracts by various combinations of, or individual application of salt fractionation, ion exchange chromatography, size exclusion chromatography, hydroxylapatite adsorption chromatography and hydrophobic interaction chromatography. In addition, recombinant TVM fusion protein can be separated from other cellular proteins by use of an immunoaffinity column made with monoclonal or polyclonal antibodies specific for a TVM protein, or polypeptide fragments of a TVM protein.

In one embodiment, the nucleic acid molecules comprising TVM fusions and the encoded fusion proteins of this invention are designed to enhance the TVM-specific immune response, relative to full-length cDNA encoding TVM, for use in vaccine development.

To further enhance the immunogenic properties of the TVM fusion sequences of the present invention, in some embodiments described herein, the polynucleotides encoding TVM fusion proteins comprise optimized codons for further high level expression in a host cell, as described below. In these embodiments, at least a portion of the codons of the TVM fusions are designed so as to use the codons preferred by the projected host cell, which in one embodiment, is a human cell. The optimized TVM fusions may be used for the development of recombinant adenovirus or plasmid-based DNA vaccines, which provide effective immunoprophylaxis against TVM-associated cancer through neutralizing antibody and cell-mediated immunity. The synthetic molecules may be used as an immunogenic composition. This invention provides codon-optimized TVM fusion polynucleotides which, when directly introduced into a vertebrate in vivo, including mammals such as primates and humans, induce the expression of encoded proteins within the animal.

In some embodiments of the present invention, the synthetic molecules comprise a sequence of nucleotides, wherein some of the nucleotides have been altered so as to use the codons preferred by a human cell, thus allowing for high-level fusion protein expression in a human host cell. The synthetic molecules may be used as a source of a TVM fusion protein, for example, TVM-LTB fusion protein, which may be used in a cancer vaccine to provide effective immunoprophylaxis against TVM-associated carcinomas through neutralizing antibody and cell mediated immunity. The nucleic acid molecules disclosed herein may also serve as the basis for a DNA-based cancer vaccine.

A "triplet" codon of four possible nucleotide bases can exist in over 60 variant forms. Because these codons provide the message for only 20 different amino acids (as well as transcription initiation and termination), some amino acids can be coded for by more than one codon, a phenomenon known as codon redundancy. For reasons not completely understood, alternative codons are not uniformly present in the endogenous DNA of differing types of cells. Indeed, there appears to exist a variable natural hierarchy or "preference" for certain codons in certain types of cells. As one example, the amino acid leucine is specified by any of six DNA codons including CTA, CTC, CTG, CTT, TTA, and TTG. Exhaustive analysis of genome codon frequencies for microorganisms has revealed endogenous DNA of *E. coli* most commonly contains the CTG leucine-specifying codon, while the DNA of yeasts and slime molds most commonly includes a TTA leucine-specifying codon.

In view of this hierarchy, it is generally believed that the likelihood of obtaining high levels of expression of a leucine-rich polypeptide by an *E. coli* host will depend to some extent on the frequency of codon use. For example, it is likely that a gene rich in TTA codons will be poorly expressed in *E. coli*, whereas a CTG rich gene will probably be highly expressed in this host. Similarly, a preferred codon for expression of a leucine-rich polypeptide in yeast host cells would be TTA.

The implications of codon preference phenomena on recombinant DNA techniques are manifest, and the phenomenon may serve to explain many prior failures to achieve high expression levels of exogenous genes in successfully transformed host organisms—a less "preferred" codon may be repeatedly present in the inserted gene and the host cell machinery for expression may not operate as efficiently. This phenomenon suggests that synthetic genes which have been designed to include a projected host cell's preferred codons provide an optimal form of foreign genetic material for practice of recombinant DNA techniques. Thus, one aspect of this invention is a TVM fusion gene that is codon-optimized for expression in a human cell. In a preferred embodiment of this invention, it has been found that the use of alternative codons encoding the same protein sequence may remove the constraints on expression of exogenous TVM fusion protein in human cells.

In accordance with some embodiments of the present invention, the nucleic acid molecules which encode the TVM fusion proteins are converted to a polynucleotide sequence having an identical translated sequence but with alternative codon usage as described by Lathe, "Synthetic Oligonucleotide Probes Deduced from Amino Acid Sequence Data: Theoretical and Practical Considerations" J. Molec. Biol. 183: 1-12 (1985), which is hereby incorporated by reference. The methodology generally consists of identifying codons in the wild-type sequence that are not commonly associated with highly expressed human genes and replacing them with optimal codons for high expression in human cells. The new gene sequence is then inspected for undesired sequences generated by these codon replacements (e.g., "ATTTA" sequences, inadvertent creation of intron splice recognition sites, unwanted restriction enzyme sites, etc.). Undesirable sequences are eliminated by substitution of the existing codons with different codons coding for the same amino acid. The synthetic gene segments are then tested for improved expression.

The methods described above were used to create synthetic gene sequences which encode TVM fusion proteins, resulting in a gene comprising codons optimized for high level expression. While the above procedure provides a summary of our methodology for designing codon optimized genes for use in cancer vaccines, it is understood by one skilled in the art that similar vaccine efficacy or increased expression of genes may be achieved by minor variations in the procedure or by minor variations in the sequence.

One of skill in the art will also recognize that additional nucleic acid molecules may be constructed that provide for high levels of TVM fusion expression in human cells, wherein only a portion of the codons of the DNA molecules are codon-optimized. For example, in some embodiments of the present invention, codons comprising the TVM portion of the TVM fusion are optimized for high-level expression in human cells, and codons comprising the adjuvant portion of the TVM fusion are substantially similar to the wild-type adjuvant-encoding nucleotide sequence. In other embodiments of the present invention, codons comprising the adjuvant portion of the TVM fusion are optimized for high-level expression in human cells, and codons comprising the TVM portion of the TVM fusion are substantially similar to a wild-type TVM gene. In still other embodiments of the present invention, both the TVM and the adjuvant portions of the TVM fusion are codon-optimized for high-level expression in human cells. TVM fusions in which only a subset of codons is optimized within the TVM and/or the adjuvant portion of the TVM fusion are also contemplated by this invention.

The nucleic acids of the present invention may be assembled into an expression cassette which comprises sequences designed to provide for efficient expression of the protein in a human cell. The cassette preferably contains TVM fusion protein-encoding gene, with related transcriptional and translations control sequences operatively linked to it, such as a promoter, and termination sequences. In one embodiment, the promoter is the cytomegalovirus promoter without the intron A sequence (CMV), although those skilled in the art will recognize that any of a number of other known promoters such as the strong immunoglobulin, or other eukaryotic gene promoters may be used. A preferred transcriptional terminator is the bovine growth hormone terminator, although other known transcriptional terminators may also be used. The combination of CMV-BGH terminator is particularly preferred.

In one embodiment, the present invention provides a polynucleotide comprising a nucleic acid sequence encoding a tumor endothelial marker (TEM)-1 fusion protein, wherein said TEM-1 fusion protein comprises a TEM-1 protein or variant thereof, fused to a substantial portion of an immuno-enhancing element selected from the group consisting of: DOM, FcIgG, CT, LTA, and LTB, and wherein said fusion protein is capable of producing an immune response in a subject.

In one embodiment, the present invention provides a polynucleotide comprising a nucleic acid sequence encoding a tumor endothelial marker (TEM)-7R fusion protein, wherein said TEM-7R fusion protein comprises a TEM-7R protein or variant thereof, fused to a substantial portion of an immuno-enhancing element selected from the group consisting of: DOM, FcIgG, CT, LTA, and LTB, and wherein said fusion protein is capable of producing an immune response in a subject. In another embodiment, TEM-7R is a tumor vasculature marker.

In one embodiment, the present invention provides a polynucleotide comprising a nucleic acid sequence encoding a tumor endothelial marker hTERT fusion protein, wherein said hTERT fusion protein comprises a hTERT protein or variant thereof, fused to a substantial portion of an immuno-enhancing element selected from the group consisting of: DOM, FcIgG, CT, LTA, and LTB, and wherein said fusion protein is capable of producing an immune response in a subject.

In one embodiment, the present invention provides a polynucleotide comprising a nucleic acid sequence encoding a tumor endothelial marker HPVE7 fusion protein, wherein said HPVE7 fusion protein comprises a HPVE7 protein or variant thereof, fused to a substantial portion of an immuno-enhancing element selected from the group consisting of: DOM, FcIgG, CT, LTA, and LTB, and wherein said fusion protein is capable of producing an immune response in a subject.

In one embodiment, the present invention provides a vector comprising the polynucleotide, which in one embodiment, is an adenovirus vector or a plasmid vector, which is one embodiment, is an Ad 5 vector.

In one embodiment, the present invention provides a host cell comprising the vector.

In one embodiment, the present invention provides a purified TEM-1 fusion protein encoded by a nucleic acid sequence encoding a tumor endothelial marker (TEM)-1 fusion protein, wherein said TEM-1 fusion protein comprises a TEM-1 protein or variant thereof, fused to a substantial portion of an immuno-enhancing element selected from the group consisting of: DOM, pDOM, FcIgG, CT, LTA, and LTB.

In one embodiment, the present invention provides an adenovirus vaccine vector comprising an adenoviral genome with a deletion in the E1 region, and an insert in the E1 region, wherein the insert comprises an expression cassette comprising: (a) a polynucleotide comprising a sequence of nucleotides that encodes a TEM-1 fusion protein, wherein the TEM-1 fusion protein comprises a TEM-1 protein or variant thereof, fused to a substantial portion of an immunoenhancing element selected from the group consisting of: DOM, pDOM, FcIgG, CT, LTA, and LTB; and wherein the fusion protein is capable of producing an immune response in a subject; and (b) a promoter operably linked to the polynucleotide, which in one embodiment, is an Ad 5 vector.

In one embodiment, the present invention provides a vaccine plasmid comprising a plasmid portion and an expression cassette portion, said expression cassette portion comprising: (a) a polynucleotide comprising a sequence of nucleotides that encodes a TEM-1 fusion protein, wherein the TEM-1 fusion protein comprises a TEM-1 protein or variant thereof, fused to a substantial portion of an immunoenhancing element selected from the group consisting of: DOM, FcIgG, CT, LTA, and LTB; and wherein the fusion protein is capable of producing an immune response in a subject; and (b) a promoter operably linked to the polynucleotide.

In one embodiment, the present invention provides compositions and methods wherein the vaccine comprises one nucleic acid construct comprising a nucleic acid sequence encoding a tumor vasculature marker (TVM) or immunogenic fragment thereof. In another embodiment, the vaccine comprises one polypeptide comprising an amino acid sequence corresponding to the amino acid sequence for a TVM. In another embodiment, the present invention provides compositions and methods wherein the vaccine comprises more than one nucleic acid construct comprising a nucleic acid sequence encoding a TVM or polypeptide comprising an amino acid sequence corresponding to the amino acid sequence for a TVM. In one embodiment, more than one refers to two, three, four, five, seven, ten, fifteen, or twenty. In other embodiments, the the present invention provides compositions and methods wherein the vaccine comprises any number of TVMs. In another embodiment, each nucleic acid construct may comprise a nucleic acid sequence encoding one or more TVMs. In another embodiment, each polypeptide may comprise an amino acid sequence corresponding to the amino acid sequence of one or more TVMs.

In one embodiment, the invention provides an immortalized endothelial cell line expressing a human tumor vasculature marker (TVM). In one embodiment, the TVM is TEM-1. In one embodiment, the endothelial cells further comprise a marker, which in one embodiment is firefly luciferase (fLuc). In one embodiment, the immortalized endothelial cells are MS1 cells, while in another embodiment, the immortalized endothelial cells are H5V cells.

In one embodiment, the invention provides a mouse comprising the endothelial cell line described hereinabove.

In one embodiment, the immortalized endothelial cells are present in a tumor, which in one embodiment, is an angioma or angiosarcoma.

In one embodiment, the present invention provides a method of immunizing a subject against a tumor, comprising administering to said subject a vaccine comprising a polypeptide comprising a tumor vasculature marker (TVM) or immunogenic fragment thereof, wherein said vaccine elicits an immune response to said TVM, thereby abrogating the growth of a tumor whose vasculature expresses said TVM.

In one embodiment, the present invention provides a method of immunizing a subject against a tumor, comprising administering to said subject a vaccine comprising a nucleic acid construct comprising a nucleic acid sequence encoding a tumor vasculature marker (TVM) or immunogenic fragment thereof, wherein said vaccine elicits an immune response to said TVM, thereby abrogating the growth of a tumor whose vasculature expresses said TVM.

In one embodiment, the present invention provides compositions and methods for immunizing a subject against a tumor. In one embodiment, immunizing a subject refers to preventing or inhibiting the growth of a tumor by inducing an immune response to a TVM that is typically expressed in the vasculature supporting the tumor type that is being inhibited. In another embodiment, immunizing a subject refers to inhibiting the recurrence of a tumor by inducing an immune response to a TVM that was expressed in the vasculature supporting said tumor. In one embodiment, a method of immunizing requires a booster in which said subject is again exposed to said TVM on a separate occasion in order to enhance the immune response to said TVM.

In another embodiment, the present invention provides a method of inhibiting the growth of a tumor in a subject, comprising administering to said subject a vaccine comprising a polypeptide comprising a tumor vasculature marker (TVM) or immunogenic fragment thereof, wherein said vaccine elicits an immune response to said TVM, thereby inhibiting the growth of a tumor whose vasculature expresses said TVM.

In one embodiment, the present invention provides a method of inhibiting the growth of a tumor in a subject, comprising administering to said subject a vaccine comprising a nucleic acid construct comprising a nucleic acid sequence encoding a tumor vasculature marker (TVM) or immunogenic fragment thereof, wherein said vaccine elicits an immune response to said TVM, thereby inhibiting the growth of a tumor whose vasculature expresses said TVM.

In another embodiment, the present invention provides a method of inhibiting tumor recurrence in a subject, comprising administering to said subject a vaccine comprising a polypeptide comprising a tumor vasculature marker (TVM) or immunogenic fragment thereof, wherein said vaccine elicits an immune response to said TVM, thereby inhibiting the recurrence of a tumor whose vasculature expresses said TVM.

In one embodiment, the present invention provides a method of inhibiting tumor recurrence in a subject, comprising administering to said subject a vaccine comprising a nucleic acid construct comprising a nucleic acid sequence encoding a tumor vasculature marker (TVM) or immunogenic fragment thereof, wherein said vaccine elicits an immune response to said TVM, thereby inhibiting the recurrence of a tumor whose vasculature expresses said TVM.

In another embodiment, the present invention provides a method of treating a tumor in a subject, comprising administering to said subject a vaccine comprising a polypeptide comprising a tumor vasculature marker (TVM) or immunogenic fragment thereof, wherein said vaccine elicits an immune response to said TVM, thereby treating a tumor whose vasculature expresses said TVM.

In one embodiment, the present invention provides a method of treating a tumor in a subject, comprising administering to said subject a vaccine comprising a nucleic acid construct comprising a nucleic acid sequence encoding a tumor vasculature marker (TVM) or immunogenic fragment thereof, wherein said vaccine elicits an immune response to said TVM, thereby treating a tumor whose vasculature expresses said TVM.

In another embodiment, the present invention provides a method of suppressing the growth of a tumor in a subject, comprising administering to said subject a vaccine comprising a polypeptide comprising a tumor vasculature marker (TVM) or immunogenic fragment thereof, wherein said vaccine elicits an immune response to said TVM, thereby suppressing the growth of a tumor whose vasculature expresses said TVM.

In another embodiment, the present invention provides a method of suppressing the growth of a tumor in a subject, comprising administering to said subject a vaccine comprising a nucleic acid construct comprising a nucleic acid sequence encoding a tumor vasculature marker (TVM) or immunogenic fragment thereof, wherein said vaccine elicits an immune response to said TVM, thereby suppressing the growth of a tumor whose vasculature expresses said TVM.

In another embodiment, the present invention provides a method of decreasing the incidence of a tumor in a subject, comprising administering to said subject a vaccine comprising a polypeptide comprising a tumor vasculature marker (TVM) or immunogenic fragment thereof, wherein said vaccine elicits an immune response to said TVM, thereby decreasing the incidence of a tumor whose vasculature expresses said TVM.

In another embodiment, the present invention provides a method of decreasing the incidence of a tumor in a subject, comprising administering to said subject a vaccine comprising a nucleic acid construct comprising a nucleic acid sequence encoding a tumor vasculature marker (TVM) or immunogenic fragment thereof, wherein said vaccine elicits an immune response to said TVM, thereby decreasing the incidence of a tumor whose vasculature expresses said TVM.

In another embodiment, the present invention provides a method of overcoming an immune tolerance to a tumor vasculature marker (TVM) in a subject, comprising administering to said subject a vaccine comprising a polypeptide comprising a tumor vasculature marker (TVM) or immunogenic fragment thereof, wherein said vaccine elicits an immune response to said TVM, thereby overcoming tolerance to said TVM.

In one embodiment, the present invention provides a method of overcoming an immune tolerance to a tumor vasculature marker (TVM) in a subject, comprising administering to said subject a vaccine comprising a nucleic acid construct comprising a nucleic acid sequence encoding a tumor vasculature marker (TVM) or immunogenic fragment thereof, wherein said vaccine elicits an immune response to said TVM, thereby overcoming an immune tolerance to said TVM.

In one embodiment, the present invention provides compositions and methods for overcoming immune tolerance. In one embodiment, immune tolerance is a state in which a host's immune system (in one embodiment, the T cells of the immune system) are unresponsive or less responsive to a particular antigen. In one embodiment, the present invention provides compositions and methods for overcoming immune tolerance to a self-antigen. "Self antigen" refers, in one embodiment, to an antigen expressed by a host's own cells and cell products. In another embodiment, the term refers to an antigen to which the host has developed a peripheral tolerance. In another embodiment, the term refers to an antigen that has been expressed in the host at a low level, thus resulting in tolerance. In another embodiment, the term refers to an antigen that has been expressed in the host at a low level for an extended period of time, thus resulting in tolerance. Each possibility represents a separate embodiment of the present invention.

In one embodiment, the method further comprises the step of boosting said subject with a second vaccine comprising said polypeptide. In some embodiments of this invention, the vaccines and methods disclosed herein are used in various prime/boost combinations in order to induce an enhanced immune response. In one embodiment, two vectors are administered in a "prime and boost" regimen. For example, the first type of vector is administered one or more times, then after a predetermined amount of time, for example, 2 weeks, 1 month, 2 months, six months, or other appropriate interval, a second type of vector is administered one or more times. In one embodiment, the vectors carry expression cassettes encoding the same polynucleotide or combination of polynucleotides. In the embodiment where a plasmid DNA is also used, it is preferred that the vector contain one or more promoters recognized by mammalian or insect cells. In a preferred embodiment, the plasmid would contain a strong promoter such as, but not limited to, the CMV promoter. The synthetic TVM fusion gene or other gene to be expressed would be linked to such a promoter. An example of such a plasmid would be the mammalian expression plasmid VtIns as described (J. Shiver et. al. in DNA Vaccines, M. Liu et al. eds., *N.Y. Acad. Sci*., N.Y., 772:198-208 (1996), which is herein incorporated by reference).

In one embodiment, the nucleic acid construct comprises a nucleic acid sequence as set forth in SEQ ID NO: 1-37, or a combination thereof. In one embodiment, the tumor is an ovarian tumor. In one embodiment, the nucleic acid construct comprises a nucleic acid sequence as set forth in SEQ ID NO: 1-35, or a combination thereof. In one embodiment, the tumor is a renal tumor. In one embodiment, the nucleic acid construct comprises a nucleic acid sequence as set forth in SEQ ID NO: 36. In one embodiment, the tumor is a breast tumor. In one embodiment, the nucleic acid construct comprises a nucleic acid sequence as set forth in SEQ ID NO: 37. In one embodiment, the vaccine is a DNA vaccine. In one embodiment, the vaccine is a recombinant viral vaccine. In one embodiment, the recombinant viral vaccine is a recombinant adenoviral vaccine. In one embodiment, the nucleic acid sequence is under the control of one or more regulatory sequences which directs the expression of said nucleic acid sequence in said subject. In one embodiment, the nucleic acid construct further comprises a nucleic acid sequence encoding an adjuvant. In one embodiment, the adjuvant is DOM, FcIgG, CT, LTA, or LTB or an immunogenic fragment thereof. In one embodiment, the adjuvant is the N-terminal domain of fragment C of tetanus toxoid (DOM). In one embodiment, the adjuvant is fused to said nucleic acid sequence. In one embodiment, the nucleic acid construct comprises a nucleic acid sequence encoding a tumor endothelial marker (TEM)-1 protein or variant thereof fused in frame to a nucleic acid sequence encoding the N-terminal domain of fragment C of tetanus toxoid (DOM). In one embodiment, the vaccine additionally comprises one or more tumor associated antigens. In one embodiment, the tumor associated antigen is a Her/2-neu antigen, High Molecular Weight Melanoma Associated Antigen (HMW-MAA), carcinoembryonic antigen (CEA), Melanoma-associated antigen (MAGE-A), Carcinoma-associated mucin (MUC-1), Renal tumor antigen 1 (RAGE), Breakpoint cluster region protein (BCR), kidney-associated antigen 1; or Carbonate dehydratase IX (CALX). In one embodiment, the method further comprises the step of boosting said subject with a second vaccine comprising said nucleic acid construct.

In one embodiment, the present invention provides a method of inhibiting the growth of a tumor in a subject, wherein the vasculature supplying said tumor comprises a tumor vasculature marker (TVM), comprising the steps of: (a) identifying expression of said TVM by said tumor by contacting said subject with a labeled compound that binds said TVM or a nucleic acid molecule encoding said TVM; (b) detecting said label; (c) contacting said subject with an antibody to said TVM, wherein said antibody is labeled with a radionuclide to deliver cytotoxic radiation to tumor vasculature expressing said TVM; and (d) contacting said subject with said TVM or with a nucleic acid construct encoding said TVM to induce an immune response against said TVM.

In one embodiment, the present invention provides a method of inhibiting tumor recurrence in a subject, wherein the vasculature supplying said tumor comprises a tumor vasculature marker (TVM), comprising the steps of: (a) identifying expression of said TVM by said tumor by contacting said subject with a labeled compound that binds said TVM or a nucleic acid molecule encoding said TVM; (b) detecting said label; (c) contacting said subject with an antibody to said TVM, wherein said antibody is labeled with a radionuclide to deliver cytotoxic radiation to tumor vasculature expressing said TVM; and (d) contacting said subject with said TVM or with a nucleic acid construct encoding said TVM to induce an immune response against said TVM.

In one embodiment, the present invention provides a method of treating a tumor in a subject, wherein the vasculature supplying said tumor comprises a tumor vasculature marker (TVM), comprising the steps of: (a) identifying expression of said TVM by said tumor by contacting said subject with a labeled compound that binds said TVM or a nucleic acid molecule encoding said TVM; (b) detecting said label; (c) contacting said subject with an antibody to said TVM, wherein said antibody is labeled with a radionuclide to deliver cytotoxic radiation to tumor vasculature expressing said TVM; and (d) contacting said subject with said TVM or with a nucleic acid construct encoding said TVM to induce an immune response against said TVM.

In one embodiment, the present invention provides a method of inhibiting the growth of a tumor in a subject, wherein the vasculature supplying said tumor comprises a tumor vasculature marker (TVM), comprising the steps of: (a) identifying expression of said TVM by said tumor by contacting said subject with a labeled compound that binds said TVM or a nucleic acid molecule encoding said TVM; (b) detecting said label; (c) contacting said subject with an antibody to said TVM, wherein said antibody is labeled with a radionuclide to deliver cytotoxic radiation to tumor vasculature expressing said TVM; and (d) contacting said subject with said TVM or with a nucleic acid construct encoding said TVM to induce an immune response against said TVM.

In one embodiment, the present invention provides a method of suppressing the growth of a tumor in a subject, wherein the vasculature supplying said tumor comprises a tumor vasculature marker (TVM), comprising the steps of: (a) identifying expression of said TVM by said tumor by contacting said subject with a labeled compound that binds said TVM or a nucleic acid molecule encoding said TVM; (b) detecting said label; (c) contacting said subject with an antibody to said TVM, wherein said antibody is labeled with a radionuclide to deliver cytotoxic radiation to tumor vasculature expressing said TVM; and (d) contacting said subject with said TVM or with a nucleic acid construct encoding said TVM to induce an immune response against said TVM.

In one embodiment, the present invention provides a method of decreasing the incidence of a tumor in a subject, wherein the vasculature supplying said tumor comprises a tumor vasculature marker (TVM), comprising the steps of: (a) identifying expression of said TVM by said tumor by contacting said subject with a labeled compound that binds said TVM or a nucleic acid molecule encoding said TVM; (b) detecting said label; (c) contacting said subject with an antibody to said TVM, wherein said antibody is labeled with a radionuclide to deliver cytotoxic radiation to tumor vasculature expressing said TVM; and (d) contacting said subject with said TVM or with a nucleic acid construct encoding said TVM to induce an immune response against said TVM.

In one embodiment, the nucleic acid sequence encoding said TVM is the sequences set forth in SEQ ID NO: 1-37. In one embodiment, the TVM is TEM-1. In one embodiment, the TVM is TEM-5, TEM-7, or TEM-8. In one embodiment, the detecting step is performed using positron emission tomography (PET) scanning. In one embodiment, the detecting step also utilizes computed tomography (CT) or magnetic resonance imaging (MRI) scanning. In one embodiment, the labeled compound is a labeled antibody.

In one embodiment, the present invention provides a method of targeting a tumor vasculature in a subject having a tumor, the method comprising the step of contacting said subject with a labeled compound that binds a) a tumor vasculature marker (TVM) or b) a nucleic acid molecule encoding said TVM.

In one embodiment, the present invention provides a method of inhibiting the growth of a tumor in a subject, the method comprising the step of contacting said subject with a labeled compound that binds a) a tumor vasculature marker (TVM) or b) a nucleic acid molecule encoding said TVM.

In one embodiment, the present invention provides a method of inhibiting tumor recurrence in a subject, the method comprising the step of contacting said subject with a labeled compound that binds a) a tumor vasculature marker (TVM) or b) a nucleic acid molecule encoding said TVM.

In one embodiment, the present invention provides a method of treating a tumor in a subject, the method comprising the step of contacting said subject with a labeled compound that binds a) a tumor vasculature marker (TVM) or b) a nucleic acid molecule encoding said TVM.

In one embodiment, the present invention provides a method of inhibiting the growth of a tumor in a subject, the method comprising the step of contacting said subject with a labeled compound that binds a) a tumor vasculature marker (TVM) or b) a nucleic acid molecule encoding said TVM.

In one embodiment, the present invention provides a method of suppressing the growth of a tumor in a subject, the method comprising the step of contacting said subject with a labeled compound that binds a) a tumor vasculature marker (TVM) or b) a nucleic acid molecule encoding said TVM.

In one embodiment, the present invention provides a method of decreasing the incidence of a tumor in a subject, the method comprising the step of contacting said subject with a labeled compound that binds a) a tumor vasculature marker (TVM) or b) a nucleic acid molecule encoding said TVM.

In one embodiment, the method further comprises the step of detecting said labeled compound, in one embodiment, in order to localize said tumor. In one embodiment, the labeled compound is an antibody. In one embodiment, the labeled compound is a ligand. In one embodiment, the labeled compound is labeled with a radionuclide, thereby delivering cytotoxic radiation to tumor vasculature expressing said TVM. In one embodiment, the radionuclide is Iodine-124. In one embodiment, the radionuclide is Astatine-211. In one embodiment, the labeled compound is labeled with a photoactivatable cytotoxic drug or pharmaceutical composition. In one embodiment, the method further comprises the step of contacting said tumor vasculature with a concentrated light source, thereby delivering said cytotoxic drug to said tumor vasculature expressing said TVM. In one embodiment, the method further comprises the step of contacting said subject with said TVM or with a nucleic acid construct encoding said TVM to induce an immune response against said TVM.

In one embodiment, the TVM is encoded by a nucleic acid sequence as set forth in SEQ ID NO: 1-37. In one embodiment, the tumor is an ovarian tumor. In one embodiment, the TVM is encoded by a nucleic acid sequence as set forth in SEQ ID NO: 1-35. In one embodiment, the tumor is a renal tumor. In one embodiment, the TVM is encoded by a nucleic acid sequence as set forth in SEQ ID NO: 36. In one embodiment, the tumor is a breast tumor. In one embodiment, the TVM is encoded by a nucleic acid sequence as set forth in SEQ ID NO: 37.

In one embodiment, patients are screened by PET for expression of a TVM, and those positive are treated with radio-immunotherapy, which is expected to result in extensive vascular damage and significant tumor destruction. Vaccine therapy targeting the TVM would then be administered to prevent tumor recurrence.

In one embodiment, the present invention provides a method of inducing an immune response against a tumor vasculature marker (TVM) in a subject, comprising administering to said subject a composition comprising a polypeptide comprising an amino acid sequence corresponding to the amino acid sequence for said TVM.

In another embodiment, the present invention provides a method of enhancing an immune response against a tumor vasculature marker (TVM) in a subject, comprising administering to said subject a composition comprising a polypeptide comprising an amino acid sequence corresponding to the amino acid sequence for said TVM.

In another embodiment, the present invention provides a method of inducing an immune response against a tumor vasculature marker (TVM) in a subject, comprising administering to said subject a composition comprising a nucleic acid construct comprising a nucleic acid sequence encoding said TVM.

In another embodiment, the present invention provides a method of enhancing an immune response against a tumor vasculature marker (TVM) in a subject, comprising administering to said subject a composition comprising a nucleic acid construct comprising a nucleic acid sequence encoding said TVM.

In another embodiment, the present invention provides a method of inhibiting the vascularization of a tumor in a subject comprising administering to said subject a composition comprising a polypeptide comprising an amino acid sequence corresponding to the amino acid sequence of a tumor vasculature marker (TVM) of the present invention.

In another embodiment, the present invention provides a method of inhibiting the vascularization of a tumor in a subject comprising administering to said subject a composition comprising a nucleic acid construct comprising a nucleic acid sequence encoding a tumor vasculature marker (TVM) of the present invention.

In another embodiment, the present invention provides a method of suppressing the vascularization of a tumor in a subject comprising administering to said subject a composition comprising a polypeptide comprising an amino acid sequence corresponding to the amino acid sequence of a tumor vasculature marker (TVM) of the present invention.

In another embodiment, the present invention provides a method of suppressing the vascularization of a tumor in a subject comprising administering to said subject a composition comprising a nucleic acid construct comprising a nucleic acid sequence encoding a tumor vasculature marker (TVM) of the present invention.

In one embodiment, the present invention provides a method of cross-priming against E7 HPV, the method comprising immunizing with a nucleic acid encoding TEM1-pDOM, whereby said cross-priming results in the stimulation of naive cytotoxic $CD8^+$ T cells against E7 HPV. In one embodiment, the present invention provides a method of cross-priming against E7 HPV, the method comprising immunizing with a nucleic acid encoding TEM1-pDOM, whereby said cross-priming results in the stimulation of splenocytes against E7 HPV. In another embodiment, the present invention provides a method of cross priming against E7 HPV, the method comprising immunizing with a nucleic acid encoding TEM1-pDOM, whereby said cross-priming results in the stimulation of naive cytotoxic $CD4^+$ T cells against E7 HPV.

In one embodiment, "treating" refers to either therapeutic treatment or prophylactic or preventative measures, wherein the object is to prevent or lessen the targeted pathologic condition or disorder as described hereinabove. Thus, in one embodiment, treating may include directly affecting or curing, suppressing, inhibiting, preventing, reducing the severity of, delaying the onset of, reducing symptoms associated with the disease, disorder or condition, or a combination thereof. Thus, in one embodiment, "treating" refers inter alia to delaying progression, expediting remission, inducing remission, augmenting remission, speeding recovery, increasing efficacy of or decreasing resistance to alternative therapeutics, or a combination thereof. In one embodiment, "suppressing" or "inhibiting" refers, inter alia, to delaying the onset of symptoms, preventing relapse to a disease, decreasing the number or frequency of relapse episodes, increasing latency between symptomatic episodes, or a combination thereof. In another embodiment, "suppressing" or "inhibiting", refers inter alia to reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

In one embodiment, symptoms are primary, while in another embodiment, symptoms are secondary. In one embodiment, "primary" refers to a symptom that is a direct result of the tumor or cancer, while in one embodiment, "secondary" refers to a symptom that is derived from or consequent to a primary cause. In one embodiment, the compositions and methods of the present invention treat primary or secondary symptoms or secondary complications related to cancer or tumors.

In another embodiment, "symptoms" may be any manifestation of cancer, comprising persistent fatigue, weight loss, changes to the skin, pain, headache, nausea, stomachache, fever, or a combination thereof.

In one embodiment, a "disorder" is any condition that would benefit from treatment with the molecules of the present invention, including the nucleic acid molecules described herein. In one embodiment, encompassed by the term "disorder" are chronic and acute disorders or diseases including those pathological conditions which predispose the mammal to the disorder in question. In one embodiment, the molecules of the present invention are intended for use as treatments for disorders or conditions characterized by aberrant cell proliferation, including, but not limited to, ovarian cancer breast cancer, and renal or kidney cancer.

"Ligand" refers, in another embodiment, to any molecule or structure capable of binding the target molecule. In another embodiment, "ligand" includes antibodies. In another embodiment, the term includes nucleotide molecules that hybridize to a target of interest. In another embodiment, the term includes small molecules with an affinity for the target. Each possibility represents a separate embodiment of the present invention.

In one embodiment, the methods and compositions of the present invention are used for imaging. "Imaging" refers, in another embodiment, to localizing a ligand of interest using an imaging or scanning technology. In another embodiment, the ligand is a fluorescent ligand. In another embodiment, the ligand is radioactive. In another embodiment, the ligand is bound by a molecule (e.g. an antibody) that is detectable by the imaging or scanning technology. In another embodiment, any suitable imaging or scanning technology known in the art may be utilized. Each possibility represents a separate embodiment of the present invention.

In one embodiment, a rapid protocol was developed and optimized for immuno-LCM of TVC, followed by extraction and amplification of RNA for array analysis of tumor vascular cells, enabling identification of the novel tumor vasculature markers (TVM). The identified transcripts and proteins encoded thereby may be validated as TVM by a number of independent lines of evidence, including enrichment in independent tumor samples, relative to normal vascular samples; enrichment in tumor tissue relative to a variety of tissue samples; and comparison of expression levels between tumor tissue and tissues with physiologic angiogenesis.

In one embodiment, certain TVM transcripts of the present invention and the proteins encoded thereby are efficacious in localizing solid tumors and vasculature thereof.

As provided in the Examples herein, certain TVM of the present invention are expressed at detectable levels only by TVC. In another embodiment, the TVM are expressed at higher levels by TVC than by healthy tissue. Thus, TVM provide a means of specifically targeting therapeutic modalities to solid tumors and their vasculature.

In another embodiment, the present invention provides a method of suppressing angiogenesis of a tumor in a subject comprising administering to said subject a composition comprising a polypeptide comprising an amino acid sequence corresponding to the amino acid sequence of a tumor vasculature marker (TVM) of the present invention.

In another embodiment, the present invention provides a method of suppressing angiogenesis of a tumor in a subject comprising administering to said subject a composition comprising a nucleic acid construct comprising a nucleic acid sequence encoding a tumor vasculature marker (TVM) of the present invention.

In one embodiment, certain TVM of the present invention are up-regulated upon differentiation of precursor cells into TVC. Thus, these TVM (both the nucleic acid molecules and the proteins encoded thereby) play important roles in the function of TVC in angiogenesis, and thus in the pathogenesis of solid tumors. Accordingly, vaccines and related methods targeting the TVMs represent an efficacious means of impeding vascularization of solid tumors.

In one embodiment, TVM are upregulated upon differentiation to TVC, both in vitro and in vivo, showing that expression levels of these proteins, and nucleotides encoding same, can be used to determine the state of a solid tumor.

In another embodiment, the present invention provides a method of treating, suppressing, or inhibiting the growth of a solid tumor in a stage-specific manner. In one embodiment, a TVM of the present invention is upregulated specifically in stage I of ovarian cancer. In another embodiment, a TVM of the present invention is upregulated specifically in stage II of ovarian cancer. In another embodiment, a TVM of the present invention is upregulated specifically in stage III of ovarian cancer. In another embodiment, a TVM of the present invention is upregulated specifically in stage IV of ovarian cancer.

In one embodiment, Adlican is detected in serum and ascites of patients with stage III ovarian cancer, but not control subjects. Thus, TVM of the present invention are efficacious for detection of tumors, by detecting their presence in bodily fluids of a subject. In one embodiment, a secreted TVM of the present invention is used in the methods of the present invention. In another embodiment, a TVM of the present invention localized to the ECM is used in the methods of the present invention. Each possibility represents a separate embodiment of the present invention.

In one embodiment, the TVMs are present in a body fluid of a subject. In another embodiment, the presence of one or more TVMs in a body fluid is detected by ligands or antibodies that bind to said TVM or TVMs. "Presence in a body fluid" refers, in another embodiment, to a detectable presence. In another embodiment, the term refers to an amount that can be detected by a method used to for detection of proteins or antigens in body fluids. In another embodiment, the term refers to an amount that generates a signal over the background in a method used to for detection of proteins or antigens in body fluids. In another embodiment, the method is ELISA. In another embodiment, the method is Western blot. In another embodiment, the method is any other method known in the art. Each possibility represents a separate embodiment of the present invention.

Methods for isolation of vascular leukocytes (VLCs) are well known in the art, and are described, for example, in Conejo-Garcia, J. R., Buckanovich, R. J., Benencia, F., Courreges, M. C., Rubin, S. C., Carroll, R. G. & Coukos, G. (2005) Blood 105: 679-81. In another embodiment, "VLC" refers to VE-cadherin+CD146+CD45+ cells. In another embodiment, the term refers to human myeloid vascular cells with endothelial-like behavior.

In another embodiment, a VLC of the present invention is a precursor of a tumor endothelial cell (TEC) of the present invention. In another embodiment, a VLC of the present invention is a separate lineage from of a TEC of the present invention. In another embodiment, VLC of the present invention cooperate with TEC of the present invention in neo-vessel formation. Each possibility represents a separate embodiment of the present invention.

In another embodiment, a TVM of the present invention is expressed by pericytes, in addition to TVC. In another embodiment, the TVM is expressed by a subset of pericytes. In another embodiment, the TVM is not expressed on pericytes.

A TVC of the present invention is, in another embodiment, an endothelial cell. In another embodiment, the TVC is a perivascular cell. In another embodiment, the TVC derives from a myeloid DC. In another embodiment, the TVC derives from a myeloid monocytic precursor. Each possibility represents a separate embodiment of the present invention.

In one embodiment, methods of the present invention inhibit, treat, or suppress the growth of a tumor by targeting the vasculature supplying nutrients to the tumor, wherein the tumor vasculature particularly expresses the TVM used in the vaccine.

In one embodiment, the term "promoter" refers to a recognition site on a DNA strand to which the RNA polymerase binds. The promoter forms an initiation complex with RNA polymerase to initiate and drive transcriptional activity. The complex can be modified by activating sequences termed "enhancers" or inhibiting sequences termed "silencers".

In one embodiment, the term "cassette" refers to a nucleotide or gene sequence that is to be expressed from a vector. In general, a cassette comprises a gene sequence that can be inserted into a vector, which in some embodiments, provides regulatory sequences for expressing the nucleotide or gene sequence. In other embodiments, the nucleotide or gene sequence provides the regulatory sequences for its expression. In further embodiments, the vector provides some regulatory sequences and the nucleotide or gene sequence provides other regulatory sequences. For example, the vector can provide a promoter for transcribing the nucleotide or gene sequence and the nucleotide or gene sequence provides a transcription termination sequence. The regulatory sequences that can be provided by the vector include, but are not limited to, enhancers, transcription termination sequences, splice acceptor and donor sequences, introns, ribosome binding sequences, and poly(A) addition sequences. In one embodiment, the term "vector" refers to some means by which DNA fragments can be introduced into a host organism or host tissue. There are various types of vectors including plasmid, virus S (including adenovirus), bacteriophages and cosmids.

In one embodiment, a "fusion protein" refers to a protein having at least two polypeptides covalently linked in which one polypeptide comes from one protein sequence or domain and the other polypeptide comes from a second protein sequence or domain.

In one embodiment, the term "effective amount" means sufficient vaccine composition is introduced to produce the adequate levels of the polypeptide, so that an immune response results.

One skilled in the art recognizes that this level may vary.

In one embodiment, the term "first generation," as used in reference to adenoviral vectors, describes adenoviral vectors that are replication-defective. First generation adenovirus vectors typically have a deleted or inactivated E1 gene region, and preferably have a deleted or inactivated E3 gene region.

In one embodiment, the present invention provides a process for expressing a TEM-1 fusion protein in a recombinant host cell, comprising: (a) introducing a vector comprising a polynucleotide comprising a nucleic acid sequence encoding a tumor endothelial marker (TEM)-1 fusion protein, wherein said TEM-1 fusion protein comprises a TEM-1 protein or variant thereof, fused to a substantial portion of an immuno-enhancing element selected from the group consisting of: DOM, FcIgG, CT, LTA, and LTB, into a suitable host cell; and (b) culturing the host cell under conditions which allow expression of said human TEM-1 fusion protein.

In one embodiment, the present invention provides a method of treating, inhibiting, reducing the incidence of, and/or suppressing cancer comprising administering to a subject a vaccine vector comprising a nucleic acid sequence encoding a tumor endothelial marker (TEM)-1 fusion protein, wherein said TEM-1 fusion protein comprises a TEM-1 protein or variant thereof, fused to a substantial portion of an immuno-enhancing element selected from the group consisting of: DOM, FcIgG, CT, LTA, and LTB. In one embodiment, the subject is human. In one embodiment, the vector is an adenovirus vector or a plasmid vector. In one embodiment, the vector is an adenoviral vector comprising a substitution of the adenovirus E1 region with an expression cassette comprising: (a) a polynucleotide comprising sequence of nucleotides that encodes a TEM-1 fusion protein, wherein the TEM-1 fusion protein comprises a TEM-1 protein or variant thereof, fused to a substantial portion of an immuno-enhancing element selected from the group consisting of: DOM, FcIgG, CT, LTA, and LTB; and wherein the fusion protein is capable of producing an immune response in a subject; and (b) a promoter operably linked to the polynucleotide.

In another embodiment, the vector is a plasmid vaccine vector, which comprises a plasmid portion and an expressible cassette comprising (a) a polynucleotide comprising a sequence of nucleotides that encodes a TEM-1 fusion protein, wherein the TEM-1 fusion protein comprises a TEM-1 protein or variant thereof, fused to a substantial portion of an immuno-enhancing element selected from the group consisting of: DOM, FcIgG, CT, LTA, and LTB; and wherein the fusion protein is capable of producing an immune response in a subject; and (b) a promoter operably linked to the polynucleotide.

In one embodiment, the present invention provides a method of treating, inhibiting, reducing the incidence of, and/or suppressing cancer in a subject suffering from or predisposed to a TEM-1-associated cancer comprising administering to a subject a vaccine vector comprising the polynucleotidethat encodes a TEM-1 fusion protein, wherein the TEM-1 fusion protein comprises a TEM-1 protein or variant thereof, fused to a substantial portion of an immunoenhancing element selected from the group consisting of: DOM, FcIgG, CT, LTA, and LTB.

In one embodiment, the TVM of the present invention exhibit the advantage over tumor cell markers that TVC are genetically stable, relative to tumor cells; thus, TVC are much less likely to switch their expression of the TVM, thus evading localization, detection and therapeutic methods of the present invention. In another embodiment, the TVM of the present invention exhibit the advantage that tumor vasculature is significantly different than physiologic vasculature. In another embodiment, the TVM of the present invention exhibit the advantage over tumor cell markers that TVC are more accessible via the bloodstream, relative to tumor cells; thus, TVC are more accessible for localization, detection and anti-tumor therapy by methods of the present invention. In another embodiment, a ligand that binds a TVM of the present invention is administered to a subject via the bloodstream. In another embodiment, the TVM of the present invention exhibit the advantage over tumor cell markers that the TVM are expressed on early as well as late stage tumors. Each possibility represents a separate embodiment of the present invention.

In another embodiment, methods and compositions of the present invention utilize a chimeric molecule, comprising a fusion of a TVM protein with a tag polypeptide that provides an epitope to which an anti-tag antibody can selectively bind. The epitope tag is placed, in other embodiments, at the amino- or carboxyl-terminus of the protein or in an internal location therein.

The presence of such epitope-tagged forms of the TVM protein is detected, in another embodiment, using an antibody against the tag polypeptide. In another embodiment, inclusion of the epitope tag enables the recombinant TVM protein to be readily purified by affinity purification using an anti-tag antibody or another type of affinity matrix that binds to the epitope tag. Various tag polypeptides and their respective antibodies are known in the art. Examples include poly-histidine (poly-his) or poly-histidine-glycine (poly-his-gly) tags; the flu HA tag polypeptide and its antibody 12CA5 (Field et al., Mol. Cell. Biol., 8: 2159-2165 (1988)); the c-myc tag and the 8F9, 3C7, 6E10, G4, B7 and 9E10 antibodies thereto (Evan et al., Molecular and Cellular Biology, 5: 3610-3616 (1985)); and the Herpes Simplex virus glycoprotein D (gD) tag and its antibody (Paborsky et al., Protein Engineering, 3(6): 547-553 (1990)). Other tag polypeptides include the Flag-peptide (Hopp et al., BioTechnology, 6: 1204-1210 (1988)); the KT3 epitope peptide et al., Science, 255: 192-194 (1992)); a tubulin epitope peptide (Skinner et al., J. Biol. Chem., 266:15163-15166 (1991)); and the T7 gene 10 protein peptide tag (Lutz-Freyermuth et al., Proc. Natl. Acad. Sci. USA, 87: 6393-6397 (1990)). In another embodiment, the chimeric molecule comprises a fusion of the TVM protein with an immunoglobulin or a particular region of an immunoglobulin. Methods for constructing fusion proteins are well known in the art, and are described, for example, in LaRochelle et al., J. Cell Biol., 139(2): 357-66 (1995); Heidaran et al., FASEB J., 9(1): 140-5 (1995); Ashkenazi et al., Int. Rev. Immunol., 10(2-3): 219-27 (1993) and Cheon et al., PNAS USA, 91(3): 989-93 (1994).

"Contacting," in another embodiment, refers to directly contacting the target cell with a composition of the present invention. In another embodiment, "contacting" refers to indirectly contacting the target cell with a composition of the present invention. Each possibility represents a separate embodiment of the present invention. In another embodiment, the composition of the present invention is carried in the subjects' bloodstream to the target cell. In another embodiment, the composition is carried by diffusion to the target cell. In another embodiment, the composition is carried by active transport to the target cell. In another embodiment, the composition is administered to the subject in such a way that it directly contacts the target cell. Each possibility represents a separate embodiment of the present invention.

In one embodiment, the term "administering" refers to bringing a subject in contact with an active compound of the present invention. In another embodiment, administration is accomplished in vitro, i.e. in a test tube. In another embodiment, administration is accomplished in vivo, i.e. in cells or tissues of a living organism. Each possibility represents a separate embodiment of the present invention.

In one embodiment, the present invention provides a method for making a codon-optimized tumor endothelial marker (TEM)-1 comprising transforming a host cell with the vector comprising a polynucleotide encoding a codon-optimized tumor endothelial marker (TEM)-1 and culturing said cell under conditions in which TEM-1 is expressed.

In one embodiment, the present invention provides a human single chain variable fragment (scFv) recognizing a TVM. In another embodiment, said scFV is biotinylated. In one embodiment, the scFv is utilized in localizing TVM-expressing vasculature.

Pharmaceutical Compositions and Methods of Administration

Pharmaceutical compositions containing compositions of the present invention can be, in another embodiment, administered to a subject by any method known to a person skilled in the art, such as parenterally, paracancerally, transmucosally, transdermally, intramuscularly, intravenously, intradermally, subcutaneously, intra-peritonealy, intra-ventricularly, intra-cranially, intra-vaginally or intra-tumorally.

In another embodiment of methods and compositions of the present invention, the pharmaceutical compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In another embodiment of the present invention, the active ingredient is formulated in a capsule. In accordance with this embodiment, the compositions of the present invention comprise, in addition to the active compound and the inert carrier or diluent, a hard gelating capsule.

In another embodiment, the pharmaceutical compositions are administered by intravenous, intra-arterial, or intramuscular injection of a liquid preparation. Suitable liquid formulations include solutions, suspensions, dispersions, emulsions, oils and the like. In another embodiment, the pharmaceutical compositions are administered intravenously and are thus formulated in a form suitable for intravenous administration. In another embodiment, the pharmaceutical compositions are administered intra-arterially and are thus formulated in a form suitable for intraarterial administration. In another embodiment, the pharmaceutical compositions are administered intra-muscularly and are thus formulated in a form suitable for intra-muscular administration.

In another embodiment, the pharmaceutical compositions are administered topically to body surfaces and are thus formulated in a form suitable for topical administration. Suitable topical formulations include gels, ointments, creams, lotions, drops and the like. In another embodiment, for topical administration, the compositions are prepared and applied as solutions, suspensions, or emulsions in a physiologically acceptable diluent with or without a pharmaceutical carrier.

In another embodiment, the active compound is delivered in a vesicle, e.g. a liposome.

In other embodiments, carriers or diluents used in methods of the present invention include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In other embodiments, pharmaceutically acceptable carriers for liquid formulations are aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of animal, vegetable, or synthetic origin, for example, peanut oil, soybean oil, olive oil, sunflower oil, fish-liver oil, another marine oil, or a lipid from milk or eggs.

In another embodiment, parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of animal, vegetable, or synthetic origin, for example, peanut oil, soybean oil, olive oil, sunflower oil, fish-liver oil, another marine oil, or a lipid from milk or eggs.

In other embodiments, the compositions further comprises binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCI, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants. Each of the above excipients represents a separate embodiment of the present invention.

The compositions also include, in another embodiment, incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions influence, in another embodiment, the physical state, solubility, stability, rate of in vivo release, and rate of in vivo clearance.

The preparation of pharmaceutical compositions that contain an active component, for example by mixing, granulating, or tablet-forming processes, is well understood in the art. The active therapeutic ingredient is often mixed with excipients that are pharmaceutically acceptable and compatible with the active ingredient. For oral administration, the active agents are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. For parenteral administration, the active agents are converted into a solution, suspension, or emulsion, if desired with the substances customary and suitable for this purpose, for example, solubilizers or other substances.

Each of the above additives, excipients, formulations and methods of administration represents a separate embodiment of the present invention.

In one embodiment, the compositions of the present invention are administered, alone, while in another embodiment, they are administered in combination with other treatments for tumors that are known in the art. In one embodiment, the compositions of the present invention are administered one time, prior to the subject demonstrating a sign or symptom of the tumor. In another embodiment, the compositions of the present invention are administered one time, subsequent to the appearance of signs or symptoms of tumor or cancer in the subject. In another embodiment, the compositions of the present invention are administered to a subject at multiple times before, during, or after diagnosis of a subject with a tumor, or a combination thereof, which in one embodiment is referred to as boosting.

"Boosting" refers, in another embodiment, to administration of an additional vaccine dose to a subject. In another embodiment of methods of the present invention, 2 boosts (or a total of 3 inoculations) are administered. In another embodiment, 3 boosts are administered. In another embodiment, 4 boosts are administered. In another embodiment, 5 boosts are administered. In another embodiment, 6 boosts are administered. In another embodiment, more than 6 boosts are administered. Each possibility represents a separate embodiment of the present invention. In one embodiment, the interval between administrations is one week, in another embodiment, two weeks, in another embodiment, one month, in another embodiment, two months, in another embodiment, six months, in another embodiment, one year, in another embodiment two years, in another embodiment, five years, in another embodiment, ten years. In one embodiment, the interval is pre-determined, while in another embodiment, a boost is administered after testing of a subject for serological evidence of lack of immunity, which in one embodiment, is a seronegative test result, which in one embodiment, is a lack of antibodies against a TVM to which said subject had prior exposure or with which said subject had been vaccinated.

In one embodiment, the methods of the present invention comprise administering an active composition or compound of the present invention as the sole active ingredient. However, also encompassed within the scope of the present invention are methods for chemotherapy that comprise administering the active composition or compound in combination with one or more therapeutic agents (e.g. anti-tumor agents or cancer chemotherapy agents).

In one embodiment, the present invention envisions using DNA vaccination as a means of generating immunity against infectious agents or tumors, or altering immune responses to various immunological diseases. In one embodiment, DNA vaccination is used in conjunction with in vivo electroporation of plasmid DNA (DNA-EP), which in one embodiment, results in increased DNA uptake, in one embodiment, leading to enhanced protein expression in the injected muscle, and, in one embodiment, a concomitant increase in immune responses to the target antigen in a variety of species. In one embodiment, replication-defective recombinant Adenovirus (Ad) is used in conjunction with the vaccines and methods of the present invention. In one embodiment, adenovirus is safe and induces strong antibody and cellular antigen-specific immune responses. In one embodiment, the present invention combines heterologous immunization modalities, which in one embodiment elicits enhanced immune responses to a target antigen by vaccinating with different vectors encoding the same immunogen; in one embodiment, such a modality is vaccination regimens using DNA-EP and Ad vector, which in one embodiment, elicit significant immune responses and antitumor effect.

The amount of expressible DNA or transcribed RNA to be introduced into a vaccine recipient will depend partially on the strength of the promoters used and on the immunogenicity of the expressed gene product. In one embodiment, an immunologically or prophylactically effective dose of about 1 ng to 100 mg, and preferably about 10 mcg to 300 mcg of a plasmid vaccine vector is administered directly into muscle tissue. In one embodiment, an effective dose for recombinant adenovirus is approximately $10^6$-$10^{12}$ particles and preferably about $10^7$-$10^{11}$ particles.

The vaccine vectors of this invention may be naked, i.e., unassociated with any proteins, or other agents which impact on the recipient's immune system. In this case, it is desirable for the vaccine vectors to be in a physiologically acceptable solution, such as, but not limited to, sterile saline or sterile buffered saline. Alternatively, it may be advantageous to administer an agent which assists in the cellular uptake of DNA, such as, but not limited to calcium ion. These agents are generally referred to as transfection facilitating reagents and pharmaceutically acceptable carriers. Those of skill in the art will be able to detennine the particular reagent or pharmaceutically acceptable carrier as well as the appropriate time and mode of administration.

The following examples are presented in order to more fully illustrate the preferred embodiments of the invention. They should in no way be construed, however, as limiting the broad scope of the invention.

EXAMPLES

TVM of the present invention are enriched in the vasculature of a wide variety of tumor cells. Immunohistochemistry-guided laser-capture microdissection was used to identify genes that were differentially expressed between vascular cells from human epithelial ovarian cancer and healthy ovaries. Tumor vascular markers (TVMs) were validated through quantitative real-time polymerase chain reaction (qRT-PCR) of immunopurified tumor endothelial cells, in situ hybridization, immunohistochemistry, and Western blot analysis. TVM expression in tumors and noncancerous tissues was assessed by qRT-PCR and was profiled using gene expression data. A tumor vascular cell profile of ovarian cancer that was distinct from the vascular profile of normal ovary and other tumors was described. Twelve novel ovarian TVMs were validated. These were expressed by immunopurified tumor endothelial cells and localized to tumor vasculature. Select TVMs were found to be specifically expressed in ovarian cancer and were absent in all normal tissues tested, including female reproductive tissues with physiologic angiogenesis. Many ovarian TVMs were expressed by a variety of other solid tumors. These methods and results, as presented in WO 2007/089513 are incorporated herein by reference.

Example 1: Expression of TVMS in Control and Tumor Tissue

Plasmid Constructs pV1J/TEM-lopt and pV1J/TEM-1 carry the codon usage-optimized and wild-type cDNA of TEM-1, respectively. All constructs encoding TEM-1 fusion proteins were generated by fusing TEM-1 cDNA with the N-terminal domain of FrC (TEM-1-DOM). DOMcoding sequences were obtained by polymerase chain reaction (PCR) amplification from pRep-TeT.C plasmid as described (Rice et al., 2002. Constructs were amplified with the following primers:

```
DOM-s:
                                        (SEQ ID NO: 48)
5'-TATTCTAGATTCAACACCAATTCCATTTTCTTATTC-3'

DOM-a:
                                        (SEQ ID NO: 49)
5'-TTAGCGGCCGCTAGTTCTGTATCATATCGTAAAGGG-3'
```

The amplified DNA was introduced at the 3' end of the TEM-1 coding sequence, generating plasmid pV1J/TEM-1-DOM.

The codon usage-optimized cDNAs of DOM was synthesized by oligonucleotide assembly (GENEART, Regensburg, Germany) and cloned in PCR-Script vector (Stratagene, La Jolla, Calif.). To generate pV1J/TEM-1-DOMopt, DOMopt was amplified by PCR with primers DOMopt-s (5'-GTTATCTAGAAGCACCCCCATCCC-3') (SEQ ID NO: 50) and DOMopt-a (5'-TTAAGATCTCTAA-GATCTGGTGTCGTATCTCAGGGG-3') (SEQ ID NO: 51). The amplified product was then inserted into the XbaI/BglII sites of plasmid pV1J/TEM-lopt.

Adenoviral Vectors

Ad/TEM-lopt and Ad/TEM-1 carry the codon usage-optimized and wild-type cDNA of TEM-1, respectively. Vectors were constructed as described previously (Mennuni et al., 2005).

Detection of TEM-1 Expression

To monitor TEM-1 expression, HeLa cells were either transfected with the indicated plasmid or infected with the selected Ad vector. After 48 hr of incubation, whole cell lysates and culture supernatant were harvested. The TEM-1 fusion protein present in the cell lysates was detected by Western blot analysis, using a specific antibody for TEM-1 and tetanus toxin. TEM-1 expression in cell lysate or supernatant was also monitored by enzyme-linked immunosorbent assay (ELISA) (Mennuni et al., 2005).

Peptides

Lyophilized TEM-1 peptides were purchased and resuspended in dimethyl sulfoxide (DMSO) at 40 mg/ml. Pools of 15-amino acid peptides overlapping by 11 residues were assembled as described (Facciabene et al., 2004). The final concentration of peptides in pool D was 0.8 mg/ml. Immune response to DOM was monitored with peptide p30 (F947NNFTVSFWLRVPKVSASHLE967) (SEQ ID NO: 58) (Rice et al., 2001).

Mouse Immunization and Tumor Challenge

All animal studies were approved by the institutional animal care and use committee. Female C57BL/6 mice were purchased from Charles River. C57BL/6 mice were subjected to two DNA injections in the quadriceps muscle followed by electrical stimulation as described (Rizzuto et al., 1999). Injections were carried out at 3-week intervals. Two weeks after the last injection, antibody and cell-mediated immune responses were analyzed. Mice were also challenged with a subcutaneous injection of $5\times10^5$ TEM-1-expressing cells. At weekly intervals, mice were examined for tumor growth.

Figure 1B:
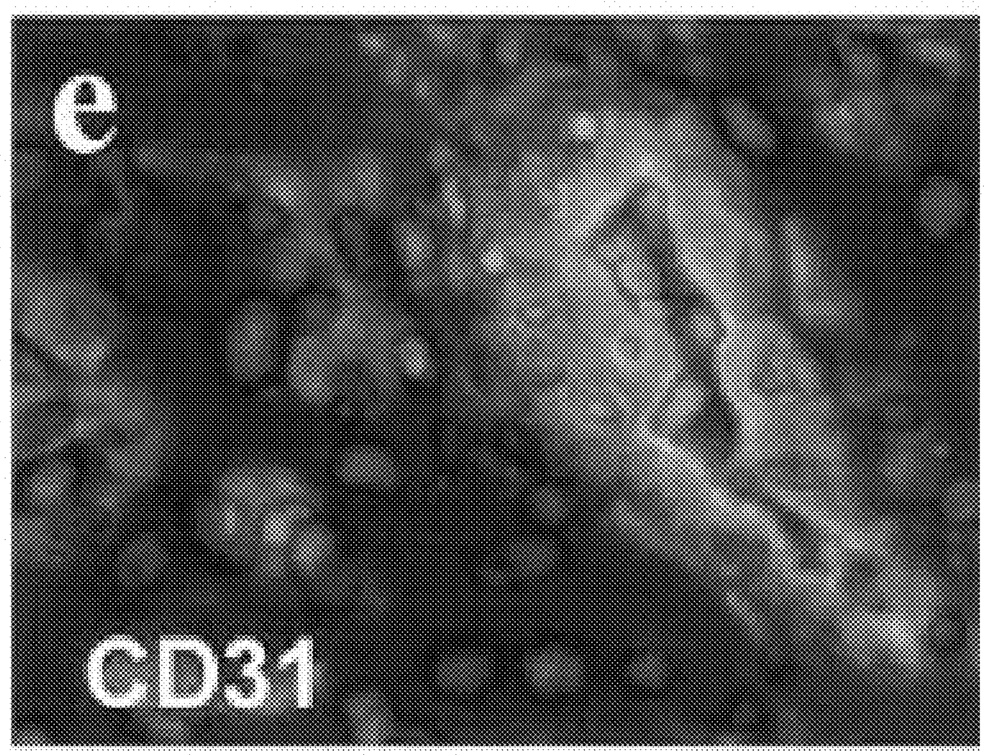
FIG. 1B, Published expression of TEM1 (green) in relation to CD31 (red) in GBM vasculature (from Brady et al. *J Neuropathol Exp Neurol* 2004, 63:1274, incorporated herein by reference).

Tumor endothelial markers (TEMs) are proteins with transmembrane domains recognized as robust tumor vascular-specific markers in the human and the mouse. TEM1 (endosialin, CD284), an 80.9 kD protein, is specifically expressed in tumor vasculature (FIG. 1) and is absent in normal blood vessels and other adult tissues using the MORAb-004 antibody (Morphotek, Exton, Pa.), a humanized monoclonal antibody (Ab) specific to the TEM1 extracellular domain TEM1 is also expressed by tumor fibroblasts. TEM1 is highly expressed by glioblastoma multiforme (GBM), where it localizes strongly to the endothelium of small and large vessels undergoing angiogenesis (FIG. 1), but is absent in normal brain vessels. It also localizes to pericytes, which are thought to contribute to angiogenesis. High expression of TEM1 was found in most GBMs and no expression in normal tissues (data not shown) using in silico analysis of recent public Affymetrix array data from approximately 100 GBMs and 44 tissues of 10 normal human donors (GSE3526; GEO, NCBI), using methods as described hereinabove.

Figure 2A:
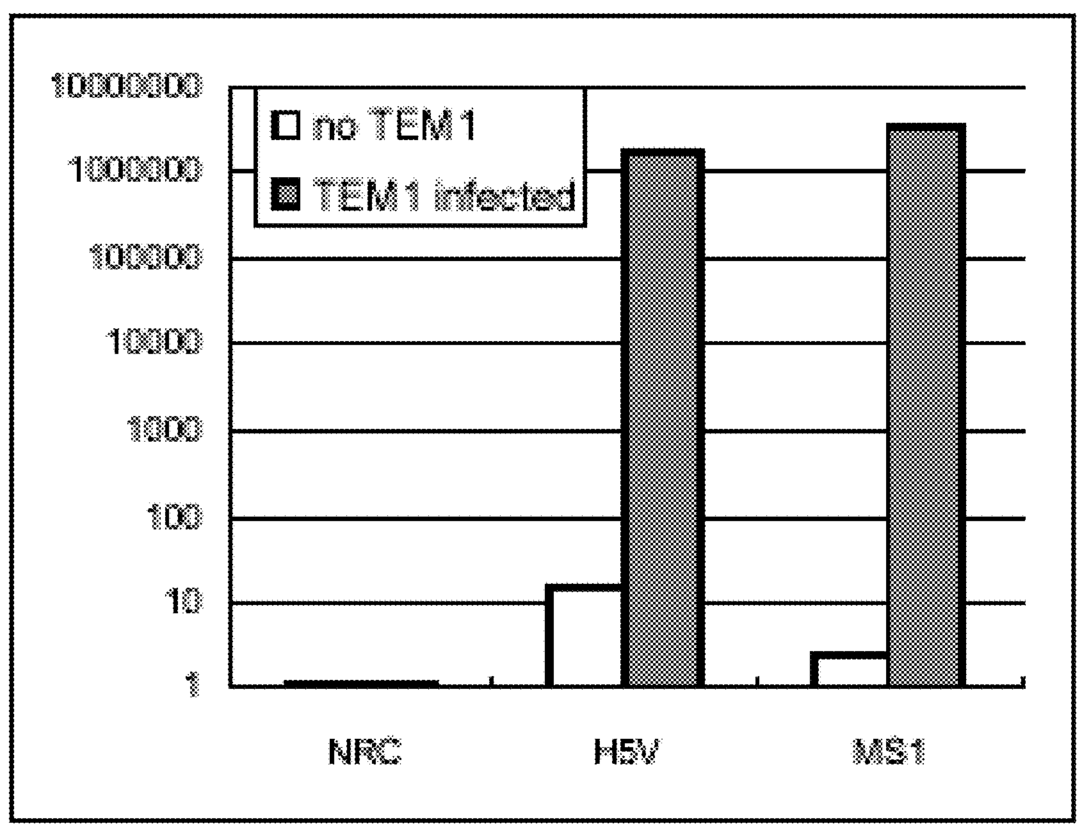
FIG. 2A. Real time PCR analysis.
Figure 2B:
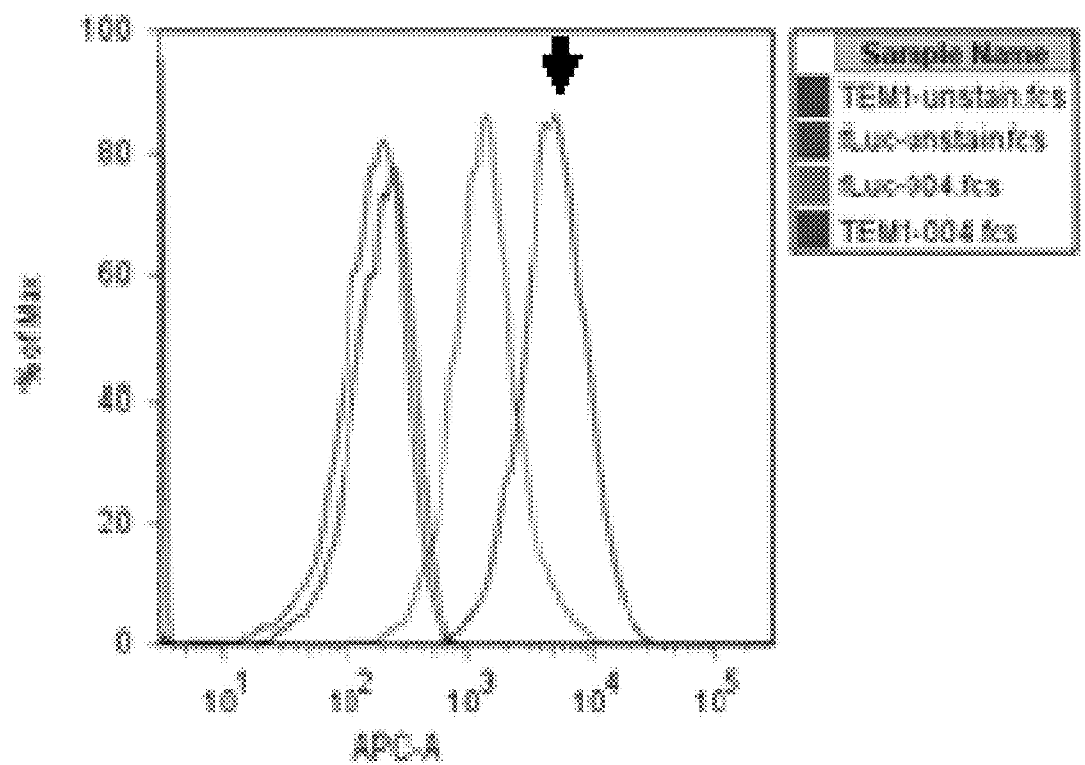
FIG. 2B. Surface expression of hTEM1 is shown by flow cytometry in MS1 cells (arrow).
Figures 3A, 3B, 3C:
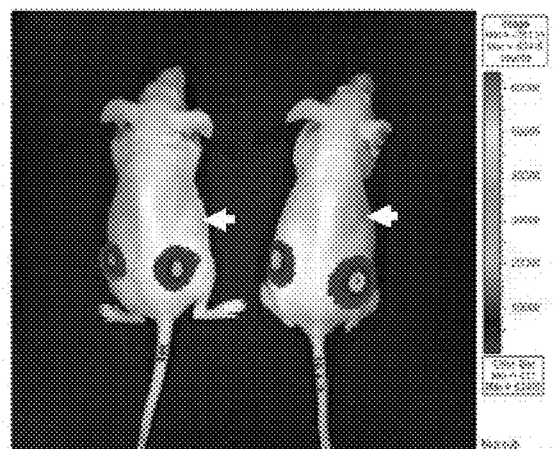
FIG. 3A. Expression of TEM1+ vascular grafts in the mouse. MS1 cells transduced with fLuc and human TEM1 were admixed with ID8 cells and implanted in flanks of Swiss nude mice. Chemiluminescent imaging was carried out following injection i.p. with 100 mc/of 30 mg/ml D-luciferin (Xenogen, Alameda, Calif.). Table (FIG. 3B) indicates the experimental conditions and cartoon (FIG. 3C) depicts the experimental design. Each mouse was inoculated with (1) ID8 tumor cells mixed with MS1 cells transduced with human fLuc only; (2) ID8 tumor cells mixed with MS1 cells transduced with human fLuc and human TEM1; and (3) non-transduced ID8 cells.
Figure 4A:
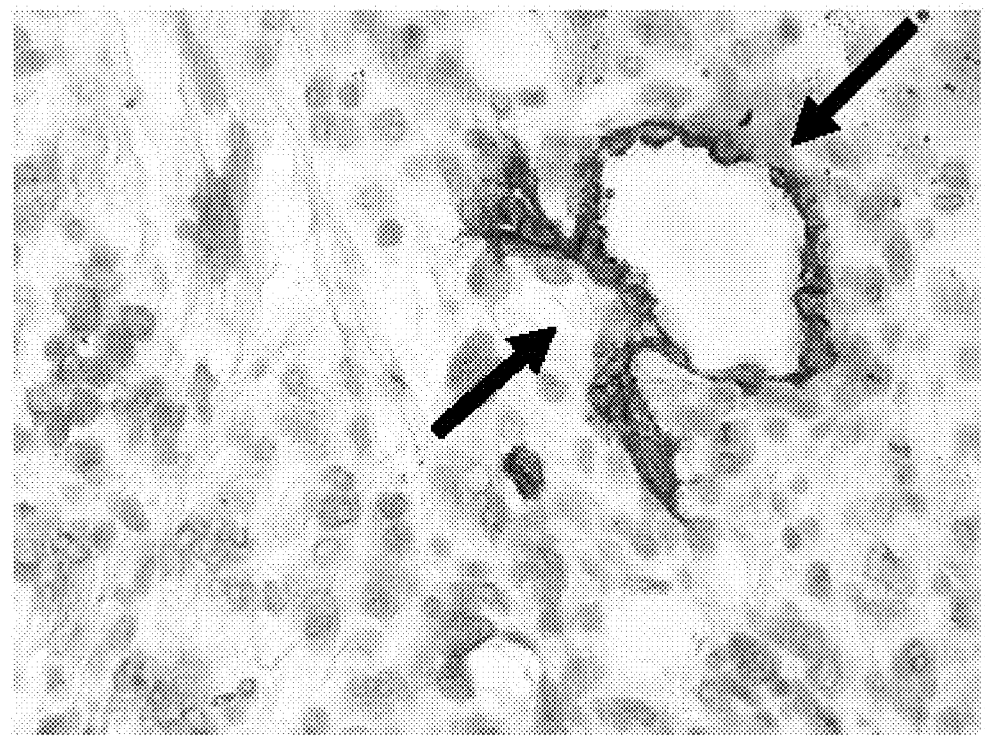
FIG. 4A, Human TEM1 expression in tumor vasculature in the mouse model from FIG. 3 (Tumor 2). Immunohistochemistry was performed using MORAb-004. hTEM1 resembles expression of TEM1 in human ovarian cancer and GBM vasculature (FIG. 1).
Figure 4B:
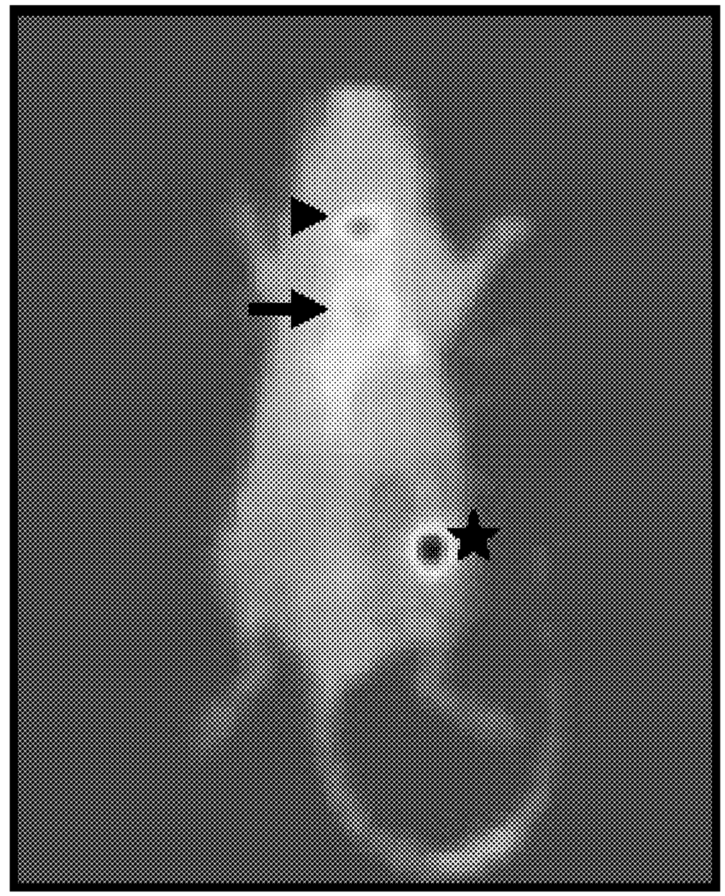
FIG. 4B, PET imaging of one mouse shown in FIG. 3. Two weeks after tumor inoculation, mice were injected with $^{124}$I-labeled MORAb-004. Mice were imaged after 16 hours using PET scan technology. Arrowhead indicates free iodine radioisotope trapped in the thyroid. Arrow shows circulating MORAb-004 in the blood pool (heart). The star indicates the site of the tumor where MORAb-004 accumulated specifically (Tumor 2). This was the tumor expressing hTEM1 shown in FIG. 4A. Note no staining of tumors that are enriched with control MS1 cells which do not express hTEM1 (Tumor 1) or of plain ID8 tumors (Tumor 3).

Example 2: Development of a Mouse Model of Tumor Endothelium Expressing Human (h) TEM1 In Vivo Murine immortalized endothelial cells MS1 and HSV, both from C57BL/6 mouse background, were transduced with hTEM1 and firefly luciferase (fLuc) using lentivirus vectors (FIG. 2). Successful subcutaneous angiosarcoma grafts were established in nude mice using fLucpos HSV. MS1 cells also establish angioma grafts with slow kinetics, which persisted for up to 24 weeks. Furthermore, as can be seen in FIG. 3, hTEM1+fLucpos MS1 cells admixed with ID8 tumor cells establish fLucpos tumors in the hips of nude mice. Immunohistochemistry against hTEM1 using MORAb-004 demonstrated clear expression of hTEM1 on the vasculature in tumors enriched with hTEM1+MS1 cells (FIG. 4) but not in tumors enriched with hTEM1-MS1 cells. This model allows for testing of human grade tools in vivo in mice.

Example 3: Pet Targeting of TVM Using TVM-Specific Antibody

MORAb-004 was labeled with iodine-124, a positron emitter with an ideal half-life of 4 days. PET studies with [$^{124}$I]-labeled antibody demonstrated successful direct attachment of iodine-124 to antibody, with retention of immunobiologic characteristics after labeling, as well as specific targeting of tumors expressing hTEM-1 in the above animal model (FIG. 3). Furthermore, titration studies to evaluate the minimum number of endothelial cells that can be detected by TEM1 PET, showed that two weeks after tumor injection, TEM1 PET can detect tumors that originally contained 5,000 hTEM1+MS1 cells (data not shown).

These experiments indicate that MORAb-004 binds to tumor vasculature expressing TEM1 in vivo, where it effectively delivers radiotracers in a very sensitive and specific manner.

In one embodiment, a phase I clinical study of TEM1 PET imaging in solid tumors is being conducted using the radio-labelled MORAD-004 described hereinabove.

In another embodiment, MORAb-008 (Morphotek), a novel monoclonal antibody recognizing mouse Tem1 is used in the studies described herein.

Example 4: Tumor Vasculature Marker Vaccines Protect Against Tumor Growth

Cell Lines

The C57BL/6 syngeneic TC-1 tumor was immortalized and transformed with the c-Ha-ras oncogene and transformed with TEM-1. TC-1 expresses low levels of TEM-1 and is highly tumorigenic. TC-1 was grown in RPMI 1640, 10% FCS, 2 mM L-glutamine, 100 U/ml penicillin, 100 μg/ml streptomycin, 100 μM nonessential amino acids, 1 mM sodium pyruvate, 50 micromolar (mcM) 2-ME, 400 microgram (mcg)/ml G418, and 10% National Collection Type Culture-109 medium at 37° with 10% $CO_2$.

Western Blotting

Bacterial strains were grown in Luria-Bertoni medium at 37° C. and were harvested at the same optical density measured at 600 nm. The supernatants were TCA precipitated and resuspended in 1× sample buffer supplemented with 0.1 N NaOH. Identical amounts of each cell pellet or each TCA-precipitated supernatant were loaded on 4-20% Tris-glycine SDS-PAGE gels (NOVEX, San Diego, Calif.). The gels were transferred to polyvinylidene difluoride and probed with an MORAb-004, then incubated with HRP-conjugated anti-mouse secondary Ab (Amersham Pharmacia Biotech, Little Chalfont, U.K.), developed with Amersham ECL detection reagents, and exposed to Hyperfilm (Amersham Pharmacia Biotech).

Measurement of Tumor Growth

Tumors were measured every other day with calipers spanning the shortest and longest surface diameters. The mean of these two measurements was plotted as the mean tumor diameter in millimeters against various time points. Mice were sacrificed when the tumor diameter reached 20 mm. Tumor measurements for each time point are shown only for surviving mice.

Effects of TEM-1 on Established Tumor Growth

Six- to 8-wk-old C57BL/6 mice (Charles River) received $2\times10^5$ TC-1 cells s.c. on the left flank. One week following tumor inoculation, the tumors had reached a palpable size of 4-5 mm in diameter. Groups of 8 mice were then treated i.p. with TEM-1, TEM-1-DOM, or saline on days 7 and 14.

Statistics

For comparisons of tumor diameters, mean and SD of tumor size for each group were determined, and statistical significance was determined by Student's t test. $p<0.05$ was considered significant.

Besides being a marker of tumor vasculature, TVMs such as TEM1 appear to be required for tumor angiogenesis. In human GBM, TEM1 is expressed specifically in vessels undergoing angiogenesis. Its recent role in endothelial cell adhesion to fibronectin and migration supports an important role in tumor angiogenesis. In fact, Tem1−/− mice are healthy, and exhibit normal wound healing, but they present a striking reduction in tumor growth and metastasis. Recent experiments showed that Tem1 mRNA was absent in all normal mouse tissues and sharply upregulated in tumor tissue.

Figure 5:
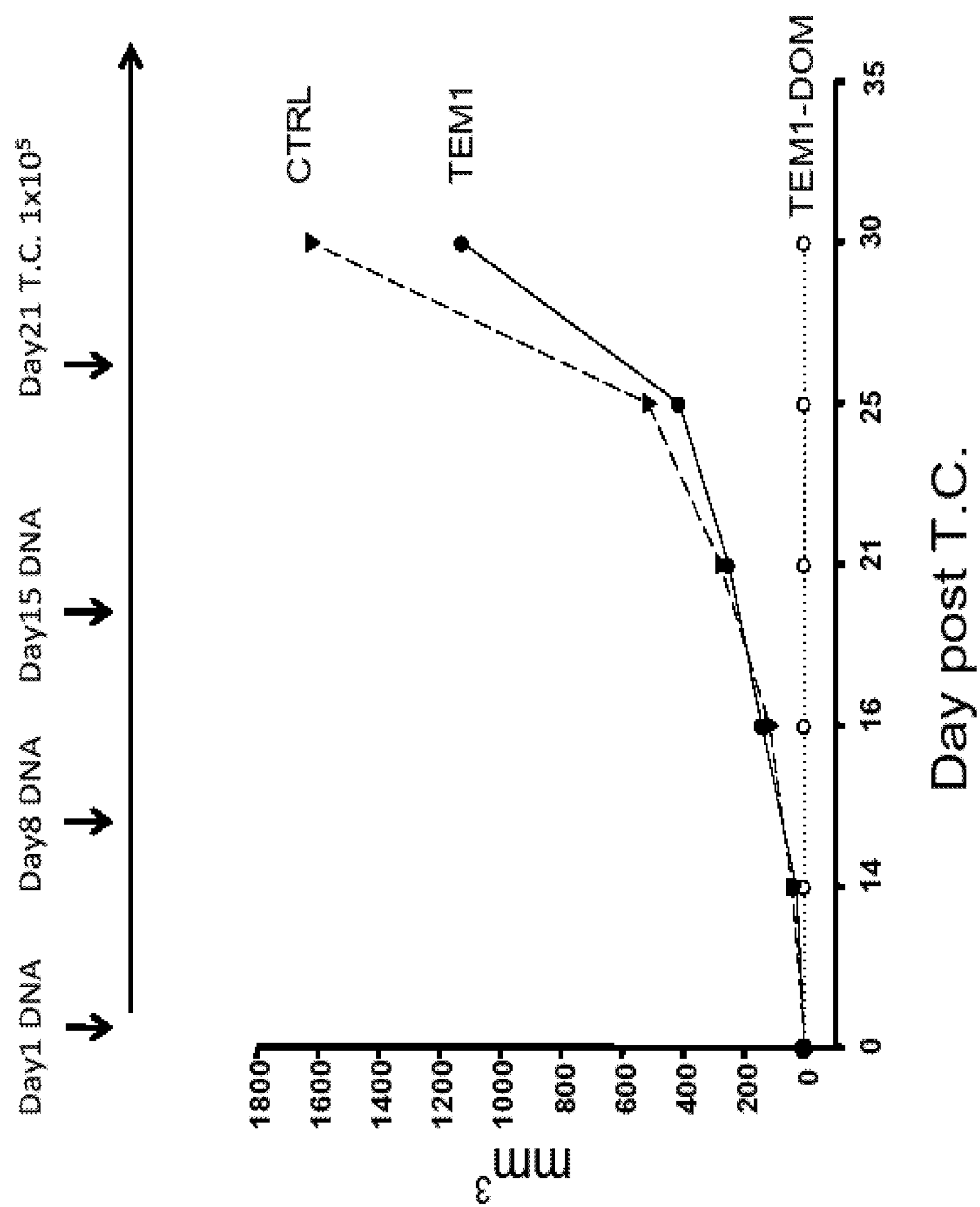
FIG. 5. Tem1 vaccination protects mice from TC-1 tumors. Top, Experimental design; Bottom, Growth curves of TC-1 tumors grown in mice vaccinated with irrelevant DNA (control); DNA vaccine comprising the full cDNA sequence of mouse Tem1 (TEM1) or DNA vaccine comprising the full cDNA sequence of mouse Tem1 fused with DOM (TEM1-DOM).

DNA constructs (Tem1-DOM) fusing the full codon-optimized murine Tem1 sequence with the minimal domain of fragment C of tetanus toxoid, DOM, which comprises two very powerful universal CD4 epitopes, P2 and P30, able to interact with many different MHC class II alleles were constructed. Mice were first vaccinated with Tem1-DOM and then injected sc so they developed TC-1 flank tumors, which express high levels of Tem1 (~1000 fold higher than background in normal murine tissues by real time PCR. As shown in FIG. 5, naïve mice vaccinated with control DNA constructs grew tumors rapidly, while mice vaccinated with Tem1-DOM DNA were 100% protected against tumor growth. Thus, the TVM-based vaccines prevent the growth of tumors whose vasculature expresses TEM1.

Example 5: Tumor Vasculature Marker Vaccines $^{51}$Cr Release Assay

C57BL/6 mice, 6-8 wk old, were immunized i.p. with TEM-1, TEM-1-DOM, or saline. Ten days post-immunization, spleens are harvested. Splenocytes are established in culture with irradiated TC-1 cells (100:1, splenocytes:TC-1) as feeder cells; stimulated in vitro for 5 days, then used in a standard $^{51}$Cr release assay. E:T cell ratios, performed in triplicate, are 80:1, 40:1, 20:1, 10:1, 5:1, and 2.5:1. Following a 4-h incubation at 37° C., cells are pelleted, and 50 μl supernatant is removed from each well. Samples are assayed with a Wallac 1450 scintillation counter (Gaithersburg, Md.). The percent specific lysis determined as [(experimental counts per minute−spontaneous counts per minute)/(total counts per minute−spontaneous counts per minute)]×100.

TC-1-Specific Proliferation

C57BL/6 mice are immunized with TVM and boosted by i.p. injection 20 days later with TVM, TVM-DOM, or control construct. Six days after boosting, spleens are harvested from immunized and naive mice. Splenocytes are established in culture at $5\times10^5$/well in flat-bottom 96-well plates with $2.5\times10^4$, $1.25\times10^4$, $6\times10^3$, or $3\times10^3$ irradiated TC-1 cells/well as a source of TVM Ag, or without TC-1 cells or with 10 μg/ml Con A. Cells are pulsed 45 h later with 0.5 [$^3$H]thymidine/well. Plates are harvested 18 h later using a Tomtec harvester 96 (Orange, Conn.), and proliferation assessed with a Wallac 1450 scintillation counter. The change in counts per minute is calculated as experimental counts per minute—no Ag counts per minute.

Flow Cytometric Analysis

C57BL/6 mice are immunized intravenously (i.v.) with TVM and boosted 30 days later. Three-color flow cytometry for CD8 (53-6.7, PE conjugated), CD62 ligand (CD62L; MEL-14, APC conjugated), and TVM H-2Db tetramer was performed using a FACSCalibur® flow cytometer with CellQuest® software (Becton Dickinson, Mountain View, Calif.). Splenocytes harvested 5 days after the boost are stained at room temperature (rt) with H-2Db tetramers loaded with a TVM peptide or a control peptide. Tetramers are used at a 1/200 dilution. Tetramer$^+$, CD8$^+$, CD62L$^{low}$ cells were analyzed.

Depletion of Specific Immune Components

CD8$^+$ cells, CD4$^+$ cells and IFN are depleted in TC-1-bearing mice by injecting the mice with 0.5 mg per mouse of mAb: 2.43, GK1.5, or xmg1.2, respectively, on days 6, 7, 8, 10, 12, and 14 post-tumor challenge. CD4$^4$ and CD8$^4$ cell populations are reduced by 99% (flow cytometric analysis). CD25$^+$ cells are depleted by i.p. injection of 0.5 mg/mouse anti-CD25 mAb (PC61, provided by Andrew J. Caton) on days 4 and 6. TGF is depleted by i.p. injection of the anti-TGF-mAb (2G7), into TC-1-bearing mice on days 6, 7, 8, 10, 12, 14, 16, 18, and 20.

Adoptive Transfer

Donor C57BL/6 mice are immunized and boosted 7 days later with the TVM construct or control. The donor splenocytes are harvested and passed over nylon wool columns to enrich for T cells. $CD8^+$ T cells are depleted in vitro by incubating with 0.1 μg 2.43 anti-CD8 mAb for 30 min at rt. The labeled cells are then treated with rabbit complement. The donor splenocytes are >60% $CD4^+$ T cells (flow cytometric analysis). TC-1 tumor-bearing recipient mice are immunized 7 days post-tumor challenge. $CD4^+$-enriched donor splenocytes ($10^7$) are transferred 9 days after tumor challenge to recipient mice by i.v. injection.

Example 6: Development of Tem1 Pet and Radio-Immunotherapy for Glioblastoma Multiforme (GBM)

GBM presents special challenges for PET imaging because signals are attenuated by the skull. to optimize the specific activity of [$^{124}$I]-antibody, linkers, which attach the radiohalide to the antibody such as MORAb-004 in a stable manner, allowing large amounts of radioactivity to be attached to the protein, are used. Thus, linkers optimize detection (when positron emitters such as iodine-124 are used) or therapy (when alpha emitters such as astatine-211 are used). The humanized tumor endothelium xenograft model is adapted to an orthotopic intracranial GBM model. Human GBM cell lines are screened to select those that permit optimal chimeric xenografts with $hTEM1^+$ MS1 endothelial cells using stereotactically injected intracranial xenograft models and brain imaging. A syngeneic mouse model of GBM, GL26, is used to develop a full portfolio of TEM1 expressing models for these studies. Based on the similarities of this model with human GBM, these tumors are expected to spontaneously express mouse (m)Tem1 on the tumor endothelium. If they do not, GL26 cells will be co-injected together with 2H11 cells which express constitutively murine (m)Tem1. Tumors injected without mouse endothelial cells or with the immortalized murine endothelial line MS1 or HSV, which do not constitutively express mouse Tem1 will be used as controls. PET studies will be conducted in GBM models as described hereinabove. In parallel, magnetic resonance imaging and 18F-deoxyglucose (FDG) PET will be conducted, to compare TEM1-based imaging to conventional imaging modalities. Our studies will be designed to test the two hypotheses as we have previously done for ovarian cancer: 1) TEM1 PET can specifically detect orthotopic GBM expressing TEM1; and 2) it can detect it earlier than conventional FDG PET or MRI.

Radio-immunotherapy (RIT) represents a major advancement for treating tumors as it can kill radiosensitive tumor cells but spare the surrounding normal tissue. To date, RIT attempts have targeted tumor cell epitopes. Perfusion of radiolabelled Abs in the extravascular space of brain tumors such as GBM may be severely limited because of the blood brain barrier (BBB). However, in the present invention, the target is mainly vascular and can readily be reached by the radio-Ab as shown by PET study. Binding of radiolabeled antibody to TEM1 causes selective, efficient and localized destruction of the tumor vasculature, resulting in thrombosis at the tumor bed and tumor necrosis. TEM1-directed radiotherapy also delivers direct radiation to the surrounding tumor cells, at a depth depending on their energy. Viable tumor cells located as far as 100 mcm from vasculature, a depth optimally targeted by alpha-emitting astatine-211, are targeted using this method. Thus, the present invention provides a highly versatile, selective and powerful tool targeting cancer vasculature that makes a seamless transition between diagnosis and therapy.

Astatine-211 is a halide that decays by alpha emission, permitting delivery of lethal radiation to tumor vasculature and perivascular tumor cells over a few cell diameters, without significant radiation delivered to normal cells. Production of astatine-211 is optimized in the 30 MeV cyclotron at University of Pennsylvania and attached in a stable manner to antibodies utilizing linkers (Dr Zalutsky), allowing for the production of a large number of clinic-grade radiometals with therapeutic potential. Among other available nuclides that may be suitable for GBM therapy are: bismuth-213 (alpha emitter, 46 minute half-life, generator-produced); copper-67 (beta-emitter, 62 hour half-life), lutetium-177 (beta emitter, 6 day half-life) as well as alpha emitters like radium-223 and beta-emitters including yttrium-90. MORAb-004 as well as MORAb-008 recognizing mTem1 are labeled with astatine-211 to demonstrate the safety and therapeutic efficacy in the animal models of GBM described hereinabove. Clinical endpoints include survival and tumor imaging by MRI and FDG PET. Morphologic evaluation of the vasculature in $TEM1^+$ and TEM1-tumors are assessed by phase microscopy, which are immunostained for mouse CD31 and tissue factor, a marker of early endothelial damage in vivo. Tumors are evaluated for apoptosis by in situ TUNEL assay and necrosis by H&E morphology and HMGB-1 immunostaining (necrosis). Systemic toxicity is assessed by examinination of all organs for thrombosis and tissue necrosis.

Example 7: Development of Additional Antibodies Against GBM Vasculature

A large scale data mining effort has been performed to assess the expression of tumor vascular markers (TVM), recently identified in the Coukos lab, in 44 normal tissues and 1,300 tumors using data from the Gene Expression Omnibus (# GSE3526 and # GSE2109, GEO, NCBI). TVM that appear highly specific for tumor vasculature and suitable for therapy applications have been selected. Recent public Affymetrix array data from approximately 100 GBMs has been analyzed as well. Many GBMs expressed four novel TVM: FZD10; ADAM12; CDCP1; and EGFL6, along with three other TVM: TEM-7; TEM-7R; and TEM-8. Human scFv recognizing both human and mouse TVM are isolated.

A novel yeast expression system, which permits the secretion of biotinylated scFv (biobodies) and the high throughput sorting of high-affinity antigen-specific scFv has been developed. In vivo biotinylation occurs through a biotin ligase expressed in the secreting pathway of diploid yeast, resulting from the mating of scFv-secreting haploid with biotin-ligase bearing haploid yeast. Biobodies form tetramers in presence of streptavidin which significantly increases their affinity (nM range). Biobodies against ovarian cancer-associated antigens have been generated and used for in vitro functional assays, serodiagnostic and as a discovery platform.

To isolate scFv recognizing both human and mouse TVM, recombinant mouse and human TVM proteins produced by different expression systems and expressing various tags (biotin, GST or His6), as well as established cell lines (CHO K1, COS7, 293T, Jurkat T) expressing TVM of interest will be used. The selection strategy includes several positive selections using gradually decreasing protein concentrations to select cross-reactive scFv of high affinity. To minimize nonspecific binding, positively selected scFv that also bind to HUVEC cell lines and control cell lines transduced with empty expression vector are depleted. Selected yeast-display scFv are then transformed into biobodies and used to screen CHO K1, COS7, 293T and Jurkat cells expressing the same tumor vascular marker. Using several cell lines sharing the TVM enhances the specificity of panning Finally, identified scFv are validated in vitro for affinity and specificity of binding to cancer vasculature. Validated scFv are grafted in an Ig frame for radiolabeling. New high affinity reagents against at least five TVM for in vivo use are identified and validated. 30 to 50% of the anti-TVM scFv are validated as biobodies for native TVM recognition, while at least half of them have to be matured by random mutagenesis to achieve the high level of affinity necessary for in vivo applications.

Figure 6:
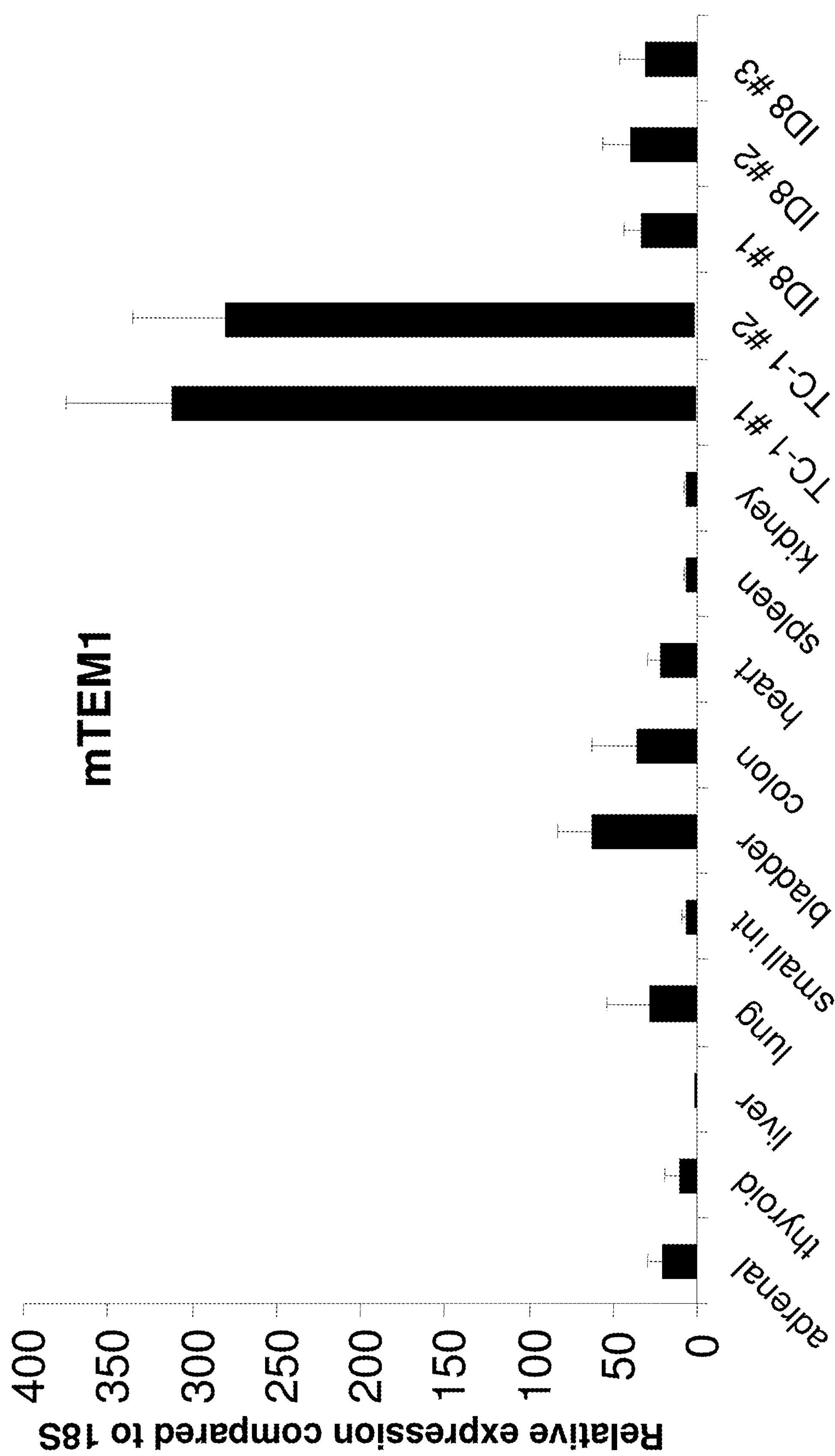
FIG. 6. TEM expression is elevated in TC1 and ID8 tumors as indicated by comparing the expression pattern to normal tissue.
Figure 7:
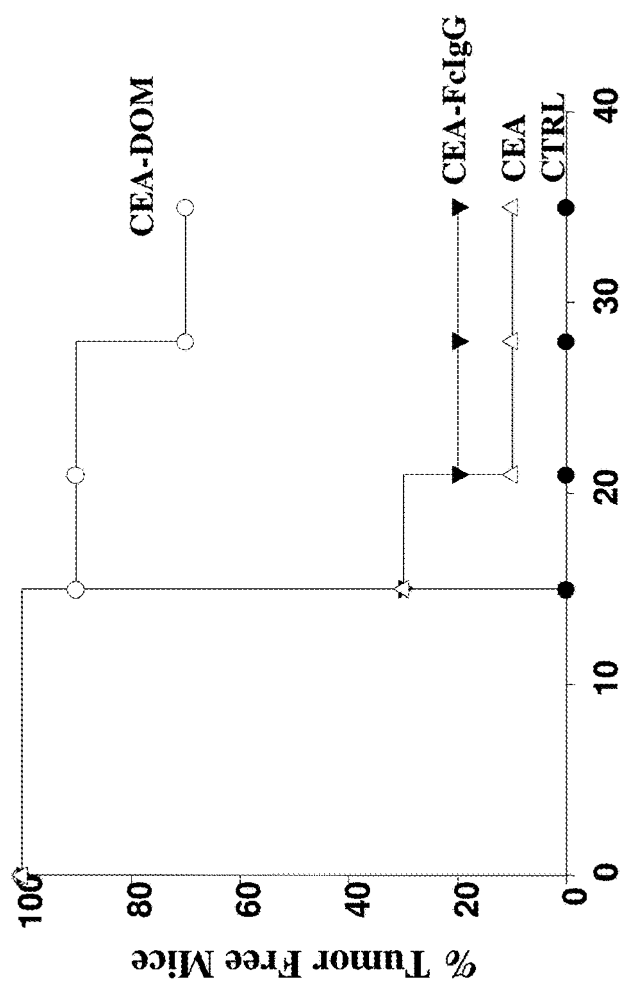
FIG. 7. Screening of various tumor associated antigen-immunoenhancing fusion DNA vaccine led to identification of the best immunoenhancing sequence, the minimized domain of tetanus toxin fragment C (DOM).
Figure 7:
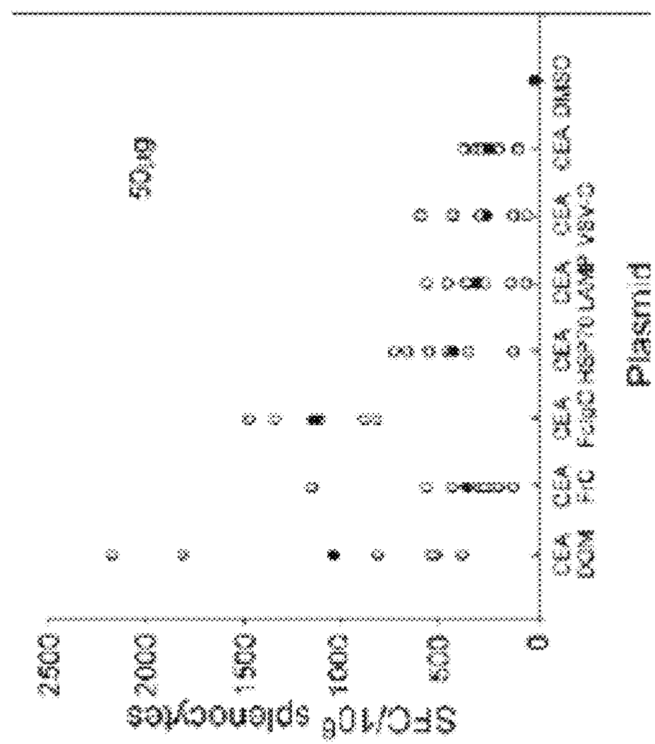

Example 8: Tem1 mRNA Expression Pattern in Normal Organs/Tissues or ID8 and TC1 Tumors TEM1 demonstrated a specific tumor expression pattern since mTEM1 mRNA expression is higher in ID8 and TC1 tumors where expression of the marker was particularly high in TC1 tumors (FIG. 6).

Example 9: Tem1-pDOM Codon Optimized DNA Plasmid Map

Figure 9:
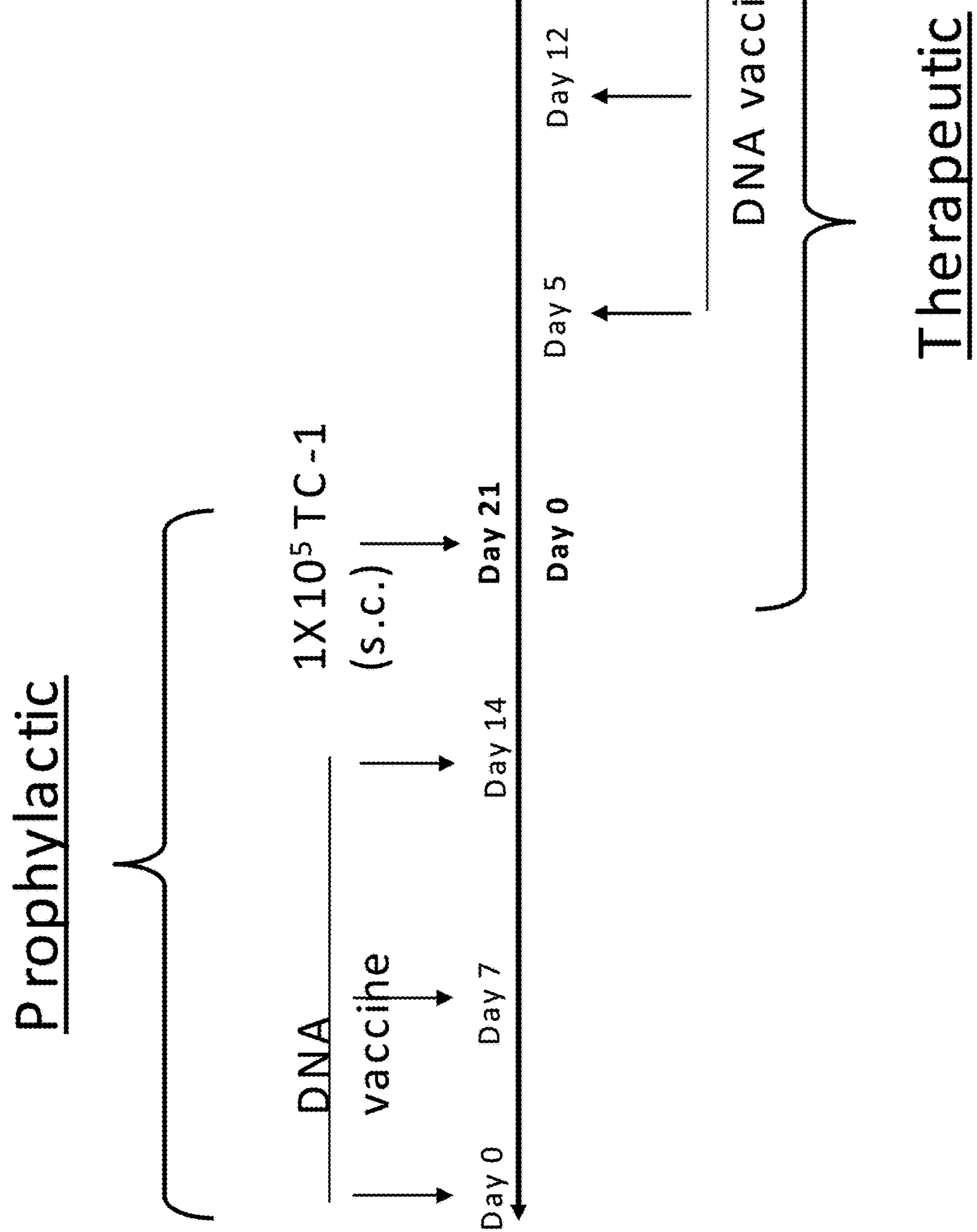
FIG. 9. For prophylactic treatment a DNA vaccine is administered early on on days 0, with boosters on days 7 and 14. For therapeutic purposes a DNA vaccine is administered on days 5, with boosters on days 12 and 19.
Figure 10:
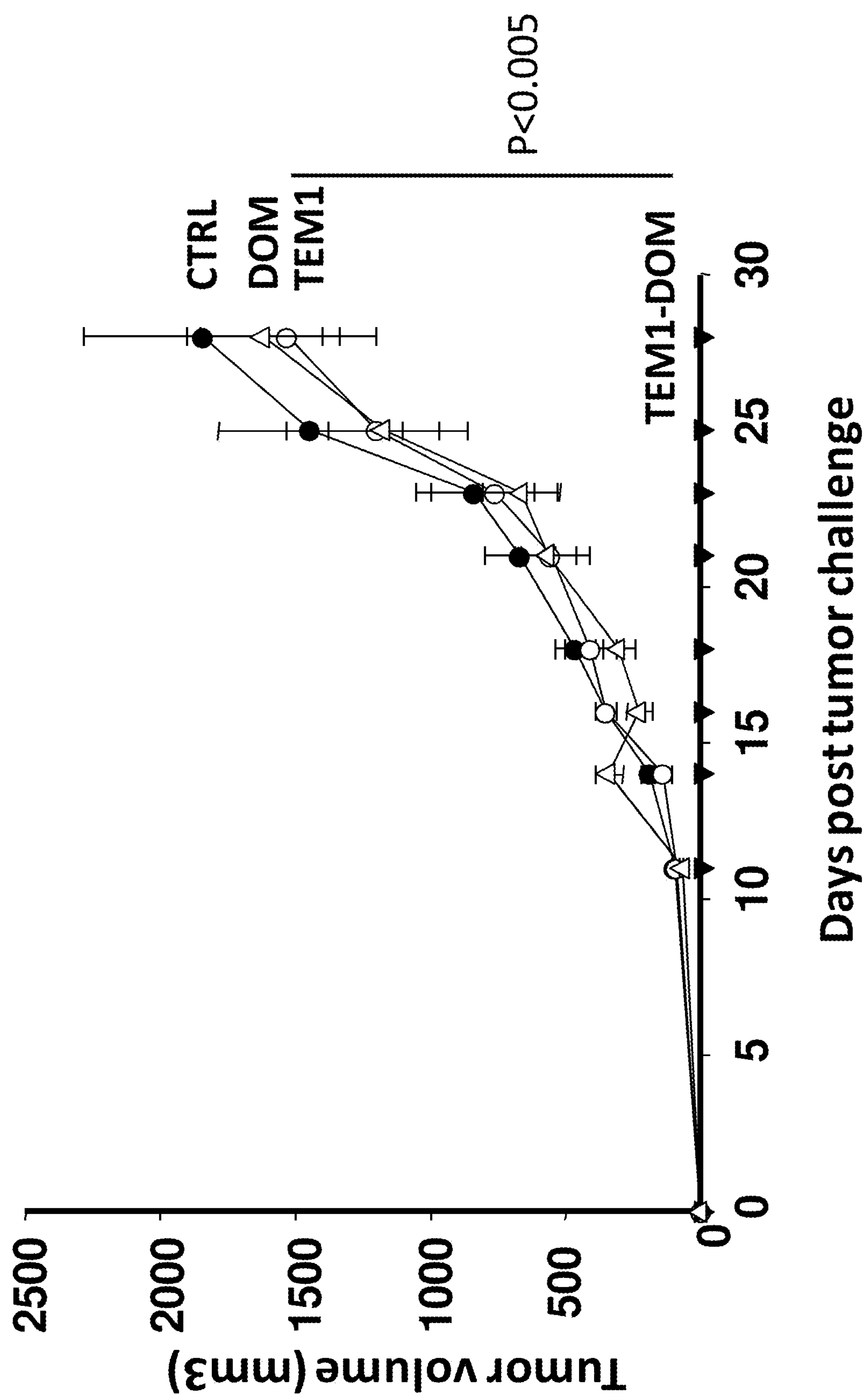
FIG. 10. Prophylactic vaccination with a TEM1-pDOM DNA vaccine prevents tumor growth.

A TEM1-pDOM (FIG. 8) was used in a system for the prevention and treatment of tumors in mice as indicated in FIG. 9. The prophylactic system results in complete tumor rejection (FIG. 10), where no tumor growth was evident with the TEM1-DOM vaccine. Therapeutic vaccination according the system in FIG. 9 results in 50% tumor rejection and significant tumor delay (see FIG. 11).

Example 10: IFN-Gamma Intracellular Staining

In another experiment, mice immunized with TEM1-pDOM demonstrated a higher percent of $CD8^+$ T cells, as opposed to mice immunized with TEM1 or pDOM alone (FIG. 12).

Figure 13:
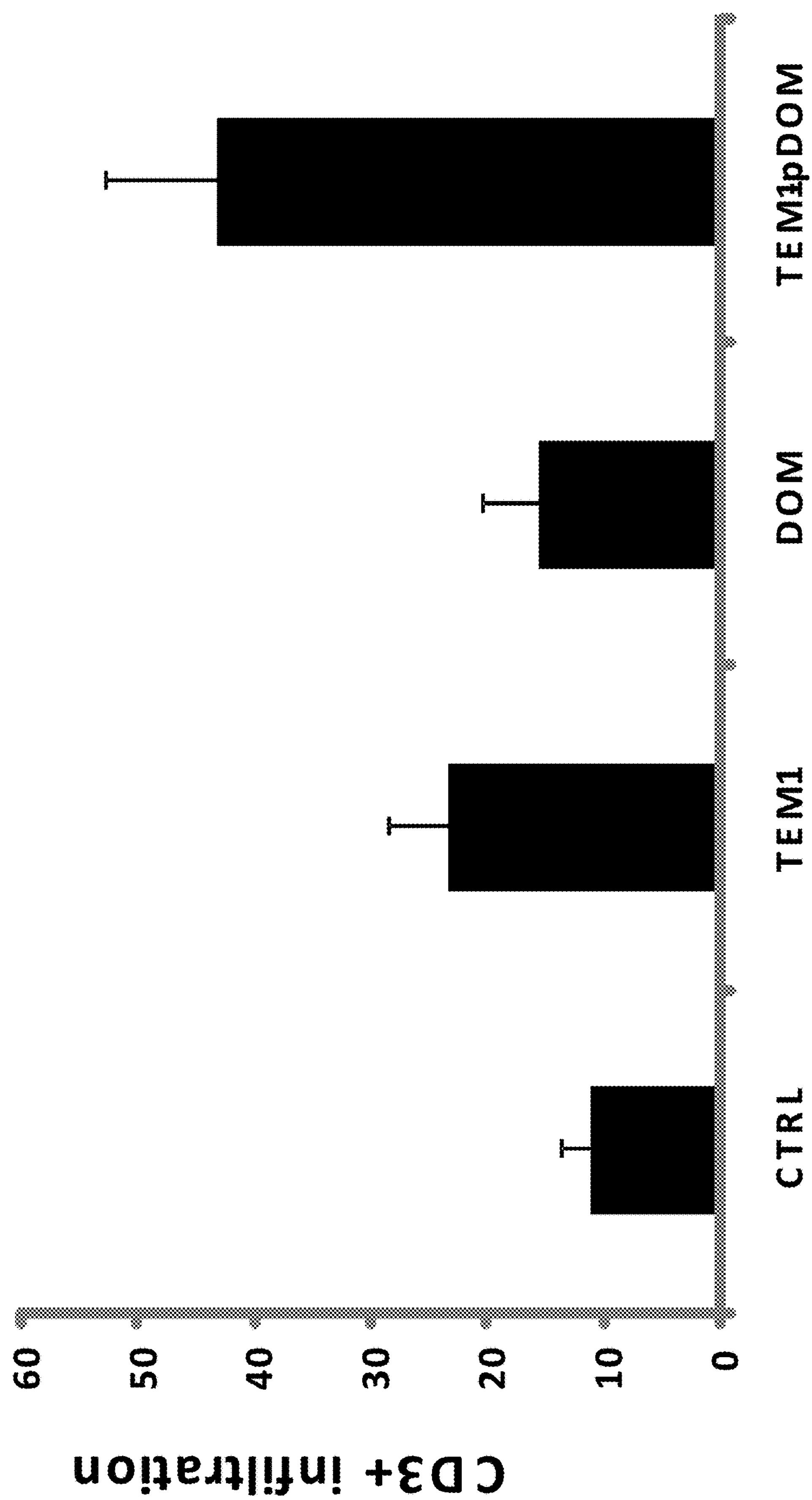
FIG. 13. TEM1-pDOM immunization results in higher T cell infiltration in the tumor FIG. 14. Cells and serum from immunized TEM1-pDOM mice were used for adoptive transfer of irratidiated mice with containing TC-1 cells.

TEM1-pDOM immunization results in higher T cell infiltration as well (FIG. 13).

Example 15: Adoptive Transfer Protocol

Figure 14:
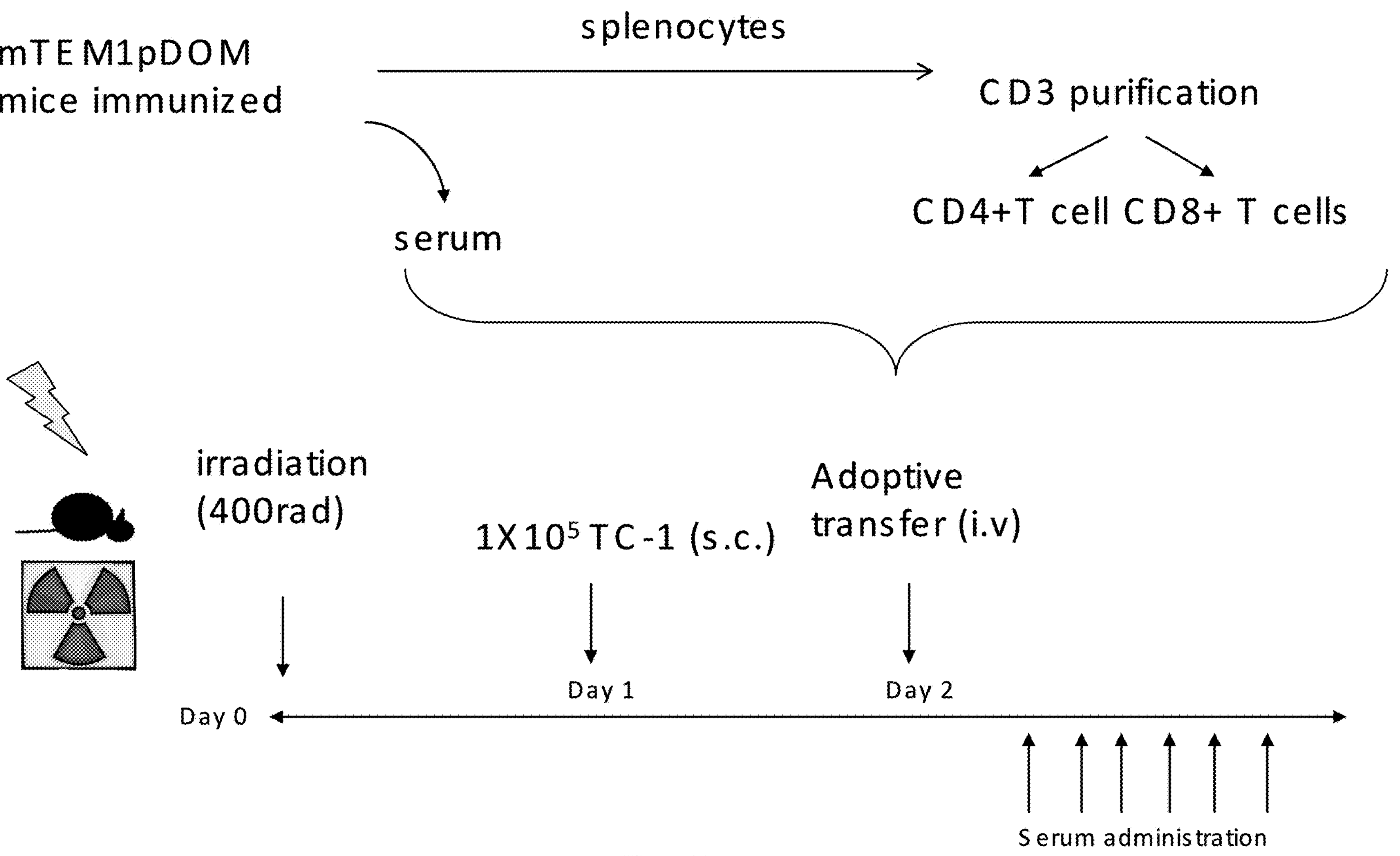
Figure 15:
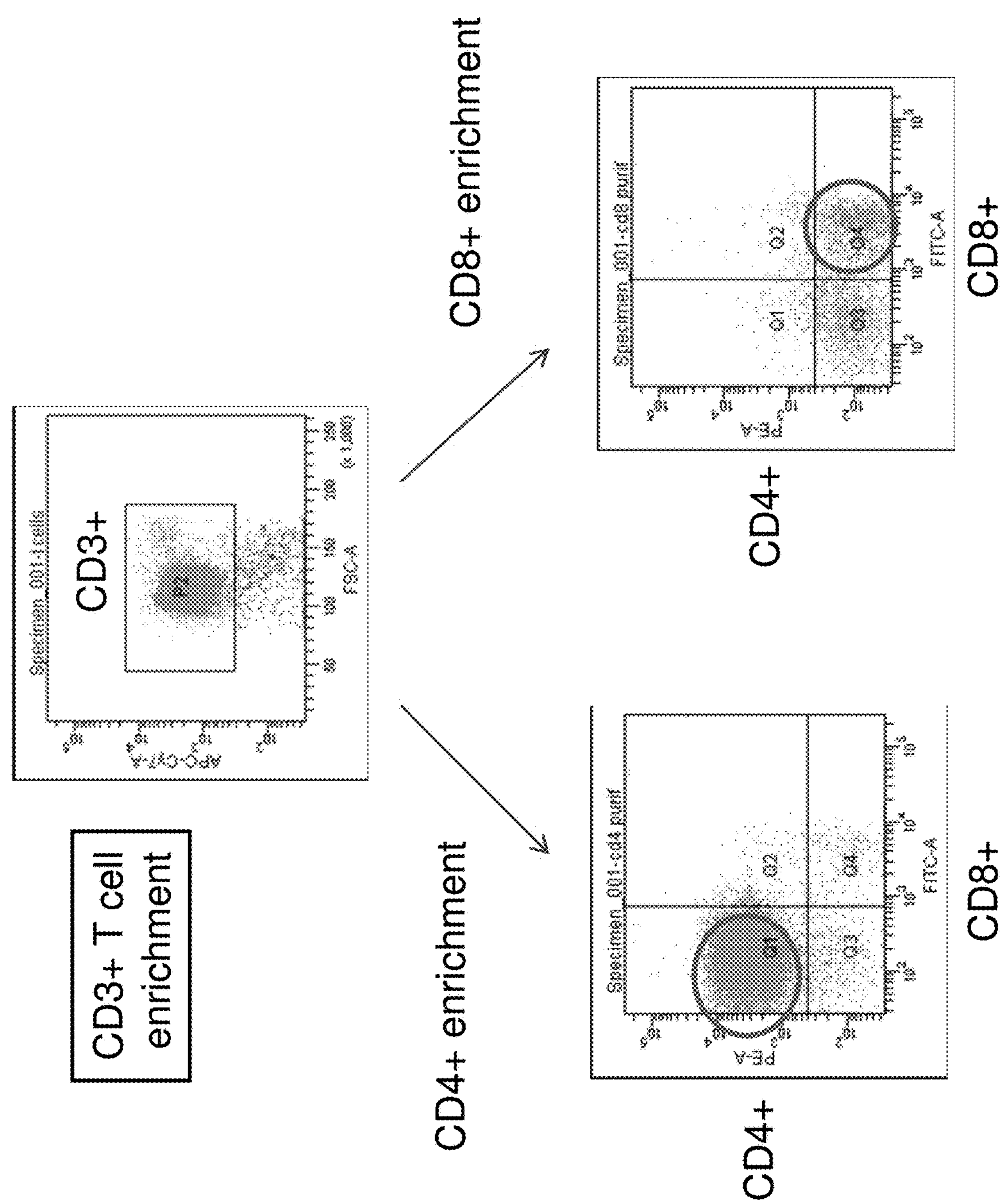
FIG. 15. CD4+ and CD8+ T cell isolation from splenocytes.
Figure 16:
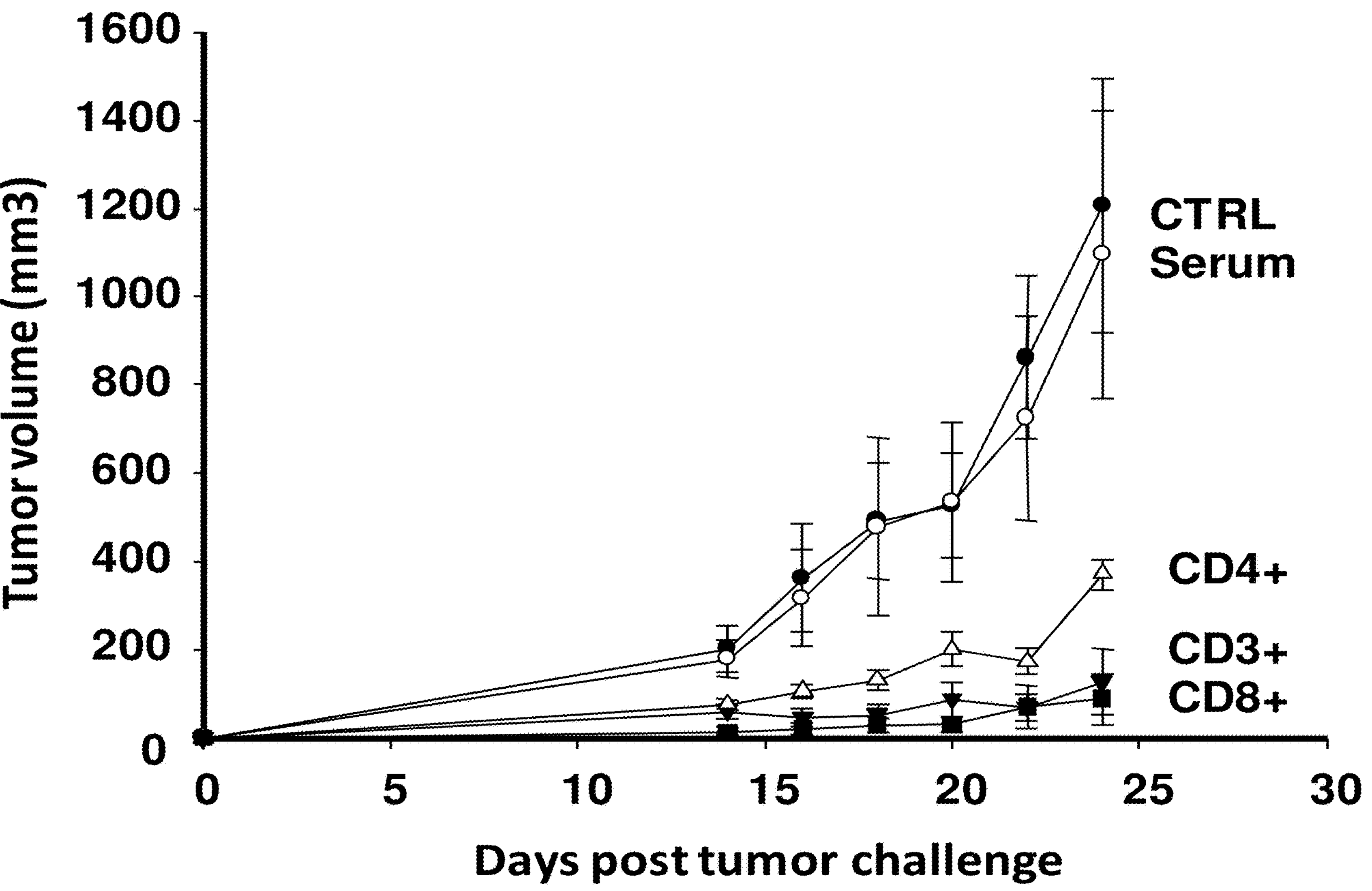
FIG. 16. Both CD4+ and CD8+ T cells are involved in tumor rejection.
Figure 17:
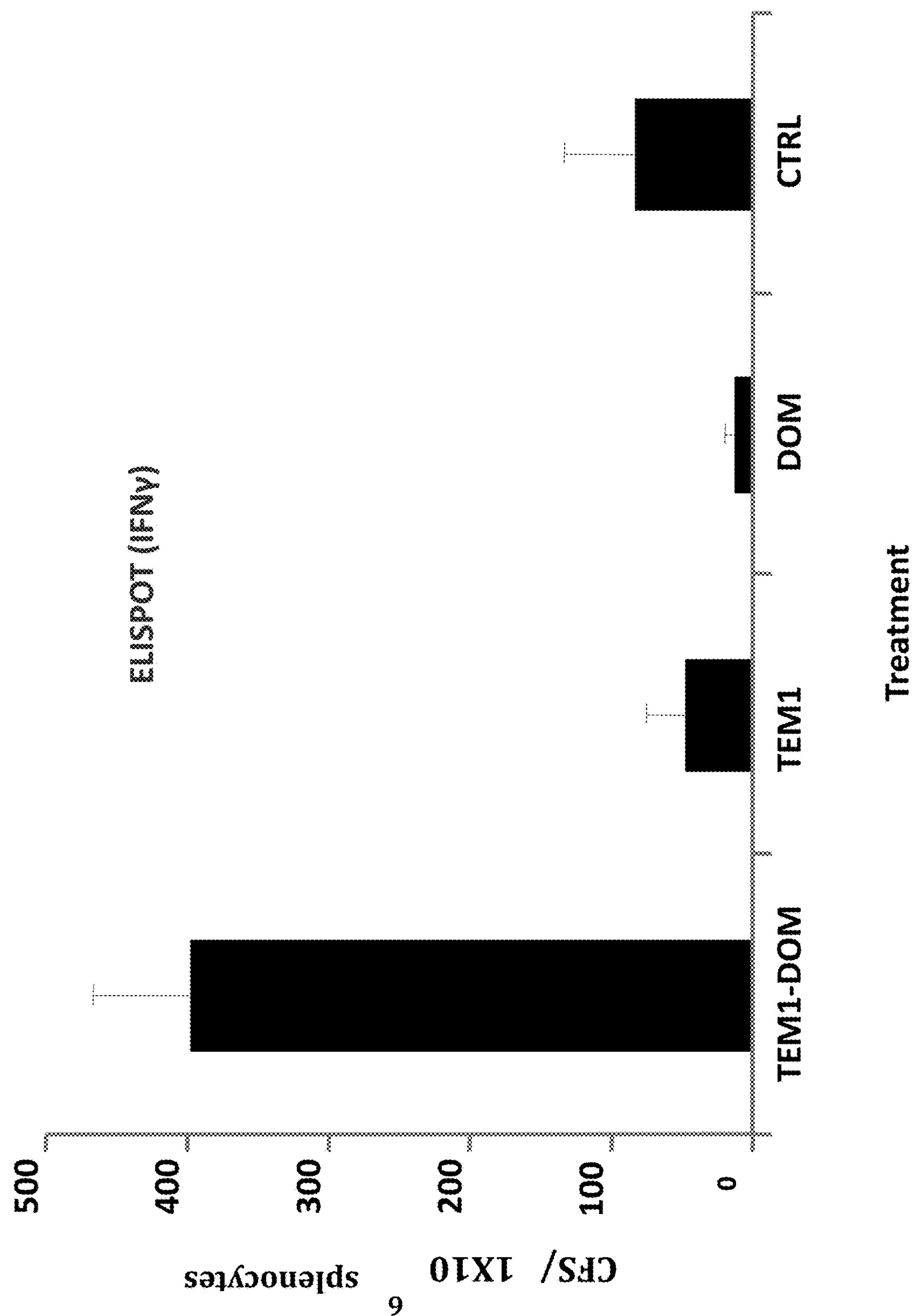
FIG. 17. TEM1-pDOM immunization results in E7 HPV cross priming.

A protocol for adoptively transferring CD4+ and CD8+ T cells into irradiated mice containing TC-1 tumors demonstrates (FIG. 14) shows that tumor rejection is mediated by T cells but not humoral immunity where both CD4+ and CD8+ cells (isolated as shown in FIG. 15) are involved in tumor rejection (FIG. 16).

Finally, immunization with TEM1 fusion with minimized domain of tetanus toxin fragment C (DOM) results in disruption of tolerance. TEM1-pDOM immunization results in E7 HPV cross-priming of splenocytes.

Figure 18:
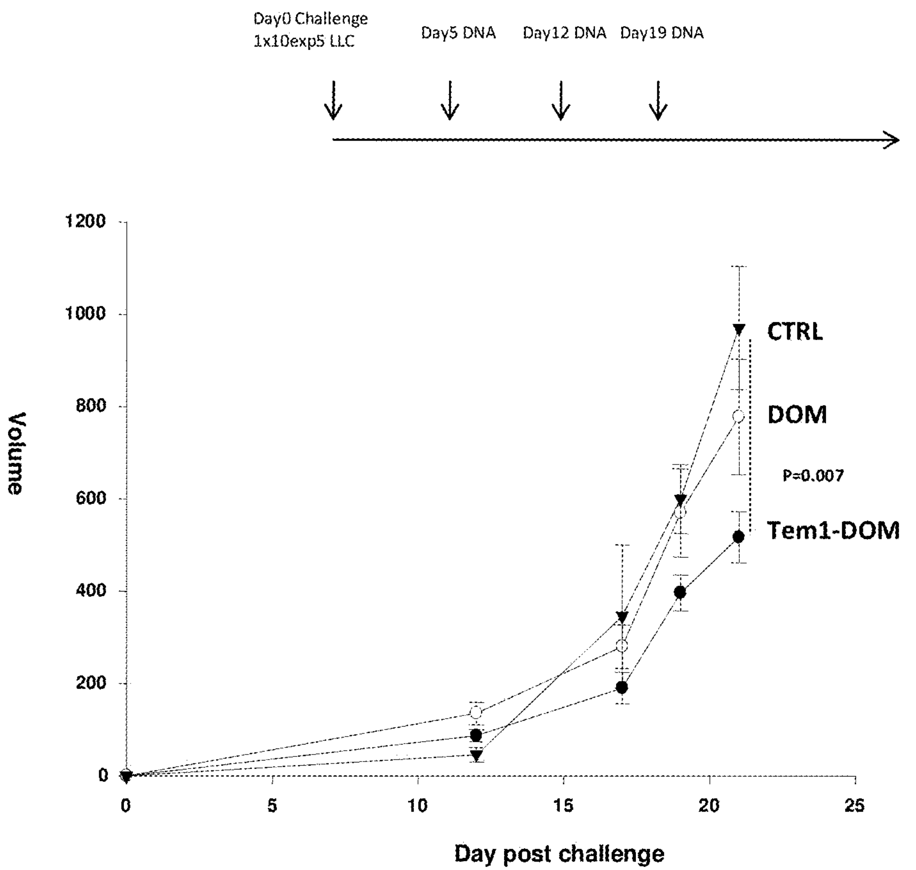
FIG. 18. Therapeutic administration of TEM-Dom DNA vaccine results in a significant Lewis lung carcinoma tumor growth impairment.

Example 16: Therapeutic Administration of TEM-Dom DNA Vaccine Results in a Significant Lewis Lung Carcinoma Tumor Growth Impairment FIG. 18 shows that therapeutic administration of TEM-Dom DNA vaccine results in a significant Lewis lung carcinoma tumor growth impairment.

TEM-Dom DNA vaccine was administered and Lewis lung carcinoma tumor volume was measured. As shown in FIG. 18, carcinoma tumor growth was impaired significantly in TEM-Dom treatment relative to control. Therefore, it is fully and clearly demonstrated that TEM-Dom DNA vaccine is effective to inhibit tumor growth.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A method of inhibiting the growth of, suppressing the growth of, decreasing the incidence, and/or recurrence of a tumor in a subject, wherein the vasculature supplying said tumor comprises a tumor endothelial marker (TEM-1) protein, comprising the steps of:

a. identifying expression of said TEM-1 by said tumor by contacting said subject with a labeled compound that binds said TEM-1 or a nucleic acid molecule encoding said TEM-1;

b. detecting said label;

c. contacting said subject with an antibody to said TEM-1, wherein said antibody is labeled with a radionuclide to deliver cytotoxic radiation to tumor vasculature expressing said TEM-1; and d. contacting said subject with a polypeptide comprising said TEM-1 protein or an immunogenic fragment thereof comprising an extracellular domain of TEM-1, said TEM-1 protein or said immunogenic fragment thereof fused to the N-terminal domain of fragment C of tetanus toxoid (DOM), or with a nucleic acid construct encoding said TEM-1 protein or said immunogenic fragment thereof, said nucleic acid fused in frame to a nucleic acid sequence encoding the N-terminal domain of fragment C of tetanus toxoid (DOM), to induce an immune response against said TEM-1.

2. The method of claim 1, wherein said detecting step is performed using positron emission tomography (PET) scanning.

3. The method of claim 2, wherein said detecting step also utilizes computed tomography (CT) or magnetic resonance imaging (MRI) scanning.

* * * * *

SEQUENCE LISTING

```
<160> NUMBER OF SEQ ID NOS: 58

<210> SEQ ID NO 1
<211> LENGTH: 5062
<212> TYPE: DNA
<213> ORGANISM: Homo sapiens

<400> SEQUENCE: 1

cactaacgct cttcctagtc cccgggccaa ctcggacagt ttgctcattt attgcaacgg     60

tcaaggctgg cttgtgccag aacggcgcgc gcgcgacgca cgcacacaca cggggggaaa    120

ctttttttaaa aatgaaaggc tagaagagct cagcggcggc gcgggccgtg cgcgagggct    180

ccggagctga ctcgccgagg caggaaatcc ctccggtcgc gacgcccggc cccgctcggc    240

gcccgcgtgg gatggtgcag cgctcgccgc cgggcccgag agctgctgca ctgaaggccg    300

gcgacgatgg cagcgcgccc gctgcccgtg tcccccgccc gcgccctcct gctcgccctg    360

gccggtgctc tgctcgcgcc ctgcgaggcc cgaggggtga gcttatggaa ccaaggaaga    420

gctgatgaag ttgtcagtgc ctctgttcgg agtggggacc tctggatccc agtgaagagc    480

ttcgactcca agaatcatcc agaagtgctg aatattcgac tacaacggga aagcaaagaa    540

ctgatcataa atctggaaag aaatgaaggt ctcattgcca gcagtttcac ggaaacccac    600
```

```
tatctgcaag acggtactga tgtctccctc gctcgaaatt acacggtaat tctgggtcac    660
tgttactacc atggacatgt acggggatat tctgattcag cagtcagtct cagcacgtgt    720
tctggtctca ggggacttat tgtgtttgaa aatgaaagct atgtcttaga accaatgaaa    780
agtgcaacca acagatacaa actcttccca gcgaagaagc tgaaaagcgt ccggggatca    840
tgtggatcac atcacaacac accaaacctc gctgcaaaga atgtgtttcc accaccctct    900
cagacatggg caagaaggca taaaagagag accctcaagg caactaagta tgtggagctg    960
gtgatcgtgg cagacaaccg agagtttcag aggcaaggaa aagatctgga aaaagttaag   1020
cagcgattaa tagagattgc taatcacgtt gacaagtttt acagaccact gaacattcgg   1080
atcgtgttgg taggcgtgga agtgtggaat gacatggaca aatgctctgt aagtcaggac   1140
ccattcacca gcctccatga atttctggac tggaggaaga tgaagcttct acctcgcaaa   1200
tcccatgaca atgcgcagct tgtcagtggg gtttatttcc aagggaccac catcggcatg   1260
gccccaatca tgagcatgtg cacggcagac cagtctgggg gaattgtcat ggaccattca   1320
gacaatcccc ttggtgcagc cgtgaccctg gcacatgagc tgggccacaa tttcgggatg   1380
aatcatgaca cactggacag ggctgtagc tgtcaaatgg cggttgagaa aggaggctgc   1440
atcatgaacg cttccaccgg gtacccattt cccatggtgt tcagcagttg cagcaggaag   1500
gacttggaga ccagcctgga gaaaggaatg gggtgtgcc tgtttaacct gccggaagtc   1560
agggagtctt tcgggggcca gaagtgtggg aacagatttg tggaagaagg agaggagtgt   1620
gactgtgggg agccagagga atgtatgaat cgctgctgca atgccaccac ctgtaccctg   1680
aagccggacg ctgtgtgcgc acatgggctg tgctgtgaag actgccagct gaagcctgca   1740
ggaacagcgt gcagggactc cagcaactcc tgtgacctcc cagagttctg cacaggggcc   1800
agccctcact gcccagccaa cgtgtacctg cacgatgggc actcatgtca ggatgtggac   1860
ggctactgct acaatggcat ctgccagact cacgagcagc agtgtgtcac actctgggga   1920
ccaggtgcta aacctgcccc tgggatctgc tttgagagag tcaattctgc aggtgatcct   1980
tatggcaact gtggcaaagt ctcgaagagt tcctttgcca aatgcgagat gagagatgct   2040
aaatgtggaa aaatccagtg tcaaggaggt gccagccggc cagtcattgg taccaatgcc   2100
gtttccatag aaacaaacat ccccctgcag caaggaggcc ggattctgtg ccgggggacc   2160
cacgtgtact tgggcgatga catgccggac ccagggcttg tgcttgcagg cacaaagtgt   2220
gcagatggaa aaatctgcct gaatcgtcaa tgtcaaaata ttagtgtctt tggggttcac   2280
gagtgtgcaa tgcagtgcca cggcagaggg gtgtgcaaca acaggaagaa ctgccactgc   2340
gaggcccact gggcacctcc cttctgtgac aagtttggct ttggaggaag cacagacagc   2400
ggccccatcc ggcaagcaga taaccaaggt ttaaccatag gaattctggt gaccatcctg   2460
tgtcttcttg ctgccggatt tgtggtttat ctcaaaagga agaccttgat acgactgctg   2520
tttacaaata agaagaccac cattgaaaaa ctaaggtgtg tgcgcccttc ccggccaccc   2580
cgtggcttcc aaccctgtca ggctcacctc ggccaccttg gaaaaggcct gatgaggaag   2640
ccgccagatt cctacccacc gaaggacaat cccaggagat tgctgcagtg tcagaatgtt   2700
gacatcagca gacccctcaa cggcctgaat gtccctcagc cccagtcaac tcagcgagtg   2760
cttcctcccc tccaccgggc cccacgtgca cctagcgtcc ctgccagacc cctgccagcc   2820
aagcctgcac ttaggcaggc ccaggggacc tgtaagccaa accccccctca gaagcctctg   2880
cctgcagatc ctctggccag aacaactcgg ctcactcatg ccttggccag gaccccagga   2940
```

```
caatgggaga ctgggctccg cctggcaccc ctcagacctg ctccacaata tccacaccaa   3000
gtgcccagat ccacccacac cgcctatatt aagtgagaag ccgacacctt ttttcaacag   3060
tgaagacaga agtttgcact atctttcagc tccagttgga gttttttgta ccaactttta   3120
ggattttttt taatgtttaa aacatcatta ctataagaac tttgagctac tgccgtcagt   3180
gctgtgctgt gctatggtgc tctgtctact tgcacaggta cttgtaaatt attaatttat   3240
gcagaatgtt gattacagtg cagtgcgctg tagtaggcat tttaccatc actgagtttt    3300
ccatggcagg aaggcttgtt gtgcttttag tattttagtg aacttgaaat atcctgcttg   3360
atgggattct ggacaggatg tgtttgcttt ctgatcaagg ccttattgga aagcagtccc   3420
ccaactaccc ccagctgtgc ttatggtacc agatgcagct caagagatcc caagtagaat   3480
ctcagttgat tttctggatt ccccatctca ggccagagcc aaggggcttc aggtccaggc   3540
tgtgtttggc tttcagggag gccctgtgcc ccttgacaac tggcaggcag gctcccaggg   3600
acacctggga gaaatctggc ttctggccag gaagctttgg tgagaacctg ggttgcagac   3660
aggaatctta aggtgtagcc acaccaggat agagactgga acactagaca agccagaact   3720
tgaccctgag ctgaccagcc gtgagcatgt ttggaagggg tctgtagtgt cactcaaggc   3780
ggtgcttgat agaaatgcca agcacttctt tttctcgctg tcctttctag agcactgcca   3840
ccagtaggtt atttagcttg ggaaaggtgg tgtttctgta agaaacctac tgcccaggca   3900
ctgcaaaccg ccacctccct atactgcttg gagctgagca aatcaccaca aactgtaata   3960
caatgatcct gtattcagac agatgaggac tttccatggg accacaacta ttttcagatg   4020
tgaaccatta accagatcta gtcaatcaag tctgtttact gcaaggttca acttattaac   4080
aattaggcag actctttatg cttgcaaaaa ctacaaccaa tggaatgtga tgttcatggg   4140
tatagttcat gtctgctatc attattcgta gatattggac aaagaacctt ctctatgggg   4200
catcctcttt ttccaacttg gctgcaggaa tctttaaaag atgcttttaa cagagtctga   4260
acctatttct taaacacttg caacctacct gttgagcatc acagaatgtg ataaggaaat   4320
caacttgctt atcaacttcc taaatattat gagatgtggc ttgggcagca tccccttgaa   4380
ctcttcactc ttcaaatgcc tgactaggga gccatgtttc acaaggtctt taaagtgact   4440
aatggcatga gaaatacaaa aatactcaga taaggtaaaa tgccatgatg cctctgtctt   4500
ctggactggt tttcacatta gaagacaatt gacaacagtt acataattca ctctgagtgt   4560
tttatgagaa agccttcttt tggggtcaac agttttccta tgctttgaaa cagaaaaata   4620
tgtaccaaga atcttggttt gccttccaga aaacaaaact gcatttcact ttcccggtgt   4680
tccccactgt atctaggcaa catagtattc atgactatgg ataaactaaa cacgtgacac   4740
aaacacacac aaaagggaac ccagctctaa tacattccaa ctcgtatagc atgcatctgt   4800
ttattctata gttattaagt tctttaaaat gtaaagccat gctggaaaat aatactgctg   4860
agatacatac agaattactg taactgatta cacttggtaa ttgtactaaa gccaaacata   4920
tatatactat taaaaaggtt tacagaattt tatggtgcat tacgtgggca ttgtcttttt   4980
agatgcccaa atccttagat ctggcatgtt agcccttcct ccaattataa gaggatatga   5040
accaaaaaaa aaaaaaaaaa aa                                            5062
```

<210> SEQ ID NO 2
<211> LENGTH: 9645
<212> TYPE: DNA
<213> ORGANISM: Homo sapiens

<400> SEQUENCE: 2

```
atgcccaagc gcgcgcactg gggggccctc tccgtggtgc tgatcctgct ttggggccat     60
ccgcgagtgg cgctggcctg cccgcatcct tgtgcctgct acgtccccag cgaggtccac    120
tgcacgttcc gatccctggc ttccgtgccc gctggcattg ctagacacgt ggaaagaatc    180
aatttggggt ttaatagcat acaggccctg tcagaaacct catttgcagg actgaccaag    240
ttggagctac ttatgattca cggcaatgag atcccaagca tccccgatgg agctttaaga    300
gacctcagct ctcttcaggt tttcaagttc agctacaaca agctgagagt gatcacagga    360
cagaccctcc agggtctctc taacttaatg aggctgcaca ttgaccacaa caagatcgag    420
tttatccacc ctcaagcttt caacggctta acgtctctga ggctactcca tttggaagga    480
aatctcctcc accagctgca ccccagcacc ttctccacgt tcacattttt ggattatttc    540
agactctcca ccataaggca cctctactta gcagagaaca tggttagaac tcttcctgcc    600
agcatgcttc ggaacatgcc gcttctggag aatctttact tgcagggaaa tccgtggacc    660
tgcgattgtg agatgagatg gtttttggaa tgggatgcaa aatccagagg aattctgaag    720
tgtaaaaagg acaaagctta tgaaggcggt cagttgtgtg caatgtgctt cagtccaaag    780
aagttgtaca aacatgagat acacaagctg aaggacatga cttgtctgaa gccttcaata    840
gagtcccctc tgagacagaa caggagcagg agtattgagg aggagcaaga acaggaagag    900
gatggtggca gccagctcat cctggagaaa ttccaactgc cccagtggag catctctttg    960
aatatgaccg acgagcacgg gaacatggtg aacttggtct gtgacatcaa gaaaccaatg   1020
gatgtgtaca agattcactt gaaccaaacg gatcctccag atattgacat aaatgcaaca   1080
gttgccttgg actttgagtg tccaatgacc cgagaaaact atgaaaagct atggaaattg   1140
atagcatact acagtgaagt tcccgtgaag ctacacagag agctcatgct cagcaaagac   1200
cccagagtca gctaccagta caggcaggat gctgatgagg aagctcttta ctacacaggt   1260
gtgagagccc agattcttgc agaaccagaa tgggtcatgc agccatccat agatatccag   1320
ctgaaccgac gtcagagtac ggccaagaag gtgctacttt cctactacac ccagtattct   1380
caaacaatat ccaccaaaga tacaaggcag gctcggggca gaagctgggt aatgattgag   1440
cctagtggag ctgtgcaaag agatcagact gtcctggaag gggtccatg ccagttgagc    1500
tgcaacgtga aagcttctga gagtccatct atcttctggg tgcttccaga tggctccatc   1560
ctgaaagcgc ccatggatga cccagacagc aagttctcca ttctcagcag tggctggctg   1620
aggatcaagt ccatggagcc atctgactca ggcttgtacc agtgcattgc tcaagtgagg   1680
gatgaaatgg accgcatggt atatagggta cttgtgcagt ctccctccac tcagccagcc   1740
gagaaagaca cagtgacaat tggcaagaac ccaggggagt cggtgacatt gccttgcaat   1800
gctttagcaa tacccgaagc ccaccttagc tggattcttc caaacagaag gataattaat   1860
gatttggcta acacatcaca tgtatacatg ttgccaaatg gaactctttc catcccaaag   1920
gtccaagtca gtgatagtgg ttactacaga tgtgtggctg tcaaccagca aggggcagac   1980
cattttacgg tgggaatcac agtgaccaag aaagggtctg gcttgccatc caaaagaggc   2040
agacgcccag gtgcaaaggc tctttccaga gtcagagaag acatcgtgga ggatgaaggg   2100
ggctcgggca tgggagatga agagaacact tcaaggagac ttctgcatcc aaaggaccaa   2160
gaggtgttcc tcaaaacaaa ggatgatgcc atcaatggag acaagaaagc caagaaaggg   2220
agaagaaagc tgaaactctg gaagcattcg gaaaaagaac cagagaccaa tgttgcagaa   2280
ggtcgcagag tgtttgaatc tagacgaagg ataaacatgg caaacaaaca gattaatccg   2340
```

```
gagcgctggg ctgatatttt agccaaagtc cgtgggaaaa atctccctaa gggcacagaa   2400
gtacccccgt tgattaaaac cacaagtcct ccatccttga gcctagaagt cacaccacct   2460
tttcctgctg tttctccccc ctcagcatct cctgtgcaga cagtaaccag tgctgaagaa   2520
tcctcagcag atgtacctct acttggtgaa gaagagcacg ttttgggtac catttcctca   2580
gccagcatgg ggctagaaca caaccacaat ggagttattc ttgttgaacc tgaagtaaca   2640
agcacacctc tggaggaagt tgttgatgac ctttctgaga agactgagga gataacttcc   2700
actgaaggag acctgaaggg gacagcagcc cctacactta tatctgagcc ttatgaacca   2760
tctcctactc tgcacacatt agacacagtc tatgaaaagc ccacccatga agagacggca   2820
acagagggtt ggtctgcagc agatgttgga tcgtcaccag agcccacatc cagtgagtat   2880
gagcctccat tggatgctgt ctccttggct gagtctgagc ccatgcaata ctttgaccca   2940
gatttggaga ctaagtcaca accagatgag gataagatga aagaagacac ctttgcacac   3000
cttactccaa cccccaccat ctgggttaat gactccagta catcacagtt atttgaggat   3060
tctactatag gggaaccagg tgtcccaggc caatcacatc tacaaggact gacagacaac   3120
atccaccttg tgaaaagtag tctaagcact caagacacct tactgattaa aaagggtatg   3180
aaagagatgt ctcagacact acagggagga aatatgctag agggagaccc cacacactcc   3240
agaagttctg agagtgaggg ccaagagagc aaatccatca ctttgcctga ctccacactg   3300
ggtataatga gcagtatgtc tccagttaag aagcctgcgg aaaccacagt tggtaccctc   3360
ctagacaaag acaccacaac agtaacaaca acaccaaggc aaaaagttgc tccgtcatcc   3420
accatgagca ctcacccttc tcgaaggaga cccaacggga gaaggagatt acgccccaac   3480
aaattccgcc accggcacaa gcaaacccca cccacaactt ttgccccatc agagactttt   3540
tctactcaac caactcaagc acctgacatt aagatttcaa gtcaagtgga gagttctctg   3600
gttcctacag cttgggtgga taacacagtt aataccccca aacagttgga aatggagaag   3660
aatgcagaac ccacatccaa gggaacacca cggagaaaac acgggaagag gccaaacaaa   3720
catcgatata ccccttctac agtgagctca agagcgtccg gatccaagcc cagcccttct   3780
ccagaaaata aacatagaaa cattgttact cccagttcag aaactatact tttgcctaga   3840
actgtttctc tgaaaactga gggcccttat gattccttag attacatgac aaccaccaga   3900
aaaatatatt catcttaccc taaagtccaa gagacacttc cagtcacata taaacccaca   3960
tcagatggaa aagaaattaa ggatgatgtt gccacaaatg ttgacaaaca taaaagtgac   4020
attttagtca ctggtgaatc aattactaat gccataccaa cttctcgctc cttggtctcc   4080
actatgggag aatttaagga agaatcctct cctgtaggct ttccaggaac tccaacctgg   4140
aatccctcaa ggacggccca gcctgggagg ctacagacag acatacctgt taccacttct   4200
ggggaaaatc ttacagaccc tccccttctt aaagagcttg aggatgtgga tttcacttcc   4260
gagtttttgt cctctttgac agtctccaca ccatttcacc aggaagaagc tggttcttcc   4320
acaactctct caagcataaa agtggaggtg gcttcaagtc aggcagaaac caccaccctt   4380
gatcaagatc atcttgaaac cactgtggct attctccttt ctgaaactag accacagaat   4440
cacaccccta ctgctgcccg gatgaaggag ccagcatcct cgtccccatc cacaattctc   4500
atgtctttgg gacaaaccac caccactaag ccagcacttc ccagtccaag aatatctcaa   4560
gcatctagag attccaagga aaatgttttc ttgaattatg tggggaatcc agaaacagaa   4620
gcaaccccag tcaacaatga aggaacacag catatgtcag ggccaaatga attatcaaca   4680
ccctcttccg accgggatgc atttaacttg tctacaaagc tggaattgga aaagcaagta   4740
```

```
tttggtagta ggagtctacc acgtggccca gatagccaac gccaggatgg aagagttcat   4800
gcttctcatc aactaaccag agtccctgcc aaacccatcc taccaacagc aacagtgagg   4860
ctacctgaaa tgtccacaca aagcgcttcc agatactttg taacttccca gtcacctcgt   4920
cactggacca acaaaccgga aataactaca tatccttctg gggctttgcc agagaacaaa   4980
cagtttacaa ctccaagatt atcaagtaca acaattcctc tcccattgca catgtccaaa   5040
cccagcattc ctagtaagtt tactgaccga agaactgacc aattcaatgg ttactccaaa   5100
gtgtttggaa ataacaacat ccctgaggca agaaacccag ttggaaagcc tcccagtcca   5160
agaattcctc attattccaa tggaagactc cctttcttta ccaacaagac tctttctttt   5220
ccacagttgg gagtcacccg gagaccccag atacccactt ctcctgcccc agtaatgaga   5280
gagagaaaag ttattccagg ttcctacaac aggatacatt cccatagcac cttccatctg   5340
gactttggcc ctccggcacc tccgttgttg cacactccgc agaccacggg atcaccctca   5400
actaacttac agaatatccc tatggtctct tccacccaga gttctatctc ctttataaca   5460
tcttctgtcc agtcctcagg aagcttccac cagagcagct caaagttctt tgcaggagga   5520
cctcctgcat ccaaattctg gtctcttggg gaaaagcccc aaatcctcac caagtcccca   5580
cagactgtgt ccgtcaccgc tgagacagac actgtgttcc cctgtgaggc aacaggaaaa   5640
ccaaagcctt tcgttacttg gacaaaggtt tccacaggag ctcttatgac tccgaatacc   5700
aggatacaac ggtttgaggt tctcaagaac ggtaccttag tgatacggaa ggttcaagta   5760
caagatcgag gccagtatat gtgcaccgcc agcaacctgc acggcctgga caggatggtg   5820
gtcttgcttt cggtcaccgt gcagcaacct caaatcctag cctcccacta ccaggacgtc   5880
actgtctacc tgggagacac cattgcaatg gagtgtctgg ccaaagggac cccagccccc   5940
caaatttcct ggatcttccc tgacaggagg gtgtggcaaa ctgtgtcccc cgtggagagc   6000
cgcatcaccc tgcacgaaaa ccggaccctt tccatcaagg aggcgtcctt ctcagacaga   6060
ggcgtctata agtgcgtggc cagcaatgca gccggggcgg acagcctggc catccgcctg   6120
cacgtggcgg cactgccccc cgttatccac caggagaagc tggagaacat ctcgctgccc   6180
ccggggctca gcattcacat tcactgcact gccaaggctg cgcccctgcc cagcgtgcgc   6240
tgggtgctcg gggacggtac ccagatccgc ccctcgcagt tcctccacgg gaacttgttt   6300
gttttcccca acgggacgct ctacatccgc aacctcgcgc ccaaggacag cgggcgctat   6360
gagtgcgtgg ccgccaacct ggtaggctcc gcgcgcagga cggtgcagct gaacgtgcag   6420
cgtgcagcag ccaacgcgcg catcacgggc acctccccgc ggaggacgga cgtcaggtac   6480
ggaggaaccc tcaagctgga ctgcagcgcc tcgggggacc cctggccgcg catcctctgg   6540
aggctgccgt ccaagaggat gatcgacgcg ctcttcagtt ttgatagcag aatcaaggtg   6600
tttgccaatg ggaccctggt ggtgaaatca gtgacggaca aagatgccgg agattacctg   6660
tgcgtagctc gaaataaggt tggtgatgac tacgtggtgc tcaaagtgga tgtggtgatg   6720
aaaccggcca agattgaaca caaggaggag aacgaccaca aagtcttcta cgggggtgac   6780
ctgaaagtgg actgtgtggc caccgggctt cccaatcccg agatctcctg gagcctccca   6840
gacgggagtc tggtgaactc cttcatgcag tcggatgaca gcggtggacg caccaagcgc   6900
tatgtcgtct tcaacaatgg gacactctac tttaacgaag tggggatgag ggaggaagga   6960
gactacacct gctttgctga aaatcaggtc gggaaggacg agatgagagt cagagtcaag   7020
gtggtgacag cgcccgccac catccggaac aagacttact tggcggttca ggtgccctat   7080
```

```
ggagacgtgg tcactgtagc ctgtgaggcc aaaggagaac ccatgcccaa ggtgacttgg   7140
ttgtccccaa ccaacaaggt gatccccacc tcctctgaga agtatcagat ataccaagat   7200
ggcactctcc ttattcagaa agcccagcgt tctgacagcg gcaactacac ctgcctggtc   7260
aggaacagcg cgggagagga taggaagacg gtgtggattc acgtcaacgt ccagccaccc   7320
aagatcaacg gtaaccccaa ccccatcacc accgtgcggg agatagcagc cgggggcagt   7380
cggaaactga ttgactgcaa agctgaaggc atccccaccc cgagggtgtt atgggctttt   7440
cccgagggtg tggttctgcc agctccatac tatggaaacc ggatcactgt ccatggcaac   7500
ggttccctgg acatcaggag tttgaggaag agcgactccg tccagctggt atgcatggca   7560
cgcaacgagg gaggggaggc gaggttgatc gtgcagctca ctgtcctgga gcccatggag   7620
aaacccatct tccacgaccc gatcagcgag aagatcacgg ccatggcggg ccacaccatc   7680
agcctcaact gctctgccgc ggggaccccg acacccagcc tggtgtgggt ccttcccaat   7740
ggcaccgatc tgcagagtgg acagcagctg cagcgcttct accacaaggc tgacggcatg   7800
ctacacatta gcggtctctc ctcggtggac gctggggcct accgctgcgt ggcccgcaat   7860
gccgctggcc acacggagag gctggtctcc ctgaaggtgg gactgaagcc agaagcaaac   7920
aagcagtatc ataacctggt cagcatcatc aatggtgaga ccctgaagct cccctgcacc   7980
cctcccgggg ctgggcaggg acgtttctcc tggacgctcc ccaatggcat gcatctggag   8040
ggcccccaaa ccctgggacg cgtttctctt ctggacaatg gcaccctcac ggttcgtgag   8100
gcctcggtgt ttgacagggg tacctatgta tgcaggatgg agacggagta cggcccttcg   8160
gtcaccagca tccccgtgat tgtgatcgcc tatcctcccc ggatcaccag cgagcccacc   8220
ccggtcatct acacccggcc cgggaacacc gtgaaactga actgcatggc tatggggatt   8280
cccaaagctg acatcacgtg ggagttaccg gataagtcgc atctgaaggc aggggttcag   8340
gctcgtctgt atggaaacag atttcttcac cccccaggat cactgaccat ccagcatgcc   8400
acacagagag atgccggctt ctacaagtgc atggcaaaaa acattctcgg cagtgactcc   8460
aaaacaactt acatccacgt cttctgaaat gtggattcca gaatgattgc ttaggaactg   8520
acaacaaagc ggggtttgta agggaagcca ggttggggaa taggagctct taaataatgt   8580
gtcacagtgc atggtggcct ctggtgggtt tcaagttgag gttgatcttg atctacaatt   8640
gttgggaaaa ggaagcaatg cagacacgag aaggagggct cagccttgct gagacacttt   8700
cttttgtgtt tacatcatgc caggggcttc attcagggtg tctgtgctct gactgcaatt   8760
tttcttcttt tgcaaatgcc actcgactgc cttcataagc gtccatagga tatctgagga   8820
acattcatca aaaataagcc atagacatga acaacacctc actaccccat tgaagacgca   8880
tcacctagtt aacctgctgc agtttttaca tgatagactt tgttccagat tgacaagtca   8940
tctttcagtt atttcctctg tcacttcaaa actccagctt gcccaataag gatttagaac   9000
cagagtgact gatatatata tatatatttt aattcagagt tacatacata cagctaccat   9060
tttatatgaa aaaagaaaaa catttcttcc tggaactcac tttttatata atgttttata   9120
tatatatttt ttcctttcaa atcagacgat gagactagaa ggagaaatac tttctgtctt   9180
attaaaatta ataaattatt ggtctttaca agacttggat acattacagc agacatggaa   9240
atataatttt aaaaaatttc tctccaacct ccttcaaatt cagtcaccac tgttatatta   9300
ccttctccag gaaccctcca gtggggaagg ctgcgatatt agatttcctt gtatgcaaag   9360
tttttgttga aagctgtgct cagaggaggt gagaggagag gaaggagaaa actgcatcat   9420
aactttacag aattgaatct agagtcttcc ccgaaaagcc cagaaacttc tctgcagtat   9480
```

```
ctggcttgtc catctggtct aaggtggctg cttcttcccc agccatgagt cagtttgtgc   9540

ccatgaataa tacacgacct gttatttcca tgactgcttt actgtatttt taaggtcaat   9600

atactgtaca tttgataata aaataatatt ctcccaaaaa aaaaa                   9645


<210> SEQ ID NO 3
<211> LENGTH: 3093
<212> TYPE: DNA
<213> ORGANISM: Homo sapiens

<400> SEQUENCE: 3

aggaagtggt gagttcggag tagagatggc cgcgcttgca ccgctgcccc cgctccccgc     60

acagttcaag agcatacagc atcatctgag gacggctcag gagcatgaca agcgagaccc    120

tgtggtggct tattactgtc gtttatacgc aatgcagact ggaatgaaga tcgatagtaa    180

aactcctgaa tgtcgcaaat ttttatcaaa gttaatggat cagttagaag ctctaaagaa    240

gcagttgggt gataatgaag ctattactca agaaatagtg ggctgtgccc atttggagaa    300

ttatgctttg aaaatgtttt tgtatgcaga caatgaagat cgtgctggac gatttcacaa    360

aaacatgatc aagtccttct atactgcaag tcttttgata gatgtcataa cagtatttgg    420

agaactcact gatgaaaatg tgaaacacag gaagtatgcc agatggaagg caacatacat    480

ccataattgt ttaaagaatg gggagactcc tcaagcaggc cctgttggaa ttgaagaaga    540

taatgatatt gaagaaaatg aagatgctgg agcagcctct ctgcccactc agccaactca    600

gccatcatca tcttcaactt atgacccaag caacatgcca tcaggcaact atactggaat    660

acagattcct ccgggtgcac acgctccagc taatacacca gcagaagtgc ctcacagcac    720

aggtgtagca agtaatacta tccaacctac tccacagact atacctgcca ttgatcccgc    780

acttttcaat acaatttccc aggggatgt tcgtctaacc ccagaagact ttgctagagc    840

tcagaagtac tgcaaatatg ctggcagtgc tttgcagtat gaagatgtaa gcactgctgt    900

ccagaatcta caaaaggctc tcaagttact gacgacaggc agagaatgaa gcctttgtat    960

gacagaccca tgtatttttg gcatgaggaa ctaacagtcc attactctat cttcagccta   1020

tcaggatcac agttttaagg aagacttggt tttgttgaat atgacaatga aatctgtgtg   1080

tatcagattt ttattgaagc attcatcagc agcctcaacc agttttcatt gtccatttac   1140

tagattcaat cgtctctgag tatatagggc tgatgttagc aagaccctaa aaatgtccat   1200

tgaaccctgc ttcaaaaaat gaaaacacac ctctataaaa tgtgtactgg gaataagctt   1260

tgtatttaca tacattaggg gaatttttta aaatctgtaa tgtttggaca aacagatgat   1320

attactttgc tataaaatta taaatgtaac ttttaataaa gatagccaga atattctaaa   1380

ttagaaatta cgtttttgtt tccctcaaga cataaaacaa atataaacat tctaaactgc   1440

tggatgaatc tgaaaagaca ttaagttcaa attttaattt attctcatat taaatataac   1500

tccattaaaa gtttaaaatt tcatgggaga aaatataata aggtaaagag gtagaatcac   1560

tttcagactt aagaataatg ttgatttccc aagtgcttta ccttatctgt taaagcgtaa   1620

gatgaattgg tatttgcttc ataggcagtt tgactgcatg tattagagaa tgaaaagaag   1680

atatttgtag taatgcctgg aaacttggtg ctttaaatta aggtactcct ctgctgctgt   1740

agaatggatt ccacacagtg gatagctatg ggtgattcag aatattatgt ttagattccc   1800

atttgttaag tttataagtt ttgtggggaa ttatgaactt actgtgtact acctgcattt   1860

gtgctgtgtg aaaaataaat acaaggattc gtttagctaa ttcaacttac tacaaagaca   1920
```

```
aatgtctgtt tttatttgcc tgctaggatt gtctttttta aaagtcattt ttatttatag   1980
gaatatgggt gtttctatag gaagaaacag gtttttttgtt ttttgttttt taagataaat   2040
ttgacaaagt taactgaaat ttatctggtc cattttattc atgctactaa gatgggaatc   2100
tttaaacaca agggtcagca agctttggcc catggattgg ccacctgtta cgtaaataaa   2160
gtttctttga aacaagccta cactcattca tttatgtttt gtctgtggtt gctttccaca   2220
actgcagagt tgtatggctt gcaagtctaa aaacatttac tatttggccc tctaagaaaa   2280
agttaagaca cctagtctaa tggccttttg ggaaaaaaca aatcactaac tcataatcat   2340
ttatatccat tattttctgc ataaatgtaa tgctattgta cagggtttgg tagaataaat   2400
attcagactg actaaactgt tctaaatcct cacaaaaaag tccccaaaca acatgcctcc   2460
taaaaaacat tttcctatct tttacaagag gtatgaacat ttgtagggtt ccacatttgc   2520
atctagaaat ccaatgctct ttagaatgtt attacgaata gaaagatggc caggatgacc   2580
tttagtgtta catgatgttc agcaaatttt aattcaaacc ttgatatgcc tggacactga   2640
aaagtaaacg catcacctcc tattttatac actaccttct ggttcccaat tgggagagca   2700
catagaggga aggagacaat atagaaacta cggagtccgc tggtagtggg ctgcatggtg   2760
tgacagagcc cttctctgta aaatggaaat gacaccacta gccatctcaa tagttacaag   2820
aattaaaaga gatacagtac ctgaagtgct tagcgcatgg tagcatttca taaatgttta   2880
gtgtcaatac taatgctcta ataatgtaaa ttgttaataa tttatttccc taatatcagg   2940
aaatcccagt tgtctatgtg gcccagtgct taaaaacgcc ttcttgcatg aggggattga   3000
actatacaat gtttgttaac tttgtatttg tattttttcc tataaaatct taaaataaaa   3060
ttaggagatg tgttccgaaa aaaaaaaaaa aaa                                 3093
```

<210> SEQ ID NO 4
<211> LENGTH: 2114
<212> TYPE: DNA
<213> ORGANISM: Homo sapiens

<400> SEQUENCE: 4

```
ccacgcgtcc gaccaatgtc atccccaaag gaagggtgag ctgaatggaa attaagccca     60
gtcattttat ttgatctatt agctctgtta tcagtgcatg atcacccaga tcaccctcct    120
cagcccacac agtgctgaac catcttccct cctgttctcc atggctatta atagtatagc    180
taaatttaga gtgcagagcc agatataagt attttggaat tatctcccag tttgtggtag    240
aagctgactg gaatacaggt tgagtatctc ttatccaaaa tgctagggac cagaaaggtt    300
tcagattttt tcagattttg gaatacttaa cagttgagca ccccaaatct gaaaggcttc    360
tgaacgtcat gtcagcactc aaaaaagtgg attttggagc acttcaaatt tcggattttt    420
ggatttggga tgctcatcct gtgtaggaga ggctactcga ttccatttaa tgactgtcct    480
agtcataatc atccaaagat aaaagccagg tagatgttga aagctctttc cagggctgaa    540
aaagtgttct tacgttctct gcatgtgact agcatcactg tggaaattaa tgctctgttc    600
ttcactagaa tgtagtaagt ggttaaactg agctatcccc cacctgatga ctattggcat    660
ccatttgcaa ggccaatggc ctggattaag ggttaggatt atttgtagct agaaggtaat    720
tttatttctg tgaaactaat tggctcatat ttgaggttag gtgtggcctt gaccttacca    780
gtacatttat acccactacc agttgactag cccagataat tgttaaatgg tgcttctttt    840
ctgcttctca gtagacttcc atgccattac aaaggaaatt tgaattacct agtgtttgta    900
tattccatga taactatgta taacttctgt tacacagctt atgtattgtt aacatttaag    960
```

```
tgtaaaccat gccacagcta acacttaaaa atgaaaacta attagttctt gcttagggaa   1020

aatgccaggt atgaagtatg gcatatactt gacactgtcc tgtgtaaccc tttactttgc   1080

tcaggctttc aagattgagt ctttttttccc ccaaattagg ttaacatgca tttgacccca   1140

acctgtgggg tttgagtaag ctggaaatct gtgacggtag gctttctagt gtcacgaggt   1200

ggtggtgact gaaggaaaag ctgggatcac aggttccttc tgatggagag gaaggtttat   1260

ttctatgccc ctcccaccac cctccaccta gagctcaccc aagcctgctc cagtcccagg   1320

ggcaggccat tctgcaaaag caggacctca cagaaacaag ggctgggttg aggtcacccc   1380

cttcagagtt ggttcctggc cagatgggta agaggcattt gtaattttaa aaatgtgaaa   1440

cttgggtttg gtgttttctt ctaagtgcct aaataagcaa gccaggctgt tgatatttta   1500

gccagagaaa tcggcaagcc aagattaacc cgaatctgaa gtttagaatc ttgagtttgc   1560

atctgcatca tatcatgctg ttttgatgag gaaacatttg ccactgagga gttggaggga   1620

gggcaagacg acagtgttaa gtcagatcat ttaatggttt cccctaagcc ctggaaaaat   1680

atttgaaaga atggcagcaa aaaggttaag aaagcaagcc agatttactg cacaatatgc   1740

agtacccagt actactttaa atcccaagag aacagtgtga tgtctaatat atacaggtct   1800

atgaaaatac tgtggaataa gcccaggaag gttagatgtg tttgcaaata agttgcccaa   1860

agggtccccc tctaagtaaa acaaatattc agaccacagg ctttaatgta aactgtcaaa   1920

aagtgggatg tggaggattt ttgttaagtg tcaatcgaag ttaaaaagca agggtttttg   1980

gccaggcgtg gtggctcacg cctgtaatcc cagcactttg ggaggccgag gccggcaaat   2040

cacctaaggt caggagttcg agaccagcct ggccaacatg gtgaaacccc gtctctacta   2100

aaaaaaaaaa aaaa                                                     2114
```

```
<210> SEQ ID NO 5
<211> LENGTH: 3450
<212> TYPE: DNA
<213> ORGANISM: Homo sapiens

<400> SEQUENCE: 5

ggcgcggagc ggtgcggcgg cgggaggcgg aggcgagggt gcgatggcgc ggagcccggg     60

acgcgcgtac gccctgctgc ttctcctgat ctgctttaac gttggaagtg gacttcactt    120

acaggtctta agcacaagaa atgaaaataa gctgcttcct aaacatcctc atttagtgcg    180

gcaaaagcgc gcctggatca ccgccccccgt ggctcttcgg gagggagagg atctgtccaa    240

gaagaatcca attgccaaga tacattctga tcttgcagaa gaaagaggac tcaaaattac    300

ttacaaatac actggaaaag ggattacaga gccacctttt ggtatatttg tctttaacaa    360

agatactgga gaactgaatg ttaccagcat tcttgatcga gaagaaacac catttttttct    420

gctaacaggt tacgctttgg atgcaagagg aaacaatgta gagaaaccct tagagctacg    480

cattaaggtt cttgatatca atgacaacga accagtgttc acacaggatg tctttgttgg    540

gtctgttgaa gagttgagtg cagcacatac tcttgtgatg aaaatcaatg caacagatgc    600

agatgagccc aataccctga attcgaaaat ttcctataga atcgtatctc tggagcctgc    660

ttatcctcca gtgttctacc taaataaaga tacaggagag atttatacaa ccagtgttac    720

cttggacaga gaggaacaca gcagctacac tttgacagta gaagcaagag atggcaatgg    780

agaagttaca gacaaacctg taaaacaagc tcaagttcag attcgtattt tggatgtcaa    840

tgacaatata cctgtagtag aaaataaagt gcttgaaggg atggttgaag aaaatcaagt    900
```

```
caacgtagaa gttacgcgca taaaagtgtt cgatgcagat gaaataggtt ctgataattg    960
gctggcaaat tttacatttg catcaggaaa tgaaggaggt tatttccaca tagaaacaga   1020
tgctcaaact aacgaaggaa ttgtgaccct tattaaggaa gtagattatg aagaaatgaa   1080
gaatcttgac ttcagtgtta ttgtcgctaa taaagcagct tttcacaagt cgattaggag   1140
taaatacaag cctacaccca ttcccatcaa ggtcaaagtg aaaaatgtga aagaaggcat   1200
tcattttaaa agcagcgtca tctcaattta tgttagcgag agcatggata gatcaagcaa   1260
aggccaaata attggaaatt ttcaagcttt tgatgaggac actggactac cagcccatgc   1320
aagatatgta aaattagaag atagagataa ttggatctct gtggattctg tcacatctga   1380
aattaaactt gcaaaacttc ctgattttga atctagatat gttcaaaatg gcacatacac   1440
tgtaaagatt gtggccatat cagaagatta tcctagaaaa accatcactg gcacagtcct   1500
tatcaatgtt gaagacatca acgacaactg tcccacactg atagagcctg tgcagacaat   1560
ctgtcacgat gcagagtatg tgaatgttac tgcagaggac ctggatggac acccaaacag   1620
tggccctttc agtttctccg tcattgacaa accacctggc atggcagaaa aatggaaaat   1680
agcacgccaa gaaagtacca gtgtgctgct gcaacaaagt gagaaaaagc ttgggagaag   1740
tgaaattcag ttcctgattt cagacaatca gggttttagt tgtcctgaaa agcaggtcct   1800
tacactcaca gtttgtgagt gtctgcatgg cagcggctgc agggaagcac agcatgactc   1860
ctatgtgggc ctgggacccg cagcaattgc gctcatgatt ttggcctttc tgctcctgct   1920
attggtacca cttttactgc tgatgtgcca ttgcggaaag ggcgccaaag gctttacccc   1980
catacctggc accatagaga tgctgcatcc ttggaataat gaaggagcac cacctgaaga   2040
caaggtggtg ccatcatttc tgccagtgga tcaagggggc agtctagtag gaagaaatgg   2100
agtaggaggt atggccaagg aagccacgat gaaaggaagt agctctgctt ccattgtcaa   2160
agggcaacat gagatgtccg agatggatgg aaggtgggaa gaacacagaa gcctgctttc   2220
tggtagagct acccagttta caggggccac aggcgctatc atgaccactg aaaccacgaa   2280
gaccgcaagg gccacagggg cttccagaga catggccgga gctcaggcag ctgctgttgc   2340
actgaacgaa gaattcttaa gaaattattt cactgataaa gcggcctctt acactgagga   2400
agatgaaaat cacacagcca aagattgcct tctggtttat tctcaggaag aaactgaatc   2460
gctgaatgct tctattggtt gttgcagttt tattgaagga gagctagatg accgcttctt   2520
agatgatttg ggacttaaat tcaagacact agctgaagtt tgcctgggtc aaaaaataga   2580
tataaataag gaaattgagc agagacaaaa acctgccaca gaaacaagta tgaacacagc   2640
ttcacattca ctctgtgagc aaactatggt taattcagag aatacctact cctctggcag   2700
tagcttccca gttccaaaat ctttgcaaga agccaatgca gagaaagtaa ctcaggaaat   2760
agtcactgaa agatctgtgt cttctaggca ggcgcaaaag gtagctacac ctcttcctga   2820
cccaatggct tctagaaatg tgatagcaac agaaacttcc tatgtcacag ggtccactat   2880
gccaccaacc actgtgatcc tgggtcctag ccagccacag agccttattg tgacagagag   2940
ggtgtatgct ccagcttcta ccttggtaga tcagccttat gctaatgaag gtacagttgt   3000
ggtcactgaa agagtaatac agcctcatgg gggtggatcg aatcctctgg aaggcactca   3060
gcatcttcaa gatgtacctt acgtcatggt gagggaaaga gagagcttcc ttgcccccag   3120
ctcaggtgtg cagcctactc tggccatgcc taatatagca gtaggacaga atgtgacagt   3180
gacagaaaga gttctagcac ctgcttccac tctgcaatcc agttaccaga ttcccactga   3240
aaattctatg acggctagga acaccacggt gtctggagct ggagtccctg gccctctgcc   3300
```

```
agattttggt ttagaggaat ctggtcattc taattctacc ataaccacat cttccaccag   3360

agttaccaag catagcactg tacagcattc ttactcctaa acagcagtca gccacaaact   3420

gacccagagt ttaattagca gtgactaatt                                    3450
```

<210> SEQ ID NO 6
<211> LENGTH: 2398
<212> TYPE: DNA
<213> ORGANISM: Homo sapiens

<400> SEQUENCE: 6

```
ccgcagagga gcctcggcca ggctagccag ggcgccccca gcccctcccc aggccgcgag     60

cgcccctgcc gcggtgcctg gcctcccctc ccagactgca gggacagcac ccggtaactg    120

cgagtggagc ggaggacccg agcggctgag gagagaggag gcggcggctt agctgctacg    180

gggtccggcc ggcgccctcc cgaggggggc tcaggaggag gaaggaggac ccgtgcgaga    240

atgcctctgc cctggagcct tgcgctcccg ctgctgctct cctgggtggc aggtggtttc    300

gggaacgcgg ccagtgcaag gcatcacggg ttgttagcat cggcacgtca gcctggggtc    360

tgtcactatg gaactaaact ggcctgctgc tacggctgga gaagaaacag caagggagtc    420

tgtgaagcta catgcgaacc tggatgtaag tttggtgagt gcgtgggacc aaacaaatgc    480

agatgctttc caggatacac cgggaaaacc tgcagtcaag atgtgaatga gtgtggaatg    540

aaaccccggc catgccaaca cagatgtgtg aatacacacg gaagctacaa gtgcttttgc    600

ctcagtggcc acatgctcat gccagatgct acgtgtgtga actctaggac atgtgccatg    660

ataaactgtc agtacagctg tgaagacaca gaagaagggc cacagtgcct gtgtccatcc    720

tcaggactcc gcctggcccc aaatggaaga gactgtctag atattgatga atgtgcctct    780

ggtaaagtca tctgtcccta caatcgaaga tgtgtgaaca catttggaag ctactactgc    840

aaatgtcaca ttggtttcga actgcaatat atcagtggac gatatgactg tatagatata    900

aatgaatgta ctatggatag ccatacgtgc agccaccatg ccaattgctt caatacccaa    960

gggtccttca agtgtaaatg caagcaggga tataaaggca atggacttcg gtgttctgct   1020

atccctgaaa attctgtgaa ggaagtcctc agagcacctg gtaccatcaa agacagaatc   1080

aagaagttgc ttgctcacaa aaacagcatg aaaaagaagg caaaaattaa aaatgttacc   1140

ccagaaccca ccaggactcc tacccctaag gtgaacttgc agcccttcaa ctatgaagag   1200

atagtttcca gaggcgggaa ctctcatgga ggtaaaaaag ggaatgaaga gaaaatgaaa   1260

gaggggcttg aggatgagaa aagagaagag aaagccctga agaatgacat agaggagcga   1320

agcctgcgag gagatgtgtt tttccctaag gtgaatgaag caggtgaatt cggcctgatt   1380

ctggtccaaa ggaaagcgct aacttccaaa ctggaacata aagatttaaa tatctcggtt   1440

gactgcagct tcaatcatgg gatctgtgac tggaaacagg atagagaaga tgattttgac   1500

tggaatcctg ctgatcgaga taatgctatt ggcttctata tggcagttcc ggccttggca   1560

ggtcacaaga aagacattgg ccgattgaaa cttctcctac ctgacctgca accccaaagc   1620

aacttctgtt tgctctttga ttaccggctg gccggagaca aagtcgggaa acttcgagtg   1680

tttgtgaaaa acagtaacaa tgccctggca tgggagaaga ccacgagtga ggatgaaaag   1740

tggaagacag ggaaaattca gttgtatcaa ggaactgatg ctaccaaaag catcattttt   1800

gaagcagaac gtggcaaggg caaaaccggc gaaatcgcag tggatggcgt cttgcttgtt   1860

tcaggcttat gtccagatag ccttttatct gtggatgact gaatgttact atctttatat   1920
```

```
ttgactttgt atgtcagttc cctggttttt ttgatattgc atcataggac ctctggcatt   1980

ttagaattac tagctgaaaa attgtaatgt accaacagaa atattattgt aagatgcctt   2040

tcttgtataa gatatgccaa tatttgcttt aaatatcata tcactgtatc ttctcagtca   2100

tttctgaatc tttccacatt atattataaa atatggaaat gtcagtttat ctcccctcct   2160

cagtatatct gatttgtata agtaagttga tgagcttctc tctacaacat ttctagaaaa   2220

tagaaaaaaa agcacagaga aatgtttaac tgtttgactc ttatgatact tcttggaaac   2280

tatgacatca aagatagact tttgcctaag tggcttagct gggtctttca tagccaaact   2340

tgtatattta aattctttgt aataataata tccaaatcat caaaaaaaaa aaaaaaaa     2398


<210> SEQ ID NO 7
<211> LENGTH: 2960
<212> TYPE: DNA
<213> ORGANISM: Homo sapiens

<400> SEQUENCE: 7

accaggtgct ccataatgag tcaaaaggga gccccacctc ggcttaccct gagcggaagg     60

ggagccccac gcctgggttt tccactcgaa gaggaagtcc aactacagga tttatcgagc    120

agaaggggag ccccacctca gcctaccccg agcgcagggg tagtccggtg ccccccgtgc    180

cggagcgcag gagcagtccg gtgccccccg tgccggagcg caggggcagc ctcaccctta    240

ccatctccgg ggagtccccg aaggccgggc ccgcggagga ggggccgagc ggccccatgg    300

aagtcttgcg caaaggctcc ttgcgtctta ggcagctgct gagccccaag ggcgagcggc    360

gcatggagga tgagggtggc ttcccagtgc cgcaggagaa cggccaaccc gagagcccgc    420

ggcgtctgtc actgggccag ggtgacagca cggaggctgc cacagaagag cggggtccgc    480

gggcgcgcct gtcctcagcc acggccaacg ccttgtacag cagcaacctt cgggatgaca    540

cgaaggccat tctggagcag atcagtgccc acggccagaa gcaccgtgcg gtccctgccc    600

cgagccccgg cccgacccac aacagccccg agctaggccg tccaccggct gctggcgtcc    660

tggccccaga tatgtccgac aaggacaagt gttcagccat cttccgctcg gacagcttgg    720

ggacccaggg ccggctgagc cgcacgctgc cagccagcgc ggaggagcgc gatcggctgc    780

tgcgccgcat ggagagcatg cgcaaggaga agcgcgtgta cagccgcttc gaggtcttct    840

gcaagaaaga ggaggccagc agccctgggg caggggaagg ccccgcggag gagggcacca    900

gggacagcaa ggtgggcaag ttcgtgccca agatcctggg cacgttcaaa agcaagaagt    960

gagtcttctg gcctggcaac ccaggccagg gtgcccgcat cgctgccccg gtcatccaga   1020

agccccgcgg aacagagagc cctgctcatg tgcttgagca gcggctgtca ggccacggcc   1080

gcttggggct tggctgagtg cgccagacct cggctccact ggaggctcac ctggcagctg   1140

ccgtctctgc cccctggcct ccccaacgct ggggctgcac ccctcgccac cagtgccttt   1200

ctcccctcag caccttcatc tctgcaccgt cagccttgcg tggcgcagcg tctggctccg   1260

ccatctcttt gtgcctcagt cccccccgcc ccctttattt ttttgagatc tagggctgga   1320

gtgcagttga gcggtctggg ctcactgcaa cctctgcctc ccgggttcca gcgattctcc   1380

tgcctcagcc tcctgagtag ctgggattac agatgtatgc taccacgccc aggtagtttt   1440

tgtattttta gtagagacag ggtttcacta tgttggccag gctggtctcc aactcctggc   1500

ctcaaatgat cagcccgctt cagcctccca aagtgggggg attacaggcg tgagccttgc   1560

accccgctaa gtcccctatc ctcttgcaag ggtctcacct ctgtgcctca attcctcatt   1620

ctctgggccc ttctcctcct cagggcctcc tgttctcagg gcctcccccc tccccgctcc   1680
```

```
ctccctctct caaggtctcc tccttccctc cccccccccc cgtctccccc ctccccccgcc   1740

tgggcttcac ttcctttcct acttggattc tcctgctcgc tgcctcccag catctttttt   1800

ggaggcccgt ctcttgctgt ggggaagact gggctggctg cgggcagttt gcaaggggtg   1860

ggtggggcgg gggggggagc tggaccagaa gatgcccctt ggagtggcaa ggaagctgga   1920

cagggcaggc ctctggggac gggacacagg gaagcccgaa ggggcgcctt ggccaggtct   1980

gccatctcct ccagcgaggc tctggccagc actgggtgag agtggggagg gggcactggc   2040

ctttgcagca cagtaaaaca tggtccagac aacctgtggc ccggcctca tgagcacccc   2100

ctgcacaggc ccagcccaag ccaggcgcta gaagggctgg ttgtggagtg cttatccttg   2160

acaggtatgg ggccaggtga gggcagggga caaggtgcag ctgaggccga gcccaactag   2220

gtcctgggca cccctgcagg tgggagtggt ccttgtcctc ctggtatcca gcagacaccc   2280

ccctctcccc accagcccca ttctcaggtc ctttcctctt tgtcaccaac accaagaatc   2340

tgtccagggt tcttggctta tcttttatct cttttcactc ctagagagga attgcaattg   2400

actcagaatg acacattttg gcaccacgtg tgtagaaagc cccactgtt agatgatagc   2460

ctcgtgaaat tcatgtttct gtattctcct atttcttttc aaaaactaat ttttttttta   2520

gtgtaataaa tcctaagagg gaactgattt aagaaacaag gccgccaaac aaaggcagca   2580

gttccgactc cagcagctgg gaaaggaagg aaagtgaccc cactttcact cctgcacagc   2640

ccactggtta ccaaaaccac cgtgcaagtc gggatgacag cagggacttc tggccaggtg   2700

ggaaaggtgc ctggaagcgg gatgcgcctg tgcgtctctt ggccatgatg ttcttgtggg   2760

catgttattc ttggtgctgc ctggggtgtt gctgagcgga caggctctcc agctggagtc   2820

catggagagg ccagaggctg gcggccctgc ctgggccttc ggagcctcct gcctgcaccc   2880

tccacctctt ctaaaccatg atgtggcaca ttttggtgtt aataaaacac aacacacaaa   2940

gtaaaaaaaa aaaaaaaaaa                                               2960
```

<210> SEQ ID NO 8
<211> LENGTH: 2811
<212> TYPE: DNA
<213> ORGANISM: Homo sapiens

<400> SEQUENCE: 8

```
acacgtccaa cgccagcatg cagcgcccgg gcccccgcct gtggctggtc ctgcaggtga     60

tgggctcgtg cgccgccatc agctccatgg acatggagcg cccgggcgac ggcaaatgcc    120

agcccatcga gatcccgatg tgcaaggaca tcggctacaa catgactcgt atgcccaacc    180

tgatgggcca cgagaaccag cgcgaggcag ccatccagtt gcacgagttc gcgccgctgg    240

tggagtacgg ctgccacggc cacctccgct tcttcctgtg ctcgctgtac gcgccgatgt    300

gcaccgagca ggtctctacc cccatccccg cctgccgggt catgtgcgag caggcccggc    360

tcaagtgctc cccgattatg gagcagttca acttcaagtg gcccgactcc ctggactgcc    420

ggaaactccc caacaagaac gaccccaact acctgtgcat ggaggcgccc aacaacggct    480

cggacgagcc cacccggggc tcgggcctgt tcccgccgct gttccggccg cagcggcccc    540

acagcgcgca ggagcacccg ctgaaggacg ggggcccgg gcgcggcggc tgcgacaacc     600

cgggcaagtt ccaccacgtg gagaagagcg cgtcgtgcgc gccgctctgc acgcccggcg    660

tggacgtgta ctggagccgc gaggacaagc gcttcgcagt ggtctggctg gccatctggg    720

cggtgctgtg cttcttctcc agcgccttca ccgtgctcac cttcctcatc gacccggccc    780
```

```
gcttccgcta ccccgagcgc cccatcatct tcctctccat gtgctactgc gtctactccg     840

tgggctacct catccgcctc ttcgccggcg ccgagagcat cgcctgcgac cgggacagcg     900

gccagctcta tgtcatccag gagggactgg agagcaccgg ctgcacgctg gtcttcctgg     960

tcctctacta cttcggcatg gccagctcgc tgtggtgggt ggtcctcacg ctcacctggt    1020

tcctggccgc cggcaagaag tggggccacg aggccatcga agccaacagc agctacttcc    1080

acctggcagc ctgggccatc ccggcggtga agaccatcct gatcctggtc atgcgcaggg    1140

tggcgggggga cgagctcacc ggggtctgct acgtgggcag catggacgtc aacgcgctca   1200

ccggcttcgt gctcattccc ctggcctgct acctggtcat cggcacgtcc ttcatcctct    1260

cgggcttcgt ggccctgttc cacatccgga gggtgatgaa gacgggcggc gagaacacgg    1320

acaagctgga gaagctcatg gtgcgtatcg ggctcttctc tgtgctgtac accgtgccgg    1380

ccacctgtgt gatcgcctgc tacttttacg aacgcctcaa catggattac tggaagatcc    1440

tggcggcgca gcacaagtgc aaaatgaaca accagactaa aacgctggac tgcctgatgg    1500

ccgcctccat ccccgccgtg gagatcttca tggtgaagat ctttatgctg ctggtggtgg    1560

ggatcaccag cgggatgtgg atttggacct ccaagactct gcagtcctgg cagcaggtgt    1620

gcagccgtag gttaaagaag aagagccgga gaaaaccggc cagcgtgatc accagcggtg    1680

ggatttacaa aaaagcccag catccccaga aaactcacca cgggaaatat gagatccctg    1740

cccagtcgcc cacctgcgtg tgaacagggc tggagggaag ggcacagggg cgcccggagc    1800

taagatgtgg tgcttttctt ggttgtgttt ttctttcttc ttcttctttt tttttttttt    1860

ataaaagcaa aagagaaata cataaaaaag tgtttaccct gaaattcagg atgctgtgat    1920

acactgaaag gaaaaatgta cttaaagggt tttgttttgt tttggttttc cagcgaaggg    1980

aagctcctcc agtgaagtag cctcttgtgt aactaatttg tggtaaagta gttgattcag    2040

ccctcagaag aaaacttttg tttagagccc tccgtaaata tacatctgtg tatttgagtt    2100

ggctttgcta cccatttaca aataagagga cagataactg ctttgcaaat tcaagagcct    2160

cccctgggtt aacaaatgag ccatccccag ggcccacccc caggaaggcc acagtgctgg    2220

gcggcatccc tgcagaggaa agacaggacc cggggcccgc ctcacacccc agtggatttg    2280

gagttgctta aaatagactc tggccttcac caatagtctc tctgcaagac agaaacctcc    2340

atcaaacctc acatttgtga actcaaacga tgtgcaatac attttttttct ctttccttga   2400

aaataaaaag agaaacaagt attttgctat atataaagac aacaaaagaa atctcctaac    2460

aaaagaacta agaggcccag ccctcagaaa cccttcagtg ctacattttg tggcttttta    2520

atggaaacca agccaatgtt atagacgttt ggactgattt gtggaaagga ggggggaaga    2580

gggagaagga tcattcaaaa gttacccaaa gggcttattg actctttcta ttgttaaaca    2640

aatgatttcc acaaacagat caggaagcac taggttggca gagacacttt gtctagtgta    2700

ttctcttcac agtgccagga aagagtggtt tctgcgtgtg tatatttgta atatatgata    2760

tttttcatgc tccactattt tattaaaaat aaaatatgtt ctttaaaaaa a             2811
```

<210> SEQ ID NO 9
<211> LENGTH: 2428
<212> TYPE: DNA
<213> ORGANISM: Homo sapiens

<400> SEQUENCE: 9

```
agtgttacct tggagcctac aatgagaggt atttcaaaat gagtgaagca tgactctcac      60

agatgaaggc ctagacgcag gatctttaat gaaaaaacac ttgggccact tcaagacgac     120
```

```
aaacgctcac tgggcaaaac accttcactg aaaagagacc tcatattatg caaaaaaaat    180
cttaaaaggc ctctgccttc agaagttaca agatgatcaa ttcaacctcc acacagcctc    240
cagatgaatc ctgctctcag aacctcctga tcactcagca gatcattcct gtgctgtact    300
gtatggtctt cattgcagga atcctactca atggagtgtc aggatggata ttcttttacg    360
tgcccagctc tgagagtttc atcatctatc tcaagaacat tgttattgct gactttgtga    420
tgagcctgac ttttcctttc aagatccttg gtgactcagg ccttggtccc tggcagctga    480
acgtgtttgt gtgcagggtc tctgccgtgc tcttctacgt caacatgtac gtcagcattg    540
tgttctttgg gctcatcagc tttgacagat attataaaat tgtaaagcct ctttggactt    600
ctttcatcca gtcagtgagt tacagcaaac ttctgtcagt gatagtatgg atgctcatgc    660
tcctccttgc tgttccaaat attattctca ccaaccagag tgttagggag gttacacaaa    720
taaaatgtat agaactgaaa agtgaactgg gacggaagtg gcacaaagca tcaaactaca    780
tcttcgtggc catcttctgg attgtgtttc ttttgttaat cgttttctat actgctatca    840
caaagaaaat ctttaagtcc caccttaagt caagtcggaa ttccacttcg gtcaaaaaga    900
aatctagccg caacatattc agcatcgtgt ttgtgttttt tgtctgtttt gtaccttacc    960
atattgccag aatcccctac acaaagagtc agaccgaagc tcattacagc tgccagtcaa   1020
aagaaatctt gcggtatatg aaagaattca ctctgctact atctgctgca aatgtatgct   1080
tggaccctat tatttatttc tttctatgcc agccgtttag ggaaatctta tgtaagaaat   1140
tgcacattcc attaaaagct cagaatgacc tagacatttc cagaatcaaa agaggaaata   1200
caacacttga aagcacagat actttgtgag ttcctaccct cttccaaaga aagaccacgt   1260
gtgcatgttg tcatcttcaa ttacataaca gaaatcaata agatatgtgc cctcatcata   1320
aatatcatct ctagcactgc catccaattt agttcaataa aattcaaata taagtttcca   1380
tgctttttttg taacatcaaa gaaaacatac ccatcagtaa tttctctaat actgaccttt   1440
ctattctcta ttaataaaaa attaatacat acaattattc aattctatta tattaaaata   1500
agttaaagtt tataaccact agtctggtca gttaatgtag aaatttaaat agtaaataaa   1560
acacaacata atcaaagaca actcactcag gcatcttctt tctctaaata ccagaatcta   1620
gtatgtaatt gttttcaaca ctgtccttaa agactaactt gaaagcaggc acagtttgat   1680
gaagggctag agagctgttt gcaataaaaa gtcaggtttt tttcctgatt tgaagaagca   1740
ggaaaagctg acacccagac aatcacttaa gaaacccctt attgatgtat ttcatggcac   1800
tgcaaaggaa gaggaatatt aattgtatac ttagcaagaa aattttttttt ttctgatagc   1860
actttgagga tattagatac atgctaaata tgttttctac aaagacttac gtcatttaat   1920
gagcctgggg ttctggtgtt agaatatttt taagtaggct ttactgagag aaactaaata   1980
ttggcatacg ttatcagcaa cttcccctgt tcaatagtat gggaaaaata agatgactgg   2040
gaaaaagaca cacccacacc gtagaacata tattaatcta ctggcgaatg ggaaaggaga   2100
ccattttctt agaaagcaaa taaacttgat ttttttaaat ctaaaattta cattaatgag   2160
tgcaaaataa cacataaaat gaaaattcac acatcacatt tttctggaaa acagacggat   2220
tttacttctg gagacatggc atacggttac tgacttatga gctaccaaaa ctaaattctt   2280
tctctgctat taactggcta gaagacattc atctattttt caaatgttct ttcaaaacat   2340
ttttataagt aatgtttgta tctatttcat gctttactgt ctatatacta ataaagaaat   2400
gttttaatac cgaaaaaaaa aaaaaaaa                                      2428
```

<210> SEQ ID NO 10
<211> LENGTH: 4205
<212> TYPE: DNA
<213> ORGANISM: Homo sapiens

<400> SEQUENCE: 10
gaagcgggct gggaggcgtc ggcggcggca gcgcacgtgg tgacgtgcga gggggtgcgg 60
cgcgagcggt cggcggcggc ggaggcagtg tctcccggtc gcgcgtggag gtcggtcgct 120
cagagctgct gggcgcagtt tctccgcctg ctgcttcggc gcggctgtat cggcgagcga 180
gcgagttccc gcgagttctc ggtggcgctc cccttccttt tcagtctcca cggactggcc 240
cctcgtcctt ctacttgacc gctcccgtct tccgccgcct tctggcgctt tccgttgggc 300
cgattcccgc ccgcttcctc ctgcttccca tcgaagctct agaaatgaat gtttccatct 360
cttcagagat gaaccagatt atgatgcatc attatcacag aagaaattcg tgtctatagc 420
ttttaaggac ttgattacat cattttcaag cctgatagtt ttggaatcac cattagagct 480
taagacacac ctgccttcat ttcaaccacc tgtcttcata ccctgacgaa gtgcaccttt 540
taacactcct ttgtccttgg attacttaag agttcccaga aatacatttg ccaccaacag 600
agtagccaaa tttataagga aaaatgattc ccaatggata tttgatgttt gaggatgaaa 660
attttattga gtcttctgtt gccaaattaa atgccctgag gaaaagtggc cagttctgtg 720
atgttcgact tcaggtctgt ggccatgaaa tgttagcaca cagagcagtg ctagcttgct 780
gcagtcccta tttatttgaa atctttaata gtgatagtga tcctcatgga atttctcacg 840
ttaaatttga tgatctcaat ccagaagctg ttgaagtctt gttgaattat gcctacactg 900
ctcagttgaa agcagataag gaattggtaa aagatgttta ttctgcagca aaaaagctga 960
agatggatcg agtaaagcag gtttgtggtg attatttact gtctagaatg gatgttacca 1020
gctgcatctc ttaccgaaat tttgcaagtt gtatgggaga ctcccgtttg ttgaataagg 1080
ttgatgctta tattcaggag catttgttac aaatttctga agaggaggag tttcttaagc 1140
ttccaaggct aaagttggag gtaatgcttg aagataatgt ttgcttgccc agcaatggca 1200
aattatatac aaaggtaatc aactgggtgc agcgtagcat ctgggagaat ggagacagtc 1260
tggaagagct gatggaagag gttcaaacct tgtactactc agctgatcac aagctgcttg 1320
atgggaacct actagatgga caggctgagg tgtttggcag tgatgatgac cacattcagt 1380
ttgtgcagaa aaagccacca cgtgagaatg gccataagca gataagtagc agttcaactg 1440
gatgtctctc ttctccaaat gctacagtac aaagccctaa gcatgagtgg aaaatcgttg 1500
cttcagaaaa gacttcaaat aacacttact tgtgcctggc tgtgctggat ggtatattct 1560
gtgtcatttt tcttcatggg agaaacagcc cacagagctc accaacaagt actccaaaac 1620
taagtaagag tttaagcttt gagatgcaac aagatgagct aatcgaaaag cccatgtctc 1680
ctatgcagta cgcacgatct ggtctgggaa cagcagagat gaatggcaaa ctcatagctg 1740
caggtggcta taacagagag gaatgtcttc gaacagtcga atgctataat ccacatacag 1800
atcactggtc ctttcttgct cccatgagaa caccaagagc ccgatttcaa atggctgtac 1860
tcatgggcca gctctatgtg gtaggtggat caaatggcca ctcagatgac ctgagttgtg 1920
gagagatgta tgattcaaac atagatgact ggattcctgt tccagaattg agaactaacc 1980
gttgtaatgc aggagtgtgt gctctgaatg gaaagttata catcgttggt ggctctgatc 2040
catatggtca aaaaggactg aaaaattgtg atgtatttga tcctgtaaca aagttgtgga 2100
caagctgtgc ccctcttaac attcggagac accagtctgc agtctgtgag cttggtggtt 2160

```
atttgtacat aatcggaggt gcagaatctt ggaattgtct gaacacagta gaacgataca   2220
atcctgaaaa taatacctgg actttaattg cacccatgaa tgtggctagg cgaggagctg   2280
gagtggctgt tcttaatgga aaactgtttg tatgtggtgg ctttgatggt tctcatgcca   2340
tcagttgtgt ggaaatgtat gatccaacta gaaatgaatg gaagatgatg ggaaatatga   2400
cttcaccaag gagcaatgct gggattgcaa ctgtagggaa caccatttat gcagtgggag   2460
gattcgatgg caatgaattt ctgaatacgg tggaagtcta taaccttgag tcaaatgaat   2520
ggagccccta tacaaagatt ttccagtttt aacaaattta agaccctctc aaactaacag   2580
gcttagtgat gtaattatgg ttagtagagg tacacttgtg aataaagagg gtgggtgggt   2640
atagatgttg ctaacagcaa cacaaagctt ttgcatattg catactatta aacatgctgt   2700
acatactttt tgggtttatt tggaaaggaa tgcaaagatg aaggtctgtt ttgtgtactt   2760
ttaagacttt ggttatttta ctttttggaa aagaataaac caagaattga ttgggcacat   2820
catttcaaga agtcccctct cctccacatt tgttttgcca atttgcacat taaatgactc   2880
ttccctcaaa tgtgtactat ggggtaaaag ggtagggtt taaagatgta gacagttggg   2940
ttttttaagg gccctttttc aataactgga acactctata acaaaggata cttatttaaa   3000
tagatgacat tgactatttt tgtttttatt aaaaggaagc ttacatgcct accaatattt   3060
aatcttttat gattgccttt ttataacttt ttatattctc agcagagtgc tttaccaatt   3120
gaagtaaaat gtggcaggct ggagttattg aagcagagtg gcagtcttca gtttgcagag   3180
taggggtctg tcttttaaac tctgagtgca aacttcagag ttcttgcctt ggctgcagtt   3240
tttttccttc aagaatgcag tactaacatt tatttgagtg gagttactga acagtaacat   3300
agctgtgatt tttggtattt gaaacactgg ttttaaatat tttgacttgt tgagggtatg   3360
ttttatatag caagacatta tatagcagta aaaaatggtg ttttatcttc tatataattc   3420
ctgtttttat tattaacaaa acagtcctaa atagcagccc tcaattgtga aaaaatttac   3480
tttaaactac attaggttgt gaatgcaggt tttatcagaa ctatgttttt gttcagttta   3540
tctgttcata tggataaata ttggttggga tgacttggtg tctaatgtgt agtgctacac   3600
acctaactta tggggccaaa atagcatgtc ctaatgcttg ctgctgattt aaacacatta   3660
aaggtacttt gcaggaaatc cttgcaccat gggattaata tccaattgct gcttgtacac   3720
tcattcatta ctaaaagttt tgagaaattt ttttttccag taatgagctt aagaaatttg   3780
tggaaaataa ctcacctggc atcttacatc tgaaataagg aatgatataa ggttttttttt   3840
tctcacagaa gatgaagcac acaggaacct aatgggccaa ctgggatgag gtgactattc   3900
tgagatgact attcagtggc taacttgggt taggaagaaa ataattaggt attttctcca   3960
aatgttcact ggtactctgc cactttattt ctctcatctg ttacacaaag aaccaccagg   4020
aaagcaaatc agtttggttg gtaactctgt aattcctaac tatcactggt ttggttctgg   4080
actaaaacta cattgacaga ttgaatttgc ctaatatgat gactgttttt aatatggatc   4140
tgtatgtgtt ctattcagca caaggaaata aaattttagt tgaggattca gcactaaaaa   4200
aaaaa                                                               4205
```

<210> SEQ ID NO 11
<211> LENGTH: 3796
<212> TYPE: DNA
<213> ORGANISM: Homo sapiens

<400> SEQUENCE: 11

```
gcatactgct agtggcgcgc ggaggagcga cgcgtggaga agcggcccac gtgtctgccc      60
agagtcaagt cctgtgttct tcccgctcct tacgcatccg cggtccaggg cgccctttca     120
gccccgctgg tgttcgccca ccccgggccg cgtgagtggg gccccacgca gctccccgca     180
ctccgtgggc caacttggcc aagcaactct gtccggggag cggtgcttgc ggggggtgag     240
taccgggcac tgcgcatgcg gagctccaaa ttcaaacagc tgttttcaga ggctggaggg     300
cgggcggact ggtagcagct ggggctagga gaggctttct ctaggaggcg gccgctcggg     360
agccatggtg gaccggggcc ctctgctcac ctcggccatc atcttctacc tggccatcgg     420
ggcggcgatc ttcgaagtgc tggaggagcc acactggaag gaggccaaga aaaactacta     480
cacacagaag ctgcatctgc tcaaggagtt cccgtgcctg ggtcaggagg gcctggacaa     540
gatcctagag gtggtatctg atgctgcagg acagggtgtg gccatcacag ggaaccagac     600
cttcaacaac tggaactggc ccaatgcaat gatttttgca gcgaccgtca ttaccaccat     660
tggatatggc aatgtggctc ccaagacccc cgccggtcgc ctcttctgtg ttttctatgg     720
tctcttcggg gtgccgctct gcctgacgtg gatcagtgcc ctgggcaagt tcttcggggg     780
acgtgccaag agactagggc agttccttac caagagaggt gtgagtctgc ggaaggcgca     840
gatcacgtgc acagtcatct tcatcgtgtg gggcgtccta gtccacctgg tgatcccacc     900
cttcgtattc atggtgactg aggggtggaa ctacatcgag ggcctctact actccttcat     960
caccatctcc accatcggct tcggtgactt tgtggccggt gtgaacccca gcgccaacta    1020
ccacgccctg taccgctact tcgtggagct ctggatctac ttggggctgg cctggctgtc    1080
cctttttgtc aactggaagg tgagcatgtt tgtggaagtc cacaaagcca ttaagaagcg    1140
gcggcggcga cggaaggagt cctttgagag ctccccacac tcccggaagg ccctgcaggt    1200
gaaggggagc acagcctcca aggacgtcaa catcttcagc tttctttcca agaaggaaga    1260
gacctacaac gacctcatca agcagatcgg gaagaaggcc atgaagacaa gcgggggtgg    1320
ggagacgggc ccgggcccag ggctggggcc tcaaggcggt gggctcccag cactgccccc    1380
ttccctggtg cccctggtag tctactccaa gaaccgggtg cccaccttgg aagaggtgtc    1440
acagacactg aggagcaaag gccacgtatc aaggtcccca gatgaggagg ctgtggcacg    1500
ggcccctgaa gacagctccc ctgcccccga ggtgttcatg aaccagctgg accgcatcag    1560
cgaggaatgc gagccatggg acgcccagga ctaccaccca ctcatcttcc aggacgccag    1620
catcaccttc gtgaacacgg aggctggcct ctcagacgag gagacctcca agtcctcgct    1680
agaggacaac ttggcagggg aggagagccc ccagcagggg gctgaagcca aggcgcccct    1740
gaacatgggc gagttcccct cctcctccga gtccaccttc accagcactg agtctgagct    1800
ctctgtgcct tacgaacagc tgatgaatga gtacaacaag gctaacagcc ccaagggcac    1860
atgaggcagg gccggctccc caccccacct ttgatggcct cttcccccct caccctaggg    1920
tgtcccgaga tgaccgggac gcctggcccc tggtgggggg gcagcctcgg aactgggagt    1980
ggggggccag gggccttcct aaccttccat catcctcagc tagatgtatg cccgggacag    2040
ggcctctgtt ctccagctga accataccct ggctgtgggg gcatctgtcc tgagcttggc    2100
tggtgtatct cacaatgcaa agacatgctg gctggcggga caggtgggca ggactgaccc    2160
tgaggaggcc ttgcctgcag ggtctttgtc tcaccatttg gtggagtatc acacggttct    2220
ctgaggtctg gggcctcagc tgtttaagtt taccggtatt actgagctcg gcatttggag    2280
agggagctct gaagtgtctg gggaggtacc gctgtgcgtg ggtcaggtg tttccgtacc     2340
acagcaggag cagggcccgc ccgcatccca gctgtgggcc tgccggtcag gtcgggcacc    2400
```

```
tactacaaac cgtagtgggg tggaggctgc tggaggtggg agtgaggaga tgagggcagg   2460

gtctcaaaca gtcctgactc acagggcctg gaaacaagtc ctatgtgggc ctggggcctg   2520

gggtcctcat cctccttgtt ggtctactca ggcccagccc agagctgtgt tccctgtctc   2580

aggtcaagca gtggcagacg caaggctttc tgtgggcccc caagtggtag gagggagagt   2640

agcagagcat gggttactgg aagccgggac tgctagggct ggtggccagg gagctgcaag   2700

agtgaggctc agctctggct ggttctgccc ttacccctcc tgcccgcctg agaactgcac   2760

accctgcccg ctggccccag gacctgcact cccaatcctg ctgtcttctc cttccctgtg   2820

ccctgaacaa ggacctcact gcccgccttc ccctcccacc agccccccttg ggccaggcag   2880

ggtgaggcca aattgctctt ggcccacaaa tgggtgatgg tcagatatgt gaatcaagct   2940

cctttctcta gctagtgttt gatgtgcacg tgtgtgtgca cagtgcgtgt gtgcacacgc   3000

acacctgtgc actcgtgtgt gtttaagaaa ggaaaggatt tgggctgggg agcaaaagat   3060

aatgtgaaac tgttggtgga ctctctggtg aggggtgggc agaacttgct gctactagag   3120

ttcttgggtt ctccatgatg ttcaccctgg ggctggccca ctgtgtcctg aatgtttttg   3180

ttattttttg ttttattttt taaacaaact gctgttttta tatacctgga atctgttgtt   3240

ggcttcagag ccagtggtta aagagcaggg tcccaaggat tgggagatct agtgtctgcc   3300

ctcctgccct gcaactcaat tgggcctttt tcggtgacct catccaaggc catgatgtca   3360

agggccatgt ccccaagcag aggtggagaa ggggacactg aggtgagcaa aagcaggaag   3420

gggcatccac tgcgggtgac tggaggccgg gcaggaagca agtcatcaga gccgctcagc   3480

tccgttcact ctctgccttc tgccccacta ctgtggggca gtggggccag agcccacctc   3540

cccaacatgt gaagacagtg atgggcacgt gcccacaccc ccacttctct agccgtttgc   3600

agaggccgcc acccagcagg ggcctgaaaa ggagctgcct cgtatttttc tgtgaaatgt   3660

tttaatgaac catgttgttg ctggttgtcc tggcatcgcg cacactgtat gtacatactg   3720

gcaacgatgt caaatgtaat ttattttaac atttttacaa taaaacatga ggtggacagg   3780

caaaaaaaaa aaaaaa                                                   3796
```

```
<210> SEQ ID NO 12
<211> LENGTH: 3240
<212> TYPE: DNA
<213> ORGANISM: Homo sapiens

<400> SEQUENCE: 12

gcccgcgccg ccaccgcctc ttccctcccc gtgtccggtc cccgtgcgtc ccgaggctcc     60

ccgccgcccg tcccggcgcg caccgcgggc gtctgtccga acgccttcca gccacctgag    120

ccctcctgcg ggcgactcgc tcagctagcc cgtgcccgcc tccaccttct ccgtcatccc    180

ctcttccttg cgtccggctc tccactgggg ctgcacagtc gagggctgct cgcgtcggga    240

aggagatgcc cagagtctct ggggcgcacc ctcccgtccc gctcagccgc acccagcttt    300

agaaggtgct ctcagcagcc actttcgggc tctagcgagg acaccctctc gcagaagtcc    360

ttgccgagac cccccgcccc agccattctc tgaaggggct gaggacactc ttatcgcgcc    420

cctcatggcc aagcctcggc tgctagttct ctacttcgct ctgattgtgg ttccggcctg    480

ggtgtccagc attgtcctca cagggacaag cgagccccca gatgcgcaga cagtggcgcc    540

tgcggaggac gagactctgc aaaacgaggc ggacaaccag gagaacgttt tatctcagtt    600

gctgggggac tatgacaagg tcaaggctat gtctgagggc tcggactgtc agtgcaagtg    660
```

```
tgtggtgaga ccccctgggcc gggatgcctg ccagaggatc aatgcggggg cctccaggaa    720
ggaagacttc tataccgtgg aaaccatcac ctcaggctcg tcgtgcaagt gtgcctgtgt    780
agcaccccca tcggccctca atccctgcga gggagacttc aggctccaga agctgcggga    840
ggcagacagc caggacttga agctctccac aatcatagac atgttggaag gagcgttcta    900
tggcctggat ctcctgaagc tacattcagt caccaccaaa ctggtggggc gagtggataa    960
actggaggag gaagtgtcta aaaacctcac caaggaaaac gaacaaatca aagaggacat   1020
ggaagaaatt cgaaccgaga tgaataagcg aggcaaagaa aattgctctg aaaacatcct   1080
agatagcatg ccagacatcc gctcagccct gcagagggat gcagcagcag cctacgccca   1140
cccagagtat gaagagcggt ttctgcagga agaaaccgtg tcccagcaga tcaactccat   1200
cgaacttctg cagacgcgac ccctggctct gcctgaggtg gtgaagtcac agcggcccct   1260
gcagaggcag gtccacctga gaggccggcc ggcctcccag cccactgtca tccggggcat   1320
cacctactat aaagccaagg tctctgaaga agagaatgac attgaagagc agcaagatga   1380
gtttttcagc ggtgacaatg gagtggattt gctgattgaa gatcagctcc tgagacacaa   1440
cggcctgatg accagtgtca cccggaggcc tgcagccacc cgtcagggac acagcactgc   1500
tgtgacaagc gacctgaacg ctcggaccgc accctggtcc tcagcactgc cacagccctc   1560
gacctcagat cccagcatcg ccaaccatgc ctcagtggga ccaacactcc aaacaacctc   1620
ggtgtctcca gatcccacaa gggagtcagt cctgcagcct tctcctcagg taccagccac   1680
cactgtggcc cacacagcca cccagcaacc agcagcccca gctcctccgg cagtgtctcc   1740
cagggaggca ttgatggaag ctatgcacac agtcccagtg cctcccacca cagtcagaac   1800
agactcgctg gggaaagatg ctcctgctgg gtggggaaca acccctgcca gccccacgct   1860
gagccccgaa gaagaagatg acatccggaa tgtcatagga aggtgcaagg acactctctc   1920
cacaatcacg gggccgacca cccagaacac atatgggcgg aatgaagggg cctggatgaa   1980
ggacccccctg gccaaggatg agcggattta cgtaaccaac tattactacg gcaacaccct   2040
ggtagagttc cggaacctgg agaacttcaa acaaggtcgc tggagcaatt cctacaagct   2100
cccgtacagc tggatcggca caggccacgt ggtatacaat ggcgccttct actacaatcg   2160
cgccttcacc cgcaacatca tcaagtacga cctgaagcag cgctacgtgg ctgcctgggc   2220
catgctgcat gacgtggcct acgaggaggc cacccccctgg cgatggcagg gccactcaga   2280
cgtggacttt gctgtggacg agaatggcct atggctcatc tacccggccc tggacgatga   2340
gggcttcagc caggaggtca ttgtcctgag caagctcaat gccgcggacc tgagcacaca   2400
gaaggagacc acatggcgca cggggctccg gaggaatttc tacggcaact gcttcgtcat   2460
ctgtggggtg ctgtatgccg tggatagcta caaccagcgg aatgccaaca tctcctacgc   2520
tttcgacacc cacaccaaca cacagatcgt ccccaggctg ctgttcgaga atgagtattc   2580
ctatacgacc cagatagact acaaccccaa ggaccgcctg ctctatgcct gggacaatgg   2640
ccaccaggtc acttaccatg tcatctttgc ctactgacac ccttgtcccc acaagcagaa   2700
gcacagaggg gtcactagca ccttgtgtgt atgtgtgtgc gcgcacgtgt gtgtaggtgg   2760
gtatgtgttg tttaaaaata tatattattt tgtataatat tgcaaatgta aaatgacaat   2820
ttgggtctat ttttttatat ggattgtaga tcaatccata cgtgtatgtg ctggtctcat   2880
cctccccagt ttatattttt gtgcaaatga acttctcctt ttgaccagta accaccttcc   2940
ttcaagcctt cagcccctcc agctccaagt ctcagatctc gaccattgaa aaggtttctt   3000
catctgggtc ttgcaggagg caggcaacac caggagcaga aatgaaagag gcaagaaaga   3060
```

agtgctatgt ggcgagaaaa aaagttttaa tgtattggag aagttttaaa aaacccagaa 3120
aaacgctttt ttttttaat aaagaagaaa tttaaaatca aaaaaaaaaa aaaaaaaaaa 3180
aaaaaaaaaa aaaaaaaaaa aaaaaaaaaa aaaaaaaaaa aaaaaaaaaa aaaaaaaaaa 3240

<210> SEQ ID NO 13
<211> LENGTH: 2998
<212> TYPE: DNA
<213> ORGANISM: Homo sapiens

<400> SEQUENCE: 13
acttttggga catcctgttc tgagtcaaga ttcctccttc tgaacatggg actttccaga 60
aggaccacag ctcctcccgt gcatccactc ggcctgggag gttctggatt ttggctgtcg 120
agggagtttg cctgcctctc cagagaaaga tggtcatgag gcccctgtgg agtctgcttc 180
tctgggaagc cctacttccc attacagtta ctggtgccca agtgctgagc aaagtcgggg 240
gctcggtgct gctggtggca gcgcgtcccc ctggcttcca agtccgtgag gctatctggc 300
gatctctctg gccttcagaa gagctcctgg ccacgttttt ccgaggctcc ctagagactc 360
tgtaccattc ccgcttcctg ggccgagccc agctacacag caacctcagc ctggagctcg 420
ggccgctgga gtctggagac agcggcaact tctccgtgtt gatggtggac acaaggggcc 480
agccctggac ccagaccctc cagctcaagg tgtacgatgc agtgcccagg cccgtggtac 540
aagtgttcat tgctgtagaa agggatgctc agccctccaa gacctgccag gttttcttgt 600
cctgttgggc ccccaacatc agcgaaataa cctatagctg gcgacgggag acaaccatgg 660
actttggtat ggaaccacac agcctcttca cagacggaca ggtgctgagc atttccctgg 720
gaccaggaga cagagatgtg gcctattcct gcattgtctc caaccctgtc agctgggact 780
tggccacagt cacgccctgg gatagctgtc atcatgaggc agcaccaggg aaggcctcct 840
acaaagatgt gctgctggtg gtggtgcctg tctcgctgct cctgatgctg gttactctct 900
tctctgcctg gcactggtgc ccctgctcag ggaaaaagaa aaaggatgtc catgctgaca 960
gagtgggtcc agagacagag aacccccttg tgcaggatct gccataaagg acaatatgaa 1020
ctgatgcctg gactatcagt aaccccactg cacaggcaca cgatgctctg ggacataact 1080
ggtgcctgga aatcaccatg gtcctcatat ctcccatggg aatcctgtcc tgcctcgaag 1140
gagcagcctg ggcagccatc acaccacgag gacaggaagc accagcacgt ttcacacctc 1200 cccccttccct ctcccatctt ctcatatcct ggctcttctc tgggcaagat gagccaagca 1260
gaacattcca tccaggacac tggaagttct ccaggatcca gatccatggg gacattaata 1320
gtccaaggca ttccctcccc caccactatt cataaagtat taaccaactg gcaccaagga 1380
attgcctcca gcctgagtcc taggctctaa aagatattac atatttgaac taatagagga 1440
actctgagtc acccatgcca gcatcagctt cagccccaga ccctgcagtt tgagatctga 1500
tgcttcctga gggccaaggc attgctgtaa gaaaaggtct agaaataggt gaaagtgaga 1560
ggtgggggac aggggtttct ctttctggcc taaggacttt caggtaatca gagttcatgg 1620
gccctcaaag gtagattgca gttgtagaca ccgaggatgg ttgacaaccc atggttgaga 1680
tgggcaccgt tttgcaggaa acaccatatt aatagacatc ctcaccatct ccatccgctc 1740
tcacgcctcc tgcaggatct gggagtgagg gtggagagtc tttcctcacg ctccagcaca 1800
gtggccagga aaagaaatac tgaatttgcc ccagccaaca ggacgttctt gcacaacttc 1860
aagaaaagca gctcagctca ggatgagtct tcctgcctga aactgagaga gtgaagaacc 1920

```
ataaaacgct atgcagaagg aacattatgg agagaaaggg tactgaggca ctctagaatc   1980
tgccacattc attttcaaat gcaaatgcag aagacttacc ttagttcaag gggaggggac   2040
aaagacccca cagcccaaca gcaggactgt agaggtcact ctgactccat caaacttttt   2100
attgtggcca tcttaggaaa atacattctg cccctgaatg attctgtcta gaaaagctct   2160
ggagtattga tcactactgg aaaaacactt aaggagctaa acttaccttc ggggattatt   2220
agctgataag gttcacagtt tctctcaccc aggtgtaact ggattttttc tggggcctca   2280
atccagtctt gataacagcg aggaaagagg tattgaagaa acaggggtgg gtttgaagta   2340
ctattttccc agggtggctt caatctcccc acctaggatg tcagccctgt ccaaggacct   2400
tccctcttct ccccagttcc tgggcaatca cttcaccttg gacaaaggat cagcacagct   2460
ggcctccaga tccacatcac cactcttcca ctcgattgtt cccagatcct ccctgcctgg   2520
cctgctcaga ggttccctgt tggtaacctg gctttatcaa attctcatcc ctttcccaca   2580
cccacttctc tcctatcacc ttcccccaag attacctgaa cagggtccat ggccactcaa   2640
cctgtcagct tgcaccatcc ccacctgcca cctacagtca ggccacatgc ctggtcactg   2700
aatcatgcaa aactggcctc agtccctaaa aatgatgtgg aaaggaaagc ccaggatctg   2760
acaatgagcc ctggtggatt tgtggggaaa aaatacacag cactccccac ctttctttcg   2820
ttcatctcca gggccccacc tcagatcaaa gcagctctgg atgagatggg acctgcagct   2880
ctccctccac aaggtgactc ttagcaacct catttcgaca gtggtttgta gcgtggtgca   2940
ccagggcctt gttgaacaga tccacactgc tctaataaag ttcccatcct taatgaag     2998
```

```
<210> SEQ ID NO 14
<211> LENGTH: 1440
<212> TYPE: DNA
<213> ORGANISM: Homo sapiens

<400> SEQUENCE: 14

cagtcacatt tcagccactg ctctgagaat ttgtgagcag cccctaacag gctgttactt     60
cactacaact gacgatatga tcatcttaat ttacttattt ctcttgctat gggaagacac    120
tcaaggatgg ggattcaagg atggaatttt tcataactcc atatggcttg aacgagcagc    180
cggtgtgtac cacagagaag cacggtctgg caaatacaag ctcacctacg cagaagctaa    240
ggcggtgtgt gaatttgaag gcggccatct cgcaacttac aagcagctag aggcagccag    300
aaaaattgga tttcatgtct gtgctgctgg atggatggct aagggcagag ttggataccc    360
cattgtgaag ccagggccca actgtggatt tggaaaaact ggcattattg attatggaat    420
ccgtctcaat aggagtgaaa gatgggatgc ctattgctac aacccacacg caaaggagtg    480
tggtggcgtc tttacagatc caaagcaaat ttttaaatct ccaggcttcc caaatgagta    540
cgaagataac caaatctgct actggcacat tagactcaag tatggtcagc gtattcacct    600
gagtttttta gattttgacc ttgaagatga cccaggttgc ttggctgatt atgttgaaat    660
atatgacagt tacgatgatg tccatggctt tgtgggaaga tactgtggag atgagcttcc    720
agatgacatc atcagtacag gaaatgtcat gaccttgaag tttctaagtg atgcttcagt    780
gacagctgga ggtttccaaa tcaaatatgt tgcaatggat cctgtatcca aatccagtca    840
aggaaaaaat acaagtacta cttctactgg aaataaaaac tttttagctg gaagatttag    900
ccacttataa aaaaaaaaaa aaggatgatc aaaacacaca gtgtttatgt tggaatcttt    960
tggaactcct ttgatctcac tgttattatt aacatttatt tattattttt ctaaatgtga   1020
aagcaataca taatttaggg aaaattggaa aatataggaa actttaaacg agaaaatgaa   1080
```

```
acctctcata atcccactgc atagaaataa caagcgttaa cattttcata tttttttctt   1140

tcagtcattt ttctatttgt ggtatatgta tatatgtacc tatatgtatt tgcatttgaa   1200

attttggaat cctgctctat gtacagtttt gtattatact ttttaaatct tgaactttat   1260

aaacattttc tgaaatcatt gattattcta caaaaacatg attttaaaca gctgtaaaat   1320

attctatgat atgaatgttt tatgcattat ttaagcctgt ctctattgtt ggaatttcag   1380

gtcattttca taaatattgt tgcaataaat atccttgaac acaaaaaaaa aaaaaaaaaa   1440
```

<210> SEQ ID NO 15
<211> LENGTH: 2806
<212> TYPE: DNA
<213> ORGANISM: Homo sapiens

<400> SEQUENCE: 15

```
gccaccttgt ctgtgagctc cctgtgcccc ccatacggtg tgtcctgtgg gttggggtgt     60

gcggaagaaa gggacagaga ctgaggatgt gcggtgtaag cagtgtgctc ggggtacctt    120

ctcagatgtg ccttctagtg tgatgaaatg caaagcatac acagactgtc tgagtcagaa    180

cctggtggtg atcaagccgg ggaccaagga gacagacaac gtctgtggca cactcccgtc    240

cttctccagc tccacctcac cttcccctgg cacagccatc tttccacgcc ctgagcacat    300

ggaaacccat gaagtccctt cctccactta tgttcccaaa ggcatgaact caacagaatc    360

caactcttct gcctctgtta gaccaaaggt actgagtagc atccaggaag ggacagtccc    420

tgacaacaca agctcagcaa gggggaagga agacgtgaac aagaccctcc caaaccttca    480

ggtagtcaac caccagcaag gcccccacca cagacacatc ctgaagctgc tgccgtccat    540

ggaggccact gggggcgaga agtccagcac gcccatcaag ggccccaaga ggggacatcc    600

tagacagaac ctacacaagc attttgacat caatgagcat ttgccctgga tgattgtgct    660

tttcctgctg ctggtgcttg tggtgattgt ggtgtgcagt atccggaaaa gctcgaggac    720

tctgaaaaag gggccccggc aggatcccag tgccattgtg gaaaaggcag ggctgaagaa    780

atccatgact ccaacccaga accgggagaa atggatctac tactgcaatg gccatggtat    840

cgatatcctg aagcttgtag cagcccaagt gggaagccag tggaaagata tctatcagtt    900

tctttgcaat gccagtgaga gggaggttgc tgctttctcc aatgggtaca cagccgacca    960

cgagcgggcc tacgcagctc tgcagcactg gaccatccgg ggccccgagg ccagcctcgc   1020

ccagctaatt agcgccctgc gccagcaccg gagaaacgat gttgtggaga agattcgtgg   1080

gctgatggaa gacaccaccc agctggaaac tgacaaacta gctctcccga tgagccccag   1140

cccgcttagc ccgagcccca tccccagccc caacgcgaaa cttgagaatt ccgctctcct   1200

gacggtggag ccttccccac aggacaagaa caagggcttc ttcgtggatg agtcggagcc   1260

ccttctccgc tgtgactcta catccagcgg ctcctccgcg ctgagcagga acggttcctt   1320

tattaccaaa gaaaagaagg acacagtgtt gcggcaggta cgcctggacc cctgtgactt   1380

gcagcctatc tttgatgaca tgctccactt tctaaatcct gaggagctgc gggtgattga   1440

agagattccc caggctgagg acaaactaga ccggctattc gaaattattg gagtcaagag   1500

ccaggaagcc agccagaccc tcctggactc tgtttatagc catcttcctg acctgctgta   1560

gaacataggg atactgcatt ctggaaatta ctcaatttag tggcagggtg gttttttaat   1620

tttcttctgt ttctgatttt tgttgtttgg ggtgtgtgtg tgtgtttgtg tgtgtgtgtg   1680

tgtgtgtgtg tgtgtgtgtt taacagagaa tatggccagt gcttgagttc tttctccttc   1740
```

```
tctctctctc ttttttttt aaataactct tctgggaagt tggtttataa gcctttgcca   1800
ggtgtaactg ttgtgaaata cccaccacta aagtttttta agttccatat tttctccatt   1860
ttgccttctt atgtattttc aagattattc tgtgcacttt aaatttactt aacttaccat   1920
aaatgcagtg tgacttttcc cacacactgg attgtgaggc tcttaacttc ttaaaagtat   1980
aatggcatct tgtgaatcct ataagcagtc tttatgtctc ttaacattca cacctacttt   2040
ttaaaaacaa atattattac tatttttatt attgtttgtc ctttataaat tttcttaaag   2100
attaagaaaa tttaagaccc cattgagtta ctgtaatgca attcaacttt gagttatctt   2160
ttaaatatgt cttgtatagt tcatattcat ggctgaaact tgaccacact attgctgatt   2220
gtatggtttt cacctggaca ccgtgtagaa tgcttgatta cttgtactct tcttatgcta   2280
atatgctctg ggctggagaa atgaaatcct caagccatca ggatttgcta tttaagtggc   2340
ttgacaactg ggccaccaaa gaacttgaac ttcacctttt aggatttgag ctgttctgga   2400
acacattgct gcactttgga aagtcaaaat caagtgccag tggcgccctt tccatagaga   2460
atttgcccag ctttgcttta aaagatgtct tgttttttat atacacataa tcaataggtc   2520
caatctgctc tcaaggcctt ggtcctggtg ggattccttc accaattact ttaattaaaa   2580
atggctgcaa ctgtaagaac ccttgtctga tatatttgca actatgctcc catttacaaa   2640
tgtaccttct aatgctcagt tgccaggttc caatgcaaag gtggcgtgga ctccctttgt   2700
gtgggtgggg tttgtgggta gtggtgaagg accgatatca gaaaaatgcc ttcaagtgta   2760
ctaatttatt aataaacatt aggtgtttgt taaaaaaaaa aaaaaa                 2806
```

<210> SEQ ID NO 16
<211> LENGTH: 1433
<212> TYPE: DNA
<213> ORGANISM: Homo sapiens

<400> SEQUENCE: 16

```
gggaggtaag tagaaaccgt tgatgggact gagaaaccag agttaaaacc tctttggagc     60
ttctgagggc tcagctggaa ccaacgggca cagttggcaa caccatcatg acatcacaac    120
ctgttcccaa tgagaccatc atagtgctcc catcaaatgt catcaacttc tcccaagcag    180
agaaacccga acccaccaac caggggcagg atagcctgaa gaaacatcta cacgcagaaa    240
tcaaagttat tgggactatc cagatcttgt gtggcatgat ggtattgagc ttggggatca    300
ttttggcatc tgcttccttc tctccaaatt ttacccaagt gacttctaca ctgttgaact    360
ctgcttaccc attcatagga ccctttttt ttatcatctc tggctctcta tcaatcgcca    420
cagagaaaag gttgaccaag cttttggtgc atagcagcct ggttggaagc attctgagtg    480
ctctgtctgc cctggtgggt ttcattatcc tgtctgtcaa acaggccacc ttaaatcctg    540
cctcactgca gtgtgagttg gacaaaaata atataccaac aagaagttat gtttcttact    600
tttatcatga ttcactttat accacggact gctatacagc caaagccagt ctggctggat    660
ccctctctct gatgctgatt tgcactctgc tggaattctg cctagctgtg ctcactgctg    720
tgctgcggtg gaaacaggct tactctgact tccctgggag tgtacttttc ctgcctcaca    780
gttacattgg taattctggc atgtcctcaa aaatgactca tgactgtgga tatgaagaac    840
tattgacttc ttaagaaaaa agggagaaat attaatcaga aagttgattc ttatgataat    900
atggaaaagt taaccattat agaaaagcaa agcttgagtt tcctaaatgt aagcttttaa    960
agtaatgaac attaaaaaaa accattattt cactgtcatt taagatatgt gttcattggg   1020
gatctcttga tttgcctgac attgacttca gcaaaagcac ggggctgtaa attaccattt   1080
```

```
actagattag ccaaatagtc tgaatttcca gaaaacaagg cagaatgatc attcccagaa   1140

acatttccca gaaaatgttt cccagaaaac tagacagaat gatcattcaa tggatcacag   1200

tgaagcaaag gacacaactt tttattgtac cccttaattg tcaacaggag ttaactgatt   1260

tgttgtggtg ctcagacttt tttatacagg tgctagtgtt ttatcctatg tattttaact   1320

cattagtgca taaaggcaag ccccatataa tgaagtctca gggtatatga aagtagctgg   1380

cttcaaaata aaatttttga gtgcaaaaaa aaaaaaaaaa aaaaaaaaaa aaa          1433


<210> SEQ ID NO 17
<211> LENGTH: 2141
<212> TYPE: DNA
<213> ORGANISM: Homo sapiens

<400> SEQUENCE: 17

ggctgaggag ctgcccagag caccgctcac actcccagag tacctgaagt cggcatttca     60

atgacaggtg acaagggtcc ccaaaggcta agcgggtcca gctatggttc catctccagc    120

ccgaccagcc cgaccagccc agggccacag caagcacctc ccagagagac ctacctgagt    180

gagaagatcc ccatcccaga cacaaaaccg ggcaccttca gcctgcggaa gctatgggcc    240

ttcacggggc ctggctttct catgagcatt gctttcctgg acccaggaaa catcgagtca    300

gatcttcagg ctggcgccgt ggcgggattc aaacttctct gggtgctgct ctgggccacc    360

gtgttgggct tgctctgcca gcgactggct gcacgtctgg gcgtggtgac aggcaaggac    420

ttgggcgagg tctgccatct ctactaccct aagtcggagt ctcgctccgt cgcccagtca    480

ggagtgcaat ggtgcgatgt cagctcactg caacctctac ctcccaggtg ccccgcaccg    540

tcctctggct gaccatcgag ctagccattg tgggctccga catgcaggaa gtcatcggca    600

cggccattgc attcaatctg ctctcagctg gacgaatccc actctggggt ggcgtcctca    660

tcaccatcgt ggacaccttc ttcttcctct tcctcgataa ctacgggctg cggaagctgg    720

aagctttttt tggactcctt ataaccatta tggccttgac ctttggctat gagtatgtgg    780

tggcgcgtcc tgagcaggga gcgcttcttc ggggcctgtt cctgccctcg tgcccgggct    840

gcggccaccc cgagctgctg caggcggtgg gcattgttgg cgccatcatc atgccccaca    900

acatctacct gcactcggcc ctggtcaagt ctcgagagat agaccgggcc cgccgagcgg    960

acatcagaga agccaacatg tacttcctga ttgaggccac catcgccctg tccgtctcct   1020

ttatcatcaa cctctttgtc atggctgtct ttgggcaggc cttctaccag aaaaccaacc   1080

aggctgcgtt caacatctgt gccaacagca gcctccacga ctacgccaag atcttcccca   1140

tgaacaacgc caccgtggcc gtggacattt accagggggg cgtgatcctg ggctgcctgt   1200

tcggccccgc ggccctctac atctgggcca taggtctcct ggcggctggg cagagctcca   1260

ccatgacggg cacctacgcg ggacagttcg tgatggaggg cttcctgagg ctgcggtggt   1320

cacgcttcgc ccgtgtcctc ctcacccgct cctgcgccat cctgcccacc gtgctcgtgg   1380

ctgtcttccg ggacctgagg gacttgtcgg gcctcaatga tctgctcaac gtgctgcaga   1440

gcctgctgct cccgttcgcc gtgctgccca tcctcacgtt caccagcatg cccaccctca   1500

tgcaggagtt tgccaatggc ctgctgaaca aggtcgtcac ctcttccatc atggtgctag   1560

tctgcgccat caacctctac ttcgtggtca gctatctgcc cagcctgccc caccctgcct   1620

acttcggcct tgcagccttg ctggccgcag cctacctggg cctcagcacc tacctggtct   1680

ggacctgttg ccttgcccac ggagccacct ttctggccca cagctcccac caccacttcc   1740
```

```
tgtatgggct ccttgaagag gaccagaaag gggagacctc tggctaggcc cacaccaggg   1800

cctggctggg agtggcatgt atgacgtgac tggcctgctg gatgtggagg gggcgcgtgc   1860

aggcagcagg atggagtggg acagttcctg agaccagcca acctgggggc tttagggacc   1920

tgctgtttcc tagcgcagcc atgtgattac cctctgggtc tcagtgtcct catctgtaaa   1980

atggagacac caccaccctt gccatggagg ttaagcactt taacacagtg tctggcactt   2040

gggacaaaaa caaacaaaca aacaaaaaac aaaaaaaaaa aaaaaaaaaa aaaaaaaaaa   2100

aaaaaaaaaa aaaaaaaaaa aaaaaaaaaa aaaaaaaaaa a                       2141
```

<210> SEQ ID NO 18
<211> LENGTH: 2031
<212> TYPE: DNA
<213> ORGANISM: Homo sapiens

<400> SEQUENCE: 18

```
gagcgcgcgc gccgccgccg ttgccgccgg gctgagagaa gagcttgcgg ggtttgcggt     60

tgatggcccc gactgaaggg ctggaggcgg tgtatgccgc tgttcttgct gtcgctcccg    120

acacctccgt ccgcttctgg tcatgagagg agacagaggc ctgaagcaaa gacatctggg    180

tcagagaaaa agtatttaag ggccatgcaa gccaatcgta gccaactgca cagtcctcca    240

ggaactggaa gcagtgagga tgcctcaacc cctcagtgtg tccacacaag attgacagga    300

gagggttctt gccctcattc tggagatgtt catatccaga taaactccat acctaaagaa    360

tgtgcagaaa atgcaagctc cagaaatata aggtcaggtg tccatagctg tgcccatgga    420

tgtgtacaca gtcgcttacg gggtcactcc cacagtgaag caaggctgac tgatgatact    480

gccgcagaat ctggagatca tggtagtagc tccttctcag aattccgcta tctcttcaag    540

tggctgcaaa aaagtcttcc atatattttg attctgagcg tcaaacttgt tatgcagcat    600

ataacaggaa tttctcttgg aattgggctg ctaacaactt ttatgtatgc aaacaaaagc    660

attgtaaatc aggtttttct aagagaaagg tcctcaaaga ttcagtgtgc ttggttactg    720

gtattcttag caggatcttc tgttctttta tattacacct ttcattctca gtcactttat    780

tacagcttaa tttttttaaa tcctactttg gaccatttga gcttctggga agtattttgg    840

attgttggaa ttacagactt cattctgaaa ttctttttca tgggcttaaa atgccttatt    900

ttattggtgc cttctttcat catgcctttt aaatctaagg gttactggta tatgctttta    960

gaagaattgt gtcaatacta ccgaactttt gttcccatac cagtttggtt tcgctacctt   1020

ataagctatg gggagtttgg taacgtaact agatggagtc ttgggatact gctggcttta   1080

ctctacctca tattaaaact tttggaattt tttgggcatc tgagaacttt cagacaggtt   1140

ttacgaatat tttttacaca accaagttat ggagtggctg ccagcaagag acagtgttca   1200

gatgtggatg atatttgttc aatatgtcaa gctgaatttc agaagccaat tcttctcatt   1260

tgtcagcata tattttgtga agagtgcatg accttatggt ttaacagaga gaaaacatgt   1320

ccactctgca gaactgtgat ttcagaccat ataaacaaat ggaaggatgg agccacttca   1380

tcacaccttc aaatatatta agttgtataa actatcaagg ccacaaaata ctaatgtcat   1440

ttggtcataa tgactactga taaggcatca gaatggattt tcagggctac cagaaaaatg   1500

tttccagatg gttttagaat gtaggactta tgatccaatt caccaaaaga ttaaatgaaa   1560

ccaccctgtg ttttaaaata tatataatgt tcaacctaat gtatatgcaa catttattct   1620

attctaatta tttgacaggt aactgcagtg ttaaattgta aatgtgtttt ctttatgtta   1680

ccaaaacagc aatttgaaat tagaactagt ggttttagag aactcaggta ttctttcctg   1740
```

acattgtttt cagaataaag aatatttttc ataatatttt aagatacata ctatctaaaa 1800
gtagaatttt gttcagcatt gacttttata attcccatcc taaaaattct taatattttc 1860
ataaaatttg tatttttaaa tgaaaattct aaatgttgta ttttatcagt aacattttct 1920
aagtgaagat taatttactg aggatgatac attatagtat tgtattattc tctgtagtaa 1980
gattagtaat aagtgaaaat aaatgattta aattcaaaaa aaaaaaaaaa a 2031

<210> SEQ ID NO 19
<211> LENGTH: 3070
<212> TYPE: DNA
<213> ORGANISM: Homo sapiens

<400> SEQUENCE: 19
gagcccagag ccagagagcg cgctgggcgg tgctgggcac ccgcggagtg gaacggggct 60
ggtggaatgc acagggtcgc agcgcttggg ccaccctcgg tcagagggcg ccgtgtccag 120
cgagcaaacg ggcgccccgg agccttgctg agaggcagct ctgggctttc ccagctccga 180
agtcaatact gagatcccag atgtgtccag agacatcctg aagaggctcg gggtggaggg 240
agccttagtg tgtccacaaa gggactcctg aaactgactg agagccagtg gatttgccag 300
cagtctgagc ttctaccgag tcttccccca cctcaatccc tgttgctatg gagactacca 360
atggaacgga gacctggtat gagagcctgc atgccgtgct gaaggctcta aatgccactc 420
ttcacagcaa tttgctctgc cggccagggc cagggctggg gccagacaac cagactgaag 480
agaggcgggc cagcctacct ggccgtgatg acaactccta catgtacatt ctctttgtca 540
tgtttctatt tgctgtaact gtgggcagcc tcatcctggg atacacccgc tcccgcaaag 600
tggacaagcg tagtgacccc tatcatgtgt atatcaagaa ccgtgtgtct atgatctaac 660
acgagagggc tgggacggtg gaagaccaag acacctgggg attgcgtctg gggcctccag 720
aactctgctg tggactgcat caggtctcag tgtccctatc tgtaagatca acaagaaaca 780
cggttaaggg aggtcgtcac tggggtggga gaagaggggc tggtagaccg aagccttgtg 840
cataaggatt ttttcccagg aaaagataga ctttataaac agtgggagcc catgaacaaa 900
catataaaag tagcaacaga taatgaccaa taactggttc agtggctgga gtattagggg 960
cctggggatt ggagaacgga gaagaagttg tagcagaggg aaatgagaca ggaagatgct 1020
ctggggacac atttttatg tgttatcttc agccatgaga agcagtgatg actatcccat 1080
atcacagata tgatttacca ccaccaccct gcccccgctc ccgtgaagaa agcagggcaa 1140
gtgctgtgct gcccatttgg gcctgcatag tgccatgatt ggaacccagg aactctggtc 1200
tccttgccta gtgcttttca aaactctgtg ctacacagga gtggatccag gcctgaaggt 1260
catacaattc tggggactct ctttaagaaa aagaattcta aaatatctta cttttgcaaa 1320
cattatgaaa atatactgcc acattaatat gttgctaggg cccctgctag gaccttaaga 1380
aggagctcat gtgagtcagg accctgaatg ttaggcctcg ttagctctat ggttcatatg 1440
cttcttgaac caagtcacag ggcacttccc agccacattg ccaggcaaca ggactaaact 1500
acctccaaag caagcagtct tttcagtttt gactgagtga tgtgagaaac ttcttttctt 1560
ttcttttctt tttttttttt tgagacagtc tccctatgtc acccaggctg tggtgcagca 1620
acccaatctt ggctcactgc aaccccccacc tcccgggttc aagcaattat cctgcctcag 1680
ccacctgagt agctgggatt acaggttcct gtcaccacac ccagttaatt tatatatata 1740
tatatatata tatatttaag tagagacagg gtttcacatg ttgcccaggc tggtctcgaa 1800
ctcctgtcct caagttatct gcccattttg gtctcccaaa gtgctgggat tacaagtgta 1860
agccaccacg actatctgag agaagttttc tgatgtcatg ttgaatctgc ttctaaaaga 1920
ctgatactgc caaggtgggc ggatcacctg aggtcaggag ttcgagacca gcctggccaa 1980
catggtgaaa ccccatctac taaaaaaata caaaaattag ccagacctgg tggcgggtgc 2040
ccgtattccc agctacttgg gaggctgagg caggagaatt gtttgaaccc gggaggtgga 2100
ggttgcagta agccaagatc acgccactgc actccagcct gggtgacaga gcaaggctct 2160
gtctcaaaaa aaaacaaaaa caaaaacaaa aaagactgat atcgcaccta aattattatt 2220
atattaaaag aagcagagta tgagagacag gtacatggtc cagtaggaag agaagcagcc 2280
ctgattctac cacttaaggt gatgtatgat cttaggctgg acacttctct ccctcatccg 2340
ttttcctctt caacataatg aaatagactt gaaagtctct aaggctctat cagttctgac 2400
attctaggct tcatatacat taagttgagc catatgtaat cactgtgttt gtaggttaga 2460
aacagctgag tatcgtagtt tcatatatgg ttccagctaa tacatgcaat gtggctggtg 2520
aacacttctg aattcagaaa ctatcccaga tctcagctag aaccatccac tgttctgttt 2580
gtccagtttc aacttaaggg atctccatgc ggtccctgga agtacccatt gaaacatgcg 2640
tatttgtgta tagcagaact ctgaaataat attctgacag cagttatctc tgaggaattg 2700
ggttataggt gattttccct ttccgcatga taaatttatg taatatttga ctgacttgac 2760
cgtaagtatg ttacttgtat aataaaagga aaaaaggtac ttctattttg aaaaaataaa 2820
aataaaagcc tttgggttct tgaatggagg atcatggaac acatttgctg ccatatgcag 2880
ttatgttgat gctctgcaaa cctgtgctga gccctgttgc tcaagccctt cctcatctct 2940
tcttgaggga gaaggtggag acttccttaa ggagatgtga catatgggaa gacaacagat 3000
tcagaaattt acgtggatag gactttagac accacccagc ccaaacttcc aaataaaata 3060
tggaacgcaa 3070

<210> SEQ ID NO 20
<211> LENGTH: 1204
<212> TYPE: DNA
<213> ORGANISM: Homo sapiens

<400> SEQUENCE: 20
agcagaagaa ccctcttgga ctggacgatt tgggaattca aaacttggga caaactgtca 60
gccttgcccc tgctgtggag gcagcctcaa tgctgaaaat ggagcctctg aacagcacgc 120
accccggcac cgccgcctcc agcagccccc tggagtcccg tgcggccggt ggcggcagcg 180
gcaatggcaa cgagtacttc tacattctgg ttgtcatgtc cttctacggc attttcttga 240
tcggaatcat gctgggctac atgaaatcca agaggcggga gaagaagtcc agcctcctgc 300
tgctgtacaa agacgaggag cggctctggg gggaggccat gaagccgctg cccgtggtgt 360
cgggcctgag gtcggtgcag gtgcccctga tgctgaacat gctgcaggag agcgtggcgc 420
ccgcgctgtc ctgcaccctc tgttccatgg aaggggacag cgtgagctcc gagtcctcct 480
ccccggacgt gcacctcacc attcaggagg agggggcaga cgaggagctg gaggagacct 540
cggagacgcc cctcaacgag agcagcgaag ggtcctcgga gaacatccat cagaattcct 600
agcacccccg ggacccctgc gggtggctcc atcagccagc aacccttagag agaggaaaga 660 cagttttcaa gtgtctggtt tcactttcac agtgcggctg ccactttgaa gagacccttg 720
gtaaacccct gattcggggt ggggtggggg actaggctca gccggaacca gcacctccaa 780
ggagtccggg aggtgcctgt ggtttgcacc caccactgaa aaagccgcgg agatgcgcag 840

```
cgcgtacact gactttgggg cctgggtgtt ggggttctga tcagaatttg gcgggatgat     900

atgcttgcca ttttctcact ggatgccctg ggtagctcct gcagggtctg cctgttccca     960

gggctgccga atgcttagga cacgctgaga gactagttgt gatttgctat tttgcctaga    1020

gctttgtcct tctagatctg attggctgta agtatctcta ctgtgtacct gtggcattcc    1080

ttcacagtgg gttacaagct tcttttggat tagaggggga tttttgatgg gagaaagctg    1140

gagatctgaa cccagcccat ttgcacacta aaaaaaaaaa aaaaaaaaaa aaaaaaaaaa    1200

aaaa                                                                 1204
```

<210> SEQ ID NO 21
<211> LENGTH: 3309
<212> TYPE: DNA
<213> ORGANISM: Homo sapiens

<400> SEQUENCE: 21

```
ttcagcccct ctcccgggct gcgcctccgc actccgggcc cgggcagaag gggggtgcgcc     60

tcggccccac cacccaggga gcagccgagc tgaaaggccg ggaaccgcgg cttgcgggga    120

ccacagctcc cgaaagcgac gttcggccac cggaggagcg ggagccaagc aggcggagct    180

cggcgggaga ggtgcgggcc gaatccgagc cgagcggaga ggaatccggc agtagagagc    240

ggactccagc cggcggaccc tgcagccctc gcctgggaca gcggcgcgct gggcaggcgc    300

ccaagagagc atcgagcagc ggaacccgcg aagccggccc gcagccgcga cccgcgcagc    360

ctgccgctct cccgccgccg gtccgggcag catgaggcgc gcggcgctct ggctctggct    420

gtgcgcgctg gcgctgagcc tgcagccggc cctgccgcaa attgtggcta ctaatttgcc    480

ccctgaagat caagatggct ctggggatga ctctgacaac ttctccggct caggtgcagg    540

tgctttgcaa gatatcacct tgtcacagca gacccccctcc acttggaagg acacgcagct    600

cctgacggct attcccacgt ctccagaacc caccggcctg gaggctacag ctgcctccac    660

ctccaccctg ccggctggag aggggcccaa ggagggagag gctgtagtcc tgccagaagt    720

ggagcctggc ctcaccgccc gggagcagga ggccaccccc cgacccaggg agaccacaca    780

gctcccgacc actcatcagg cctcaacgac cacagccacc acggcccagg agcccgccac    840

ctcccacccc cacagggaca tgcagcctgg ccaccatgag acctcaaccc ctgcaggacc    900

cagccaagct gaccttcaca ctccccacac agaggatgga ggtccttctg ccaccgagag    960

ggctgctgag gatggagcct ccagtcagct cccagcagca gagggctctg gggagcagga   1020

cttcaccttt gaaacctcgg gggagaatac ggctgtagtg gccgtggagc ctgaccgccg   1080

gaaccagtcc ccagtggatc agggggccac gggggcctca cagggcctcc tggacaggaa   1140

agaggtgctg ggaggggtca ttgccggagg cctcgtgggg ctcatctttg ctgtgtgcct   1200

ggtgggtttc atgctgtacc gcatgaagaa gaaggacgaa ggcagctact ccttggagga   1260

gccgaaacaa gccaacggcg gggcctacca gaagcccacc aaacaggagg aattctatgc   1320

ctgacgcggg agccatgcgc cccctccgcc ctgccactca ctaggccccc acttgcctct   1380

tccttgaaga actgcaggcc ctggcctccc ctgccaccag gccacctccc cagcattcca   1440

gcccctctgg tcgctcctgc ccacggagtc gtggggtgtg ctgggagctc cactctgctt   1500

ctctgacttc tgcctggaga cttagggcac caggggtttc tcgcatagga cctttccacc   1560

acagccagca cctggcatcg caccattctg actcggtttc tccaaactga agcagcctct   1620

ccccaggtcc agctctggag gggagggggga tccgactgct ttggacctaa atggcctcat   1680
```

```
gtggctggaa gatcctgcgg gtggggcttg gggctcacac acctgtagca cttactggta   1740
ggaccaagca tcttgggggg gtggccgctg agtggcaggg gacaggagtc cactttgttt   1800
cgtggggagg tctaatctag atatcgactt gtttttgcac atgtttcctc tagttctttg   1860
ttcatagccc agtagacctt gttacttctg aggtaagtta agtaagttga ttcggtatcc   1920
ccccatcttg cttccctaat ctatggtcgg gagacagcat cagggttaag aagacttttt   1980
tttttttttt ttaaactagg agaaccaaat ctggaagcca aaatgtaggc ttagtttgtg   2040
tgttgtctct tgagtttgtc gctcatgtgt gcaacagggt atggactatc tgtctggtgg   2100
ccccgtttct ggtggtctgt tggcaggctg gccagtccag gctgccgtgg ggccgccgcc   2160
tctttcaagc agtcgtgcct gtgtccatgc gctcagggcc atgctgaggc ctgggccgct   2220
gccacgttgg agaagcccgt gtgagaagtg aatgctggga ctcagccttc agacagagag   2280
gactgtaggg agggcggcag gggcctggag atcctcctgc agaccacgcc cgtcctgcct   2340
gtggcgccgt ctccaggggc tgcttcctcc tggaaattga cgaggggtgt cttgggcaga   2400
gctggctctg agcgcctcca tccaaggcca ggttctccgt tagctcctgt ggccccaccc   2460
tgggccctgg gctggaatca ggaatatttt ccaaagagtg atagtctttt gcttttggca   2520
aaactctact taatccaatg ggtttttccc tgtacagtag attttccaaa tgtaataaac   2580
tttaatataa agtagtcctg tgaatgccac tgccttcgct tcttgcctct gtgctgtgtg   2640
tgacgtgacc ggacttttct gcaaacacca acatgttggg aaacttggct cgaatctctg   2700
tgccttcgtc tttcccatgg ggagggattc tggttccagg gtccctctgt gtatttgctt   2760
ttttgttttg gctgaaattc tcctggaggt cggtaggttc agccaaggtt ttataaggct   2820
gatgtcaatt tctgtgttgc caagctccaa gccccatctt ctaaatggca aaggaaggtg   2880
gatggcccca gcacagcttg acctgaggct gtggtcacag cggaggtgtg gagccgaggc   2940
ctaccccgca gacaccttgg acatcctcct cccacccggc tgcagaggcc agaggccccc   3000
agcccagggc tcctgcactt acttgcttat ttgacaacgt ttcagcgact ccgttggcca   3060
ctccgagagg tgggccagtc tgtggatcag agatgcacca ccaagccaag ggaacctgtg   3120
tccggtattc gatactgcga ctttctgcct ggagtgtatg actgcacatg actcgggggt   3180
ggggaaaggg gtcggctgac catgctcatc tgctggtccg tgggacggtg cccaagccag   3240
aggctgggtt catttgtgta acgacaataa acggtacttg tcatttcggg caaaaaaaaa   3300
aaaaaaaaa                                                            3309
```

<210> SEQ ID NO 22
<211> LENGTH: 3273
<212> TYPE: DNA
<213> ORGANISM: Homo sapiens

<400> SEQUENCE: 22

```
cgctgggcct gcccggaatc ccgccgcctg cgccccgcgc cccgcgccct gcgggccatg     60
ggagccggcc gccggcaggg acgacgcctg tgagacccgc gagcggcctc ggggaccatg    120
gggagcgatc gggcccgcaa gggcggaggg ggcccgaagg acttcggcgc gggactcaag    180
tacaactccc ggcacgagaa agtgaatggc ttggaggaag gcgtggagtt cctgccagtc    240
aacaacgtca agaaggtgga aaagcatggc ccggggcgct gggtggtgct ggcagccgtg    300
ctgatcggcc tcctcttggt cttgctgggg atcggcttcc tggtgtggca tttgcagtac    360
cgggacgtgc gtgtccagaa ggtcttcaat ggctacatga ggatcacaaa tgagaatttt    420
gtggatgcct acgagaactc caactccact gagtttgtaa gcctggccag caaggtgaag    480
```

```
gacgcgctga agctgctgta cagcggagtc ccattcctgg gcccctacca caaggagtcg    540
gctgtgacgg ccttcagcga gggcagcgtc atcgcctact actggtctga gttcagcatc    600
ccgcagcacc tggtggagga ggccgagcgc gtcatggccg aggagcgcgt agtcatgctg    660
cccccgcggg cgcgctccct gaagtccttt gtggtcacct cagtggtggc tttccccacg    720
gactccaaaa cagtacagag gacccaggac aacagctgca gctttggcct gcacgcccgc    780
ggtgtggagc tgatgcgctt caccacgccc ggcttccctg acagccccta ccccgctcat    840
gcccgctgcc agtgggccct gcggggggac gccgactcag tgctgagcct caccttccgc    900
agctttgacc ttgcgtcctg cgacgagcgc ggcagcgacc tggtgacggt gtacaacacc    960
ctgagcccca tggagcccca cgccctggtg cagttgtgtg gcacctaccc tccctcctac   1020
aacctgacct tccactcctc ccagaacgtc ctgctcatca cactgataac caacactgag   1080
cggcggcatc ccggctttga ggccaccttc ttccagctgc ctaggatgag cagctgtgga   1140
ggccgcttac gtaaagccca ggggacattc aacagcccct actacccagg ccactaccca   1200
cccaacattg actgcacatg gaacattgag gtgcccaaca accagcatgt gaaggtgcgc   1260
ttcaaattct tctacctgct ggagcccggc gtgcctgcgg gcacctgccc caaggactac   1320
gtggagatca atggggagaa atactgcgga gagaggtccc agttcgtcgt caccagcaac   1380
agcaacaaga tcacagttcg cttccactca gatcagtcct acaccgacac cggcttctta   1440
gctgaatacc tctcctacga ctccagtgac ccatgcccgg ggcagttcac gtgccgcacg   1500
gggcggtgta tccggaagga gctgcgctgt gatggctggg ccgactgcac cgaccacagc   1560
gatgagctca actgcagttg cgacgccggc caccagttca cgtgcaagaa caagttctgc   1620
aagcccctct tctgggtctg cgacagtgtg aacgactgcg gagacaacag cgacgagcag   1680
gggtgcagtt gtccggccca gaccttcagg tgttccaatg ggaagtgcct ctcgaaaagc   1740
cagcagtgca atgggaagga cgactgtggg gacggctccg acgaggcctc ctgccccaag   1800
gtgaacgtcg tcacttgtac caaacacacc taccgctgcc tcaatgggct ctgcttgagc   1860
aagggcaacc ctgagtgtga cgggaaggag gactgtagcg acggctcaga tgagaaggac   1920
tgcgactgtg ggctgcggtc attcacgaga caggctcgtg ttgttggggg cacggatgcg   1980
gatgagggcg agtggccctg gcaggtaagc ctgcatgctc tgggccaggg ccacatctgc   2040
ggtgcttccc tcatctctcc caactggctg gtctctgccg cacactgcta catcgatgac   2100
agaggattca ggtactcaga ccccacgcag tggacggcct tcctgggctt gcacgaccag   2160
agccagcgca gcgcccctgg ggtgcaggag cgcaggctca agcgcatcat ctcccacccc   2220
ttcttcaatg acttcacctt cgactatgac atcgcgctgc tggagctgga gaaaccggca   2280
gagtacagct ccatggtgcg gcccatctgc ctgccggacg cctcccatgt cttccctgcc   2340
ggcaaggcca tctgggtcac gggctgggga cacacccagt atggaggcac tggcgcgctg   2400
atcctgcaaa agggtgagat ccgcgtcatc aaccagacca cctgcgagaa cctcctgccg   2460
cagcagatca cgccgcgcat gatgtgcgtg ggcttcctca gcggcggcgt ggactcctgc   2520
cagggtgatt ccgggggacc cctgtccagc gtggaggcgg atgggcggat cttccaggcc   2580
ggtgtggtga gctggggaga cggctgcgct cagaggaaca agccaggcgt gtacacaagg   2640
ctccctctgt ttcgggactg gatcaaagag aacactgggg tataggggcc ggggccaccc   2700
aaatgtgtac acctgcgggg ccacccatcg tccaccccag tgtgcacgcc tgcaggctgg   2760
agactggacc gctgactgca ccagcgcccc cagaacatac actgtgaact caatctccag   2820
```

```
ggctccaaat ctgcctagaa aacctctcgc ttcctcagcc tccaaagtgg agctgggagg   2880

tagaagggga ggacactggt ggttctactg acccaactgg gggcaaaggt ttgaagacac   2940

agcctccccc gccagcccca agctgggccg aggcgcgttt gtgcatatct gcctcccctg   3000

tctctaagga gcagcgggaa cggagcttcg gggcctcctc agtgaaggtg gtggggctgc   3060

cggatctggg ctgtggggcc cttgggccac gctcttgagg aagcccaggc tcggaggacc   3120

ctggaaaaca gacgggtctg agactgaaat tgttttacca gctcccaggg tggacttcag   3180

tgtgtgtatt tgtgtaaatg agtaaaacat tttatttctt tttaaaaaaa aaaaaaaaaa   3240

aaaaaaaaaa aaaaaaaaaa aaaaaaaaaa aaa                                 3273
```

<210> SEQ ID NO 23
<211> LENGTH: 1410
<212> TYPE: DNA
<213> ORGANISM: Homo sapiens

<400> SEQUENCE: 23

```
gggcggggct cgggccggtc cgcccgcgcg caggtgagtg agccagggcg gagcgcagct     60

gcgccgggct tgggcgcctg gggccgccgc tccccaccgt cgttttcccc accgaggccg    120

aggcgtcccg gagtcatggc cggcctgaac tgcggggtct ctatcgcact gctaggggtt    180

ctgctgctgg gtgcggcgcg cctgccgcgc ggggcagaag cttttgagat tgctctgcca    240

cgagaaagca acattacagt tctcataaag ctggggaccc cgactctgct ggcaaaaccc    300

tgttacatcg tcatttctaa aagacatata accatgttgt ccatcaagtc tggagaaaga    360

atagtcttta cctttagctg ccagagtcct gagaatcact ttgtcataga gatccagaaa    420

aatattgact gtatgtcagg cccatgtcct tttggggagg ttcagcttca gccctcgaca    480

tcgttgttgc ctaccctcaa cagaactttc atctgggatg tcaaagctca taagagcatc    540

ggtttagagc tgcagttttc catccctcgc ctgaggcaga tcggtccggg tgagagctgc    600

ccagacggag tcactcactc catcagcggc cgaatcgatg ccaccgtggt caggatcgga    660

accttctgca gcaatggcac tgtgtcccgg atcaagatgc aagaaggagt gaaaatggcc    720

ttacacctcc catggttcca ccccagaaat gtctccggct tcagcattgc aaaccgctca    780

tctataaaac gtctgtgcat catcgagtct gtgtttgagg gtgaaggctc agcaaccctg    840

atgtctgcca actacccaga aggcttccct gaggatgagc tcatgacgtg gcagtttgtc    900

gttcctgcac acctgcgggc cagcgtctcc ttcctcaact tcaacctctc caactgtgag    960

aggaaggagg agcgggttga atactacatc ccgggctcca ccaccaaccc cgaggtgttc   1020

aagctggagg acaagcagcc tgggaacatg gcggggaact tcaacctctc tctgcaaggc   1080

tgtgaccaag atgcccaaag tccagggatc ctccggctgc agttccaagt tttggtccaa   1140

catccacaaa atgaaagcag tgagtgagcc ccactttcct ttttcttcct cctccagcac   1200

cttcgttgtt tcctgggtag tctgcctggg tgaggctccc ttcctgtttc tcatctgtgg   1260

cttctgaaac acttagactc tggacccagc aagagtttca ggaagtgggt tgctaggcag   1320

ttagacaggc ttgttggtga acacccggta tgtagttcca tttcagcaca ataaaaagaa   1380

atcttgcatt caaaaaaaaa aaaaaaaaaa                                    1410
```

<210> SEQ ID NO 24
<211> LENGTH: 566
<212> TYPE: DNA
<213> ORGANISM: Homo sapiens

<400> SEQUENCE: 24

```
caccatgcct gcttgtcgcc taggcccgct agccgccgcc ctcctcctca gcctgctgct      60

gttcggcttc accctagtct caggcacagg agcagagaag actggcgtgt gccccgagct     120

ccaggctgac cagaactgca cgcaagagtg cgtctcggac agcgaatgcg ccgacaacct     180

caagtgctgc agcgcgggct gtgccacctt ctgctctctg cccaatgata aggagggttc     240

ctgcccccag gtgaacatta actttcccca gctcggcctc tgtcgggacc agtgccaggt     300

ggacagccag tgtcctggcc agatgaaatg ctgccgcaat ggctgtggga aggtgtcctg     360

tgtcactccc aatttctgag ctccagccac caccaggctg agcagtgagg agagaaagtt     420

tctgcctggc cctgcatctg gttccagccc acctgccctc ccctttttcg ggactctgta     480

ttccctcttg ggctgaccac agcttctccc tttcccaacc aataaagtaa ccactttcag     540

caaaaaaaaa aaaaaaaaaa aaaaaa                                         566


<210> SEQ ID NO 25
<211> LENGTH: 1486
<212> TYPE: DNA
<213> ORGANISM: Homo sapiens

<400> SEQUENCE: 25

agcagcagga ggaggcagag cacagcatcg tcgggaccag actcgtctca ggccagttgc      60

agccttctca gccaaacgcc gaccaaggaa aactcactac catgagaatt gcagtgattt     120

gcttttgcct cctaggcatc acctgtgcca taccagttaa acaggctgat tctggaagtt     180

ctgaggaaaa gcagctttac aacaaatacc cagatgctgt ggccacatgg ctaaaccctg     240

acccatctca gaagcagaat ctcctagccc cacagaccct tccaagtaag tccaacgaaa     300

gccatgacca catggatgat atggatgatg aagatgatga tgaccatgtg gacagccagg     360

actccattga ctcgaacgac tctgatgatg tagatgacac tgatgattct caccagtctg     420

atgagtctca ccattctgat gaatctgatg aactggtcac tgattttccc acggacctgc     480

cagcaaccga agttttcact ccagttgtcc ccacagtaga cacatatgat ggccgaggtg     540

atagtgtggt ttatggactg aggtcaaaat ctaagaagtt tcgcagacct gacatccagt     600

accctgatgc tacagacgag gacatcacct cacacatgga aagcgaggag ttgaatggtg     660

catacaaggc catccccgtt gcccaggacc tgaacgcgcc ttctgattgg gacagccgtg     720

ggaaggacag ttatgaaacg agtcagctgg atgaccagag tgctgaaacc cacagccaca     780

agcagtccag attatataag cggaaagcca atgatgagag caatgagcat tccgatgtga     840

ttgatagtca ggaactttcc aaagtcagcc gtgaattcca cagccatgaa tttcacagcc     900

atgaagatat gctggttgta gaccccaaaa gtaaggaaga agataaacac ctgaaatttc     960

gtatttctca tgaattagat agtgcatctt ctgaggtcaa ttaaaaggag aaaaaataca    1020

atttctcact ttgcatttag tcaaaagaaa aaatgcttta tagcaaaatg aaagagaaca    1080

tgaaatgctt ctttctcagt ttattggttg aatgtgtatc tatttgagtc tggaaataac    1140

taatgtgttt gataattagt ttagtttgtg gcttcatgga aactccctgt aaactaaaag    1200

cttcagggtt atgtctatgt tcattctata gaagaaatgc aaactatcac tgtattttaa    1260

tatttgttat tctctcatga atagaaattt atgtagaagc aaacaaaata cttttaccca    1320

cttaaaaaga gaatataaca ttttatgtca ctataatctt ttgtttttta agttagtgta    1380

tattttgttg tgattatctt tttgtggtgt gaataaatct tttatcttga atgtaataag    1440

aaaaaaaaaa aaaaaataaa aaaaaaaaaa aaaaaaaaaa aaaaaa                   1486
```

<210> SEQ ID NO 26
<211> LENGTH: 1652
<212> TYPE: DNA
<213> ORGANISM: Homo sapiens

<400> SEQUENCE: 26
gtggcccgga tgttcggtgc agctgccaga tccgctgatc tagtgcttct cgaaaaaaac 60
cttcaggcgg cccatggcat gccttggact ttattgtggg aagaccctat tatttaaaaa 120
tggctcaact gaaatatatg gagaatgtgg ggtatgccca agaggacaga gaacgaatgc 180
acagaaatat tgtcagcctt gcacagaatc tcctgaactt tatgattggc tctatcttgg 240
atttatggca atgcttcctc tggttttaca ttggttcttc attgaatggt actcggggaa 300
aaagagttcc agcgcacttt tccaacacat cactgcatta tttgaatgca gcatggcagc 360
tattatcacc ttacttgtga gtgatccagt tggtgttctt tatattcgtt catgtcgagt 420
attgatgctt tctgactggt acacgatgct ttacaaccca agtccagatt acgttaccac 480
agtacactgt actcatgaag ccgtctaccc actatatacc attgtattta tctattacgc 540
attctgcttg gtattaatga tgctgctccg acctcttctg gtgaagaaga ttgcatgtgg 600
gttagggaaa tctgatcgat ttaaaagtat ttatgctgca ctttacttct tcccaatttt 660
aaccgtgctt caggcagttg gtggaggcct tttatattac gccttcccat acattatatt 720
agtgttatct ttggttactc tggctgtgta catgtctgct tctgaaatag agaactgcta 780
tgatcttctg gtcagaaaga aaagacttat tgttctcttc agccactggt tacttcatgc 840
ctatggaata atctccattt ccagagtgga taaacttgag caagatttgc cccttttggc 900
tttggtacct acaccagccc ttttttactt gttcactgca aaatttaccg aaccttcaag 960
gatactctca gaaggagcca atggacactg agtgtagaca tgtgaaatgc caaaaacctg 1020
agaagtgctc ctaataaaaa agtaaatcaa tcttaacagt gtatgagaac tattctatca 1080
tatatgggaa caagattgtc agtatatctt aatgtttggg tttgtctttg ttttgtttat 1140
ggttagactt acagacttgg aaaatgcaaa actctgtaat actctgttac acagggtaat 1200
attatctgct acactggaag gccgctagga agcccttgct tctctcaaca gttcagctgt 1260
tctttagggc aaaatcatgt ttctgtgtac ctagcaatgt gttcccattt tattaagaaa 1320
agctttaaca cgtgtaatct gcagtcctta acagtggcgt aattgtacgt acctgttgtg 1380
tttcagtttg tttttcacct ataatgaatt gtaaaaacaa acatacttgt ggggtctgat 1440
agcaaacata gaaatgatgt atattgtttt ttgttatcta tttattttca tcaatacagt 1500
attttgatgt attgcaaaaa tagataataa tttatataac aggttttctg tttatagatt 1560
ggttcaagat ttgtttggat tattgttcct gtaaagaaaa caataataaa aagcttacct 1620
acaaaaaaaa aaaaaaaaaa aaaaaaaaaa aa 1652

<210> SEQ ID NO 27
<211> LENGTH: 548
<212> TYPE: DNA
<213> ORGANISM: Homo sapiens

<400> SEQUENCE: 27
ggggacagca acttccttga tccctgccac gcacgactga acacagacag cagccgcctc 60
gccatgaagc tgctgatggt cctcatgctg gcggccctcc tcctgcactg ctatgcagat 120
tctggctgca aactcctgga ggacatggtt gaaaagacca tcaattccga catatctata 180
cctgaataca aagagcttct tcaagagttc atagacagtg atgccgctgc agaggctatg 240

```
gggaaattca agcagtgttt cctcaaccag tcacatagaa ctctgaaaaa ctttggactg    300
atgatgcata cagtgtacga cagcatttgg tgtaatatga agagtaatta actttaccca    360
aggcgtttgg ctcagagggc tacagactat ggccagaact catctgttga ttgctagaaa    420
ccacttttct ttcttgtgtt gtctttttat gtggaaactg ctagacaact gttgaaacct    480
caaattcatt tccatttcaa taaactaact gcaaatctaa aaaaaaaaaa aaaaaaaaaa    540
aaaaaaaa                                                             548
```

<210> SEQ ID NO 28
<211> LENGTH: 2543
<212> TYPE: DNA
<213> ORGANISM: Homo sapiens

<400> SEQUENCE: 28

```
gaggcgggca aggcgggcgc cgaggtttgc aaaggctcgc agcggccaga aacccggctc     60
cgagcggcgg cggcccggct tccgctgccc gtgagctaag gacggtccgc tccctctagc    120
cagctccgaa tcctgatcca ggcgggggcc aggggcccct cgcctcccct ctgaggaccg    180
aagatgagct tcctcttcag cagccgctct tctaaaacat tcaaaccaaa gaagaatatc    240
cctgaaggat ctcatcagta tgaactctta aaacatgcag aagcaactct aggaagtggg    300
aatctgagac aagctgttat gttgcctgag ggagaggatc tcaatgaatg gattgctgtg    360
aacactgtgg atttctttaa ccagatcaac atgttatatg gaactattac agaattctgc    420
actgaagcaa gctgtccagt catgtctgca ggtccgagat atgaatatca ctgggcagat    480
ggtactaata ttaaaaagcc aatcaaatgt tctgcaccaa aatacattga ctatttgatg    540
acttgggttc aagatcagct tgatgatgaa actctttttc cttctaagat tggtgtccca    600
tttcccaaaa actttatgtc tgtggcaaag actattctaa agcgtctgtt cagggtttat    660
gcccatattt atcaccagca ctttgattct gtgatgcagc tgcaagaggg ggcccacctc    720
aacacctcct ttaagcactt tattttcttt gttcaggagt ttaatctgat tgataggcgt    780
gagctggcac ctcttcaaga attaatagag aaacttggat caaaagacag ataaatgttt    840
cttctagaac acagttaccc ccttgcttca tctattgcta gaactatctc attgctatct    900
gttatagact agtgatacaa actttaagaa aacaggataa aaagataccc attgcctgtg    960
tctactgata aaattatccc aaaggtaggt tggtgtgata gtttccgagt aagaccttaa   1020
ggacacagcc aaatcttaag tactgtgtga ccactcttgt tgttatcaca tagtcatact   1080
tggttgtaat atgtgatggt taacctgtag cttataaatt tacttattat tcttttactc   1140
atttactcag tcatttcttt acaagaaaat gattgaatct gttttaggtg acagcacaat   1200
ggacattaag aatttccatc aataatttat gaataagttt ccagaacaaa tttcctaata   1260
acacaatcag attggtttta ttcttttatt ttacgaataa aaaatgtatt tttcagtatc   1320
cttgagattt agaacatctg tgtcacttca gataacattt tagtttcaag tttgtatggt   1380
agtgttttta tagataagat acgtctattt tttcaaaatt catgattgca gtttaaatca   1440
tcatatgacg tgtgggtggg agcaaccaaa gttattttta cagggacttt atttttttgat   1500
ctttatttga gattgttttc atatctatct aaattattag gagtgtgtgt atcagaagta   1560
attttttaat gtcttctaag gatggtcttc caggctttta aactgaaaag cttaattcag   1620
atagtagctt ttggctgaga aaaggaatcc aaaatattaa taaatttaga tctcaaaacc   1680
actattttta ttatttcatt atttttcaga ggccttaaaa ttctggataa gagaatggag   1740
```

```
gaaaatactc agagtacttg attattttat ttccttttat taaaaaatta cttctatgtt   1800
tttattgtct cttgagcctt agttaagagt agtgtagaaa tgcatgaact tcatcctaat   1860
aaggataaaa cttaaggaaa accacaataa accatgaagg tgtacacatc ctataacaca   1920
gataaagttt tggtgtgcta cctattcttg agagagtgag tgagtgtatg tgtttaaagg   1980
aaacaaaatg ggagaaataa gttttaaaaa aatcctcatt ttgttaatat tcaaaagatg   2040
gactgagctt ccacttgggt tttatcttgt tttaattgtt tttgtatcaa aacttgaaat   2100
tcctctattt ctattgggat ataaaagcct tccccttcag tgaagaaaac atttattttt   2160
tatttgattc ctaggattta gtaaactcta gctgtctatt taaaatgtac tgaggcacaa   2220
caagtattat actggaagac ttgccaaact ggcaaagctt taagttcatc agcattctat   2280
gtggttcaga gctgtgattt ttgcaaagta ttttaccaac ctcctcgatg gctttgataa   2340
aggttagatt tgatgttttt tttttagatt tattttttctt actccactaa actataaaga   2400
aaataattac ttagaaactc cattttaaat aatcatttcc tagaaattct taaatatata   2460
cagaatttta aagaaaacat ttcatctgat ttagttagca tccacatatc attgaggaat   2520
taaagtgtgg gacagtcatt att                                           2543
```

<210> SEQ ID NO 29
<211> LENGTH: 2906
<212> TYPE: DNA
<213> ORGANISM: Homo sapiens

<400> SEQUENCE: 29

```
aagaagcgac gtgtcccact gtcctggctc cgtgggtcca gtgagattgg gcctgggcgc     60
tggagctgct gtggctcccg ccgcggcggc tgccatggag gccatgccag agcccagaac    120
tcacgccggg ggaggccgag acagccggcg gtactcatag atgaggcagc ggcggcggcg    180
gcggcggcgg cagcccgggc tctccatgag caggcggcgg cggcgacggg tgcggcggca    240
ccggcagttt tcggtcccca gggaggatga agacactgtt tgaagagatc aaagcatcaa    300
ttaaaaataa ctataaccaa gatcgatcat tttgtaggcc tgttcttcct tggggggtg    360
tttttactat caaagctggc cgcaaagcag tatcctgtac accactctat gttgaaataa    420
gactgaaaaa tacctgcacc atagatggat tcttgatgtt attatatgtc attcttaatg    480
aaaatgaaaa cttccctagg gaactctctc ttcattttgg tagagagttt gtagactgtt    540
ttctttactt aatggacacc tacagtttta caactgtgaa gctactttgg atttgggaca    600
agatggaaaa acagcaatac aaatctgaag tccataaagc ttcattaata attgatttgt    660
ttgggaatga gcatgataat tttacaaaaa atcttgaaaa tctcatgtct accattcaag    720
agagttactg ttccaactgg cgatgcccaa ctcgagtgca ggaggatcag cagcgcacaa    780
ttaatataaa tcctccccaa gaaattccac atggaaactt gataagactg gctgtgaatg    840
agttattctg ttccaagatt gaactgtgtg aagagcatgg gtgtggtggc ttaagagaat    900
tttcccaacg aattttctgc catggggcac cccctttttgt tgtcttaaat atgcaacatt    960
ggaaatctga agatctggcg tatgtaccct attacttgga tttgtctgat cacaagtatt   1020
tgttggaagg tgccacatta tttaacaaag aggaacatca ttattctgca gctttccaga   1080
ttggtggaca ttggatgcac tatgatgggc tcagaaatgt gaatttaatt ttgttaaata   1140
aacccccaga gtttctcctc ttgtcatcat tggtttatat tcgagcaaca gagaaataaa   1200
tatagattga tgctaaaagt tgttttccct cctgcccatg ctctcccaga tgaagggctt   1260
ttattttgtg tatacttggt atccaagaaa atagttcaac tatactagtt tcagaagtgt   1320
```

```
attttcagtg tttaacccca ggtaaatgtt ttatatagag gatctgtgca aaaatgtttg   1380
taattttttt atatttcctg agttattttt atatgagcat attttatgtt ggaataaaat   1440
atatcttgtg gcctttgtat tttttattta tatgtacctc aaagattttt acaattctgt   1500
ctttgaattc aagaaatact ttgtcatctg aattctaaat ttttcttttt ggatattcga   1560
gtaaaaccta ggtaaaagta ttttaagttt atataattta acagttcaaa atatatctga   1620
ctgtatttct ttgccctacc tcactataat ccaaagtgca ctatttgatc tagtatggat   1680
ttgaatgtac aatttatcga tggcttagtt tattagttcg atttgcctag tatccctgca   1740
gcaatttttt aaaatgtctg agaaattttt cagagcttaa actatttctt tataatggca   1800
aattactttt aactacttcc taaagtatta taaacctgcc agtggatttt aagtgatagc   1860
taagcttcca agcttaattc acgttattac aaataaatta tataactatc ttaaatgttt   1920
atcttataat taaatgtaat ttgaaatgct ctaatgtatt ttgcagataa aacaactata   1980
aacaatatta ggcaactgga tgtttactag tgtcggacta gcaatagaaa tgcactttaa   2040
atatatattt aaggggaaat gcgtgcctgg aaatacttct tttcctagtg aagttttata   2100
ttgacacaga gaaaagaata cttaaaattt tgagtgatgt ctactggctt ccttgtaagt   2160
agtgattgat agcatgcggc tttgacttgc aatacaaatc attacgattt tatagttatc   2220
agaacattac gtttctttat aaagacccta aggtcactct tctttttgca acttaaggga   2280
aaaaatattc tcaagggaaa atacttttttg aaatttatca ccattttagt gtttacattt   2340
caataaatag ttcacttcag gtttgggatt gagattagtt gcaatatatt tagaagctcc   2400
tacatgacag cacagatcac tgccatctgc tgaactgcta aagtgcttgg tgccatgttg   2460
agaaaactta cccaagaatg gataaatatg ggtgaaacat tactgagaat gcctcacgtt   2520
agcaaatact atgaaaattc ttgtttatat atcaaactga tttattttac aaaaaaaaaa   2580
aattcacccc aagatttatt tagtttccca agtgtatctg attaggattt aatttagagt   2640
aaacttttct ggggacacct gattgcatga actgaagtat acaataacac aaatattaca   2700
gtaaacataa atggtgtcat taacaaaatt attcctaatg cagatttatt ctttcaggaa   2760
atgcacttta tttggaatac tagtttatca tgaaacaatg acttacctac ctcacagggt   2820
tgttgtgagg attaagatgt ttgttaaaat cttgactacc ttgaacatgc taataaaaaa   2880
acatttttct acctctttta tttgca                                        2906
```

<210> SEQ ID NO 30
<211> LENGTH: 2758
<212> TYPE: DNA
<213> ORGANISM: Homo sapiens

<400> SEQUENCE: 30

```
ggaagaggag gctttctaag gcggtcgctc cgggaaatcc gggccctagg attgtccact     60
catcccagta tcagcgagat acggggagat agagttagcg acaacgtgag ccagagctgg    120
agcacgtttg gtgagagacc agaaagcaat ggaggccgga gaggggaagg agcgcgttcc    180
gaaacaaagg caagtcctga tattctttgt tttgctgggc atagctcagg ctagttgcca    240
gcctaggcac tattcagtgg ccgaggaaac ggagagtggc tcctttgtgg ccaatttgtt    300
aaaagacctg ggctggaga taggagaact tgctgtgagg ggggccaggg tcgtttccaa    360
aggaaaaaaa atgcatttgc agttcgatag gcagaccggg gatttgttgt taaatgagaa    420
attggaccgg gaggagctgt gcggccccac agagccctgt gtcctacctt tccaggtgtt    480
```

```
actagaaaat cccttgcagt tttttcaggc ggagctacgg attagggacg taaatgatca    540
ttccccagtt ttcctagaca aagaaatact tttgaaaatt ccagaaagta tcactcctgg    600
aactactttc ttaatagaac gtgcccagga cttggatgta ggaaccaaca gtctccaaaa    660
ttacacaatc agtcccaatt tccactttca tcttaattta caagacagtc tcgatggcat    720
aatattacca cagctggtgc tgaacagagc cctggatcgc gaggagcagc ctgagatcag    780
gttaaccctc acagcgctag atggcgggag tccacccagg tccggcacgg ccctggtacg    840
gattgaagtt gtggacatca atgacaacgt cccagagttt gcaaagctgc tctatgaggt    900
gcagatcccg gaggacagcc ccgttggatc ccaggttgcc atcgtctctg ccagggattt    960
agacattgga actaatggag aaatatctta tgcattttcc caagcatctg aagacattcg   1020
caaaacgttt cgattaagtg caaaatcggg agaactgctt ttaagacaga aactggattt   1080
cgaatccatc cagacataca cagtaaatat tcaggcgaca gatggtgggg gcctatctgg   1140
aacttgtgtg gtatttgtcc aagtgatgga tttgaatgac aatcctccgg aactaactat   1200
gtcgacactt atcaatcaga tcccagaaaa cttgcaggac accctcattg ctgtattcag   1260
cgtttcagat cctgactccg gagacaacgg aaggatggtg tgctccatcc aagatgatct   1320
tcctttttc ttgaaacctt ctgttgagaa cttttacact ctggtgataa gcacggccct    1380
ggaccgggag accagatccg aatacaacat caccatcacc gtcaccgact tcgggacacc   1440
caggctgaaa accgagcaca acataaccgt gctggtctcc gacgtcaatg acaacgcccc   1500
cgccttcacc caaacctcct acaccctgtt cgtccgcgag aacaacagcc ccgccctgca   1560
catcggcagc gtcagcgcca cagacagaga ctcgggcacc aacgcccagg tcacctactc   1620
gctgctgccg ccccaggacc cgcacctgcc cctcgcctcc ctggtctcca tcaacgcgga   1680
caacggccac ctgttcgctc tccagtcgct ggactacgag gccctgcagg cgttcgagtt   1740
ccgcgtgggc gccgcagacc gcggctcccc ggcgttgagc agcgaggcgc tggtgcgcgt   1800
gctggtgctg gacgccaacg acaactcgcc cttcgtgctg tacccgctgc agaacggctc   1860
cgcgccctgc accgagctgg tgccccgggc ggccgagccg ggctacctgg tgaccaaggt   1920
ggtggcggtg gacggcgact cgggccagaa cgcctggctg tcgtaccagc tgctcaaggc   1980
cacggagccc gggctgttcg gcgtgtgggc gcacaatggc gaggtgcgca ccgccaggct   2040
gctgagggag cgcgacgctg ccaagcagag gctggtggtg ctggtcaagg acaatggcga   2100
gcctccgcgc tcggccaccg ccacgctgca cgtgctcctg gtggacggct tctcccagcc   2160
ctacctgctg ctcccggagg cggcaccggc ccaggcccag gccgacttgc tcaccgtcta   2220
cctggtggtg gcattggcct cggtgtcttc gctcttcctc ttctcggtgc tcctgttcgt   2280
ggcggtgcgg ctgtgcagga ggagcagggc ggcctcggtg ggtcgctgct cggtgcccga   2340
gggcccottt ccagggcaga tggtggacgt gagcggcacc gggaccctgt cccagagcta   2400
ccagtacgag gtgtgtctga ctggagaatc cgggacaaat gagttcaagt tcctgaagcc   2460
aattatcccc aacttcgttg ctcagggtgc agagagggtt agcgaggcaa atcccagttt   2520
caggaagagc tttgaattca cttaagtgtt aataaggatc tactgaggct agtctcgttt   2580
aatttgtgga aagtcctttt ttactgcttt gcccattgga ggtgtctcct tttattagaa   2640
agtaaccatc ttattccaat tctatgcatg ttactggtat ttataaatgt atgagttttt   2700
ttgcggtata ataaatgtaa attttctttg tattctaaaa aaaaaaaaaa aaaaaaaa     2758
```

<210> SEQ ID NO 31
<211> LENGTH: 1584

<212> TYPE: DNA
<213> ORGANISM: Homo sapiens

<400> SEQUENCE: 31

```
cgctaagcgt cccagccgca tccctcccgc agcgacggcg gcccgggacc cgcgggctgt     60
gaaccatgaa cacccgcaat agagtggtga actccgggct cggcgcctcc cctgcctccc    120
gcccgacccg ggatccccag gacccttctg ggcggcaagg ggagctgagc cccgtggaag    180
accagagaga gggtttggag gcagccccta agggcccttc gcgggagagc gtcgtgcacg    240
cgggccagag gcgcacaagt gcatacacct tgatagcacc aaatataaac cggagaaatg    300
agatacaaag aattgcggag caggagctgg ccaacctgga gaagtggaag gagcagaaca    360
gagctaaacc ggttcacctg gtgcccagac ggctaggtgg aagccagtca gaaactgaag    420
tcagacagaa acaacaactc cagctgatgc aatctaaata caagcaaaag ctaaaaagag    480
aagaatctgt aagaatcaag aaggaagctg aagaagctga actccaaaaa atgaaggcaa    540
ttcagagaga gaagagcaat aaactggagg agaaaaaaag acttcaagaa aaccttagaa    600
gagaagcatt tagagagcat cagcaataca aaaccgctga gttcttgagc aaactgaaca    660
cagaatcgcc agacagaagt gcctgtcaaa gtgctgtttg tggcccacaa tcctcaacat    720
ggaaacttcc tatcctgcct agggatcaca gctgggccag aagctgggct tacagagatt    780
ctctaaaggc agaagaaaac agaaaattgc aaaagatgaa ggatgaacaa catcaaaaga    840
gtgaattact ggaactgaaa cggcagcagc aagagcaaga aagagccaaa atccaccaga    900
ctgaacacag gagggtaaat aatgcttttc tggaccgact ccaaggcaaa agtcaaccag    960
gtggcctcga gcaatctgga ggctgttgga atatgaatag cggtaacagc tggggttctc   1020
tattagtttt ttcgaggcac ctaagggtat atgagaaaat attgactcct atctggcctt   1080
catcaactga cctcgaaaag cctcatgaga tgctttttct taatgtgatt ttgttcagcc   1140
tcactgtttt taccttaatt tcaactgccc acacacttga ccgtgcagtc aggagtgact   1200
ggcttctcct tgtcctcatt tatgcatgtt tggaggagct gattcctgaa ctcatattta   1260
atctctactg ccagggaaat gctacattat ttttctaatt ggaagtataa ttagagtgat   1320
gttggtaggg tagaaaaaga gggagtcact tgatgctttc aggttaatca gagctatggg   1380
tgctacaggc ttgtctttct aagtgacata ttcttatcta attctcagat caggttttga   1440
aaagctttgg gggtcttttt agattttaat ccctactttc tttatggtac aaatatgtac   1500
aaaagaaaaa ggtcttatat tcttttacac aaatttataa ataaattttg aactccttct   1560
gtaaaaaaaa aaaaaaaaaa aaaa                                          1584
```

<210> SEQ ID NO 32
<211> LENGTH: 4171
<212> TYPE: DNA
<213> ORGANISM: Homo sapiens

<400> SEQUENCE: 32

```
ctggagccgc tgagcccccg ctgcggccgg gagctgcatg ggggagcgcc ggcagcgctt     60
gggaagatgc cccggccgga gctgcccctg ccggagggct gggaggaggc gcgcgacttc    120
gacggcaagg tctactacat agaccacacg aaccgcacca ccagctggat cgacccgcgg    180
gacaggtaca ccaaaccgct cacctttgct gactgcatta gtgatgagtt gccgctagga    240
tgggaagagg catatgaccc acaggttgga gattacttca tagaccacaa caccaaaacc    300
actcagattg aggatcctcg agtacaatgg cggcgggagc aggaacatat gctgaaggat    360
```

```
tacctggtgg tggcccagga ggctctgagt gcacaaaagg agatctacca ggtgaagcag    420
cagcgcctgg agcttgcaca gcaggagtac cagcaactgc atgccgtctg ggagcataag    480
ctgggctccc aggtcagctt ggtctctggt tcatcatcca gctccaagta tgaccctgag    540
atcctgaaag ctgaaattgc cactgcaaaa tcccgggtca acaagctgaa gagagagatg    600
gttcacctcc agcacgagct gcagttcaaa gagcgtggct ttcagaccct gaagaaaatc    660
gataagaaaa tgtctgatgc tcagggcagc tacaaactgg atgaagctca ggctgtcttg    720
agagaaacaa aagccatcaa aaaggctatt acctgtgggg aaaaggaaaa gcaagatctc    780
attaagagcc ttgccatgtt gaaggacggc ttccgcactg acaggggggtc tcactcagac    840
ctgtggtcca gcagcagctc tctggagagt tcgagtttcc cgctaccgaa acagtacctg    900
gatgtgagct cccagacaga catctcggga agcttcggca tcaacagcaa caatcagttg    960
gcagagaagg tcagattgcg ccttcgatat gaagaggcta agagaaggat cgccaacctg   1020
aagatccagc tggccaagct tgacagtgag gcctggcctg ggtgctgga ctcagagagg   1080
gaccggctga tccttatcaa cgagaaggag gagctgctga aggagatgcg cttcatcagc   1140
ccccgcaagt ggacccaggg ggaggtggag cagctggaga tggcccggaa gcggctggaa   1200
aaggacctgc aggcagcccg ggacacccag agcaaggcgc tgacggagag gttaaagtta   1260
aacagtaaga ggaaccagct tgtgagagaa ctggaggaag ccacccggca ggtggcaact   1320
ctgcactccc agctgaaaag tctctcaagc agcatgcagt ccctgtcctc aggcagcagc   1380
cccggatccc tcacgtccag ccggggctcc ctggttgcat ccagcctgga ctcctccact   1440
tcagccagct tcactgacct ctactatgac ccctttgagc agctggactc agagctgcag   1500
agcaaggtgg agttcctgct cctggagggg gccaccggct tccggccctc aggctgcatc   1560
accaccatcc acgaggatga ggtggccaag acccagaagg cagagggagg tggccgcctg   1620
caggctctgc gttccctgtc tggcacccca aagtccatga cctccctatc cccacgttcc   1680
tctctctcct ccccctcccc accctgttcc cctctcatgg ctgacccccct cctggctggt   1740
gatgccttcc tcaactcctt ggagtttgaa gacccggagc tgagtgccac tctttgtgaa   1800
ctgagccttg gtaacagcgc ccaggaaaga taccggctgg aggaaccagg aacggagggc   1860
aagcagctgg gccaagctgt gaatacggcc caggggtgtg gcctgaaagt ggcctgtgtc   1920
tcagccgccg tatcggacga gtcagtggct ggagacagtg gtgtgtacga ggcttccgtg   1980
cagagactgg gtgcttcaga agctgctgca tttgacagtg acgaatcgga agcagtgggt   2040
gcgacccgaa ttcagattgc cctgaagtat gatgagaaga ataagcaatt tgcaatatta   2100
atcatccagc tgagtaacct ttctgctctg ttgcagcaac aagaccagaa agtgaatatc   2160
cgcgtggctg tccttccttg ctctgaaagc acaacctgcc tgttccggac ccggcctctg   2220
gacgcctcag acactctagt gttcaatgag gtgttctggg tatccatgtc ctatccagcc   2280
cttcaccaga agaccttaag agtcgatgtc tgtaccaccg acaggagcca tctggaagag   2340
tgcctgggag gcgcccagat cagcctggcg gaggtctgcc ggtctgggga gaggtcgact   2400
cgctggtaca accttctcag ctacaaatac ttgaagaagc agagcaggga gctcaagcca   2460
gtgggagtta tggcccctgc ctcagggcct gccagcacgg acgctgtgtc tgctctgttg   2520
gaacagacag cagtggagct ggagaagagg caggagggca ggagcagcac acagacactg   2580
gaagacagct ggaggtatga ggagaccagt gagaatgagg cagtagccga ggaagaggag   2640
gaggaggtgg aggaggagga gggagaagag gatgttttca ccgagaaagc ctcacctgat   2700
atggatgggt acccagcatt aaaggtggac aaagagacca acacggagac cccggcccca   2760
```

```
tcccccacag tggtgcgacc taaggaccgg agagtgggca ccccgtccca ggggccattt   2820
cttcgaggga gcaccatcat ccgctctaag accttctccc caggacccca gagccagtac   2880
gtgtgccggc tgaatcggag tgatagtgac agctccactc tgtccaaaaa gccacctttt   2940
gttcgaaact ccctggagcg acgcagcgtc cggatgaagc ggccttcctc ggtcaagtcg   3000
ctgcgctccg agcgtctgat ccgtacctcg ctggacctgg agttagacct gcaggcgaca   3060
agaacctggc acagccaact gacccaggag atctcggtgc tgaaggagct caaggagcag   3120
ctggaacaag ccaagagcca cggggagaag gagctgccac agtggttgcg tgaggacgag   3180
cgtttccgcc tgctgctgag gatgctggag aagcggcaga tggaccgagc ggagcacaag   3240
ggtgagcttc agacagacaa gatgatgagg gcagctgcca aggatgtgca caggctccga   3300
ggccagagct gtaaggaacc cccagaagtt cagtctttca gggagaagat ggcatttttc   3360
acccggcctc ggatgaatat cccagctctc tctgcagatg acgtctaatc gccagaaaag   3420
tatttccttt gttccactga ccaggctgtg aacattgact gtggctaaag ttatttatgt   3480
ggtgttatat gaaggtactg agtcacaagt cctctagtgc tcttgttggt ttgaagatga   3540
accgactttt tagtttgggt cctactgttg ttattaaaaa cagaacaaaa acaaaacaca   3600
cacacacaca aaaacagaaa caaaaaaaac cagcattaaa ataataagat tgtatagttt   3660
gtatatttag gagtgtattt ttgggaaaga aaatttaaat gaactaaagc agtattgagt   3720
tgctgctctt cttaaaatcg tttagatttt ttttggtttg tacagctcca ccttttagag   3780
gtcttactgc aataagaagt aatgcctggg ggacggtaat cctaatagga cgtcccgcac   3840
ttgtcacagt acagctaatt tttcctagtt aacatatttt gtacaatatt aaaaaaatgc   3900
acagaaacca ttggggggga ttcagaggtg catccacgga tcttcttgag ctgtgacgtg   3960
tttttatgtg gctgcccaac gtggagcggg cagtgtgata ggctgggtgg gctaagcagc   4020
ctagtctatg tgggtgacag gccacgctgg tctcagatgc ccagtgaagc cactaacatg   4080
agtgagggga gggctgtggg gaactccatt cagttttatc tccatcaata aagtggcctt   4140
tcaaaaagaa aaaaaaaaaa aaaaaaaaaa a                                  4171
```

```
<210> SEQ ID NO 33
<211> LENGTH: 3084
<212> TYPE: DNA
<213> ORGANISM: Homo sapiens

<400> SEQUENCE: 33

aatcggttga gagctgagct ggacttggcg gtgggagccg gagcctgctt gttgcagctg     60
tgggtgagga cggctctagc tagttccctt ttagactatg gcgacatacc tggagttcat    120
ccagcagaat gaagaacggg atggtgtgcg ttttagttgg aacgtgtggc cttccagccg    180
gctggaggct acaagaatgg ttgtacccct ggcttgtctc cttactcctt tgaaagaacg    240
tccagaccta cctcctgtac aatatgaacc tgtgctttgc agcaggccaa cttgtaaagc    300
tgttctcaac ccactttgtc aggttgatta tcgagcaaaa ctttgggcct gtaatttctg    360
ttttcaaaga aatcagtttc ctccagctta tggaggcata tctgaggtga atcaacctgc    420
cgaattgatg ccccagtttt ctacaattga gtacgtgata cagcgaggtg ctcagtcccc    480
tctgatcttt ctctatgtgg ttgacacatg cctggaggaa gatgaccttc aagcactcaa    540
agagtccctg cagatgtccc tgagtcttct tcctccagat gctctggtgg gtctgatcac    600
atttggaagg atggtgcagg ttcatgagct aagctgtgaa ggaatctcca aaagttatgt    660
```

```
cttccgaggg accaaggatt taactgcaaa gcaaatacag gatatgttgg gcctgaccaa    720
gccagccatg cccatgcagc aagcacgacc tgcacaacca caggagcacc cttttgcttc    780
aagcagattt ctgcagcctg ttcacaagat tgatatgaac ctcactgatc ttcttgggga    840
gctacagagg gacccatggc cagtaactca ggggaagaga cctttgcgat ccactggtgt    900
ggctttgtcc attgctgttg gcttgctgga gggcactttt ccaaacacag gagccaggat    960
catgctgttt actggaggtc cccctaccca agggcctggc atggtggttg gagatgaatt   1020
aaagattcct attcgttctt ggcatgatat tgagaaagat aatgcacgat tcatgaaaaa   1080
ggcaaccaag cactatgaga tgcttgctaa tcgaacagct gcaaatggtc actgcattga   1140
tatttatgct tgtgcccttg atcaaactgg acttttggag atgaagtgtt gtgcaaatct   1200
tactggaggc tacatggtaa tgggagattc tttcaacact tctctcttca agcagacatt   1260
ccaaagaatc tttactaaag attttaatgg agatttccga atggcatttg gtgctacttt   1320
ggacgtaaag acctctcggg aactgaagat tgcaggagcc attggtccat gcgtatctct   1380
gaatgtgaaa ggactgtgtg tgtcagaaaa tgagcttggt gttggtggca cgagtcagtg   1440
gaaaatctgt ggcctagatc ctacatctac acttggcatc tattttgaag ttgtcaatca   1500
gcacaacacc ccgatccccc aaggaggcag aggagccatc cagtttgtca cgcattatca   1560
gcactccagc acccagagac gcatccgcgt gaccaccatc gcccgaaatt gggcagatgt   1620
acagagtcag ctcaggcaca tagaagcagc atttgaccag gaggctgcgg cagtgttgat   1680
ggcacggctt ggggtgttcc gagcggagtc agaggagggg cccgatgtgc tccggtggct   1740
ggaccgacaa ctcatccgac tgtgtcaaaa gtttggacag tataacaaag aagaccccac   1800
ttcttttagg ttatcagatt ccttttctct atatcctcag tttatgttcc atctgagaag   1860
atctccattt cttcaagtgt ttaacaacag tcctgatgag tcgtcatatt acagacatca   1920
ttttgcccgg caggacctga cccagtccct catcatgatc cagcccattc tctactctta   1980
ctcctttcat gggccaccag agccagtact cttggatagc agcagcattc tagctgacag   2040
aattttgctg atggatactt tctttcaaat tgtcatttat cttggtgaga ccatagccca   2100
gtggcgtaaa gctggctacc aggacatgcc cgagtatgaa aacttcaagc accttctgca   2160
ggcaccactg gatgatgctc aagaaattct gcaagcacgc ttcccgatgc cacgttacat   2220
caacacggag catggaggca gtcaggctcg attccttttg tccaaagtga acccatctca   2280
gacacacaat aacctgtatg cttggggaca ggaaactgga gcacccatcc taactgatga   2340
tgttagcctg caggtgttca tggaccattt gaagaagctg gctgtctcca gtgcctgtta   2400
agctgaggat acaaccagga aatgcaacgg tgtcagattg tgttcaaaat gtctagaaag   2460
gcttgataac attcctgtta cttttctagc agattttaac aaataatcaa ggacatttta   2520
tatgtaactc tttagattat aatttatttg tattcctgtc tttgtccttt ttcttgcact   2580
ataaaattat aaggtcataa atgttttggt acttgtagat gtttatgtgc tttttgtatc   2640
ctaactttta gaatctaaat aaaatcagag gtaatgtatt ttggcagctt gtttaggtga   2700
gaatcttaat gatcataaaa ggaaataaat ctagatgcag aaagtactgg ctaaaatatt   2760
gctaatacaa atgtgatttc ctgaggtctc tgtgtgagtg tgtatgtgtt ttaagtgact   2820
tccttaagag gtgtttcctg aacctaattc tcataattaa agtaatgtat atgcaggatc   2880
aaaatgaaac aaatatacct tatcctaaag agctcataac aaataagtta cctccactct   2940
ataaactcag acctactttt tgaagataac tgcttttaac ctctccttac aagatttttg   3000
ttgttgatgt atttaatttt agcccatgtc tcaattctca ttttcaaaga atcaatatat   3060
```

taatatacaa aaaaaaaaaa aaaa 3084

<210> SEQ ID NO 34
<211> LENGTH: 2461
<212> TYPE: DNA
<213> ORGANISM: Homo sapiens

<400> SEQUENCE: 34
atgctgggta cgctgcgcgc catggagggc gaggacgtgg aagacgacca gctgctgcag 60
aagctcaggg ccagtcgccg ccgcttccag aggcgcatgc agcggctgat agagaagtac 120
aaccagccct tcgaggacac cccggtggtg caaatggcca cgctgaccta cgagacgcca 180
cagggattga gaatttgggg tggaagacta ataaaggaaa gaaacaaagg agagatccag 240
gactcctcca tgaagcccgc ggacaggaca gatggctccg tgcaagctgc agcctggggt 300
cctgagcttc cctcgcaccg cacagtcctg ggagccgatt caaaaagcgg tgaggtcgat 360
gccacgtcag accaggaaga gtcagttgct tgggccttag cacctgcagt gcctcaaagc 420
cctttgaaaa atgaattaag aaggaaatac ttgacccaag tggatatact gctacaaggt 480
gcagagtatt ttgagtgtgc aggtaacaga gctggaaggg atgtacgtgt gactccgctg 540
ccttcactgg cctcacctgc cgtgcctgcc cccggatact gcagtcgtat ctccggaaag 600
agtcctggtg acccagcgaa accagcttca tctcccagag aatgggatcc tttgcatcct 660
tcctccacag acatggcctt agtacctaga aatgacagcc tctccctaca agagaccagt 720
agcagcagct tcttaagcag ccagcccttt gaagatgatg acatttgcaa tgtgaccatc 780
agtgacctgt acgcagggat gctgcactcc atgagccggc tgttgagcac aaagccatca 840
agcatcatct ccaccaaaac gttcatcatg caaaactgga actgcaggag gaggcacaga 900
tataagagca ggatgaacaa aacatattgc aaaggagcca gacgttctca gaggagctcc 960
aaggagaact tcataccctg ctctgagcct gtgaaaggga caggggcatt aagagattgc 1020
aagaacgtat tagatgtttc ttgccgtaag acaggtttaa aattggaaaa agcttttctt 1080
gaagtcaaca gaccccaaat ccataagtta gatccaagtt ggaaggagcg caaagtgaca 1140
ccctcgaagt attcttcctt gatttacttc gactccagtg caacatataa tcttgatgag 1200
gaaaatagat ttaggacatt aaaatggtta atttctcctg taaaaatagt ttccagacca 1260
acaatacgac agggccatgg agagaaccgt cagagggaga ttgaaatccg atttgatcag 1320
cttcatcggg aatattgcct gagtcccagg aaccagcctc gccggatgtg cctcccggac 1380
tcctgggcca tgaacatgta cagagggggt cctgcgagtc ctggtggcct tcagggctta 1440
gaaacccgca ggctgagttt accttccagc aaagcaaaag caaaaagttt aagtgaggct 1500
tttgaaaacc taggcaaaag atctctggaa gcaggtaggt gcctgcccaa gagcgattca 1560
tcttcatcac ttccaaagac caaccccaca cacagcgcaa ctcgcccgca gcagacatct 1620
gaccttcacg ttcagggaaa tagttctgga atatttagaa agtcagtgtc acccagcaaa 1680
actctttcag tcccagataa agaagtgcca ggccacggaa ggaatcgtta cgatgaaatt 1740
aaagaagaat ttgacaagct tcatcaaaag tattgcctca aatctcctgg gcagatgaca 1800
gtgcctttat gtattggagt gtctacagat aaagcaagta tggaagttcg atatcaaaca 1860
gaaggcttct taggaaaatt aaatccagac cctcacttcc agggtttcca gaagttgcca 1920
tcatcacccc tggggtgcag aaaaagtcta ctgggctcaa ctgcaattga ggctccttca 1980
tctacatgtg ttgctcgtgc catcacgagg gatggcacga gggaccatca gttccctgca 2040
aaaagaccca ggctatcaga accccagggc tccggacgcc agggcaattc cctgggtgcc 2100
tcagatgggg tggacaacac cgtcagaccg ggagaccagg gcagctcttc acagcccaac 2160
tcagaagaga gaggagagaa cacgtcttac aggatggaag agaaaagtga tttcatgcta 2220
gaaaaattgg aaactaaaag tgtgtagcta ggttatttcg gagtgttatt tatcttccca 2280
cttgctctct gtttgtattt ttgttttgtt tttgattctt gagactgtga ggacttggtt 2340
gacttctctg cccttaaagt aaatattagt gaaattggtt ccatcagaga taacctcgag 2400
ttcttggtgt agaaattatg tgaataaagt tgctcaatta gaaaaaaaaa aaaaaaaaaa 2460
a 2461

<210> SEQ ID NO 35
<211> LENGTH: 3625
<212> TYPE: DNA
<213> ORGANISM: Homo sapiens

<400> SEQUENCE: 35
ccgctcgccg tccttgcagg ctctgccgtc ggaaagccgc tcattctcgc ttccccttcc 60
ctttcccggc tcaagtcctt cctctctctt tcctttcttt ccgcctatct tttttctgct 120
gccgctccgg gtccgggcca ttttccgggc cgggcgcact aaggtgcgcg gccccggggc 180
ccagtatatg acccgccgtc ctgctatcct tcgcttcccc cgccccatgt ggctgcgggg 240
ccgcggcggc gctgcccact atggcccgga aagtagttag caggaagcgg aaagcgcccg 300
cctcgccggg agctgggagc gacgctcagg gcccgcagtt tggctgggat cactcgcttc 360
acaaaaggaa aagacttcct cctgtgaaga gatccttagt atactacttg aagaaccggg 420
aagtcaggct acagaatgaa accagctact ctcgagtgtt gcatggttat gcagcacagc 480
aacttcccag tctcctgaag gagagagagt ttcaccttgg gacccttaat aaagtgtttg 540
catctcagtg gttgaatcat aggcaagtgg tgtgtggcac aaaatgcaac acgctatttg 600
tcgtagatgt ccagacaagc cagatcacca agatccccat tctgaaagac caggagcctg 660
gaggtgtgac ccagcagggc tgtggtatcc atgccatcga gctgaatcct tctagaacac 720
tgctagccac tggaggagac aaccccaaca gtcttgccat ctatcgacta cctacgctgg 780
atcctgtgtg tgtaggagat gatggacaca aggactggat cttttccatc gcatggatca 840
gcgacactat ggcagtgtct ggctcacgtg atggttctat gggactctgg gaggtgacag 900
atgatgtttt gaccaaaagt gatgcgagac acaatgtgtc acgggtccct gtgtatgcac 960
acatcactca caaggcctta aaggacatcc ccaaagaaga cacaaaccct gacaactgca 1020
aggttcgggc tctggccttc aacaacaaga acaaggaact gggagcagtg tctctggatg 1080
gctactttca tctctggaag gctgaaaata cactatctaa gctcctctcc accaaactgc 1140
catattgccg tgagaatgtg tgtctggctt atggtagtga atggtcagtt tatgcagtgg 1200
gctcccaagc tcatgtctcc ttcttggatc cacggcagcc atcatacaac gtcaagtctg 1260
tctgttccag ggagcgaggc agtggaatcc ggtcagtgag tttctacgag cacatcatca 1320
ctgtgggaac agggcagggc tccctgctgt tctatgacat ccgagctcag agatttctgg 1380
aagagaggct ctcagcttgt tatgggtcca agcccagact agcaggggag aatctgaaac 1440
taaccactgg caaaggctgg ctgaatcatg atgaaacctg gaggaattac ttttcagaca 1500
ttgacttctt ccccaatgct gtttacaccc actgctacga ctcgtctgga acgaaactct 1560
ttgtggcagg aggtcccctc ccttcagggc tccatggaaa ctatgctggg ctctggagtt 1620
aatgacaact ccccaaatgc agagatttac actaacttcc attctcagtt tccttgtttc 1680

```
ttttgatttt ttttttccta attgtgtgag gctcttgtgt tttagtggga acaccaaagt   1740
ttgcctatag tttaggcact taataggaag aagctctgta cagaaatctg aaagttgttt   1800
tgctttttgt tttccccttt ggtaatcaaa attttactat cttttattat ttctggcttt   1860
tcaaccaaac attgttgcta atccctattt ttctttaagt gacacacatt ctcctgtctc   1920
tggcttcttc aggctgaaat gacatagtct ttctcaccct tacttcactc ttgagaggta   1980
gggctccttt ataattacat ggttgctctc agactttctg tgaaagtttg ggagctgtgt   2040
gtgtctgtgt gtgtgtgaga gagagatctt gtctgcgtgt gtgtgtgtga tcttgtgtgc   2100
ctgtaggtac tgtgtgtcac tgaaattacc tggagtgagg attacttgta attaaaatat   2160
ttataaaaga aacaacttta ttcacagagt ccagctttgg gactagtctg tatcttgttt   2220
tttaagtcta acaacactga taataggaag taaaaacaga aaggaaaaga aattaccact   2280
gggaaaatct ttttagttag attgtaggct tcctggggcc tcccatgcca ggactgcaaa   2340
gtgatccagc cctacctgtc ttcccacctg tgtgtccccc gtgtgggaag ttggtgtcac   2400
ttccccttcc caccctcaca tctgcttagc cagtagccac accccttaaaa catcagactc   2460
accatccagg tgcagctcca gaggctacaa aaggcttcat gggacttgaa tccccatcct   2520
agcttctctc tccttcccct caagacctga tctggtttta aggggcctgg agctgggagt   2580
ctcaagtctg ctaagattca catccatagc cccccatggct ttgaggagaa tcctctctgc   2640
cattcttcca atctccccag tgggttttgc tattattttc taaattgggt taagtctaag   2700
aaggtggggg tgagcagggg gtttatctgt gtgtagtgag tgcttcatgt gtggaatatt   2760
cattttctta ctgcagtggg acttggggtt gaagccaccc ctcctactct gttggcttag   2820
ccctgagatg gtgacaggct ggcctgcagt cagcatcatt gtgcatgtga cagcatcaat   2880
gtgattagta atttgtctgt tcctcccttg aactgtctgt ttagtctgag gtttttaaac   2940
ttgcaggcag ctgactgtga tgtccacttg ttccctgatt tttacacatc atgtcaaaga   3000
taacagctgt tcccacccac cagttcctct aagcacatac tctgcttttc tgtcaacatc   3060
ccattttggg gaaaggaaaa gtcatattta ttcctgcacc ccagtttttt aacttgttct   3120
cccagttgtc cccctcttct ctgggtgtaa gaagggaaat tggaaaaaaa attatatata   3180
tattctcctt ttaatggtgg ggggctactg gagaggagag acagcaagtc caccctaact   3240
tgttacacag cacataccac aggttctgga attctcatct tcgaacctag agaaataggt   3300
gctataaaca gggaattaag caaaatgctg gatgctatag atcttttaat tgtcttaatt   3360
ttttttctat tattaaacta caggctgtag atttcttagt tctcacagaa cttctatcat   3420
tttaaactga cttgtatatt taaaaaaaaa atcttcagta ggatgttttg tactattgct   3480
agaccctctt ctgtaatggg taatgcgttt gattgtttga gattttctgt ttttaaaaat   3540
gtagcacttg actttttgcc aaggaaaaaa ataaaaatta ttccagtgca aaaaaaaaaa   3600
aaaaaaaaaa aaaaaaaaaa aaaaa                                          3625
```

<210> SEQ ID NO 36
<211> LENGTH: 1634
<212> TYPE: DNA
<213> ORGANISM: Homo sapiens

<400> SEQUENCE: 36

```
gctgcttccc accagcaaag accacgactg gagagccgag ccggaggcag ctgggaaaca     60
tgaagagcgt cttgctgctg accacgctcc tcgtgcctgc acacctggtg gccgcctgga    120
```

```
gcaataatta tgcggtggac tgccctcaac actgtgacag cagtgagtgc aaaagcagcc    180
cgcgctgcga gaggacagtg ctcgacgact gtggctgctg ccgagtgtgc gctgcagggc    240
ggggagaaac ttgctaccgc acagtctcag gcatggatgg catgaagtgt ggcccggggc    300
tgaggtgtca gccttctaat ggggaggatc cttttggtga agagtttggt atctgcaaag    360
actgtcccta cggcaccttc gggatggatt gcagagagac ctgcaactgc cagtcaggca    420
tctgtgacag gggggacgga aaatgcctga aattcccctt cttccaatat tcagtaacca    480
agtcttccaa cagatttgtt tctctcacgg agcatgacat ggcatctgga gatggcaata    540
ttgtgagaga agaagttgtg aaagagaatg ctgccgggtc tcccgtaatg aggaaatggt    600
taaatccacg ctgatcccgg ctgtgatttc tgagagaagg ctctattttc gtgattgttc    660
aacacacagc caacatttta ggaactttct agattatagc ataaggacat gtaatttttg    720
aagaccaaat gtgatgcatg gtggatccag aaaacaaaaa gtaggatact tacaatccat    780
aacatccata tgactgaaca cttgtatgtg tttgttaaat attcgaatgc atgtagattt    840
gttaaatgtg tgtgtatagt aacactgaag aactaaaaat gcaatttagg taatcttaca    900
tggagacagg tcaaccaaag agggagctag gcaaagctga agaccgcagt gagtcaaatt    960
agttctttga ctttgatgta cattaatgtt gggatatgga atgaagactt aagagcagga   1020
gaagatgggg agggggtggg agtgggaaat aaaatattta gcccttcctt ggtaggtagc   1080
ttctctagaa tttaattgtg cttttttttt ttggctttgg gaaaagtcaa aataaaacaa   1140
ccagaaaacc cctgaaggaa gtaagatgtt tgaagcttat ggaaatttga gtaacaaaca   1200
gctttgaact gagagcaatt tcaaaaggct gctgatgtag ttcccgggtt acctgtatct   1260
gaaggacggt tctggggcat aggaaacaca tacacttcca taaatagctt taacgtatgc   1320
cacctcagag ataaatctaa gaagtatttt acccactggt ggtttgtgtg tgtatgaagg   1380
taaatattta tatattttta taaataaatg tgttagtgca agtcatcttc cctacccata   1440
tttatcatcc tcttgaggaa agaaatctag tattatttgt tgaaaatggt tagaataaaa   1500
ctatgactct ataaggtttt caaacatctg aggcatgata aatttattat ccataattat   1560
agtaataata accttaataa gcataagaaa aacagagtca ctctggattt caaaaatgtc   1620
aaaaaaaaaa aaaa                                                     1634
```

<210> SEQ ID NO 37
<211> LENGTH: 7291
<212> TYPE: DNA
<213> ORGANISM: Homo sapiens

<400> SEQUENCE: 37

```
acacagtact ctcagcttgt tggtggaagc ccctcatctg ccttcattct gaaggcaggg     60
cccggcagag gaaggatcag agggtcgcgg ccggagggtc ccggccggtg gggccaactc    120
agagggagag gaaagggcta gagacacgaa gaacgcaaac catcaaattt agaagaaaaa    180
gccctttgac tttttccccc tctccctccc caatggctgt gtagcaaaca tccctggcga    240
taccttggaa aggacgaagt tggtctgcag tcgcaatttc gtgggttgag ttcacagttg    300
tgagtgcggg gctcggagat ggagccgtgg tcctctaggt ggaaaacgaa acggtggctc    360
tgggatttca ccgtaacaac cctcgcattg accttcctct tccaagctag agaggtcaga    420
ggagctgctc cagttgatgt actaaaagca ctagattttc acaattctcc agagggaata    480
tcaaaaacaa cgggattttg cacaaacaga aagaattcta aaggctcaga tactgcttac    540
agagtttcaa agcaagcaca actcagtgcc ccaacaaaac agttatttcc aggtggaact    600
```

```
ttcccagaag acttttcaat actatttaca gtaaaaccaa aaaaaggaat tcagtctttc    660
cttttatcta tatataatga gcatggtatt cagcaaattg gtgttgaggt tgggagatca    720
cctgtttttc tgtttgaaga ccacactgga aaacctgccc cagaagacta tcccctcttc    780
agaactgtta acatcgctga cgggaagtgg catcgggtag caatcagcgt ggagaagaaa    840
actgtgacaa tgattgttga ttgtaagaag aaaaccacga aaccacttga tagaagtgag    900
agagcaattg ttgataccaa tggaatcacg gtttttggaa caaggatttt ggatgaagaa    960
gtttttgagg gggacattca gcagtttttg atcacaggtg atcccaaggc agcatatgac   1020
tactgtgagc attatagtcc agactgtgac tcttcagcac ccaaggctgc tcaagctcag   1080
gaacctcaga tagatgagta tgcaccagag gatataatcg aatatgacta tgagtatggg   1140
gaagcagagt ataaagaggc tgaaagtgta acagagggac ccactgtaac tgaggagaca   1200
atagcacaga cggaggcaaa catcgttgat gattttcaag aatacaacta tggaacaatg   1260
gaaagttacc agacagaagc tcctaggcat gtttctggga caaatgagcc aaatccagtt   1320
gaagaaatat ttactgaaga atatctaacg ggagaggatt atgattccca gaggaaaaat   1380
tctgaggata cactatatga aaacaaagaa atagacggca gggattctga tcttctggta   1440
gatggagatt taggcgaata tgatttttat gaatataaag aatatgaaga taaaccaaca   1500
agccccccta atgaagaatt tggtccaggt gtaccagcag aaactgatat tacagaaaca   1560
agcataaatg gccatggtgc atatggagag aaaggacaga aaggagaacc agcagtggtt   1620
gagcctggta tgcttgtcga aggaccacca ggaccagcag gacctgcagg tattatgggt   1680
cctccaggtc tacaaggccc cactggaccc cctggtgacc ctggcgatag gggccccca   1740
ggacgtcctg gcttaccagg ggctgatggt ctacctggtc ctcctggtac tatgttgatg   1800
ttaccgttcc gttatggtgg tgatggttcc aaaggaccaa ccatctctgc tcaggaagct   1860
caggctcaag ctattcttca gcaggctcgg attgctctga gaggcccacc tggcccaatg   1920
ggtctaactg gaagaccagg tcctgtgggg gggcctggtt catctggggc caaaggtgag   1980
agtggtgatc caggtcctca gggccctcga ggcgtccagg gtccccctgg tccaacggga   2040
aaacctggaa aaaggggtcg tccaggtgca gatggaggaa gaggaatgcc aggagaacct   2100
ggggcaaagg gagatcgagg gtttgatgga cttccgggtc tgccaggtga caaaggtcac   2160
aggggtgaac gaggtcctca aggtcctcca ggtcctcctg gtgatgatgg aatgaggga   2220
gaagatggag aaattggacc aagaggtctt ccaggtgaag ctggcccacg aggtttgctg   2280
ggtccaaggg gaactccagg agctccaggg cagcctggta tggcaggtgt agatggcccc   2340
ccaggaccaa aagggaacat gggtccccaa ggggagcctg ggcctccagg tcaacaaggg   2400
aatccaggac ctcagggtct tcctggtcca caaggtccaa ttggtcctcc tggtgaaaaa   2460
ggaccacaag gaaaaccagg acttgctgga cttcctggtg ctgatgggcc tcctggtcat   2520
cctgggaaag aaggccagtc tggagaaaag ggggctctgg gtccccctgg tccacaaggt   2580
cctattggat acccgggccc ccggggagta aagggagcag atggtgtcag aggtctcaag   2640
ggatctaaag gtgaaaaggg tgaagatggt tttccaggat tcaaaggtga catgggtcta   2700
aaaggtgaca gaggagaagt tggtcaaatt ggcccaagag gggaagatgg ccctgaagga   2760
cccaaaggtc gagcaggccc aactggagac ccaggtcctt caggtcaagc aggagaaaag   2820
ggaaaacttg gagttccagg attaccagga tatccaggaa gacaaggtcc aaagggttcc   2880
actggattcc ctgggtttcc aggtgccaat ggagagaaag gtgcacgggg agtagctggc   2940
```

```
aaaccaggcc ctcggggtca gcgtggtcca acgggtcctc gaggttcaag aggtgcaaga   3000
ggtcccactg ggaaacctgg gccaaagggc acttcaggtg gcgatggccc tcctggccct   3060
ccaggtgaaa gaggtcctca aggacctcag ggtccagttg gattccctgg accaaaaggc   3120
cctcctggac cacctgggaa ggatgggctg ccaggacacc ctgggcaacg tggggagact   3180
ggatttcaag gcaagaccgg ccctcctggg ccagggggag tggttggacc acagggacca   3240
accggtgaga ctggtccaat aggggaacgt gggcatcctg gccctcctgg ccctcctggt   3300
gagcaaggtc ttcctggtgc tgcaggaaaa gaaggtgcaa agggtgatcc aggtcctcaa   3360
ggtatctcag ggaaagatgg accagcagga ttacgtggtt tcccagggga aagaggtctt   3420
cctggagctc agggtgcacc tggactgaaa ggaggggaag gtccccaggg cccaccaggt   3480
ccagttggct caccaggaga acgtgggtca gcaggtacag ctggcccaat tggtttacca   3540
gggcgcccgg gacctcaggg tcctcctggt ccagctggag agaaaggtgc tcctggagaa   3600
aaaggtcccc aagggcctgc agggagagat ggagttcaag gtcctgttgg tctcccaggg   3660
ccagctggtc ctgccggctc ccctggggaa gacggagaca agggtgaaat tggtgagccg   3720
ggacaaaaag gcagcaaggg tgacaaggga gaaaatggcc ctcccggtcc cccaggtctt   3780
caaggaccag ttggtgcccc tggaattgct ggaggtgatg gtgaaccagg tcctagagga   3840
cagcagggga tgtttgggca aaaaggtgat gagggtgcca gaggcttccc tggacctcct   3900
ggtccaatag gtcttcaggg tctgccaggc ccacctggtg aaaaaggtga aaatggggat   3960
gttggtccca tggggccacc tggtcctcca ggcccaagag gccctcaagg tcccaatgga   4020
gctgatggac cacaaggacc cccagggtct gttggttcag ttggtggtgt tggagaaaag   4080
ggtgaacctg gagaagcagg gaacccaggg cctcctgggg aagcaggtgt aggcggtccc   4140
aaaggagaaa gaggagagaa aggggaagct ggtccacctg gagctgctgg acctccaggt   4200
gccaaggggc caccaggtga tgatggccct aagggtaacc cgggtcctgt tggttttcct   4260
ggagatcctg gtcctcctgg ggaacctggc cctgcaggtc aagatggtgt tggtggtgac   4320
aagggtgaag atggagatcc tggtcaaccg ggtcctcctg gcccatctgg tgaggctggc   4380
ccaccaggtc ctcctggaaa acgaggtcct cctggagctg caggtgcaga gggaagacaa   4440
ggtgaaaaag gtgctaaggg ggaagcaggt gcagaaggtc ctcctggaaa aaccggccca   4500
gtcggtcctc agggacctgc aggaaagcct ggtccagaag gtcttcgggg catccctggt   4560
cctgtgggag aacaaggtct ccctggagct gcaggccaag atggaccacc tggtcctatg   4620
ggacctcctg gcttacctgg tctcaaaggt gaccctggct ccaagggtga aaagggacat   4680
cctggtttaa ttggcctgat tggtcctcca ggagaacaag gggaaaaagg tgaccgaggg   4740
ctccctggaa ctcaaggatc tccaggagca aaaggggatg gggaattcc tggtcctgct   4800
ggtcccttag gtccacctgg tcctccaggt ttaccaggtc ctcaaggccc aaagggtaac   4860
aaaggctcta ctggacccgc tggccagaaa ggtgacagtg gtcttccagg gcctcctggg   4920
tctccaggtc cacctggtga agtcattcag cctttaccaa tcttgtcctc caaaaaaacg   4980
agaagacata ctgaaggcat gcaagcagat gcagatgata atattcttga ttactcggat   5040
ggaatggaag aaatatttgg ttccctcaat tccctgaaac aagacattga gcatatgaaa   5100
tttccaatgg gtactcagac caatccagcc cgaacttgta aagacctgca actcagccat   5160
cctgacttcc cagatggtga atattggatt gatcctaacc aaggttgctc aggagattcc   5220
ttcaaagttt actgtaattt cacatctggt ggtgagactt gcatttatcc agacaaaaaa   5280
tctgagggag taagaatttc atcatggcca aaggagaaac caggaagttg gtttagtgaa   5340
```

```
tttaagaggg gaaaactgct ttcatactta gatgttgaag gaaattccat caatatggtg   5400
caaatgacat tcctgaaact tctgactgcc tctgctcggc aaaatttcac ctaccactgt   5460
catcagtcag cagcctggta tgatgtgtca tcaggaagtt atgacaaagc acttcgcttc   5520
ctgggatcaa atgatgagga gatgtcctat gacaataatc cttttatcaa aacactgtat   5580
gatggttgtg cgtccagaaa aggctatgaa aagactgtca ttgaaatcaa tacaccaaaa   5640
attgatcaag tacctattgt tgatgtcatg atcaatgact ttggtgatca gaatcagaag   5700
ttcggatttg aagttggtcc tgtttgtttt cttggctaag attaagacaa agaacatatc   5760
aaatcaacag aaaatatacc ttggtgccac caacccattt tgtgccacat gcaagttttg   5820
aataaggatg gtatagaaaa caacgctgca tatacaggta ccatttagga aataccgatg   5880
cctttgtggg ggcagaatca catggcaaaa gctttgaaaa tcataaagat ataagttggt   5940
gtggctaaga tggaaacagg gctgattctt gattcccaat tctcaactct ccttttccta   6000
tttgaatttc tttggtgctg tagaaaacaa aaaaagaaaa atatatattc ataaaaaata   6060
tggtgctcat tctcatccat ccaggatgta ctaaaacagt gtgtttaata aattgtaatt   6120
attttgtgta cagttctata ctgttatctg tgtccatttc caaaacttgc acgtgtccct   6180
gaattccatc tgactctaat tttatgagaa ttgcagaact ctgatggcaa taaatatatg   6240
tattatgaaa aaataaagtt gtaatttctg atgactctaa gtccctttct ttggttaata   6300
ataaaatgcc tttgtatata ttgatgttga agagttcaat tatttgatgt cgccaacaaa   6360
attctcagag ggcaaaaatc tggaagactt ttggaagcac actctgatca actcttctct   6420
gccgacagtc attttgctga atttcagcca aaaatattat gcattttgat gctttattca   6480
aggctatacc tcaaactttt tcttctcaga atccaggatt tcacaggata cttgtatata   6540
tggaaaacaa gcaagtttat atttttggac agggaaatgt gtgtaagaaa gtatattaac   6600
aaatcaatgc ctccgtcaag caaacaatca tatgtatact ttttttctac gttatctcat   6660
ctccttgttt tcagtgtgct tcaataatgc aggttaatat taaagatgga aattaagcaa   6720
ttatttatga atttgtgcaa tgttagattt tcttatcaat caagttcttg aatttgattc   6780
taagttgcat attataacag tctcgaaaat tattttactt gcccaacaaa tattactttt   6840
ttcctttcaa gataatttta taaatcattt gacctaccta attgctaaat gaataacata   6900
tggtggactg ttattaagag tatttgtttt aagtcattca ggaaaatcta aacttttttt   6960
tccactaagg tatttacttt aaggtagctt gaaatagcaa tacaatttaa aaattaaaaa   7020
ctgaattttg tatctatttt aagtaatata tgtaagactt gaaaataaat gttttatttc   7080
ttatataaag tgttaaatta attgatacca gatttcactg gaacagtttc aactgataat   7140
ttatgacaaa agaacatacc tgtaatattg aaattaaaaa gtgaaatttg tcataaagaa   7200
tttcttttat ttttgaaatc gagtttgtaa atgtcctttt aagaagggag atatgaatcc   7260
aataaataaa ctcaagtctt ggctacctgg a                                  7291
```

<210> SEQ ID NO 38
<211> LENGTH: 2565
<212> TYPE: DNA
<213> ORGANISM: Homo sapiens

<400> SEQUENCE: 38

```
tcgcgatgct gctgcgcctg ttgctggcct gggcggccgc agggcccaca ctgggccagg     60
acccctgggc tgctgagccc cgtgccgcct gcggccccag cagctgctac gctctcttcc    120
```

```
cacggcgccg caccttcctg gaggcctggc gggcctgccg cgagctgggg ggcgacctgg    180
ccactcctcg gacccccgag gaggcccagc gtgtggacag cctggtgggt gcgggcccag    240
ccagccggct gctgtggatc gggctgcagc ggcaggcccg gcaatgccag ctgcagcgcc    300
cactgcgcgg cttcacgtgg accacagggg accaggacac ggctttcacc aactgggccc    360
agccagcctc tggaggcccc tgcccggccc agcgctgtgt ggccctggag gcaagtggcg    420
agcaccgctg gctggagggc tcgtgcacgc tggctgtcga cggctacctg tgccagtttg    480
gcttcgaggg cgcctgcccg gcgctgcaag atgaggcggg ccaggccggc ccagccgtgt    540
ataccacgcc cttccacctg gtctccacag agtttgagtg gctgcccttc ggctctgtgg    600
ccgctgtgca gtgccaggct ggcaggggag cctctctgct ctgcgtgaag cagcctgagg    660
gaggtgtggg ctggtcacgg gctgggcccc tgtgcctggg gactggctgc agccctgaca    720
acgggggctg cgaacacgaa tgtgtggagg aggtggatgg tcacgtgtcc tgccgctgca    780
ctgagggctt ccggctggca gcagacgggc gcagttgcga ggacccctgt gcccaggctc    840
cgtgcgagca gcagtgtgag cccggtgggc cacaaggcta cagctgccac tgtcgcctgg    900
gtttccggcc agcggaggat gatccgcacc gctgtgtgga cacagatgag tgccagattg    960
ccggtgtgtg ccagcagatg tgtgtcaact acgttggtgg cttcgagtgt tattgtagcg   1020
agggacatga gctggaggct gatggcatca gctgcagccc tgcaggggcc atgggtgccc   1080
aggcttccca ggacctcgga gatgagttgc tggatgacgg ggaggatgag gaagatgaag   1140
acgaggcctg gaaggccttc aacggtggct ggacggagat gcctgggatc ctgtggatgg   1200
agcctacgca gccgcctgac tttgccctgg cctatagacc gagcttccca gaggacagag   1260
agccacagat accctacccg gagcccacct ggccaccccc gctcagtgcc cccagggtcc   1320
cctaccactc ctcagtgctc tccgtcaccc ggcctgtggt ggtctctgcc acgcatccca   1380
cactgccttc tgcccaccag cctcctgtga tccctgccac acacccagct ttgtcccgtg   1440
accaccagat ccccgtgatc gcagccaact atccagatct gccttctgcc taccaacccg   1500
gtattctctc tgtctctcat tcagcacagc ctcctgccca ccagcccccct atgatctcaa   1560
ccaaatatcc ggagctcttc cctgcccacc agtcccccat gtttccagac acccgggtcg   1620
ctggcaccca gaccaccact catttgcctg gaatcccacc taaccatgcc cctctggtca   1680
ccaccctcgg tgcccagcta ccccctcaag ccccagatgc ccttgtcctc agaacccagg   1740
ccacccagct tcccattatc ccaactgccc agccctctct gaccaccacc tccaggtccc   1800
ctgtgtctcc tgcccatcaa atctctgtgc ctgctgccac ccagcccgca gccctcccca   1860
ccctcctgcc ctctcagagc cccactaacc agacctcacc catcagccct acacatcccc   1920
attccaaagc cccccaaatc ccaagggaag atggccccag tcccaagttg gccctgtggc   1980
tgccctcacc agctcccaca gcagccccaa cagccctggg ggaggctggt cttgccgagc   2040
acagccagag ggatgaccgg tggctgctgg tggcactcct ggtgccaacg tgtgtctttt   2100
tggtggtcct gcttgcactg ggcatcgtgt actgcacccg ctgtggcccc catgcaccca   2160
acaagcgcat cactgactgc tatcgctggg tcatccatgc tgggagcaag agcccaacag   2220
aacccatgcc ccccaggggc agcctcacag ggtgcagac ctgcagaacc agcgtgtgat   2280
ggggtgcaga cccccctcat ggagtatggg gcgctggaca catggccggg gctgcaccag   2340
ggacccatgg gggctgccca gctggacaga tggcttcctg ctccccaggc ccagccaggg   2400
tcctctctca accactagac ttggctctca ggaactctgc ttcctggccc agcgctcgtg   2460
accaaggata caccaaagcc cttaagacct caggggggcgg gtgctggggt cttctccaat   2520
```

aaatggggtg tcaaccttaa aaaaaaaaaa aaaaaaaaaa aaaaa 2565

<210> SEQ ID NO 39
<211> LENGTH: 757
<212> TYPE: PRT
<213> ORGANISM: Homo sapiens

<400> SEQUENCE: 39

Met Leu Leu Arg Leu Leu Leu Ala Trp Ala Ala Ala Gly Pro Thr Leu
1 5 10 15

Gly Gln Asp Pro Trp Ala Ala Glu Pro Arg Ala Ala Cys Gly Pro Ser
20 25 30

Ser Cys Tyr Ala Leu Phe Pro Arg Arg Arg Thr Phe Leu Glu Ala Trp
35 40 45

Arg Ala Cys Arg Glu Leu Gly Gly Asp Leu Ala Thr Pro Arg Thr Pro
50 55 60

Glu Glu Ala Gln Arg Val Asp Ser Leu Val Gly Ala Gly Pro Ala Ser
65 70 75 80

Arg Leu Leu Trp Ile Gly Leu Gln Arg Gln Ala Arg Gln Cys Gln Leu
85 90 95

Gln Arg Pro Leu Arg Gly Phe Thr Trp Thr Thr Gly Asp Gln Asp Thr
100 105 110

Ala Phe Thr Asn Trp Ala Gln Pro Ala Ser Gly Gly Pro Cys Pro Ala
115 120 125

Gln Arg Cys Val Ala Leu Glu Ala Ser Gly Glu His Arg Trp Leu Glu
130 135 140

Gly Ser Cys Thr Leu Ala Val Asp Gly Tyr Leu Cys Gln Phe Gly Phe
145 150 155 160

Glu Gly Ala Cys Pro Ala Leu Gln Asp Glu Ala Gly Gln Ala Gly Pro
165 170 175

Ala Val Tyr Thr Thr Pro Phe His Leu Val Ser Thr Glu Phe Glu Trp
180 185 190

Leu Pro Phe Gly Ser Val Ala Ala Val Gln Cys Gln Ala Gly Arg Gly
195 200 205

Ala Ser Leu Leu Cys Val Lys Gln Pro Glu Gly Gly Val Gly Trp Ser
210 215 220

Arg Ala Gly Pro Leu Cys Leu Gly Thr Gly Cys Ser Pro Asp Asn Gly
225 230 235 240

Gly Cys Glu His Glu Cys Val Glu Glu Val Asp Gly His Val Ser Cys
245 250 255

Arg Cys Thr Glu Gly Phe Arg Leu Ala Ala Asp Gly Arg Ser Cys Glu
260 265 270

Asp Pro Cys Ala Gln Ala Pro Cys Glu Gln Gln Cys Glu Pro Gly Gly
275 280 285

Pro Gln Gly Tyr Ser Cys His Cys Arg Leu Gly Phe Arg Pro Ala Glu
290 295 300

Asp Asp Pro His Arg Cys Val Asp Thr Asp Glu Cys Gln Ile Ala Gly
305 310 315 320

Val Cys Gln Gln Met Cys Val Asn Tyr Val Gly Gly Phe Glu Cys Tyr
325 330 335

Cys Ser Glu Gly His Glu Leu Glu Ala Asp Gly Ile Ser Cys Ser Pro
340 345 350

Ala Gly Ala Met Gly Ala Gln Ala Ser Gln Asp Leu Gly Asp Glu Leu
355 360 365

```
Leu Asp Asp Gly Glu Asp Glu Glu Asp Glu Asp Glu Ala Trp Lys Ala
    370                 375                 380

Phe Asn Gly Gly Trp Thr Glu Met Pro Gly Ile Leu Trp Met Glu Pro
385                 390                 395                 400

Thr Gln Pro Pro Asp Phe Ala Leu Ala Tyr Arg Pro Ser Phe Pro Glu
                405                 410                 415

Asp Arg Glu Pro Gln Ile Pro Tyr Pro Glu Pro Thr Trp Pro Pro Pro
            420                 425                 430

Leu Ser Ala Pro Arg Val Pro Tyr His Ser Ser Val Leu Ser Val Thr
        435                 440                 445

Arg Pro Val Val Val Ser Ala Thr His Pro Thr Leu Pro Ser Ala His
    450                 455                 460

Gln Pro Pro Val Ile Pro Ala Thr His Pro Ala Leu Ser Arg Asp His
465                 470                 475                 480

Gln Ile Pro Val Ile Ala Ala Asn Tyr Pro Asp Leu Pro Ser Ala Tyr
                485                 490                 495

Gln Pro Gly Ile Leu Ser Val Ser His Ser Ala Gln Pro Pro Ala His
            500                 505                 510

Gln Pro Pro Met Ile Ser Thr Lys Tyr Pro Glu Leu Phe Pro Ala His
        515                 520                 525

Gln Ser Pro Met Phe Pro Asp Thr Arg Val Ala Gly Thr Gln Thr Thr
    530                 535                 540

Thr His Leu Pro Gly Ile Pro Pro Asn His Ala Pro Leu Val Thr Thr
545                 550                 555                 560

Leu Gly Ala Gln Leu Pro Pro Gln Ala Pro Asp Ala Leu Val Leu Arg
                565                 570                 575

Thr Gln Ala Thr Gln Leu Pro Ile Ile Pro Thr Ala Gln Pro Ser Leu
            580                 585                 590

Thr Thr Thr Ser Arg Ser Pro Val Ser Pro Ala His Gln Ile Ser Val
        595                 600                 605

Pro Ala Ala Thr Gln Pro Ala Ala Leu Pro Thr Leu Leu Pro Ser Gln
    610                 615                 620

Ser Pro Thr Asn Gln Thr Ser Pro Ile Ser Pro Thr His Pro His Ser
625                 630                 635                 640

Lys Ala Pro Gln Ile Pro Arg Glu Asp Gly Pro Ser Pro Lys Leu Ala
                645                 650                 655

Leu Trp Leu Pro Ser Pro Ala Pro Thr Ala Ala Pro Thr Ala Leu Gly
            660                 665                 670

Glu Ala Gly Leu Ala Glu His Ser Gln Arg Asp Asp Arg Trp Leu Leu
        675                 680                 685

Val Ala Leu Leu Val Pro Thr Cys Val Phe Leu Val Val Leu Leu Ala
    690                 695                 700

Leu Gly Ile Val Tyr Cys Thr Arg Cys Gly Pro His Ala Pro Asn Lys
705                 710                 715                 720

Arg Ile Thr Asp Cys Tyr Arg Trp Val Ile His Ala Gly Ser Lys Ser
                725                 730                 735

Pro Thr Glu Pro Met Pro Pro Arg Gly Ser Leu Thr Gly Val Gln Thr
            740                 745                 750

Cys Arg Thr Ser Val
        755
```

<210> SEQ ID NO 40
<211> LENGTH: 7288

<212> TYPE: DNA
<213> ORGANISM: Homo sapiens

<400> SEQUENCE: 40

```
catagagcca gcgggcgcgg gcgggacggg cgccccgcgg ccggacccag ccagggcacc     60
acgctgcccg gccctgcgcc gccaggcact tctttccggg gctcctaggg acgccagaag    120
gaagtcaacc tctgctgctt ctccttggcc tgcgttggac cttccttttt ttgttgtttt    180
tttttgtttt tccccttcct tccttttgaa ttaactggct tcttggctgg atgttttcaa    240
cttctttcct ggctgcgaac ttttccccaa ttgttttcct tttacaacag ggggagaaag    300
tgctctgtgg tccgaggcga gccgtgaagt tgcgtgtgcg tggcagtgtg cgtggcagga    360
tgtgcgtgcg tgtgtaaccc gagccgcccg atctgtttcg atctgcgccg cggagccctc    420
cctcaaggcc cgctccacct gctgcggtta cgcggcgctc gtgggtgttc gtgcctcgga    480
gcagctaacc ggcgggtgct gggcgacggt ggaggagtat cgtctcgctg ctgcccgagt    540
cagggctgag tcacccagct gatgtagaca gtggctgcct tccgaagagt gcgtgtttgc    600
atgtgtgtga ctctgcggct gctcaactcc caacaaacca gaggaccagc cacaaactta    660
accaacatcc ccaaacccga gttcacagat gtgggagagc tgtagaaccc tgagtgtcat    720
cgactgggcc ttcttatgat tgttgtttta agattagctg aagatctctg aaacgctgaa    780
ttttctgcac tgagcgtttt gacagaattc attgagagaa cagagaacat gacaagtact    840
tctagctcag cactgctcca actactgaag ctgattttca aggctactta aaaaaatctg    900
cagcgtacat taatggattt ctgttgtgtt taaattctcc acagattgta ttgtaaatat    960
tttatgaagt agagcatatg tatatattta tatatacgtg cacatacatt agtagcacta   1020
cctttggaag tctcagctct tgcttttcgg gactgaagcc agttttgcat gataaaagtg   1080
gccttgttac gggagataat tgtgttctgt tgggacttta gacaaaactc acctgcaaaa   1140
aactgacagg cattaactac tggaacttcc aaataatgtg tttgctgatc gttttactct   1200
tcgcataaat attttaggaa gtgtatgaga attttgcctt caggaacttt tctaacagcc   1260
aaagacagaa cttaacctct gcaagcaaga ttcgtggaag atagtctcca ctttttaatg   1320
cactaagcaa tcggttgcta ggagcccatc ctgggtcaga ggccgatccg cagaaccaga   1380
acgttttccc ctcctggact gttagtaact tagtctccct cctcccctaa ccaccccccgc   1440
cccccccac ccccgcagt aataaaggcc cctgaacgtg tatgttggtc tcccgggagc   1500
tgcttgctga agatccgcgc ccctgtcgcc gtctggtagg agctgtttgc agggtcctaa   1560
ctcaatcggc ttgttgtgat gcgtatcccc gtagatgcca gcacgagccg ccgcttcacg   1620
ccgccttcca ccgcgctgag cccaggcaag atgagcgagg cgttgccgct gggcgccccg   1680
gacgccggcg ctgccctggc cggcaagctg aggagcggcg accgcagcat ggtggaggtg   1740
ctggccgacc acccgggcga gctggtgcgc accgacagcc ccaacttcct ctgctccgtg   1800
ctgcctacgc actggcgctg caacaagacc ctgcccatcg ctttcaaggt ggtggcccta   1860
ggggatgttc cagatggcac tctggtcact gtgatggctg gcaatgatga aaactactcg   1920
gctgagctga gaaatgctac cgcagccatg aagaaccagg ttgcaagatt taatgacctc   1980
aggtttgtcg gtcgaagtgg aagagggaaa agcttcactc tgaccatcac tgtcttcaca   2040
aacccaccgc aagtcgccac ctaccacaga gccatcaaaa tcacagtgga tgggccccga   2100
gaacctcgaa gacatcggca gaaactagat gatcagacca agcccgggag cttgtccttt   2160
tccgagcggc tcagtgaact ggagcagctg cggcgcacag ccatgagggt cagcccacac   2220
```

```
cacccagccc ccacgcccaa ccctcgtgcc tccctgaacc actccactgc ctttaaccct   2280
cagcctcaga gtcagatgca ggatacaagg cagatccaac catccccacc gtggtcctac   2340
gatcagtcct accaatacct gggatccatt gcctctcctt ctgtgcaccc agcaacgccc   2400
atttcacctg gacgtgccag cggcatgaca accctctctg cagaactttc cagtcgactc   2460
tcaacggcac ccgacctgac agcgttcagc gacccgcgcc agttccccgc gctgccctcc   2520
atctccgacc cccgcatgca ctatccaggc gccttcacct actccccgac gccggtcacc   2580
tcgggcatcg gcatcggcat gtcggccatg ggctcggcca cgcgctacca cacctacctg   2640
ccgccgccct accccggctc gtcgcaagcg cagggaggcc cgttccaagc cagctcgccc   2700
tcctaccacc tgtactacgg cgcctcggcc ggctcctacc agttctccat ggtgggcggc   2760
gagcgctcgc cgccgcgcat cctgccgccc tgcaccaacg cctccaccgg ctccgcgctg   2820
ctcaacccca gcctcccgaa ccagagcgac gtggtggagg ccgagggcag ccacagcaac   2880
tcccccacca acatggcgcc ctccgcgcgc ctggaggagg ccgtgtggag gccctactga   2940
ggcgccaggc ctggcccggc tgggccccgc gggccgccgc cttcgcctcc gggcgcgcgg   3000
gcctcctgtt cgcgacaagc ccgccgggat cccgggccct gggcccggcc accgtcctgg   3060
ggccgagggc gcccgacggc caggatctcg ctgtaggtca ggcccgcgca gcctcctgcg   3120
cccagaagcc cacgccgccg ccgtctgctg gcgccccggc cctcgcggag gtgtccgagg   3180
cgacgcacct cgagggtgtc cgccggcccc agcacccagg ggacgcgctg gaaagcaaac   3240
aggaagattc ccggagggaa actgtgaatg cttctgattt agcaatgctg tgaataaaaa   3300
gaaagatttt ataccottga cttaactttt taaccaagtt gtttattcca aagagtgtgg   3360
aattttggtt ggggtggggg gagaggaggg atgcaactcg ccctgtttgg catctaattc   3420
ttatttttaa tttttccgca ccttatcaat tgcaaaatgc gtatttgcat ttgggtggtt   3480
tttattttta tatacgttta tataaatata tataaattga gcttgcttct ttcttgcttt   3540
gaccatggaa agaaatatga ttccctttc tttaagtttt atttaacttt tcttttggac   3600
ttttgggtag ttgttttttt ttgttttgtt ttgttttttt gagaaacagc tacagctttg   3660
ggtcattttt aactactgta ttcccacaag gaatccccag atatttatgt atcttgatgt   3720
tcagacattt atgtgttgat aattttttaa ttatttaaat gtacttatat taagaaaaat   3780
atcaagtact acattttctt ttgttcttga tagtagccaa agttaaatgt atcacattga   3840
agaaggctag aaaaaaagaa tgagtaatgt gatcgcttgg ttatccagaa gtattgttta   3900
cattaaactc cctttcatgt taatcaaaca agtgagtagc tcacgcagca acgtttttaa   3960
taggattttt agacactgag ggtcactcca aggatcagaa gtatggaatt ttctgccagg   4020
ctcaacaagg gtctcatatc taacttcctc cttaaaacag agaaggtcaa tctagttcca   4080
gagggttgag gcaggtgcca ataattacat ctttggagag gatttgattt ctgcccaggg   4140
atttgctcac cccaaggtca tctgataatt tcacagatgc tgtgtaacag aacacagcca   4200
aagtaaactg tgtaggggag ccacatttac ataggaacca aatcaatgaa tttaggggtt   4260
acgattatag caatttaagg gccaccagaa gcaggcctcg aggagtcaat ttgcctctgt   4320
gtgcctcagt ggagacaagt gggaaaacat ggtcccacct gtgcgagacc ccctgtcctg   4380
tgctgctcac tcaacaacat ctttgtgttg ctttcaccag gctgagaccc taccctatgg   4440
ggtatatggg cttttacctg tgcaccagtg tgacaggaaa gattcatgtc actactgtcc   4500
gtggctacaa ttcaaaggta tccaatgtcg ctgtaaattt tatggcacta tttttattgg   4560
aggatttggt cagaatgcag ttgttgtaca actcataaat actaactgct gattttgaca   4620
```

```
catgtgtgct ccaaatgatc tggtggttat ttaacgtacc tcttaaaatt cgttgaaacg   4680
atttcaggtc aactctgaag agtatttgaa agcaggactt cagaacagtg tttgattttt   4740
attttataaa tttaagcatt caaattaggc aaatctttgg ctgcaggcag caaaaacagc   4800
tggacttatt taaaacaact tgtttttgag ttttcttata tatatattga ttatttgttt   4860
tacacacatg cagtagcact ttggtaagag ttaaagagta aagcagctta tgttgtcagg   4920
tcgttcttat ctagagaaga gctatagcag atctcggaca aactcagaat atattcactt   4980
tcatttttga caggattccc tccacaactc agtttcatat attattccgt attacatttt   5040
tgcagctaaa ttaccataaa atgtcagcaa atgtaaaaat ttaatttctg aaaagcacca   5100
ttagcccatt tcccccaaat taaacgtaaa tgtttttttt cagcacatgt taccatgtct   5160
gacctgcaaa aatgctggag aaaaatgaag gaaaaaatta tgtttttcag tttaattctg   5220
ttaactgaag atattccaac tcaaaaccag cctcatgctc tgattagata atcttttaca   5280
ttgaaccttt actctcaaag ccatgtgtgg agggggcttg tcactattgt aggctcactg   5340
gattggtcat ttagagtttc acagactctt accagcatat atagtattta attgtttcaa   5400
aaaaaatcaa actgtagttg ttttggcgat aggtctcacg caacacattt ttgtatgtgt   5460
gtgtgtgtgc gtgtgtgtgt gtgtgtgtga aaaattgcat tcattgactt caggtagatt   5520
aaggtatctt tttattcatt gccctcagga aagttaaggt atcaatgaga cccttaagcc   5580
aatcatgtaa taactgcatg tgtctggtcc aggagaagta ttgaataagc catttctact   5640
gcttactcat gtccctattt atgatttcaa catggataca tatttcagtt ctttcttttt   5700
ctcactatct gaaaatacat ttccctccct ctcttccccc caatatctcc cttttttttct   5760
ctcttcctct atcttccaaa ccccactttc tccctcctcc ttttcctgtg ttctcttaag   5820
cagatagcac atacccccac ccagtaccaa atttcagaac acaagaaggt ccagttcttc   5880
ccccttcaca taaaggaaca tggtttgtca gcctttctcc tgtttatggg tttcttccag   5940
cagaacagag acattgccaa ccatattgga tctgcttgct gtccaaacca gcaaactttc   6000
ctgggcaaat cacaatcagt gagtaaatag acagcctttc tgctgccttg ggtttctgtg   6060
cagataaaca gaaatgctct gattagaaag gaaatgaatg gttccactca aatgtcctgc   6120
aatttaggat tgcagatttc tgccttgaaa tacctgtttc tttgggacat tccgtcctga   6180
tgatttttat ttttgttggt ttttattttt ggggggaatg acatgtttgg gtcttttata   6240
catgaaaatt tgtttgacaa taatctcaca aaacatattt tacatctgaa caaaatgcct   6300
ttttgtttac cgtagcgtat acatttgttt tgggattttt gtgtgtttgt tgggaatttt   6360
gtttttagcc aggtcagtat tgatgaggct gatcatttgg ctcttttttt ccttccagaa   6420
gagttgcatc aacaaagtta attgtattta tgtatgtaaa tagattttaa gcttcattat   6480
aaaatattgt taatgcctat aacttttttt caattttttt gtgtgtgttt ctaaggactt   6540
tttcttaggt ttgctaaata ctgtagggaa aaaaatgctt ctttctactt tgtttatttt   6600
agactttaaa atgagctact tcttattcac ttttgtaaac agctaatagc atggttccaa   6660
tttttttaa gttcactttt tttgttctag gggaaatgaa tgtgcaaaaa aagaaaaaga   6720
actgttggtt atttgtgtta ttctggatgt ataaaaatca atggaaaaaa ataaactttc   6780
aaattgaaat gacggtataa cacatctact gaaaaagcaa cgggaaatgt ggtcctattt   6840
aagccagccc ccacctaggg tctatttgtg tggcagttat tgggtttggt cacaaaacat   6900
cctgaaaatt cgtgcgtggg cttctttctc cctggtacaa acgtatggaa tgcttcttaa   6960
```

aggggaactg tcaagctggt gtcttcagcc agatgacatg agagaatatc ccagaaccct 7020
ctctccaagg tgtttctaga tagcacagga gagcaggcac tgcactgtcc acagtccacg 7080
gtacacagtc gggtgggccg cctcccctct cctgggagca ttcgtcgtgc ccagcctgag 7140
cagggcagct ggactgctgc tgttcaggag ccaccagagc cttcctctct ttgtaccaca 7200
gtttcttctg taaatccagt gttacaatca gtgtgaatgg caaataaaca gtttgacaag 7260
tacatacacc ataaaaaaaa aaaaaaaa 7288

<210> SEQ ID NO 41
<211> LENGTH: 7291
<212> TYPE: DNA
<213> ORGANISM: Homo sapiens

<400> SEQUENCE: 41
acacagtact ctcagcttgt tggtggaagc ccctcatctg ccttcattct gaaggcaggg 60
cccggcagag gaaggatcag agggtcgcgg ccggagggtc ccggccggtg gggccaactc 120
agagggagag gaaagggcta gagacacgaa gaacgcaaac catcaaattt agaagaaaaa 180
gccctttgac tttttccccc tctccctccc caatggctgt gtagcaaaca tccctggcga 240
taccttggaa aggacgaagt tggtctgcag tcgcaatttc gtgggttgag ttcacagttg 300
tgagtgcggg gctcggagat ggagccgtgg tcctctaggt ggaaaacgaa acggtggctc 360
tgggatttca ccgtaacaac cctcgcattg accttcctct tccaagctag agaggtcaga 420
ggagctgctc cagttgatgt actaaaagca ctagattttc acaattctcc agagggaata 480
tcaaaaacaa cgggattttg cacaaacaga aagaattcta aaggctcaga tactgcttac 540
agagtttcaa agcaagcaca actcagtgcc ccaacaaaac agttatttcc aggtggaact 600
ttcccagaag acttttcaat actatttaca gtaaaaccaa aaaaaggaat tcagtctttc 660
cttttatcta tatataatga gcatggtatt cagcaaattg gtgttgaggt tgggagatca 720
cctgtttttc tgtttgaaga ccacactgga aaacctgccc cagaagacta tcccctcttc 780
agaactgtta acatcgctga cgggaagtgg catcgggtag caatcagcgt ggagaagaaa 840
actgtgacaa tgattgttga ttgtaagaag aaaaccacga aaccacttga tagaagtgag 900
agagcaattg ttgataccaa tggaatcacg gtttttggaa caaggatttt ggatgaagaa 960
gtttttgagg gggacattca gcagtttttg atcacaggtg atcccaaggc agcatatgac 1020
tactgtgagc attatagtcc agactgtgac tcttcagcac ccaaggctgc tcaagctcag 1080
gaacctcaga tagatgagta tgcaccagag gatataatcg aatatgacta tgagtatggg 1140
gaagcagagt ataaagaggc tgaaagtgta acagagggac ccactgtaac tgaggagaca 1200
atagcacaga cggaggcaaa catcgttgat gattttcaag aatacaacta tggaacaatg 1260
gaaagttacc agacagaagc tcctaggcat gtttctggga caaatgagcc aaatccagtt 1320
gaagaaatat ttactgaaga atatctaacg ggagaggatt atgattccca gaggaaaaat 1380
tctgaggata cactatatga aaacaaagaa atagacggca gggattctga tcttctggta 1440
gatggagatt taggcgaata tgatttttat gaatataaag aatatgaaga taaaccaaca 1500 agcccccccta atgaagaatt tggtccaggt gtaccagcag aaactgatat tacagaaaca 1560
agcataaatg gccatggtgc atatggagag aaaggacaga aaggagaacc agcagtggtt 1620
gagcctggta tgcttgtcga aggaccacca ggaccagcag gacctgcagg tattatgggt 1680
cctccaggtc tacaaggccc cactggaccc cctggtgacc ctggcgatag gggcccccca 1740
ggacgtcctg gcttaccagg ggctgatggt ctacctggtc ctcctggtac tatgttgatg 1800

```
ttaccgttcc gttatggtgg tgatggttcc aaaggaccaa ccatctctgc tcaggaagct   1860
caggctcaag ctattcttca gcaggctcgg attgctctga gaggcccacc tggcccaatg   1920
ggtctaactg gaagaccagg tcctgtgggg gggcctggtt catctggggc caaaggtgag   1980
agtggtgatc caggtcctca gggccctcga ggcgtccagg gtccccctgg tccaacggga   2040
aaacctggaa aaaggggtcg tccaggtgca gatggaggaa gaggaatgcc aggagaacct   2100
ggggcaaagg gagatcgagg gtttgatgga cttccgggtc tgccaggtga caaaggtcac   2160
aggggtgaac gaggtcctca aggtcctcca ggtcctcctg gtgatgatgg aatgagggga   2220
gaagatggag aaattggacc aagaggtctt ccaggtgaag ctggcccacg aggtttgctg   2280
ggtccaaggg gaactccagg agctccaggg cagcctggta tggcaggtgt agatggcccc   2340
ccaggaccaa aagggaacat gggtccccaa ggggagcctg ggcctccagg tcaacaaggg   2400
aatccaggac ctcagggtct tcctggtcca caaggtccaa ttggtcctcc tggtgaaaaa   2460
ggaccacaag gaaaaccagg acttgctgga cttcctggtg ctgatgggcc tcctggtcat   2520
cctgggaaag aaggccagtc tggagaaaag gggggctctgg gtccccctgg tccacaaggt   2580
cctattggat acccgggccc ccggggagta aagggagcag atggtgtcag aggtctcaag   2640
ggatctaaag gtgaaaaggg tgaagatggt tttccaggat tcaaaggtga catgggtcta   2700
aaaggtgaca gaggagaagt tggtcaaatt ggcccaagag gggaagatgg ccctgaagga   2760
cccaaaggtc gagcaggccc aactggagac ccaggtcctt caggtcaagc aggagaaaag   2820
ggaaaacttg gagttccagg attaccagga tatccaggaa gacaaggtcc aaagggttcc   2880
actggattcc ctgggtttcc aggtgccaat ggagagaaag gtgcacgggg agtagctggc   2940
aaaccaggcc ctcggggtca gcgtggtcca acgggtcctc gaggttcaag aggtgcaaga   3000
ggtcccactg ggaaacctgg gccaaagggc acttcaggtg gcgatggccc tcctggccct   3060
ccaggtgaaa gaggtcctca aggacctcag ggtccagttg gattccctgg accaaaaggc   3120
cctcctggac cacctgggaa ggatgggctg ccaggacacc ctgggcaacg tggggagact   3180
ggatttcaag gcaagaccgg ccctcctggg ccagggggag tggttggacc acagggacca   3240
accggtgaga ctggtccaat aggggaacgt gggcatcctg gccctcctgg ccctcctggt   3300
gagcaaggtc ttcctggtgc tgcaggaaaa gaaggtgcaa agggtgatcc aggtcctcaa   3360
ggtatctcag ggaaagatgg accagcagga ttacgtggtt tcccagggga aagaggtctt   3420
cctggagctc agggtgcacc tggactgaaa ggaggggaag gtccccaggg cccaccaggt   3480
ccagttggct caccaggaga acgtgggtca gcaggtacag ctggcccaat tggtttacca   3540
gggcgcccgg gacctcaggg tcctcctggt ccagctggag agaaaggtgc tcctggagaa   3600
aaaggtcccc aagggcctgc agggagagat ggagttcaag gtcctgttgg tctcccaggg   3660
ccagctggtc ctgccggctc ccctggggaa gacggagaca agggtgaaat tggtgagccg   3720
ggacaaaaag gcagcaaggg tgacaaggga gaaaatggcc ctcccggtcc cccaggtctt   3780
caaggaccag ttggtgcccc tggaattgct ggaggtgatg gtgaaccagg tcctagagga   3840
cagcagggga tgtttgggca aaaaggtgat gagggtgcca gaggcttccc tggacctcct   3900
ggtccaatag gtcttcaggg tctgccaggc ccacctggtg aaaaaggtga aaatggggat   3960
gttggtccca tggggccacc tggtcctcca ggcccaagag gccctcaagg tcccaatgga   4020
gctgatggac cacaaggacc cccagggtct gttggttcag ttggtggtgt tggagaaaag   4080
ggtgaacctg gagaagcagg gaacccaggg cctcctgggg aagcaggtgt aggcggtccc   4140
```

```
aaaggagaaa gaggagagaa aggggaagct ggtccacctg gagctgctgg acctccaggt   4200
gccaaggggc caccaggtga tgatggccct aagggtaacc cgggtcctgt tggttttcct   4260
ggagatcctg gtcctcctgg ggaacctggc cctgcaggtc aagatggtgt tggtggtgac   4320
aagggtgaag atggagatcc tggtcaaccg ggtcctcctg gcccatctgg tgaggctggc   4380
ccaccaggtc ctcctggaaa acgaggtcct cctggagctg caggtgcaga gggaagacaa   4440
ggtgaaaaag gtgctaaggg ggaagcaggt gcagaaggtc ctcctggaaa aaccggccca   4500
gtcggtcctc agggacctgc aggaaagcct ggtccagaag gtcttcgggg catccctggt   4560
cctgtgggag aacaaggtct ccctggagct gcaggccaag atggaccacc tggtcctatg   4620
ggacctcctg gcttacctgg tctcaaaggt gaccctggct ccaagggtga aaagggacat   4680
cctggtttaa ttggcctgat tggtcctcca ggagaacaag ggaaaaaagg tgaccgaggg   4740
ctccctggaa ctcaaggatc tccaggagca aaaggggatg gggaattcc tggtcctgct   4800
ggtcccttag gtccacctgg tcctccaggt ttaccaggtc ctcaaggccc aaagggtaac   4860
aaaggctcta ctggacccgc tggccagaaa ggtgacagtg gtcttccagg gcctcctggg   4920
tctccaggtc cacctggtga agtcattcag cctttaccaa tcttgtcctc caaaaaaacg   4980
agaagacata ctgaaggcat gcaagcagat gcagatgata atattcttga ttactcggat   5040
ggaatggaag aaatatttgg ttccctcaat tccctgaaac aagacattga gcatatgaaa   5100
tttccaatgg gtactcagac caatccagcc cgaacttgta aagacctgca actcagccat   5160
cctgacttcc cagatggtga atattggatt gatcctaacc aaggttgctc aggagattcc   5220
ttcaaagttt actgtaattt cacatctggt ggtgagactt gcatttatcc agacaaaaaa   5280
tctgagggag taagaatttc atcatggcca aaggagaaac caggaagttg gtttagtgaa   5340
tttaagaggg gaaaactgct ttcatactta gatgttgaag gaaattccat caatatggtg   5400
caaatgacat tcctgaaact tctgactgcc tctgctcggc aaaatttcac ctaccactgt   5460
catcagtcag cagcctggta tgatgtgtca tcaggaagtt atgacaaagc acttcgcttc   5520
ctgggatcaa atgatgagga gatgtcctat gacaataatc cttttatcaa aacactgtat   5580
gatggttgtg cgtccagaaa aggctatgaa aagactgtca ttgaaatcaa tacaccaaaa   5640
attgatcaag tacctattgt tgatgtcatg atcaatgact ttggtgatca gaatcagaag   5700
ttcggatttg aagttggtcc tgtttgtttt cttggctaag attaagacaa agaacatatc   5760
aaatcaacag aaaatatacc ttggtgccac caacccattt tgtgccacat gcaagttttg   5820
aataaggatg gtatagaaaa caacgctgca tatacaggta ccatttagga aataccgatg   5880
cctttgtggg ggcagaatca catggcaaaa gctttgaaaa tcataaagat ataagttggt   5940
gtggctaaga tggaaacagg gctgattctt gattcccaat tctcaactct ccttttccta   6000
tttgaatttc tttggtgctg tagaaaacaa aaaaagaaaa atatatattc ataaaaaata   6060
tggtgctcat tctcatccat ccaggatgta ctaaaacagt gtgtttaata aattgtaatt   6120
attttgtgta cagttctata ctgttatctg tgtccatttc caaaacttgc acgtgtccct   6180
gaattccatc tgactctaat tttatgagaa ttgcagaact ctgatggcaa taaatatatg   6240
tattatgaaa aaataaagtt gtaatttctg atgactctaa gtccctttct ttggttaata   6300
ataaaatgcc tttgtatata ttgatgttga agagttcaat tatttgatgt cgccaacaaa   6360
attctcagag ggcaaaaatc tggaagactt ttggaagcac actctgatca actcttctct   6420
gccgacagtc attttgctga atttcagcca aaaatattat gcattttgat gctttattca   6480
aggctatacc tcaaactttt tcttctcaga atccaggatt tcacaggata cttgtatata   6540
```

```
tggaaaacaa gcaagtttat atttttggac agggaaatgt gtgtaagaaa gtatattaac   6600
aaatcaatgc ctccgtcaag caaacaatca tatgtatact ttttttctac gttatctcat   6660
ctccttgttt tcagtgtgct tcaataatgc aggttaatat taaagatgga aattaagcaa   6720
ttatttatga atttgtgcaa tgttagattt tcttatcaat caagttcttg aatttgattc   6780
taagttgcat attataacag tctcgaaaat tattttactt gcccaacaaa tattactttt   6840
ttcctttcaa gataatttta taaatcattt gacctaccta attgctaaat gaataacata   6900
tggtggactg ttattaagag tatttgtttt aagtcattca ggaaaatcta aacttttttt   6960
tccactaagg tatttacttt aaggtagctt gaaatagcaa tacaatttaa aaattaaaaa   7020
ctgaattttg tatctatttt aagtaatata tgtaagactt gaaaataaat gttttatttc   7080
ttatataaag tgttaaatta attgatacca gatttcactg gaacagtttc aactgataat   7140
ttatgacaaa agaacatacc tgtaatattg aaattaaaaa gtgaaatttg tcataaagaa   7200
tttcttttat ttttgaaatc gagtttgtaa atgtcctttt aagaagggag atatgaatcc   7260
aataaataaa ctcaagtctt ggctacctgg a                                  7291
```

<210> SEQ ID NO 42
<211> LENGTH: 2056
<212> TYPE: DNA
<213> ORGANISM: Homo sapiens

<400> SEQUENCE: 42

```
agtttcataa tttccgtggg tcgggccggg cgggccaggc gctgggcacg gtgatggcca     60
ccactggggc cctgggcaac tactacgtgg actcgttcct gctgggcgcc gacgccgcgg    120
atgagctgag cgttggccgc tatgcgccgg ggaccctggg ccagcctccc cggcaggcgg    180
cgacgctggc cgagcacccc gacttcagcc cgtgcagctt ccagtccaag gcgacggtgt    240
ttggcgcctc gtggaaccca gtgcacgcgg cgggcgccaa cgctgtaccc gctgcggtgt    300
accaccacca tcaccaccac ccctacgtgc acccccaggc gcccgtggcg gcggcggcgc    360
cggacggcag gtacatgcgc tcctggctgg agcccacgcc cggtgcgctc tccttcgcgg    420
gcttgccctc cagccggcct tatggcatta aacctgaacc gctgtcggcc agaaggggtg    480
actgtcccac gcttgacact cacactttgt ccctgactga ctatgcttgt ggttctcctc    540
cagttgatag agaaaaacaa cccagcgaag gcgccttctc tgaaaacaat gctgagaatg    600
agagcggcgg agacaagccc cccatcgatc ccaataaccc agcagccaac tggcttcatg    660
cgcgctccac tcggaaaaag cggtgcccct atacaaaaca ccagaccctg gaactggaga    720
aagagtttct gttcaacatg tacctcacca gggaccgcag gtacgaggtg gctcgactgc    780
tcaacctcac cgagaggcag gtcaagatct ggttccagaa ccgcaggatg aaaatgaaga    840
aaatcaacaa agaccgagca aaagacgagt gatgccattt gggcttattt agaaaaaagg    900
gtaagctaga gagaaaaaga aagaactgtc cgtcccccctt ccgccttctc cctttttctca   960
cccccaccct agcctccacc atccccgcac aaagcggctc taaacctcag gccacatctt   1020
ttccaaggca aaccctgttc aggctggctc gtaggcctgc cgctttgatg gaggaggtat   1080
tgtaagcttt ccattttcta taagaaaaag gaaaagttga ggggggggca ttagtgctga   1140
tagctgtgtg tgttagcttg tatatatatt tttaaaaatc tacctgttcc tgacttaaaa   1200
caaaaggaaa gaaactacct ttttataatg cacaactgtt gatggtaggc tgtatagttt   1260
ttagtctgtg tagttaattt aatttgcagt ttgtgcggca gattgctctg ccaagatact   1320
```

```
tgaacactgt gttttattgt ggtaattatg ttttgtgatt caaacttctg tgtactgggt   1380

gatgcaccca ttgtgattgt ggaagataga attcaatttg aactcaggtt gtttatgagg   1440

ggaaaaaaac agttgcatag agtatagctc tgtagtggaa tatgtcttct gtataactag   1500

gctgttaacc tatgattgta aagtagctgt aagaatttcc cagtgaaata aaaaaaaatt   1560

ttaagtgttc tcggggatgc atagattcat cattttctcc accttaaaaa tgcgggcatt   1620

taagtctgtc cattatctat atagtcctgt cttgtctatt gtatatataa tctatatgat   1680

taaagaaaat atgcataatc agacaagctt gaatattgtt tttgcaccag acgaacagtg   1740

aggaaattcg gagctataca tatgtgcaga aggttactac ctagggttta tgcttaattt   1800

taatcggagg aaatgaatgc tgattgtaac ggagttaatt ttattgataa taaattatac   1860

actatgaaac cgccattggg ctactgtaga tttgtatcct tgatgaatct ggggtttcca   1920

tcagactgaa cttacactgt atattttgca atagttacct caaggcctac tgaccaaatt   1980

gttgtgttga gatgatattt aactttttgc caaataaaat atattgattc ttttctaaaa   2040

aaaaaaaaaa aaaaaa                                                     2056
```

<210> SEQ ID NO 43
<211> LENGTH: 625
<212> TYPE: DNA
<213> ORGANISM: Homo sapiens

<400> SEQUENCE: 43

```
agagtcactc ctgccttcac catgaagtcc agcggcctct tccccttcct ggtgctgctt     60

gccctgggaa ctctggcacc ttgggctgtg gaaggctctg gaaagtcctt caaagctgga    120

gtctgtcctc ctaagaaatc tgcccagtgc cttagataca agaaacctga gtgccagagt    180

gactggcagt gtccagggaa gaagagatgt tgtcctgaca cttgtggcat caaatgcctg    240

gatcctgttg acaccccaaa cccaacaagg aggaagcctg ggaagtgccc agtgacttat    300

ggccaatgtt tgatgcttaa cccccccaat ttctgtgaga tggatggcca gtgcaagcgt    360

gacttgaagt gttgcatggg catgtgtggg aaatcctgcg tttcccctgt gaaagcttga    420

ttcctgccat atggaggagg ctctggagtc ctgctctgtg tggtccaggt cctttccacc    480

ctgagacttg gctccaccac tgatatcctc ctttggggaa aggcttggca cacagcaggc    540

tttcaagaag tgccagttga tcaatgaata aataaacgag cctatttctc tttgcaaaaa    600

aaaaaaaaaa aaaaaaaaaa aaaaa                                          625
```

<210> SEQ ID NO 44
<211> LENGTH: 1211
<212> TYPE: DNA
<213> ORGANISM: Homo sapiens

<400> SEQUENCE: 44

```
caaccttctc agctacaaat acttgaagaa acagagcagg gagctcaagc cagtgggagt     60

catggcccct gcctcagggc ctgccagcac ggacgctgtg tctgctctgt tggaacagac    120

agcagtggag ctggagaaga ggcaggaggg caggagcagc acacagacac tggaagacag    180

ctggaggtat gaggagacca gtgagaatga ggcagtagcc gaggaagagg aggaggaggt    240

ggaggaggag gagggagaag aggatgtttt caccgagaaa gcctcacctg atatggatgg    300

gtacccagca ttaaaggtgg acaaagagac caacacggag accccggccc catcccccac    360

agtggtgcga cctaaggacc ggagagtggg caccccgtcc caggggccat ttcttcgagg    420

gagcaccatc atccgctcta agaccttctc cccaggaccc cagagccagt acgtgtgccg    480
```

```
gctgaatcgg agtgatagtg acagctccac tctgtccaaa aagccacctt ttgttcgaaa    540
ctccctggag cgacgcagcg tccggatgaa gcggccttcc tcggtcaagt cgctgcgctc    600
cgagcgtctg atccgtacct cgctggacct ggagttagac ctgcaggcga caagaacctg    660
gcacagccaa ttgacccagg agatctcggt gctgaaggag ctcaaggagc agctggaaca    720
agccaagagc cacggggaga aggagctgcc acagtggttg cgtgaggacg agcgtttccg    780
cctgctgctg aggatgctgg agaagcggca gatggaccga gcggagcaca agggtgagct    840
tcagacagac aagatgatga gggcagctgc caaggatgtg cacaggctcc gaggccagag    900
ctgtaaggaa cccccagaag ttcagtcttt cagggagaag atggcatttt tcacccggcc    960
tcggatgaat atcccagctc tctctgcaga tgacgtctaa tcgccagaaa agtatttcct   1020
ttgttccact gaccaggctg tgaacattga ctgtggctaa agttatttat gtggtgttat   1080
atgaaggtac tgagtcacaa gtcctctagt gctcttgttg gtttgaagat gaaccgactt   1140
tttagtttgg gtcctactgt tgttattaaa aaaaaaaaaa aaacaaaaaa aaaaaaaaaa   1200
aaaaaaaaaa a                                                         1211
```

<210> SEQ ID NO 45
<211> LENGTH: 3691
<212> TYPE: DNA
<213> ORGANISM: Homo sapiens

<400> SEQUENCE: 45

```
tggaggcgcg caggccggct ccgctccggc cccggacgat gcggcgcgcc caggatgctg     60
ccgtgcctcg tagtgctgct ggcggcgctc ctcagcctcc gtcttggctc agacgctcat    120
gggacagagc tgcccagccc tccgtctgtg tggtttgaag cagaattttt ccaccacatc    180
ctccactgga cacccatccc aaatcagtct gaaagtacct gctatgaagt ggcactcctg    240
aggtatggaa tagagtcctg gaactccatc tccaactgta gccagaccct gtcctatgac    300
cttaccgcag tgaccttgga cctgtaccac agcaatggct accgggccag agtgcgggct    360
gtggacggca gccggcactc caactggacc gtcaccaaca cccgcttctc tgtggatgaa    420
gtgactctga cagttggcag tgtgaaccta gagatccaca atggcttcat cctcgggaag    480
attcagctac ccaggcccaa gatggccccc gcaaatgaca catatgaaag catcttcagt    540
cacttccgag agtatgagat tgccattcgc aaggtgccgg gaaacttcac gttcacacac    600
aagaaagtaa aacatgaaaa cttcagcctc ctaacctctg gagaagtggg agagttctgt    660
gtccaggtga aaccatctgt cgcttcccga agtaacaagg ggatgtggtc taaagaggag    720
tgcatctccc tcaccaggca gtatttcacc gtgaccaacg tcatcatctt ctttgccttt    780
gtcctgctgc tctccggagc cctcgcctac tgcctggccc tccagctgta tgtgcggcgc    840
cgaaagaagc tacccagtgt cctgctcttc aagaagccca gccccttcat cttcatcagc    900
cagcgtccct ccccagagac ccaagacacc atccacccgc ttgatgagga ggcctttttg    960
aaggtgtccc cagagctgaa gaacttggac ctgcacggca gcacagacag tggctttggc   1020
agcaccaagc catccctgca gactgaagag ccccagttcc tcctccctga ccctcacccc   1080
caggctgaca gaacgctggg aaacggggag ccccctgtgc tgggggacag ctgcagtagt   1140
ggcagcagca atagcacaga cagcgggatc tgcctgcagg agcccagcct gagccccagc   1200
acagggccca cctgggagca acaggtgggg agcaacagca ggggccagga tgacagtggc   1260
attgacttag ttcaaaactc tgagggccgg gctggggaca cacagggtgg ctcggccttg   1320
```

-continued

```
ggccaccaca gtcccccgga gcctgaggtg cctggggaag aagacccagc tgctgtggca   1380
ttccagggtt acctgaggca gaccagatgt gctgaagaga aggcaaccaa gacaggctgc   1440
ctggaggaag aatcgccctt gacagatggc cttggcccca aattcgggag atgcctggtt   1500
gatgaggcag gcttgcatcc accagccctg gccaagggct atttgaaaca ggatcctcta   1560
gaaatgactc tggcttcctc aggggcccca acgggacagt ggaaccagcc cactgaggaa   1620
tggtcactcc tggccttgag cagctgcagt gacctgggaa tatctgactg gagctttgcc   1680
catgaccttg cccctctagg ctgtgtggca gccccaggtg gtctcctggg cagctttaac   1740
tcagacctgg tcaccctgcc cctcatctct agcctgcagt caagtgagtg actcgggctg   1800
agaggctgct tttgatttta gccatgcctg ctcctctgcc tggaccagga ggagggcccc   1860
tggggcagaa gttaggcacg aggcagtctg ggcacttttc tgcaagtcca ctggggctgg   1920
ccccagccag gccctgcagg gctggtcagg gtgtctgggg caggaggagg ccaactcact   1980
gaactagtgc agggtatgtg ggtggcactg acctgttctg ttgactgggg ccctgcagac   2040
tctggcagag ctgagaaggg cagggacctt ctccctccta ggaactcttt cctgtatcat   2100
aaaggattat ttgctcaggg gaaccatggg gctttctgga gttgtggtga ggccaccagg   2160
ctgaagtcag ctcagaccca gacctccctg cttaggccac tcgagcatca gagcttccag   2220
caggaggaag ggctgtagga atggaagctt cagggccttg ctgctggggt catttttagg   2280
ggaaaaagga ggatatgatg gtcacatggg gaacctcccc tcatcgggcc tctggggcag   2340
gaagcttgtc actggaagat cttaaggtat atattttctg gacactcaaa cacatcataa   2400
tggattcact gaggggagac aaagggagcc gagaccctgg atggggcttc cagctcagaa   2460
cccatccctc tggtgggtac ctctggcacc catctgcaaa tatctccctc tctccaacaa   2520
atggagtagc atccccctgg ggcacttgct gaggccaagc cactcacatc ctcactttgc   2580
tgccccacca tcttgctgac aacttccaga gaagccatgg tttttgtat tggtcataac    2640
tcagcccttt gggcggcctc tgggcttggg caccagctca tgccagcccc agagggtcag   2700
ggttggaggc ctgtgcttgt gtttgctgct aatgtccagc tacagaccca gaggataagc   2760
cactgggcac tgggctgggg tccctgcctt gttggtgttc agctgtgtga ttttggacta   2820
gccacttgtc agagggcctc aatctcccat ctgtgaaata aggactccac ctttagggga   2880
ccctccatgt ttgctgggta ttagccaagc tggtcctggg agaatgcaga tactgtccgt   2940
ggactaccaa gctggcttgt ttcttatgcc agaggctaac agatccaatg ggagtccatg   3000
gtgtcatgcc aagacagtat cagacacagc cccagaaggg ggcattatgg gccctgcctc   3060
cccataggcc atttggactc tgccttcaaa caaaggcagt tcagtccaca ggcatggaag   3120
ctgtgagggg acaggcctgt gcgtgccatc cagagtcatc tcagccctgc ctttctctgg   3180
agcattctga aaacagatat tctggcccag ggaatccagc catgaccccc acccctctgc   3240
caaagtactc ttaggtgcca gtctggtaac tgaactccct ctggaggcag gcttgaggga   3300
ggattcctca gggttccctt gaaagcttta tttatttatt ttgttcattt atttattgga   3360
gaggcagcat tgcacagtga aagaattctg gatatctcag gagccccgaa attctagctc   3420
tgactttgct gtttccagtg gtatgacctt ggagaagtca cttatcctct tggagcctca   3480
gtttcctcat ctgcagaata atgactgact tgtctaattc gtagggatgt gaggttctgc   3540
tgaggaaatg ggtatgaatg tgccttgaac acaaagctct gtcaataagt gatacatgtt   3600
ttttattcca ataaattgtc aagaccacaa aaaaaaaaaa aaaaaaaaaa aaaaaaaaaa   3660
aaaaaaaaaa aaaaaaaaaa aaaaaaaaaa a                                  3691
```

<210> SEQ ID NO 46
<211> LENGTH: 4950
<212> TYPE: DNA
<213> ORGANISM: Homo sapiens

<400> SEQUENCE: 46
cagagcaggg tggagagggc ggtgggaggc gtgtgcctga gtgggctcta ctgccttgtt 60
ccatattatt ttgtgcacat tttccctggc actctgggtt gctagccccg ccgggcactg 120
ggcctcagac actgcgcggt tccctcggag cagcaagcta aagaaagccc ccagtgccgg 180
cgaggaagga ggcggcgggg aaagatgcgc ggcgttggct ggcagatgct gtccctgtcg 240
ctggggttag tgctggcgat cctgaacaag gtggcaccgc aggcgtgccc ggcgcagtgc 300
tcttgctcgg gcagcacagt ggactgtcac gggctggcgc tgcgcagcgt gcccaggaat 360
atcccccgca acaccgagag actggattta aatggaaata acatcacaag aattacgaag 420
acagattttg ctggtcttag acatctaaga gttcttcagc ttatggagaa taagattagc 480
accattgaaa gaggagcatt ccaggatctt aaagaactag agagactgcg tttaaacaga 540
aatcaccttc agctgtttcc tgagttgctg tttcttggga ctgcgaagct atacaggctt 600
gatctcagtg aaaaccaaat tcaggcaatc ccaaggaaag ctttccgtgg ggcagttgac 660
ataaaaaatt tgcaactgga ttacaaccag atcagctgta ttgaagatgg ggcattcagg 720
gctctccggg acctggaagt gctcactctc aacaataaca acattactag actttctgtg 780
gcaagtttca accatatgcc taaacttagg acttttcgac tgcattcaaa caacctgtat 840
tgtgactgcc acctggcctg gctctccgac tggcttcgcc aaaggcctcg ggttggtctg 900
tacactcagt gtatgggccc ctcccacctg agaggccata atgtagccga ggttcaaaaa 960
cgagaatttg tctgcagtgg tcaccagtca tttatggctc cttcttgtag tgttttgcac 1020
tgccctgccg cctgtacctg tagcaacaat atcgtagact gtcgtgggaa aggtctcact 1080
gagatcccca caaatcttcc agagaccatc acagaaatac gtttggaaca gaacacaatc 1140
aaagtcatcc ctcctggagc tttctcacca tataaaaagc ttagacgaat tgacctgagc 1200
aataatcaga tctctgaact tgcaccagat gctttccaag gactacgctc tctgaattca 1260
cttgtcctct atggaaataa aatcacagaa ctccccaaaa gtttatttga aggactgttt 1320
tccttacagc tcctattatt gaatgccaac aagataaact gccttcgggt agatgctttt 1380
caggatctcc acaacttgaa ccttctctcc ctatatgaca acaagcttca gaccatcgcc 1440
aaggggacct tttcacctct tcgggccatt caaactatgc atttggccca gaaccccttt 1500
atttgtgact gccatctcaa gtggctagcg gattatctcc ataccaaccc gattgagacc 1560
agtggtgccc gttgcaccag cccccgccgc ctggcaaaca aaagaattgg acagatcaaa 1620
agcaagaaat tccgttgttc agctaaagaa cagtatttca ttccaggtac agaagattat 1680
cgatcaaaat taagtggaga ctgctttgcg gatctggctt gccctgaaaa gtgtcgctgt 1740
gaaggaacca cagtagattg ctctaatcaa aagctcaaca aaatcccgga gcacattccc 1800
cagtacactg cagagttgcg tctcaataat aatgaattta ccgtgttgga agccacagga 1860
atctttaaga aacttcctca attacgtaaa ataaacttta gcaacaataa gatcacagat 1920
attgaggagg gagcatttga aggagcatct ggtgtaaatg aaatacttct tacgagtaat 1980
cgtttggaaa atgtgcagca taagatgttc aagggattgg aaagcctcaa aactttgatg 2040
ttgagaagca atcgaataac ctgtgtgggg aatgacagtt tcataggact cagttctgtg 2100

```
cgtttgcttt ctttgtatga taatcaaatt actacagttg caccaggggc atttgatact   2160
ctccattctt tatctactct aaacctcttg gccaatcctt ttaactgtaa ctgctacctg   2220
gcttggttgg gagagtggct gagaaagaag agaattgtca cgggaaatcc tagatgtcaa   2280
aaaccatact tcctgaaaga aatacccatc caggatgtgg ccattcagga cttcacttgt   2340
gatgacggaa atgatgacaa tagttgctcc ccactttctc gctgtcctac tgaatgtact   2400
tgcttggata cagtcgtccg atgtagcaac aagggtttga aggtcttgcc gaaaggtatt   2460
ccaagagatg tcacagagtt gtatctggat ggaaaccaat ttacactggt tcccaaggaa   2520
ctctccaact acaaacattt aacacttata gacttaagta acaacagaat aagcacgctt   2580
tctaatcaga gcttcagcaa catgacccag ctcctcacct taattcttag ttacaaccgt   2640
ctgagatgta ttcctcctcg cacctttgat ggattaaagt ctcttcgatt actttctcta   2700
catggaaatg acatttctgt tgtgcctgaa ggtgctttca atgatctttc tgcattatca   2760
catctagcaa ttggagccaa ccctctttac tgtgattgta acatgcagtg gttatccgac   2820
tgggtgaagt cggaatataa ggagcctgga attgctcgtt gtgctggtcc tggagaaatg   2880
gcagataaac ttttactcac aactccctcc aaaaaattta cctgtcaagg tcctgtggat   2940
gtcaatattc tagctaagtg taacccctgc ctatcaaatc cgtgtaaaaa tgatggcaca   3000
tgtaatagtg atccagttga cttttaccga tgcacctgtc catatggttt caaggggcag   3060
gactgtgatg tcccaattca tgcctgcatc agtaacccat gtaaacatgg aggaacttgc   3120
cacttaaagg aaggagaaga agatggattc tggtgtattt gtgctgatgg atttgaagga   3180
gaaaattgtg aagtcaacgt tgatgattgt gaagataatg actgtgaaaa taattctaca   3240
tgtgtcgatg gcattaataa ctacacatgc ctttgcccac ctgagtatac aggtgagttg   3300
tgtgaggaga agctggactt ctgtgcccag gacctgaacc cctgccagca cgattcaaag   3360
tgcatcctaa ctccaaaggg attcaaatgt gactgcacac cagggtacgt aggtgaacac   3420
tgcgacatcg attttgacga ctgccaagac aacaagtgta aaaacggagc ccactgcaca   3480
gatgcagtga acggctatac gtgcatatgc cccgaaggtt acagtggctt gttctgtgag   3540
ttttctccac ccatggtcct ccctcgtacc agcccctgtg ataattttga ttgtcagaat   3600
ggagctcagt gtatcgtcag aataaatgag ccaatatgtc agtgtttgcc tggctatcag   3660
ggagaaaagt gtgaaaaatt ggttagtgtg aattttataa acaaagagtc ttatcttcag   3720
attccttcag ccaaggttcg gcctcagacg aacataacac ttcagattgc cacagatgaa   3780
gacagcggaa tcctcctgta taagggtgac aaagaccata tcgcggtaga actctatcgg   3840
gggcgtgttc gtgccagcta tgacaccggc tctcatccag cttctgccat ttacagtgtg   3900
gagacaatca atgatggaaa cttccacatt gtggaactac ttgccttgga tcagagtctc   3960
tctttgtccg tggatggtgg gaaccccaaa atcatcacta acttgtcaaa gcagtccact   4020
ctgaattttg actctccact ctatgtagga ggcatgccag ggaagagtaa cgtggcatct   4080
ctgcgccagg cccctgggca gaacggaacc agcttccacg gctgcatccg gaacctttac   4140
atcaacagtg agctgcagga cttccagaag gtgccgatgc aaacaggcat tttgcctggc   4200
tgtgagccat gccacaagaa ggtgtgtgcc catggcacat gccagcccag cagccaggca   4260
ggcttcacct gcgagtgcca ggaaggatgg atggggcccc tctgtgacca acggaccaat   4320
gacccttgcc ttggaaataa atgcgtacat ggcacctgct tgcccatcaa tgcgttctcc   4380
tacagctgta agtgcttgga gggccatgga ggtgtcctct gtgatgaaga ggaggatctg   4440
tttaacccat gccaggcgat caagtgcaag cacgggaagt gcaggctttc aggtctgggg   4500
```

```
cagccctact gtgaatgcag cagtggatac acgggggaca gctgtgatcg agaaatctct   4560

tgtcgagggg aaaggataag agattattac caaaagcagc agggctatgc tgcttgccaa   4620

acaaccaaga aggtgtcccg attagagtgc agaggtgggt gtgcaggagg gcagtgctgt   4680

ggaccgctga ggagcaagcg gcggaaatac tctttcgaat gcactgacgg ctcctccttt   4740

gtggacgagg ttgagaaagt ggtgaagtgc ggctgtacga ggtgtgtgtc ctaaacacac   4800

tcccggcagc tctgtctttg gaaaaggttg tatacttctt gaccatgtgg gactaatgaa   4860

tgcttcatag tggaaatatt tgaaatatat tgtaaaatac agaacagact tatttttatt   4920

atgagaataa agactttttt tctgcatttg                                    4950
```

<210> SEQ ID NO 47
<211> LENGTH: 1410
<212> TYPE: DNA
<213> ORGANISM: Homo sapiens

<400> SEQUENCE: 47

```
gggcggggct cgggccggtc cgcccgcgcg caggtgagtg agccagggcg gagcgcagct     60

gcgccgggct tgggcgcctg ggccgccgc tccccaccgt cgttttcccc accgaggccg     120

aggcgtcccg gagtcatggc cggcctgaac tgcggggtct ctatcgcact gctaggggtt    180

ctgctgctgg gtgcggcgcg cctgccgcgc ggggcagaag cttttgagat tgctctgcca    240

cgagaaagca acattacagt tctcataaag ctggggaccc cgactctgct ggcaaaaccc    300

tgttacatcg tcatttctaa aagacatata accatgttgt ccatcaagtc tggagaaaga    360

atagtcttta cctttagctg ccagagtcct gagaatcact ttgtcataga gatccagaaa    420

aatattgact gtatgtcagg cccatgtcct tttggggagg ttcagcttca gccctcgaca    480

tcgttgttgc ctaccctcaa cagaactttc atctgggatg tcaaagctca taagagcatc    540

ggtttagagc tgcagttttc catccctcgc ctgaggcaga tcggtccggg tgagagctgc    600

ccagacggag tcactcactc catcagcggc cgaatcgatg ccaccgtggt caggatcgga    660

accttctgca gcaatggcac tgtgtcccgg atcaagatgc aagaaggagt gaaaatggcc    720

ttacacctcc catggttcca ccccagaaat gtctccggct tcagcattgc aaaccgctca    780

tctataaaac gtctgtgcat catcgagtct gtgtttgagg gtgaaggctc agcaaccctg    840

atgtctgcca actacccaga aggcttccct gaggatgagc tcatgacgtg gcagtttgtc    900

gttcctgcac acctgcgggc cagcgtctcc ttcctcaact tcaacctctc caactgtgag    960

aggaaggagg agcgggttga atactacatc ccgggctcca ccaccaaccc cgaggtgttc   1020

aagctggagg acaagcagcc tgggaacatg gcggggaact tcaacctctc tctgcaaggc   1080

tgtgaccaag atgcccaaag tccagggatc ctccggctgc agttccaagt tttggtccaa   1140

catccacaaa atgaaagcag tgagtgagcc ccactttcct tttcttcct cctccagcac    1200

cttcgttgtt tcctgggtag tctgcctggg tgaggctccc ttcctgtttc tcatctgtgg   1260

cttctgaaac acttagactc tggacccagc aagagtttca ggaagtgggt tgctaggcag   1320

ttagacaggc ttgttggtga acacccggta tgtagttcca tttcagcaca ataaaaagaa   1380

atcttgcatt caaaaaaaaa aaaaaaaaaa                                    1410
```

<210> SEQ ID NO 48
<211> LENGTH: 36
<212> TYPE: DNA
<213> ORGANISM: Homo sapiens

```
<400> SEQUENCE: 48

tattctagat tcaacaccaa ttccattttc ttattc                              36


<210> SEQ ID NO 49
<211> LENGTH: 36
<212> TYPE: DNA
<213> ORGANISM: Homo sapiens

<400> SEQUENCE: 49

ttagcggccg ctagttctgt atcatatcgt aaaggg                              36


<210> SEQ ID NO 50
<211> LENGTH: 24
<212> TYPE: DNA
<213> ORGANISM: Homo sapiens

<400> SEQUENCE: 50

gttatctaga agcacccccca tccc                                           24


<210> SEQ ID NO 51
<211> LENGTH: 36
<212> TYPE: DNA
<213> ORGANISM: Homo sapiens

<400> SEQUENCE: 51

ttaagatctc taagatctgg tgtcgtatct cagggg                              36


<210> SEQ ID NO 52
<211> LENGTH: 389
<212> TYPE: DNA
<213> ORGANISM: Homo sapiens

<400> SEQUENCE: 52

ctccaaagga gccagcgtct ccccagttcc tgaaatcctg ggtgttgcct gccagtcgcc     60

atgagaactt cctaccttct gctgtttact ctctgcttac ttttgtctga gatggcctca    120

ggtggtaact ttctcacagg ccttggccac agatctgatc attacaattg cgtcagcagt    180

ggagggcaat gtctctattc tgcctgcccg atctttacca aaattcaagg cacctgttac    240

agagggaagg ccaagtgctg caagtgagct gggagtgacc agaagaaatg acgcagaagt    300

gaaatgaact ttttataagc attcttttaa taaaggaaaa ttgcttttga agtataaaaa    360

aaaaaaaaaa aaaaaaaaaa aaaaaaaaa                                      389


<210> SEQ ID NO 53
<211> LENGTH: 709
<212> TYPE: DNA
<213> ORGANISM: Homo sapiens

<400> SEQUENCE: 53

atttacaata aatgaagatt accctcaaat gctagaagct gtctaggtcc gtccggtgtg     60

tcagattttc ctcagattag atgtgccaat aaccaagttt attcagtaaa caacttgtac    120

ttgtttcatc tggttttatt actctcaccc ataaacagga atgactcttt gaccctctgg    180

aaatatgtaa tgcttccaat cttgctttgt gtatctcatt taatttgtta taaggtagta    240

ctgattttag catattaatg cgatttcttc cttgttgttt gctttggtct gtgttcaatc    300

cagagagctt aaattgtcat tattttggga agaaaacctg tatttttgtt agtttacaat    360

attatgaaat ttcacttcag gagaaactgc tgggcttcct gtggctttgt tttcttagtt    420

actttttccg tgccgtgtat tttttaattg atttttcttc ttttacttga aaagaaagtg    480
```

```
ttttattttc aaatctggtc catatttaca ttctagttca gagccaagcc ttaaactgta    540

cagaatttcc actgtaatta aaactattta gtgttagtta taaatagcct tcaaaaagag    600

agattctcca ttcacgatca cctgcatcac agcccatggt gaatgtatgt ttctgcatag    660

cgaaataaaa atggcaaatg caaaaaaaaa aaaaaaaaaa aaaaaaaaa                709
```

<210> SEQ ID NO 54
<211> LENGTH: 2813
<212> TYPE: DNA
<213> ORGANISM: Homo sapiens

<400> SEQUENCE: 54

```
ctgactttct ctcggtgcgt ccagtggagc tctgagtttc gaatcggtgg cggcggattc     60

cccgcgcgcc cggcgtcggg gcttccagga ggatgcggag ccccagcgcg gcgtggctgc    120

tgggggccgc catcctgcta gcagcctctc tctcctgcag tggcaccatc caaggaacca    180

atagatcctc taaaggaaga agccttattg gtaaggttga tggcacatcc cacgtcactg    240

gaaaaggagt tacagttgaa acagtctttt ctgtggatga gttttctgca tctgtcctca    300

ctggaaaact gaccactgtc ttccttccaa ttgtctacac aattgtgttt gtggtgggtt    360

tgccaagtaa cggcatggcc ctgtgggtct ttcttttccg aactaagaag aagcaccctg    420

ctgtgattta catggccaat ctggccttgg ctgacctcct ctctgtcatc tggttcccct    480

tgaagattgc ctatcacata catggcaaca actggattta tggggaagct ctttgtaatg    540

tgcttattgg ctttttctat ggcaacatgt actgttccat tctcttcatg acctgcctca    600

gtgtgcagag gtattgggtc atcgtgaacc ccatggggca ctccaggaag aaggcaaaca    660

ttgccattgg catctccctg gcaatatggc tgctgattct gctggtcacc atccctttgt    720

atgtcgtgaa gcagaccatc ttcattcctg ccctgaacat cacgacctgt catgatgttt    780

tgcctgagca gctcttggtg ggagacatgt tcaattactt cctctctctg gccattgggg    840

tctttctgtt cccagccttc ctcacagcct ctgcctatgt gctgatgatc agaatgctgc    900

gatcttctgc catggatgaa aactcagaga agaaaaggaa gagggccatc aaactcattg    960

tcactgtcct ggccatgtac ctgatctgct tcactcctag taaccttctg cttgtggtgc   1020

attattttct gattaagagc cagggccaga gccatgtcta tgccctgtac attgtagccc   1080

tctgcctctc tacccttaac agctgcatcg acccctttgt ctattacttt gtttcacatg   1140

atttcaggga tcatgcaaag aacgctctcc tttgccgaag tgtccgcact gtaaagcaga   1200

tgcaagtatc cctcacctca aagaaacact ccaggaaatc cagctcttac tcttcaagtt   1260

caaccactgt taagacctcc tattgagttt tccaggtcct cagatgggaa ttgcacagta   1320

ggatgtggaa cctgtttaat gttatgagga cgtgtctgtt atttcctaat caaaaaggtc   1380

tcaccacata ccatgtggat gcagcacctc tcaggattgc taggagctcc cctgtttgca   1440

tgagaaaagt agtcccccaa attaacatca gtgtctgttt cagaatctct ctactcagat   1500

gaccccagaa actgaaccaa cagaagcaga cttttcagaa gatggtgaag acagaaaccc   1560

agtaacttgc aaaaagtaga cttggtgtga agactcactt ctcagctgaa attatatata   1620

tacacatata tatatatatt ttacatctgg gatcatgata gacttgttag ggcttcaagg   1680

ccctcagaga tgatcagtcc aactgaacga ccttacaaat gaggaaacca agataaatga   1740

gctgccagaa tcaggtttcc aatcaacagc agtgagatgg gattggacag tagaatttca   1800

atgtccagtg agtgaggttc ttgtaccact tcatcaaaat catggatctt ggctgggtgc   1860
```

```
ggtgcctcat gcctgtaatc ctagcacttt gggaggctga ggcaggcaat cacttgaggt   1920

caggagttcg agaccagcct ggccatcatg gcgaaacctc atctctacta aaaatacaaa   1980

agttaaccag gtgtgtggtg cacgtttgta atcccagtta ctcaggaggc tgaggcacaa   2040

gaattgagta tcactttaac tcaggaggca gaggttgcag tgagccgaga ttgcaccact   2100

gcactccagc ttgggtgata aaataaaata aaatagtcgt gaatcttgtt caaaatgcag   2160

attcctcaga ttcaataatg agagctcaga ctgggaacag ggcccaggaa tctgtgtggt   2220

acaaacctgc atggtgttta tgcacacaga gatttgagaa ccattgttct gaatgctgct   2280

tccatttgac aaagtgccgt gataattttt gaaaagagaa gcaaacaatg gtgtctcttt   2340

tatgttcagc ttataatgaa atctgtttgt tgacttatta ggactttgaa ttatttcttt   2400

attaaccctc tgagtttttg tatgtattat tattaaagaa aaatgcaatc aggattttaa   2460

acatgtaaat acaaatttg tataactttt gatgacttca gtgaaatttt caggtagtct   2520

gagtaataga ttgttttgcc acttagaata gcatttgcca cttagtattt taaaaaataa   2580

ttgttggagt atttattgtc agttttgttc acttgttatc taatacaaaa ttataaagcc   2640

ttcagagggt ttggaccaca tctctttgga aaatagtttg caacatattt aagagatact   2700

tgatgccaaa atgactttat acaacgattg tatttgtgac ttttaaaaat aattatttta   2760

ttgtgtaatt gatttataaa taacaaaatt ttttttacaa cttaaaaaaa aaa          2813
```

<210> SEQ ID NO 55
<211> LENGTH: 1473
<212> TYPE: DNA
<213> ORGANISM: Homo sapiens

<400> SEQUENCE: 55

```
ggagtccaaa agaaaaggaa gaggaggaaa aacaagtgtg tgttgggggg aacaggggga     60

aaagcatttt tggtggatgg tatgaagcca gccatggaaa ctgcagccga ggaaaatact    120

gaacaaagcc aagagagaaa aggctgcttt gaatgctgca tcaagtgtct gggaggagtc    180

ccctacgcct ccctggtggc caccatcctc tgcttctccg ggtggcctt attctgcggc    240

tgtgggcatg tggctctcgc aggcaccgtg gcgattcttg agcaacactt ctccaccaac    300

gccagtgacc atgccttgct gagcgaggtg atacaactga tgcagtatgt catctatgga    360

attgcgtcct ttttcttctt gtatgggatc attctgttgg cagaaggctt ttacaccaca    420

agtgcagtga aagaactgca cggtgagttt aaaacaaccg cttgtggccg atgcatcagt    480

ggaatgttcg ttttcctcac ctatgtgctt ggagtggcct ggctgggtgt gtttggtttc    540

tcagcggtgc ccgtgtttat gttctacaac atatggtcaa cttgtgaagt catcaagtca    600

ccgcagacca acgggaccac gggtgtggag cagatctgtg tggatatccg acaatacggt    660

atcattcctt ggaatgcttt ccccggaaaa atatgtggct ctgccctgga gaacatctgc    720

aacacaaacg agttctacat gtcctatcac ctgttcattg tggcctgtgc aggagctggt    780

gccaccgtca ttgccctgct gatctacatg atggctacta catataacta tgcggttttg    840

aagtttaaga gtcgggaaga ttgctgcact aaattctaaa ttgcataagg agttttagag    900

agctatgctc tgtagcatga aatatcactg acactccaga ctaaagcaga gtctaggttt    960

ctgcaatttt gttacagtaa tttgtaaata gctttagtaa actcaccttg catggtagat   1020

taataagatg acttactgta catgaattac acaataatga gatctggtgg ctatttccac   1080

attttgaaaa ggattcagtt atttactgac agtggtgagc atccttttta aaataatgtt   1140

ctcatactta aacattagag agcagtatct ttaaatgaat tattaacact ttggaatact   1200
```

```
tacattttct gttatttttg attgcctgat aaccagtttc aatgatgaaa atgaaaacaa   1260
gtgctgaaga tgaaatggaa gagaaccgtt ttaatctgga ttttgttttg tcacacctgg   1320
aaaatacttt gcaaatatgt tctaaattga aaacaatttt ttttatgatc acatggttca   1380
ctaccaaatg accctcaaat aagccagatg aaaatttgaa gaaaaaggtc acccagttct   1440
ctggaaaaaa aaaaaaaaaa aaaaaaaaaa aaa                                1473
```

<210> SEQ ID NO 56
<211> LENGTH: 5400
<212> TYPE: DNA
<213> ORGANISM: Homo sapiens

<400> SEQUENCE: 56

```
ccgccaagca tattgctagg cacagagcag gtgtgcaaca aaagttattt ctcaggcttt     60
ccctcctctg agcgccgtcc tccagagggt ccggagtgta gctgggggtt ggagcagcag    120
cctcctaggc gatgggacag agcccacagg gtccggtatg ccacggtttc ttcgtcagac    180
cctgggaatc caacgtcgca aaataaacac ggccgcgccg ctaatcgcca gttcggagga    240
aacaaaacag cgctgcgctg ggggatctgg gcaaaatcag ccctccctcc tcccgctcct    300
tcgccgcggc cctcccctcc tcgcgctgct ctcgttcgct tggctcagct cagctcagct    360
cagcgcagct ccgcggccgc caagccgagg cgggcacggt ctccgagtcg cggacgccag    420
ctccgagctc cctctctccg ccgcgcctcc gccaggtcgc gccttcgtcg ggaccacttc    480
gggcaggagt cgcgtggcga aggcctgcgg ccgcggcaca aagttggggg ccgcgaagat    540
gaggctgtcc ccggcgcccc tgaagctgag ccggactccg gcactgctgg ccctggcgct    600
gcccctggcc gcggcgctgg ccttctccga cgagaccctg gacaaagtgc ccaagtcaga    660
gggctactgc agccgtatcc tgcgcgccca gggcacgcgg cgcgagggct acaccgagtt    720
cagcctccgc gtggagggcg accccgactt ctacaagccg ggaaccagct accgcgtaac    780
actttcagct gctcctccct cctacttcag aggattcaca ttaattgccc tcagagagaa    840
cagagagggt gataaggaag aagaccatgc tgggaccttc cagatcatag acgaagaaga    900
aactcagttt atgagcaatt gccctgttgc agtcactgaa agcactccac ggaggaggac    960
ccggatccag gtgttttgga tagcaccacc agcgggaaca ggctgcgtga ttctgaaggc   1020
cagcatcgta caaaaacgca ttatttattt tcaagatgag ggctctctga ccaagaaact   1080
ttgtgaacaa gattccacat ttgatggggt gactgacaaa cccatcttag actgctgtgc   1140
ctgcggaact gccaagtaca gactcacatt ttatgggaat tggtccgaga agacacaccc   1200
aaaggattac cctcgtcggg ccaaccactg gtctgcgatc atcggaggat cccactccaa   1260
gaattatgta ctgtgggaat atggaggata tgccagcgaa ggcgtcaaac aagttgcaga   1320
attgggctca cccgtgaaaa tggaggaaga aattcgacaa cagagtgatg aggtcctcac   1380
cgtcatcaaa gccaaagccc aatggccagc ctggcagcct ctcaacgtga gagcagcacc   1440
ttcagctgaa ttttccgtgg acagaacgcg ccatttaatg tccttcctga ccatgatggg   1500
ccctagtccc gactggaacg taggcttatc tgcagaagat ctgtgcacca aggaatgtgg   1560
ctgggtccag aaggtggtgc aagacctgat tccctgggac gctggcaccg acagcggggt   1620
gacctatgag tcacccaaca aacccaccat tccccaggag aaaatccggc ccctgaccag   1680
cctggaccat cctcagagtc ctttctatga cccagagggt gggtccatca ctcaagtagc   1740
cagagttgtc atcgagagaa tcgcacggaa gggtgaacaa tgcaatattg tacctgacaa   1800
```

```
tgtcgatgat attgtagctg acctggctcc agaagagaaa gatgaagatg acacccctga   1860
aacctgcatc tactccaact ggtccccatg gtccgcctgc agctcctcca cctgtgacaa   1920
aggcaagagg atgcgacagc gcatgctgaa agcacagctg gacctcagcg tcccctgccc   1980
tgacacccag gacttccagc cctgcatggg ccctggctgc agtgacgaag acggctccac   2040
ctgcaccatg tccgagtgga tcacctggtc gccctgcagc atctcctgcg gcatgggcat   2100
gaggtcccgg gagaggtatg tgaagcagtt cccggaggac ggctccgtgt gcacgctgcc   2160
cactgaggaa acggagaagt gcacggtcaa cgaggagtgc tctcccagca gctgcctgat   2220
gaccgagtgg ggcgagtggg acgagtgcag cgccacctgc ggcatgggca tgaagaagcg   2280
gcaccgcatg atcaagatga accccgcaga tggctccatg tgcaaagccg agacatcaca   2340
ggcagagaag tgcatgatgc cagagtgcca caccatccca tgcttgctgt ccccatggtc   2400
cgagtggagt gactgcagcg tgacctgcgg gaagggcatg cgaacccgac agcggatgct   2460
caagtctctg gcagaacttg gagactgcaa tgaggatctg gagcaggtgg agaagtgcat   2520
gctccctgaa tgccccattg actgtgagct caccgagtgg tcccagtggt cggaatgtaa   2580
caagtcatgt gggaaaggcc acgtgattcg aacccggatg atccaaatgg agcctcagtt   2640
tggaggtgca ccctgcccag agactgtgca gcgaaaaaag tgccgcatcc gaaaatgcct   2700
tcgaaatcca tccatccaaa agctacgctg gagggaggcc cgagagagcc ggcggagtga   2760
gcagctgaag gaagagtctg aaggggagca gttcccaggt tgtaggatgc gcccatggac   2820
ggcctggtca gaatgcacca aactgtgcgg aggtggaatt caggaacgtt acatgactgt   2880
aaagaagaga ttcaaaagct cccagtttac cagctgcaaa gacaagaagg agatcagagc   2940
atgcaatgtt catccttgtt agcaagggta cgagttcccc agggctgcac tctagattcc   3000
agagtcacca atggctggat tatttgcttg tttaagacaa tttaaattgt gtacgctagt   3060
tttcattttt gcagtgtggt tcgcccagta gtcttgtgga tgccagagac atcctttctg   3120
aatacttctt gatgggtaca ggctgagtgg ggcgccctca cctccagcca gcctcttcct   3180
gcagaggagt agtgtcagcc accttgtact aagctgaaac atgtccctct ggagcttcca   3240
cctggccagg gaggacggag actttgacct actccacatg gagaggcaac catgtctgga   3300
agtgactatg cctgagtccc agggtgcggc aggtaggaaa cattcacaga tgaagacagc   3360
agattcccca cattctcatc tttggcctgt tcaatgaaac cattgtttgc ccatctcttc   3420
ttagtggaac tttaggtctc ttttcaagtc tcctcagtca tcaatagttc ctggggaaaa   3480
acagagctgg tagacttgaa gaggagcatt gatgttgggt ggcttttgtt ctttcactga   3540
gaaattcgga atacatttgt ctcacccctg atattggttc ctgatgcccc cccaacaaaa   3600
ataaataaat aaattatggc tgctttattt aaatataagg tagctagttt ttacacctga   3660
gataaataat aagcttagag tgtatttttc ccttgctttt gggggttcag aggagtatgt   3720
acaattcttc tgggaagcca gccttctgaa ctttttggta ctaaatcctt attggaacca   3780
agacaaagga agcaaaattg gtctctttag agaccaattt gcctaaattt taaaatcttc   3840
ctacacacat ctagacgttc aagtttgcaa atcagttttt agcaagaaaa catttttgct   3900
atacaaacat tttgctaagt ctgcccaaag ccccccccaat gcattccttc aacaaaatac   3960
aatctctgta ctttaaagtt attttagtca tgaaatttta tatgcagaga gaaaaagtta   4020
ccgagacaga aaacaaatct aagggaaagg aatattatgg gattaagctg agcaagcaat   4080
tctggtggaa agtcaaacct gtcagtgctc cacaccaggg ctgtggtcct cccagacatg   4140
cataggaatg gccacaggtt tacactgcct tcccagcaat tataagcaca ccagattcag   4200
```

```
ggagactgac caccaaggga tagtgtaaaa ggacattttc tcagttgggt ccatcagcag   4260
tttttcttcc tgcatttatt gttgaaaact attgtttcat ttcttctttt ataggcctta   4320
ttactgctta atccaaatgt gtaccattgg tgagacacat acaatgctct gaatacacta   4380
cgaatttgta ttaaacacat cagaatattt ccaaatacaa catagtatag tcctgaatat   4440
gtacttttaa cacaagagag actattcaat aaaaactcac tgggtctttc atgtctttaa   4500
gctaagtaag tgttcagaag gttctttttt atattgtcct ccacctccat cattttcaat   4560
aaaagatagg gcttttgctc ccttgttctt ggagggacca ttattacatc tctgaactac   4620
ctttgtatcc aacatgtttt aaatccttaa atgaattgct ttctcccaaa aaaagcacaa   4680
tataaagaaa cacaagattt aattattttt ctacttgggg ggaaaaaagt cctcatgtag   4740
aagcacccac ttttgcaatg ttgttctaag ctatctatct aactctcagc ccatgataaa   4800
gttccttaag ctggtgattc ctaatcaagg acaagccacc ctagtgtctc atgtttgtat   4860
ttggtcccag ttgggtacat tttaaaatcc tgattttgga gacttaaaac caggttaatg   4920
gctaagaatg ggtaacatga ctcttgttgg attgttattt tttgtttgca atggggaatt   4980
tataagaagc atcaagtctc tttcttacca aagtcttgtt aggtggttta tagttctttt   5040
ggctaacaaa tcattttgga aataaagatt ttttactaca aaaatgaaat ttgtttggac   5100
ttccacttga gacagtaaag agagtattag acacccagta aaaactgcca tataaagaag   5160
ttgtaattgt ttgttgtgta tgtatttttt tcaatgccaa accagctgtg atccaattta   5220
catccacatt ttaggtccaa cagcaagaag ttcagagaga gatttcccaa ccagacattg   5280
ggtcactcac tggtcacctt gccagtgcat tttattagaa gggaatctgt tgtagcaaat   5340
gggaataaac ctgggtttct atagacccag aactgaaaaa ataaaaaaaa aaaaaaaaaa   5400
```

<210> SEQ ID NO 57
<211> LENGTH: 1947
<212> TYPE: DNA
<213> ORGANISM: Homo sapiens

<400> SEQUENCE: 57

```
catccctgcc attgccgggc actcgcggcg ctgctaacgg cctggtcaca tgctctccgg     60
agagctacgg gagggcgctg ggtaacctct atccgagccg cggccgcgag gaggagggaa    120
aaggcgagca aaaaggaaga gtgggaggag gaggggaagc ggcgaaggag gaagaggagg    180
aggaggaaga ggggagcaca aaggatccag gtctcccgac gggaggttaa taccaagaac    240
catgtgtgcc gagcggctgg gccagttcat gaccctggct ttggtgttgg ccacctttga    300
cccggcgcgg gggaccgacg ccaccaaccc acccgagggt ccccaagaca ggagctccca    360
gcagaaaggc cgcctgtccc tgcagaatac agcggagatc cagcactgtt tggtcaacgc    420
tggcgatgtg gggtgtggcg tgtttgaatg tttcgagaac aactcttgtg agattcgggg    480
cttacatggg atttgcatga cttttctgca caacgctgga aaatttgatg cccagggcaa    540
gtcattcatc aaagacgcct tgaaatgtaa ggcccacgct ctgcggcaca ggttcggctg    600
cataagccgg aagtgcccgg ccatcaggga aatggtgtcc cagttgcagc gggaatgcta    660
cctcaagcac gacctgtgcg cggctgccca ggagaacacc cgggtgatag tggagatgat    720
ccatttcaag gacttgctgc tgcacgaacc ctacgtggac ctcgtgaact tgctgctgac    780
ctgtggggag gaggtgaagg aggccatcac ccacagcgtg caggttcagt gtgagcagaa    840
ctggggaagc ctgtgctcca tcttgagctt ctgcacctcg gccatccaga agcctcccac    900
```

-continued

```
ggcgcccccc gagcgccagc cccaggtgga cagaaccaag ctctccaggg cccaccacgg    960

ggaagcagga catcacctcc cagagcccag cagtagggag actggccgag gtgccaaggg   1020

tgagcgaggt agcaagagcc acccaaacgc ccatgcccga ggcagagtcg gggccttgg    1080

ggctcaggga ccttccggaa gcagcgagtg ggaagacgaa cagtctgagt attctgatat   1140

ccggaggtga aatgaaaggc ctggccacga aatctttcct ccacgccgtc cattttctta   1200

tctatggaca ttccaaaaca tttaccatta gagagggggg atgtcacacg caggattctg   1260

tggggactgt ggacttcatc gaggtgtgtg ttcgcggaac ggacaggtga gatggagacc   1320

cctggggccg tggggtctca ggggtgcctg gtgaattctg cacttacacg tactcaaggg   1380

agcgcgcccg cgttatcctc gtacctttgt cttctttcca tctgtggagt cagtgggtgt   1440

cggccgctct gttgtggggg aggtgaacca gggaggggca gggcaaggca gggcccccag   1500

agctgggcca cacagtgggt gctgggcctc gccccgaagc ttctggtgca gcagcctctg   1560

gtgctgtctc cgcggaagtc agggcggctg gattccagga caggagtgaa tgtaaaaata   1620

aatatcgctt agaatgcagg agaagggtgg agaggaggca ggggccgagg gggtgcttgg   1680

tgccaaactg aaattcagtt tcttgtgtgg ggccttgcgg ttcagagctc ttggcgaggg   1740

tggagggagg agtgtcattt ctatgtgtaa tttctgagcc attgtactgt ctgggctggg   1800

ggggacactg tccaagggag tggcccctat gagtttatat tttaaccact gcttcaaatc   1860

tcgatttcac ttttttattt tatccagtta tatctacata tctgtcatct aaataaatgg   1920

ctttcaaaca aaaaaaaaaa aaaaaaa                                       1947


<210> SEQ ID NO 58
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 58

Asn Asn Phe Thr Val Ser Phe Trp Leu Arg Val Pro Lys Val Ser Ala
1               5                   10                  15

Ser His Leu Glu
            20
```